US010112926B2

(12) United States Patent
Bellenie et al.

(10) Patent No.: US 10,112,926 B2
(45) Date of Patent: Oct. 30, 2018

(54) AMINO PYRIDINE DERIVATIVES AS PHOSPHATIDYLINOSITOL 3-KINASE INHIBITORS

(71) Applicants: Benjamin Richard Bellenie, Horsham (GB); Graham Charles Bloomfield, Horsham (GB); Ian Bruce, Tyne and Wear (GB); Andrew James Culshaw, Middlesex (GB); Edward Charles Hall, Cambridge, MA (US); Gregory John Hollingworth, Kent (GB); James Neef, Cambridge, MA (US); Matthew Spendiff, Horsham (GB); Simon James Watson, Horsham (GB)

(72) Inventors: Benjamin Richard Bellenie, Horsham (GB); Graham Charles Bloomfield, Horsham (GB); Ian Bruce, Tyne and Wear (GB); Andrew James Culshaw, Middlesex (GB); Edward Charles Hall, Cambridge, MA (US); Gregory John Hollingworth, Kent (GB); James Neef, Cambridge, MA (US); Matthew Spendiff, Horsham (GB); Simon James Watson, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/303,879

(22) PCT Filed: Apr. 24, 2014

(86) PCT No.: PCT/IB2014/060985

§ 371 (c)(1),
(2) Date: Oct. 13, 2016

(87) PCT Pub. No.: WO2015/162456

PCT Pub. Date: Oct. 29, 2015

(65) Prior Publication Data

US 2017/0037032 A1 Feb. 9, 2017

(51) Int. Cl.

| | |
|---|---|
| *C07D 401/14* | (2006.01) |
| *C07D 413/14* | (2006.01) |
| *C07D 401/04* | (2006.01) |
| *C07D 413/04* | (2006.01) |
| *C07D 417/04* | (2006.01) |
| *C07D 417/14* | (2006.01) |
| *C07D 213/73* | (2006.01) |
| *C07D 491/107* | (2006.01) |
| *A61K 31/4439* | (2006.01) |
| *A61K 31/444* | (2006.01) |
| *A61K 31/4545* | (2006.01) |
| *A61K 31/496* | (2006.01) |

(Continued)

(52) U.S. Cl.

CPC .......... *C07D 401/14* (2013.01); *A61K 31/444* (2013.01); *A61K 31/4439* (2013.01); *A61K 31/4545* (2013.01); *A61K 31/496* (2013.01); *A61K 31/5377* (2013.01); *A61K 31/55* (2013.01); *C07D 213/73* (2013.01); *C07D 401/04* (2013.01); *C07D 413/04* (2013.01); *C07D 413/14* (2013.01); *C07D 417/04* (2013.01); *C07D 417/14* (2013.01); *C07D 491/107* (2013.01)

(58) Field of Classification Search

CPC .. C07D 401/14; C07D 213/73; C07D 401/04; C07D 413/04; C07D 413/14; C07D 417/04; C07D 417/14; C07D 491/107

See application file for complete search history.

(56) References Cited

U.S. PATENT DOCUMENTS

2009/0118305 A1 5/2009 Barlaam et al.
2009/0239847 A1 9/2009 Bruce et al.
2012/0071662 A1 3/2012 Sander et al.

(Continued)

FOREIGN PATENT DOCUMENTS

WO WO2003077918 A1 9/2003
WO WO2003093297 A2 11/2003

(Continued)

OTHER PUBLICATIONS

International Search Report and Written Opinion for International Application No. PCT/IB2014/060985, dated Jul. 17, 2014 (7 pages).

(Continued)

*Primary Examiner* — Rebecca L Anderson
(74) *Attorney, Agent, or Firm* — Michelle Han

(57) ABSTRACT

The present invention provides compounds of formula (I) which inhibit the activity of PI 3-kinase gamma isoform, which are useful for the treatment of diseases mediated by the activation of PI 3-kinase gamma isoform.

(I)

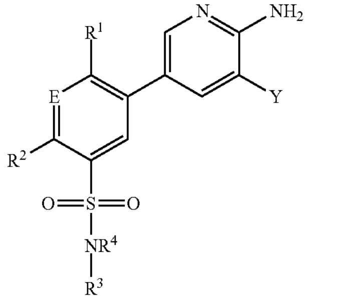

14 Claims, No Drawings

(51) Int. Cl.
*A61K 31/5377* (2006.01)
*A61K 31/55* (2006.01)

(56) References Cited

U.S. PATENT DOCUMENTS

| | | | | |
|---|---|---|---|---|
| 2012/0295905 | A1* | 11/2012 | Witty .................. | C07D 213/73 514/235.5 |
| 2017/0029414 | A1 | 2/2017 | Bellenie et al. | |
| 2017/0042889 | A1 | 2/2017 | Bellenie et al. | |

FOREIGN PATENT DOCUMENTS

| | | | |
|---|---|---|---|
| WO | WO2006124874 | A2 | 11/2006 |
| WO | WO2007110337 | A1 | 10/2007 |
| WO | WO2007111904 | A2 | 10/2007 |
| WO | WO2008006583 | A1 | 1/2008 |
| WO | WO2008025820 | A1 | 3/2008 |
| WO | WO2009007390 | A2 | 1/2009 |
| WO | WO2009013348 | A2 | 1/2009 |
| WO | WO2009053737 | A2 | 4/2009 |
| WO | WO2009087212 | A2 | 7/2009 |
| WO | 2009/115517 | A2 | 9/2009 |
| WO | WO2010071837 | A1 | 6/2010 |
| WO | WO2011086531 | A2 | 7/2011 |
| WO | WO2015162459 | A1 | 10/2015 |
| WO | WO2015162461 | A1 | 10/2015 |

OTHER PUBLICATIONS

Leahy et al., "Discovery of a novel series of potent and orally bioavailable phosphoinositide 3-kinase γ inhibitors," J Med Chem. Jun. 14, 2012;55(11):5467-82.

* cited by examiner

AMINO PYRIDINE DERIVATIVES AS PHOSPHATIDYLINOSITOL 3-KINASE INHIBITORS

TECHNICAL FIELD

The present invention relates to novel amino pyridine derivatives which are PI 3-kinase gamma isoform selective inhibitors, processes for their preparation, pharmaceutical compositions and medicaments containing them and to their use in diseases and disorders mediated by the activation of PI 3-kinase gamma isoform, particularly asthma.

BACKGROUND

Phosphatidylinositol 3-kinases (PI 3-kinases), a family of enzymes which catalyse the phosphorylation of the 3'-OH of the inositol ring, play a central role in regulating a wide range of cellular processes including metabolism, survival, motility and cell activation (Vanhaesebroeck, B. et al., Annu. Rev. Biochem. 2001, 70, 535). These lipid kinases are divided into 3 major classes, I, II & III, according to their structure and in vitro substrate specificity (Wymann, M. et al.; Biochem. Biophys. Acta, 1998, 1436, 127). The most widely understood class I family is further subdivided into subclasses IA and IB. Class IA PI 3-kinases consist of an 85 kDa regulatory/adapter protein and three 110 kDa catalytic subunits (p110α, p110β and p110δ) which are activated in the tyrosine kinase system whilst class IB consists of a single p110γ isoform (PI 3-kinase gamma isoform) which is activated by G protein-coupled receptors. The three members of class II PI 3-kinases (C2α, C2β and C2γ) and single member of class III PI 3 kinases (Vps34) are less well understood. In addition there are also four PI 4-kinases and several PI 3-kinase related protein kinases (termed PIKK's or class IV) including DNA-PK, mTOR, ATM and ATR, all of which have a similar catalytic domain (Abraham R. T. et al.; DNA repair 2004, 3(8-9), 883).

A key role for PI 3-kinase gamma isoform in processes such as leukocyte activation, leukocyte chemotaxis and mast cell degranulation has been shown, thereby generating interest in this target for the treatment of autoimmune and inflammatory disorders (Ghigo et al., Bioessays, 2010, 32, p 185-196; Reif et al., J. Immunol., 2004, 173, p 2236-2240; Laffargue et al., Immunity, 2002, 16, p 441-451; Rommel et al, Nature Rev. Immunology, 2007, 7, p 191; Cushing et al J. Med. Chem., 2012, 55, p 8559; Bergamini et al, Nature Chem. Biol., 2012, 8, p 576). Specifically, numerous publications suggest the potential utility of PI3 Kinase gamma isoform inhibitors for the treatment of asthma (e.g. Thomas et al, Immunology, 2008, 126, p 413; Jiang et al, J. Pharm. Exp. Ther., 2012, 342, p 305; Takeda et al, Int. Arch. Allergy Immunol. 2010, 152 (suppl 1), p 90-95). There are also reports linking inhibition of the PI 3-kinase gamma isoform as having potential therapeutic value in numerous other indications such as cancer (Beagle and Fruman, Cancer Cell, 2011, 19, p 693; Schmid et al, Cancer Cell, 2011, 19, p 715; Xie et al, Biochem. Pharm., 2013, 85, p 1454; Subramaniam et al, Cancer Cell, 2012, 21, p 459), diabetes (Kobayashi et al, Proc. Nat. Acad. Sci, 2011, 108, p 5753; Azzi et al, Diabetes, 2012, 61, p 1509), cardiovascular disease (Fougerat et al, Clin. Sci., 2009, 116, p 791; Fougerat et al, Circulation, 2008, 117, p 1310; Chang et al, Proc. Nat. Acad. Sci., 2007, 104, p 8077; Fougerat et al, Br. J. Pharm., 2012, 166, p 1643), obesity (Becattini et al, Proc. Nat. Acad. Sci., 2011, 108, pE854), Alzheimer's disease (Passos et al, Brain, Behaviour and Immunity, 2010, 24, 493) and pancreatitis (Lupia et al, Am. J. Path, 2004, 165, p 2003). A recent review of PI 3-Kinase isoforms as drug targets is given in Blajecka et al, Current Drug Targets, 2011, 12, p 1056-1081.

WO2009/115517 (Novartis) describes amino pyrazine and pyridine derivatives as PI 3-kinase inhibitors.

WO2009/013348 (Novartis) describes amino pyrimidine derivatives as PI 3-kinase inhibitors.

WO2003/093297 (Exelixis) describes protein kinase modulators and methods of use of such modulators.

Leahy et al., *J. Med. Chem.*, 2012, 55 (11), pp 5467-5482, describe PI 3-kinase gamma isoform inhibitors.

Hence, there is a need for potent, selective inhibitors of PI 3-kinase gamma isoform.

SUMMARY OF THE INVENTION

In a first aspect, the invention relates to a compound of formula (I)

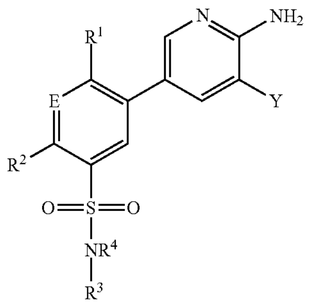

(I)

or a pharmaceutically acceptable salt thereof, wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

$R^3$ is selected from (i) $C_{1-4}$ alkyl which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(ii) $C_{1-4}$ alkoxy which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) a —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) a pyridyl wherein the pyridyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$; and (viii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$ alkyl, $C_{1-4}$hydroxyalkyl, $C_{1-4}$ alkoxy, $C_{1-4}$ haloalkoxy, halogen, —($C_{0-3}$ alkyl)-NR'R", —($C_{0-3}$ alkyl)-$C_{3-7}$ cycloalkyl, —($C_{0-3}$ alkyl)-$C_{3-7}$ heterocyclyl, —(C═O)—$C_{3-7}$ heterocyclyl, —(C═O)—NR'R", —($C_{0-3}$ alkyl)-phenyl and —($C_{0-3}$ alkyl)-5-6-membered heteroaryl;

R' and R" are independently selected from H and $C_{1-4}$ alkyl.

In other aspects, the invention relates to pharmaceutical compositions and combinations comprising compounds of the first aspect, and to the use of such compounds of the first aspect in the treatment of a disorder or disease mediated by the activation of PI 3-kinase gamma isoform.

DESCRIPTION OF THE EMBODIMENTS

In an embodiment 1 of the invention, there is provided a compound of formula (I)

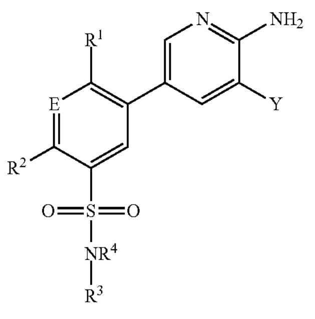

(I)

wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

$R^3$ is selected from (i) $C_{1-4}$ alkyl which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(ii) $C_{1-4}$ alkoxy which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) a —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) a pyridyl wherein the pyridyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$; and (viii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$ alkyl, $C_{1-4}$hydroxyalkyl, $C_{1-4}$ alkoxy, $C_{1-4}$ haloalkoxy, halogen, —($C_{0-3}$ alkyl)-NR'R", —($C_{0-3}$ alkyl)-$C_{3-7}$ cycloalkyl, —($C_{0-3}$ alkyl)-$C_{3-7}$ heterocyclyl, —(C═O)—$C_{3-7}$ heterocyclyl, —(C═O)—NR'R", —($C_{0-3}$ alkyl)-phenyl and —($C_{0-3}$ alkyl)-5-6-membered heteroaryl;

R' and R" are independently selected from H and $C_{1-4}$ alkyl; or a pharmaceutically acceptable salt thereof.

In an embodiment 1.1 of the invention, there is provided a compound of formula (I)

(I)

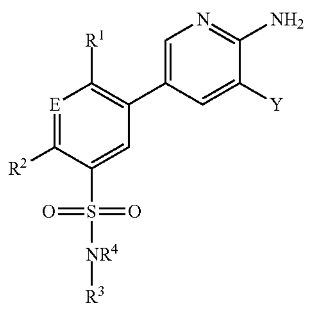

wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy and $C_{3-6}$ cycloalkyl;

$R^3$ is selected from (i) $C_{1-4}$ alkyl which is unsubstituted or substituted with 1 to 3 substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;

(ii) $C_{1-4}$ alkoxy which is unsubstituted or substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;

(iii) —$C_{3-6}$ cycloalkyl or —O—$C_{3-6}$ cycloalkyl wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;

(iv) a —($C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the $C_{3-6}$ cycloalkyl or $C_{0-6}$ heterocyclyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;

(v) a —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

(vi) a —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

(vii) a pyridyl wherein the pyridyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

$R^4$ is selected from H and $C_{1-4}$ alkyl; or $R^3$ and $R^4$ together with the nitrogen atom to which they are attached form a $C_{3-6}$ heterocyclyl, which $C_{3-6}$ heterocyclyl is optionally spiro fused to a second $C_{3-6}$ heterocyclyl or a $C_{3-6}$ cycloalkyl by one single carbon atom, and which $C_{3-6}$ heterocyclyl and $C_{3-6}$ cycloalkyl are unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl;

Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$ alkyl, $C_{1-4}$hydroxyalkyl, $C_{1-4}$ alkoxy, $C_{1-4}$ haloalkoxy, halogen, $C_{1-4}$ hydroxyalkyl, $C_{1-4}$ alkoxyalkyl, —($C_{0-3}$ alkyl)-$NR^{3a}R^{3b}$, —($C_{0-3}$ alkyl)-$C_{3-6}$ cycloalkyl and —($C_{0-3}$ alkyl)-$C_{3-6}$ heterocyclyl; or a pharmaceutically acceptable salt thereof.

Definitions

"Halo" or "halogen", as used herein, may be fluoro, chloro, bromo or iodo.

"$C_{1-4}$ alkyl", as used herein, denotes straight chain or branched alkyl having 1-4 carbon atoms. If a different number of carbon atoms is specified, such as $C_6$ or $C_3$, then the definition is to be amended accordingly, such as "$C_1$-$C_4$ alkyl" will represent methyl, ethyl, propyl, isopropyl, butyl, isobutyl, sec-butyl and tert-butyl.

"$C_{1-4}$ alkoxy", as used herein, refers to an —O—$C_{1-4}$ alkyl group wherein $C_{1-4}$ alkyl is as defined herein. Examples of such groups include methoxy, ethoxy, propoxy, butoxy, pentoxy or hexoxy and the like. As for alkyl unless a particular structure is specified the terms propoxy, butoxy etc include all straight and branched chain forms having the appropriate number of carbon atoms e.g. propoxy includes n-propoxy and isopropoxy.

"$C_{1-4}$ haloalkoxy" as used herein refers to an —O—$C_{1-4}$ alkyl group wherein $C_{1-4}$ alkyl is as defined herein and substituted with one or more halogen groups, e.g. —O—$CF_3$.

"$C_{1-4}$ haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_{3-7}$ cycloalkyl" as used herein refers to a saturated monocyclic hydrocarbon ring of 3 to 7 carbon atoms. Examples of such groups include cyclopropyl, cyclobutyl, cyclopentyl and cyclohexyl. If a different number of carbon atoms is specified, then the definition is to be amended accordingly.

The term "hydroxy" or "hydroxyl" refers to —OH.

"$C_{1-4}$ hydroxyalkyl", as used herein, denotes a straight chain or branched alkyl having 1-4 carbon atoms with at least one hydrogen substituted with a hydroxy group. If a different number of carbon atoms is specified, such as $C_6$ or $C_3$, then the definition is to be amended accordingly, such as "$C_1$-$C_4$ hydroxyalkyl" will represent methyl, ethyl, propyl, isopropyl, butyl, isobutyl, sec-butyl and tert-butyl that have at least one hydrogen substituted with hydroxy.

"$C_{3-7}$ heterocyclyl ring" refers to a 3 to 7 membered saturated or partially unsaturated aliphatic ring system which contains 1 to 3 heteroatoms selected from oxygen, nitrogen and sulfur. Suitable examples of such ring systems include pyrrolidinyl, piperidinyl, piperazinyl, morpholinyl, tetrahydrofuranyl, tetrahydropyranyl, pyrrolinyl, thienyl or oxazolinyl.

"5-6 membered heteroaryl" refers to a 5-6 membered aromatic ring system which contains 1 to 3 heteroatoms selected from oxygen, nitrogen or sulfur. Examples of 5-membered heteroaryl rings in this instance include furanyl, pyrrolyl, oxazolyl, thiazolyl, imidazolyl, oxadiazolyl, thiadiazolyl, triazolyl, isothiazolyl, isoxazolyl, thiophenyl, or pyrazolyl. Examples of 6-membered heteroaryl rings include pyridinyl, pyridazinyl, pyrimidinyl, pyrazinyl, or triazinyl.

"Oxo" refers to =O.

The term "a," "an," "the" and similar terms used in the context of the present invention (especially in the context of the claims) are to be construed to cover both the singular and plural unless otherwise indicated herein or clearly contradicted by the context.

The term "treatment" as used herein refers to both to symptomatic and prophylactic treatment, particularly symptomatic.

Various embodiments of the invention are described herein. It will be recognized that features specified in each embodiment may be combined with other specified features to provide further embodiments.

As used herein, when one embodiment refers to several other embodiments by using the term "according to any one of", for example "according to any one of embodiments 1 to 5", then said embodiment refers not only to embodiments indicated by the integers such as 1 and 2 but also to embodiments indicated by numbers with a decimal component such as 1.1, 1.2 or 2.1, 2.2, 2.3. For example, "according to any one of embodiments 1 to 4" means according to any one of embodiments 1, 1.1, 2, 2.1, 3, 3.1, 4, 4.1, 4.2. The same applies when referring to exemplified compounds.

In an embodiment 2 of the invention, there is provided a compound of formula (Ia)

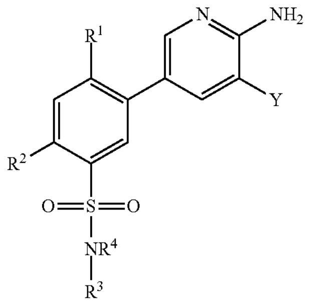

(Ia)

wherein $R^1$ is independently selected from H, halogen, $C_{1-4}$ alkyl, $C_{1-4}$ alkoxy, $C_{1-4}$ haloalkyl, $C_{1-4}$ haloalkoxy, hydroxyalkyl and $C_{3-6}$ cycloalkyl;

$R^2$ is selected from H, halogen, trifluoromethyl and methyl;

$R^3$ is selected from (i) $C_{1-4}$ alkyl which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(ii) $C_{1-4}$ alkoxy which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) a —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{0-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) a —($C_{0-3}$ alkyl)-$C_{3-7}$ heterocyclyl or —(O—$C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) a pyridyl wherein the pyridyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$; and (viii) H;

$R^{3a}$ and $R^{3b}$ are independently selected from H, $C_{1-4}$ alkyl and $C_{1-4}$ haloalkyl;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$ alkyl, $C_{1-4}$hydroxyalkyl, $C_{1-4}$ alkoxy, $C_{1-4}$ haloalkoxy, halogen, $C_{1-4}$ hydroxyalkyl, $C_{1-4}$ alkoxyalkyl, —($C_{0-3}$ alkyl)-NR'R", —($C_{0-3}$ alkyl)-$C_{3-6}$ cycloalkyl, —($C_{0-3}$ alkyl)-$C_{3-6}$ heterocyclyl, —(C═O)—$C_{3-6}$ heterocyclyl, —(C═O)—NR'R", —($C_{0-3}$ alkyl)-phenyl and —($C_{0-3}$ alkyl)-5-6-membered heteroaryl;

R' and R" are independently selected from H and $C_{1-4}$ alkyl;

or a pharmaceutically acceptable salt thereof.

In an embodiment 2.1 of the invention, there is provided a compound of formula (I) according to embodiment 1 or 1.1, wherein E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy and $C_{3-6}$ cycloalkyl;

$R^3$ is selected from (i) $C_{1-4}$ alkyl which is substituted with 1 to 3 substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, —$NR^{3a}R^{3b}$ and $C_{3-6}$cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;

(ii) $C_{1-4}$ alkoxy which is substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, $C_{3-6}$ cycloalkyl, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;

(iii) —$C_{0-6}$ cycloalkyl or —O—$C_{3-6}$ cycloalkyl wherein the $C_{3-6}$ cycloalkyl is substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;

(iv) a —($C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;

(v) a —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

(vi) a —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein said $C_{3-6}$ heterocyclyl or $C_{3-6}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

(vii) a pyridyl wherein the pyridyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

$R^4$ is selected from H and $C_{1-4}$ alkyl; or $R^3$ and $R^4$ together with the nitrogen atom to which they are attached form a $C_{3-6}$ heterocyclyl, which heterocyclyl is optionally spiro fused to a second $C_{3-6}$ heterocyclyl or a $C_{3-6}$ cycloalkyl by one single carbon atom, and which $C_{3-6}$ heterocyclyl and $C_{3-6}$ cycloalkyl are unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl;

Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$ alkyl, $C_{1-4}$hydroxyalkyl, $C_{1-4}$ alkoxy, $C_{1-4}$ haloalkoxy, halogen, $C_{1-4}$ hydroxyalkyl, $C_{1-4}$ alkoxyalkyl, —($C_{0-3}$ alkyl)-$NR^{3a}R^{3b}$, —($C_{0-3}$ alkyl)-$C_{3-6}$ cycloalkyl and —($C_{0-3}$ alkyl)-$C_{3-6}$ heterocyclyl;

or a pharmaceutically acceptable salt thereof.

In an embodiment 3 of the invention, there is provided a compound according to embodiment 1, wherein $R^1$ is independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

$R^2$ is selected from H, halogen, $CF_3$ and methyl;

E is $CR^E$ and $R^E$ is H;

$R^3$ is selected from (i) $C_{1-4}$ alkyl which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(ii) $C_{1-4}$ alkoxy which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$-alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) a —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) a —($C_{0-3}$ alkyl)-$C_{3-7}$ heterocyclyl or —(O—$C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is selected from the group consisting of thiazolyl,
thiadiazolyl,
isothiazolyl,
pyrazolyl,
pyridyl,
pyrimidinyl,
triazolyl,
imidazolyl,
oxadiazolyl,
isoxazolyl,
oxazolyl,
pyrrolyl,
thienyl, and
furanyl;

each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, —($C_{0-3}$ alkyl)-NR'R", —($C_{0-3}$ alkyl)-$C_{3-7}$ cycloalkyl, —($C_{0-3}$ alkyl)-$C_{3-7}$ heterocyclyl, —(C═O)—$C_{3-7}$ heterocyclyl, —(C═O)—NR'R", —($C_{0-3}$ alkyl)-phenyl and —($C_{0-3}$ alkyl)-5-6-membered heteroaryl;

R' and R" are independently selected from H and $C_{1-4}$ alkyl; or a pharmaceutically acceptable salt thereof.

In an embodiment 3.1 of the invention, there is provided a compound or salt according to any one of embodiments 1 to 2 wherein E is $CR^E$ and $R^E$ is H.

In an embodiment 4 of the invention, there is provided a compound according to embodiment 1, 2 or 3, wherein $R^1$ is selected from H and $C_{1-4}$ alkyl;

$R^2$ is selected from H, halogen, $CF_3$ and methyl;

$R^3$ is selected from (i) $C_{1-4}$ alkyl which is substituted with 1 or more substituents, particularly 1 to 3 substituents, independently selected from hydroxy, halogen and $C_{1-4}$ alkyl;

(ii) $C_{1-4}$ alkoxy which is unsubstituted or substituted with 1 or more substituents, particularly 1 to 3 substituents, independently selected from hydroxyl, halogen and $C_{1-4}$ alkyl;

(iii) —(O—$C_{0-3}$ alkyl)-$C_{3-6}$ heterocyclyl and wherein said $C_{3-6}$ heterocyclyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;

(iv) —O—($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;

(v) —($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;

(vi) —($C_{0-3}$ alkyl)-$C_{3-6}$ heterocyclyl which is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;

(vii) a —($C_{0-3}$ alkyl)-$C_{3-6}$ cycloalkyl or —O—($C_{0-3}$ alkyl)-$C_{3-6}$ cycloalkyl wherein the $C_{3-6}$ cycloalkyl is spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;

(viii) a —($C_{0-3}$ alkyl)-$C_{3-6}$ heterocyclyl or —O—($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;

(ix) H;

Y is selected from the group consisting of thiazolyl,
thiadiazolyl,
isothiazolyl,
pyrazolyl,
pyridyl,
triazolyl,
imidazolyl,
oxadiazolyl,
isoxazolyl,
oxazolyl,
pyrrolyl,
thienyl, and
furanyl;

each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, —($C_{0-3}$ alkyl)-NR'R", —($C_{0-3}$ alkyl)-$C_{3-7}$ cycloalkyl and —($C_{0-3}$ alkyl)-$C_{3-7}$ heterocyclyl, —(C═O)—$C_{3-7}$ heterocyclyl, —(C═O)—NR'R", —($C_{0-3}$ alkyl)-phenyl and —($C_{0-3}$ alkyl)-5-6-membered heteroaryl;

R' and R" are independently selected from H and $C_{1-4}$ alkyl;

or a pharmaceutically acceptable salt thereof.

In an embodiment 4.1 of the invention, there is provided a compound or salt according to any of embodiments 1 to 4, wherein $R^1$ is selected from methyl and H, particularly methyl.

In an embodiment 4.2 of the invention, there is provided a compound or salt according to any one of embodiments 1 to 4, wherein $R^2$ is selected from H, fluoro, chloro and methyl, particularly H and fluoro, more particularly H.

In an embodiment 5 of the invention, there is provided a compound according to any one of embodiments 1 to 4, wherein Y is selected from the group consisting of oxazol-2-yl,
oxazol-5-yl,
oxazol-4-yl,
thiazol-5-yl,
thiazol-2-yl,
thiazol-4-yl,
1,3,4-thiadiazol-2-yl,
isothiazol-5-yl,
pyrazol-4-yl,
pyrazol-3-yl,
pyrazol-1-yl,
pyrid-4-yl,
pyrid-3-yl,
pyrid-2-yl,
1,2,4-triazol-1-yl,
1,2,3-triazol-4-yl,
imidazol-1-yl,
1,2,4-oxadiazol-5-yl,
1,3,4-oxadiazol-2-yl,
1,2,4-oxadiazol-3-yl,
isoxazol-5-yl,
isoxazol-3-yl,
isoxazol-4-yl,
pyrrol-3-yl,
thien-2-yl,
thien-3-yl, and
furan-3-yl, each of which is unsubstituted or substituted with 1 to 3 substituents independently selected from $C_{1-4}$ alkyl, $C_{1-4}$ haloalkyl, $C_{1-4}$hydroxyalkyl, —($C_{0-3}$ alkyl)-$C_{3-7}$ cycloalkyl, —(C═O)—$C_{3-7}$ heterocyclyl, —($C_{0-3}$ alkyl)-NR'R", —(C═O)—NR'R", —($C_{0-3}$ alkyl)-phenyl and —($C_{0-3}$ alkyl)-pyridyl;

R' and R" are independently selected from H and $C_{1-4}$ alkyl;

or a pharmaceutically acceptable salt thereof.

In an embodiment 5.1 of the invention, there is provided a compound according to any one of embodiments 1 to 4, wherein Y is selected from the group consisting of oxazol-5-yl,
thiazol-5-yl,
thiazol-2-yl,
thiazol-4-yl,
isothiazol-5-yl,
pyrazol-4-yl,
pyrazol-1-yl,
pyrid-4-yl,
1,2,4-triazol-1-yl,
1,2,3-triazol-4-yl,
1,2,4-oxadiazol-5-yl,
1,3,4-oxadiazol-2-yl,
isoxazol-5-yl,
isoxazol-4-yl, and
pyrrol-3-yl, each of which is unsubstituted or substituted with 1 to 3 substituents independently selected from $C_{1-4}$ alkyl, $C_{1-4}$ haloalkyl, —(C═O)—$C_{3-7}$ heterocyclyl, —($C_{0-3}$ alkyl)-NR'R" and —(C═O)—NR'R";

R' and R" are independently selected from H and $C_{1-4}$ alkyl;

or a pharmaceutically acceptable salt thereof.

In an embodiment 6 of the invention, there is provided a compound according to any one of embodiments 1 to 5, wherein Y is selected from the group consisting of

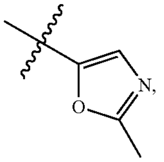 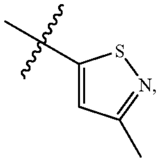

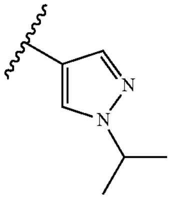 , 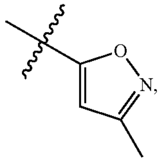

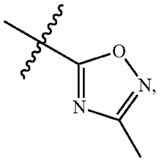 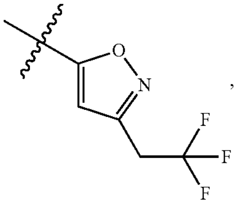 ,

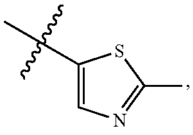 , 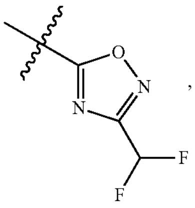 ,

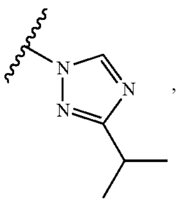 , 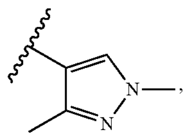

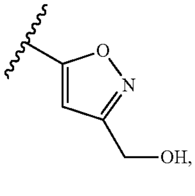 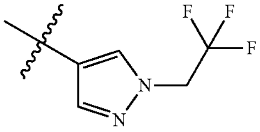 ,

-continued
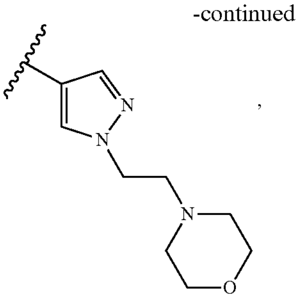, 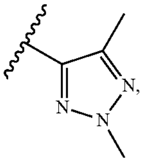
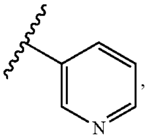 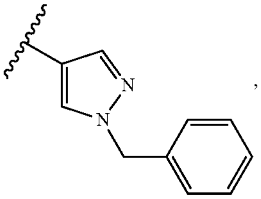,
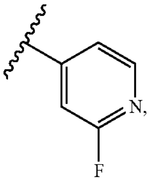 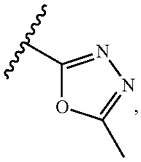
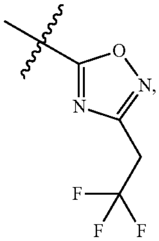 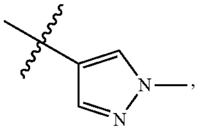
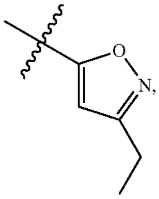 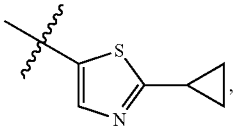
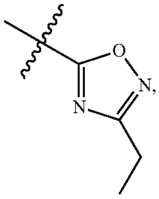 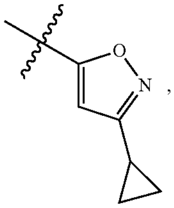
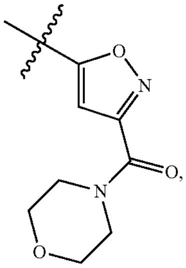 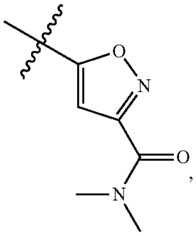
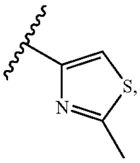 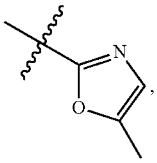
-continued
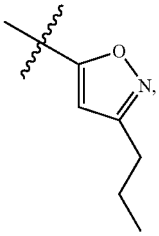 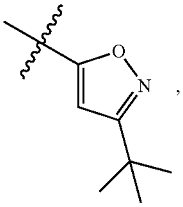,
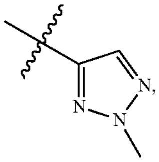 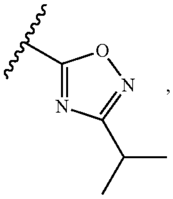,
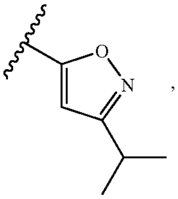, 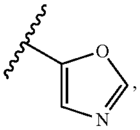
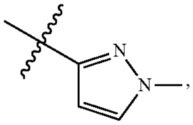 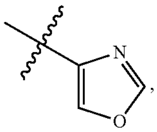
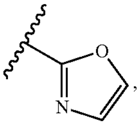 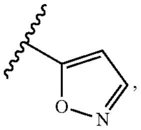
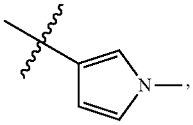 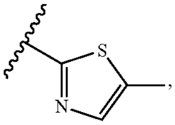
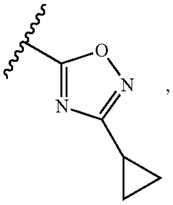, 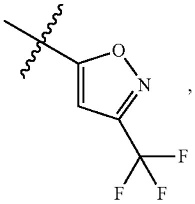,
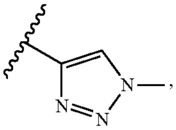 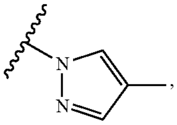
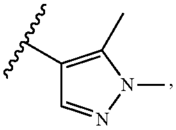 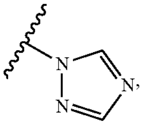
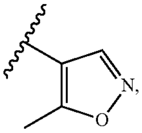 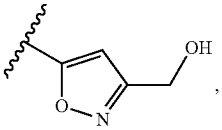

-continued
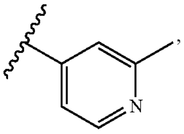 ,
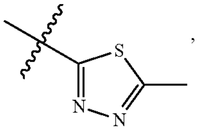 ,
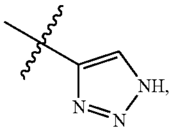 ,
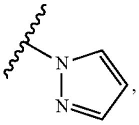 ,
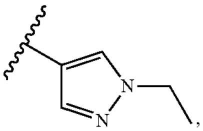 ,
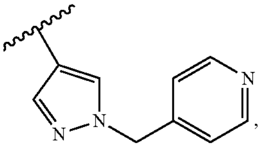 ,
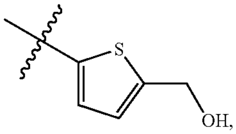 ,
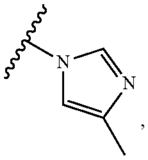 ,
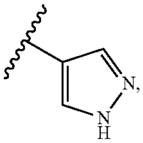 ,
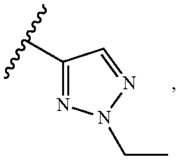 ,
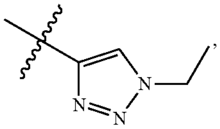 ,
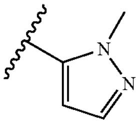 ,
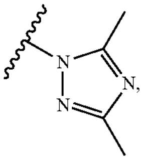 ,
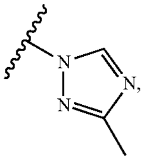 ,
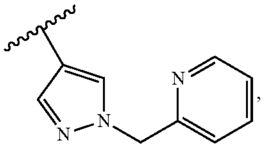 ,
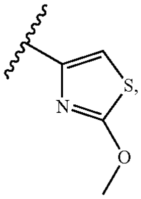 ,
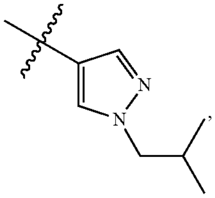 ,
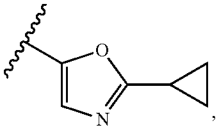 ,
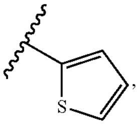 ,
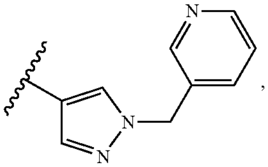 ,
-continued
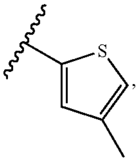 ,
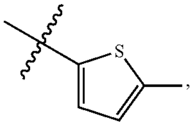 ,
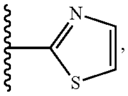 ,
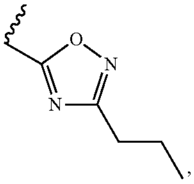 ,
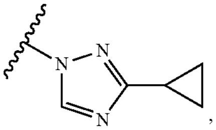 ,
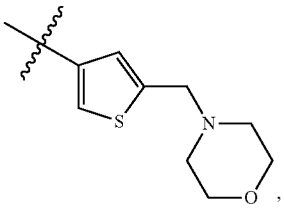 ,
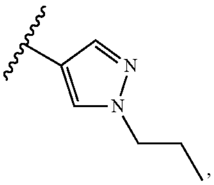 ,
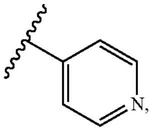 ,
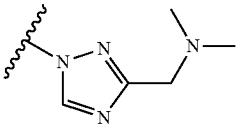 ,
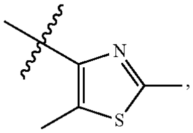 ,
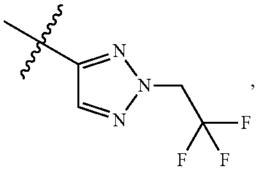 ,
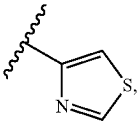 ,
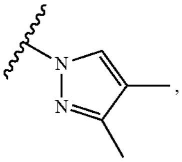 ,
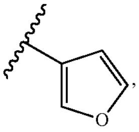 ,
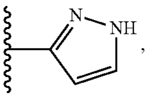 ,
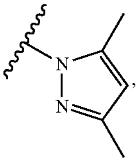 ,
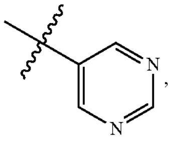 ,
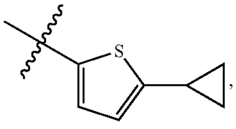 ,
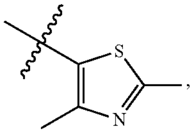 ,
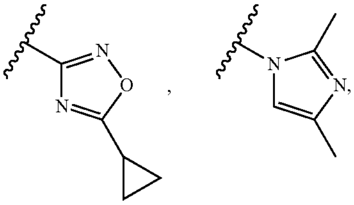

-continued
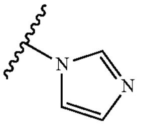
and
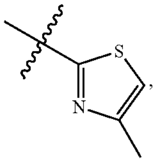
or a pharmaceutically acceptable salt thereof.
In an embodiment 7 of the invention, there is provided a compound according to any one of embodiments 1 to 5, wherein
Y is selected from the group consisting of
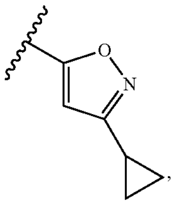
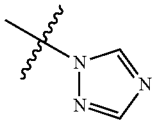
,
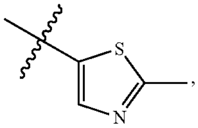
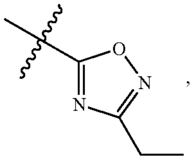
,
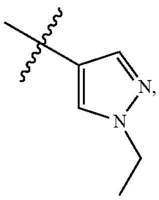
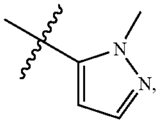
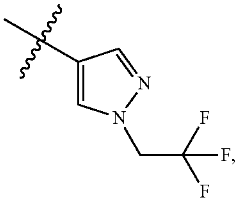
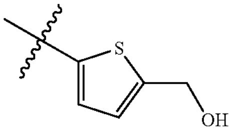
,
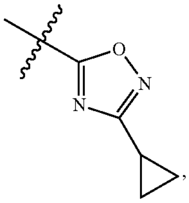
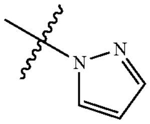
,
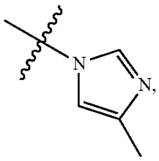
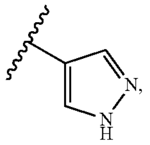
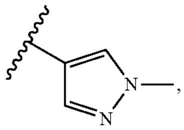
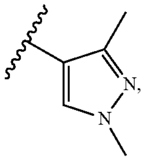
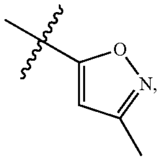
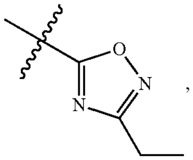
,
-continued
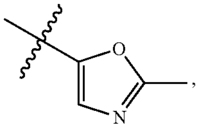
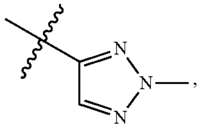
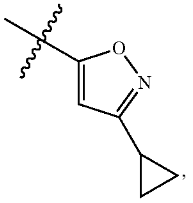
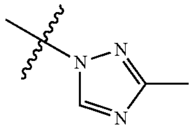
,
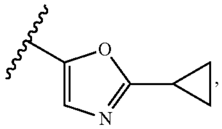
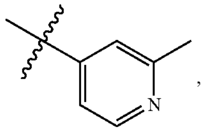
,
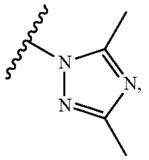
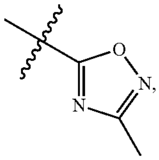
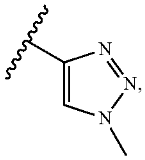
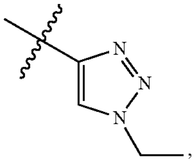
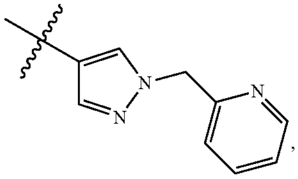
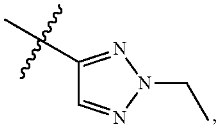
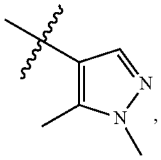
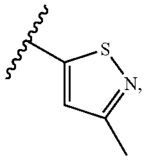
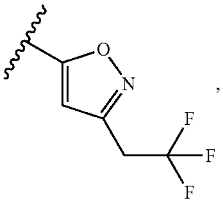
,
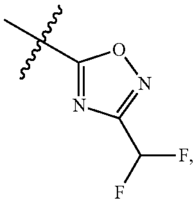
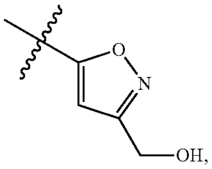
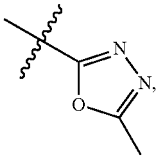
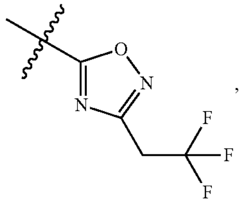
, -continued

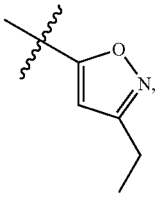

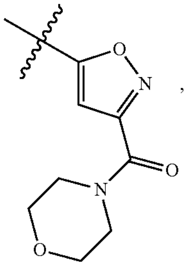

,

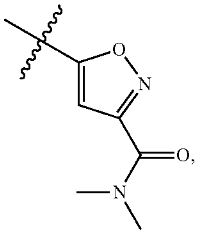

and

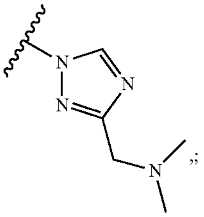

or a pharmaceutically acceptable salt thereof.

In an embodiment 8 of the invention, there is provided a compound according to any one of embodiments 1 to 5, wherein Y is selected from the group consisting of

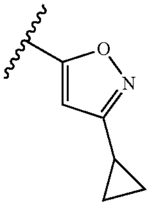

,

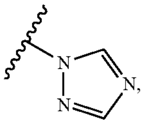

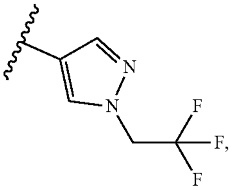

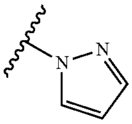

,

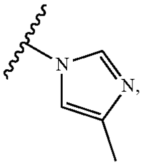

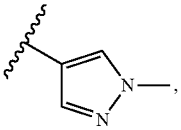

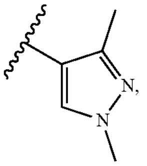

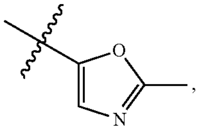

,

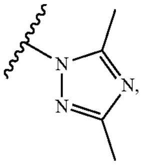

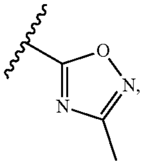

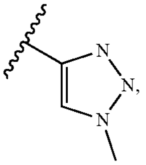

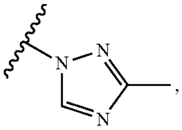

,

-continued

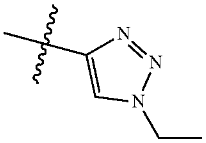

and

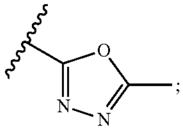

or a pharmaceutically acceptable salt thereof.

In an embodiment 9 of the invention, there is provided a compound according to any one of embodiments 1 to 5, wherein Y is selected from the group consisting of

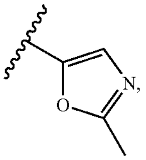

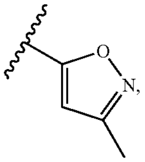

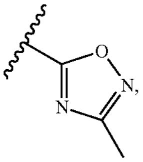

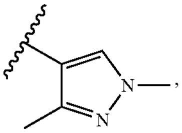

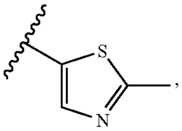

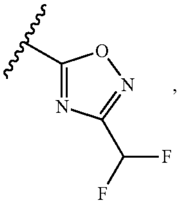

, and

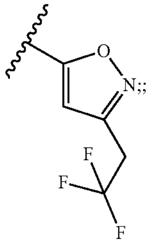

or a pharmaceutically acceptable salt thereof.

In an embodiment 9.1 of the invention, there is provided a compound or salt according to any one of embodiment 1 to 5, wherein Y is selected from thiazolyl,
pyrazolyl,
pyridyl,
triazolyl,
imidazolyl,
oxadiazolyl,
pyrimidinyl,
isoxazolyl,
oxazolyl, and
thienyl;

each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, $C_{1-4}$ hydroxyalkyl, $C_{1-4}$ alkoxyalkyl, —$NR^{3a}R^{3b}$, —($C_{0-3}$ alkyl)-$C_{3-6}$ cycloalkyl and —($C_{0-3}$ alkyl)-$C_{3-6}$ heterocyclyl.

In an embodiment 9.2 of the invention, there is provided a compound or salt according to any one of embodiment 1 to 5, wherein Y is selected from oxazol-2-yl,
thiazol-5-yl,
pyrazol-4-yl,
pyrazol-5-yl,
pyrazol-1-yl,
pyrid-4-yl,
pyrid-3-yl, 1,2,4-triazol-1-yl,
1,2,3-triazol-4-yl,
imidazol-1-yl,
1,2,4-oxadiazol-5-yl,
1,3,4-oxadiazol-2-yl,
oxazol-5-yl,
isoxazol-5-yl,
pyrimidin-5-yl,
thien-3-yl,
each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy and —($C_{0-3}$ alkyl)-$C_{3-6}$ cycloalkyl.

In an embodiment 9.3 of the invention, there is provided a compound or salt according to any one of embodiment 1 to 5, wherein Y is selected from
oxazol-2-yl,
thiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
imidazol-1-yl,
1,2,4-oxadiazol-5-yl,
oxazol-5-yl,
isoxazol-5-yl,
pyrimidin-5-yl,
thien-3-yl,
each of which is unsubstituted or substituted with 1 to 3 substituents independently selected from methyl, ethyl, propyl, isopropyl, cyclopropyl, $CF_3$, $CF_3CH_2$—, hydroxyethyl, methoxyethyl and methoxy.

In an embodiment 9.4 of the invention, there is provided a compound or salt according to any one of embodiment 1 to 5, wherein Y is selected from
5-methyl-oxazol-2-yl,
5-morpholin-4-ylmethyl-thien-3-yl,
3-cyclopropyl-[1,2,4]triazol-1-yl,
2-cyclopropyl-thiazol-5-yl,
2,5-dimethyl-2H-[1,2,3]triazol-4-yl,
2-methylthiazol-5-yl,
1,3-dimethyl-1H-pyrazol-4-yl,
1,2,4-triazol-1-yl,
3-isopropyl-1,2,4-oxadiazol-5-yl,
3-methyl-[1,2,4]oxadiazol-5-yl,
1-methyl-1H-pyrazol-4-yl,
1H-pyrazol-1-yl,
3-ethyl-1,2,4-oxadiazol-5-yl,
2-methyl-2H-1,2,3-triazol-4-yl,
(2,2,2-trifluoro-ethyl)-1H-pyrazol-4-yl
1H-pyrazol-4-yl,
3-methylisoxazol-5-yl,
2-methylpyridin-4-yl)pyrazin-2-yl,
1H-1,2,4-triazol-1-yl,
3-propyl-1,2,4-oxadiazol-5-yl,
2-methyl-oxazol-5-yl,
pyrimidin-5-yl,
3-methyl-1H-1,2,4-triazol-1-yl,
5-methyl-1,3,4-oxadiazol-2-yl,
1-methyl-1H-pyrazol-5-yl,
pyrid-3-yl,
pyrid-4-yl,
2-methyl-pyrid-4-yl,
3-methyl-1,2,4-oxadiazol-5-yl,
2-methylthiazol-4-yl,
4-methyl-1H-imidazol-1-yl,
1-ethyl-1H-pyrazol-4-yl,
3,5-dimethyl-1H-pyrazol-1-yl,
3-cyclopropyl-1,2,4-oxadiazol-5-yl,
1-isopropyl-1H-pyrazol-4-yl,
1H-1,2,4-triazol-1-yl,
1-propyl-1H-pyrazol-4-yl,
4-methoxypyridin-3-yl,
pyrazol-3-yl,
3-methylisoxazol-5-yl, and
1-(2-methoxyethyl)-1H-pyrazol-4-yl.

In an embodiment 9.5 of the invention, there is provided a compound or salt according to any one of embodiment 1 to 5, wherein Y is selected from
oxazolyl,
thiazolyl,
oxadiazolyl,
isoxazolyl,
pyrazolyl,
pyridyl, and
triazolyl,
each of which is unsubstituted or substituted with 1 to 3 substituents independently selected from $C_{1-4}$ alkyl, $C_{1-4}$ haloalkyl, $C_{1-4}$ alkoxy, $C_{1-4}$ haloalkoxy, —($C_{0-3}$ alkyl)-$C_{3-6}$ cycloalkyl and —($C_{0-3}$ alkyl)-$C_{3-6}$ heterocyclyl.

In an embodiment 9.6 of the invention, there is provided a compound or salt according to any one of embodiment 1 to 5, wherein Y is selected from
oxazol-5-yl,
oxazol-2-yl,
thiazol-5-yl,
isoxazol-5-yl,
oxadiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
each of which is unsubstituted or substituted with 1 or 2 substituents independently selected from methyl, ethyl, propyl and isopropyl.

In an embodiment 10 of the invention, there is provided a compound according to any one of embodiments 1 to 9, wherein
$R^3$ is selected from
(i) $C_{1-4}$ alkyl which is substituted with 1 to 3 substituents independently selected from hydroxyl, halogen and $C_{1-4}$ alkyl;
(ii) $C_{1-4}$ alkoxy which is unsubstituted or substituted with 1 to 3 substituents independently selected from hydroxyl, halogen and $C_{1-4}$ alkyl;
(iii) —O—($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(iv) —O—($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(v) —($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;

(vi) —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;

(vii) a —($C_{0-3}$ alkyl)-$C_{3-6}$ cycloalkyl or —O—($C_{0-3}$ alkyl)-$C_{3-6}$ cycloalkyl wherein the $C_{3-6}$ cycloalkyl is spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;

(viii) a —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;

or a pharmaceutically acceptable salt thereof.

In an embodiment 10.1 of the invention, there is provided a compound according to any one of embodiments 1 to 9, wherein $R^3$ is selected from (i) $C_{1-4}$ alkyl which is substituted with 1 to 3 substituents independently selected from hydroxy, halogen and $C_{1-4}$ alkyl;

(ii) $C_{1-4}$ alkoxy which is unsubstituted or substituted with 1 to 3 substituents selected from $C_{1-4}$ alkyl;

(iii) —O—($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted;

(iv) —O—($C_{0-3}$ alkyl)-$C_{3-6}$ cycloalkyl wherein the $C_{3-6}$ cycloalkyl is unsubstituted or substituted with 1 to 3 substituents independently selected from hydroxy;

(v) —($C_{0-3}$ alkyl)-$C_{3-6}$ cycloalkyl wherein the $C_{3-6}$ cycloalkyl is unsubstituted or substituted with 1 to 3 substituents independently selected from hydroxyl and $C_{1-4}$ hydroxyalkyl;

(vi) —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, hydroxy, $C_{1-4}$ hydroxyalkyl and oxo;

(vii) a —($C_{0-3}$ alkyl)-$C_{3-6}$ cycloalkyl or —O—($C_{0-3}$ alkyl)-$C_{3-6}$ cycloalkyl wherein the $C_{3-6}$ cycloalkyl is spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is substituted with 1 to 3 substituents independently selected from hydroxy;

or a pharmaceutically acceptable salt thereof.

In an embodiment 11 of the invention, there is provided a compound according to any one of embodiments 1 to 9, wherein $R^3$ is selected from (i) $C_{1-4}$ alkyl which is substituted with 1 to 3 substituents independently selected from hydroxyl, halogen and $C_{1-4}$ alkyl;

(ii) $C_{1-4}$ alkoxy which is unsubstituted or substituted with 1 to 3 substituents independently selected from hydroxyl, halogen and $C_{1-4}$ alkyl;

(iii) —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;

(iv) —O—($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;

(v) —($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;

(vi) —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;

(vii) a —($C_{0-3}$ alkyl)-$C_{3-6}$ cycloalkyl or —(O—$C_{0-3}$ alkyl)-$C_{3-6}$ cycloalkyl wherein the $C_{3-6}$ cycloalkyl is spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;

or a pharmaceutically acceptable salt thereof.

In an embodiment 12 of the invention, there is provided a compound according to any one of embodiments 1 to 9, wherein $R^3$ is selected from (i) $C_{1-4}$ alkyl which is substituted with 1 to 3 substituents independently selected from hydroxyl, halogen and $C_{1-4}$ alkyl;

(ii) $C_{1-4}$ alkoxy which is unsubstituted or substituted with 1 to 3 substituents independently selected from hydroxyl, halogen and $C_{1-4}$ alkyl;

(iii) —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;

(iv) —O—($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;

(v) —($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;

or a pharmaceutically acceptable salt thereof.

In an embodiment 13 of the invention, there is provided a compound according to any one of embodiments 1 to 9, wherein $R^3$ is selected from (i) $C_{1-4}$ alkyl which is substituted with 1 to 3 substituents independently selected from hydroxyl, halogen and $C_{1-4}$ alkyl;

(ii) $C_{1-4}$ alkoxy which is unsubstituted or substituted with 1 to 3 substituents independently selected from hydroxyl and $C_{1-4}$ alkyl;

(iii) —O—($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;

(iv) —O—($C_{0-3}$ alkyl)-$C_{3-6}$ cycloalkyl wherein the $C_{3-6}$ cycloalkyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;

or a pharmaceutically acceptable salt thereof.

In an embodiment 14 of the invention, there is provided a compound according to any one of embodiments 1 to 9, wherein $R^3$ is selected from (i) $C_{1-4}$ alkyl which is substituted with 1 to 3 substituents independently selected from hydroxyl, halogen and $C_{1-4}$ alkyl;

(ii) $C_{1-4}$ alkoxy which is unsubstituted or substituted with 1 to 3 substituents independently selected from hydroxyl and $C_{1-4}$ alkyl;

or a pharmaceutically acceptable salt thereof.

In an embodiment 15 of the invention, there is provided a compound according to any one of embodiments 1 to 9, wherein $R^3$ is selected from

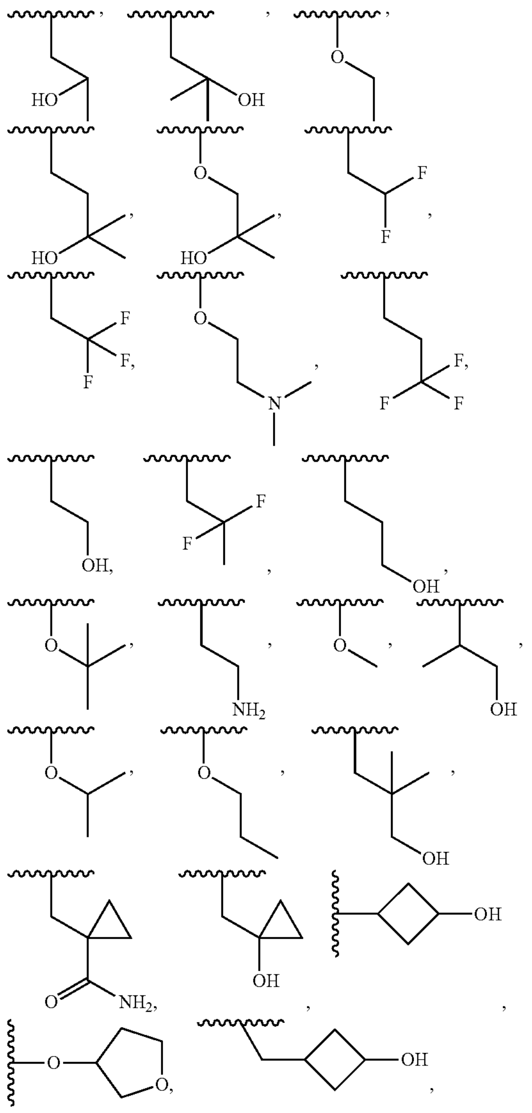

-continued

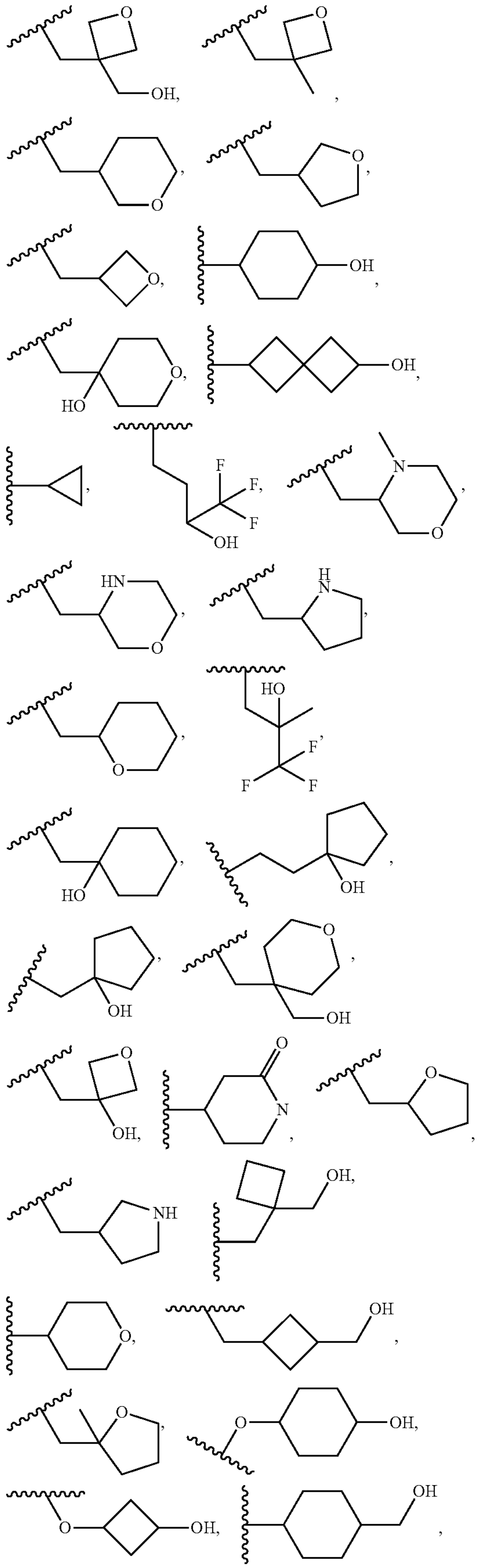

-continued
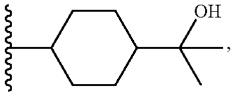,
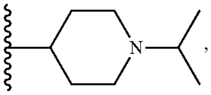,
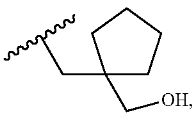
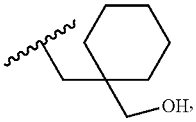
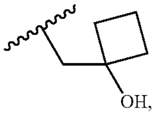
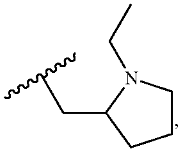,
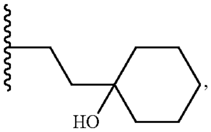,
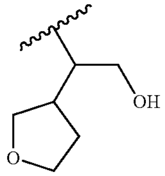
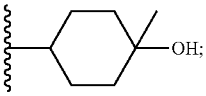
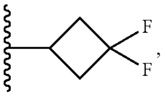,
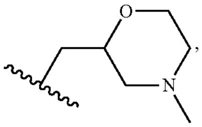,
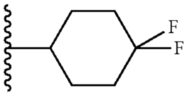
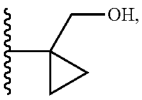
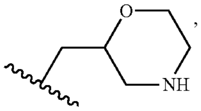,
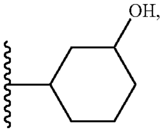
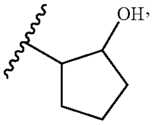
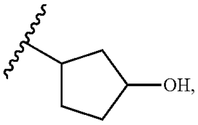
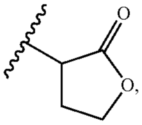
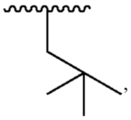,
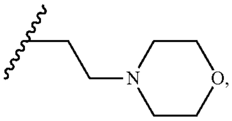
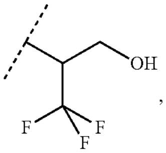,
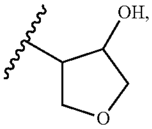
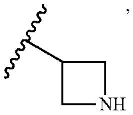,
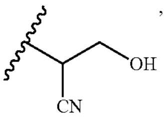,
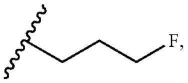
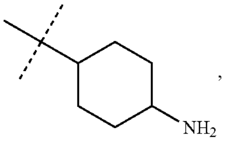,
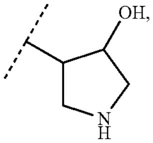
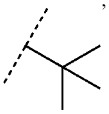,
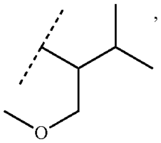,
-continued
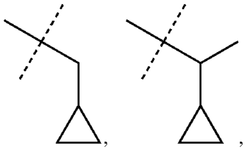,
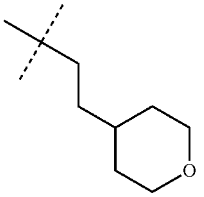 and
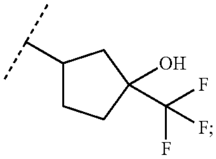
or a pharmaceutically acceptable salt thereof.
In an embodiment 16 of the invention, there is provided a compound according to any one of embodiments 1 to 9, wherein
$R^3$ is selected from
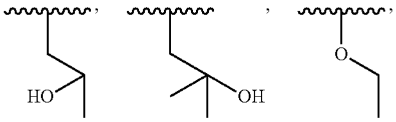
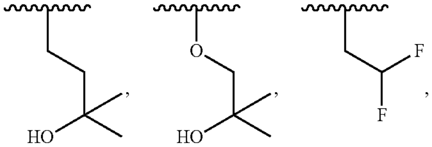
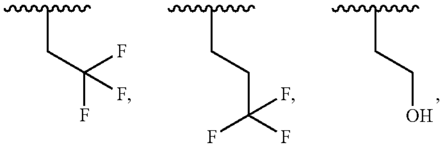
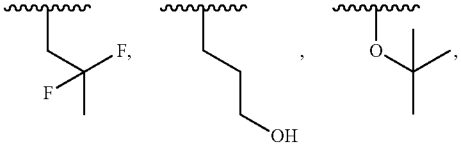
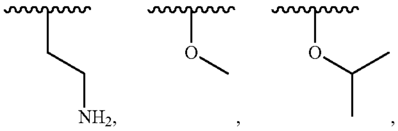
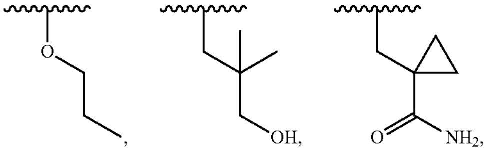
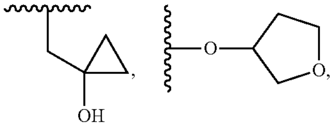
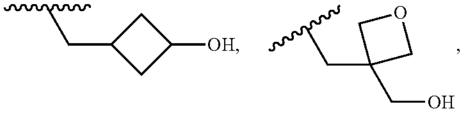, -continued
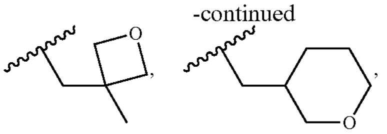
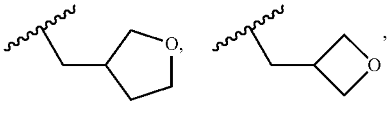
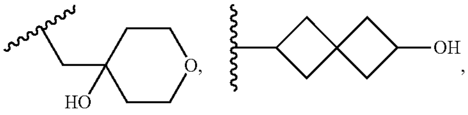
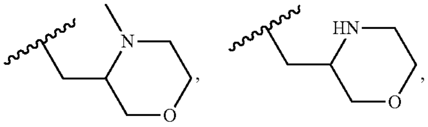
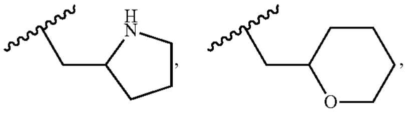
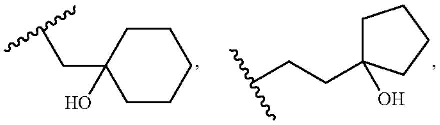
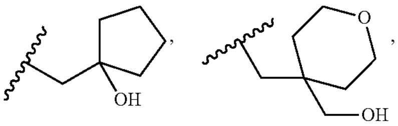
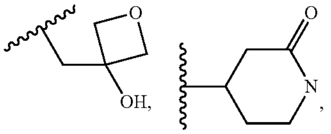
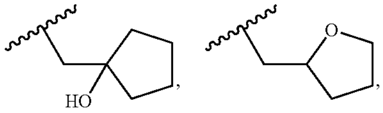
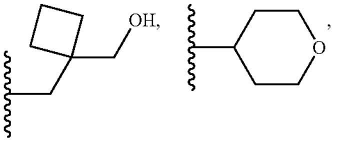
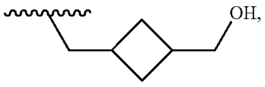
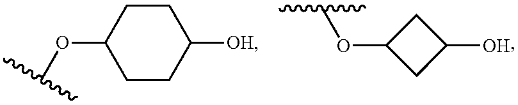
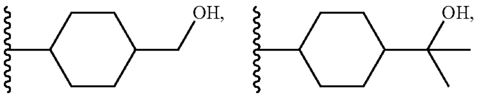
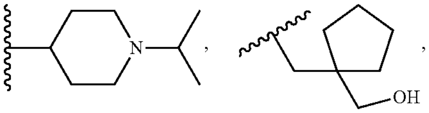
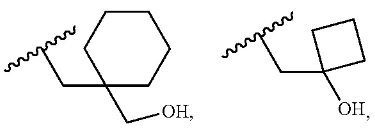
-continued
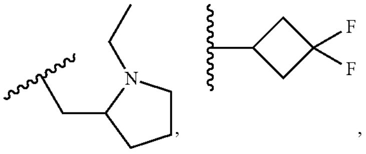
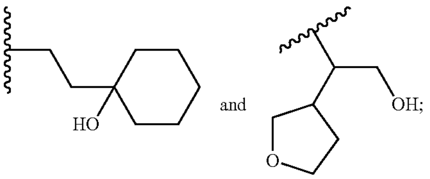
or a pharmaceutically acceptable salt thereof.
In an embodiment 17 of the invention, there is provided a compound according to an one of embodiments 1 to 9, wherein
$R^3$ is selected from
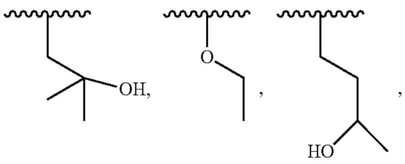
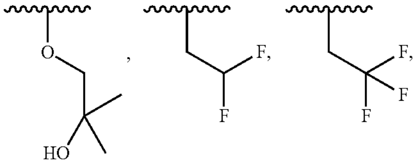
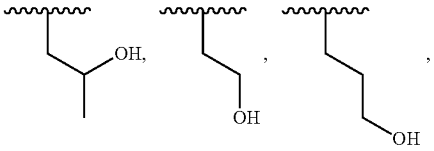
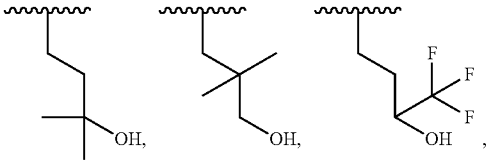
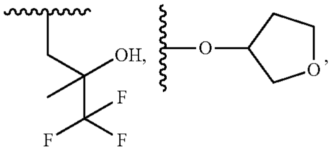
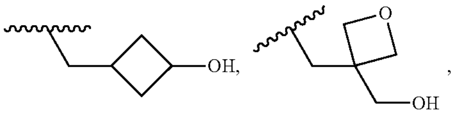
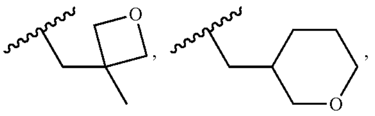
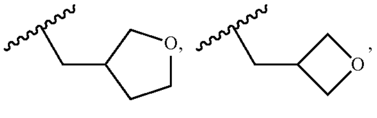

-continued

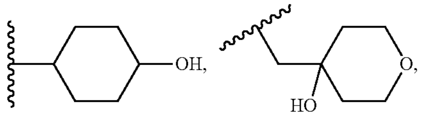

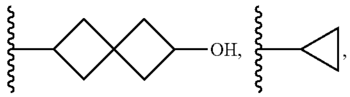

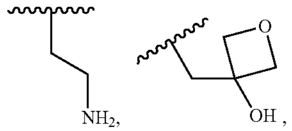

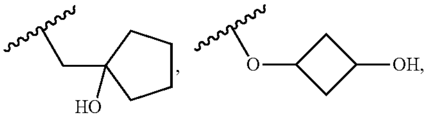

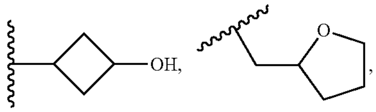

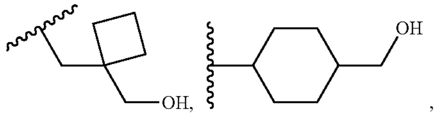

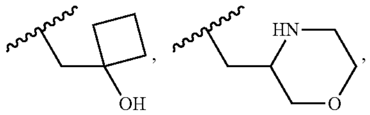

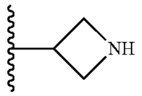
and
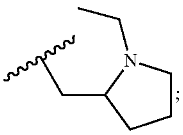

or a pharmaceutically acceptable salt thereof.

In an embodiment 18 of the invention, there is provided a compound according to an one of embodiments 1 to 9, wherein $R^3$ is selected from

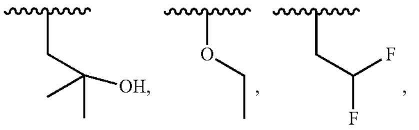

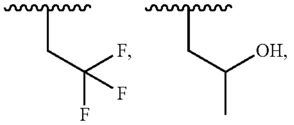

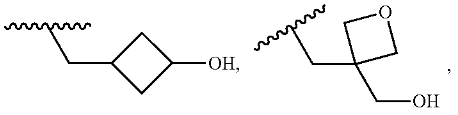

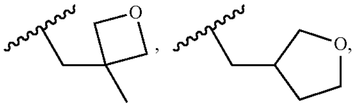

-continued

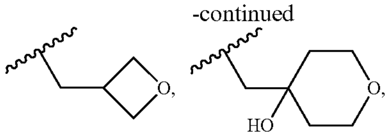

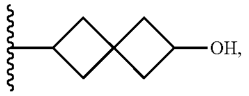

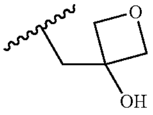
and
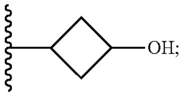

or a pharmaceutically acceptable salt thereof.

In an embodiment 19 of the invention, there is provided a compound according to any one of embodiments 1 to 9, wherein $R^3$ is selected from

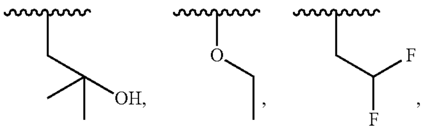

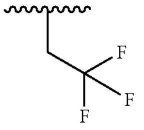
and
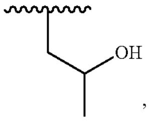

or a pharmaceutically acceptable salt thereof.

In an embodiment 20 of the invention, there is provided a compound according to any one of embodiments 1 to 9, wherein $R^3$ is selected from

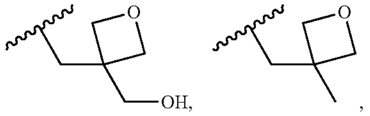

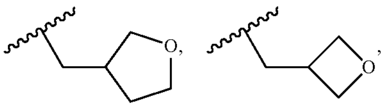

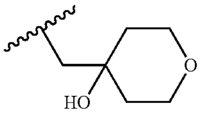
and
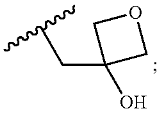

or a pharmaceutically acceptable salt thereof.

In an embodiment 21 of the invention, there is provided a compound according to any one of embodiments 1 to 7, wherein $R^3$ is selected from

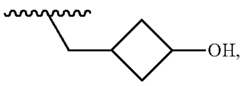

-continued

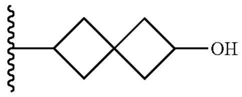

and

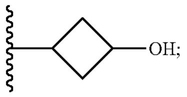

or a pharmaceutically acceptable salt thereof.

In an embodiment 22 of the invention, there is provided a compound according to any one of embodiments 1 to 9, wherein $R^3$ is selected from

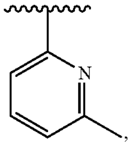 [SMILES: *c1cccc(C)n1]

or a pharmaceutically acceptable salt thereof.

In an embodiment 22.1 of the invention, there is provided a compound according to any one of embodiments 1 to 9, wherein $R^3$ is H, or a pharmaceutically acceptable salt thereof.

In an embodiment 23 of the invention, there is provided a compound according to any one of embodiments 1 to 9, wherein $R^3$ and $R^4$ together with the nitrogen atom to which they are attached form a ring selected from

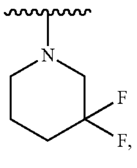 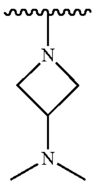, 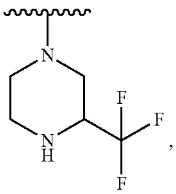,

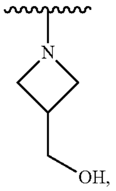 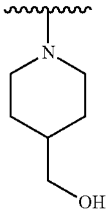, 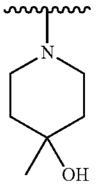, 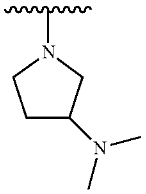,

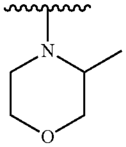, 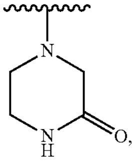 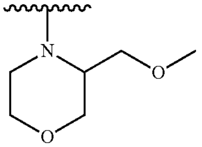,

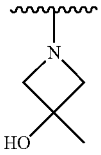, 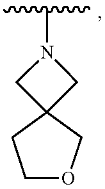, 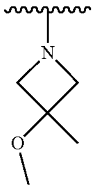, 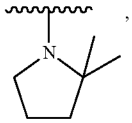,

-continued

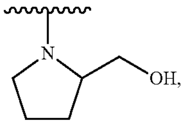 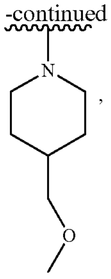,

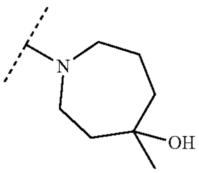 and 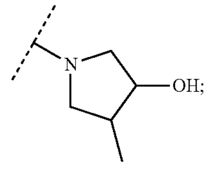

or a pharmaceutically acceptable salt thereof.

In an embodiment 23.1 of the invention, there is provided a compound or salt according to any one of embodiments 1 to 9, wherein $R^3$ is selected from (i) $C_{1-4}$ alkyl substituted with 1 to 3 substituents independently selected from hydroxy, $C_{1-4}$ alkyl, halogen, oxo, and $-NR^{3a}R^{3b}$;

(ii) $C_{1-4}$ alkoxy substituted with 1 to 3 substituents independently selected from hydroxy, halogen and $C_{1-4}$ alkyl;

(iii) $-(C_{0-3}$ alkyl)-$C_{3-6}$ cycloalkyl wherein the $C_{3-6}$ cycloalkyl is substituted with 1 to 3 substituents independently selected from hydroxy, $C_{1-4}$ hydroxyalkyl and halogen;

(iv) a $-(C_{0-3}$ alkyl)-$C_{3-6}$ cycloalkyl spiro fused to a second $C_{3-6}$ cycloalkyl by one single carbon atom, wherein the second $C_{3-6}$ cycloalkyl is substituted with 1 to 3 substituents independently selected from hydroxy and halogen; and (v) a $-(C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from hydroxy, $C_{1-4}$ alkyl and $C_{1-4}$ hydroxyalkyl;

(vi) a $-(C_{0-3}$ alkyl)-$C_{3-6}$ heterocyclyl wherein the $C_{3-6}$ heterocyclyl contains at least one heteroatom selected from O and N, and wherein the $C_{3-6}$ heterocyclyl is spiro fused to a second $C_{3-6}$ heterocyclyl or a $C_{3-6}$ cycloalkyl by one single carbon atom, and wherein said second $C_{3-6}$ heterocyclyl or $C_{3-6}$ cycloalkyl is unsubstituted or substituted with 1 to 3 substituents independently selected from $C_{1-4}$ alkyl, hydroxy and $C_{1-4}$ hydroxyalkyl;

$R^{3a}$ and $R^{3b}$ are independently selected from H and $C_{1-4}$ alkyl;

$R^4$ is selected from H and $C_{1-4}$alkyl; or $R^3$ and $R^4$ together with the nitrogen atom to which they are attached form a $C_{3-6}$ heterocyclyl, which $C_{3-6}$ heterocyclyl is unsubstituted or substituted with 1 to 3 substituents independently selected from hydroxy, $C_{1-4}$ hydroxyalkyl and $C_{1-4}$ alkyl.

In an embodiment 23.2 of the invention, there is provided a compound or salt according to any one of embodiments 1 to 9, wherein $R^3$ is $C_{1-4}$ alkyl which is unsubstituted or substituted with 1 to 3 substituents independently selected from hydroxy, $C_{1-4}$ alkyl, halogen, oxo, and $-NR^{3a}R^{3b}$.

In an embodiment 23.3 of the invention, there is provided a compound or salt according to any one of embodiments 1 to 9, wherein $R^3$ is selected from propyl, butyl and pentyl substituted with 1 to 3 substituents independently selected from hydroxy, $C_{1-4}$ alkyl, halogen, $-NR^{3a}R^{3b}$ and oxo.

In an embodiment 23.4 of the invention, there is provided a compound or salt according to any one of embodiments 1 to 9, wherein $R^3$ is selected from
3-hydroxypropyl-;
3-hydroxy-2,2-dimethylpropyl-;
3-hydroxy-3-methylbutyl-;
2-hydroxy-2-methylpropyl-;
4,4,4-trifluoro-3-hydroxybutyl-;
2,2-difluoroethyl-;
3,3-dimethyl-2-oxo-butyl; and
3,3,3-trifluoro-2-hydroxy-2-methylpropyl-.

In an embodiment 23.5 of the invention, there is provided a compound or salt according to any one of embodiments 1 to 9, wherein $R^3$ is selected from
3-hydroxypropyl-;
3-hydroxy-2,2-dimethylpropyl-;
2-hydroxy-2-methylpropyl; and
3-hydroxy-3-methylbutyl-.

In an embodiment 23.6 of the invention, there is provided a compound or salt according to any one of embodiments 1 to 9, wherein $R^3$ is $C_{1-4}$ alkoxy which is unsubstituted or substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl.

In an embodiment 23.7 of the invention, there is provided a compound or salt according to any one of embodiments 1 to 9, wherein $R^3$ is selected from propoxy, butoxy and pentoxy substituted with 1 to 3 substituents selected from hydroxy, $C_{1-4}$ alkyl and halogen.

In an embodiment 23.8 of the invention, there is provided a compound or salt according to any one of embodiments 1 to 9, wherein $R^3$ is 2-hydroxy-2-methylpropoxy-.

In an embodiment 23.9 of the invention, there is provided a compound or salt according to any one of embodiments 1 to 9, wherein $R^3$ is —($C_{0-3}$ alkyl)-$C_{3-6}$ cycloalkyl or —($C_{0-3}$ alkyl)-O—$C_{3-6}$ cycloalkyl wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$.

In an embodiment 23.10 of the invention, there is provided a compound or salt according to any one of embodiments 1 to 9, wherein $R^3$ is selected from —($C_{0-3}$ alkyl)-cyclohexyl, —($C_{0-3}$ alkyl)-cyclobutyl and —($C_{0-3}$ alkyl)-cyclopropyl, and wherein the cyclohexyl, cyclobutyl and cyclopropyl are substituted with 1 or 2 substituents independently selected from hydroxy, $C_{1-4}$ hydroxyalkyl and halogen.

In an embodiment 23.11 of the invention, there is provided a compound or salt according to any one of embodiments 1 to 9, wherein $R^3$ is selected from
3-hydroxycyclobutyl-;
4-hydroxycyclohexyl-;
3-hydroxycyclobutyl-methyl-;
1-hydroxycyclobutyl-methyl-;
1-(hydroxymethyl)cyclopropyl; and
1-hydroxycyclopropyl-methyl-.

In an embodiment 23.12 of the invention, there is provided a compound or salt according to any one of embodiments 1 to 9, wherein $R^3$ is selected from
3-hydroxycyclobutyl-; and
4-hydroxycyclohexyl-.

In an embodiment 23.13 of the invention, there is provided a compound or salt according to any one of embodiments 1 to 9, wherein $R^3$ is —($C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$.

In an embodiment 23.14 of the invention, there is provided a compound or salt according to any one of embodiments 1 to 9, wherein $R^3$ is selected from spiro[3.3]heptan-2-yl, spiro[3.4]octan-6-yl, spiro[4.4]nonan-2-yl and spiro[3.4]undecan-3-yl, which is substituted with 1 to 3 substituents selected from hydroxy and halogen.

In an embodiment 23.15 of the invention, there is provided a compound or salt according to any one of embodiments 1 to 9, wherein $R^3$ is 6-hydroxyspiro[3.3]heptan-2-yl.

In an embodiment 23.16 of the invention, there is provided a compound or salt according to any one of embodiments 1 to 9, wherein $R^3$ is —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from hydroxy, $C_{1-4}$ alkyl and $C_{1-4}$ hydroxyalkyl;
or —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$.

In an embodiment 23.17 of the invention, there is provided a compound or salt according to any one of embodiments 1 to 9, wherein $R^3$ is selected from a —($C_{0-3}$ alkyl)-tetrahydrofuranyl, —($C_{0-3}$ alkyl)-oxetanyl, —($C_{0-3}$ alkyl)-pyrrolidinyl, and —($C_{0-3}$ alkyl)-tetrahydropyranyl, each of which is unsubstituted or substituted with 1 to 3 substituents independently selected from hydroxy, $C_{1-4}$ alkyl and $C_{1-4}$ hydroxyalkyl.

In an embodiment 23.18 of the invention, there is provided a compound or salt according to any one of embodiments 1 to 9, wherein $R^3$ is selected from
(1-ethylpyrrolidin-2-yl)methyl,
(tetrahydro-2H-pyran-4-yl,
(3-hydroxyoxetan-3-yl)methyl,
(3-methyloxetan-3-yl)methyl,
(4-hydroxy-tetrahydropyran)methyl,
(3-hydroxymethyl-oxetan-3-yl)methyl, and
(tetrahydrofuran-3-yl)methyl.

In an embodiment 23.19 of the invention, there is provided a compound or salt according to any one of embodiments 1 to 9, wherein $R^4$ is H or methyl.

In an embodiment 23.20 of the invention, there is provided a compound or salt according to any one of embodiments 1 to 9, wherein $R^3$ and $R^4$ together with the nitrogen atom to which they are attached form a $C_{3-6}$ heterocyclyl, which heterocyclyl is unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl.

In an embodiment 23.21 of the invention, there is provided a compound or salt according to any one of embodiments 1 to 9, wherein $R^3$ and $R^4$ together with the nitrogen atom to which they are attached form a piperazinyl, piperidinyl, or azetidinyl, which are unsubstituted or substituted with 1 to 3 substituents independently selected from hydroxy, $C_{1-4}$ hydroxyalkyl and $C_{1-4}$ alkyl.

In an embodiment 23.22 of the invention, there is provided a compound or salt according to any one of embodiments 1 to 9, wherein $R^3$ and $R^4$ together with the nitrogen atom to which they are attached form a 3-(trifluoromethyl)piperazin-1-yl, 3,3-difluoropiperidin-1-yl, or 1-(hydroxymethyl)azetidin-3-yl.

In an embodiment 23.23 of the invention, there is provided a compound or salt according to any one of embodiments 1 to 9, wherein $R^3$ is pyridyl wherein the pyridyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$.

In an embodiment 23.24 of the invention, there is provided a compound or salt according to any one of embodiments 1 to 9, wherein $R^3$ is pyridyl wherein the pyridyl is unsubstituted or substituted with 1 to 3 substituents independently selected from $C_{1-4}$ alkyl, $C_{1-4}$ alkoxy and hydroxy, particularly $C_{1-4}$ alkyl.

In an particular embodiment 24 of the invention, there is provided a compound of formula (I)

(I)

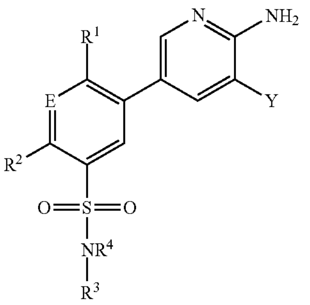

wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

Y is selected from the group consisting of

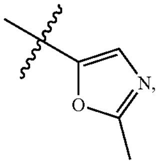 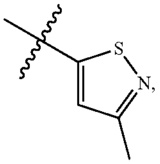

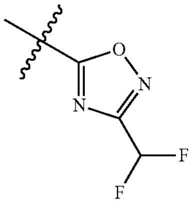, 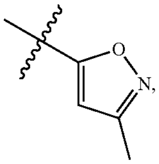

-continued

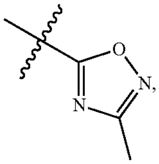 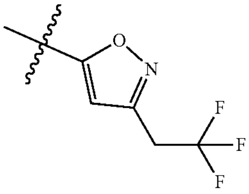,

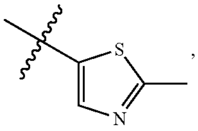, 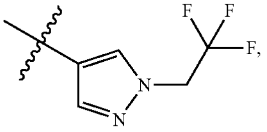

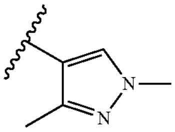, 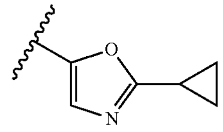,

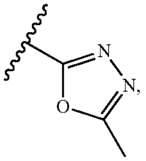 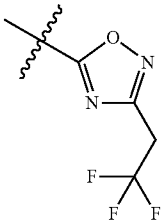,

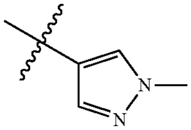, 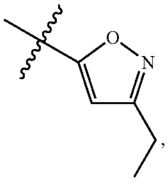,

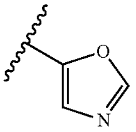, 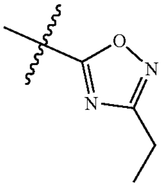, 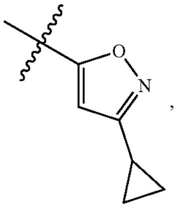,

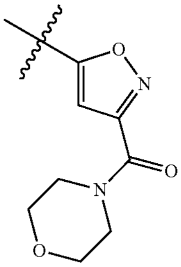, 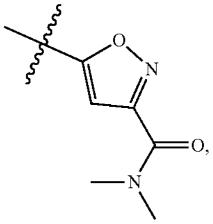

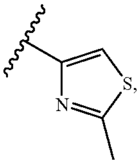 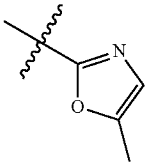, 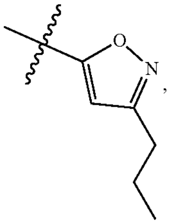

-continued
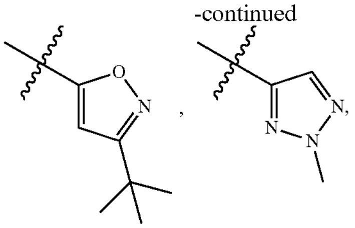
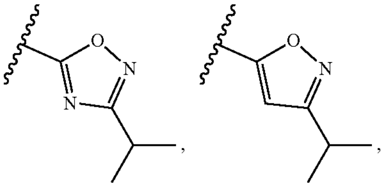
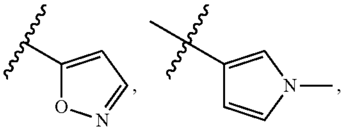
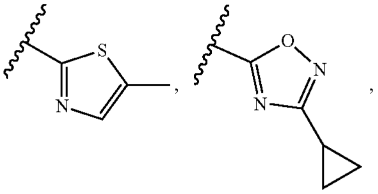
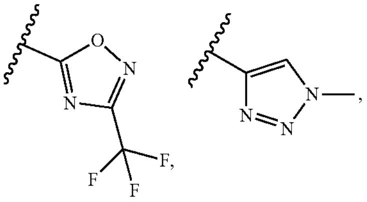
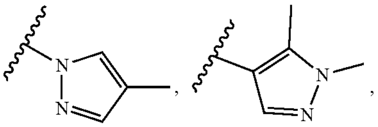
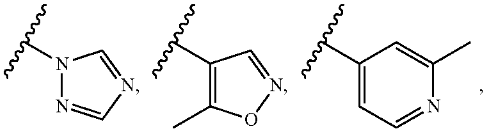
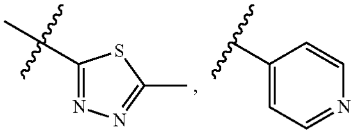
and
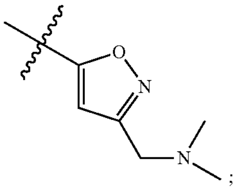
$R^4$ is H and $R^3$ is selected from the group consisting of
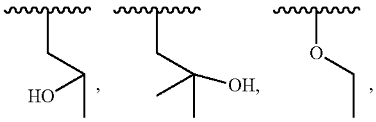
-continued
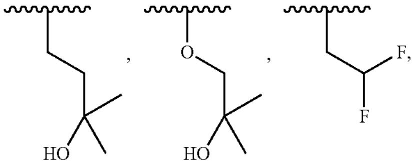
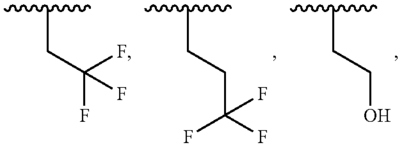
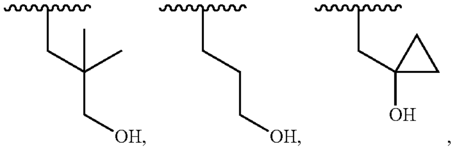
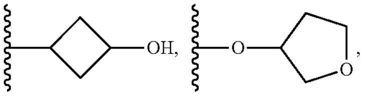
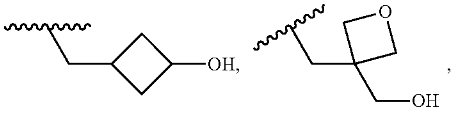
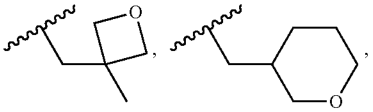
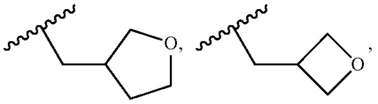
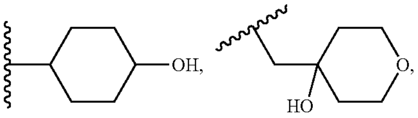
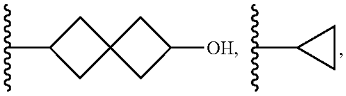
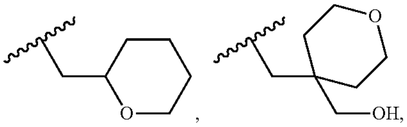
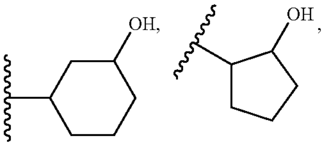
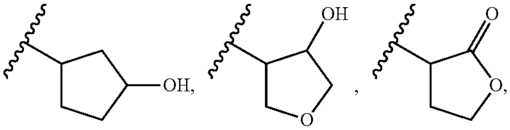
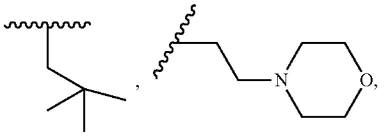

-continued

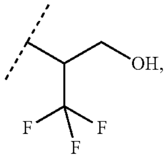
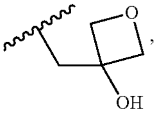
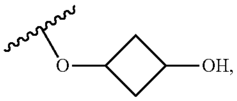
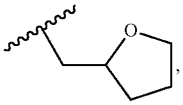
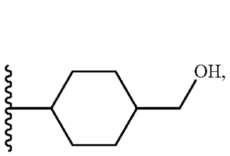
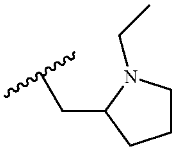
and
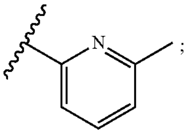

or $R^3$ and $R^4$ together with the nitrogen atom to which they are attached form a $C_{3-7}$ heterocyclyl selected from the group consisting of

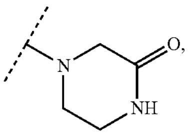
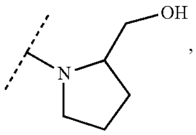
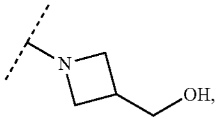
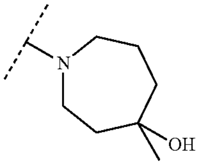
and
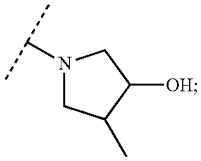

or a pharmaceutically acceptable salt thereof.

In a further particular embodiment 25 of the invention, there is provided a compound of formula (Ib)

(Ib)

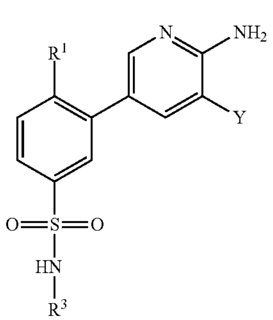

wherein $R^1$ is H or $C_{1-4}$ alkyl, particularly $C_{1-4}$ alkyl, more particularly methyl;

Y is selected from the group consisting of

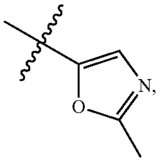
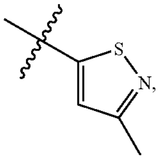
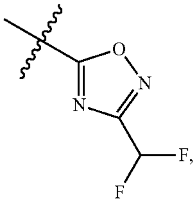
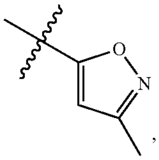
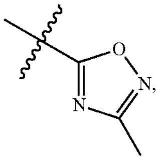
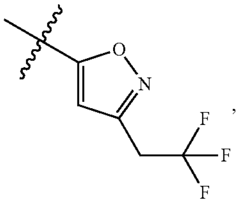
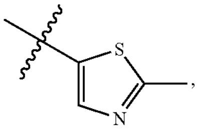
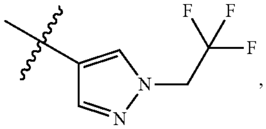
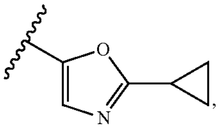
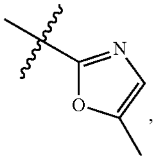
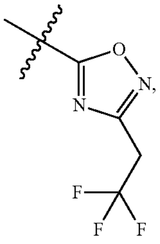
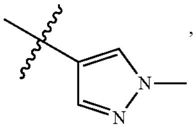
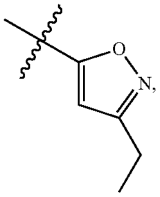
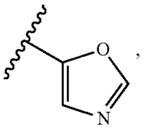
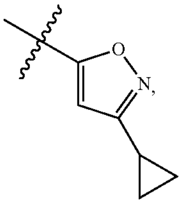
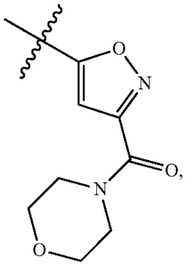
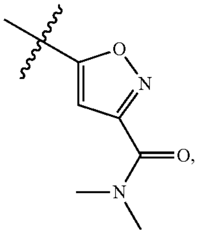

-continued
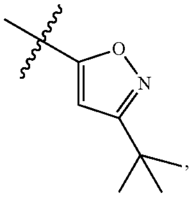,
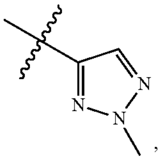,
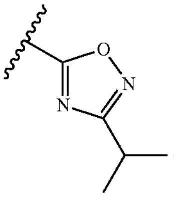,
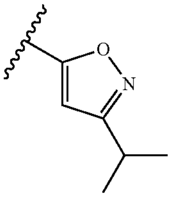,
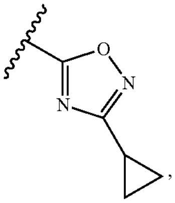,
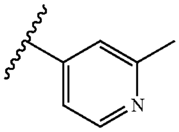
and
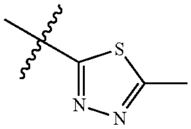,
$R^3$ is selected from the group consisting of
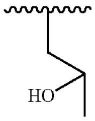,
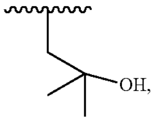
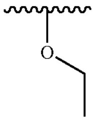,
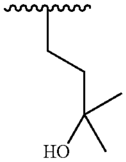,
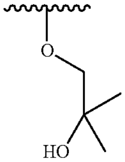,
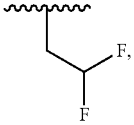
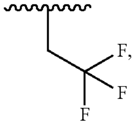
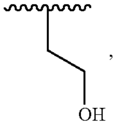,
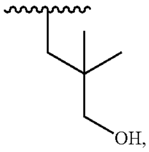
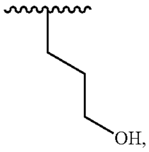
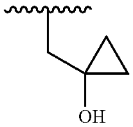,
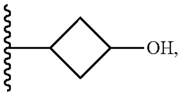
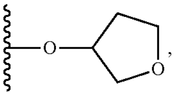,
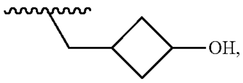
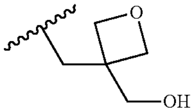,
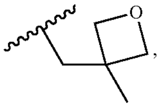
-continued
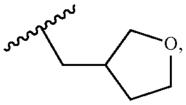
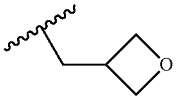
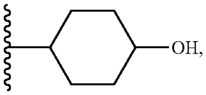
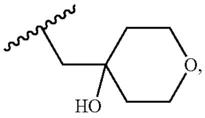
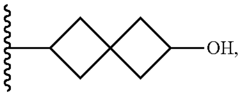
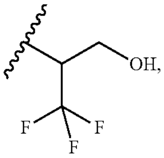
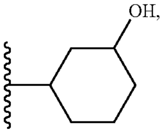
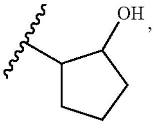
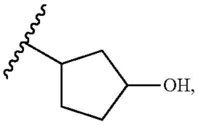
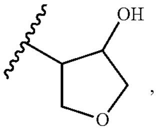,
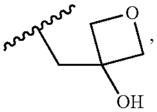
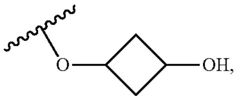
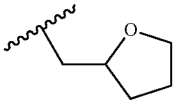
and
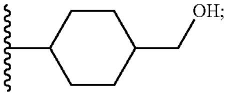
or a pharmaceutically acceptable salt thereof.
In a further particular embodiment 26 of the invention, there is provided a compound of formula (Ib)
(Ib)
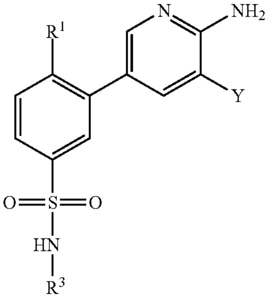
wherein
$R^1$ is H or $C_{1-4}$ alkyl, particularly $C_{1-4}$ alkyl, more particularly methyl;

Y is selected from the group consisting of

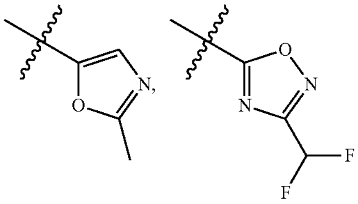

,

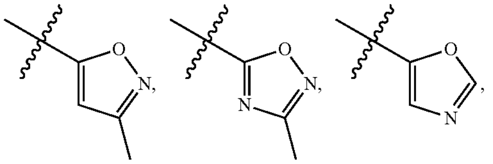

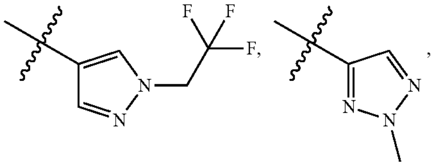

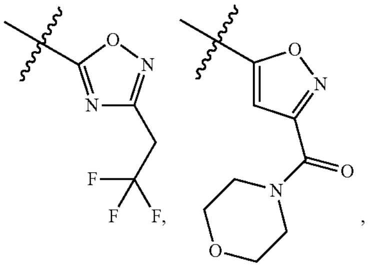

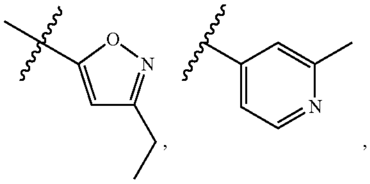

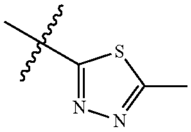

and

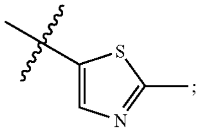

R[3] is selected from the group consisting of

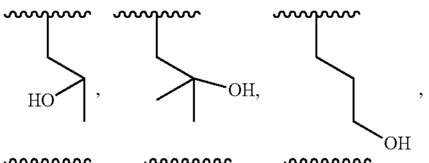

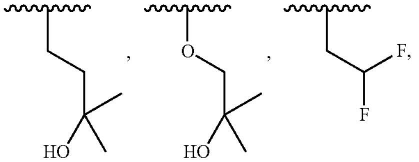

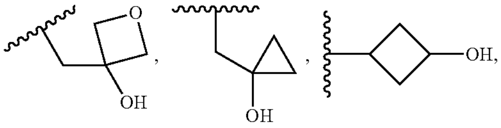

-continued

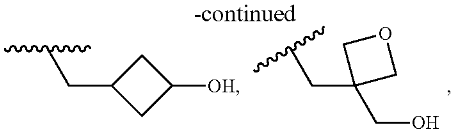

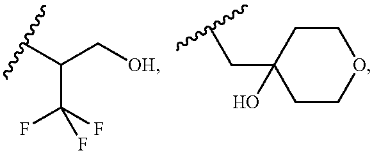

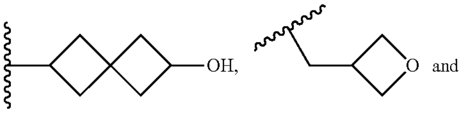

and

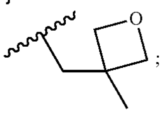

or a pharmaceutically acceptable salt thereof.

In another particular embodiment 27 of the invention, there is provided a compound of formula (Ib)

(Ib)

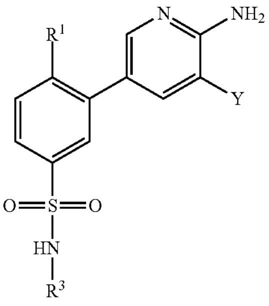

wherein $R^1$ is H or $C_{1-4}$ alkyl, particularly $C_{1-4}$ alkyl, more particularly methyl;

Y is selected from the group consisting of

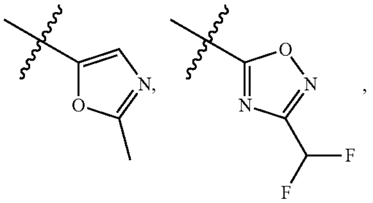

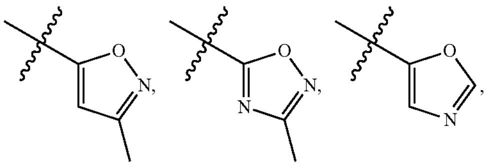

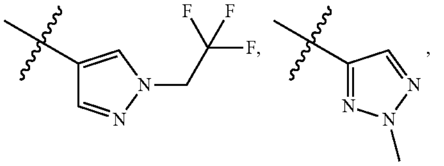

-continued

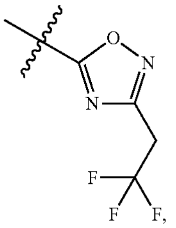 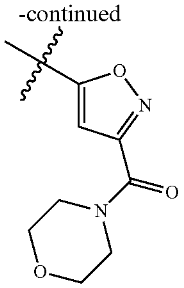 ,

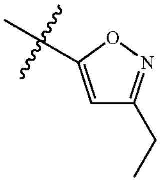 , 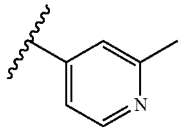 ,

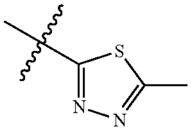 and 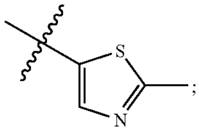 ;

$R^3$ is selected from the group consisting of

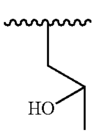 , 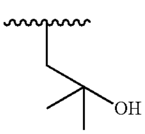 , 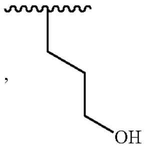 ,

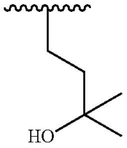 , 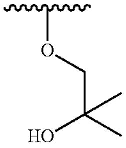 , 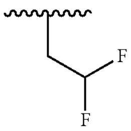 and

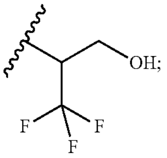

or a pharmaceutically acceptable salt thereof.

In another particular embodiment 28 of the invention, there is provided a compound of formula (Ib)

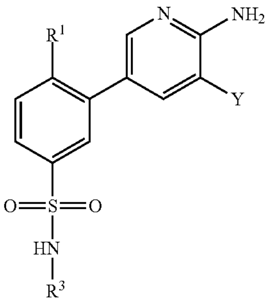

(Ib)

wherein $R^1$ is H or $C_{1-4}$ alkyl, particularly $C_{1-4}$ alkyl, more particularly methyl;

Y is selected from the group consisting of

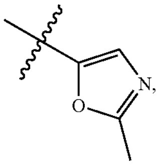 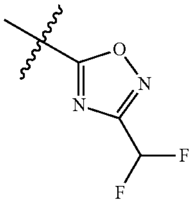 ,

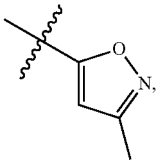 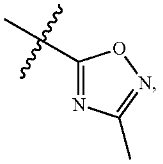 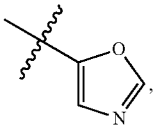

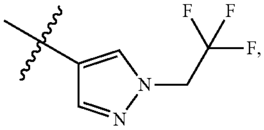 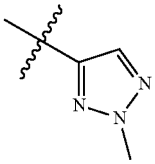 ,

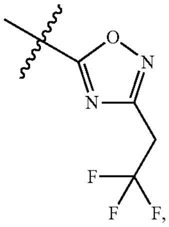 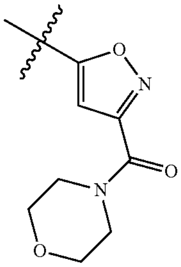 ,

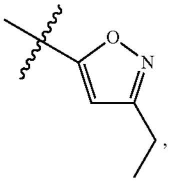 , 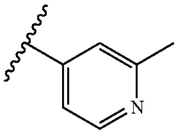 ,

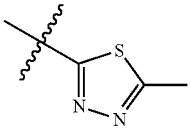 and 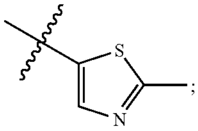 ;

$R^3$ is selected from the group consisting of

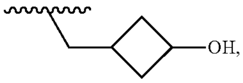 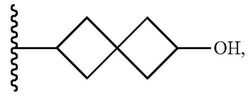

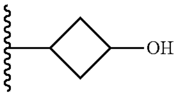 and 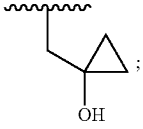 ;

or a pharmaceutically acceptable salt thereof.

In another particular embodiment 29 of the invention, there is provided a compound of formula (Ib)

(Ib)

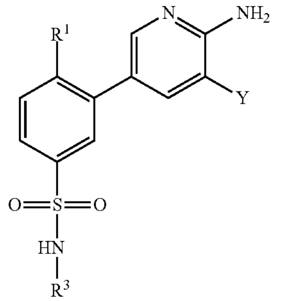

wherein $R^1$ is H or $C_{1-4}$ alkyl, particularly $C_{1-4}$ alkyl, more particularly methyl;

Y is selected from the group consisting of

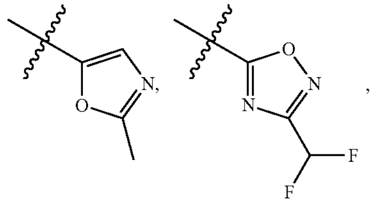

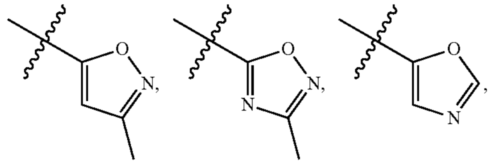

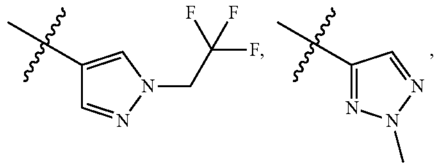

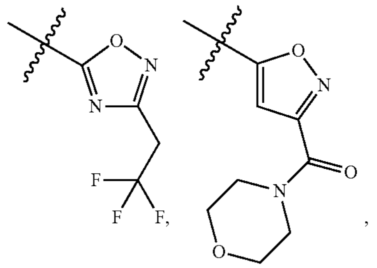

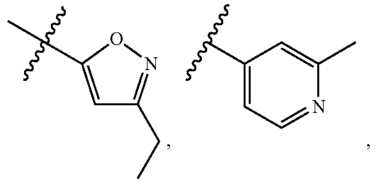

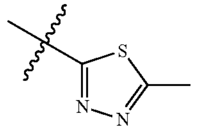

and

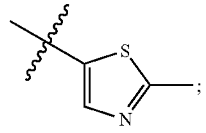

$R^3$ is selected from the group consisting of

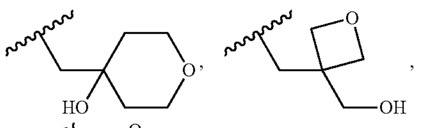

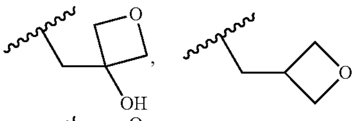

and

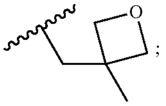

or a pharmaceutically acceptable salt thereof.

In an embodiment 30 of the invention, there is provided a compound according to embodiment 1 selected from 3-(6-amino-5-(1-(2,2,2-trifluoroethyl)-1H-pyrazol-4-yl)pyridin-3-yl)-4-methyl-N-(6-methylpyridin-2-yl)benzenesulfonamide;

3-(6-amino-5-(1-methyl-1H-pyrazol-4-yl)pyridin-3-yl)-N-(3-hydroxy-3-methylbutyl)-4-methylbenzenesulfonamide;

3-(6-amino-5-(1-(2,2,2-trifluoroethyl)-1H-pyrazol-4-yl)pyridin-3-yl)-N-(3-hydroxy-3-methylbutyl)-4-methylbenzenesulfonamide;

3-(6-amino-5-(2-methylthiazol-5-yl)pyridin-3-yl)-N-(3-hydroxy-3-methylbutyl)-4-methylbenzenesulfonamide;

3-(6-amino-5-(1-methyl-1H-pyrazol-4-yl)pyridin-3-yl)-N-((1r,4r)-4-hydroxycyclohexyl)-4-methylbenzenesulfonamide;

3-(6-amino-5-(1-(2,2,2-trifluoroethyl)-1H-pyrazol-4-yl)pyridin-3-yl)-N-((1r,4r)-4-hydroxycyclohexyl)-4-methylbenzenesulfonamide;

3-(2-amino-2'-methyl-3,4'-bipyridin-5-yl)-N-((1r,4r)-4-hydroxycyclohexyl)-4-methylbenzenesulfonamide;

3-(6-amino-5-(2-methyl-2H-1,2,3-triazol-4-yl)pyridin-3-yl)-N-(2-hydroxy-2-methylpropyl)-4-methylbenzenesulfonamide;

3-(6-amino-5-(2-methyl-2H-1,2,3-triazol-4-yl)pyridin-3-yl)-N-((1r,4r)-4-hydroxycyclohexyl)-4-methylbenzenesulfonamide;

3-(6-amino-5-(3-ethylisoxazol-5-yl)pyridin-3-yl)-N-(2-hydroxy-2-methylpropyl)-4-methylbenzenesulfonamide;

(R)-3-(6-amino-5-(3-methylisoxazol-5-yl)pyridin-3-yl)-4-methyl-N-((tetrahydrofuran-3-yl)methyl)benzenesulfonamide;

3-(6-amino-5-(3-methylisothiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-4-methyl-N-((3-methyloxetan-3-yl)methyl)benzenesulfonamide;

3-(6-amino-5-(3-methyl-1,2,4-oxadiazol-5-yl)pyridin-3-yl)-N-(3-hydroxy-3-methylbutyl)-4-methylbenzenesulfonamide;

3-(6-amino-5-(3-isopropyl-1,2,4-oxadiazol-5-yl)pyridin-3-yl)-N-(2-hydroxy-2-methylpropyl)-4-methylbenzenesulfonamide;

3-(6-amino-5-(5-methyloxazol-2-yl)pyridin-3-yl)-N-((1r,4r)-4-hydroxycyclohexyl)-4-methylbenzenesulfonamide;

3-(6-amino-5-(3-ethyl-1,2,4-oxadiazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1r,4r)-4-hydroxycyclohexyl)-4-methylbenzenesulfonamide;

3-(6-amino-5-(3-methyl-1,2,4-oxadiazol-5-yl)pyridin-3-yl)-N-(3-hydroxycyclobutyl)-4-methylbenzenesulfonamide;
3-(6-amino-5-(3-methyl-1,2,4-oxadiazol-5-yl)pyridin-3-yl)-N-((1s,3s)-3-hydroxycyclobutyl)-4-methylbenzenesulfonamide;
3-(6-amino-5-(5-methyl-1,3,4-oxadiazol-2-yl)pyridin-3-yl)-N-(3-hydroxy-3-methylbutyl)-4-methylbenzenesulfonamide;
3-(6-amino-5-(2-methyloxazol-5-yl)pyridin-3-yl)-N-(2-hydroxy-2-methylpropyl)-4-methylbenzenesulfonamide;
3-(6-amino-5-(3-methylisoxazol-5-yl)pyridin-3-yl)-N-(2-hydroxy-2-methylpropyl)-4-methylbenzenesulfonamide;
3-(6-amino-5-(3-methyl-1,2,4-oxadiazol-5-yl)pyridin-3-yl)-N-(6-hydroxyspiro[3.3]heptan-2-yl)-4-methylbenzenesulfonamide;
3-(6-amino-5-(3-methyl-1,2,4-oxadiazol-5-yl)pyridin-3-yl)-N-(6-hydroxyspiro[3.3]heptan-2-yl)-4-methylbenzenesulfonamide;
3-(6-amino-5-(3-methyl-1,2,4-oxadiazol-5-yl)pyridin-3-yl)-N-(6-hydroxyspiro[3.3]heptan-2-yl)-4-methylbenzenesulfonamide;
3-(6-amino-5-(2-methylthiazol-5-yl)pyridin-3-yl)-N-(3-hydroxypropyl)-4-methylbenzenesulfonamide;
3-(6-amino-5-(3-methyl-1,2,4-oxadiazol-5-yl)pyridin-3-yl)-N-(2-hydroxy-2-methylpropyl)-4-methylbenzenesulfonamide;
3-(6-amino-5-(3-methyl-1,2,4-oxadiazol-5-yl)pyridin-3-yl)-N-(2-hydroxy-2-methylpropoxy)-4-methylbenzenesulfonamide;
3-(6-amino-5-(3-methyl-1,2,4-oxadiazol-5-yl)pyridin-3-yl)-N-((1r,4r)-4-hydroxycyclohexyl)-4-methylbenzenesulfonamide;
3-(6-amino-5-(2-methyloxazol-5-yl)pyridin-3-yl)-N-(3-hydroxy-3-methylbutyl)-4-methylbenzenesulfonamide;
3-(6-amino-5-(3-methylisoxazol-5-yl)pyridin-3-yl)-N-(3-hydroxy-3-methylbutyl)-4-methylbenzenesulfonamide;
3-(6-amino-5-(2-methylthiazol-5-yl)pyridin-3-yl)-N-(2-hydroxy-2-methylpropyl)-4-methylbenzenesulfonamide;
3-(2-amino-2'-methyl-3,4'-bipyridin-5-yl)-N-(3-hydroxy-3-methylbutyl)-4-methylbenzenesulfonamide;
3-(6-amino-5-(3-methylisoxazol-5-yl)pyridin-3-yl)-4-methyl-N-((3-methyloxetan-3-yl)methyl)benzenesulfonamide;
3-(2-amino-3,4'-bipyridin-5-yl)-N-(3-hydroxy-3-methylbutyl)-4-methylbenzenesulfonamide;
3-(6-amino-5-(3-methyl-1,2,4-oxadiazol-5-yl)pyridin-3-yl)-N-((1r,4r)-4-(hydroxymethyl)cyclohexyl)-4-methylbenzenesulfonamide;
5-(5-(6-oxa-2-azaspiro[3.4]octan-2-ylsulfonyl)-2-methylphenyl)-3-(3-methylisoxazol-5-yl)pyridin-2-amine;
3-(6-amino-5-(3-methylisoxazol-5-yl)pyridin-3-yl)-4-methyl-N-(2-oxotetrahydrofuran-3-yl)benzenesulfonamide;
3-(6-amino-5-(3-methylisoxazol-5-yl)pyridin-3-yl)-N-((1r,4r)-4-aminocyclohexyl)-4-methylbenzenesulfonamide;
3-(6-amino-5-(3-methylisoxazol-5-yl)pyridin-3-yl)-N-((3R,4R)-4-hydroxypyrrolidin-3-yl)-4-methylbenzenesulfonamide;
(S)-5-(2-methyl-5-(3-methylmorpholinosulfonyl)phenyl)-3-(3-methylisoxazol-5-yl)pyridin-2-amine;
(R)-5-(2-methyl-5-(3-methylmorpholinosulfonyl)phenyl)-3-(3-methylisoxazol-5-yl)pyridin-2-amine;
3-(6-amino-5-(3-methylisoxazol-5-yl)pyridin-3-yl)-4-methyl-N-neopentylbenzenesulfonamide;
3-(6-amino-5-(3-methylisoxazol-5-yl)pyridin-3-yl)-N-tert-butyl-4-methylbenzenesulfonamide
5-(5-(2,2-dimethylpyrrolidin-1-ylsulfonyl)-2-methylphenyl)-3-(3-methylisoxazol-5-yl)pyridin-2-amine;
3-(6-amino-5-(3-methylisoxazol-5-yl)pyridin-3-yl)-N-((1-hydroxycyclopropyl)methyl)-4-methylbenzenesulfonamide;
3-(6-amino-5-(3-methylisoxazol-5-yl)pyridin-3-yl)-N-(1-methoxy-3-methylbutan-2-yl)-4-methylbenzenesulfonamide;
3-(6-amino-5-(3-methylisoxazol-5-yl)pyridin-3-yl)-4-methyl-N-(2-(tetrahydro-2H-pyran-4-yl)ethyl)benzenesulfonamide;
(S)-3-(6-amino-5-(3-methylisoxazol-5-yl)pyridin-3-yl)-N-(1-cyclopropylethyl)-4-methylbenzenesulfonamide;
(S)-(1-(3-(6-amino-5-(3-methylisoxazol-5-yl)pyridin-3-yl)-4-methylphenylsulfonyl)pyrrolidin-2-yl)methanol;
3-(6-amino-5-(3-methylisoxazol-5-yl)pyridin-3-yl)-N-((1S,3S)-3-hydroxycyclohexyl)-4-methylbenzenesulfonamide;
4-(3-(6-amino-5-(3-methylisoxazol-5-yl)pyridin-3-yl)-4-methylphenylsulfonyl)piperazin-2-one;
5-(5-(4-(methoxymethyl)piperidin-1-ylsulfonyl)-2-methylphenyl)-3-(3-methylisoxazol-5-yl)pyridin-2-amine;
5-(5-(3-(dimethylamino)azetidin-1-ylsulfonyl)-2-methylphenyl)-3-(3-methylisoxazol-5-yl)pyridin-2-amine;
(R)-5-(5-(3-(methoxymethyl)morpholinosulfonyl)-2-methylphenyl)-3-(3-methylisoxazol-5-yl)pyridin-2-amine;
3-(6-amino-5-(3-methylisoxazol-5-yl)pyridin-3-yl)-N-(2-hydroxy-2-methylpropoxy)-4-methylbenzenesulfonamide;
3-(6-amino-5-(3-methylisoxazol-5-yl)pyridin-3-yl)-4-methyl-N-(tetrahydrofuran-3-yloxy)benzenesulfonamide;
3-(6-amino-5-(3-methylisoxazol-5-yl)pyridin-3-yl)-4-methyl-N-(tetrahydrofuran-3-yloxy)benzenesulfonamide;
3-(6-amino-5-(3-methylisoxazol-5-yl)pyridin-3-yl)-N-ethoxy-4-methylbenzenesulfonamide;
3-(6-amino-5-(3-methylisoxazol-5-yl)pyridin-3-yl)-4-methyl-N-((tetrahydro-2H-pyran-3-yl)methyl)benzenesulfonamide;
3-(6-amino-5-(3-methylisoxazol-5-yl)pyridin-3-yl)-4-methyl-N-((tetrahydro-2H-pyran-3-yl)methyl)benzenesulfonamide;
(R)-3-(6-amino-5-(3-methylisoxazol-5-yl)pyridin-3-yl)-N-(2-hydroxypropyl)-4-methylbenzenesulfonamide;
3-(6-amino-5-(3-methylisoxazol-5-yl)pyridin-3-yl)-4-methyl-N-(oxetan-3-ylmethyl)benzenesulfonamide;
3-(6-amino-5-(1,3-dimethyl-1H-pyrazol-4-yl)pyridin-3-yl)-N-(6-hydroxyspiro[3.3]heptan-2-yl)-4-methylbenzenesulfonamide;
3-(6-amino-5-(3-methylisoxazol-5-yl)pyridin-3-yl)-N-(2,2-difluoroethyl)-4-methylbenzenesulfonamide;
3-(6-amino-5-(2-methylthiazol-5-yl)pyridin-3-yl)-N-(6-hydroxyspiro[3.3]heptan-2-yl)-4-methylbenzenesulfonamide;
3-(6-amino-5-(3-methyl-1,2,4-oxadiazol-5-yl)pyridin-3-yl)-4-methyl-N-((tetrahydrofuran-3-yl)methyl)benzenesulfonamide;
3-(6-amino-5-(1-methyl-1H-pyrazol-4-yl)pyridin-3-yl)-4-methyl-N-(6-methylpyridin-2-yl)benzenesulfonamide;
3-(6-amino-5-(3-methylisoxazol-5-yl)pyridin-3-yl)-N-cyclopropyl-4-methylbenzenesulfonamide;
3-(6-amino-5-(3-methylisoxazol-5-yl)pyridin-3-yl)-4-methylbenzenesulfonamide;
3-(6-amino-5-(2-methyloxazol-5-yl)pyridin-3-yl)-4-methylbenzenesulfonamide;
3-(6-amino-5-(1-(2,2,2-trifluoroethyl)-1H-pyrazol-4-yl)pyridin-3-yl)-N-(2-hydroxy-2-methylpropoxy)-4-methylbenzenesulfonamide 3-(6-amino-5-(3-(2,2,2-trifluoroethyl)isoxazol-5-yl)pyridin-3-yl)-N-(2-hydroxy-2-methylpropyl)-4-methylbenzenesulfonamide;

3-(6-amino-5-(3-propylisoxazol-5-yl)pyridin-3-yl)-N-(2-hydroxy-2-methylpropyl)-4-methylbenzenesulfonamide;

3-(6-amino-5-(3-tert-butylisoxazol-5-yl)pyridin-3-yl)-N-((1r,4r)-4-hydroxycyclohexyl)-4-methylbenzenesulfonamide;

3-(6-amino-5-(3-cyclopropylisoxazol-5-yl)pyridin-3-yl)-N-(2-hydroxy-2-methylpropyl)-4-methylbenzenesulfonamide;

3-(6-amino-5-(3-isopropylisoxazol-5-yl)pyridin-3-yl)-N-(3-hydroxy-3-methylbutyl)-4-methylbenzenesulfonamide;

3-(6-amino-5-(3-tert-butylisoxazol-5-yl)pyridin-3-yl)-N-(2-hydroxy-2-methylpropyl)-4-methylbenzenesulfonamide;

3-(6-amino-5-(3-isopropylisoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1s,3s)-3-hydroxycyclobutyl)-4-methylbenzenesulfonamide;

3-(6-amino-5-(3-methylisoxazol-5-yl)pyridin-3-yl)-N-((1r,3r)-3-hydroxycyclobutyl)-4-methylbenzenesulfonamide;

(S)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-N-((4-(hydroxymethyl)tetrahydro-2H-pyran-4-yl)methyl)-4-methylbenzenesulfonamide;

5-(5-(3-methoxy-3-methylazetidin-1-ylsulfonyl)-2-methylphenyl)-3-(3-methyl-1,2,4-oxadiazol-5-yl)pyridin-2-amine;

3-(6-amino-5-(3-methylisoxazol-5-yl)pyridin-3-yl)-N-((1-(hydroxymethyl)cyclohexyl)methyl)-4-methylbenzenesulfonamide;

(R)-3-(6-amino-5-(3-methylisoxazol-5-yl)pyridin-3-yl)-4-methyl-N-(2-oxopiperidin-4-yl)benzenesulfonamide;

(R)-3-(6-amino-5-(3-methyl-1,2,4-oxadiazol-5-yl)pyridin-3-yl)-4-methyl-N-((tetrahydrofuran-2-yl)methyl)benzenesulfonamide;

3-(6-amino-5-(3-methylisoxazol-5-yl)pyridin-3-yl)-N-((1-(hydroxymethyl)cyclobutyl)methyl)-4-methylbenzenesulfonamide;

3-(6-amino-5-(3-methylisoxazol-5-yl)pyridin-3-yl)-N-(3-hydroxy-2,2-dimethylpropyl)-4-methylbenzenesulfonamide;

3-(6-amino-5-(3-methylisoxazol-5-yl)pyridin-3-yl)-4-methyl-N-(tetrahydro-2H-pyran-4-yl)benzenesulfonamide;

3-(6-amino-5-(3-methylisoxazol-5-yl)pyridin-3-yl)-N-((1-hydroxycyclohexyl)methyl)-4-methylbenzenesulfonamide;

3-(6-amino-5-(3-methyl-1,2,4-oxadiazol-5-yl)pyridin-3-yl)-N-((4-(hydroxymethyl)tetrahydro-2H-pyran-4-yl)methyl)-4-methylbenzenesulfonamide;

3-(6-amino-5-(3-methyl-1,2,4-oxadiazol-5-yl)pyridin-3-yl)-N-(2-(1-hydroxycyclopentyl)ethyl)-4-methylbenzenesulfonamide;

(1-(3-(6-amino-5-(3-methylisoxazol-5-yl)pyridin-3-yl)-4-methylphenylsulfonyl)azetidin-3-yl)methanol;

3-(6-amino-5-(3-methyl-1,2,4-oxadiazol-5-yl)pyridin-3-yl)-N-((1-(hydroxymethyl)cyclopentyl)methyl)-4-methylbenzenesulfonamide;

3-(6-amino-5-(3-methylisoxazol-5-yl)pyridin-3-yl)-4-methyl-N-(3,3,3-trifluoropropyl)benzenesulfonamide;

3-(6-amino-5-(3-methyl-1,2,4-oxadiazol-5-yl)pyridin-3-yl)-N-((1-hydroxycyclobutyl)methyl)-4-methylbenzenesulfonamide;

3-(6-amino-5-(3-methylisoxazol-5-yl)pyridin-3-yl)-N-(2-(1-hydroxycyclopentyl)ethyl)-4-methylbenzenesulfonamide;

3-(6-amino-5-(3-methyl-1,2,4-oxadiazol-5-yl)pyridin-3-yl)-N-(3,3-difluorocyclobutyl)-4-methylbenzenesulfonamide;

3-(6-amino-5-(3-methyl-1,2,4-oxadiazol-5-yl)pyridin-3-yl)-N-(3-hydroxy-2,2-dimethylpropyl)-4-methylbenzenesulfonamide;

3-(6-amino-5-(3-methyl-1,2,4-oxadiazol-5-yl)pyridin-3-yl)-N-((1-hydroxycyclopropyl)methyl)-4-methylbenzenesulfonamide;

5-(5-(3-methoxy-3-methylazetidin-1-ylsulfonyl)-2-methylphenyl)-3-(3-methylisoxazol-5-yl)pyridin-2-amine;

3-(6-amino-5-(3-methyl-1,2,4-oxadiazol-5-yl)pyridin-3-yl)-N-(2-hydroxy-1-(tetrahydrofuran-3-yl)ethyl)-4-methylbenzenesulfonamide;

3-(6-amino-5-(3-methylisoxazol-5-yl)pyridin-3-yl)-N-methoxy-N,4-dimethylbenzenesulfonamide;

3-(6-amino-5-(3-methylisoxazol-5-yl)pyridin-3-yl)-N-((1-(hydroxymethyl)cyclopentyl)methyl)-4-methylbenzenesulfonamide;

(R)-1-(3-(6-amino-5-(3-methylisoxazol-5-yl)pyridin-3-yl)-4-methylphenylsulfonyl)pyrrolidin-3-ol;

(R)-3-(6-amino-5-(3-methyl-1,2,4-oxadiazol-5-yl)pyridin-3-yl)-4-methyl-N-(2-oxopiperidin-4-yl)benzenesulfonamide;

3-(6-amino-5-(3-methyl-1,2,4-oxadiazol-5-yl)pyridin-3-yl)-N-((1-(hydroxymethyl)cyclobutyl)methyl)-4-methylbenzenesulfonamide;

(R)-3-(6-amino-5-(3-methylisoxazol-5-yl)pyridin-3-yl)-N-((1-ethylpyrrolidin-2-yl)methyl)-4-methylbenzenesulfonamide;

1-(3-(6-amino-5-(3-methylisoxazol-5-yl)pyridin-3-yl)-4-methylphenylsulfonyl)-3-methylazetidin-3-ol;

3-(6-amino-5-(3-methyl-1,2,4-oxadiazol-5-yl)pyridin-3-yl)-N-(2-aminoethyl)-4-methylbenzenesulfonamide;

3-(6-amino-5-(3-methylisoxazol-5-yl)pyridin-3-yl)-N-(2-(1-hydroxycyclohexyl)ethyl)-4-methylbenzenesulfonamide;

3-(6-amino-5-(3-methyl-1,2,4-oxadiazol-5-yl)pyridin-3-yl)-N-(2-(1-hydroxycyclohexyl)ethyl)-4-methylbenzenesulfonamide;

(S)-1-(3-(6-amino-5-(3-methyl-1,2,4-oxadiazol-5-yl)pyridin-3-yl)-4-methylphenylsulfonyl)pyrrolidin-3-ol;

(S)-3-(6-amino-5-(3-methylisoxazol-5-yl)pyridin-3-yl)-N-((1-ethylpyrrolidin-2-yl)methyl)-4-methylbenzenesulfonamide;

3-(6-amino-5-(3-methyl-1,2,4-oxadiazol-5-yl)pyridin-3-yl)-N-(1-isopropylpiperidin-4-yl)-4-methylbenzenesulfonamide;

3-(6-amino-5-(3-methylisoxazol-5-yl)pyridin-3-yl)-N-((1-hydroxycyclobutyl)methyl)-4-methylbenzenesulfonamide;

3-(6-amino-5-(3-methylisoxazol-5-yl)pyridin-3-yl)-4-methyl-N-((tetrahydro-2H-pyran-2-yl)methyl)benzenesulfonamide;

3-(6-amino-5-(3-methylisoxazol-5-yl)pyridin-3-yl)-4-methyl-N-((tetrahydro-2H-pyran-2-yl)methyl)benzenesulfonamide;

3-(6-amino-5-(3-methyl-1,2,4-oxadiazol-5-yl)pyridin-3-yl)-N-(2,2-difluoropropyl)-4-methylbenzenesulfonamide;

(1-(3-(6-amino-5-(3-methyl-1,2,4-oxadiazol-5-yl)pyridin-3-yl)-4-methylphenylsulfonyl)azetidin-3-yl)methanol;

(S)-3-(6-amino-5-(3-methylisoxazol-5-yl)pyridin-3-yl)-4-methyl-N-((tetrahydrofuran-3-yl)methyl)benzenesulfonamide;

3-(6-amino-5-(3-methylisoxazol-5-yl)pyridin-3-yl)-4-methyl-N-(2,2,2-trifluoroethyl)benzenesulfonamide;

(S)-3-(6-amino-5-(3-methylisoxazol-5-yl)pyridin-3-yl)-4-methyl-N-((tetrahydrofuran-2-yl)methyl)benzenesulfonamide;

3-(6-amino-5-(3-(hydroxymethyl)isoxazol-5-yl)pyridin-3-yl)-N-(2-hydroxy-2-methylpropyl)-4-methylbenzenesulfonamide;

3-(6-amino-5-(3-(morpholine-4-carbonyl)isoxazol-5-yl)pyridin-3-yl)-N-(2-hydroxy-2-methylpropyl)-4-methylbenzenesulfonamide;

5-(2-amino-5-(5-(N-(2-hydroxy-2-methylpropyl)sulfamoyl)-2-methylphenyl)pyridin-3-yl)-N,N-dimethylisoxazole-3-carboxamide;

3-(6-amino-5-(3-methyl-1,2,4-oxadiazol-5-yl)pyridin-3-yl)-4-methyl-N-propoxybenzenesulfonamide;

3-(6-amino-5-(3-methyl-1,2,4-oxadiazol-5-yl)pyridin-3-yl)-N-isopropoxy-4-methylbenzenesulfonamide 3-(6-amino-5-(3-methyl-1,2,4-oxadiazol-5-yl)pyridin-3-yl)-N-methoxy-4-methylbenzenesulfonamide;

3-(6-amino-5-(3-methyl-1,2,4-oxadiazol-5-yl)pyridin-3-yl)-N-tert-butoxy-4-methylbenzenesulfonamide;

3-(6-amino-5-(3-methyl-1,2,4-oxadiazol-5-yl)pyridin-3-yl)-4-methyl-N-(3,3,3-trifluoropropyl)benzenesulfonamide;

3-(6-amino-5-(3-methyl-1,2,4-oxadiazol-5-yl)pyridin-3-yl)-4-methyl-N-(tetrahydro-2H-pyran-4-yl)benzenesulfonamide;

3-(6-amino-5-(3-methylisoxazol-5-yl)pyridin-3-yl)-N-((3-(hydroxymethyl)oxetan-3-yl)methyl)-4-methylbenzenesulfonamide;

3-(6-amino-5-(3-methyl-1,2,4-oxadiazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((3-(hydroxymethyl)oxetan-3-yl)methyl)-4-methylbenzenesulfonamide;

3-(6-amino-5-(3-methylisoxazol-5-yl)pyridin-3-yl)-N-((1-hydroxycyclopentyl)methyl)-4-methylbenzenesulfonamide;

3-(6-amino-5-(3-methylisoxazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((1r,3r)-3-hydroxycyclobutoxy)-4-methylbenzenesulfonamide;

3-(6-amino-5-(3-methyl-1,2,4-oxadiazol-5-yl)pyridin-3-yl)-N-((3-hydroxyoxetan-3-yl)methyl)-4-methylbenzenesulfonamide;

3-(6-amino-5-(3-methyl-1,2,4-oxadiazol-5-yl)pyridin-3-yl)-4-methyl-N-((tetrahydrofuran-2-yl)methyl)benzenesulfonamide;

3-(6-amino-5-(1-methyl-1H-pyrrol-3-yl)pyridin-3-yl)-N-(2-hydroxy-2-methylpropyl)-4-methylbenzenesulfonamide;

3-(6-amino-5-(2-methylthiazol-4-yl)pyridin-3-yl)-N-(2-hydroxy-2-methylpropyl)-4-methylbenzenesulfonamide;

3-(6-amino-5-(4-methyl-1H-pyrazol-1-yl)pyridin-3-yl)-N-(2-hydroxy-2-methylpropyl)-4-methylbenzenesulfonamide;

3-(6-amino-5-(1,5-dimethyl-1H-pyrazol-4-yl)pyridin-3-yl)-N-(2-hydroxy-2-methylpropyl)-4-methylbenzenesulfonamide;

3-(6-amino-5-(5-methylisoxazol-4-yl)pyridin-3-yl)-N-(2-hydroxy-2-methylpropyl)-4-methylbenzenesulfonamide;

3-(6-amino-5-(1-methyl-1H-1,2,3-triazol-4-yl)pyridin-3-yl)-N-(2-hydroxy-2-methylpropyl)-4-methylbenzenesulfonamide;

3-(6-amino-5-(isoxazol-5-yl)pyridin-3-yl)-N-(2-hydroxy-2-methylpropyl)-4-methylbenzenesulfonamide;

3-(6-amino-5-(3-(trifluoromethyl)isoxazol-5-yl)pyridin-3-yl)-N-(2-hydroxy-2-methylpropyl)-4-methylbenzenesulfonamide;

3-(6-amino-5-(3-((dimethylamino)methyl)isoxazol-5-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((3-(hydroxymethyl)oxetan-3-yl)methyl)-4-methylbenzenesulfonamide;

3-(6-amino-5-(2-methylthiazol-5-yl)pyridin-3-yl)-N-((3-(hydroxymethyl) oxetan-3-yl)methyl)-4-methylbenzenesulfonamide;

3-(6-amino-5-(2-methyloxazol-5-yl)pyridin-3-yl)-4-methyl-N-((3-methyl oxetan-3-yl)methyl)benzenesulfonamide;

3-(6-amino-5-(3-(difluoromethyl)-1,2,4-oxadiazol-5-yl)pyridin-3-yl)-N-((1r,4r)-4-hydroxycyclohexyl)-4-methylbenzenesulfonamide;

3-(6-amino-5-(3-(difluoromethyl)-1,2,4-oxadiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-4-methyl-N-(6-methylpyridin-2-yl)benzenesulfonamide;

3-(6-amino-5-(3-methylisoxazol-5-yl)pyridin-3-yl)-N-(2-hydroxyethyl)-4-methylbenzenesulfonamide;

3-(6-amino-5-(2-methylthiazol-5-yl)pyridin-3-yl)-4-methylbenzenesulfonamide;

3-(6-amino-5-(3-methyl-1,2,4-oxadiazol-5-yl)pyridin-3-yl)-4-methylbenzenesulfonamide;

3-(6-amino-5-(3-methyl-1,2,4-oxadiazol-5-yl)pyridin-3-yl)-N-((1s,3s)-3-(hydroxymethyl)cyclobutyl)-4-methylbenzenesulfonamide;

3-(6-amino-5-(3-methyl-1,2,4-oxadiazol-5-yl)pyridin-3-yl)-N-((1r,3r)-3-(hydroxymethyl)cyclobutyl)-4-methylbenzenesulfonamide;

3-(2-amino-2'-methyl-3,4'-bipyridin-5-yl)-N-((1r,4r)-4-(hydroxymethyl)cyclohexyl)-4-methylbenzenesulfonamide;

3-(6-amino-5-(3-(2,2,2-trifluoroethyl)-1,2,4-oxadiazol-5-yl)pyridin-3-yl)-N-((1r,4r)-4-hydroxycyclohexyl)-4-methylbenzenesulfonamide;

3-(6-amino-5-(3-(2,2,2-trifluoroethyl)-1,2,4-oxadiazol-5-yl)pyridin-3-yl)-N-(3-hydroxy-3-methylbutyl)-4-methylbenzenesulfonamide;

3-(6-amino-5-(3-cyclopropyl-1,2,4-oxadiazol-5-yl)pyridin-3-yl)-N-(2-hydroxy-2-methylpropyl)-4-methylbenzenesulfonamide;

3-(6-amino-5-(1H-1,2,4-triazol-1-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((1r,3r)-3-hydroxycyclobutyl)-4-methylbenzenesulfonamide;

3-(6-amino-5-(2-methyloxazol-5-yl)pyridin-3-yl)-N-((1s,3s)-3-hydroxycyclobutyl)-4-methylbenzenesulfonamide;

3-(6-amino-5-(2-methylthiazol-5-yl)pyridin-3-yl)-N-((3-hydroxycyclobutyl)methyl)-4-methylbenzenesulfonamide;

(1-(3-(6-amino-5-(2-methylthiazol-5-yl)pyridin-3-yl)-4-methylphenylsulfonyl)azetidin-3-yl)methanol;

3-(6-amino-5-(2-methylthiazol-5-yl)pyridin-3-yl)-4-methyl-N-(oxetan-3-ylmethyl)benzenesulfonamide;

3-(6-amino-5-(2-methylthiazol-5-yl)pyridin-3-yl)-N-((3-hydroxyoxetan-3-yl)methyl)-4-methylbenzenesulfonamide 3-(6-amino-5-(2-methylthiazol-5-yl)pyridin-3-yl)-N-(3-hydroxy-2,2-dimethylpropyl)-4-methylbenzenesulfonamide;

3-(6-amino-5-(2-methylthiazol-5-yl)pyridin-3-yl)-N-(2-hydroxyethyl)-4-methylbenzenesulfonamide;

3-(6-amino-5-(3-methylisoxazol-5-yl)pyridin-3-yl)-N-(((1s,3s)-3-hydroxycyclobutyl)methyl)-4-methylbenzenesulfonamide;

5-(6-amino-5-(3-methyl-1,2,4-oxadiazol-5-yl)pyridin-3-yl)-2-fluoro-N-(2-hydroxy-2-methylpropyl)-4-methylbenzenesulfonamide;

(R)-3-(6-amino-5-(3-methyl-1,2,4-oxadiazol-5-yl)pyridin-3-yl)-4-methyl-N-((tetrahydrofuran-3-yl)methyl)benzenesulfonamide;

(S)-3-(6-amino-5-(3-methyl-1,2,4-oxadiazol-5-yl)pyridin-3-yl)-4-methyl-N-((tetrahydrofuran-3-yl)methyl)benzenesulfonamide;

5-(6-amino-5-(3-methylisoxazol-5-yl)pyridin-3-yl)-2-chloro-N-(2-hydroxy-2-methylpropyl)-4-methylbenzenesulfonamide;

5-(6-amino-5-(3-methyl-1,2,4-oxadiazol-5-yl)pyridin-3-yl)-2-chloro-N-(2-hydroxy-2-methylpropyl)-4-methylbenzenesulfonamide;

3-(6-amino-5-(5-methylthiazol-2-yl)pyridin-3-yl)-N-(2-hydroxy-2-methylpropyl)-4-methylbenzenesulfonamide;

3-(6-amino-5-(5-methylthiazol-2-yl)pyridin-3-yl)-N-(3-hydroxy-3-methylbutyl)-4-methylbenzenesulfonamide;

3-(6-amino-5-(2-methylthiazol-4-yl)pyridin-3-yl)-N-((1r,4r)-4-hydroxycyclohexyl)-4-methylbenzenesulfonamide;

3-(6-amino-5-(2-methylthiazol-4-yl)pyridin-3-yl)-N-(3-hydroxy-3-methylbutyl)-4-methylbenzenesulfonamide;

3-(6-amino-5-(oxazol-5-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((1-hydroxycyclopropyl)methyl)-4-methylbenzenesulfonamide;

3-(6-amino-5-(2-methyloxazol-5-yl)pyridin-3-yl)-4-methyl-N-(2,2,2-trifluoroethyl)benzenesulfonamide;

3-(6-amino-5-(2-methyloxazol-5-yl)pyridin-3-yl)-N-(2-hydroxypropyl)-4-methylbenzenesulfonamide;

3-(6-amino-5-(2-methyloxazol-5-yl)pyridin-3-yl)-N-(2,2-difluoroethyl)-4-methylbenzenesulfonamide;

3-(6-amino-5-(2-methyloxazol-5-yl)pyridin-3-yl)-N-(3-hydroxy-2,2-dimethylpropyl)-4-methylbenzenesulfonamide;

3-(6-amino-5-(2-methyloxazol-5-yl)pyridin-3-yl)-4-methyl-N-(oxetan-3-ylmethyl)benzenesulfonamide;

3-(6-amino-5-(2-methyloxazol-5-yl)pyridin-3-yl)-4-methyl-N-((tetrahydrofuran-3-yl)methyl)benzenesulfonamide;

3-(6-amino-5-(2-methyloxazol-5-yl)pyridin-3-yl)-N-((3-hydroxycyclobutyl)methyl)-4-methylbenzenesulfonamide; and 3-(6-amino-5-(2-methyloxazol-5-yl)pyridin-3-yl)-N-cyclopropyl-4-methylbenzenesulfonamide.

3-(6-amino-5-(3-methylisoxazol-5-yl)pyridin-3-yl)-N-((1r,3r)-3-hydroxycyclobutoxy)-4-methylbenzenesulfonamide;

trans-3-(6-amino-5-(3-methylisoxazol-5-yl)pyridin-3-yl)-N-(3-hydroxycyclopentyl)-4-methylbenzenesulfonamide;

3-(6-amino-5-(2-methylthiazol-5-yl)pyridin-3-yl)-N-((1r,4r)-4-hydroxycyclohexyl)-4-methylbenzenesulfonamide;

3-(6-amino-5-(2-methyloxazol-5-yl)pyridin-3-yl)-N-((1r,4r)-4-hydroxycyclohexyl)-4-methylbenzenesulfonamide hydrochloride;

5-(6-amino-5-(3-methylisoxazol-5-yl)pyridin-3-yl)-2-fluoro-N-(2-hydroxy-2-methylpropoxy)-4-methylbenzenesulfonamide;

5-(6-amino-5-(3-methyl-1,2,4-oxadiazol-5-yl)pyridin-3-yl)-N-(2-hydroxy-2-methylpropyl)-2,4-dimethylbenzenesulfonamide;

3-(6-amino-5-(3-methylisoxazol-5-yl)pyridin-3-yl)-N-(trans-4-hydroxytetrahydrofuran-3-yl)-4-methylbenzenesulfonamide:trifluoroacetic acid;

3-(6-amino-5-(3-methylisoxazol-5-yl)pyridin-3-yl)-N-((trans)-2-hydroxycyclopentyl)-4-methylbenzenesulfonamide;

trans-1-((3-(6-amino-5-(3-methylisoxazol-5-yl)pyridin-3-yl)-4-methylphenyl)sulfonyl)-4-methylpyrrolidin-3-ol;

3-(6-amino-5-(5-methyl-1,3,4-thiadiazol-2-yl)pyridin-3-yl)-N-(2-hydroxy-2-methylpropyl)-4-methylbenzenesulfonamide;

(R)-3-(6-amino-5-(3-methylisoxazol-5-yl)pyridin-3-yl)-4-methyl-N-(1,1,1-trifluoro-3-hydroxypropan-2-yl)benzenesulfonamide;

(S)-3-(6-amino-5-(3-methylisoxazol-5-yl)pyridin-3-yl)-4-methyl-N-(1,1,1,1-trifluoro-3-hydroxypropan-2-yl)benzenesulfonamide;

3-(6-amino-5-(2-methyloxazol-5-yl)pyridin-3-yl)-N-((3-hydroxycyclobutyl)methyl)-4-methylbenzenesulfonamide;

3-(6-amino-5-(2-methyloxazol-5-yl)pyridin-3-yl)-N-(3-hydroxy-2,2-dimethylpropyl)-4-methylbenzenesulfonamide;

3-(6-amino-5-(2-methyloxazol-5-yl)pyridin-3-yl)-4-methyl-N-(oxetan-3-ylmethyl)benzenesulfonamide;

(+/−)trans-3-(6-amino-5-(2-methyloxazol-5-yl)pyridin-3-yl)-N-(3-hydroxycyclopentyl)-4-methylbenzenesulfonamide;

3-(6-amino-5-(2-methyloxazol-5-yl)pyridin-3-yl)-N-(2-hydroxyethyl)-4-methylbenzenesulfonamide;

3-(6-amino-5-(2-methyloxazol-5-yl)pyridin-3-yl)-N-(3-hydroxypropyl)-4-methylbenzenesulfonamide;

3-(6-amino-5-(2-methyloxazol-5-yl)pyridin-3-yl)-N-((3-hydroxyoxetan-3-yl)methyl)-4-methylbenzenesulfonamide;

3-(6-amino-5-(2-methyloxazol-5-yl)pyridin-3-yl)-4-methyl-N-((tetrahydro-2H-pyran-3-yl)methyl)benzenesulfonamide;

3-(6-amino-5-(2-methyloxazol-5-yl)pyridin-3-yl)-4-methyl-N-(2,2,2-trifluoroethyl)benzenesulfonamide;

3-(6-amino-5-(2-methyloxazol-5-yl)pyridin-3-yl)-N-(2,2-difluoroethyl)-4-methylbenzenesulfonamide;

3-(6-amino-5-(2-methyloxazol-5-yl)pyridin-3-yl)-N-((1r,4r)-4-(hydroxymethyl)cyclohexyl)-4-methylbenzenesulfonamide;

3-(6-amino-5-(2-methyloxazol-5-yl)pyridin-3-yl)-N-(cyclopropyl methyl)-4-methylbenzenesulfonamide;

3-(6-amino-5-(2-methyloxazol-5-yl)pyridin-3-yl)-N-((4-(hydroxymethyl)tetrahydro-2H-pyran-4-yl)methyl)-4-methylbenzenesulfonamide;

3-(6-amino-5-(2-methyloxazol-5-yl)pyridin-3-yl)-N-cyclopropyl-4 methylbenzenesulfonamide;

rac-3-(6-amino-5-(2-methyloxazol-5-yl)pyridin-3-yl)-N-(2-hydroxypropyl)-4-methylbenzenesulfonamide;

(+/−)-cis-3-(6-amino-5-(2-methyloxazol-5-yl)pyridin-3-yl)-N-(3-hydroxycyclopentyl)-4-methylbenzenesulfonamide;

or a pharmaceutically acceptable salt thereof.

In an embodiment 31 of the invention, there is provided a compound according to embodiment 1 selected from 3-(6-amino-5-(1-(2,2,2-trifluoroethyl)-1H-pyrazol-4-yl)pyridin-3-yl)-4-methyl-N-(6-methylpyridin-2-yl)benzenesulfonamide;

3-(6-amino-5-(1-methyl-1H-pyrazol-4-yl)pyridin-3-yl)-N-(3-hydroxy-3-methylbutyl)-4-methylbenzenesulfonamide;

3-(6-amino-5-(1-(2,2,2-trifluoroethyl)-1H-pyrazol-4-yl)pyridin-3-yl)-N-(3-hydroxy-3-methylbutyl)-4-methylbenzenesulfonamide;

3-(6-amino-5-(2-methylthiazol-5-yl)pyridin-3-yl)-N-(3-hydroxy-3-methylbutyl)-4-methylbenzenesulfonamide;

3-(6-amino-5-(1-methyl-1H-pyrazol-4-yl)pyridin-3-yl)-N-((1r,4r)-4-hydroxycyclohexyl)-4-methylbenzenesulfonamide;

3-(6-amino-5-(1-(2,2,2-trifluoroethyl)-1H-pyrazol-4-yl)pyridin-3-yl)-N-((1r,4r)-4-hydroxycyclohexyl)-4-methylbenzenesulfonamide;

3-(2-amino-2'-methyl-3,4'-bipyridin-5-yl)-N-((1r,4r)-4-hydroxycyclohexyl)-4-methylbenzenesulfonamide;

3-(6-amino-5-(2-methyl-2H-1,2,3-triazol-4-yl)pyridin-3-yl)-N-(2-hydroxy-2-methylpropyl)-4-methylbenzenesulfonamide;

3-(6-amino-5-(2-methyl-2H-1,2,3-triazol-4-yl)pyridin-3-yl)-N-((1r,4r)-4-hydroxycyclohexyl)-4-methylbenzenesulfonamide;

3-(6-amino-5-(3-ethylisoxazol-5-yl)pyridin-3-yl)-N-(2-hydroxy-2-methylpropyl)-4-methylbenzenesulfonamide;

(R)-3-(6-amino-5-(3-methylisoxazol-5-yl)pyridin-3-yl)-4-methyl-N-((tetrahydrofuran-3-yl)methyl)benzenesulfonamide;

3-(6-amino-5-(3-methylisothiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-4-methyl-N-((3-methyloxetan-3-yl)methyl)benzenesulfonamide;

3-(6-amino-5-(3-methyl-1,2,4-oxadiazol-5-yl)pyridin-3-yl)-N-(3-hydroxy-3-methylbutyl)-4-methylbenzenesulfonamide;

3-(6-amino-5-(3-isopropyl-1,2,4-oxadiazol-5-yl)pyridin-3-yl)-N-(2-hydroxy-2-methylpropyl)-4-methylbenzenesulfonamide;

3-(6-amino-5-(5-methyloxazol-2-yl)pyridin-3-yl)-N-((1r,4r)-4-hydroxycyclohexyl)-4-methylbenzenesulfonamide;

3-(6-amino-5-(3-ethyl-1,2,4-oxadiazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1r,4r)-4-hydroxycyclohexyl)-4-methylbenzenesulfonamide;

3-(6-amino-5-(3-methyl-1,2,4-oxadiazol-5-yl)pyridin-3-yl)-N-(3-hydroxycyclobutyl)-4-methylbenzenesulfonamide;

3-(6-amino-5-(3-methyl-1,2,4-oxadiazol-5-yl)pyridin-3-yl)-N-((1s,3s)-3-hydroxycyclobutyl)-4-methylbenzenesulfonamide;

3-(6-amino-5-(5-methyl-1,3,4-oxadiazol-2-yl)pyridin-3-yl)-N-(3-hydroxy-3-methylbutyl)-4-methylbenzenesulfonamide;

3-(6-amino-5-(2-methyloxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-N-(6-hydroxyspiro[3.3]heptan-2-yl)-4-methylbenzenesulfonamide;

3-(6-amino-5-(3-methyl-1,2,4-oxadiazol-5-yl)pyridin-3-yl)-N-(6-hydroxyspiro[3.3]heptan-2-yl)-4-methylbenzenesulfonamide;

3-(6-amino-5-(3-methyl-1,2,4-oxadiazol-5-yl)pyridin-3-yl)-N-(6-hydroxyspiro[3.3]heptan-2-yl)-4-methylbenzenesulfonamide;

3-(6-amino-5-(2-methylthiazol-5-yl)pyridin-3-yl)-N-(3-hydroxypropyl)-4-methylbenzenesulfonamide;

3-(6-amino-5-(3-methyl-1,2,4-oxadiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-N-(2-hydroxy-2-methylpropoxy)-4-methylbenzenesulfonamide;

3-(6-amino-5-(3-methyl-1,2,4-oxadiazol-5-yl)pyridin-3-yl)-N-((1r,4r)-4-hydroxycyclohexyl)-4-methylbenzenesulfonamide;

3-(6-amino-5-(2-methyloxazol-5-yl)pyridin-3-yl)-N-(3-hydroxy-3-methylbutyl)-4-methylbenzenesulfonamide;

3-(6-amino-5-(3-methylisoxazol-5-yl)pyridin-3-yl)-N-(3-hydroxy-3-methyl butyl)-4-methylbenzenesulfonamide;

3-(6-amino-5-(2-methylthiazol-5-yl)pyridin-3-yl)-N-(2-hydroxy-2-methylpropyl)-4-methylbenzenesulfonamide;

3-(2-amino-2'-methyl-3,4-bipyridin-5-yl)-N-(3-hydroxy-3-methyl butyl)-4-methylbenzenesulfonamide;

3-(6-amino-5-(3-methylisoxazol-5-yl)pyridin-3-yl)-4-methyl-N-((3-methyloxetan-3-yl)methyl)benzenesulfonamide;

3-(2-amino-3,4'-bipyridin-5-yl)-N-(3-hydroxy-3-methylbutyl)-4-methylbenzenesulfonamide;

3-(6-amino-5-(3-methyl-1,2,4-oxadiazol-5-yl)pyridin-3-yl)-N-((1r,4r)-4-(hydroxymethyl)cyclohexyl)-4-methylbenzenesulfonamide;

5-(5-(6-oxa-2-azaspiro[3.4]octan-2-ylsulfonyl)-2-methylphenyl)-3-(3-methylisoxazol-5-yl)pyridin-2-amine;

3-(6-amino-5-(3-methylisoxazol-5-yl)pyridin-3-yl)-4-methyl-N-(2-oxotetrahydrofuran-3-yl)benzenesulfonamide;

3-(6-amino-5-(3-methylisoxazol-5-yl)pyridin-3-yl)-N-((1r,4r)-4-aminocyclohexyl)-4-methylbenzenesulfonamide;

3-(6-amino-5-(3-methylisoxazol-5-yl)pyridin-3-yl)-N-((3R,4R)-4-hydroxypyrrolidin-3-yl)-4-methylbenzenesulfonamide;

(S)-5-(2-methyl-5-(3-methylmorpholinosulfonyl)phenyl)-3-(3-methylisoxazol-5-yl)pyridin-2-amine;

(R)-5-(2-methyl-5-(3-methylmorpholinosulfonyl)phenyl)-3-(3-methylisoxazol-5-yl)pyridin-2-amine;

3-(6-amino-5-(3-methylisoxazol-5-yl)pyridin-3-yl)-4-methyl-N-neopentylbenzenesulfonamide;

3-(6-amino-5-(3-methylisoxazol-5-yl)pyridin-3-yl)-N-tert-butyl-4-methylbenzenesulfonamide 5-(5-(2,2-dimethylpyrrolidin-1-ylsulfonyl)-2-methylphenyl)-3-(3-methylisoxazol-5-yl)pyridin-2-amine;

3-(6-amino-5-(3-methylisoxazol-5-yl)pyridin-3-yl)-N-((1-hydroxycyclopropyl)methyl)-4-methylbenzenesulfonamide;

3-(6-amino-5-(3-methylisoxazol-5-yl)pyridin-3-yl)-N-(1-methoxy-3-methyl butan-2-yl)-4-methylbenzenesulfonamide;

3-(6-amino-5-(3-methylisoxazol-5-yl)pyridin-3-yl)-4-methyl-N-(2-(tetrahydro-2H-pyran-4-yl)ethyl)benzenesulfonamide;

(S)-3-(6-amino-5-(3-methylisoxazol-5-yl)pyridin-3-yl)-N-(1-cyclopropylethyl)-4-methylbenzenesulfonamide;

(S)-(1-(3-(6-amino-5-(3-methylisoxazol-5-yl)pyridin-3-yl)-4-methylphenylsulfonyl)pyrrolidin-2-yl)methanol;

3-(6-amino-5-(3-methylisoxazol-5-yl)pyridin-3-yl)-N-((1S,3S)-3-hydroxycyclohexyl)-4-methylbenzenesulfonamide;

4-(3-(6-amino-5-(3-methylisoxazol-5-yl)pyridin-3-yl)-4-methylphenylsulfonyl)piperazin-2-one;

5-(5-(4-(methoxymethyl)piperidin-1-ylsulfonyl)-2-methylphenyl)-3-(3-methylisoxazol-5-yl)pyridin-2-amine;

5-(5-(3-(di methylamino)azetidin-1-ylsulfonyl)-2-methylphenyl)-3-(3-methylisoxazol-5-yl)pyridin-2-amine;

(R)-5-(5-(3-(methoxymethyl)morpholinosulfonyl)-2-methylphenyl)-3-(3-methylisoxazol-5-yl)pyridin-2-amine;

3-(6-amino-5-(3-methylisoxazol-5-yl)pyridin-3-yl)-N-(2-hydroxy-2-methyl propoxy)-4-methylbenzenesulfonamide;

3-(6-amino-5-(3-methylisoxazol-5-yl)pyridin-3-yl)-4-methyl-N-(tetrahydrofuran-3-yloxy)benzenesulfonamide;
3-(6-amino-5-(3-methylisoxazol-5-yl)pyridin-3-yl)-4-methyl-N-(tetrahydrofuran-3-yloxy)benzenesulfonamide;
3-(6-amino-5-(3-methylisoxazol-5-yl)pyridin-3-yl)-N-ethoxy-4-methyl benzenesulfonamide;
3-(6-amino-5-(3-methylisoxazol-5-yl)pyridin-3-yl)-4-methyl-N-((tetrahydro-2H-pyran-3-yl)methyl)benzenesulfonamide;
3-(6-amino-5-(3-methylisoxazol-5-yl)pyridin-3-yl)-4-methyl-N-((tetrahydro-2H-pyran-3-yl)methyl)benzenesulfonamide;
(R)-3-(6-amino-5-(3-methylisoxazol-5-yl)pyridin-3-yl)-N-(2-hydroxypropyl)-4-methylbenzenesulfonamide;
3-(6-amino-5-(3-methylisoxazol-5-yl)pyridin-3-yl)-4-methyl-N-(oxetan-3-ylmethyl)benzenesulfonamide;
3-(6-amino-5-(1,3-dimethyl-1H-pyrazol-4-yl)pyridin-3-yl)-N-(6-hydroxyspiro[3.3]heptan-2-yl)-4-methylbenzenesulfonamide;
3-(6-amino-5-(3-methylisoxazol-5-yl)pyridin-3-yl)-N-(2,2-difluoroethyl)-4-methylbenzenesulfonamide;
3-(6-amino-5-(2-methylthiazol-5-yl)pyridin-3-yl)-N-(6-hydroxyspiro[3.3]heptan-2-yl)-4-methylbenzenesulfonamide;
3-(6-amino-5-(3-methyl-1,2,4-oxadiazol-5-yl)pyridin-3-yl)-4-methyl-N-((tetrahydrofuran-3-yl)methyl)benzenesulfonamide;
3-(6-amino-5-(1-methyl-1H-pyrazol-4-yl)pyridin-3-yl)-4-methyl-N-(6-methylpyridin-2-yl)benzenesulfonamide;
3-(6-amino-5-(3-methylisoxazol-5-yl)pyridin-3-yl)-N-cyclopropyl-4-methylbenzenesulfonamide;
3-(6-amino-5-(3-methylisoxazol-5-yl)pyridin-3-yl)-4-methylbenzenesulfonamide;
3-(6-amino-5-(2-methyloxazol-5-yl)pyridin-3-yl)-4-methylbenzenesulfonamide;
3-(6-amino-5-(1-(2,2,2-trifluoroethyl)-1H-pyrazol-4-yl)pyridin-3-yl)-N-(2-hydroxy-2-methylpropoxy)-4-methylbenzenesulfonamide
3-(6-amino-5-(3-(2,2,2-trifluoroethyl)isoxazol-5-yl)pyridin-3-yl)-N-(2-hydroxy-2-methylpropyl)-4-methylbenzenesulfonamide;
3-(6-amino-5-(3-propylisoxazol-5-yl)pyridin-3-yl)-N-(2-hydroxy-2-methylpropyl)-4-methylbenzenesulfonamide;
3-(6-amino-5-(3-tert-butylisoxazol-5-yl)pyridin-3-yl)-N-((1r,4r)-4-hydroxycyclohexyl)-4-methylbenzenesulfonamide;
3-(6-amino-5-(3-cyclopropylisoxazol-5-yl)pyridin-3-yl)-N-(2-hydroxy-2-methylpropyl)-4-methylbenzenesulfonamide;
3-(6-amino-5-(3-isopropylisoxazol-5-yl)pyridin-3-yl)-N-(3-hydroxy-3-methylbutyl)-4-methylbenzenesulfonamide;
3-(6-amino-5-(3-tert-butylisoxazol-5-yl)pyridin-3-yl)-N-(2-hydroxy-2-methylpropyl)-4-methylbenzenesulfonamide;
3-(6-amino-5-(3-isopropylisoxazol-5-yl)pyridin-3-yl)-N-(2-hydroxy-2-methylpropyl)-4-methylbenzenesulfonamide;
3-(6-amino-5-(3-methylisoxazol-5-yl)pyridin-3-yl)-N-((1s,3s)-3-hydroxycyclobutyl)-4-methylbenzenesulfonamide;
3-(6-amino-5-(3-methylisoxazol-5-yl)pyridin-3-yl)-N-((1r,3r)-3-hydroxycyclobutyl)-4-methylbenzenesulfonamide;
(S)-3-(6-amino-5-(3-methylisoxazol-5-yl)pyridin-3-yl)-N-(2-hydroxypropyl)-4-methylbenzenesulfonamide;
3-(6-amino-5-(3-methylisoxazol-5-yl)pyridin-3-yl)-N-((4-(hydroxymethyl)tetrahydro-2H-pyran-4-yl)methyl)-4-methylbenzenesulfonamide;
5-(5-(3-methoxy-3-methylazetidin-1-ylsulfonyl)-2-methylphenyl)-3-(3-methyl-1,2,4-oxadiazol-5-yl)pyridin-2-amine;
3-(6-amino-5-(3-methylisoxazol-5-yl)pyridin-3-yl)-N-((1-(hydroxymethyl)cyclohexyl)methyl)-4-methylbenzenesulfonamide;
(R)-3-(6-amino-5-(3-methylisoxazol-5-yl)pyridin-3-yl)-4-methyl-N-(2-oxopiperidin-4-yl)benzenesulfonamide;
(R)-3-(6-amino-5-(3-methyl-1,2,4-oxadiazol-5-yl)pyridin-3-yl)-4-methyl-N-((tetrahydrofuran-2-yl)methyl)benzenesulfonamide;
3-(6-amino-5-(3-methylisoxazol-5-yl)pyridin-3-yl)-N-((1-(hydroxymethyl)cyclobutyl)methyl)-4-methylbenzenesulfonamide;
3-(6-amino-5-(3-methylisoxazol-5-yl)pyridin-3-yl)-N-(3-hydroxy-2,2-dimethylpropyl)-4-methylbenzenesulfonamide;
3-(6-amino-5-(3-methylisoxazol-5-yl)pyridin-3-yl)-4-methyl-N-(tetrahydro-2H-pyran-4-yl)benzenesulfonamide;
3-(6-amino-5-(3-methylisoxazol-5-yl)pyridin-3-yl)-N-((1-hydroxycyclohexyl)methyl)-4-methylbenzenesulfonamide;
3-(6-amino-5-(3-methyl-1,2,4-oxadiazol-5-yl)pyridin-3-yl)-N-((4-(hydroxymethyl)tetrahydro-2H-pyran-4-yl)methyl)-4-methylbenzenesulfonamide;
3-(6-amino-5-(3-methyl-1,2,4-oxadiazol-5-yl)pyridin-3-yl)-N-(2-(1-hydroxycyclopentyl)ethyl)-4-methylbenzenesulfonamide;
(1-(3-(6-amino-5-(3-methylisoxazol-5-yl)pyridin-3-yl)-4-methylphenylsulfonyl)azetidin-3-yl)methanol;
3-(6-amino-5-(3-methyl-1,2,4-oxadiazol-5-yl)pyridin-3-yl)-N-((1-(hydroxymethyl)cyclopentyl)methyl)-4-methylbenzenesulfonamide;
3-(6-amino-5-(3-methylisoxazol-5-yl)pyridin-3-yl)-4-methyl-N-(3,3,3-trifluoropropyl)benzenesulfonamide;
3-(6-amino-5-(3-methyl-1,2,4-oxadiazol-5-yl)pyridin-3-yl)-N-((1-hydroxycyclobutyl)methyl)-4-methylbenzenesulfonamide;
3-(6-amino-5-(3-methylisoxazol-5-yl)pyridin-3-yl)-N-(2-(1-hydroxycyclopentyl)ethyl)-4-methylbenzenesulfonamide;
3-(6-amino-5-(3-methyl-1,2,4-oxadiazol-5-yl)pyridin-3-yl)-N-(3,3-difluorocyclobutyl)-4-methylbenzenesulfonamide;
3-(6-amino-5-(3-methyl-1,2,4-oxadiazol-5-yl)pyridin-3-yl)-N-(3-hydroxy-2,2-di methylpropyl)-4-methylbenzenesulfonamide;
3-(6-amino-5-(3-methyl-1,2,4-oxadiazol-5-yl)pyridin-3-yl)-N-((1-hydroxycyclopropyl)methyl)-4-methylbenzenesulfonamide;
5-(5-(3-methoxy-3-methylazetidin-1-ylsulfonyl)-2-methylphenyl)-3-(3-methylisoxazol-5-yl)pyridin-2-amine;
3-(6-amino-5-(3-methyl-1,2,4-oxadiazol-5-yl)pyridin-3-yl)-N-(2-hydroxy-1-(tetrahydrofuran-3-yl)ethyl)-4-methylbenzenesulfonamide;
3-(6-amino-5-(3-methylisoxazol-5-yl)pyridin-3-yl)-N-methoxy-N,4-dimethylbenzenesulfonamide;
3-(6-amino-5-(3-methylisoxazol-5-yl)pyridin-3-yl)-N-((1-(hydroxymethyl)cyclopentyl)methyl)-4-methylbenzenesulfonamide;
(R)-1-(3-(6-amino-5-(3-methylisoxazol-5-yl)pyridin-3-yl)-4-methylphenylsulfonyl)pyrrolidin-3-ol;
(R)-3-(6-amino-5-(3-methyl-1,2,4-oxadiazol-5-yl)pyridin-3-yl)-4-methyl-N-(2-oxopiperidin-4-yl)benzenesulfonamide;
3-(6-amino-5-(3-methyl-1,2,4-oxadiazol-5-yl)pyridin-3-yl)-N-((1-(hydroxymethyl)cyclobutyl)methyl)-4-methylbenzenesulfonamide;

(R)-3-(6-amino-5-(3-methylisoxazol-5-yl)pyridin-3-yl)-N-((1-ethylpyrrolidin-2-yl)methyl)-4-methylbenzenesulfonamide;

1-(3-(6-amino-5-(3-methylisoxazol-5-yl)pyridin-3-yl)-4-methylphenylsulfonyl)-3-methylazetidin-3-ol;

3-(6-amino-5-(3-methyl-1,2,4-oxadiazol-5-yl)pyridin-3-yl)-N-(2-aminoethyl)-4-methylbenzenesulfonamide;

3-(6-amino-5-(3-methylisoxazol-5-yl)pyridin-3-yl)-N-(2-(1-hydroxycyclohexyl)ethyl)-4-methylbenzenesulfonamide;

3-(6-amino-5-(3-methyl-1,2,4-oxadiazol-5-yl)pyridin-3-yl)-N-(2-(1-hydroxycyclohexyl)ethyl)-4-methylbenzenesulfonamide;

(S)-1-(3-(6-amino-5-(3-methyl-1,2,4-oxadiazol-5-yl)pyridin-3-yl)-4-methylphenylsulfonyl)pyrrolidin-3-ol;

(S)-3-(6-amino-5-(3-methylisoxazol-5-yl)pyridin-3-yl)-N-((1-ethylpyrrolidin-2-yl)methyl)-4-methylbenzenesulfonamide;

3-(6-amino-5-(3-methyl-1,2,4-oxadiazol-5-yl)pyridin-3-yl)-N-(1-isopropylpiperidin-4-yl)-4-methylbenzenesulfonamide;

3-(6-amino-5-(3-methylisoxazol-5-yl)pyridin-3-yl)-N-((1-hydroxycyclobutyl)methyl)-4-methylbenzenesulfonamide;

3-(6-amino-5-(3-methylisoxazol-5-yl)pyridin-3-yl)-4-methyl-N-((tetrahydro-2H-pyran-2-yl)methyl)benzenesulfonamide;

3-(6-amino-5-(3-methylisoxazol-5-yl)pyridin-3-yl)-4-methyl-N-((tetrahydro-2H-pyran-2-yl)methyl)benzenesulfonamide;

3-(6-amino-5-(3-methyl-1,2,4-oxadiazol-5-yl)pyridin-3-yl)-N-(2,2-difluoropropyl)-4-methylbenzenesulfonamide;

(1-(3-(6-amino-5-(3-methyl-1,2,4-oxadiazol-5-yl)pyridin-3-yl)-4-methylphenylsulfonyl)azetidin-3-yl)methanol;

(S)-3-(6-amino-5-(3-methylisoxazol-5-yl)pyridin-3-yl)-4-methyl-N-((tetrahydrofuran-3-yl)methyl)benzenesulfonamide;

3-(6-amino-5-(3-methylisoxazol-5-yl)pyridin-3-yl)-4-methyl-N-(2,2,2-trifluoroethyl)benzenesulfonamide;

(S)-3-(6-amino-5-(3-methylisoxazol-5-yl)pyridin-3-yl)-4-methyl-N-((tetrahydrofuran-2-yl)methyl)benzenesulfonamide;

3-(6-amino-5-(3-(hydroxymethyl)isoxazol-5-yl)pyridin-3-yl)-N-(2-hydroxy-2-methylpropyl)-4-methylbenzenesulfonamide;

3-(6-amino-5-(3-(morpholine-4-carbonyl)isoxazol-5-yl)pyridin-3-yl)-N-(2-hydroxy-2-methylpropyl)-4-methylbenzenesulfonamide;

5-(2-amino-5-(5-(N-(2-hydroxy-2-methylpropyl)sulfamoyl)-2-methylphenyl)pyridin-3-yl)-N,N-dimethylisoxazole-3-carboxamide;

3-(6-amino-5-(3-methyl-1,2,4-oxadiazol-5-yl)pyridin-3-yl)-4-methyl-N-propoxybenzenesulfonamide;

3-(6-amino-5-(3-methyl-1,2,4-oxadiazol-5-yl)pyridin-3-yl)-N-isopropoxy-4-methylbenzenesulfonamide 3-(6-amino-5-(3-methyl-1,2,4-oxadiazol-5-yl)pyridin-3-yl)-N-methoxy-4-methylbenzenesulfonamide;

3-(6-amino-5-(3-methyl-1,2,4-oxadiazol-5-yl)pyridin-3-yl)-N-tert-butoxy-4-methylbenzenesulfonamide;

3-(6-amino-5-(3-methyl-1,2,4-oxadiazol-5-yl)pyridin-3-yl)-4-methyl-N-(3,3,3-trifluoropropyl)benzenesulfonamide;

3-(6-amino-5-(3-methyl-1,2,4-oxadiazol-5-yl)pyridin-3-yl)-4-methyl-N-(tetrahydro-2H-pyran-4-yl)benzenesulfonamide;

3-(6-amino-5-(3-methylisoxazol-5-yl)pyridin-3-yl)-N-((3-(hydroxymethyl)oxetan-3-yl)methyl)-4-methylbenzenesulfonamide;

3-(6-amino-5-(3-methyl-1,2,4-oxadiazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((3-(hydroxymethyl)oxetan-3-yl)methyl)-4-methylbenzenesulfonamide;

3-(6-amino-5-(3-methylisoxazol-5-yl)pyridin-3-yl)-N-((1-hydroxycyclopentyl)methyl)-4-methylbenzenesulfonamide;

3-(6-amino-5-(3-methylisoxazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((1r,3r)-3-hydroxycyclobutoxy)-4-methylbenzenesulfonamide;

3-(6-amino-5-(3-methyl-1,2,4-oxadiazol-5-yl)pyridin-3-yl)-N-((3-hydroxyoxetan-3-yl)methyl)-4-methylbenzenesulfonamide;

3-(6-amino-5-(3-methyl-1,2,4-oxadiazol-5-yl)pyridin-3-yl)-4-methyl-N-((tetrahydrofuran-2-yl)methyl)benzenesulfonamide;

3-(6-amino-5-(1-methyl-1H-pyrrol-3-yl)pyridin-3-yl)-N-(2-hydroxy-2-methylpropyl)-4-methylbenzenesulfonamide;

3-(6-amino-5-(2-methylthiazol-4-yl)pyridin-3-yl)-N-(2-hydroxy-2-methylpropyl)-4-methylbenzenesulfonamide;

3-(6-amino-5-(4-methyl-1H-pyrazol-1-yl)pyridin-3-yl)-N-(2-hydroxy-2-methylpropyl)-4-methylbenzenesulfonamide;

3-(6-amino-5-(1,5-dimethyl-1H-pyrazol-4-yl)pyridin-3-yl)-N-(2-hydroxy-2-methylpropyl)-4-methylbenzenesulfonamide;

3-(6-amino-5-(5-methylisoxazol-4-yl)pyridin-3-yl)-N-(2-hydroxy-2-methylpropyl)-4-methylbenzenesulfonamide;

3-(6-amino-5-(1-methyl-1H-1,2,3-triazol-4-yl)pyridin-3-yl)-N-(2-hydroxy-2-methylpropyl)-4-methylbenzenesulfonamide;

3-(6-amino-5-(isoxazol-5-yl)pyridin-3-yl)-N-(2-hydroxy-2-methylpropyl)-4-methylbenzenesulfonamide;

3-(6-amino-5-(3-(trifluoromethyl)isoxazol-5-yl)pyridin-3-yl)-N-(2-hydroxy-2-methylpropyl)-4-methylbenzenesulfonamide;

3-(6-amino-5-(3-((dimethylamino)methyl)isoxazol-5-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((3-(hydroxymethyl)oxetan-3-yl)methyl)-4-methylbenzenesulfonamide;

3-(6-amino-5-(2-methylthiazol-5-yl)pyridin-3-yl)-N-((3-(hydroxymethyl)oxetan-3-yl)methyl)-4-methylbenzenesulfonamide;

3-(6-amino-5-(2-methyloxazol-5-yl)pyridin-3-yl)-4-methyl-N-((3-methyloxetan-3-yl)methyl)benzenesulfonamide;

3-(6-amino-5-(3-(difluoromethyl)-1,2,4-oxadiazol-5-yl)pyridin-3-yl)-N-((1r,4r)-4-hydroxycyclohexyl)-4-methylbenzenesulfonamide;

3-(6-amino-5-(3-(difluoromethyl)-1,2,4-oxadiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-4-methyl-N-(6-methylpyridin-2-yl)benzenesulfonamide;

3-(6-amino-5-(3-methylisoxazol-5-yl)pyridin-3-yl)-N-(2-hydroxyethyl)-4-methylbenzenesulfonamide;

3-(6-amino-5-(2-methylthiazol-5-yl)pyridin-3-yl)-4-methylbenzenesulfonamide;

3-(6-amino-5-(3-methyl-1,2,4-oxadiazol-5-yl)pyridin-3-yl)-4-methylbenzenesulfonamide;

3-(6-amino-5-(3-methyl-1,2,4-oxadiazol-5-yl)pyridin-3-yl)-N-((1s,3s)-3-(hydroxymethyl)cyclobutyl)-4-methylbenzenesulfonamide;
3-(6-amino-5-(3-methyl-1,2,4-oxadiazol-5-yl)pyridin-3-yl)-N-((1r,3r)-3-(hydroxymethyl)cyclobutyl)-4-methylbenzenesulfonamide;
3-(2-amino-2'-methyl-3,4'-bipyridin-5-yl)-N-((1r,4r)-4-(hydroxymethyl)cyclohexyl)-4-methylbenzenesulfonamide;
3-(6-amino-5-(3-(2,2,2-trifluoroethyl)-1,2,4-oxadiazol-5-yl)pyridin-3-yl)-N-((1r,4r)-4-hydroxycyclohexyl)-4-methylbenzenesulfonamide;
3-(6-amino-5-(3-(2,2,2-trifluoroethyl)-1,2,4-oxadiazol-5-yl)pyridin-3-yl)-N-(3-hydroxy-3-methylbutyl)-4-methylbenzenesulfonamide;
3-(6-amino-5-(3-cyclopropyl-1,2,4-oxadiazol-5-yl)pyridin-3-yl)-N-(2-hydroxy-2-methylpropyl)-4-methylbenzenesulfonamide;
3-(6-amino-5-(1H-1,2,4-triazol-1-yl)pyridin-3-yl)-N-(2-hydroxy-2-methylpropyl)-4-methylbenzenesulfonamide;
3-(6-amino-5-(2-methyloxazol-5-yl)pyridin-3-yl)-N-((1r,3r)-3-hydroxycyclobutyl)-4-methylbenzenesulfonamide;
3-(6-amino-5-(2-methyloxazol-5-yl)pyridin-3-yl)-N-((1s,3s)-3-hydroxycyclobutyl)-4-methylbenzenesulfonamide;
3-(6-amino-5-(2-methylthiazol-5-yl)pyridin-3-yl)-N-((3-hydroxycyclobutyl)methyl)-4-methylbenzenesulfonamide;
(1-(3-(6-amino-5-(2-methylthiazol-5-yl)pyridin-3-yl)-4-methylphenylsulfonyl)azetidin-3-yl)methanol;
3-(6-amino-5-(2-methylthiazol-5-yl)pyridin-3-yl)-4-methyl-N-(oxetan-3-ylmethyl)benzenesulfonamide;
3-(6-amino-5-(2-methylthiazol-5-yl)pyridin-3-yl)-N-((3-hydroxyoxetan-3-yl)methyl)-4-methylbenzenesulfonamide
3-(6-amino-5-(2-methylthiazol-5-yl)pyridin-3-yl)-N-(3-hydroxy-2,2-dimethylpropyl)-4-methylbenzenesulfonamide;
3-(6-amino-5-(2-methylthiazol-5-yl)pyridin-3-yl)-N-(2-hydroxyethyl)-4-methylbenzenesulfonamide;
3-(6-amino-5-(3-methylisoxazol-5-yl)pyridin-3-yl)-N-(((1s,3s)-3-hydroxycyclobutyl)methyl)-4-methylbenzenesulfonamide;
5-(6-amino-5-(3-methyl-1,2,4-oxadiazol-5-yl)pyridin-3-yl)-2-fluoro-N-(2-hydroxy-2-methylpropyl)-4-methylbenzenesulfonamide;
(R)-3-(6-amino-5-(3-methyl-1,2,4-oxadiazol-5-yl)pyridin-3-yl)-4-methyl-N-((tetrahydrofuran-3-yl)methyl)benzenesulfonamide;
(S)-3-(6-amino-5-(3-methyl-1,2,4-oxadiazol-5-yl)pyridin-3-yl)-4-methyl-N-((tetrahydrofuran-3-yl)methyl)benzenesulfonamide;
5-(6-amino-5-(3-methylisoxazol-5-yl)pyridin-3-yl)-2-chloro-N-(2-hydroxy-2-methylpropyl)-4-methylbenzenesulfonamide;
5-(6-amino-5-(3-methyl-1,2,4-oxadiazol-5-yl)pyridin-3-yl)-2-chloro-N-(2-hydroxy-2-methylpropyl)-4-methylbenzenesulfonamide;
3-(6-amino-5-(5-methylthiazol-2-yl)pyridin-3-yl)-N-(2-hydroxy-2-methylpropyl)-4-methylbenzenesulfonamide;
3-(6-amino-5-(5-methylthiazol-2-yl)pyridin-3-yl)-N-(3-hydroxy-3-methylbutyl)-4-methylbenzenesulfonamide;
3-(6-amino-5-(2-methylthiazol-4-yl)pyridin-3-yl)-N-((1r,4r)-4-hydroxycyclohexyl)-4-methylbenzenesulfonamide;
3-(6-amino-5-(2-methylthiazol-4-yl)pyridin-3-yl)-N-(3-hydroxy-3-methylbutyl)-4-methylbenzenesulfonamide;
3-(6-amino-5-(oxazol-5-yl)pyridin-3-yl)-N-(2-hydroxy-2-methylpropyl)-4-methylbenzenesulfonamide;
3-(6-amino-5-(2-methyloxazol-5-yl)pyridin-3-yl)-N-((1-hydroxycyclopropyl)methyl)-4-methylbenzenesulfonamide;
3-(6-amino-5-(2-methyloxazol-5-yl)pyridin-3-yl)-4-methyl-N-(2,2,2-trifluoroethyl)benzenesulfonamide;
3-(6-amino-5-(2-methyloxazol-5-yl)pyridin-3-yl)-N-(2-hydroxypropyl)-4-methylbenzenesulfonamide;
3-(6-amino-5-(2-methyloxazol-5-yl)pyridin-3-yl)-N-(2,2-difluoroethyl)-4-methylbenzenesulfonamide;
3-(6-amino-5-(2-methyloxazol-5-yl)pyridin-3-yl)-N-(3-hydroxy-2,2-dimethylpropyl)-4-methylbenzenesulfonamide;
3-(6-amino-5-(2-methyloxazol-5-yl)pyridin-3-yl)-4-methyl-N-(oxetan-3-ylmethyl)benzenesulfonamide;
3-(6-amino-5-(2-methyloxazol-5-yl)pyridin-3-yl)-4-methyl-N-((tetrahydrofuran-3-yl)methyl)benzenesulfonamide;
3-(6-amino-5-(2-methyloxazol-5-yl)pyridin-3-yl)-N-((3-hydroxycyclobutyl)methyl)-4-methylbenzenesulfonamide; and
3-(6-amino-5-(2-methyloxazol-5-yl)pyridin-3-yl)-N-cyclopropyl-4-methylbenzenesulfonamide;
or a pharmaceutically acceptable salt thereof.

In an embodiment 32 of the invention, there is provided a compound according to embodiment 1 selected from
3-(6-amino-5-(1-(2,2,2-trifluoroethyl)-1H-pyrazol-4-yl)pyridin-3-yl)-4-methyl-N-(6-methylpyridin-2-yl)benzenesulfonamide;
3-(6-amino-5-(1-methyl-1H-pyrazol-4-yl)pyridin-3-yl)-N-(3-hydroxy-3-methylbutyl)-4-methylbenzenesulfonamide;
3-(6-amino-5-(1-(2,2,2-trifluoroethyl)-1H-pyrazol-4-yl)pyridin-3-yl)-N-(3-hydroxy-3-methylbutyl)-4-methylbenzenesulfonamide;
3-(6-amino-5-(2-methylthiazol-5-yl)pyridin-3-yl)-N-(3-hydroxy-3-methylbutyl)-4-methylbenzenesulfonamide;
3-(6-amino-5-(1-methyl-1H-pyrazol-4-yl)pyridin-3-yl)-N-((1r,4r)-4-hydroxycyclohexyl)-4-methylbenzenesulfonamide;
3-(6-amino-5-(1-(2,2,2-trifluoroethyl)-1H-pyrazol-4-yl)pyridin-3-yl)-N-((1r,4r)-4-hydroxycyclohexyl)-4-methylbenzenesulfonamide;
3-(2-amino-2'-methyl-3,4'-bipyridin-5-yl)-N-((1r,4r)-4-hydroxycyclohexyl)-4-methylbenzenesulfonamide;
3-(6-amino-5-(2-methyl-2H-1,2,3-triazol-4-yl)pyridin-3-yl)-N-(2-hydroxy-2-methylpropyl)-4-methylbenzenesulfonamide;
3-(6-amino-5-(2-methyl-2H-1,2,3-triazol-4-yl)pyridin-3-yl)-N-((1r,4r)-4-hydroxycyclohexyl)-4-methylbenzenesulfonamide;
3-(6-amino-5-(3-ethylisoxazol-5-yl)pyridin-3-yl)-N-(2-hydroxy-2-methylpropyl)-4-methylbenzenesulfonamide;
(R)-3-(6-amino-5-(3-methylisoxazol-5-yl)pyridin-3-yl)-4-methyl-N-((tetrahydrofuran-3-yl)methyl)benzenesulfonamide;
3-(6-amino-5-(3-methyl isothiazol-5-yl)pyridin-3-yl)-N-(2-hydroxy-2-methylpropyl)-4-methylbenzenesulfonamide;
3-(6-amino-5-(3-methyl-1,2,4-oxadiazol-5-yl)pyridin-3-yl)-4-methyl-N-((3-methyloxetan-3-yl)methyl)benzenesulfonamide
3-(6-amino-5-(3-methyl-1,2,4-oxadiazol-5-yl)pyridin-3-yl)-N-(3-hydroxy-3-methylbutyl)-4-methylbenzenesulfonamide;
3-(6-amino-5-(3-isopropyl-1,2,4-oxadiazol-5-yl)pyridin-3-yl)-N-(2-hydroxy-2-methylpropyl)-4-methylbenzenesulfonamide;
3-(6-amino-5-(5-methyloxazol-2-yl)pyridin-3-yl)-N-((1r,4r)-4-hydroxycyclohexyl)-4-methylbenzenesulfonamide;
3-(6-amino-5-(3-ethyl-1,2,4-oxadiazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1r, 4r)-4-hydroxycyclohexyl)-4-methylbenzenesulfonamide;
3-(6-amino-5-(3-methyl-1,2,4-oxadiazol-5-yl)pyridin-3-yl)-N-(3-hydroxycyclobutyl)-4-methylbenzenesulfonamide;
3-(6-amino-5-(3-methyl-1,2,4-oxadiazol-5-yl)pyridin-3-yl)-N-((1s,3s)-3-hydroxycyclobutyl)-4-methylbenzenesulfonamide;
3-(6-amino-5-(5-methyl-1,3,4-oxadiazol-2-yl)pyridin-3-yl)-N-(3-hydroxy-3-methylbutyl)-4-methylbenzenesulfonamide;
3-(6-amino-5-(2-methyloxazol-5-yl)pyridin-3-yl)-N-(2-hydroxy-2-methylpropyl)-4-methylbenzenesulfonamide;
3-(6-amino-5-(3-methylisoxazol-5-yl)pyridin-3-yl)-N-(2-hydroxy-2-methylpropyl)-4-methylbenzenesulfonamide;
3-(6-amino-5-(3-methyl-1,2,4-oxadiazol-5-yl)pyridin-3-yl)-N-(6-hydroxyspiro[3.3]heptan-2-yl)-4-methylbenzenesulfonamide;
3-(6-amino-5-(3-methyl-1,2,4-oxadiazol-5-yl)pyridin-3-yl)-N-(6-hydroxyspiro[3.3]heptan-2-yl)-4-methylbenzenesulfonamide;
3-(6-amino-5-(3-methyl-1,2,4-oxadiazol-5-yl)pyridin-3-yl)-N-(6-hydroxyspiro[3.3]heptan-2-yl)-4-methylbenzenesulfonamide;
3-(6-amino-5-(2-methylthiazol-5-yl)pyridin-3-yl)-N-(3-hydroxypropyl)-4-methylbenzenesulfonamide;
3-(6-amino-5-(3-methyl-1,2,4-oxadiazol-5-yl)pyridin-3-yl)-N-(2-hydroxy-2-methylpropyl)-4-methylbenzenesulfonamide;
3-(6-amino-5-(3-methyl-1,2,4-oxadiazol-5-yl)pyridin-3-yl)-N-(2-hydroxy-2-methylpropoxy)-4-methylbenzenesulfonamide;
3-(6-amino-5-(3-methyl-1,2,4-oxadiazol-5-yl)pyridin-3-yl)-N-((1r,4r)-4-hydroxycyclohexyl)-4-methylbenzenesulfonamide;
3-(6-amino-5-(2-methyloxazol-5-yl)pyridin-3-yl)-N-(3-hydroxy-3-methylbutyl)-4-methylbenzenesulfonamide;
3-(6-amino-5-(3-methylisoxazol-5-yl)pyridin-3-yl)-N-(3-hydroxy-3-methylbutyl)-4-methylbenzenesulfonamide;
3-(6-amino-5-(2-methylthiazol-5-yl)pyridin-3-yl)-N-(2-hydroxy-2-methylpropyl)-4-methylbenzenesulfonamide;
3-(2-amino-2'-methyl-3,4-bipyridin-5-yl)-N-(3-hydroxy-3-methylbutyl)-4-methylbenzenesulfonamide;
3-(6-amino-5-(3-methylisoxazol-5-yl)pyridin-3-yl)-4-methyl-N-((3-methyloxetan-3-yl)methyl)benzenesulfonamide;
3-(2-amino-3,4'-bipyridin-5-yl)-N-(3-hydroxy-3-methylbutyl)-4-methylbenzenesulfonamide;
3-(6-amino-5-(3-methyl-1,2,4-oxadiazol-5-yl)pyridin-3-yl)-N-((1r,4r)-4-(hydroxymethyl)cyclohexyl)-4-methylbenzenesulfonamide;
5-(5-(6-oxa-2-azaspiro[3.4]octan-2-ylsulfonyl)-2-methylphenyl)-3-(3-methylisoxazol-5-yl)pyridin-2-amine;
3-(6-amino-5-(3-methylisoxazol-5-yl)pyridin-3-yl)-4-methyl-N-(2-oxotetrahydrofuran-3-yl)benzenesulfonamide;
3-(6-amino-5-(3-methylisoxazol-5-yl)pyridin-3-yl)-N-((1r, 4r)-4-aminocyclohexyl)-4-methylbenzenesulfonamide;
3-(6-amino-5-(3-methylisoxazol-5-yl)pyridin-3-yl)-N-((3R, 4R)-4-hydroxypyrrolidin-3-yl)-4-methylbenzenesulfonamide;
(S)-5-(2-methyl-5-(3-methylmorpholinosulfonyl)phenyl)-3-(3-methylisoxazol-5-yl)pyridin-2-amine;
(R)-5-(2-methyl-5-(3-methylmorpholinosulfonyl)phenyl)-3-(3-methylisoxazol-5-yl)pyridin-2-amine;
3-(6-amino-5-(3-methylisoxazol-5-yl)pyridin-3-yl)-4-methyl-N-neopentylbenzenesulfonamide;
3-(6-amino-5-(3-methylisoxazol-5-yl)pyridin-3-yl)-N-tert-butyl-4-methylbenzenesulfonamide;
5-(5-(2,2-dimethylpyrrolidin-1-ylsulfonyl)-2-methylphenyl)-3-(3-methylisoxazol-5-yl)pyridin-2-amine;
3-(6-amino-5-(3-methylisoxazol-5-yl)pyridin-3-yl)-N-((1-hydroxycyclopropyl)methyl)-4-methylbenzenesulfonamide;
3-(6-amino-5-(3-methylisoxazol-5-yl)pyridin-3-yl)-N-(1-methoxy-3-methylbutan-2-yl)-4-methylbenzenesulfonamide;
3-(6-amino-5-(3-methylisoxazol-5-yl)pyridin-3-yl)-4-methyl-N-(2-(tetrahydro-2H-pyran-4-yl)ethyl)benzenesulfonamide;
(S)-3-(6-amino-5-(3-methylisoxazol-5-yl)pyridin-3-yl)-N-(1-cyclopropylethyl)-4-methylbenzenesulfonamide;
(S)-(1-(3-(6-amino-5-(3-methylisoxazol-5-yl)pyridin-3-yl)-4-methylphenylsulfonyl)pyrrolidin-2-yl)methanol;
3-(6-amino-5-(3-methylisoxazol-5-yl)pyridin-3-yl)-N-((1S, 3S)-3-hydroxycyclohexyl)-4-methylbenzenesulfonamide;
4-(3-(6-amino-5-(3-methylisoxazol-5-yl)pyridin-3-yl)-4-methylphenylsulfonyl) piperazin-2-one;
5-(5-(4-(methoxymethyl)piperidin-1-ylsulfonyl)-2-methylphenyl)-3-(3-methylisoxazol-5-yl)pyridin-2-amine;
5-(5-(3-(dimethylamino)azetidin-1-ylsulfonyl)-2-methylphenyl)-3-(3-methylisoxazol-5-yl)pyridin-2-amine;
(R)-5-(5-(3-(methoxymethyl)morpholinosulfonyl)-2-methylphenyl)-3-(3-methylisoxazol-5-yl)pyridin-2-amine;
3-(6-amino-5-(3-methylisoxazol-5-yl)pyridin-3-yl)-N-(2-hydroxy-2-methylpropoxy)-4-methylbenzenesulfonamide;
3-(6-amino-5-(3-methylisoxazol-5-yl)pyridin-3-yl)-4-methyl-N-(tetrahydrofuran-3-yloxy)benzenesulfonamide;
3-(6-amino-5-(3-methylisoxazol-5-yl)pyridin-3-yl)-4-methyl-N-(tetrahydrofuran-3-yloxy)benzenesulfonamide;
3-(6-amino-5-(3-methylisoxazol-5-yl)pyridin-3-yl)-N-ethoxy-4-methylbenzenesulfonamide;
3-(6-amino-5-(3-methylisoxazol-5-yl)pyridin-3-yl)-4-methyl-N-((tetrahydro-2H-pyran-3-yl)methyl)benzenesulfonamide;
3-(6-amino-5-(3-methylisoxazol-5-yl)pyridin-3-yl)-4-methyl-N-((tetrahydro-2H-pyran-3-yl)methyl)benzenesulfonamide;
(R)-3-(6-amino-5-(3-methylisoxazol-5-yl)pyridin-3-yl)-N-(2-hydroxypropyl)-4-methylbenzenesulfonamide;
3-(6-amino-5-(3-methylisoxazol-5-yl)pyridin-3-yl)-4-methyl-N-(oxetan-3-ylmethyl)benzenesulfonamide;
3-(6-amino-5-(1,3-dimethyl-1H-pyrazol-4-yl)pyridin-3-yl)-N-(6-hydroxyspiro[3.3]heptan-2-yl)-4-methylbenzenesulfonamide;
3-(6-amino-5-(3-methylisoxazol-5-yl)pyridin-3-yl)-N-(2,2-difluoroethyl)-4-methylbenzenesulfonamide;
3-(6-amino-5-(2-methylthiazol-5-yl)pyridin-3-yl)-N-(6-hydroxyspiro[3.3]heptan-2-yl)-4-methylbenzenesulfonamide;
3-(6-amino-5-(3-methyl-1,2,4-oxadiazol-5-yl)pyridin-3-yl)-4-methyl-N-((tetrahydrofuran-3-yl)methyl)benzenesulfonamide;
3-(6-amino-5-(1-methyl-1H-pyrazol-4-yl)pyridin-3-yl)-4-methyl-N-(6-methylpyridin-2-yl)benzenesulfonamide;
3-(6-amino-5-(3-methylisoxazol-5-yl)pyridin-3-yl)-N-cyclopropyl-4-methylbenzenesulfonamide;
3-(6-amino-5-(3-methylisoxazol-5-yl)pyridin-3-yl)-4-methylbenzenesulfonamide;
3-(6-amino-5-(2-methyloxazol-5-yl)pyridin-3-yl)-4-methylbenzenesulfonamide;

3-(6-amino-5-(1-(2,2,2-trifluoroethyl)-1H-pyrazol-4-yl)pyridin-3-yl)-N-(2-hydroxy-2-methylpropoxy)-4-methylbenzenesulfonamide;

3-(6-amino-5-(3-(2,2,2-trifluoroethyl)isoxazol-5-yl)pyridin-3-yl)-N-(2-hydroxy-2-methylpropyl)-4-methylbenzenesulfonamide;

3-(6-amino-5-(3-propylisoxazol-5-yl)pyridin-3-yl)-N-(2-hydroxy-2-methylpropyl)-4-methylbenzenesulfonamide;

3-(6-amino-5-(3-tert-butylisoxazol-5-yl)pyridin-3-yl)-N-((1r,4r)-4-hydroxycyclohexyl)-4-methylbenzenesulfonamide;

3-(6-amino-5-(3-cyclopropylisoxazol-5-yl)pyridin-3-yl)-N-(2-hydroxy-2-methylpropyl)-4-methylbenzenesulfonamide;

3-(6-amino-5-(3-isopropylisoxazol-5-yl)pyridin-3-yl)-N-(3-hydroxy-3-methylbutyl)-4-methylbenzenesulfonamide;

3-(6-amino-5-(3-tert-butylisoxazol-5-yl)pyridin-3-yl)-N-(2-hydroxy-2-methylpropyl)-4-methylbenzenesulfonamide;

3-(6-amino-5-(3-isopropylisoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1s,3s)-3-hydroxycyclobutyl)-4-methylbenzenesulfonamide;

3-(6-amino-5-(3-methylisoxazol-5-yl)pyridin-3-yl)-N-((1r,3r)-3-hydroxycyclobutyl)-4-methylbenzenesulfonamide;

(S)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-N-((4-(hydroxymethyl)tetrahydro-2H-pyran-4-yl)methyl)-4-methylbenzenesulfonamide;

5-(5-(3-methoxy-3-methylazetidin-1-ylsulfonyl)-2-methylphenyl)-3-(3-methyl-1,2,4-oxadiazol-5-yl)pyridin-2-amine;

3-(6-amino-5-(3-methylisoxazol-5-yl)pyridin-3-yl)-N-((1-(hydroxymethyl)cyclohexyl)methyl)-4-methylbenzenesulfonamide;

(R)-3-(6-amino-5-(3-methylisoxazol-5-yl)pyridin-3-yl)-4-methyl-N-(2-oxopiperidin-4-yl)benzenesulfonamide;

(R)-3-(6-amino-5-(3-methyl-1,2,4-oxadiazol-5-yl)pyridin-3-yl)-4-methyl-N-((tetrahydrofuran-2-yl)methyl)benzenesulfonamide;

3-(6-amino-5-(3-methylisoxazol-5-yl)pyridin-3-yl)-N-((1-(hydroxymethyl)cyclobutyl)methyl)-4-methylbenzenesulfonamide;

3-(6-amino-5-(3-methylisoxazol-5-yl)pyridin-3-yl)-N-(3-hydroxy-2,2-dimethylpropyl)-4-methylbenzenesulfonamide;

3-(6-amino-5-(3-methylisoxazol-5-yl)pyridin-3-yl)-4-methyl-N-(tetrahydro-2H-pyran-4-yl)benzenesulfonamide;

3-(6-amino-5-(3-methylisoxazol-5-yl)pyridin-3-yl)-N-((1-hydroxycyclohexyl)methyl)-4-methylbenzenesulfonamide;

3-(6-amino-5-(3-methyl-1,2,4-oxadiazol-5-yl)pyridin-3-yl)-N-((4-(hydroxymethyl)tetrahydro-2H-pyran-4-yl)methyl)-4-methylbenzenesulfonamide;

3-(6-amino-5-(3-methyl-1,2,4-oxadiazol-5-yl)pyridin-3-yl)-N-(2-(1-hydroxycyclopentyl)ethyl)-4-methylbenzenesulfonamide;

(1-(3-(6-amino-5-(3-methylisoxazol-5-yl)pyridin-3-yl)-4-methylphenylsulfonyl)azetidin-3-yl)methanol;

3-(6-amino-5-(3-methyl-1,2,4-oxadiazol-5-yl)pyridin-3-yl)-N-((1-(hydroxymethyl)cyclopentyl)methyl)-4-methylbenzenesulfonamide;

3-(6-amino-5-(3-methylisoxazol-5-yl)pyridin-3-yl)-4-methyl-N-(3,3,3-trifluoropropyl)benzenesulfonamide;

3-(6-amino-5-(3-methyl-1,2,4-oxadiazol-5-yl)pyridin-3-yl)-N-((1-hydroxycyclobutyl)methyl)-4-methylbenzenesulfonamide;

3-(6-amino-5-(3-methylisoxazol-5-yl)pyridin-3-yl)-N-(2-(1-hydroxycyclopentyl)ethyl)-4-methylbenzenesulfonamide;

3-(6-amino-5-(3-methyl-1,2,4-oxadiazol-5-yl)pyridin-3-yl)-N-(3,3-difluorocyclobutyl)-4-methylbenzenesulfonamide;

3-(6-amino-5-(3-methyl-1,2,4-oxadiazol-5-yl)pyridin-3-yl)-N-(3-hydroxy-2,2-dimethylpropyl)-4-methylbenzenesulfonamide;

3-(6-amino-5-(3-methyl-1,2,4-oxadiazol-5-yl)pyridin-3-yl)-N-((1-hydroxycyclopropyl)methyl)-4-methylbenzenesulfonamide;

5-(5-(3-methoxy-3-methylazetidin-1-ylsulfonyl)-2-methylphenyl)-3-(3-methylisoxazol-5-yl)pyridin-2-amine;

3-(6-amino-5-(3-methyl-1,2,4-oxadiazol-5-yl)pyridin-3-yl)-N-(2-hydroxy-1-(tetrahydrofuran-3-yl)ethyl)-4-methylbenzenesulfonamide;

3-(6-amino-5-(3-methylisoxazol-5-yl)pyridin-3-yl)-N-methoxy-N,4-dimethylbenzenesulfonamide;

3-(6-amino-5-(3-methylisoxazol-5-yl)pyridin-3-yl)-N-((1-(hydroxymethyl)cyclopentyl)methyl)-4-methylbenzenesulfonamide;

(R)-1-(3-(6-amino-5-(3-methylisoxazol-5-yl)pyridin-3-yl)-4-methylphenylsulfonyl)pyrrolidin-3-ol;

(R)-3-(6-amino-5-(3-methyl-1,2,4-oxadiazol-5-yl)pyridin-3-yl)-4-methyl-N-(2-oxopiperidin-4-yl)benzenesulfonamide;

3-(6-amino-5-(3-methyl-1,2,4-oxadiazol-5-yl)pyridin-3-yl)-N-((1-(hydroxymethyl)cyclobutyl)methyl)-4-methylbenzenesulfonamide;

(R)-3-(6-amino-5-(3-methylisoxazol-5-yl)pyridin-3-yl)-N-((1-ethylpyrrolidin-2-yl)methyl)-4-methylbenzenesulfonamide;

1-(3-(6-amino-5-(3-methylisoxazol-5-yl)pyridin-3-yl)-4-methylphenylsulfonyl)-3-methylazetidin-3-ol;

3-(6-amino-5-(3-methyl-1,2,4-oxadiazol-5-yl)pyridin-3-yl)-N-(2-aminoethyl)-4-methylbenzenesulfonamide;

3-(6-amino-5-(3-methylisoxazol-5-yl)pyridin-3-yl)-N-(2-(1-hydroxycyclohexyl)ethyl)-4-methylbenzenesulfonamide;

3-(6-amino-5-(3-methyl-1,2,4-oxadiazol-5-yl)pyridin-3-yl)-N-(2-(1-hydroxycyclohexyl)ethyl)-4-methylbenzenesulfonamide;

(S)-1-(3-(6-amino-5-(3-methyl-1,2,4-oxadiazol-5-yl)pyridin-3-yl)-4-methylphenylsulfonyl)pyrrolidin-3-ol;

(S)-3-(6-amino-5-(3-methylisoxazol-5-yl)pyridin-3-yl)-N-((1-ethylpyrrolidin-2-yl)methyl)-4-methylbenzenesulfonamide;

3-(6-amino-5-(3-methyl-1,2,4-oxadiazol-5-yl)pyridin-3-yl)-N-(1-isopropylpiperidin-4-yl)-4-methylbenzenesulfonamide;

3-(6-amino-5-(3-methylisoxazol-5-yl)pyridin-3-yl)-N-((1-hydroxycyclobutyl)methyl)-4-methylbenzenesulfonamide;

3-(6-amino-5-(3-methylisoxazol-5-yl)pyridin-3-yl)-4-methyl-N-((tetrahydro-2H-pyran-2-yl)methyl)benzenesulfonamide;

3-(6-amino-5-(3-methylisoxazol-5-yl)pyridin-3-yl)-4-methyl-N-((tetrahydro-2H-pyran-2-yl)methyl)benzenesulfonamide;

3-(6-amino-5-(3-methyl-1,2,4-oxadiazol-5-yl)pyridin-3-yl)-N-(2,2-difluoropropyl)-4-methylbenzenesulfonamide;

(1-(3-(6-amino-5-(3-methyl-1,2,4-oxadiazol-5-yl)pyridin-3-yl)-4-methylphenylsulfonyl)azetidin-3-yl)methanol;

(S)-3-(6-amino-5-(3-methylisoxazol-5-yl)pyridin-3-yl)-4-methyl-N-((tetrahydrofuran-3-yl)methyl)benzenesulfonamide;

3-(6-amino-5-(3-methylisoxazol-5-yl)pyridin-3-yl)-4-methyl-N-(2,2,2-trifluoroethyl)benzenesulfonamide;

(S)-3-(6-amino-5-(3-methylisoxazol-5-yl)pyridin-3-yl)-4-methyl-N-((tetrahydrofuran-2-yl)methyl)benzenesulfonamide;

3-(6-amino-5-(3-(hydroxymethyl)isoxazol-5-yl)pyridin-3-yl)-N-(2-hydroxy-2-methylpropyl)-4-methylbenzenesulfonamide;

3-(6-amino-5-(3-(morpholine-4-carbonyl)isoxazol-5-yl)pyridin-3-yl)-N-(2-hydroxy-2-methylpropyl)-4-methylbenzenesulfonamide;

5-(2-amino-5-(5-(N-(2-hydroxy-2-methylpropyl)sulfamoyl)-2-methylphenyl)pyridin-3-yl)-N,N-dimethylisoxazole-3-carboxamide;

3-(6-amino-5-(3-methyl-1,2,4-oxadiazol-5-yl)pyridin-3-yl)-4-methyl-N-propoxybenzenesulfonamide;

3-(6-amino-5-(3-methyl-1,2,4-oxadiazol-5-yl)pyridin-3-yl)-N-isopropoxy-4-methylbenzenesulfonamide;

3-(6-amino-5-(3-methyl-1,2,4-oxadiazol-5-yl)pyridin-3-yl)-N-methoxy-4-methylbenzenesulfonamide;

3-(6-amino-5-(3-methyl-1,2,4-oxadiazol-5-yl)pyridin-3-yl)-N-tert-butoxy-4-methylbenzenesulfonamide;

3-(6-amino-5-(3-methyl-1,2,4-oxadiazol-5-yl)pyridin-3-yl)-4-methyl-N-(3,3,3-trifluoropropyl)benzenesulfonamide;

3-(6-amino-5-(3-methyl-1,2,4-oxadiazol-5-yl)pyridin-3-yl)-4-methyl-N-(tetrahydro-2H-pyran-4-yl)benzenesulfonamide;

3-(6-amino-5-(3-methylisoxazol-5-yl)pyridin-3-yl)-N-((3-(hydroxymethyl)oxetan-3-yl)methyl)-4-methylbenzenesulfonamide;

3-(6-amino-5-(3-methyl-1,2,4-oxadiazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((3-(hydroxymethyl)oxetan-3-yl)methyl)-4-methylbenzenesulfonamide;

3-(6-amino-5-(3-methylisoxazol-5-yl)pyridin-3-yl)-N-((1-hydroxycyclopentyl)methyl)-4-methylbenzenesulfonamide;

3-(6-amino-5-(3-methylisoxazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((1r,3r)-3-hydroxycyclobutoxy)-4-methylbenzenesulfonamide;

3-(6-amino-5-(3-methyl-1,2,4-oxadiazol-5-yl)pyridin-3-yl)-N-((3-hydroxyoxetan-3-yl)methyl)-4-methylbenzenesulfonamide;

3-(6-amino-5-(3-methyl-1,2,4-oxadiazol-5-yl)pyridin-3-yl)-4-methyl-N-((tetrahydrofuran-2-yl)methyl)benzenesulfonamide;

3-(6-amino-5-(1-methyl-1H-pyrrol-3-yl)pyridin-3-yl)-N-(2-hydroxy-2-methylpropyl)-4-methylbenzenesulfonamide;

3-(6-amino-5-(2-methylthiazol-4-yl)pyridin-3-yl)-N-(2-hydroxy-2-methylpropyl)-4-methylbenzenesulfonamide;

3-(6-amino-5-(4-methyl-1H-pyrazol-1-yl)pyridin-3-yl)-N-(2-hydroxy-2-methylpropyl)-4-methylbenzenesulfonamide;

3-(6-amino-5-(1,5-dimethyl-1H-pyrazol-4-yl)pyridin-3-yl)-N-(2-hydroxy-2-methylpropyl)-4-methylbenzenesulfonamide;

3-(6-amino-5-(5-methylisoxazol-4-yl)pyridin-3-yl)-N-(2-hydroxy-2-methylpropyl)-4-methylbenzenesulfonamide;

3-(6-amino-5-(1-methyl-1H-1,2,3-triazol-4-yl)pyridin-3-yl)-N-(2-hydroxy-2-methylpropyl)-4-methylbenzenesulfonamide;

3-(6-amino-5-(isoxazol-5-yl)pyridin-3-yl)-N-(2-hydroxy-2-methylpropyl)-4-methylbenzenesulfonamide;

3-(6-amino-5-(3-(trifluoromethyl)isoxazol-5-yl)pyridin-3-yl)-N-(2-hydroxy-2-methylpropyl)-4-methylbenzenesulfonamide;

3-(6-amino-5-(3-((dimethylamino)methyl)isoxazol-5-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((3-(hydroxymethyl)oxetan-3-yl)methyl)-4-methylbenzenesulfonamide;

3-(6-amino-5-(2-methylthiazol-5-yl)pyridin-3-yl)-N-((3-(hydroxymethyl)oxetan-3-yl)methyl)-4-methylbenzenesulfonamide;

3-(6-amino-5-(2-methyloxazol-5-yl)pyridin-3-yl)-4-methyl-N-((3-methyloxetan-3-yl)methyl)benzenesulfonamide;

3-(6-amino-5-(3-(difluoromethyl)-1,2,4-oxadiazol-5-yl)pyridin-3-yl)-N-((1r,4r)-4-hydroxycyclohexyl)-4-methylbenzenesulfonamide;

3-(6-amino-5-(3-(difluoromethyl)-1,2,4-oxadiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-4-methyl-N-(6-methylpyridin-2-yl)benzenesulfonamide;

3-(6-amino-5-(3-methylisoxazol-5-yl)pyridin-3-yl)-N-(2-hydroxyethyl)-4-methylbenzenesulfonamide;

3-(6-amino-5-(2-methylthiazol-5-yl)pyridin-3-yl)-4-methylbenzenesulfonamide;

3-(6-amino-5-(3-methyl-1,2,4-oxadiazol-5-yl)pyridin-3-yl)-4-methylbenzenesulfonamide;

3-(6-amino-5-(3-methyl-1,2,4-oxadiazol-5-yl)pyridin-3-yl)-N-((1s,3s)-3-(hydroxymethyl)cyclobutyl)-4-methylbenzenesulfonamide;

3-(6-amino-5-(3-methyl-1,2,4-oxadiazol-5-yl)pyridin-3-yl)-N-((1r,3r)-3-(hydroxymethyl)cyclobutyl)-4-methylbenzenesulfonamide;

3-(2-amino-2'-methyl-3,4-bipyridin-5-yl)-N-((1r,4r)-4-(hydroxymethyl)cyclohexyl)-4-methylbenzenesulfonamide;

3-(6-amino-5-(3-(2,2,2-trifluoroethyl)-1,2,4-oxadiazol-5-yl)pyridin-3-yl)-N-((1r,4r)-4-hydroxycyclohexyl)-4-methylbenzenesulfonamide;

3-(6-amino-5-(3-(2,2,2-trifluoroethyl)-1,2,4-oxadiazol-5-yl)pyridin-3-yl)-N-(3-hydroxy-3-methylbutyl)-4-methylbenzenesulfonamide;

3-(6-amino-5-(3-cyclopropyl-1,2,4-oxadiazol-5-yl)pyridin-3-yl)-N-(2-hydroxy-2-methylpropyl)-4-methylbenzenesulfonamide;

3-(6-amino-5-(1H-1,2,4-triazol-1-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((1r,3r)-3-hydroxycyclobutyl)-4-methylbenzenesulfonamide;

3-(6-amino-5-(2-methyloxazol-5-yl)pyridin-3-yl)-N-((1s,3s)-3-hydroxycyclobutyl)-4-methylbenzenesulfonamide;

3-(6-amino-5-(2-methylthiazol-5-yl)pyridin-3-yl)-N-((3-hydroxycyclobutyl)methyl)-4-methylbenzenesulfonamide;

(1-(3-(6-amino-5-(2-methylthiazol-5-yl)pyridin-3-yl)-4-methylphenylsulfonyl)azetidin-3-yl)methanol;

3-(6-amino-5-(2-methylthiazol-5-yl)pyridin-3-yl)-4-methyl-N-(oxetan-3-ylmethyl)benzenesulfonamide;

3-(6-amino-5-(2-methylthiazol-5-yl)pyridin-3-yl)-N-((3-hydroxyoxetan-3-yl)methyl)-4-methylbenzenesulfonamide;

3-(6-amino-5-(2-methylthiazol-5-yl)pyridin-3-yl)-N-(3-hydroxy-2,2-dimethylpropyl)-4-methylbenzenesulfonamide;

3-(6-amino-5-(2-methylthiazol-5-yl)pyridin-3-yl)-N-(2-hydroxyethyl)-4-methylbenzenesulfonamide;

3-(6-amino-5-(3-methylisoxazol-5-yl)pyridin-3-yl)-N-(((1s,3s)-3-hydroxycyclobutyl)methyl)-4-methylbenzenesulfonamide;

5-(6-amino-5-(3-methyl-1,2,4-oxadiazol-5-yl)pyridin-3-yl)-2-fluoro-N-(2-hydroxy-2-methylpropyl)-4-methylbenzenesulfonamide;

(R)-3-(6-amino-5-(3-methyl-1,2,4-oxadiazol-5-yl)pyridin-3-yl)-4-methyl-N-((tetrahydrofuran-3-yl)methyl)benzenesulfonamide;

(S)-3-(6-amino-5-(3-methyl-1,2,4-oxadiazol-5-yl)pyridin-3-yl)-4-methyl-N-((tetrahydrofuran-3-yl)methyl)benzenesulfonamide;

5-(6-amino-5-(3-methylisoxazol-5-yl)pyridin-3-yl)-2-chloro-N-(2-hydroxy-2-methylpropyl)-4-methylbenzenesulfonamide;

5-(6-amino-5-(3-methyl-1,2,4-oxadiazol-5-yl)pyridin-3-yl)-2-chloro-N-(2-hydroxy-2-methylpropyl)-4-methylbenzenesulfonamide;

3-(6-amino-5-(5-methylthiazol-2-yl)pyridin-3-yl)-N-(2-hydroxy-2-methylpropyl)-4-methylbenzenesulfonamide;

3-(6-amino-5-(5-methylthiazol-2-yl)pyridin-3-yl)-N-(3-hydroxy-3-methylbutyl)-4-methylbenzenesulfonamide;

3-(6-amino-5-(2-methylthiazol-4-yl)pyridin-3-yl)-N-((1r,4r)-4-hydroxycyclohexyl)-4-methylbenzenesulfonamide;

3-(6-amino-5-(2-methylthiazol-4-yl)pyridin-3-yl)-N-(3-hydroxy-3-methylbutyl)-4-methylbenzenesulfonamide; and 3-(6-amino-5-(oxazol-5-yl)pyridin-3-yl)-N-(2-hydroxy-2-methylpropyl)-4-methylbenzenesulfonamide;

or a pharmaceutically acceptable salt thereof.

In an embodiment 33 of the invention, there is provided a compound according to embodiment 1 selected from 3-{6-Amino-5-[1-(2,2,2-trifluoro-ethyl)-1H-pyrazol-4-yl]-pyridin-3-yl}-4-methyl-N-(6-methyl-pyridin-2-yl)-benzenesulfonamide;

3-(6-Amino-5-(1-methyl-1H-pyrazol-4-yl)pyridin-3-yl)-N-(3-hydroxy-3-methylbutyl)-4-methylbenzenesulfonamide;

3-(6-Amino-5-(1-(2,2,2-trifluoroethyl)-1H-pyrazol-4-yl) pyridin-3-yl)-N-(3-hydroxy-3-methylbutyl)-4-methylbenzenesulfonamide;

3-(6-Amino-5-(2-methylthiazol-5-yl)pyridin-3-yl)-N-(3-hydroxy-3-methylbutyl)-4-methylbenzenesulfonamide;

3-[6-Amino-5-(3-methyl-[1,2,4]oxadiazol-5-yl)-pyridin-3-yl]-N-(3-hydroxy-3-methyl-butyl)-4-methyl-benzenesulfonamide;

3-[6-Amino-5-(2-methyl-oxazol-5-yl)-pyridin-3-yl]-N-(2-hydroxy-2-methyl-propyl)-4-methyl-benzenesulfonamide;

3-[6-Amino-5-(3-methyl-isoxazol-5-yl)-pyridin-3-yl]-N-(2-hydroxy-2-methyl-propyl)-4-methyl-benzenesulfonamide;

3-[6-Amino-5-(3-methyl-[1,2,4]oxadiazol-5-yl)-pyridin-3-yl]-N-(6-hydroxy-spiro[3.3]hept-2-yl)-4-methyl-benzenesulfonamide;

3-[6-Amino-5-(2-methyl-thiazol-5-yl)-pyridin-3-yl]-N-(3-hydroxy-propyl)-4-methyl-benzenesulfonamide;

3-(6-amino-5-(3-methyl-1,2,4-oxadiazol-5-yl)pyridin-3-yl)-N-(2-hydroxy-2-methylpropyl)-4-methylbenzenesulfonamide;

3-[6-Amino-5-(3-methyl-[1,2,4]oxadiazol-5-yl)-pyridin-3-yl]-N-(2-hydroxy-2-methyl-propoxy)-4-methyl-benzenesulfonamide;

Trans 3-[6-Amino-5-(3-methyl-[1,2,4]oxadiazol-5-yl)-pyridin-3-yl]-N-(4-hydroxy-cyclohexyl)-4-methyl-benzenesulfonamide;

3-[6-Amino-5-(2-methyl-oxazol-5-yl)-pyridin-3-yl]-N-(3-hydroxy-3-methyl-butyl)-4-methyl-benzenesulfonamide;

3-[6-Amino-5-(3-methyl-isoxazol-5-yl)-pyridin-3-yl]-N-(3-hydroxy-3-methyl-butyl)-4-methyl-benzenesulfonamide;

3-[6-Amino-5-(2-methyl-thiazol-5-yl)-pyridin-3-yl]-N-(2-hydroxy-2-methyl-propyl)-4-methyl-benzenesulfonamide;

3-(2-Amino-2'-methyl-[3,4']bipyridinyl-5-yl)-N-(3-hydroxy-3-methyl-butyl)-4-methyl-benzenesulfonamide;

3-[6-Amino-5-(3-methyl-isoxazol-5-yl)-pyridin-3-yl]-4-methyl-N-(3-methyl-oxetan-3-ylmethyl)-benzenesulfonamide;

3-(2-Amino-[3,4']bipyridinyl-5-yl)-N-(3-hydroxy-3-methyl-butyl)-4-methyl-benzenesulfonamide;

trans 3-[6-Amino-5-(3-methyl-[1,2,4]oxadiazol-5-yl)-pyridin-3-yl]-N-(4-hydroxymethyl-cyclohexyl)-4-methyl-benzenesulfonamide;

trans 3-(6-Amino-5-(1-methyl-1H-pyrazol-4-yl)pyridin-3-yl)-N-(4-hydroxy cyclohexyl)-4-methylbenzenesulfonamide;

trans 3-(6-Amino-5-(1-(2,2,2-trifluoroethyl)-1H-pyrazol-4-yl)pyridin-3-yl)-N-(4-hydroxy cyclohexyl)-4-methylbenzenesulfonamide;

trans 3-(2-Amino-2'-methyl-[3,4'-bi pyridin]-5-yl)-N-(4-hydroxy cyclohexyl)-4-methylbenzenesulfonamide;

3-(6-Amino-5-(2-methyl-2H-1,2,3-triazol-4-yl)pyridin-3-yl)-N-(2-hydroxy-2-methylpropyl)-4-methylbenzenesulfonamide;

trans 3-(6-Amino-5-(2-methyl-2H-1,2,3-triazol-4-yl)pyridin-3-yl)-N-(4-hydroxy cyclohexyl)-4-methylbenzene sulfonamide;

3-(6-Amino-5-(3-ethylisoxazol-5-yl)pyridin-3-yl)-N-(2-hydroxy-2-methylpropyl)-4-methylbenzenesulfonamide;

(R)-3-(6-Amino-5-(3-methylisoxazol-5-yl)pyridin-3-yl)-4-methyl-N-((tetra hydrofuran-3-yl)methyl)benzenesulfonamide;

3-(6-Amino-5-(3-methylisothiazol-5-yl)pyridin-3-yl)-N-(2-hydroxy-2-methylpropyl)-4-methylbenzenesulfonamide;

3-(6-Amino-5-(3-methyl-1,2,4-oxadiazol-5-yl)pyridin-3-yl)-4-methyl-N-((3-methyloxetan-3-yl)methyl)benzenesulfonamide;

3-(6-Amino-5-(3-isopropyl-1,2,4-oxadiazol-5-yl)pyridin-3-yl)-N-(2-hydroxy-2-methylpropyl)-4-methylbenzenesulfonamide;

trans 3-(6-Amino-5-(5-methyloxazol-2-yl)pyridin-3-yl)-N-(4-hydroxy cyclohexyl)-4-methylbenzene sulfonamide;

3-(6-Amino-5-(3-ethyl-1,2,4-oxa diazol-5-yl)pyridin-3-yl)-N-(2-hydroxy-2-methylpropyl)-4-methylbenzenesulfonamide;

trans 3-(6-Amino-5-(3-methylisoxazol-5-yl)pyridin-3-yl)-N-(–4-hydroxy cyclohexyl)-4-methylbenzenesulfonamide;

Diastereomers of 3-(6-Amino-5-(3-methyl-1,2,4-oxadiazol-5-yl)pyridin-3-yl)-N-(3-hydroxy cyclobutyl)-4-methylbenzene sulfonamide;

3-(6-Amino-5-(5-methyl-1,3,4-oxa diazol-2-yl)pyridin-3-yl)-N-(3-hydroxy-3-methylbutyl)-4-methylbenzenesulfonamide; and 3-(6-Amino-5-(3-methylisoxazol-5-yl)pyridin-3-yl)-N-(2-hydroxy-2-methylpropoxy)-4-methylbenzenesulfonamide;

or a pharmaceutically acceptable salt thereof.

In an embodiment 34 of the invention, there is provided a compound according to embodiment 1 selected from 3-(6-amino-5-(1-(2,2,2-trifluoroethyl)-1H-pyrazol-4-yl) pyridin-3-yl)-4-methyl-N-(6-methylpyridin-2-yl)benzenesulfonamide;

3-(6-amino-5-(1-(2,2,2-trifluoroethyl)-1H-pyrazol-4-yl)pyridin-3-yl)-N-(3-hydroxy-3-methylbutyl)-4-methylbenzenesulfonamide;

3-(6-amino-5-(2-methylthiazol-5-yl)pyridin-3-yl)-N-(3-hydroxy-3-methylbutyl)-4-methylbenzenesulfonamide;

3-(6-amino-5-(2-methyl-2H-1,2,3-triazol-4-yl)pyridin-3-yl)-N-(2-hydroxy-2-methylpropyl)-4-methylbenzenesulfonamide;

3-(6-amino-5-(2-methyl-2H-1,2,3-triazol-4-yl)pyridin-3-yl)-N-((1r,4r)-4-hydroxycyclohexyl)-4-methylbenzenesulfonamide;

3-(6-amino-5-(3-ethylisoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1r,4r)-4-hydroxycyclohexyl)-4-methylbenzenesulfonamide;

3-(6-amino-5-(2-methyloxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-(2-hydroxy-2-methylpropyl)-4-methylbenzenesulfonamide;

3-(6-amino-5-(2-methylthiazol-5-yl)pyridin-3-yl)-N-(3-hydroxypropyl)-4-methylbenzenesulfonamide;

3-(6-amino-5-(3-methyl-1,2,4-oxadiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-N-(2-hydroxy-2-methylpropoxy)-4-methylbenzenesulfonamide;

3-(6-amino-5-(3-methyl-1,2,4-oxadiazol-5-yl)pyridin-3-yl)-N-((1r,4r)-4-hydroxycyclohexyl)-4-methylbenzenesulfonamide;

3-(6-amino-5-(2-methyloxazol-5-yl)pyridin-3-yl)-N-(3-hydroxy-3-methylbutyl)-4-methylbenzenesulfonamide;

3-(6-amino-5-(3-methylisoxazol-5-yl)pyridin-3-yl)-N-((1S,3S)-3-hydroxycyclohexyl)-4-methylbenzenesulfonamide;

3-(6-amino-5-(3-methylisoxazol-5-yl)pyridin-3-yl)-N-(2-hydroxy-2-methyl propoxy)-4-methylbenzenesulfonamide;

(R)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-4-methyl-N-(oxetan-3-ylmethyl)benzenesulfonamide;

3-(6-amino-5-(3-methylisoxazol-5-yl)pyridin-3-yl)-N-(2,2-difluoroethyl)-4-methylbenzenesulfonamide;

3-(6-amino-5-(1-(2,2,2-trifluoroethyl)-1H-pyrazol-4-yl)pyridin-3-yl)-N-(2-hydroxy-2-methylpropoxy)-4-methylbenzenesulfonamide;

3-(6-amino-5-(3-(2,2,2-trifluoroethyl)isoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1s,3s)-3-hydroxycyclobutyl)-4-methylbenzenesulfonamide;

(S)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-4-methyl-N-(2,2,2-trifluoroethyl)benzenesulfonamide;

3-(6-amino-5-(3-(morpholine-4-carbonyl)isoxazol-5-yl)pyridin-3-yl)-N-(2-hydroxy-2-methylpropyl)-4-methylbenzenesulfonamide;

5-(2-amino-5-(5-(N-(2-hydroxy-2-methylpropyl)sulfamoyl)-2-methylphenyl)pyridin-3-yl)-N,N-dimethylisoxazole-3-carboxamide;

3-(6-amino-5-(3-methylisoxazol-5-yl)pyridin-3-yl)-N-((3-(hydroxymethyl)oxetan-3-yl)methyl)-4-methylbenzenesulfonamide;

3-(6-amino-5-(3-methyl-1,2,4-oxadiazol-5-yl)pyridin-3-yl)-N-((4-hydroxytetrahydro-2H-pyran-4-yl)methyl)-4-methylbenzenesulfonamide;

3-(6-amino-5-(3-methylisoxazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((3-hydroxyoxetan-3-yl)methyl)-4-methylbenzenesulfonamide;

3-(6-amino-5-(2-methyloxazol-5-yl)pyridin-3-yl)-N-((3-(hydroxymethyl)oxetan-3-yl)methyl)-4-methylbenzenesulfonamide;

3-(6-amino-5-(2-methylthiazol-5-yl)pyridin-3-yl)-N-((3-(hydroxymethyl)oxetan-3-yl)methyl)-4-methylbenzenesulfonamide;

3-(6-amino-5-(2-methyloxazol-5-yl)pyridin-3-yl)-4-methyl-N-((3-methyloxetan-3-yl)methyl)benzenesulfonamide;

3-(2-amino-2'-methyl-3,4'-bipyridin-5-yl)-N-((1r,4r)-4-(hydroxymethyl)cyclohexyl)-4-methylbenzenesulfonamide;

3-(6-amino-5-(3-(2,2,2-trifluoroethyl)-1,2,4-oxadiazol-5-yl)pyridin-3-yl)-N-((1r,4r)-4-hydroxycyclohexyl)-4-methylbenzenesulfonamide;

3-(6-amino-5-(2-methyloxazol-5-yl)pyridin-3-yl)-N-((1r,3r)-3-hydroxycyclobutyl)-4-methylbenzenesulfonamide;

5-(6-amino-5-(3-methyl-1,2,4-oxadiazol-5-yl)pyridin-3-yl)-2-fluoro-N-(2-hydroxy-2-methylpropyl)-4-methylbenzenesulfonamide;

3-(6-amino-5-(oxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1r,3r)-3-hydroxycyclobutoxy)-4-methylbenzenesulfonamide;

3-(6-amino-5-(3-methylisoxazol-5-yl)pyridin-3-yl)-N-(3-hydroxycyclopentyl)-4-methylbenzenesulfonamide;

3-(6-amino-5-(2-methyloxazol-5-yl)pyridin-3-yl)-N-((1r,4r)-4-hydroxycyclohexyl)-4-methylbenzenesulfonamide;

3-(6-amino-5-(5-methyl-1,3,4-thiadiazol-2-yl)pyridin-3-yl)-N-(2-hydroxy-2-methylpropyl)-4-methylbenzenesulfonamide;

3-(6-amino-5-(3-methylisoxazol-5-yl)pyridin-3-yl)-4-methyl-N-(1,1,1-trifluoro-3-hydroxypropan-2-yl)benzenesulfonamide;

3-(6-amino-5-(3-methylisoxazol-5-yl)pyridin-3-yl)-4-methyl-N-(1,1,1-trifluoro-3-hydroxypropan-2-yl)benzenesulfonamide;

3-(6-amino-5-(1-methyl-1H-pyrazol-4-yl)pyridin-3-yl)-N-((1r,4r)-4-hydroxycyclohexyl)-4-methylbenzenesulfonamide;

3-(6-amino-5-(3-methyl-1,2,4-oxadiazol-5-yl)pyridin-3-yl)-N-(3-hydroxycyclobutyl)-4-methylbenzenesulfonamide;

3-(6-amino-5-(2-methylthiazol-5-yl)pyridin-3-yl)-N-((3-hydroxyoxetan-3-yl)methyl)-4-methylbenzenesulfonamide;

3-(6-amino-5-(3-(hydroxymethyl)isoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1-hydroxycyclopropyl)methyl)-4-methylbenzenesulfonamide;

3-(6-amino-5-(1-methyl-1H-pyrazol-4-yl)pyridin-3-yl)-N-(3-hydroxy-3-methylbutyl)-4-methylbenzenesulfonamide;

3-(6-amino-5-(3-methylisoxazol-5-yl)pyridin-3-yl)-4-methylbenzenesulfonamide; and 3-(6-amino-5-(3-methylisoxazol-5-yl)pyridin-3-yl)-N-((3S,4R)-4-hydroxytetrahydrofuran-3-yl)-4-methylbenzenesulfonamide;

or a pharmaceutically acceptable salt thereof.

In an embodiment 35 of the invention, there is provided a compound according to embodiment 1 selected from 3-(6-amino-5-(1-(2,2,2-trifluoroethyl)-1H-pyrazol-4-yl)pyridin-3-yl)-4-methyl-N-(6-methylpyridin-2-yl)benzenesulfonamide;

3-(6-amino-5-(1-(2,2,2-trifluoroethyl)-1H-pyrazol-4-yl)pyridin-3-yl)-N-(3-hydroxy-3-methylbutyl)-4-methylbenzenesulfonamide;

3-(6-amino-5-(2-methyl-2H-1,2,3-triazol-4-yl)pyridin-3-yl)-N-(2-hydroxy-2-methylpropyl)-4-methylbenzenesulfonamide;

3-(6-amino-5-(2-methyl-2H-1,2,3-triazol-4-yl)pyridin-3-yl)-N-((1r,4r)-4-hydroxycyclohexyl)-4-methylbenzenesulfonamide;

3-(6-amino-5-(3-methylisoxazol-5-yl)pyridin-3-yl)-N-((1r,4r)-4-hydroxycyclohexyl)-4-methylbenzenesulfonamide;

3-(6-amino-5-(2-methyloxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-(2-hydroxy-2-methylpropyl)-4-methylbenzenesulfonamide;

3-(6-amino-5-(2-methylthiazol-5-yl)pyridin-3-yl)-N-(3-hydroxypropyl)-4-methylbenzenesulfonamide;

3-(6-amino-5-(3-methyl-1,2,4-oxadiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-N-(2-hydroxy-2-methylpropoxy)-4-methylbenzenesulfonamide;

3-(6-amino-5-(3-methyl-1,2,4-oxadiazol-5-yl)pyridin-3-yl)-N-((1r,4r)-4-hydroxycyclohexyl)-4-methylbenzenesulfonamide;

3-(6-amino-5-(3-methylisoxazol-5-yl)pyridin-3-yl)-N-((1S,3S)-3-hydroxycyclohexyl)-4-methylbenzenesulfonamide;

3-(6-amino-5-(3-methylisoxazol-5-yl)pyridin-3-yl)-N-(2-hydroxy-2-methylpropoxy)-4-methylbenzenesulfonamide;

(R)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-N-(2,2-difluoroethyl)-4-methylbenzenesulfonamide;

3-(6-amino-5-(1-(2,2,2-trifluoroethyl)-1H-pyrazol-4-yl)pyridin-3-yl)-N-(2-hydroxy-2-methylpropoxy)-4-methylbenzenesulfonamide;

3-(6-amino-5-(3-methylisoxazol-5-yl)pyridin-3-yl)-N-((1s,3s)-3-hydroxycyclobutyl)-4-methylbenzenesulfonamide;

(S)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-4-methyl-N-(2,2,2-trifluoroethyl)benzenesulfonamide;

3-(6-amino-5-(3-methyl-1,2,4-oxadiazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((3-hydroxyoxetan-3-yl)methyl)-4-methylbenzenesulfonamide;

3-(6-amino-5-(2-methyloxazol-5-yl)pyridin-3-yl)-N-((3-(hydroxymethyl)oxetan-3-yl)methyl)-4-methylbenzenesulfonamide;

3-(6-amino-5-(2-methylthiazol-5-yl)pyridin-3-yl)-N-((3-(hydroxymethyl)oxetan-3-yl)methyl)-4-methylbenzenesulfonamide;

3-(6-amino-5-(2-methyloxazol-5-yl)pyridin-3-yl)-4-methyl-N-((3-methyl oxetan-3-yl)methyl)benzenesulfonamide;

3-(2-amino-2'-methyl-3,4'-bipyridin-5-yl)-N-((1r,4r)-4-(hydroxymethyl)cyclohexyl)-4-methylbenzenesulfonamide;

3-(6-amino-5-(2-methyloxazol-5-yl)pyridin-3-yl)-N-((1r,3r)-3-hydroxycyclobutyl)-4-methylbenzenesulfonamide;

5-(6-amino-5-(3-methyl-1,2,4-oxadiazol-5-yl)pyridin-3-yl)-2-fluoro-N-(2-hydroxy-2-methylpropyl)-4-methylbenzenesulfonamide;

3-(6-amino-5-(oxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1r,3r)-3-hydroxycyclobutoxy)-4-methylbenzenesulfonamide;

3-(6-amino-5-(3-methylisoxazol-5-yl)pyridin-3-yl)-N-(3-hydroxycyclopentyl)-4-methylbenzenesulfonamide;

3-(6-amino-5-(5-methyl-1,3,4-thiadiazol-2-yl)pyridin-3-yl)-N-(2-hydroxy-2-methylpropyl)-4-methylbenzenesulfonamide;

3-(6-amino-5-(3-methylisoxazol-5-yl)pyridin-3-yl)-4-methyl-N-(1,1,1-trifluoro-3-hydroxypropan-2-yl)benzenesulfonamide;

3-(6-amino-5-(3-methylisoxazol-5-yl)pyridin-3-yl)-4-methyl-N-(1,1,1-trifluoro-3-hydroxypropan-2-yl)benzenesulfonamide;

3-(6-amino-5-(1-methyl-1H-pyrazol-4-yl)pyridin-3-yl)-N-((1r,4r)-4-hydroxycyclohexyl)-4-methylbenzenesulfonamide;

3-(6-amino-5-(3-methyl-1,2,4-oxadiazol-5-yl)pyridin-3-yl)-N-(3-hydroxycyclobutyl)-4-methylbenzenesulfonamide;

3-(6-amino-5-(2-methylthiazol-5-yl)pyridin-3-yl)-N-((3-hydroxyoxetan-3-yl)methyl)-4-methylbenzenesulfonamide;

3-(6-amino-5-(3-(hydroxymethyl)isoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1-hydroxycyclopropyl)methyl)-4-methylbenzenesulfonamide;

3-(6-amino-5-(1-methyl-1H-pyrazol-4-yl)pyridin-3-yl)-N-(3-hydroxy-3-methylbutyl)-4-methylbenzenesulfonamide;

3-(6-amino-5-(3-methylisoxazol-5-yl)pyridin-3-yl)-4-methylbenzenesulfonamide; and 3-(6-amino-5-(3-methylisoxazol-5-yl)pyridin-3-yl)-N-((3S,4R)-4-hydroxytetrahydrofuran-3-yl)-4-methylbenzenesulfonamide;

or a pharmaceutically acceptable salt thereof.

In an embodiment 35.1 of the invention, there is provided a compound according to embodiment 1 selected from 3-(6-amino-5-(2-methyl-2H-1,2,3-triazol-4-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1S,2S)-2-hydroxycyclopentyl)-4-methylbenzenesulfonamide;

3-(6-amino-5-(3-methylisoxazol-5-yl)pyridin-3-yl)-N-(2-hydroxy-2-methylpropyl)-4-methylbenzenesulfonamide;

3-(6-amino-5-(5-methyl-1,3,4-thiadiazol-2-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-N-(2-hydroxy-2-methylpropyl)-4-methylbenzenesulfonamide;

5-(6-amino-5-(3-methyl-1,2,4-oxadiazol-5-yl)pyridin-3-yl)-N-(2-hydroxy-2-methylpropyl)-2,4-dimethylbenzenesulfonamide;

3-(6-amino-5-(2-methyloxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1S,3S)-3-hydroxycyclohexyl)-4-methylbenzenesulfonamide;

3-(6-amino-5-(2-methylthiazol-5-yl)pyridin-3-yl)-N-((3-hydroxyoxetan-3-yl)methyl)-4-methylbenzenesulfonamide;

3-(6-amino-5-(2-methylthiazol-5-yl)pyridin-3-yl)-N-((3-(hydroxymethyl) oxetan-3-yl)methyl)-4-methylbenzenesulfonamide;

3-(6-amino-5-(3-methylisoxazol-5-yl)pyridin-3-yl)-N-((1r,3r)-3-hydroxycyclobutyl)-4-methylbenzenesulfonamide;

3-(6-amino-5-(3-(morpholine-4-carbonyl)isoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((3-(hydroxymethyl)oxetan-3-yl)methyl)-4-methylbenzenesulfonamide;

3-(6-amino-5-(3-methylisoxazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((1s,3s)-3-hydroxycyclobutyl)-4-methylbenzenesulfonamide;

3-(6-amino-5-(3-methylisoxazol-5-yl)pyridin-3-yl)-N-(3-hydroxycyclopentyl)-4-methylbenzenesulfonamide;

3-(6-amino-5-(3-methylisoxazol-5-yl)pyridin-3-yl)-N-((1-hydroxycyclopropyl)methyl)-4-methylbenzenesulfonamide;

(S)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-N-((1r,3r)-3-hydroxycyclobutoxy)-4-methylbenzenesulfonamide;

(R)-3-(6-amino-5-(3-methylisoxazol-5-yl)pyridin-3-yl)-N-(2-hydroxypropyl)-4-methylbenzenesulfonamide 3-(6-amino-5-(3-methyl-1,2,4-oxadiazol-5-yl)pyridin-3-yl)-N-((3-hydroxyoxetan-3-yl)methyl)-4-methylbenzenesulfonamide;

3-(6-amino-5-(3-methylisoxazol-5-yl)pyridin-3-yl)-4-methyl-N-(1,1,1-trifluoro-3-hydroxypropan-2-yl)benzenesulfonamide;

3-(6-amino-5-(3-methylisoxazol-5-yl)pyridin-3-yl)-4-methyl-N-(1,1,1-trifluoro-3-hydroxypropan-2-yl)benzenesulfonamide;

3-(6-amino-5-(1-(2,2,2-trifluoroethyl)-1H-pyrazol-4-yl)pyridin-3-yl)-N-(2-hydroxy-2-methylpropoxy)-4-methylbenzenesulfonamide;

3-(6-amino-5-(3-(hydroxymethyl)isoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-(2-hydroxy-2-methylpropoxy)-4-methylbenzenesulfonamide;

5-(6-amino-5-(3-methyl-1,2,4-oxadiazol-5-yl)pyridin-3-yl)-2-fluoro-N-(2-hydroxy-2-methylpropyl)-4-methylbenzenesulfonamide;

3-(6-amino-5-(3-methylisoxazol-5-yl)pyridin-3-yl)-N-((3S,4R)-4-hydroxytetrahydrofuran-3-yl)-4-methylbenzenesulfonamide;

3-(6-amino-5-(3-methylisoxazol-5-yl)pyridin-3-yl)-N-(((1s,3s)-3-hydroxycyclobutyl)methyl)-4-methylbenzenesulfonamide;

3-(6-amino-5-(3-methylisoxazol-5-yl)pyridin-3-yl)-4-methyl-N-(2,2,2-trifluoroethyl)benzenesulfonamide; and 3-(6-amino-5-(3-methylisoxazol-5-yl)pyridin-3-yl)-N-(2-hydroxyethyl)-4-methylbenzenesulfonamide;

or a pharmaceutically acceptable salt thereof.

In an embodiment 35.2 of the invention, there is provided a compound according to embodiment 1 selected from 3-(6-amino-5-(2-methyl-2H-1,2,3-triazol-4-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1S,2S)-2-hydroxycyclopentyl)-4-methylbenzenesulfonamide;

3-(6-amino-5-(3-methylisoxazol-5-yl)pyridin-3-yl)-N-(2-hydroxy-2-methylpropyl)-4-methylbenzenesulfonamide;

3-(6-amino-5-(5-methyl-1,3,4-thiadiazol-2-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-N-(2-hydroxy-2-methylpropyl)-4-methylbenzenesulfonamide;

5-(6-amino-5-(3-methyl-1,2,4-oxadiazol-5-yl)pyridin-3-yl)-N-(2-hydroxy-2-methylpropyl)-2,4-dimethylbenzenesulfonamide;

3-(6-amino-5-(2-methyloxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1S,3S)-3-hydroxycyclohexyl)-4-methylbenzenesulfonamide;

3-(6-amino-5-(2-methylthiazol-5-yl)pyridin-3-yl)-N-((3-hydroxyoxetan-3-yl)methyl)-4-methylbenzenesulfonamide; and 3-(6-amino-5-(3-methylisoxazol-5-yl)pyridin-3-yl)-N-((1r,3r)-3-hydroxycyclobutoxy)-4-methylbenzenesulfonamide;

or a pharmaceutically acceptable salt thereof.

In an embodiment 36 of the invention, there is provided a compound or salt according to any one of embodiments 1-35, or a pharmaceutically acceptable salt thereof, for use in medicine.

In an embodiment 37 of the invention, there is provided a compound or salt according to any one of embodiments 1-35 for use in the treatment of a disorder or disease mediated by the activation of PI 3-kinase gamma isoform (p110-γ).

In an embodiment 38 of the invention, there is provided a compound or salt according to any one of embodiments 1-35 for use in the treatment of inflammatory, obstructive or allergic conditions.

In an embodiment 39 of the invention, there is provided a compound or salt according to any one of embodiments 1-35 for use in the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 40 of the invention, there is provided a compound or salt according to any one of embodiments 1-35 for use in the treatment of respiratory diseases, particularly asthma, COPD, COAD, COLD, chronic bronchitis, dyspnea or emphysema, more particularly asthma.

In an embodiment 41 of the invention, there is provided the use of a compound according to any one of embodiments 1-35, or a pharmaceutically acceptable salt thereof, in the manufacture of a medicament for the treatment of a disorder or disease mediated by the activation of PI 3-kinase gamma isoform (p110-γ).

In an embodiment 42 of the invention, there is provided the use of a compound according to any one of embodiments 1-35, or a pharmaceutically acceptable salt thereof, in the manufacture of a medicament for the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 43 of the invention, there is provided the use of a compound according to any one of embodiments 1-35, or a pharmaceutically acceptable salt thereof, in the manufacture of a medicament for the treatment of respiratory diseases, particularly asthma, COPD, COAD, COLD, chronic bronchitis, dyspnea or emphysema, more particularly asthma.

In an embodiment 44 of the invention, there is provided the use of a compound according to any one of embodiments 1-35, or a pharmaceutically acceptable salt thereof, for the treatment of a disorder or disease mediated by the activation of PI 3-kinase gamma isoform (p110-γ).

In an embodiment 45 of the invention, there is provided the use of a compound according to any one of embodiments 1-35, or a pharmaceutically acceptable salt thereof, for the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 46 of the invention, there is provided the use of a compound according to any one of embodiments 1-35, or a pharmaceutically acceptable salt thereof, for the treatment of respiratory diseases, particularly asthma, COPD, COAD, COLD, chronic bronchitis, dyspnea or emphysema, more particularly asthma.

In an embodiment 47 of the invention, there is provided a method of treating a disorder or disease mediated by the activation of PI 3-kinase gamma isoform (p110-γ), comprising administering to a subject in need thereof a therapeutically effective amount of a compound according to any one of embodiments 1-35, or a pharmaceutically acceptable salt thereof.

In an embodiment 48 of the invention, there is provided a method of treating respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis, comprising administering to a subject in need thereof a therapeutically effective amount of a compound according to any one of embodiments 1-35, or a pharmaceutically acceptable salt thereof.

In an embodiment 49 of the invention, there is provided a method of treating respiratory diseases, particularly asthma, COPD, COAD, COLD, chronic bronchitis, dyspnea or emphysema, more particularly asthma, comprising administering to a subject in need thereof a therapeutically effective amount of a compound according to any one of embodiments 1-35, or a pharmaceutically acceptable salt thereof.

In an embodiment 50 of the invention, there is provided a pharmaceutical composition comprising:

a therapeutically effective amount of the compound according to any one of embodiments 1-35, or a pharmaceutically acceptable salt thereof, and one or more pharmaceutically acceptable carriers.

In an embodiment 51 of the invention, there is provided a pharmaceutical combination, comprising:

a therapeutically effective amount of the compound according to any one of embodiments 1 to 35, or a pharmaceutically acceptable salt thereof, and a second active agent.

In an embodiment 52 of the invention, there is provided a pharmaceutical combination according to embodiment 51, wherein the second active agent is selected from an anti-inflammatory, bronchodilatory or antihistamine drug substance.

In another embodiment, individual compounds according to the invention are those listed in the Examples section below.

The term "compounds of the present invention" or "a compound of the present invention" refers to a compound as defined in any one of embodiments 1-35.

The compounds as defined in embodiments 1-35 may be synthesized by the general synthetic routes below, specific examples of which are described in the Example section.

Scheme 1

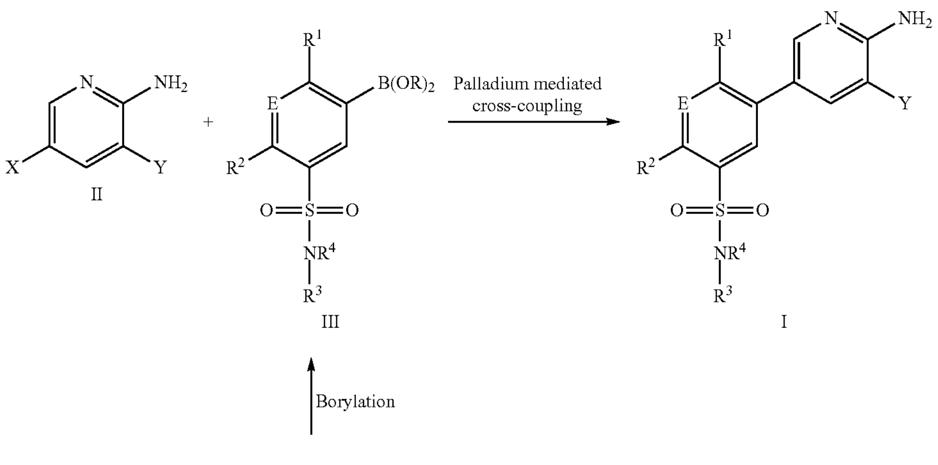

-continued

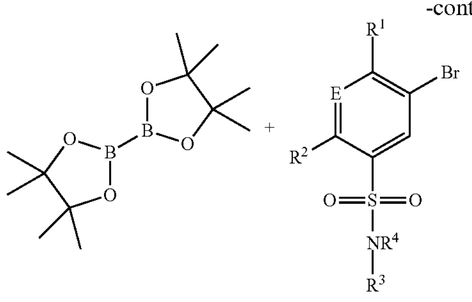

IV wherein Y, $R^1$, $R^2$, $R^3$, $R^4$ and E are defined as in embodiment 1, and X is a halogen such as I, Br or Cl.

The reaction between compound II and boronic acid or boronic ester III to form compounds of formula I as shown in Scheme 1 may be carried out using a suitable palladium catalyst, such as $Pd(PPh_3)_2Cl_2$, $PdCl_2(dtbpf)$, $Pd(dppf)Cl_2$ or its adduct with dichloromethane, in a suitable solvent or mixture of solvents, such as DME, acetonitrile, 1,4-dioxane or toluene/ethanol. The reaction typically requires a base, such as aqueous sodium carbonate or aqueous potassium phosphate and may be carried out at elevated temperatures, using conventional or microwave heating.

Compounds of formula II may be obtained from commercial suppliers, prepared as described in Schemes 2a, 2d, 3a, 6, 6a, 6b, 6c, 6d or 6e, or by other methods known in the art.

Compounds of formula III may be obtained from commercial suppliers or prepared by borylation of an aryl bromide of formula IV with a boron source such as bis (pinacolato)diboron (Scheme 1) at elevated temperature using conventional or microwave heating. This reaction is typically catalysed by a palladium catalyst such as $Pd(dppf)Cl_2.CH_2Cl_2$, and utilises a suitable base such as potassium acetate in an appropriate solvent such as DME or dioxane.

In a variation of scheme 1, this borylation of IV to form III may be followed without isolation of III by the subsequent coupling with compound II in a 'one-pot' procedure to form compound I.

In a further variation of scheme 1, the 'one-pot' procedure can be carried out by borylation of II and subsequent coupling with IV.

Compounds of formula IV may be obtained from commercial suppliers, prepared as described in Scheme 4, or by other methods known in the art.

Scheme 2

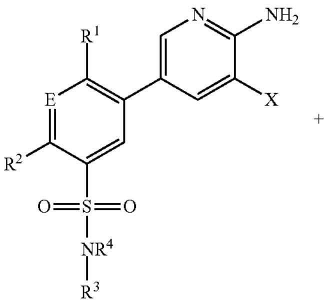

V

-continued

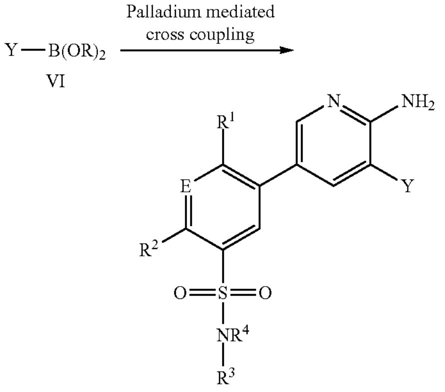

I' wherein Y, $R^1$, $R^2$, $R^3$, $R^4$ and E are defined as in embodiment 1, and X is a halogen such as I, Br or Cl.

Where Y is attached to the pyridine ring by a carbon-carbon bond, compounds of formula I' may be prepared as shown in Scheme 2 via a reaction between compounds V and boronic acid or ester VI, carried out using a suitable palladium catalyst, such as $Pd(dppf)Cl_2.CH_2Cl_2$ or $Pd(PPh_3)_2Cl_2$ in a suitable solvent, such as DME or MeCN. The reaction typically requires a base, such as aqueous sodium carbonate and may be carried out at elevated temperatures using conventional or microwave heating.

Scheme 2a

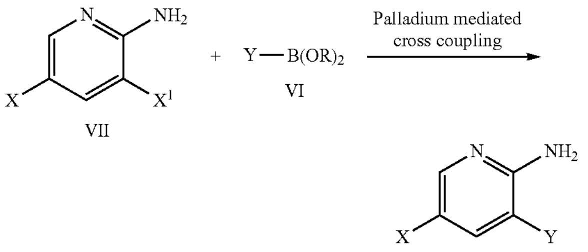

II wherein Y is defined as in embodiment 1, and X and X1 are halogens such as I, Br or Cl.

The same general method as in Scheme 2 can be used to prepare compounds of formula II, where Y is attached to the pyridine ring by a carbon-carbon bond, via a reaction between a compound of formula VII, such as 5-bromo-3-iodopyridin-2-amine and boronic ester or acid VI as shown in Scheme 2a.

Scheme 2b

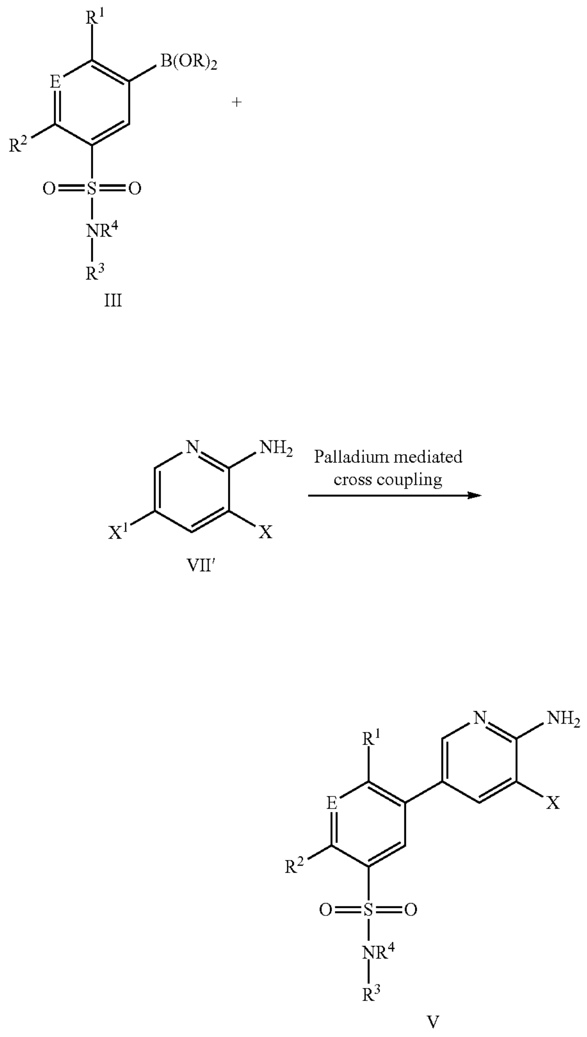

wherein $R^1$, $R^2$, $R^3$, $R^4$ and E are defined as in embodiment 1, and X and X1 are halogens such as I, Br or Cl.

The same general method as in Scheme 2 can be used to prepare compounds of formula V, via a reaction between a compound of formula III and a compound of formula VII' where X and X1 are halogens, such as 3-bromo-5-iodopyridin-2-amine, as shown in Scheme 2b.

Scheme 2c

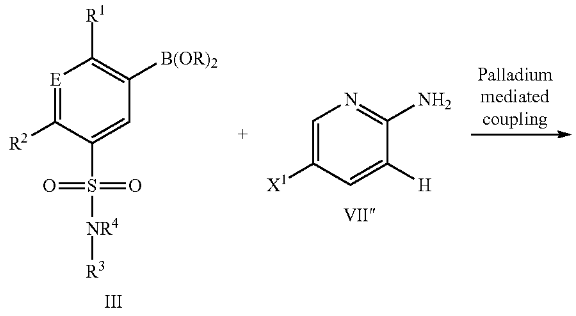

-continued

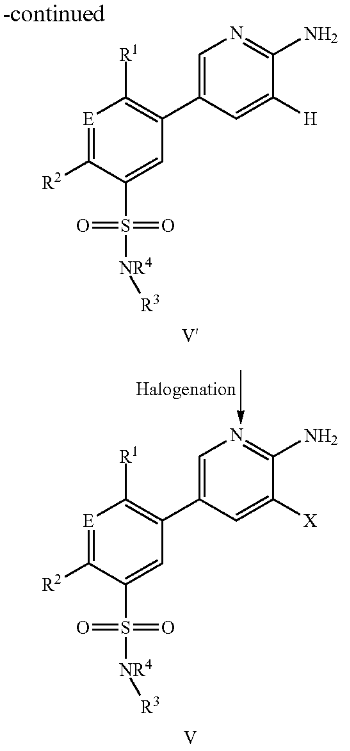

wherein Y, $R^1$, $R^2$, $R^3$, $R^4$ and E are defined as in embodiment 1, and X and X1 are halogens such as I, Br or Cl.

The same general method as in Scheme 2 can be used to prepare compounds of formula V' as shown in Scheme 2c, which can then be converted into a compound of formula V via a halogenation. Typically the halogenation could be carried out with a halogenating agent such as N-bromosuccinimide in an appropriate solvent such as DCM.

Scheme 2d

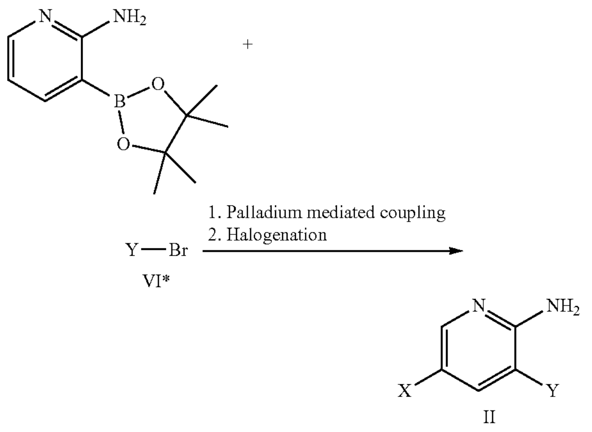

wherein Y is defined as in embodiment 1, and X is a halogen such as I, Br or Cl.

The same general method can be used to prepare compounds of formula II, where Y is attached to the pyridine ring by a carbon-carbon bond, as shown in Scheme 2d, via the reaction of a heteroaryl bromide VI* with 2-aminopyridine-3-boronic acid pinacol ester (available commercially or prepared by known methods) followed by halogenation.

Compounds of formula VI, VII, VII' and VII" are commercially available or may be prepared according to known methods.

Scheme 2e

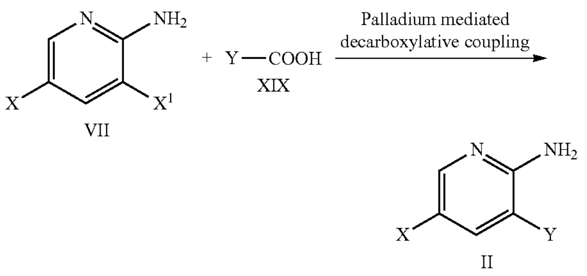

VII XIX II wherein Y is defined as in embodiment 1, and X and X1 are halogens such as I, Br or Cl.

Compounds of formula II may be prepared by a decarboxylative cross-coupling of carboxylic acid XIX (obtained from commercial suppliers or prepared by known methods) with compound VII. Reagents for the coupling are known in the art and include a suitable palladium catalyst, such as $Pd(PPh_3)_2Cl_2$ and a base (preferentially a silver salt such as silver carbonate) in an appropriate solvent such as NMP (N-methylpyrrolidinone) at elevated temperature.

Scheme 3

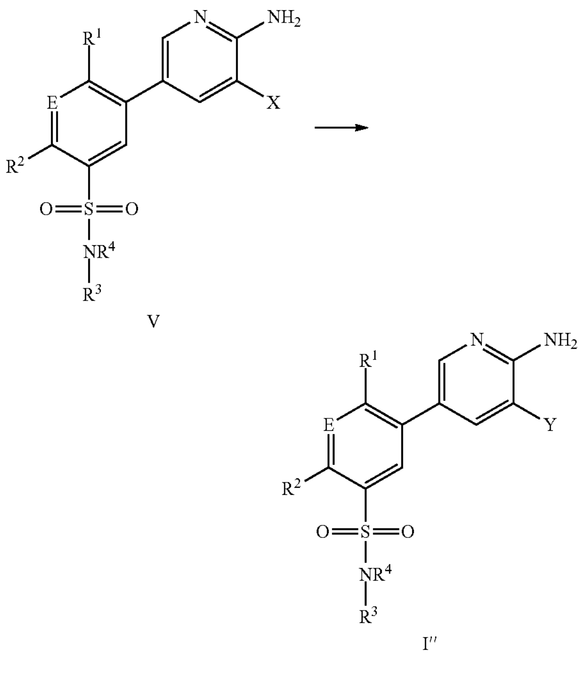

V I"

wherein Y, $R^1$, $R^2$, $R^3$, $R^4$ and E are defined as in embodiment 1, and where Y can be attached to the pyridine ring by a nitrogen-carbon bond, and X is a halogen such as I, Br or Cl.

Compounds of formula I" may be prepared by a reaction of compound V with an appropriate heteroaryl containing an NH group, such as (optionally substituted) 1,2,4-triazole or pyrazole.

This reaction is typically carried out in the presence of a suitable base such as cesium carbonate, in a suitable solvent such as dimethyl acetamide (DMA), optionally in the presence of an appropriate catalyst system such as CuI and N,N-dimethylglycine at an elevated temperature such as 150-180° C. using, for example, microwave heating.

Scheme 3a

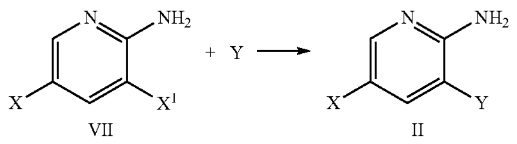

VII II wherein Y is defined as in embodiment 1, and where Y is attached to the pyridine ring by a nitrogen-carbon bond, and X and X1 are halogen atoms such as I, Br or Cl.

The same method as in Scheme 3 can be used to prepare compounds of formula II as shown in Scheme 3a, via reaction between a compound of formula VII, such as 5-bromo-3-iodopyridin-2-amine and an appropriate heteroaryl containing an NH group, such as (optionally substituted) 1,2,4-triazole or pyrazole.

Scheme 3b

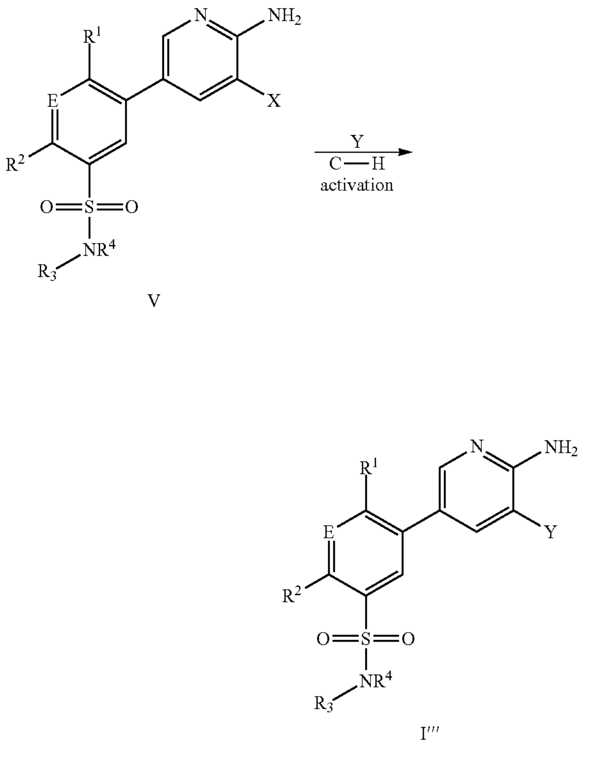

V I'''

In certain cases compounds (I''') can also be prepared directly from aminopyridine halides and heterocycles, such as oxazole (to give I''' where Y is oxazol-5-yl), using a palladium catalysed C—H activation protocol as shown in Scheme B. Typical conditions use palladium acetate with an added ligand such as di(adamant-1-yl)-n-butyl phosphine, with a base such as potassium carbonate and an additive such as pivalic acid in a solvent such as dimethylacetamide, heating at temperatures such as 110° C.

Scheme 4

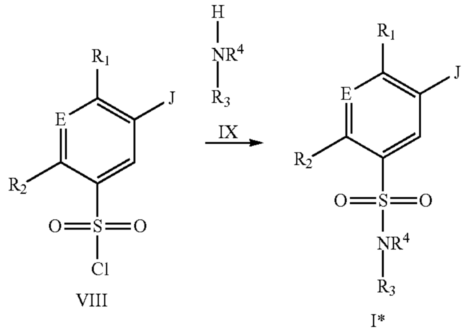

VIII I* wherein J is

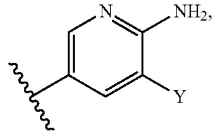

and Y, $R^1$, $R^2$, $R^3$, $R^4$ and E are defined as in embodiment 1,

Compound of formula (I*) may be prepared by reacting VIII with an amine IX in the presence of a suitable base such as pyridine, triethylamine or diisopropylethylamine, in a suitable solvent such as DCM, THF, pyridine or dimethylacetamide.

Where J is bromo, the same method can be used to prepare compounds of formula IV. Compounds of formula IX are commercially available or may be prepared by known methods.

Compounds of formula VIII are commercially available or may be prepared according to the following Scheme 5, wherein J is bromo or

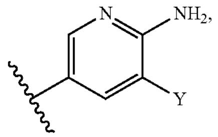

and Y, $R^1$, $R^2$ and E are defined as in embodiment 1, by chlorosulfonation of a compound of formula X, typically using chlorosulfonic acid in an appropriate solvent such as chloroform, at ambient temperature or with cooling such as to 0° C.

Scheme 5

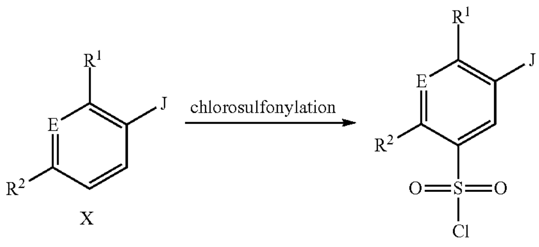

X VIII

Scheme 6

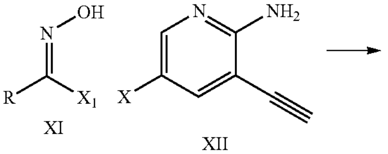

XI XII

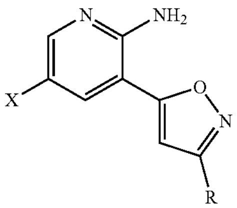

II'

Wherein R is one of the substitutents as listed in the definition of Y in embodiment 1, and X and X1 are independently halogens such as Br, Cl or I.

Compounds of formula II' (compounds of formula II where Y is isoxazol-5-yl substituted in the 3 position) can be prepared according to the route shown in Scheme 6 by the reaction of a compound of formula XI with an alkyne of formula XII. Typical conditions for this transformation use copper (II) sulfate, sodium ascorbate and sodium bicarbonate in appropriate solvent mixtures such as t-BuOH and water, under a nitrogen atmosphere at ambient temperature.

Compounds of formulae X and XII are commercially available or can be prepared by known methods. Compounds of formula XI are commercially available, or can be prepared by known methods, or prepared in situ. For example compounds of formula XI can be prepared by halogenation of aldehyde oximes.

Compounds of formula II' can also be formed by cycloisomerization of acetylenic oximes as shown in scheme 6a.

Scheme 6a

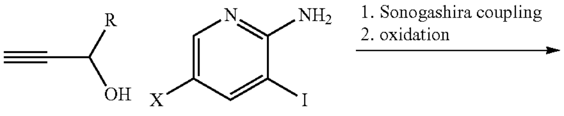

XIV

-continued

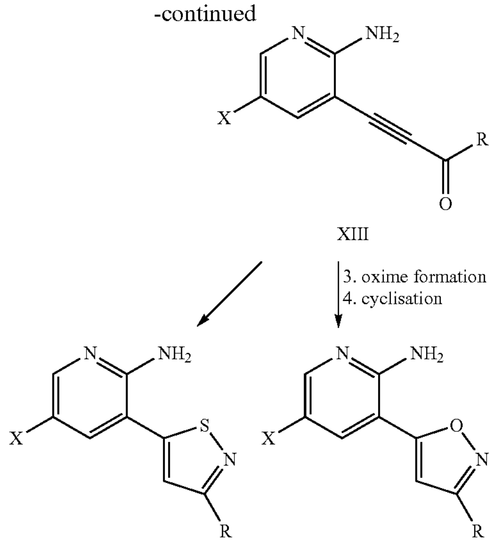

XIII

II*

II' wherein R and X are as defined in Scheme 6.

Following oxime formation using hydroxylamine by known methods, the cyclisation in step 4 is typically catalysed by acid (such as aqueous HCl in AcOH) or by gold catalysis as described in Synlett, 2010, No. 5, pp 0777-0781.

Compound II* can also be formed from compound XIII, for example by treatment with hydroxylamine-O-sulfonic acid, sodium bicarbonate and sodium hydrogen sulfide in an appropriate solvent mixture such as THF/water.

Compound XIII can be formed from a dihaloaminopyridine such as 3-iodo-5-bromopyridin-2-amine using known methods, for example Sonagashira coupling with propargylic alcohol XIV, followed by oxidation using an oxidising agent such as manganese dioxide.

Compounds of formula XIV are commercially available or can be prepared by known methods.

Scheme 6b

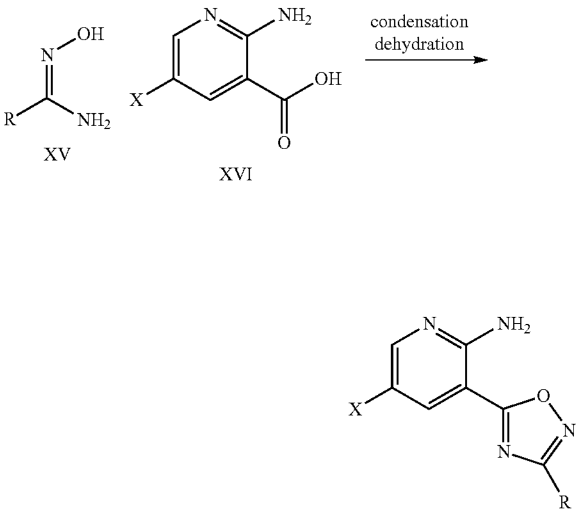

XV

XVI

II"

Scheme 6c

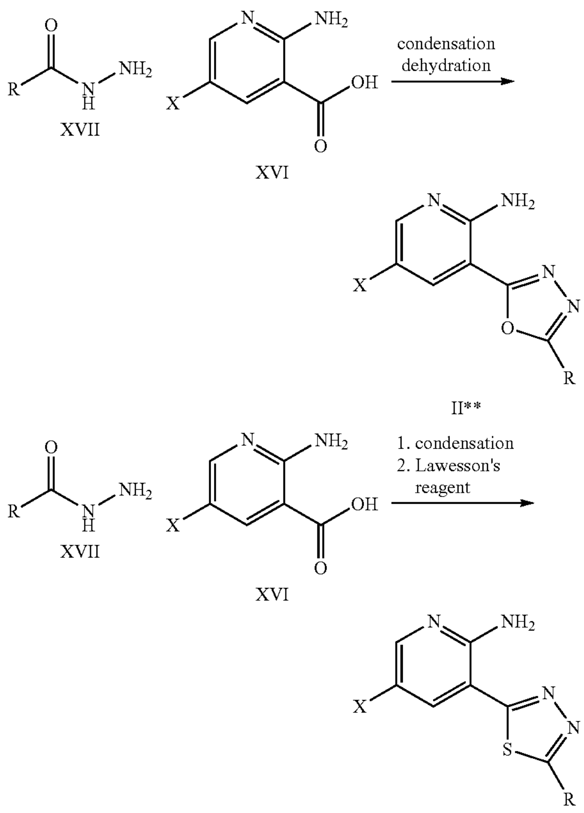

XVII

XVI

II**

XVII

XVI

II*** wherein R and X are as defined in Scheme 6.

Compounds of formula II" (compounds of formula II where Y is [1,2,4]oxadiazol-5-yl substituted in the 3 position) may be prepared by condensation and dehydration of amidoxime XV and acid XVI as shown in Scheme 6b. Suitable reagents for the condensation and dehydration are known in the art and include 1-Chloro-N,N,2-trimethyl-1-propenylamine (Ghosez' reagent), T3P, HATU in an appropriate solvent such as DCM, THF or toluene, in the presence of an appropriate base such as DIPEA. In a related reaction shown in Scheme 6c, compounds of formula II are prepared by condensation and dehydration of compounds XVI and XVII using conditions known in the art, typically using phosphorus oxychloride. Similarly, condensation of compounds XVI and XVII, typically using T3P, followed by treatment of the resulting N-acylhydrazide with Lawesson's reagent can be used to prepare compounds of formula II*.

Compounds of formulae XV, XVI and XVII are commercially available or can be prepared by known methods.

Scheme 6d

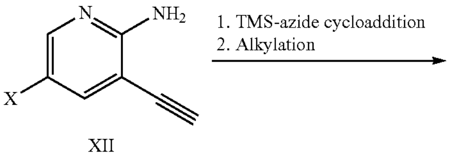

XII

-continued

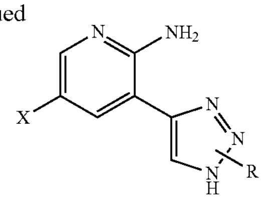

II''' wherein X and R are as defined in Scheme 6.

Compounds of formula II''' (compounds of formula II where Y is 1,2,3-triazol-4-yl optionally substituted in the 1 or 2 position) are prepared by reaction of alkyne XII with trimethylsilyl azide as shown in scheme 6d. Typical conditions for this transformation use copper (II) sulfate, sodium ascorbate and sodium bicarbonate in appropriate solvent mixtures such as t-BuOH and water, at elevated temperature such as 90° C. Alkylation by known methods (such as iodomethane, TBAF, THF at 0° C.) gives rise to compounds of formula II''' as a separable mixture of N1 and N2-alkylated products.

Scheme 6e

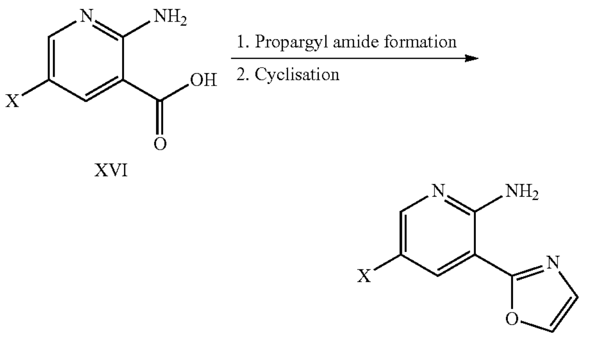

XVI

II# wherein X is a halogen such as Br, Cl and I.

Compounds of formula II# can be prepared from compound XVI by formation of a propargyl amide using known conditions, followed by cyclisation, for example using gold (III) chloride in a solvent such as DCM.

Scheme 7

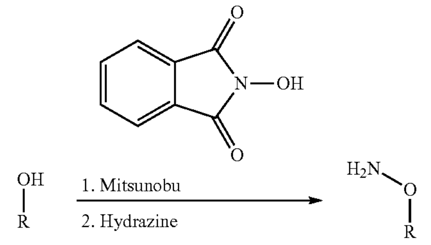

XVIII

IX'

Compounds of formula IX' can be prepared from alcohols XVIII by treatment with N-hydroxyphthalamide under Mitsunobu-type conditions known in the art (for example using PS-triphenylphosphine and di-tert-butyl azodicarboxylate in a solvent such as THF), followed by deprotection of the phthalamide group using conditions known in the art, typically by treatment with hydrazine.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under “Additional process steps”.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning. The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl $4^{th}$ Ed. 1952, Methods of Organic Synthesis, Thieme, Volume 21).

The term “an optical isomer” or “a stereoisomer” refers to any of the various stereoisomeric configurations which may exist for a given compound of the present invention and includes geometric isomers. It is understood that a substituent may be attached at a chiral center of a carbon atom. The term “chiral” refers to molecules which have the property of non-superimposability on their mirror image partner, while the term “achiral” refers to molecules which are superimposable on their mirror image partner. Therefore, the invention includes enantiomers, diastereomers or racemates of the compound. “Enantiomers” are a pair of stereoisomers that are non-superimposable mirror images of each other. A 1:1 mixture of a pair of enantiomers is a “racemic” mixture. The term is used to designate a racemic mixture where appropriate. “Diastereoisomers” are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

The compounds of the present invention are potent inhibitors of the PI 3-kinase gamma isoform. This is shown in Table 4, assay E. Furthermore and importantly, the compounds of the present invention are selective for the PI 3-kinase gamma isoform over the other class 1 PI 3-kinase isoforms alpha, beta and delta, which is shown in Table 4, assays A, B and F, and over related lipid kinases Vps34 and PI 4-kinase beta, which is shown in Table 4, assays C and D, and also over the PI 3-kinase related protein kinases such as mTOR (Table 4, assay G). Selectivity for PI 3-kinase gamma isoform is preferred in order to avoid possible unwanted side effects when treating patients. Particularly, selectivity for the PI 3-kinase gamma isoform over the PI 3-kinase alpha isoform is preferred as the PI 3-kinase alpha isoform is widely expressed in the body and has shown to be important in insulin receptor signalling.

The target enzyme of the compounds of the present invention, i.e. PI 3-kinase gamma isoform, is an intracellular target. Thus, compounds of the present invention which retain their activity in a cellular environment are preferred. The compounds of the present invention have thus been tested in cellular assays (see Table 5, assays H1, H2, I1, I2, J1, J2, K1 and K2). In assays K1 and K2, the compounds were tested for their ability to inhibit the production of phosphorylated AKT (Protein Kinase B) generated in a PI 3-kinase gamma isoform-dependent process in a U937 human cell line. Activity of a particular compound in a cellular assay depends on a variety of different factors such as potency of that compound at the target (see Table 4), solubility of the compound, Log P and permeability. Thus, good cellular activity of compounds of the present invention results from the combination of structural features conveying a good overall balance of molecular properties. Generally, preferred compounds of the present invention have high potency at the target (see Table 4) and show good activity in the cellular assays (Table 5).

In order to effectively inhibit the PI 3-kinase gamma isoform target (present in leukocytes) in an in vivo system, a drug compound will preferably need to show sufficient activity in whole blood. Hence, compounds of the present invention have been tested for their ability to inhibit neutrophil shape change in response to the chemotactic factor interleukin-8 (IL-8), which is a PI 3-kinase gamma isoform-dependent event, in human whole blood (Table 5, assay L). Activity in whole blood is dependent on additional factors such as plasma protein binding and plasma stability of a particular compound. Preferred compounds of the present invention thus have besides of potency at the PI 3-kinase gamma isoform target (Table 4) and sufficient cellular potency (Table 5) also sufficient activity in human whole blood as tested in assay L. More preferably, compounds of the present invention have IC50 values of in this human whole blood assay of <1 μM.

Additionally to the on-target potency (Table 4, assay E)), selectivity (Table 4, assays A, B, C, D, F and G), activity in cellular assays (Table 5, assays H1, H2, I1, I2, J1, J2, K1 and K2) and human whole blood assay (Table 5, assay L), the maintenance of sufficient drug concentration in vivo after oral administration to inhibit the target is required. Such pharmacokinetic properties are dependent on a variety of factors such as Log P, permeability, aqueous solubility and stability against oxidative metabolism. Compounds of the present invention have been tested for stability against oxidative metabolism using an in vitro microsomal stability assay (Table 5, assay M). Preferred compounds of the present invention show sufficient stability in this liver microsomal assay. Furthermore, preferred compounds of the present invention also have sufficient aqueous solubility.

Thus, the compounds of the present invention may be useful in the treatment of conditions which are mediated by the activation of PI 3-kinase gamma isoform, particularly inflammatory or allergic conditions.

Compounds of the present invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, compounds of the present invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the present invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Compounds of the present invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, leishmaniasis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with compounds of the present invention include thrombosis, hypertension, heart ischaemia and pancreatitis, (Nature review November 2006 Vol 5), treatment of anaemia including haemolytic anaemia, aplastic anaemia and pure red cell anaemia (WO 2006/040318), septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

Agents of the present invention may be useful in the treatment or prevention of heart failure such as (acute and chronic) congestive heart failure, left ventricular dysfunction including impaired cardiac contractility, hypertrophic cardiomyopathy, diabetic cardiac myopathy and other types of detrimental cardiac dysfunction and remodelling.

The compounds of the present invention may also be useful in the treatment of visceral disorders, inflammatory bowel disease, inflammatory bowel disorder, cystitis, e.g. interstitial cystitis and urinary incontinence including bladder detrusor hyper-reflexia and bladder hypersensitivity.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The compounds of the present invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosage or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition.

The compounds of the present invention are also useful as co-therapeutic agents for use in combination with PI 3-Kinase delta inhibitors, for example in allergic asthma or in immune-mediated inflammatory diseases, such as rheumatoid arthritis or multiple sclerosis. Such an effect could be potentially achieved through co-administration of a selective inhibitor of PI 3-kinase gamma isoform with a selective inhibitor of PI 3-kinase delta isoform.

Useful combinations of PI 3-kinase inhibitors with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-aminium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula:

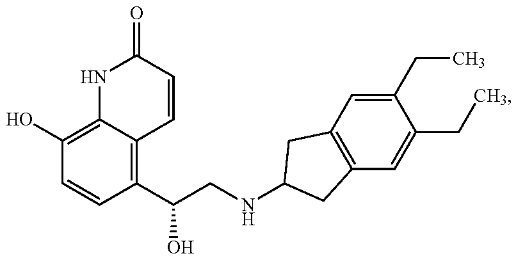 [SMILES: CCc1cc2c(cc1CC)CC(NC[C@H](O)c1ccc(O)c3[nH]c(=O)ccc13)C2]

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841

Pi3 kinase inhibitors, e.g. those compounds of the invention, may be combined with an angiotensin receptor blocker, e.g. valsartan (an angiotensin receptor blocker) and achieve greater therapeutic effect than the administration of valsartan alone. The combination regimen also surprisingly reduces the rate of progression of cardiac, renal and cerebral end-organ damage. The combination elicits enhanced antihypertensive effects (whether malignant, essential, reno-vascular, diabetic, isolated systolic, or other secondary type of hypertension) and lessening of pulse pressure. The combination is also effective in treating supraventricular and ventricular arrhythmias, atrial fibrillation, atrial flutter or detrimental vascular remodeling. It can further be shown that the combination is beneficial in the treatment and prevention of myocardial infarction and its sequelae, and is useful in treating atherosclerosis, angina (whether stable or unstable), renal insufficiency (diabetic and non-diabetic), peripheral vascular disease, cognitive dysfunction, and stroke. Furthermore, the improvement in endothelial function with the combination therapy provides benefit in diseases in which normal endothelial function is disrupted such as heart failure, angina pectoris and diabetes. Furthermore, the combination may be used for the treatment or prevention of primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke.

Compounds of the present invention may also be useful in the treatment of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, Graves ophthalmopathy, alopecia areata and others, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis and further eczematous dermatitises, seborrhoeic dermatitis, cutaneous manifestations of immunologically-mediated disorders, inflammatory eye disease, myocarditis or hepatitis, gut ischemia, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

Compounds of the present invention may be administered in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, biolimus-7 or biolimus-9; an ascomycin having immuno-suppressive properties, e.g. ABT-281 or ASM981; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline](WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; a S1P receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists.

The compounds of the present invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

Thus, in a further aspect, there is provided a compound of the present invention for use in therapy. In a further embodiment, the therapy is selected from a disease or disorder which is mediated by the activation of PI 3-kinase gamma isoform. In a further embodiment, the therapy is selected from a disease which may be treated by inhibiting of PI 3-kinase gamma isoform. In another embodiment, the therapy is selected from a disease which may be treated by inhibiting of PI 3-kinase gamma isoform selectively over PI 3-kinase delta isoform.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by the activation of PI 3-kinase, particularly the gamma isoform, or (ii) associated with PI 3-kinase gamma isoform activity, or (iii) characterized by activity (normal or abnormal) of PI 3-kinase gamma isoform; or (2) reducing or inhibiting the activity of PI 3-kinase gamma isoform. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of PI 3-kinase gamma isoform.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the present invention may be useful as pharmaceuticals and are thus usually formulated in the form of a pharmaceutical composition.

Hence, in another aspect, the present invention provides a pharmaceutical composition comprising a compound of the present invention and a pharmaceutically acceptable carrier.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in a mixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 μl, e.g. 25 to 50 μl, of the composition, i.e. a device known as a metered dose inhaler.

Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 μl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

Hence, the invention also includes (A) an agent of the invention, or a pharmaceutically acceptable salt or solvate thereof, in inhalable form; (B) an inhalable medicament comprising a compound of the present invention in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of compounds of the present invention employed in practicing the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

In a further aspect, there is provided a pharmaceutical combination comprising a compound of the present invention and at least one other therapeutic agent, for example for simultaneous, separate or sequential use in therapy. In one embodiment, the therapy is the treatment of a disease or disorder mediated by the activation of PI 3-kinase, particularly the gamma isoform. Products provided as a pharmaceutical combination include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical combination comprising a compound of the present invention and another therapeutic agent(s). Optionally, the pharmaceutical composition may comprise a pharmaceutically acceptable excipient, as described above.

In one embodiment, there is provided a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit may be used for administering different dosage forms, for example, oral and parenteral, for administering the separate compositions at different dosage intervals, or for titrating the separate compositions against one another. To assist compliance, the kit of the invention typically comprises directions for administration.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound of the present invention, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

PI 3-kinase antagonists such as the compounds of the present invention are also useful as co-therapeutic agents for use in combination with a second active agent such as for example an organic nitrate and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO- and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In a particular embodiment, there is provided a pharmaceutical combination comprising the compounds of the present invention and a second agent wherein the second agent is a PDE 5 inhibitor or neutral endopeptidase inhibitor.

The compounds of the present invention may be mixed with a second agent in a fixed pharmaceutical composition or it may be administered separately, before, simultaneously with or after the other drug substance.

Particularly, the invention includes in a further aspect a combination of a PI 3-kinase inhibitor such a compound of the present invention with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the TPH1 antagonist and the further drug substance may be in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Accordingly, the invention includes as a further aspect a combination of PI 3-kinase inhibitors such the compounds of the present invention with second agents that are IP receptor agonist, particularly the compounds disclosed in WO2012/007539.

Accordingly, the invention includes as a further aspect a combination of PI 3-kinase inhibitors such the compounds of the present invention with second agents that are multi-kinase inhibitors, such as imatinib mysilate, Gleevec. Imatinib functions as a specific inhibitor of a number of tyrosine kinase enzymes. It occupies the TK active site, leading to a decrease in activity. TK enzymes in the body, include the insulin receptor. Imatinib is specific for the TK domain in the Abelson proto-oncogene, c-kit and PDGF-R (platelet-derived growth factor receptor).

In a particular embodiment, there is provided a pharmaceutical combination comprising a compound of the present invention and a second active agent selected from phosphodiesterase V inhibitors, neutral endopeptidase 1 inhibitors, ALK-5 inhibitors, rho-kinase inhibitors, TPH1 inhibitors, multi-kinase inhibitors, endothelin antagonist, diuretic, aldosteron receptor blocker, and endothelin receptor blocker.

In another embodiment, there is provided a pharmaceutical combination comprising a compound of the present invention and a second active agent selected from phosphodiesterase V inhibitors, neutral endopeptidase 1 inhibitors, ALK-5 inhibitors, rho-kinase inhibitors, TPH1 inhibitors, multi-kinase inhibitors.

Compounds according to any one of embodiments 1-35 where both $R^3$ and $R^4$ are H have been found to be metabolites of the compounds of the present invention.

EXPERIMENTAL

The present invention is illustrated by the following examplified compounds.

From the foregoing it will be appreciated that, although specific embodiments of the invention have been described herein for purposes of illustration, various modifications may be made without deviating from the spirit and scope of the invention. Accordingly, the invention is not limited except as by the appended claims.

General Conditions:

Mass spectra were run on LCMS systems using electrospray ionization. These were either Agilent 1100 HPLC/Micromass Platform Mass Spectrometer combinations or Waters Acquity UPLC with SQD Mass Spectrometer. $[M+H]^+$ refers to mono-isotopic molecular weights. NMR spectra were run on Bruker AVANCE 400 MHz or 500 MHz NMR spectrometers using ICON-NMR. Spectra were measured at 298K and were referenced using the solvent peak.

As a person skilled in the art understands, when running a $^1H$ NMR in deuterated DMSO for compounds according to any one of embodiments 1-35 with $R^1$=methyl, the signal of said methyl protons is often obscured due to the DMSO solvent peak at δ of around 2.5 ppm.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 30 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations:

AcOH acetic acid
aq. aqueous
br broad
BuOH butanol
Celite® diatomaceous earth filter material
conc. concentrated
d doublet
dd doublet of doublets
DCM dichloromethane
DCC N,N'-dicyclohexylcarbodiimide
DCE 1,2-dichloroethane
DEAD diethyl azodicarboxylate
DIPEA diisopropylethylamine
DMA dimethylacetamide
DME 1,2-dimethoxyethane
DMF N,N-dimethylformamide
DMSO dimethylsulfoxide
$Et_2O$ diethyl ether
EtOAc ethyl acetate
EtOH ethanol
h hour(s)
HATU O-(7-azabenzotriazol-1-yl)-N,N,N,N-tetramethyluronium hexafluorophosphate
HOBt. $H_2O$ 1-Hydroxybenzotriazole hydrate
HPLC High Performance Liquid Chromatography
IPA iso-propyl alcohol
KOAc Potassium acetate
KOtBu Potassium tert-butoxide
LCMS liquid chromatography and mass spectrometry
MeOH methanol
MeCN acetonitrile
MP macroporous
MS mass spectrometry
m multiplet
min minute
ml milliliter(s)
m/z mass to charge ratio
NBS N-bromosuccinimide
NMR nuclear magnetic resonance
NOESY nuclear Overhauser effect spectroscopy
$Pd_2(dba)_3$ tris(dibenzylideneacetone)dipalladium(0)
$PdCl_2(dppf).CH_2Cl_2$ adduct [1,1-Bis(diphenylphosphino)ferrocene]dichloropalladium (II) dichloromethane adduct.
$Pd(PPh_3)_2Cl_2$ bis(triphenylphosphine)palladium(II) dichloride
Pd 118, $PdCl_2$(dtbpf) dichloro[1,1' bis(di-tert-butylphosphino)]ferrocene palladium(II)
ppm parts per million
PS polymer supported
Rt retention time
RT room temperature
s singlet
sat. saturated
SCX-2 strong cation exchange (e.g. Isolute® SCX-2 columns from Biotage)
SFC supercritical fluid chromatography
Si-TMT Isolute® Si-TMT is the silica bound equivalent of 2,4,6-trimercaptotriazine (0.3 mmol/g)
t triplet
TBAF tetrabutylammonium fluoride
TBME methyl-tert-butyl ether
TEA triethylamine
TFA trifluoroacetic acid
THF tetrahydrofuran
TLC thin layer chromatography
T3P® propylphosphonic anhydride
XPhos 2-dicyclohexylphosphino-2',4',6'-triisopropylbiphenyl Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

Where microwave heating was employed, this was carried out using a Biotage Initiator Sixty microwave in dedicated reaction vials at the temperature shown and for the time indicated.

If not indicated otherwise, the analytical LCMS conditions are as follows:

Method A

Column: Cynergi 2.5 uMMax-RP100A (20×4.0) mm.

Mobile Phase: A: Water+0.1% Formic Acid B:Acetonitrile

Gradient 0.0-0.5 min 20% B, 2.5-4.5 mins 95% B, 5.0 min 20% B

Method 2 minLC_v003

Column Waters BEH C18 50×2.1 mm, 1.7 W

Column Temperature 50° C.

Eluents A: $H_2O$, B: acetonitrile, both containing 0.1% TFA

Flow Rate 0.8 ml/min

Gradient 0.20 min 5% B; 5% to 95% B in 1.30 min, 0.25 min 95% B

Method 2 minLowpH

Column: Waters Acquity CSH 1.7 μm, 2.1×50 mm

Temperature: 50° C.

Mobile Phase: A: Water+0.1% Formic Acid B: Acetonitrile+ 0.1% Formic Acid

Flow rate: 1.0 mL/min

Gradient: 0.0 min 5% B, 0.2-1.3 min 5-98% B, 1.3-1.55 min 98% B, 1.55-1.6 min 98-5% B Method 2 minLowpHv01

Column: Waters Acquity CSH 1.7 μm, 2.1×50 mm

Temperature: 50° C.

Mobile Phase: A: Water+0.1% Formic Acid B: Acetonitrile+ 0.1% Formic Acid

Flow rate: 1.0 mL/min

Gradient: 0.0 min 5% B, 0.2-1.55 min 5-98% B, 1.55-1.75 min 98% B, 1.75-1.8 min 98-5% B Method 2 minLowpHv02

Column: Acquity CSH C18 50×2.1 mm

Temperature: 50° C.

Eluents A: Water B: Acetonitrile both with +0.1% TFA

Flow Rate: 1.0 mL/min

Gradient: 0.0 min 5% B, 0.2-1.55 min 5-98% B, 1.55-1.75 min 98% B, 1.75-1.8 min 98-5% B Method 2 minLowpHv03:

Column: Waters Acquity CSH 1.7 μm, 2.1×50 mm

Temperature: 50° C.

Mobile Phase: A: Water+0.1% Formic Acid B: Acetonitrile+ 0.1% Formic Acid

Flow rate: 1.0 mL/min

Gradient: 0.0 min 5% B, 0.2-1.8 min 5-98% B, 1.8-2.1 min 98% B, 2.1-2.3 min 98% B Method 8 minLowpHv01:

Column: Waters Acquity CSH 1.7 μm, 2.1×100 mm

Temperature: 50° C.

Mobile Phase: A: Water+0.1% Formic Acid B: Acetonitrile+ 0.1% Formic Acid

Flow rate: 0.7 mL/min

Gradient: 0.0 min 2% B, 0.3-6.5 min 2-98% B, 6.5-7.5 min 98% B, 7.5-8.0 min 5-98% B Method 10 minLowpH Column: Waters Acquity CSH 1.7 μm, 2.1×100 mm Temperature: 50° C.

Mobile Phase: A: Water+0.1% Formic Acid B: Acetonitrile+ 0.1% Formic Acid

Flow rate: 0.7 mL/min

Gradient: 0.0 min 2% B, 0.5-8.0 min 2-98% B, 8.0-9.0 min 98% B, 9.0-9.1 min 98-2% B Method 10 minHighpH Column: Waters Acquity CSH 1.7 μm, 2.1×100 mm Temperature: 50° C.

Mobile Phase: A: Water+0.1% Ammonia B: Acetonitrile+ 0.1% Ammonia

Flow rate: 0.7 mL/min

Gradient: 0.0 min 2% B, 0.5-8.0 min 2-98% B, 8.0-9.0 min 98% B, 9.0-9.1 min 98-2% B Unless indicated otherwise, preparative HPLC was carried out using an appropriate column and a mobile phase of 0.1% TFA in acetonitrile and 0.1% aqueous TFA with an appropriate gradient. Where a particular method is specified, the conditions (column, mobile phase and gradient) are those listed below:

Method 10-35% Gradient lowpH

Column: Waters Sunfire C18, 150×30 mm, 5 mic

Mobile Phase: A=0.1% TFA in Water, B=0.1% TFA in MeCN

Gradient: 0.0-0.5 min 10% B 30 mL/min, 0.5-1.0 min 10% B 30-50 mL/min, 1.0-7.25 min 10-35% B, 7.25-7.3 min 35-98% B, 7.3-8.3 min 98% B, 8.3-8.5 min 98-100% B 50 mL/min

Example 1

3-{6-Amino-5-[1-(2,2,2-trifluoro-ethyl)-1H-pyrazol-4-yl]-pyridin-3-yl}-4-methyl-N-(6-methyl-pyridin-2-yl)-benzenesulfonamide

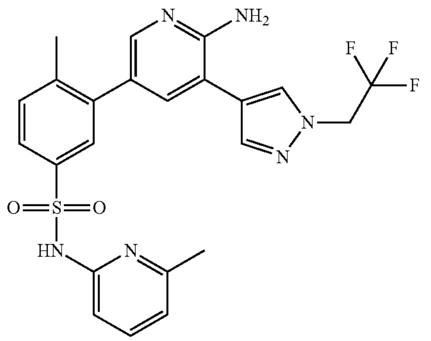 [SMILES: Cc1cccc(NS(=O)(=O)c2ccc(C)c(-c3cnc(N)c(-c4cnn(CC(F)(F)F)c4)c3)c2)n1]

Sodium carbonate (1.0 ml of a 2M solution, 2 mmol) was added to a mixture of 4-methyl-N-(6-methylpyridin-2-yl)-3-(4,4,5,5-tetramethyl-1,3,2-dioxaborolan-2-yl)benzenesulfonamide (Intermediate B6) (0.266 g, 0.865 mmol), 5-bromo-3-(1-(2,2,2-trifluoroethyl)1H-pyrazol-4-yl)pyridin-2-amine (Intermediate C1) (0.20 g, 0.623 mmol) and $Pd(PPh_3)_2Cl_2$ (0.022 g, 0.031 mmol) in DME (4 ml). The mixture was de-gassed several times under nitrogen then heated at 85° C. for 5 h. The reaction mixture was diluted with water, extracted with EtOAc and washed with brine. The organic extract was separated, dried over $MgSO_4$ and the solvent removed to give an oil. Chromatography on silica, eluting with 30% EtOH in chloroform afforded the product which was crystallised from MeOH to give a white crystalline solid;

LCMS: Rt 0.71 mins; MS m/z 503.5 [M+H]+, Method 2 minLC_v003

$^1H$ NMR (400 MHz, MeOD-d4) δ 8.12 (1H, s), 7.91 (1H, d), 7.88 (1H, s), 7.81 (1H, d), 7.79 (1H, s), 7.60 (1H, t), 7.55 (1H, s), 7.45 (1H, d), 7.13 (1H, d), 6.68 (1H, d), 5.02 (2H, q), 2.35 (3H, s), 2.36 (3H, s).

Example 2

3-(6-Amino-5-(1-methyl-1H-pyrazol-4-yl)pyridin-3-yl)-N-(3-hydroxy-3-methylbutyl)-4-methylbenzene-sulfonamide

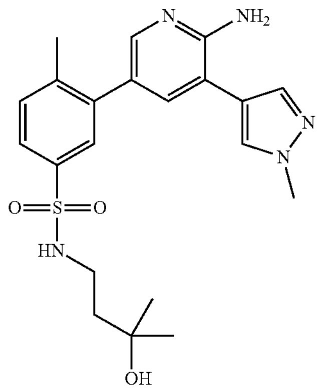 [SMILES: Cc1ccc(S(=O)(=O)NCCC(C)(C)O)cc1-c1cnc(N)c(-c2cnn(C)c2)c1]

The title compound was prepared from 5-bromo-3-(1-methyl-1H-pyrazol-4-yl)pyridin-2-amine (Intermediate C2) and N-(3-hydroxy-3-methylbutyl)-4-methyl-3-(4,4,5,5-tetramethyl-1,3,2-dioxaborolan-2-yl)benzenesulfonamide (Intermediate B3) under analogous conditions to those of Example 1;

LCMS: Rt 0.62 mins; MS m/z 430.3 [M+H]+, Method 2 minLowpH $^1$H NMR (400 MHz, MeOH-d4) δH 7.96 (1H, s), 7.90 (1H, d), 7.78 (1H, s), 7.74 (1H, dd), 7.70 (1H, d), 7.56 (1H, d), 7.52 (1H, d), 3.98 (3H, s), 3.00 (2H, m), 2.41 (3H, s), 1.65 (2H, m), 1.15 (6H, s).

Example 3

3-(6-Amino-5-(1-(2,2,2-trifluoroethyl)-1H-pyrazol-4-yl)pyridin-3-yl)-N-(3-hydroxy-3-methylbutyl)-4-methylbenzenesulfonamide

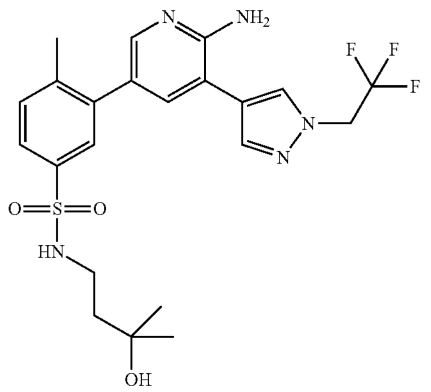 [SMILES: Cc1ccc(S(=O)(=O)NCCC(C)(C)O)cc1-c1cnc(N)c(-c2cnn(CC(F)(F)F)c2)c1]

The title compound was prepared under analogous conditions to those of Example 1 using N-(3-hydroxy-3-methylbutyl)-4-methyl-3-(4,4,5,5-tetramethyl-1,3,2-dioxaborolan-2-yl) benzenesulfonamide (Intermediate B3) and 5-bromo-3-(1-(2,2,2-trifluoroethyl)1H-pyrazol-4-yl)pyridin-2-amine (Intermediate C1);

LCMS: Rt 0.73 mins; MS m/z 498.5 [M+H]+; Method 2 minLC_v003

$^1$H NMR (400 MHz, DMSO-d6) δ 8.28 (1H, s), 7.98 (1H, s), 7.93 (1H, d), 7.65 (1H, dd), 7.62 (1H, d), 7.58 (1H, d), 7.52 (1H, d), 7.39 (1H, t), 5.88 (2H, br s), 5.15 (2H, q), 4.25 (1H, s), 2.82 (2H, m), 2.37 (3H, s), 1.50 (2H, m), 1.00 (6H, s).

Example 4

3-(6-Amino-5-(2-methylthiazol-5-yl)pyridin-3-yl)-N-(3-hydroxy-3-methylbutyl)-4-methylbenzenesulfonamide

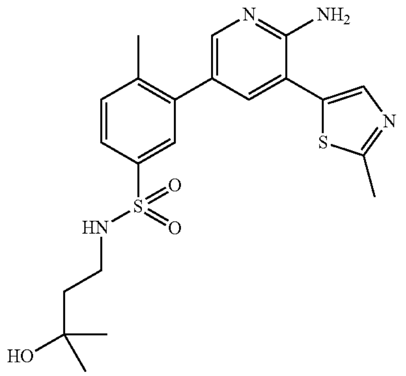 [SMILES: Cc1ncc(-c2cc(-c3cc(S(=O)(=O)NCCC(C)(C)O)ccc3C)cnc2N)s1]

To a mixture comprising 3-(6-amino-5-bromopyridin-3-yl)-N-(3-hydroxy-3-methylbutyl)-4-methylbenzene sulfonamide (Intermediate E1) (85 mg, 0.198 mmol), 2-methyl-5-(4,4,5,5-tetramethyl-1,3,2-dioxaborolan-2-yl)thiazole (67 mg, 0.298 mmol) and $PdCl_2(dppf).CH_2Cl_2$ adduct (16 mg, 0.02 mmol) in DME (2 mL) in a 2-5 mL microwave tube equipped with stirrer bar was added a solution of sodium carbonate (63 mg, 0.595 mmol) in water (0.4 mL). The tube was capped and the mixture heated for 1 hour at 120° C. in the Biotage Initiator microwave.

The mixture was diluted with water (5 mL) and extracted with EtOAc (3×5 mL). The EtOAc extracts were combined, washed with sat brine (5 mL), dried ($MgSO_4$), filtered and evaporated to give a orange oil. The orange oil was loaded onto an Isolute SCX cartridge. The MeOH eluate was discarded and the 2M ammonia in MeOH eluate was collected. This did not result in pure material so the product-containing fractions were combined and dry loaded onto silica gel and purified by chromatography on Isco using a 24 g pre-packed silica gel column and 0-50% methanol in TBME as eluant. Further purification by preparative reverse phase HPLC afforded the title compound;

LCMS: RT 0.71 mins; MS m/z 447.6 [M+H]+; Method 2 minLowpH $^1$H NMR (400 MHz, MeOH-d4) δH 8.01 (1H, d), 7.81 (1H, s), 7.75 (1H, dd), 7.70 (1H, d), 7.58 (1H, d), 7.52 (1H, d), 3.00 (2H, m), 2.76 (3H, s), 2.40 (3H, s), 1.65 (2H, m), 1.15 (6H, s).

The compounds of the following tabulated examples were prepared analogously to Example 4 from the appropriate starting compounds.

Where hydrochloride salt is shown, this was prepared by standard conditions, for example treating the free base compound formed with 4M HCl in dioxane, followed by recrystallisation where necessary, for example from ethanol.

TABLE 1

| Ex. | Structure | Name | [M + H]+/NMR |
|---|---|---|---|
| 4.1 | 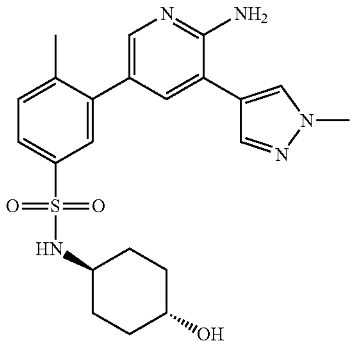 [SMILES: Cc1ccc(S(=O)(=O)N[C@H]2CC[C@H](O)CC2)cc1-c1cnc(N)c(-c2cnn(C)c2)c1] | trans 3-(6-Amino-5-(1-methyl-1H-pyrazol-4-yl)pyridin-3-yl)-N-(4-hydroxy cyclohexyl)-4-methylbenzene-sulfonamide | LCMS Rt 0.73 min. MS m/z 442.3 [M + H]+), Method: 2minLowpHv02 $^1$H NMR (400 MHz, MeOD-d4) δ 7.94 (1H, s), 7.87 (1H, d), 7.77 (1H, d), 7.74 (1H, dd), 7.70 (1H, d), 7.55 (1H, d), 7.49 (1H, d), 3.97 (3H, s), 3.46 (1H, m), 3.03 (1H, m), 2.39 (3H, s), 1.85 (2H, m), 1.76 (2H, m), 1.24 (4H, m). |
| 4.2 | 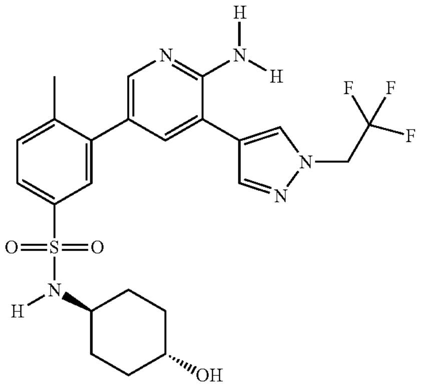 [SMILES: Cc1ccc(S(=O)(=O)N[C@H]2CC[C@H](O)CC2)cc1-c1cnc(N)c(-c2cnn(CC(F)(F)F)c2)c1] | trans 3-(6-Amino-5-(1-(2,2,2-trifluoro ethyl)-1H-pyrazol-4-yl)pyridin-3-yl)-N-(4-hydroxy cyclohexyl)-4-methyl-benzenesulfonamide | LCMS: Rt 0.81 mins; MS m/z 510.3 [M + H]+; Method 2minLowpHv02. $^1$H NMR (400 MHz, MeOD-d4) δ 8.12 (1H, s), 7.91 (2H, m), 7.74 (1H, dd), 7.71 (1H, d), 7.59 (1H, d), 7.50 (1H, d), 5.02 (2H, q), 3.48 (1H, m), 3.03 (1H, m), 2.39 (3H, s), 1.85 (2H, m), 1.76 (2H, m), 1.24 (4H, m). |
| 4.3 | 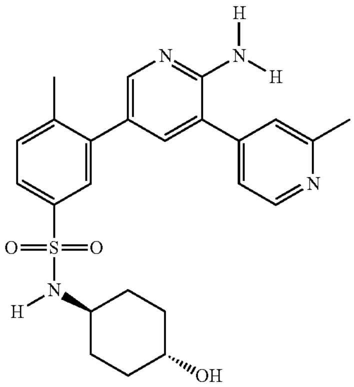 [SMILES: Cc1cc(-c2cc(-c3cc(S(=O)(=O)N[C@H]4CC[C@H](O)CC4)ccc3C)cnc2N)ccn1] | trans 3-(2-Amino-2'-methyl-[3,4'-bi pyridin]-5-yl)-N-(4-hydroxy cyclohexyl)-4-methyl-benzenesulfonamide | LCMS: Rt 0.64 mins; MS m/z 453.3 [M + H]+; Method 2minLowpHv02 $^1$H NMR (400 MHz, MeOD-d4) δ 8.51 (1H, d), 8.01 (1H, d), 7.75 (1H, dd), 7.72 (1H, d), 7.51 (3H, m), 7.43 (1H, dd), 3.47 (1H, m), 3.03 (1H, m), 2.61 (3H, s), 2.41 (3H, s), 1.85 (2H, m), 1.76 (2H, m), 1.24 (4H, m). |
| 4.4 | 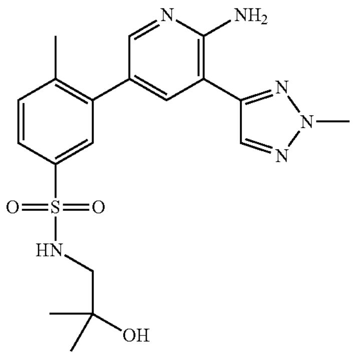 [SMILES: Cc1ccc(S(=O)(=O)NCC(C)(C)O)cc1-c1cnc(N)c(-c2cnn(C)n2)c1] | 3-(6-Amino-5-(2-methyl-2H-1,2,3-triazol-4-yl)pyridin-3-yl)-N-(2-hydroxy-2-methylpropyl)-4-methyl-benzenesulfonamide hydrochloride | LCMS: Rt = 0.71 mins MS m/z 417.6 [M + H]+; Method 2minLowpHv01. $^1$H NMR (400 MHz, DMSO-d6) δ 8.58 (1H, s), 8.56 (1H, d), 8.19 (1H, d superimposed on 2H, br), 7.76 (2H, mult), 7.59 (1H, d), 7.53 (1H, t), 4.29 (3H, s), 2.63 (2H, d), 2.38 (3H, s), 1.07 (6H, s). |

TABLE 1-continued

| Ex. | Structure | Name | [M + H]+/NMR |
|---|---|---|---|
| 4.5 | 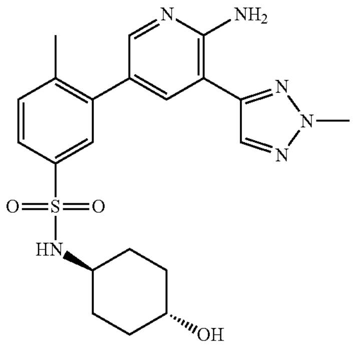 [SMILES: Cc1ccc(S(=O)(=O)N[C@H]2CC[C@H](O)CC2)cc1-c1cnc(N)c(-c2cnn(C)n2)c1] | trans 3-(6-Amino-5-(2-methyl-2H-1,2,3-triazol-4-yl)pyridin-3-yl)-N-(4-hydroxy cyclohexyl)-4-methylbenzene sulfonamide hydrochloride | LCMS: Rt = 0.68 mins MS m/z 443.8 [M + H]+; Method 2minLowpHv01. $^{1}$H NMR (400 MHz, DMSO-d6) δ 8.58 (1H, s), 8.54 (1H, s), 8.20 (1H, br), 8.17 (1H, d), 7.78 (1H, dd), 7.74 (1H, d), 7.64 (1H, d), 7.58 (1H, d), 4.29 (3H, s), 3.30 (1H, mult), 2.93 (1H, mult), 2.38 (3H, s), 1.71 (2H, mult), 1.62 (2H, mult), 1.13 (4H, mult). |
| 4.6 | 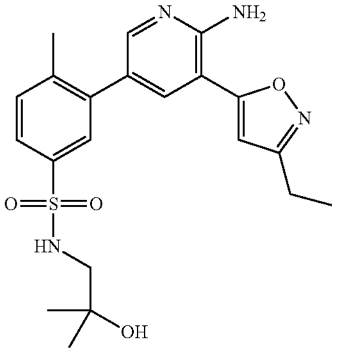 [SMILES: CCc1cc(-c2cc(-c3cc(S(=O)(=O)NCC(C)(C)O)ccc3C)cnc2N)on1] | 3-(6-Amino-5-(3-ethylisoxazol-5-yl)pyridin-3-yl)-N-(2-hydroxy-2-methylpropyl)-4-methyl-benzenesulfonamide hydrochloride | LCMS: Rt = 0.89 mins MS m/z 431.7 [M + H]+; Method 2minLowpHv01. $^{1}$H NMR (400 MHz, DMSO-d6) δ 8.25 (2H, mult), 7.74 (2H, mult), 7.56 (1H, d), 7.50 (1H, t), 7.09 (1H, s), 2.72 (2H, mult), 2.63 (2H, d), 2.37 (3H, s), 1.26 (3H, t), 1.06 (6H, s). |
| 4.7 | 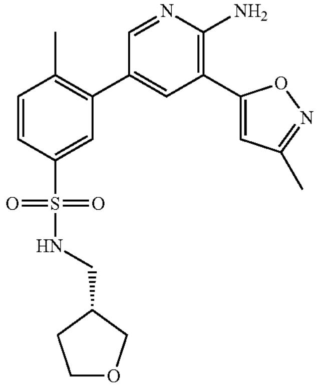 [SMILES: Cc1cc(-c2cc(-c3cc(S(=O)(=O)NC[C@H]4CCOC4)ccc3C)cnc2N)on1] | (R)-3-(6-Amino-5-(3-methylisoxazol-5-yl)pyridin-3-yl)-4-methyl-N-((tetra hydrofuran-3-yl)methyl)benzene-sulfonamide hydrochloride | LCMS: Rt = 0.85 mins MS m/z 429.6 [M + H]+; Method 2minLowpHv01. $^{1}$H NMR (400 MHz, DMSO-d6) δ 8.28 (2H, s), 7.78 (1H, t), 7.73 (1H, dd), 7.71 (1H, d), 7.57 (1H, d), 7.04 (1H, s), 3.63 (3H, mult), 3.36 (1H, mult), 2.73 (2H, t), 2.37 (3H, s), 2.33 (3H, s), 2.28 (1H, mult), 1.88 (1H, mult), 1.49 (1H, mult). |
| 4.8 | 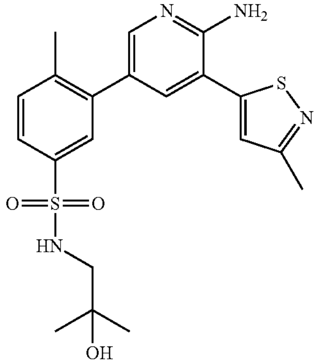 [SMILES: Cc1cc(-c2cc(-c3cc(S(=O)(=O)NCC(C)(C)O)ccc3C)cnc2N)sn1] | 3-(6-Amino-5-(3-methylisothiazol-5-yl)pyridin-3-yl)-N-(2-hydroxy-2-methylpropyl)-4-methyl-benzenesulfonamide hydrochloride | LC-MS: Rt 0.85 mins; MS m/z 433.6 [M + H]+; Method 2minLowpHv01 $^{1}$H NMR (400 MHz, DMSO-d6) δ 8.17 (1H, d), 7.94 (1H, m), 7.72 (2H, m), 7.54 (2H, m), 7.47 (1H, t), 7.34 (1H, br), 2.61 (2H, d), 2.49 (3H, s, partially obscured by DMSO peak), 2.37 (3H, s), 1.06 (6H, s). |

TABLE 1-continued

| Ex. | Structure | Name | [M + H]+/NMR |
| --- | --- | --- | --- |
| 4.9 | 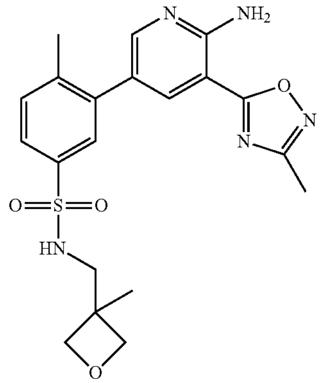 [SMILES: Cc1noc(-c2cc(-c3cc(S(=O)(=O)NCC4(C)COC4)ccc3C)cnc2N)n1] | 3-(6-Amino-5-(3-methyl-1,2,4-oxadiazol-5-yl)pyridin-3-yl)-4-methyl-N-((3-methyloxetan-3-yl)methyl)benzene-sulfonamide | LCMS: Rt = 0.99 mins; MS m/z 430.2 [M + H]+; Method 2minLowpHv01 $^1$H NMR (400 MHz, $CDCl_3$) δ 8.30 (2H, s), 7.86 (1H, d), 7.78 (1H, s), 7.50 (1H, d), 7.05 (1H, br s), 4.38 (4H, s), 3.18 (2H, m), 2.55 (3H, s), 1.91 (3H, s), 1.28 (3H, s). |

Example 4.4

3-(6-amino-5-(2-methyl-2H-1,2,3-triazol-4-yl)pyridin-3-yl)-N-(2-hydroxy-2-methylpropyl)-4-methylbenzenesulfonamide hydrochloride

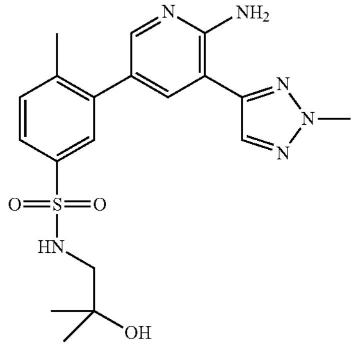 [SMILES: Cc1ccc(S(=O)(=O)NCC(C)(C)O)cc1-c1cnc(N)c(-c2cnn(C)n2)c1]

A mixture of N-(2-hydroxy-2-methylpropyl)-4-methyl-3-(4,4,5,5-tetramethyl-1,3,2-dioxaborolan-2-yl)benzenesulfonamide (Intermediate B2, 104 mg, 0.281 mmol), 5-bromo-3-(2-methyl-2H-1,2,3-triazol-4-yl)pyridin-2-amine (Intermediate C11, 65 mg, 0.256 mmol), and $PdCl_2$(dppf).$CH_2Cl_2$ adduct (10.5 mg, 0.013 mmol) and sodium carbonate (0.32 mL, 0.64 mmol) in DME (3 ml) was heated in the microwave at 120° C. for 2 hours, then extracted into ethyl acetate, washed with water, brine, the organic layer separated, dried over MgSO4, filtered and the solvent removed under reduced pressure. The crude product was loaded onto silica and purified by flash column chromatography, eluting with TBME:MeOH (0-10%) on a 12 g silica cartridge. The required fractions were combined and the solvent removed under reduced pressure to yield a yellow residue. The residue was taken up in 4M HCl in dioxane (5 ml) and the solvent removed under reduced pressure. The product was recrystallised from ethanol with cooling, collected by filtration and dried in the oven to give a yellow solid.

LCMS: Rt=0.71 mins MS m/z 417.6 [M+H]+; Method 2 minLowpHv01.

$^1$H NMR (400 MHz, DMSO-d6) δ 8.58 (1H, s), 8.56 (1H, d), 8.19 (1H, d superimposed on 2H, br), 7.76 (2H, mult), 7.59 (1H, d), 7.53 (1H, t), 4.29 (3H, s), 2.63 (2H, d), 2.38 (3H, s), 1.07 (6H, s).

Example 5

3-[6-Amino-5-(3-methyl-[1,2,4]oxadiazol-5-yl)-pyridin-3-yl]-N-(3-hydroxy-3-methyl-butyl)-4-methyl-benzenesulfonamide hydrochloride

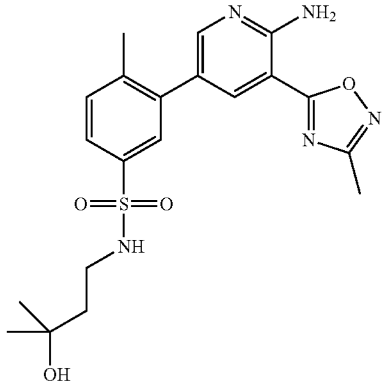 [SMILES: Cc1noc(-c2cc(-c3cc(S(=O)(=O)NCCC(C)(C)O)ccc3C)cnc2N)n1]

The title compound was prepared from N-(3-hydroxy-3-methyl butyl)-4-methyl-3-(4,4,5,5-tetramethyl-1,3,2-dioxaborolan-2-yl)benzenesulfonamide (Intermediate B3) and 5-bromo-3-[1,2,4]oxadiazol-5-yl-pyridin-2-ylamine (Intermediate C3) under analogous conditions to those of Example 1. The purified product was taken up in 4M HCl in dioxane (2 ml). After 5 min the volatiles were evaporated and the residue was recrystallised from hot EtOH to give a solid;

LCMS: Rt 1.00 mins; MS m/z 432.4 [M+H]+; Method 2 minLowpH $^1$H NMR (400 MHz, DMSO-d6) δ 8.37 (1H, s), 8.24 (1H, s), 7.87-7.61 (4H, br m), 7.56 (1H, br d), 7.42 (1H, br s), 2.91-2.78 (2H, br m), 2.48 (3H, s), 2.38 (3H, s), 1.58-1.42 (2H, br m), 1.02 (6H, s).

Example 5.1

3-(6-Amino-5-(3-isopropyl-1,2,4-oxadiazol-5-yl)pyridin-3-yl)-N-(2-hydroxy-2-methylpropyl)-4-methylbenzenesulfonamide hydrochloride

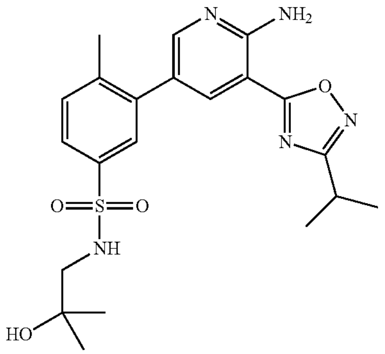 [SMILES: Cc1ccc(S(=O)(=O)NCC(C)(C)O)cc1-c1cnc(N)c(-c2nc(C(C)C)no2)c1]

The title compound was prepared analogously to Example 5 from 5-bromo-3-(3-isopropyl-1,2,4-oxadiazol-5-yl)pyridin-2-amine (Intermediate C8) and N-(2-hydroxy-2-methylpropyl)-4-methyl-3-(4,4,5,5-tetramethyl[1,3,2]dioxaborolan-2-yl)benzenesulfonamide (Intermediate B2);

LCMS: Rt=1.13 mins; MS m/z 444.3 [M−H]−; Method 2 minLowpHv01.

$^1$H NMR (400 MHz, DMSO-d6) δ 8.39 (1H, d), 8.28 (1H, d), 7.78 (1H, br s), 7.71 (2H, m), 7.54 (1H, m), 7.48 (1H, t), 3.19 (1H, m), 2.63 (2H, d), 2.37 (3H, s), 1.35 (6H, d), 1.06 (6H, s).

The compounds of the following tabulated examples were prepared analogously to Example 5 from the appropriate starting compounds. For Example 5.6, the hydrochloride salt was not formed

TABLE 2

| Ex. | Structure | Name | [M + H]$^+$/NMR |
|---|---|---|---|
| 5.2 | 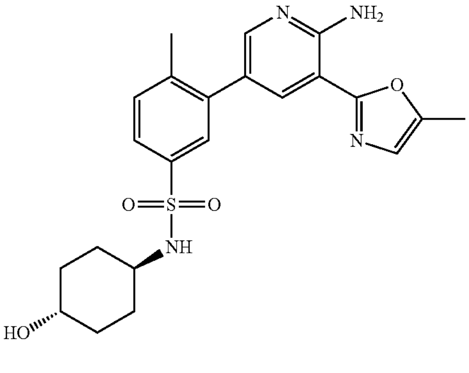 [SMILES: Cc1cnc(-c2cc(-c3cc(S(=O)(=O)N[C@H]4CC[C@H](O)CC4)ccc3C)cnc2N)o1] | trans 3-(6-Amino-5-(5-methyloxazol-2-yl)pyridin-3-yl)-N-(4-hydroxy cyclohexyl)-4-methylbenzene sulfonamide hydrochloride | LCMS Rt 0.83 min. MS m/z 443.7 [M + H]+), Method: 2minLowpHv01 $^1$H NMR (400 MHz, DMSO-d6) δ 8.25 (3H, br s), 7.75 (1H, d), 7.71 (1H, s), 7.61 (1H, d), 7.56 (1H, d), 7.20 (1H, s), 3.30 (1H, m), 2.95 (1H, m), 2.42 (3H, s), 2.37 (3H, s), 1.67 (4H, dd), 1.13 (4H, m). |
| 5.3 | 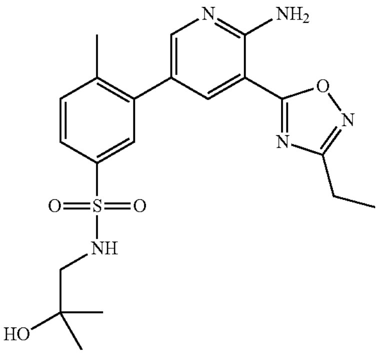 [SMILES: CCc1noc(-c2cc(-c3cc(S(=O)(=O)NCC(C)(C)O)ccc3C)cnc2N)n1] | 3-(6-Amino-5-(3-ethyl-1,2,4-oxadiazol-5-yl)pyridin-3-yl)-N-(2-hydroxy-2-methylpropyl)-4-methylbenzenesulfonamide hydrochloride | LCMS: Rt = 1.10 mins; MS m/z 432.6 [M + H]+; Method 2minLowpHv01 $^1$H NMR-(400 MHz, DMSO-d6) δ 8.41 (1H, s), 8.35 (1H, s), 7.93 (1H, br s), 7.72 (2H, m), 7.55 (1H, d), 7.49 (1H, t), 2.86 (2H, m), 2.63 (2H, d), 2.38 (3H, s), 1.32 (3H, t), 1.06 (6H, s). |

TABLE 2-continued

| Ex. | Structure | Name | [M + H]$^+$/NMR |
|---|---|---|---|
| 5.4 | 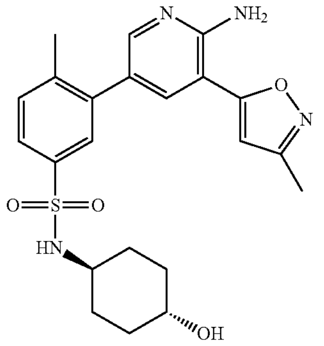 [SMILES: Cc1cc(-c2cc(-c3cc(S(=O)(=O)N[C@H]4CC[C@H](O)CC4)ccc3C)cnc2N)on1] | trans 3-(6-Amino-5-(3-methylisoxazol-5-yl)pyridin-3-yl)-N-(-4-hydroxy cyclohexyl)-4-methylbenzenesulfonamide hydrochloride | LCMS: Rt = 0.82 mins MS m/z 443.5 [M + H]+; Method 2minLowpHv01. $^1$H NMR (400 MHz, DMSO-d6) δ 8.22 (1H, mult), 8.20 (1H, br), 7.73 (1H, dd), 7.70 (1H, s), 7.60 (1H, d), 7.54 (1H, d), 7.00 (1H, s), 3.29 (1H, mult), 2.91 (1H, mult), 2.37 (3H, s), 2.33 (3H, s), 1.71 (2H, br), 1.62 (2H, br), 1.13 (4H, mult). |
| 5.5 | 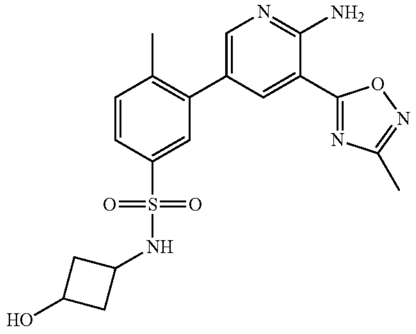 [SMILES: Cc1noc(-c2cc(-c3cc(S(=O)(=O)NC4CC(O)C4)ccc3C)cnc2N)n1] | Diastereomers of 3-(6-Amino-5-(3-methyl-1,2,4-oxadiazol-5-yl)pyridin-3-yl)-N-(3-hydroxy cyclobutyl)-4-methylbenzene sulfonamide hydrochloride | LCMS: Rt = 0.80 and 0.82 mins; MS m/z 416.1 [M + H]+; Method 2minLowpHv01 $^1$H NMR (400 MHz, DMSO-d6) δ 8.38 (1H, s), 8.29 (1H, s), 7.85 (2H, m), 7.67 (3H, m), 7.54 (1H, m), 3.74 (0.7H, m), 3.66 (0.7H, m), 3.13 (0.7H, m), 2.38 (3H, s), 2.24 (1.4H, m), 1.98 (0.8H, m), 1.60 (1.3H, m). |
| 5.6 | 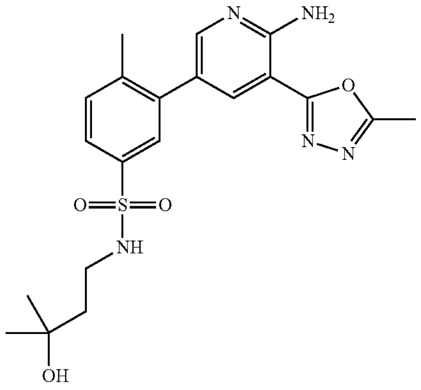 [SMILES: Cc1nnc(-c2cc(-c3cc(S(=O)(=O)NCCC(C)(C)O)ccc3C)cnc2N)o1] | 3-(6-Amino-5-(5-methyl-1,3,4-oxadiazol-2-yl)pyridin-3-yl)-N-(3-hydroxy-3-methylbutyl)-4-methylbenzenesulfonamide | LCMS: Rt = 0.86; MS m/z 432.6 [M + H]+; Method 2minLowpHv01 $^1$H NMR (400 MHz, DMSO-d6), δ, 8.28 (1H, s), 7.98 (1H, s), 7.57 (6H, m), 4.28 (1H, s), 2.83 (2H, m), 2.58 (3H, s), 2.37 (3H, s), 1.51 (2H, s), 1.03 (6H, s) |

Example 5.5a 3-(6-Amino-5-(3-methyl-1,2,4-oxadiazol-5-yl)pyridin-3-yl)-N-((1s,3s)-3-hydroxycyclobutyl)-4-methylbenzenesulfonamide

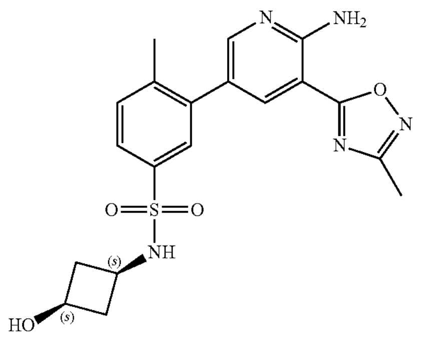 [SMILES: Cc1noc(-c2cc(-c3cc(S(=O)(=O)N[C@H]4C[C@@H](O)C4)ccc3C)cnc2N)n1]

3-(6-Amino-5-(3-methyl-1,2,4-oxadiazol-5-yl)pyridin-3-yl)-N-(3-hydroxy cyclobutyl)-4-methylbenzene sulfonamide (Example 5.5) (100 mg, 0.241 mmol) was separated by chiral SFC according to the following conditions to afford the title compound as the first eluted peak:

SFC Retention Time=3.476 mins. NOESY experiment confirmed correct stereochemistry.

LCMS: Rt=0.90 mins; MS m/z 416.6 [M+H]+; Method 2 minLowpHv01

$^1$H NMR (400 MHz, DMSO-d6) δ 8.35 (1H, d), 8.17 (1H, d), 7.82 (1H, d), 7.68 (1H, d), 7.65 (1H, s), 7.60 (2H, s), 7.53 (1H, d), 5.00 (1H, d), 3.66 (1H, m), 3.13 (1H, m), 2.47 (3H, s), 2.38 (3H, s), 2.24 (2H, m), 1.60 (2H, s).

Method Details:

Column: LUX A2, 250×10 mm, 5 um @35 deg C.;
Mobile phase: 50% Isopropanol+0.1% v/v DEA/50% $CO_2$;
Flow: 10 ml/min; Detection: UV @ 254 nm;
Instrument: Berger Minigram SFC2

Example 6

3-(6-Amino-5-(2-methyloxazol-5-yl)pyridin-3-yl)-N-(2-hydroxy-2-methylpropyl)-4-methylbenzenesulfonamide

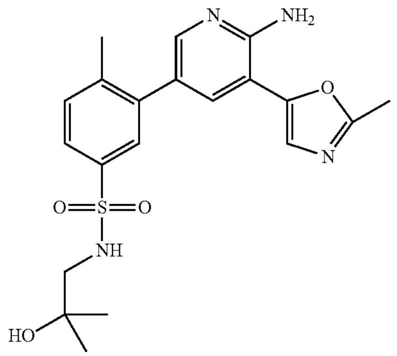 [SMILES: Cc1ncc(-c2cc(-c3cc(S(=O)(=O)NCC(C)(C)O)ccc3C)cnc2N)o1]

To a mixture comprising 5-bromo-3-(2-methyl-oxazol-5-yl)-pyridin-2-ylamine (Intermediate C4) (1.3 g, 5.12 mmol) and N-(2-hydroxy-2-methyl-propyl)-4-methyl-3-(4,4,5,5-tetramethyl[1,3,2]dioxaborolan-2-yl)benzenesulfonamide (Intermediate B2) (2.83 g, 7.67 mmol) in DME (1,2-dimethoxyethane) (25.6 ml) under nitrogen gas, was added sequentially, catalyst bis(triphenylphosphine)palladium(II) chloride (0.180 g, 0.256 mmol) followed by 2 M $Na_2CO_3$ (aq.) (7.67 ml, 15.35 mmol). The resulting mixture was heated to 80° C. for 3 hours. After cooling to RT, the mixture was allowed to stand overnight. The mixture was partitioned between EtOAc (75 mL) and sat. $NaHCO_3$ to give a biphasic mixture. The organic layer was separated, washed with brine (75 mL), dried over $MgSO_4$, filtered under vacuum and concentrated under reduced pressure to give a crude brown oil. The crude material was loaded onto a 120 g silica column (RediSep®), primed with TBME (tert-butylmethyl ether). The product was eluted using a TBME/MeOH (10-20%) gradient, UV collection trigger 254 nm. The product fractions were combined and concentrated to give a viscous yellow oil/foam. The isolated oil/foam was dissolved in MeOH and re-concentrated under reduced pressure and the resulting oil/gum was sonicated in TBME (~80 mL) for 2 hours to give a yellow solid. The solid was filtered under vacuum and dried at 40° C. for 2 hours to give the title compound;

LCMS: Rt 0.79 mins; MS m/z 417.3 [M+H]+; Method 2 minLowpHv03

$^1$H NMR (400 MHz, DMSO-d6) δ 8.04 (1H, d), 7.72 (1H, d), 7.66 (1H, dd), 7.64 (1H, d), 7.50 (1H, d), 7.49 (1H, s), 7.43 (1H, t), 6.29 (2H, s), 4.38 (1H, s), 2.61 (2H, d), 2.47 (3H, s), 2.34 (3H, s), 1.05 (6H, s).

Re-crystallization of 3-(6-Amino-5-(2-methyloxazol-5-yl)pyridin-3-yl)-N-(2-hydroxy-2-methylpropyl)-4-methylbenzenesulfonamide (Example 6)

3-(6-Amino-5-(2-methyloxazol-5-yl)pyridin-3-yl)-N-(2-hydroxy-2-methylpropyl)-4-methylbenzenesulfonamide (may be prepared as in Example 6; 16.5 g) was slurried in EtOH (110 ml) and heated in a reactor to 50° C. Seed crystal slurry (A) (0.9 g, 39.6 mmol) in ethanol (6 ml) was added to this solution and the reaction mixture cycled overnight using the following cycling program:

Heating from 5° C. to 50° C. at 5° C./min, holding at 50° C. for 5 min, cooling from 50° C. to 5° C. at 0.27° C./min, holding at 5° C. for 25 mins. Total cycle time 215 mins. Stirring speed 1000 rpm.

After 6 cycles were completed, the resulting slurry was filtered and the filtrate washed with minimal ethanol. This filtrate was dried in vacuo at 40° C. for 2.5 hrs (yield 13.4 g). Differential scanning calorimetry showed a melting point of 157° C. for this material.

The seed crystal slurry (A) was prepared as follows:

3-(6-Amino-5-(2-methyloxazol-5-yl)pyridin-3-yl)-N-(2-hydroxy-2-methylpropyl)-4-methylbenzenesulfonamide (may be prepared as described in Example 6; 0.9 g) was slurried in EtOH (6 ml) and heated in a reactor to 50° C. Seed crystals (B) (12 mg) were added to this hazy solution at 50° C. in the first cycle and the reaction mixture cycled overnight using the following cycling program:

Heating from 5° C. to 50° C. at 5° C./min, holding at 50° C. for 5 min, cooling from 50° C. to 5° C. at 0.27° C./min, holding at 5° C. for 25 mins. Total cycle time 205 mins. Stirring speed 1000 rpm Seed crystals (B) were prepared as follows:

3-(6-Amino-5-(2-methyloxazol-5-yl)pyridin-3-yl)-N-(2-hydroxy-2-methylpropyl)-4-methylbenzenesulfonamide (may be prepared as described in Example 6; 150 mg) was added to 1 ml ethanol which gave a hazy solution at 50° C. The reaction mixture was cycled for 6 hours using the following cycling program:

Heating from 5° C. to 50° C. at 5° C./min, holding at 50° C. for 1 min, cooling from 50° C. to 5° C. at 0.5° C./min, holding at 5° C. for 25 mins. Total cycle time 125 mins. Stirring speed 1000 rpm. This heat/cool cycle was modified with a slower cooling rate, reduced from 0.5° C. to 0.27° C.

The reaction mixture was further cycled for 65 hours (25 cycles) using the following cycling program:

Heating from 5° C. to 50° C. at 5° C./min, holding at 50° C. for 1 min, cooling from 50° C. to 5° C. at 0.27° C./min, holding at 5° C. for 25 mins. Total cycle time 205 mins. Stirring speed 1000 rpm.

This reaction mixture was then filtered and dried in vacuo at 40° C. for 2 hrs (yield: 80 mg).

Preparation of HCl salt of 3-(6-Amino-5-(2-methyloxazol-5-yl)pyridin-3-yl)-N-(2-hydroxy-2-methylpropyl)-4-methylbenzenesulfonamide (Example 6)

1 ml of 95% of IPA containing 20 μl of 12N HCl was added to the solid of 3-(6-Amino-5-(2-methyloxazol-5-yl) pyridin-3-yl)-N-(2-hydroxy-2-methylpropyl)-4-methylbenzenesulfonamide (Example 6; 100 mg) at room temperature and then placed in a reactor. The reaction mixture was cycled (1 cycle) using the following cycling program:

Heating from 25° C. to 50° C. in 30 min, holding at 50° C. for 1 hours, cooling from 50° C. to 5° C. within 2 hours, holding at 5° C. for 1 h. Stirring speed: 500 rpm stirring.

The precipitate was collected by centrifugation and dried in vacuum overnight to get a white solid.

Preparation of fumarate salt of 3-(6-Amino-5-(2-methyloxazol-5-yl)pyridin-3-yl)-N-(2-hydroxy-2-methylpropyl)-4-methylbenzenesulfonamide (Example 6)

500 μl of EtOAc was added to the solid mixture of 50 mg 3-(6-Amino-5-(2-methyloxazol-5-yl)pyridin-3-yl)-N-(2-hydroxy-2-methylpropyl)-4-methylbenzenesulfonamide (Example 6) and 14 mg fumaric acid at room temperature in a reactor. The reaction mixture was cycled (6 cycles) using the following cycling program:

Heating from 25° C.-50° C. in 30 min, holding at 50° C. for 1 h, cooling from 50° C. to 5° C. in 2 h, holing at 5° C. for 1 h)

The precipitate was collected by centrifugation and dried in vacuum overnight to get a white solid.

Example 7

3-(6-Amino-5-(3-methylisoxazol-5-yl)pyridin-3-yl)-N-(2-hydroxy-2-methylpropyl)-4-methylbenzenesulfonamide

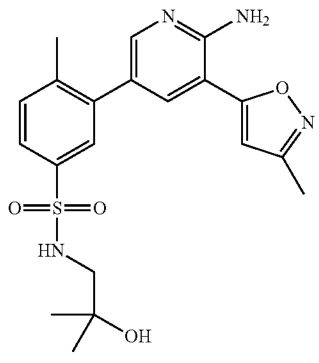 [SMILES: Cc1cc(-c2cc(-c3cc(S(=O)(=O)NCC(C)(C)O)ccc3C)cnc2N)on1]

A mixture comprising 5-bromo-3-(3-methyl-isoxazol-5-yl)-pyridin-2-ylamine (Intermediate C5) (1.5 g, 5.90 mmol) in 1,4-dioxane (12 mL), potassium phosphate (2.506 g, 11.81 mmol), N-(2-hydroxy-2-methyl-propyl)-4-methyl-3-(4,4,5,5-tetramethyl[1,3,2] dioxaborolan-2-yl) benzenesulfonamide (Intermediate B2) (2.180 g, 5.90 mmol) and [1,1'-bis(di-tert-butylphosphino)ferrocene]dichloropalladium(II) (0.192 g, 0.295 mmol) in water (3.00 mL) was heated using microwave radiation at 100° C. for 25 mins. The resulting mixture was poured into water and extracted with EtOAc. The organic layer was separated and washed with water, brine and dried over $MgSO_4$. Si-TMT resin was added and after stirring for 1 h, the mixture was filtered. The solvent was removed under reduced pressure and the crude product was suspended in EtOH (50 ml) and heated to reflux. After cooling to RT, the mixture was allowed to stand at RT for 3 days. The resulting solid was collected by filtration and dried in a vacuum oven at 150° C. for 7 h to afford the title compound;

LCMS: Rt 2.81 mins; MS m/z 417.5 [M+H]+; Method 8 minLowpHv01

$^1$H NMR (400 MHz, DMSO-d6) δ 8.16 (1H, d), 7.91 (1H, d), 7.71-7.64 (2H, m), 7.55-7.42 (2H, m), 6.90 (1H, s), 6.50 (2H, s), 4.40 (1H, s), 2.62 (2H, d), 2.37 (3H, s), 2.30 (3H, s), 1.06 (6H, s).

Example 8

3-[6-Amino-5-(3-methyl-[1,2,4]oxadiazol-5-yl)-pyridin-3-yl]-N-(6-hydroxy-spiro[3.3]hept-2-yl)-4-methyl-benzenesulfonamide (racemate)

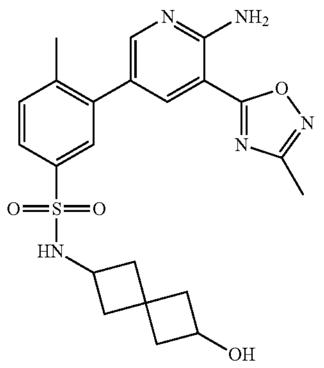 [SMILES: Cc1noc(-c2cc(-c3cc(S(=O)(=O)NC4CC5(CC(O)C5)C4)ccc3C)cnc2N)n1]

A stirring mixture of racemic 3-bromo-N-(6-hydroxyspiro[3.3]heptan-2-yl)-4-methylbenzenesulfonamide (Intermediate A8) (353 mg, 0.980 mmol), KOAc (144 mg, 1.470 mmol), $PdCl_2$(dppf).$CH_2Cl_2$ adduct (40.0 mg, 0.049 mmol), and bis(pinacolato)diboron (274 mg, 1.078 mmol) in DME (4901 μL), under $N_2$, was heated at 90° C. for 18 h. 5-Bromo-3-(3-methyl-1,2,4-oxadiazol-5-yl)pyridin-2-amine (Intermediate C3) (250 mg, 0.980 mmol), 2M aqueous $Na_2CO_3$ (1470 μL, 2.94 mmol), and $PdCl_2$(dppf).$CH_2Cl_2$ adduct (40.0 mg, 0.049 mmol) was added and reaction was heated in a microwave for 45 mins at 120° C. The reaction was added to water (100 ml), and product extracted into EtOAc (2×90 ml). The organic phase was washed with brine, dried over $MgSO_4$ and polymer supported trimethyl thiol to scavenge Pd. This mixture was swirled occasionally over 1 hour. The solids were removed by filtration, washed with EtOAc and concentrated under vacuo. The crude was purified by ISCO combiflash chromatography, eluting with 0-10% gradient of (2M $NH_3$ in MeOH) in DCM on a 24 g Si-column, loading with DCM to afford racemic 3-[6-amino-5-(3-methyl-[1,2,4]oxadiazol-5-yl)-pyridin-3-yl]-N-(6-hydroxy-spiro[3.3]hept-2-yl)-4-methyl-benzenesulfonamide (Example 8);

LCMS: Rt=0.99 mins; MS m/z 456.1 [M+H]+; Method 2 minLowpHv01

Example 8.1: (R) or (S)-3-[6-Amino-5-(3-methyl-[1,2,4]oxadiazol-5-yl)-pyridin-3-yl]-N-(6-hydroxy-spiro[3.3]hept-2-yl)-4-methyl-benzenesulfonamide hydrochloride

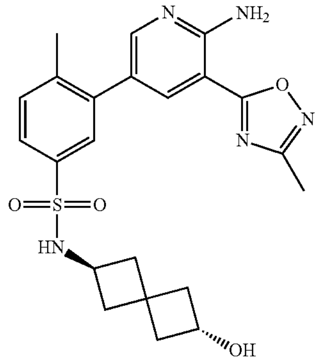

or

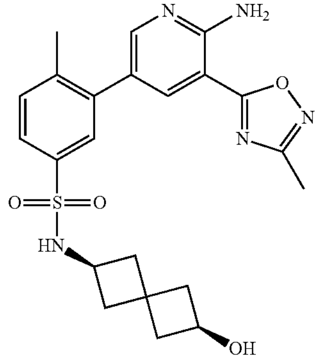

Chiral separation of the racemate in Example 8 was carried out under the following conditions:

Column: 2× Chiralpak AD-H, 250×10 mm 5 um @ 35 deg C.

Mobile phase: 35% Isopropanol+0.1% v/v DEA/65% $CO_2$

Flow: 10 ml/min

Detection: UV @ 220 nm

Instrument: Berger Minigram SFC1

The first eluted compound was dissolved in MeOH (0.5 ml) and 4.0M HCl in dioxane was added (0.5 ml). After 5 mins the mixture was concentrated to dryness and the resulting solid recrystallised from EtOH (~2 ml) to afford the title compound; (single enantiomer, unknown stereochemistry).

LCMS: Rt 0.98 mins; MS m/z 456.5 [M+H]+; Method 2 minLowpHv01.

$^1$H NMR (400 MHz, DMSO-d6) δ 8.38 (1H, s), 8.28 (1H, s), 7.86 (1H, d), 7.72-7.62 (2H, m), 7.53 (1H, d), 3.91-3.80 (1H, m), 3.59-3.48 (1H, m), 2.48 (3H, s), 2.38 (3H, s), 2.27.2.18 (1H, m), 2.09-1.98 (2H, m), 1.97-1.85 (1H, m), 1.82-1.63, (4H, m).

Example 8.2: (R) or (S)-3-[6-Amino-5-(3-methyl-[1,2,4]oxadiazol-5-yl)-pyridin-3-yl]-N-(6-hydroxy-spiro[3.3]hept-2-yl)-4-methyl-benzenesulfonamide hydrochloride

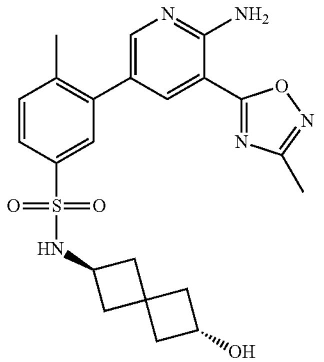

or

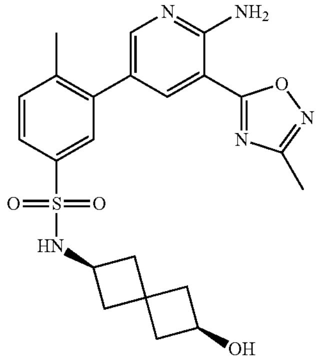

The second eluted compound eluted was dissolved in MeOH (0.5 ml) and 4.0M HCl in dioxane was added (0.5 ml). After 5 mins the mixture was concentrated to dryness and the resulting solid recrystallised from EtOH (~2 ml) to afford the title compound; (single enantiomer, unknown stereochemistry).

LCMS: Rt 1.05 mins; MS m/z 457.2 [M+H]+; Method 2 minLowpHv01.

$^1$H NMR (400 MHz, DMSO-d6) δ 8.38 (1H, s), 8.28 (1H, s), 7.86 (1H, d), 7.72-7.62 (2H, m), 7.53 (1H, d), 3.91-3.80 (1H, m), 3.59-3.48 (1H, m), 2.48 (3H, s), 2.38 (3H, s), 2.27.2.18 (1H, m), 2.09-1.98 (2H, m), 1.97-1.85 (1H, m), 1.82-1.63, (4H, m).

Example 9

3-[6-Amino-5-(2-methyl-thiazol-5-yl)-pyridin-3-yl]-N-(3-hydroxy-propyl)-4-methyl-benzenesulfonamide

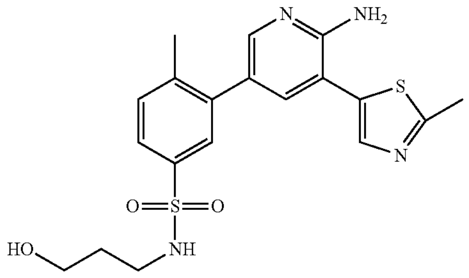 [SMILES: Cc1ncc(-c2cc(-c3cc(S(=O)(=O)NCCCO)ccc3C)cnc2N)s1]

A mixture of 5-Bromo-3-(2-methyl-thiazol-5-yl)-pyridin-2-ylamine (Intermediate C6) (40 mg, 0.148 mmol), N-(3-Hydroxypropyl)-4-methyl-3-(4,4,5,5-tetramethyl-1,3,2-dioxaborolan-2-yl)benzenesulfonamide (Intermediate B1) (65 mg, 0.183 mmol), bis(triphenylphosphine) palladium(II) chloride (11 mg, 0.016 mmol) and sodium carbonate 2M aqueous (225 μL, 0.450 mmol) in Toluene (0.6 ml) and Ethanol (300 μL) was heated in the microwave to 120° C. for 1 hour. DCM, was added and the layers separated using a phase separator cartridge. The organic layer was evaporated under reduced pressure and purified by flash column chromatography using solid loading (ISCO, 4 g silica, 0-20% methanol in TBME) to give the product as a yellow-orange oil. Crystallised from ethanol to give an orange solid (31 mg);

LCMS: Rt 0.66 min; MS m/z 419.2 [M+H]+; Method 2 minLowpH.

$^1$H NMR (400 MHz, DMSO-d6) δ 8.03 (1H, d); 7.83 (1H, s); 7.64 (1H); 7.60 (1H); 7.53-7.48 (2H, m); 7.45 (1H, br); 6.13 (2H, s); 4.40 (1H, br); 3.36 (2H, br m); 2.78 (2H, br t); 2.69 (3H, s); 2.36 (3H, s); 1.52 (2H, m).

Example 10

3-(6-Amino-5-(3-methyl-1,2,4-oxadiazol-5-yl)pyridin-3-yl)-N-(2-hydroxy-2-methylpropyl)-4-methylbenzenesulfonamide, hydrochloride salt

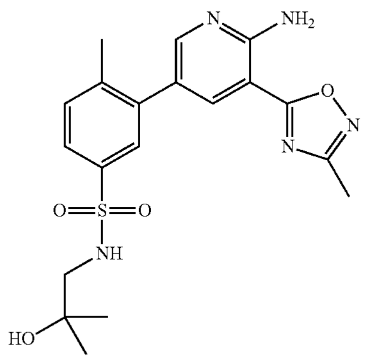 [SMILES: Cc1noc(-c2cc(-c3cc(S(=O)(=O)NCC(C)(C)O)ccc3C)cnc2N)n1]

To a solution of N-(2-hydroxy-2-methylpropyl)-4-methyl-3-(4,4,5,5-tetramethyl-1,3,2-dioxaborolan-2-yl)benzenesulfonamide (Intermediate B2) (2.82 g, 7.64 mmol) in DME (25.5 mL) was added 5-bromo-3-(3-methyl-1,2,4-oxadiazol-5-yl)pyridin-2-amine (Intermediate C3)(1.3 g, 5.10 mmol), bis(triphenylphosphine)palladium(II) chloride (0.179 g, 0.255 mmol) and $Na_2CO_3$ (aq. 2.0M) (7.64 mL, 15.29 mmol). The reaction was heated in a microwave at 120° C. for 30 mins. A further 1 g of N-(2-hydroxy-2-methylpropyl)-4-methyl-3-(4,4,5,5-tetramethyl-1,3,2-dioxaborolan-2-yl)benzenesulfonamide was added and bis(triphenylphosphine)palladium(II) chloride (0.179 g, 0.255 mmol) and reaction microwaved at 120° C. for 30 mins.

The reaction was added to water (400 ml), and product extracted into EtOAc (2×200 ml). The organic phase was washed with brine, dried over $MgSO_4$ and polymer supported trimethyl thiol to scavange Pd. This mixture was swirled occasionally over 1 hour. The solids were removed by filtration, washed with EtOAc and concentrated under reduced pressure. The crude product was purified by ISCO combiflash chromatography, eluting with a modified 0-10% gradient (DCM_2M NH3 in MeOH) on a 80 g si-column, loading with DCM. The resulting gum was dissolved in TBME (~3 ml). This was heated and concentrated to ~1 ml. The solution was left to cool overnight. The resulting solid was collected by filtration and dried to give a pale yellow solid. The purified product was taken up in 4M HCl in dioxane (2 ml). After 5 min the volatiles were evaporated and the residue was recrystallised from hot EtOH to give a solid;

LCMS: Rt 0.96 mins; MS m/z 418.3 [M+H]+; Method 2 minLowpHv01

$^1$H NMR (400 MHz, DMSO-d6) δ 8.36 (1H, d), 8.23 (1H, d), 7.85-7.50 (2H, br s), 7.69 (2H, d), 7.68 (1H, dd), 7.53 (1H, d), 7.45 (1H, t), 2.61 (2H, d), 2.46 (3H, s), 2.37 (3H, s), 1.05 (6H, s).

Example 11

3-[6-Amino-5-(3-methyl-[1,2,4]oxadiazol-5-yl)-pyridin-3-yl]-N-(2-hydroxy-2-methyl-propoxy)-4-methyl-benzenesulfonamide, hydrochloride salt

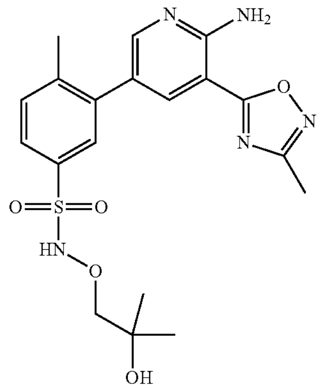 [SMILES: Cc1noc(-c2cc(-c3cc(S(=O)(=O)NOCC(C)(C)O)ccc3C)cnc2N)n1]

Prepared from N-(2-Hydroxy-2-methyl-propoxy)-4-methyl-3-(4,4,5,5-tetramethyl-[1,3,2]dioxaborolan-2-yl) benzenesulfonamide (Intermediate B4) and 5-bromo-3-(3-methyl-1,2,4-oxadiazol-5-yl)pyridin-2-amine (Intermediate C3) under analogous conditions to those of Example 1. The purified product was taken up in 4M HCl in dioxane (2 ml). After 5 min the volatiles were evaporated and the residue was recrystallised from hot EtOH to give a solid;

LCMS: Rt 0.90 mins; MS m/z 434.3 [M+H]+; Method 2 minLowpHv01

$^1$H NMR (400 MHz, DMSO-d6) δ 10.44 (1H, s), 8.40 (1H, s), 8.32 (1H, d), 7.78 (1H, d), 7.73 (1H, s), 7.61 (1H, d), 3.73 (2H, s), 2.49 (3H, s), 2.41 (3H, s), 1.06 (6H, s).

Example 12 trans 3-[6-Amino-5-(3-methyl-[1,2,4]oxadiazol-5-yl)-pyridin-3-yl]-N-(4-hydroxy-cyclohexyl)-4-methyl-benzenesulfonamide, hydrochloride salt

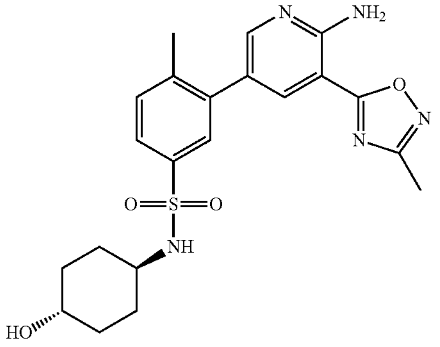 [SMILES: Cc1noc(-c2cc(-c3cc(S(=O)(=O)N[C@H]4CC[C@H](O)CC4)ccc3C)cnc2N)n1]

Prepared from trans N-(4-Hydroxy-cyclohexyl)-4-methyl-3-(4,4,5,5-tetramethyl-[1,3,2]dioxaborolan-2-yl)-benzenesulfonamide (Intermediate B5) and 5-bromo-3-(3-methyl-1,2,4-oxadiazol-5-yl)pyridin-2-amine (Intermediate C3) under analogous conditions to those of Example 1. The purified product was taken up in 4M HCl in dioxane (2 ml). After 5 min the volatiles were evaporated and the residue was recrystallised from hot EtOH to give a solid;

LCMS: Rt 0.93 mins; MS m/z 442.3 [M−H]−; Method 2 minLowpHv01

$^{1}$H NMR (400 MHz, DMSO-d6) δ 8.38 (1H, s), 8.24 (1H, s), 7.80-7.65 (3H, m), 7.62-7.50 (2H, m), 7.61 (1H, d), 3.37-3.34 (1H, m), 3.00-2.87 (1H, m), 2.39 (3H, s), 1.79-1.55 (4H, m), 1.27-1.00 (4H, m).

Example 13

3-[6-Amino-5-(2-methyl-oxazol-5-yl)-pyridin-3-yl]-N-(3-hydroxy-3-methyl-butyl)-4-methyl-benzenesulfonamide, hydrochloride salt

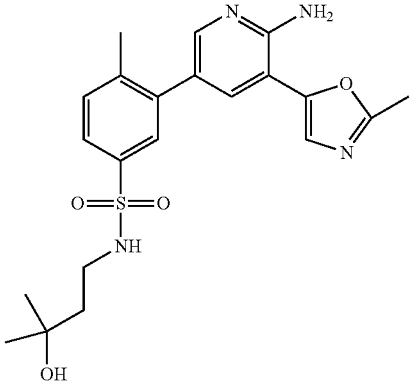 [SMILES: Cc1ncc(-c2cc(-c3cc(S(=O)(=O)NCCC(C)(C)O)ccc3C)cnc2N)o1]

The title compound was prepared from N-(3-hydroxy-3-methyl butyl)-4-methyl-3-(4,4,5,5-tetramethyl-1,3,2-dioxaborolan-2-yl)benzenesulfonamide (Intermediate B3) and 5-Bromo-3-(2-methyl-oxazol-5-yl)-pyridin-2-ylamine (Intermediate C4) under analogous conditions to those of Example 1. The purified product was taken up in 4M HCl in dioxane (2 ml). After 5 min the volatiles were evaporated and the residue was recrystallised from hot EtOH to give a solid;

LCMS: Rt 0.78 mins; MS m/z 431.4 [M+H]+; Method 2 minLowpHv01

$^{1}$H (400 MHz, DMSO-d6) δ 8.24 (2H, s), 8.15 (1H, br), 7.76 (1H, dd), 7.71 (1H, d), 7.69 (1H, s), 7.59 (1H, d), 7.50 (1H, br t), 5.20 (2H, br), 2.82 (2H, m), 2.50 (3H, s, partially obscured by DMSO), 2.37 (3H, s), 1.50 (2H, m), 1.03 (6H, s).

Example 14

3-[6-Amino-5-(3-methyl-isoxazol-5-yl)-pyridin-3-yl]-N-(3-hydroxy-3-methyl-butyl)-4-methyl-benzenesulfonamide, hydrochloride salt

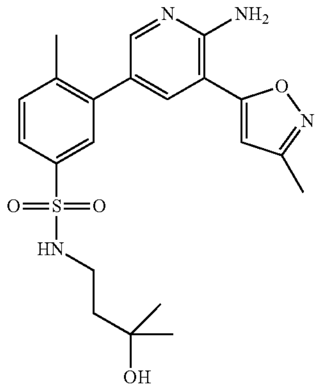 [SMILES: Cc1cc(-c2cc(-c3cc(S(=O)(=O)NCCC(C)(C)O)ccc3C)cnc2N)on1]

Prepared from N-(3-hydroxy-3-methylbutyl)-4-methyl-3-(4,4,5,5-tetramethyl-1,3,2-dioxaborolan-2-yl)benzenesulfonamide (Intermediate B3) and 5-bromo-3-(3-methyl-isoxazol-5-yl)-pyridin-2-ylamine (Intermediate C5) under analogous conditions to those of Example 1. The purified product was taken up in 4M HCl in dioxane (2 ml). After 5 min the volatiles were evaporated and the residue was recrystallised from hot EtOH to give a solid;

LCMS: Rt 0.86 mins; MS m/z 431.6 [M+H]+; Method 2 minLowpHv01

$^{1}$H NMR (400 MHz, DMSO-d6) δ 8.22 (1H, d), 8.17 (1H, s), 7.71 (1H, dd), 7.67 (1H, s), 7.56 (1H, d), 7.44 (1H, t), 6.99 (1H, s), 2.83 (2H, m), 2.37 (3H, s), 2.32 (3H, s), 1.50 (2H, m), 1.02 (6H, s).

Example 15

3-[6-Amino-5-(2-methyl-thiazol-5-yl)-pyridin-3-yl]-N-(2-hydroxy-2-methyl-propyl)-4-methyl-benzene-sulfonamide

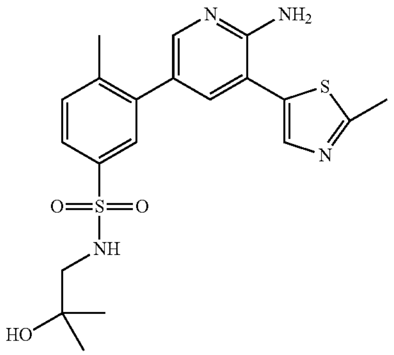 [SMILES: Cc1ncc(-c2cc(-c3cc(S(=O)(=O)NCC(C)(C)O)ccc3C)cnc2N)s1]

A mixture of 3-bromo-N-(2-hydroxy-2-methylpropyl)-4-methylbenzenesulfonamide (Intermediate A2) (48 mg, 0.149 mmol), potassium acetate (22 mg, 0.224 mmol), $PdCl_2(dppf).CH_2Cl_2$ adduct (6 mg, 7.35 μmol) and bis(pinacolato) diboron (42 mg, 0.165 mmol) in DME (0.7 mL) was heated in the microwave to 90° C. for 3 hours. 5-bromo-3-(2-methylthiazol-5-yl)pyridin-2-amine (Intermediate C6) (40 mg, 0.148 mmol), $PdCl_2(dppf).CH_2Cl_2$ adduct (6 mg, 7.35 μmol) and aqueous sodium carbonate (2M, 0.25 mL, 0.500 mmol) were added and the reaction was heated in the microwave to 120° C. for 45 mins. DCM was added and the mixture was partitioned using a phase separator column, loaded onto silica and purified by flash column chromatography (ISCO, 4 g silica, 0-12% methanol in TBME) to give the product as a brown solid;

LCMS: Rt 0.69 min; MS m/z 433.2 [M+H]+; Method 2 minLowpH.

$^1$H NMR (400 MHz, DMSO-d6) δ 8.04 (1H, d); 7.83 (1H, s); 7.67-7.62 (2H, m); 7.53-7.47 (2H, m); 7.42 (1H, t); 6.13 (2H, s); 4.38 (1H, s); 2.69 (3H, s); 2.60 (2H, d); 2.36 (3H, s); 1.05 (6H, s).

Example 16

3-(2-Amino-2'-methyl-[3,4']bipyridinyl-5-yl)-N-(3-hydroxy-3-methyl-butyl)-4-methyl-benzenesulfonamide

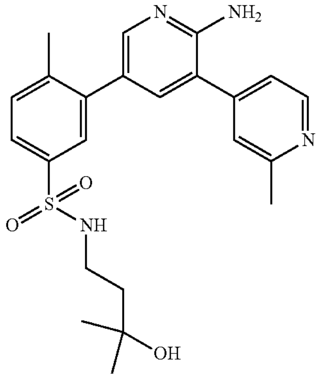 [SMILES: Cc1cc(-c2cc(-c3cc(S(=O)(=O)NCCC(C)(C)O)ccc3C)cnc2N)ccn1]

Prepared from N-(3-hydroxy-3-methylbutyl)-4-methyl-3-(4,4,5,5-tetramethyl-1,3,2-dioxaborolan-2-yl)benzenesulfonamide (Intermediate B3) and 5-bromo-2'-methyl-[3,4']bipyridinyl-2-ylamine (Intermediate C7) under analogous conditions to those of Example 9;

LCMS: Rt 0.58 mins; MS m/z 441.2 [M+H]+; Method 2 minLowpHv01

$^1$H NMR (400 MHz, MeOH-d4) δ 8.52 (1H, d), 8.04 (1H, d), 7.75 (1H, dd), 7.71 (1H, d), 7.52 (3H, m), 7.43 (1H, m), 3.00 (2H, m), 2.62 (3H, s), 2.42 (3H, s), 1.65 (2H, m), 1.15 (6H, s).

Example 17

3-[6-Amino-5-(3-methyl-isoxazol-5-yl)-pyridin-3-yl]-4-methyl-N-(3-methyl-oxetan-3-ylmethyl)-benzenesulfonamide hydrochloride

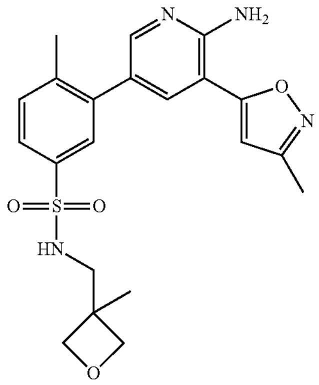 [SMILES: Cc1cc(-c2cc(-c3cc(S(=O)(=O)NCC4(C)COC4)ccc3C)cnc2N)on1]

The title compound was prepared from 4-methyl-N-(3-methyl-oxetan-3-ylmethyl)-3-(4,4,5,5)tetramethyl-[1,3,2]dioxaborolan-2-yl)-benzenesulfonamide (Intermediate B7) and 5-bromo-3-(3-methyl-isoxazol-5-yl)-pyridin-2-ylamine (Intermediate C5) under analogous conditions to those of Example 1;

LCMS: Rt 0.85 mins; MS m/z 429.3. [M+H]+; Method 2 minLowpHv01

$^1$H NMR (400 MHz, DMSO-d6) δ 8.27 (2H, m), 7.73 (2H, m), 7.59 (2H, m), 7.03 (1H, s), 3.52 (2H, d), 3.24 (2H, d), 2.71 (2H, d), 2.37 (3H, s), 2.33 (3H, s), 0.86 (3H, s).

Example 18

3-(2-Amino-[3,4']bipyridinyl-5-yl)-N-(3-hydroxy-3-methyl-butyl)-4-methyl-benzenesulfonamide

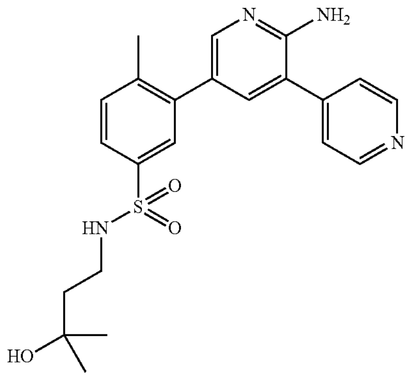 [SMILES: Cc1ccc(S(=O)(=O)NCCC(C)(C)O)cc1-c1cnc(N)c(-c2ccncc2)c1]

To a 2 mL microwave tube equipped with stirrer bar was added potassium carbonate (116 mg, 0.84 mmol), copper(I) iodide (16 mg, 0.084 mmol), 6-methyl-2-(pyridin-4-yl)-1,3,6,2-dioxazaborocane-4,8-dione (59 mg, 0.252 mmol), 3-(6-amino-5-bromopyridin-3-yl)-N-(3-hydroxy-3-methylbutyl)-4-methylbenzene sulfonamide (Intermediate E1) (72 mg, 0.168 mmol) and XPhos (32 mg, 0.067 mmol). DMF (2 mL) and IPA (0.4 mL) were added, followed by $Pd_2(dba)_3$ (15 mg, 0.17 mmol). The mixture was heated in the Biotage microwave for 1 hour at 100° C. Pyridine-4-boronic acid (31 mg, 0.252 mmol) was added and the mixture was heated in the microwave for a further 1 hour. 2M sodium carbonate (1 mL) added and the reaction was heated for a further 2 h. The reaction was diluted with water (5 mL) and extracted with EtOAc (3×5 mL). Evaporation gave a brown oil. Purification on an preparative HPLC system gave the product as a brown oil;

LCMS: Rt 0.59 mins; MS m/z 427.2 [M+H]+; Method 2 minLowpH.

$^1$H NMR (400 MHz, MeOH-d4) d 8.54 (2H, d), 7.93 (1H, d), 7.63 (1H, dd), 7.60 (1H, d), 7.53 (2H, d), 7.43 (1H, d), 7.40 (1H, d), 2.88 (2H, m), 2.30 (3H, s), 1.53 (2H, m), 1.02 (6H, s).

Example 19 trans 3-[6-Amino-5-(3-methyl-[1,2,4]oxadiazol-5-yl)-pyridin-3-yl]-N-(4-hydroxymethyl-cyclohexyl)-4-methyl-benzenesulfonamide hydrochloride

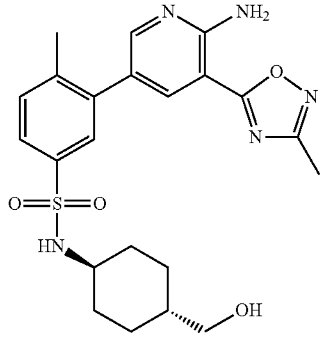 [SMILES: Cc1noc(-c2cc(-c3cc(S(=O)(=O)N[C@H]4CC[C@H](CO)CC4)ccc3C)cnc2N)n1]

To a stirring solution of 3-(6-amino-5-(3-methyl-1,2,4-oxadiazol-5-yl)pyridin-3-yl)-4-methylbenzene-1-sulfonyl chloride (Intermediate E2) (50 mg, 0.137 mmol) in DMA (685 µl), under $N_2$, was added trans (4-amino-cyclohexyl)-methanol (26.6 mg, 0.206 mmol) & DIPEA (59.8 µl, 0.343 mmol). The reaction was stirred for 4 hours at RT. The reaction mixture was added to sat aqueous $NaHCO_3$ (50 ml) and the product extracted into EtOAc (2×40 ml). Organic phases were combined, washed with brine, dried over $MgSO_4$, and concentrated to dryness. The crude product was purified by ISCO combiflash chromatography, eluting with 0-10% gradient of (2.0M $NH_3$ in MeOH) in DCM on a 4 g Si-column, loading with DCM. The resulting oil was dissolved in a small amount of MeOH (1 ml) and HCl in dioxane (4M) was added (1 ml). The mixture was concentrated to dryness and the solid recrystalised from hot EtOH to give a crystalline solid (65 mg, 96%). The purified product was taken up in 4M HCl in dioxane (2 ml). After 5 min the volatiles were evaporated and the residue was recrystallised from hot EtOH to give a solid;

LCMS: Rt 1.01 mins; MS m/z 458.5 [M+H]+; Method 2 minLowpHv01.

$^1$H NMR (400 MHz, DMSO-d6) d 8.37 (1H, d), 8.26 (1H, d), 8.05-7.65 (3H, m superimposed over br), 7.60 (1H, d), 7.54 (1H, d), 3.14 (2H, d), 2.90 (1H, br), 2.48 (3H, s), 2.38 (3H, s), 1.66 (4H, m), 1.14 (3H, m), 0.82 (2H, m).

The following examples 19.1 to 19.20 were prepared according to the following method starting from an appropriate commercially available amine.

Each amine (0.206 mmol) was treated with a solution of diisopropylethylamine (0.048 ml, 0.275 mmol) in DMA (0.5 ml) and sonicated to ensure all material had dissolved. Each solution was then treated with a solution of 3-(6-amino-5-(3-methylisoxazol-5-yl)pyridin-3-yl)-4-methylbenzene-1-sulfonyl chloride (Intermediate E3) (50 mg, 0.137 mmol) in DMA (1 ml) and the reaction mixtures shaken for 4 hours. For examples 19.3 and 19.4, mono boc-protected diamines were used to ensure reaction on the correct nitrogen, and the boc group removed prior to purification by treatment with Trifluoroacetic acid (1 ml) and shaking overnight. The reaction mixtures were then evaporated to dryness, re-dissolved in DMA (1.5 ml) and taken on to purification. The reaction mixtures were purified by MS directed reverse phase preparative HPLC [Column details: Waters XSelect CSH Prep C18, 5 um OBD, 30×100 mm; Column temperature: Ambient (room) Temperature; Gradient: 5 to 100% Acetonitrile in water (+0.1% TFA) over 9.0 minutes], resulting in the formation of trifluoroacetic acid salts. For examples 19.3, 19.4, 19.19, 19.22, additional purification was carried out using an Isolute® PE-AX column, resulting in the formation of acetic acid salts. The solutions from each reaction were evaporated to dryness and analyzed using LCMS Method 2 minLowpHv02. Preparation of the amine used in example 19.16 is described in Brocklehurst et al., *Org. Proc. Res. Dev*, 2011, 15, 294-300.

| Ex # | Structure | Name | RT (min) | MS [M + H]+ |
|---|---|---|---|---|
| 19.1 | 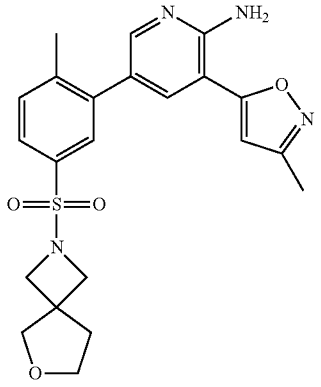 [SMILES: Cc1cc(-c2cc(-c3cc(S(=O)(=O)N4CC5(CCOC5)C4)ccc3C)cnc2N)on1] | 5-(5-(6-oxa-2-azaspiro[3.4]octan-2-ylsulfonyl)-2-methylphenyl)-3-(3-methylisoxazol-5-yl)pyridin-2-amine trifluoroacetic acid salt | 0.84 | 441.5 |

-continued

| Ex # | Structure | Name | RT (min) | MS [M + H]+ |
|---|---|---|---|---|
| 19.2 | 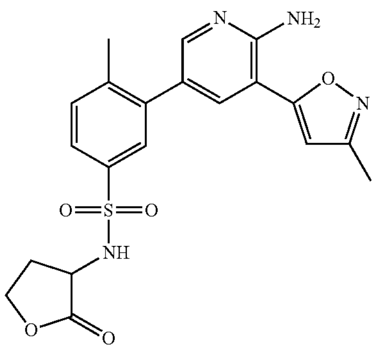 [SMILES: Cc1cc(-c2cc(-c3cc(S(=O)(=O)NC4CCOC4=O)ccc3C)cnc2N)on1] | 3-(6-amino-5-(3-methylisoxazol-5-yl)pyridin-3-yl)-4-methyl-N-(2-oxotetrahydrofuran-3-yl)benzene sulfonamide trifluoroacetic acid salt | 0.78 | 429.4 |
| 19.3 | 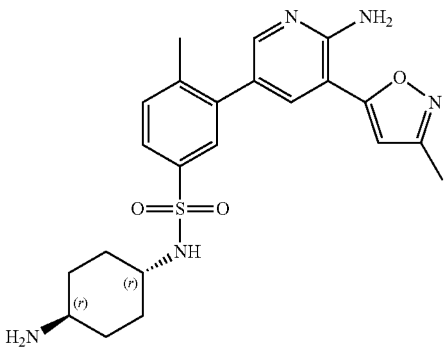 [SMILES: Cc1cc(-c2cc(-c3cc(S(=O)(=O)N[C@H]4CC[C@H](N)CC4)ccc3C)cnc2N)on1] | 3-(6-amino-5-(3-methylisoxazol-5-yl)pyridin-3-yl)-N-(trans-4-aminocyclohexyl)-4-methylbenzenesulfonamide acetic acid salt | 0.68 | 442.5 |
| 19.4 | 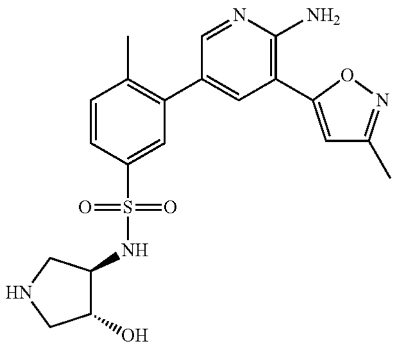 [SMILES: Cc1cc(-c2cc(-c3cc(S(=O)(=O)N[C@@H]4CNC[C@H]4O)ccc3C)cnc2N)on1] | 3-(6-amino-5-(3-methylisoxazol-5-yl)pyridin-3-yl)-N-(trans-4-hydroxypyrrolidin-3-yl)-4-methylbenzenesulfonamide acetic acid salt ( | 0.66 | 430.5 |
| 19.5 | 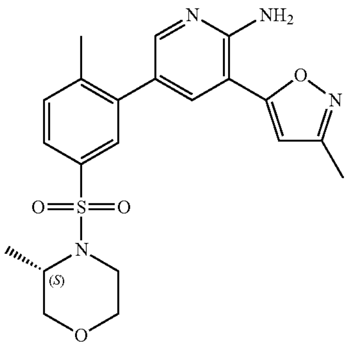 | (S)-5-(2-methyl-5-((3-methylmorpholino)sulfonyl)phenyl)-3-(3-methylisoxazol-5-yl)pyridin-2-amine trifluoroacetic acid salt | 0.88 | 429.5 |

-continued

| Ex # | Structure | Name | RT (min) | MS [M + H]+ |
|---|---|---|---|---|
| 19.6 | 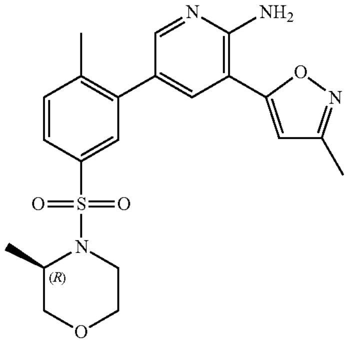 | (R)-5-(2-methyl-5-((3-methylmorpholino)sulfon-yl)phenyl)-3-(3-methylisoxazol-5-yl)pyridin-2-amine trifluoroacetic acid salt | 0.88 | 429.5 |
| 19.7 | 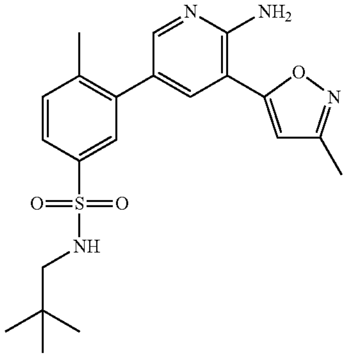 [SMILES: Cc1cc(-c2cc(-c3cc(S(=O)(=O)NCC(C)(C)C)ccc3C)cnc2N)on1] | 3-(6-amino-5-(3-methylisoxazol-5-yl)pyridin-3-yl)-4-methyl-N-neopentylbenzenesulfon-amide trifluoroacetic acid salt | 0.98 | 415.5 |
| 19.8 | 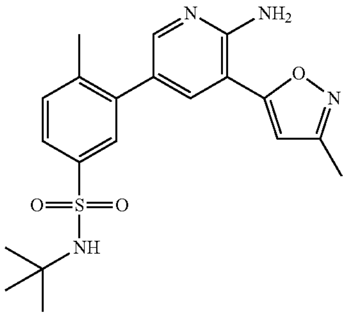 [SMILES: Cc1cc(-c2cc(-c3cc(S(=O)(=O)NC(C)(C)C)ccc3C)cnc2N)on1] | 3-(6-amino-5-(3-methylisoxazol-5-yl)pyridin-3-yl)-N-(tert-butyl)-4-methylbenzenesulfon-amide trifluoroacetic acid salt | 0.91 | 401.5 |
| 19.9 | 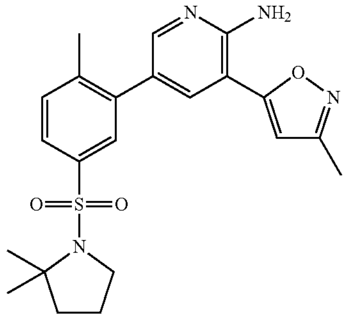 | 5-(5-((2,2-dimethylpyrrolidin-1-yl)sulfonyl)-2-methylphenyl)-3-(3-methylisoxazol-5-yl)pyridin-2-amine trifluoroacetic acid salt | 0.98 | 427.5 |

-continued

| Ex # | Structure | Name | RT (min) | MS [M + H]+ |
|---|---|---|---|---|
| 19.10 | 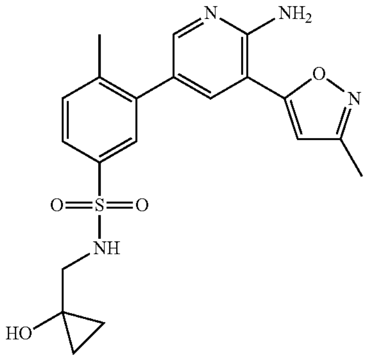 [SMILES: Cc1cc(-c2cc(-c3cc(S(=O)(=O)NCC4(O)CC4)ccc3C)cnc2N)on1] | 3-(6-amino-5-(3-methylisoxazol-5-yl)pyridin-3-yl)-N-((1-hydroxycyclopropyl)methyl)-4-methylbenzenesulfonamide trifluoroacetic acid salt | 0.78 | 415.5 |
| 19.11 | 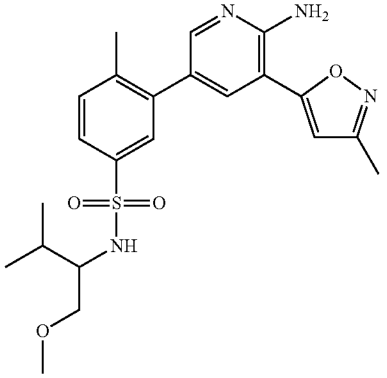 [SMILES: COCC(NS(=O)(=O)c1ccc(C)c(-c2cnc(N)c(-c3cc(C)no3)c2)c1)C(C)C] | 3-(6-amino-5-(3-methylisoxazol-5-yl)pyridin-3-yl)-N-(1-methoxy-3-methylbutan-2-yl)-4-methylbenzenesulfonamide trifluoroacetic acid salt | 0.94 | 445.5 |
| 19.12 | 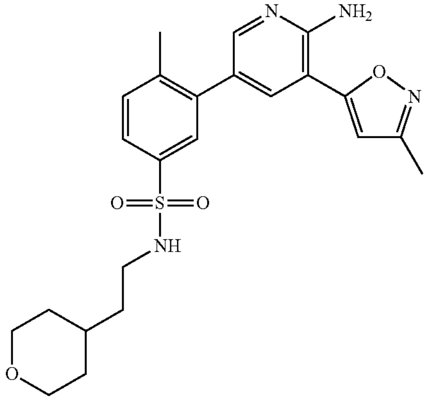 [SMILES: Cc1cc(-c2cc(-c3cc(S(=O)(=O)NCCC4CCOCC4)ccc3C)cnc2N)on1] | 3-(6-amino-5-(3-methylisoxazol-5-yl)pyridin-3-yl)-4-methyl-N-(2-(tetrahydro-2H-pyran-4-yl)ethyl)benzenesulfonamide trifluoroacetic acid salt | 0.87 | 457.5 |
| 19.13 | 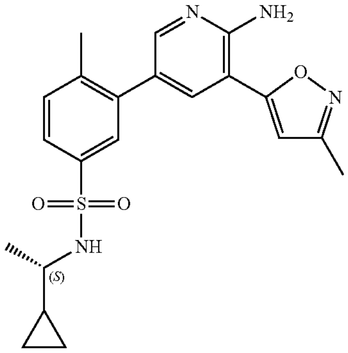 | (S)-3-(6-amino-5-(3-methylisoxazol-5-yl)pyridin-3-yl)-N-(1-cyclopropylethyl)-4-methylbenzenesulfonamide trifluoroacetic acid salt | 0.93 | 413.5 |

-continued

| Ex # | Structure | Name | RT (min) | MS [M + H]+ |
|---|---|---|---|---|
| 19.15 | 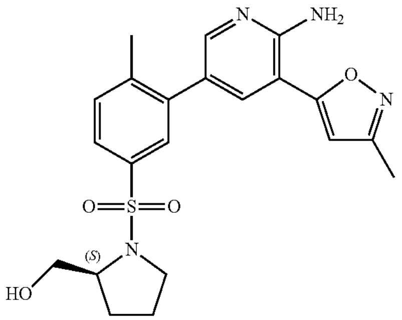 | (S)-(1-((3-(6-amino-5-(3-methylisoxazol-5-yl)pyridin-3-yl)-4-methylphenyl)sulfonyl) pyrrolidin-2-yl)methanol trifluoroacetic acid salt | 0.81 | 429.5 |
| 19.16 | 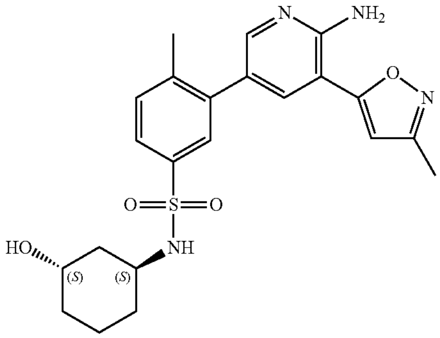 | 3-(6-amino-5-(3-methylisoxazol-5-yl)pyridin-3-yl)-N-((1S,3S)-3-hydroxycyclohexyl)-4-methylbenzenesulfon-amide trifluoroacetic acid salt | 0.8 | 443.5 |
| 19.17 | 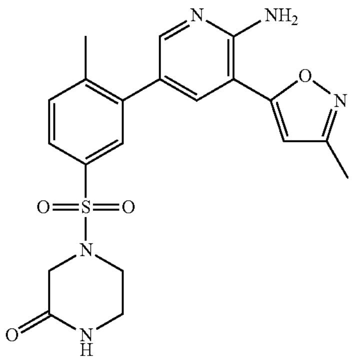 [SMILES: Cc1cc(-c2cc(-c3cc(S(=O)(=O)N4CCNC(=O)C4)ccc3C)cnc2N)on1] | 4-((3-(6-amino-5-(3-methylisoxazol-5-yl)pyridin-3-yl)-4-methylphenyl)sulfonyl) piperazin-2-one trifluoroacetic acid salt | 0.76 | 428.5 |
| 19.18 | 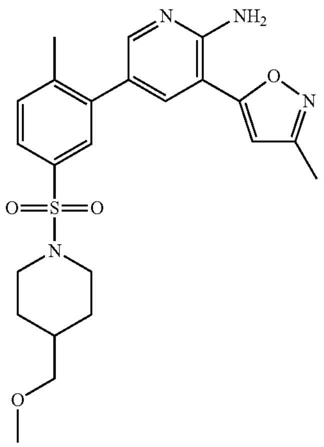 [SMILES: COCC1CCN(S(=O)(=O)c2ccc(C)c(-c3cnc(N)c(-c4cc(C)no4)c3)c2)CC1] | 5-(5-((4-(methoxymethyl)piperidin-1-yl)sulfonyl)-2-methylphenyl)-3-(3-methylisoxazol-5-yl)pyridin-2-amine trifluoroacetic acid salt | 0.95 | 457.5 |

-continued

| Ex # | Structure | Name | RT (min) | MS [M + H]+ |
|---|---|---|---|---|
| 19.19 | 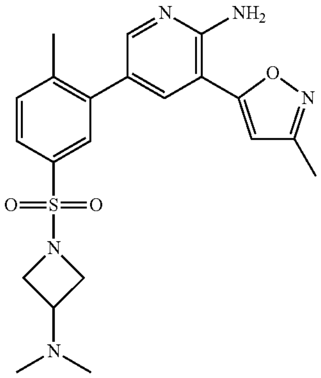 [SMILES: Cc1cc(-c2cc(-c3cc(S(=O)(=O)N4CC(N(C)C)C4)ccc3C)cnc2N)on1] | 5-(5-((3-(dimethylamino)azetidin-1-yl)sulfonyl)-2-methylphenyl)-3-(3-methylisoxazol-5-yl)pyridin-2-amine acetic acid salt | 0.69 | 428.5 |
| 19.20 | 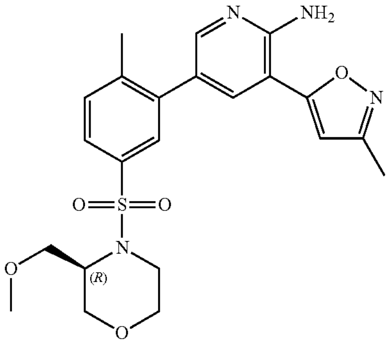 | (R)-5-(5-((3-(methoxymethyl)morpholino)sulfonyl)-2-methylphenyl)-3-(3-methylisoxazol-5-yl)pyridin-2-amine trifluoroacetic acid salt | 0.86 | 459.5 |
| 19.21 | 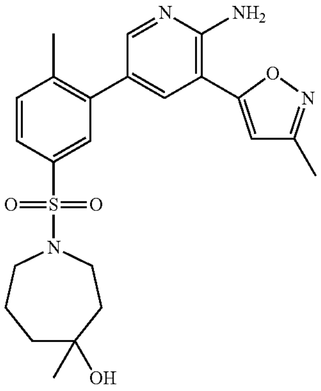 [SMILES: Cc1cc(-c2cc(-c3cc(S(=O)(=O)N4CCCC(C)(O)CC4)ccc3C)cnc2N)on1] | 1-((3-(6-amino-5-(3-methylisoxazol-5-yl)pyridin-3-yl)-4-methylphenyl)sulfonyl)-4-methylazepan-4-ol trifluoroacetic acid salt | 0.86 | 457.6 |
| 19.22 | 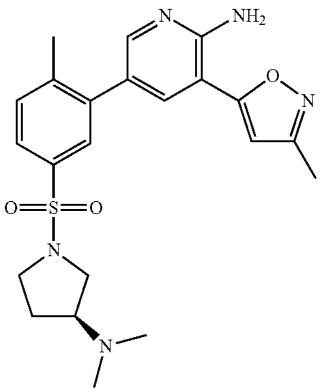 [SMILES: Cc1cc(-c2cc(-c3cc(S(=O)(=O)N4CC[C@H](N(C)C)C4)ccc3C)cnc2N)on1] | (S)-5-(5-((3-(dimethylamino)pyrrolidin-1-yl)sulfonyl)-2-methylphenyl)-3-(3-methylisoxazol-5-yl)pyridin-2-amine acetic acid salt | 0.7 | 442.55 |

Example 20

3-(6-Amino-5-(3-methylisoxazol-5-yl)pyridin-3-yl)-N-(2-hydroxy-2-methylpropoxy)-4-methylbenzene-sulfonamide hydrochloride

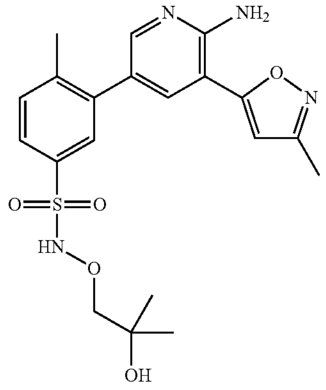 [SMILES: Cc1cc(-c2cc(-c3cc(S(=O)(=O)NOCC(C)(C)O)ccc3C)cnc2N)on1]

To a stirred solution of pyridine (0.066 ml, 0.813 mmol) and 1-(aminooxy)-2-methylpropan-2-ol (86 mg, 0.813 mmol) in THF (6 ml) to give a yellow solution was added 3-(6-Amino-5-(3-methylisoxazol-5-yl)pyridin-3-yl)-4-methylbenzene-1-sulfonyl chloride (Intermediate E3) (26 9 mg, 0.739 mmol). The reaction was stirred at 0° C. for 30 min and allowed to warm to RT overnight. The resulting mixture was extracted with DCM and the organic portion was washed with water, brine, and dried using $MgSO_4$, filtered and concentrated under reduced pressure.

The crude product was purified by flash column chromatography using the flash column chromatography, elution with TBME:MeOH (0-10%) on a 24 g silica cartridge. The required fractions were combined and the solvent removed under reduced pressure to yield a yellow solid. The solid was dissolved in 4M HCl in dioxane and the solvent removed under reduced pressure to yield a yellow residue. The yellow residue was dissolved in isohexane:ethanol (1:1) and recrystallised over several days to afford the title compound as off-white crystals;

LCMS: Rt 0.87 mins; MS m/z 433.5 [M+H]+; Method 2 minlowpHv01

$^1H$ NMR (400 MHz, DMSO-d6) δ 10.45 (1H, s), 8.24 (2H, mult), 7.78 (1H, d), 7.75 (1H, s), 7.61 (1H, d), 7.02 (1H, s), 3.72 (2H, s), 2.40 (3H, s), 2.33 (3H, s), 1.05 (6H, s).

Example 21a: (R or S)-3-(6-Amino-5-(3-methylisoxazol-5-yl)pyridin-3-yl)-4-methyl-N-((tetrahydrofuran-3-yl)oxy)benzenesulfonamide and Example 21 b: (R or S)-3-(6-aminoamino-5-(3-methylisoxazol-5-yl)pyridin-3-yl)-4-methyl-N-((tetrahydrofuran-3-yl)oxy)benzene sulfonamide

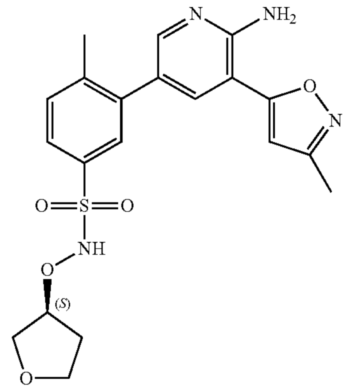

and

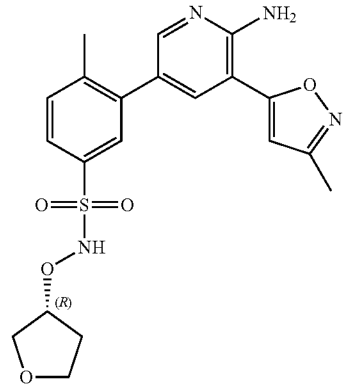

Step 1: 2-((Tetrahydrofuran-3-yl)oxy)isoindoline-1,3-dione

Literature References:

Synlett (1998), (5), 471-472

Organic Preparations and Procedures International (1996), 28(2), 127-64. (see page 144).

To a stirring solution of N-hydroxyphthalimide (5 g, 30.7 mmol) in THF (200 ml) at 00° C., PS-triphenylphosphine (loading 1.88 mmol/g) (19.56 g, 36.8 mmol) was added followed by tetrahydrofuran-3-ol (2.477 ml, 30.7 mmol) and di-tert-butyl azodicarboxylate (7.06 g, 30.7 mmol). The mixture was stirred at 0° C. for 10 mins, then for 21 hours at RT. The mixture was filtered, and solvent removed under reduced pressure. The resulting yellow solid was triturated with ether and the solid collected by filtration, washing with more ether to give a pale yellow solid. The mother liquors were evaporated under reduced pressure and triturated again with ether to give a pale yellow solid;

LCMS: Rt 0.82 min; MS m/z 234.4[M+H]+; Method: 2 minLowpHv01.

Step 2. O-(Tetrahydrofuran-3-yl)hydroxylamine

To a stirred solution of 2-((tetrahydrofuran-3-yl)oxy) isoindoline-1,3-dione (step 1) (3.07 g, 13.16 mmol) in MeOH (60 mL) was added hydrazine hydrate (1.097 mL, 14.48 mmol). The resulting mixture was stirred at RT for 16 hours overnight, yielding a yellow solution with a suspension of a white solid. The white solid was removed by filtration, and the filtrate was evaporated under reduced pressure. This was triturated with DCM and the solid again removed by filtration. The filtrate was evaporated under reduced pressure to give a yellow oil, which was used without further purification in the subsequent step.

Step 3. (S)-3-(6-Amino-5-(3-methylisoxazol-5-yl)pyridin-3-yl)-4-methyl-N-((tetrahydrofuran-3-yl)oxy)benzenesulfonamide and (R)-3-(6-amino-5-(3-methylisoxazol-5-yl)pyridin-3-yl)-4-methyl-N-((tetrahydrofuran-3-yl)oxy)benzene sulfonamide To O-(tetrahydrofuran-3-yl)hydroxylamine (step 2) (75 mg, 0.727 mmol) was added pyridine (0.2 mL, 2.473 mmol) followed immediately by a freshly prepared solution of (3-(6-amino-5-(3-methylisoxazol-5-yl)pyridin-3-yl)-4-methylbenzene-1-sulfonyl chloride (Intermediate E3)) (150 mg, 0.375 mmol) in N,N-dimethylacetamide (3 mL). The resulting mixture was stirred at room temperature for 3 days. The reaction mixture was partitioned between dichloromethane (9 mL) and saturated aqueous sodium bicarbonate (6 mL), shaken and separated using a phase separator. The aqueous was further extracted with ethyl acetate (6 mL), this organic phase was dried over magnesium sulfate and filtered. Organic extracts were combined and evaporated under reduced pressure to give a brown oily residue, which was purified by flash column chromatography (12 g silica, 2-7% methanol in DCM). Fractions eluting between 3.5-4.5% were combined, evaporated under reduced pressure and dried in a vacuum oven overnight to give the racemate. Chiral separation of the racemate using Supercritical Fluid Chromatography afforded the individual enantiomers (Example 21a and 21b).

Fractions collected were analysed by analytical chiral SFC using the following method Chiralpak IC-3, 150×2.1 mm 3 um @ 40 C, 0.4 ml/min, UV @ 220 nm and 254 nm Mobile phase: 40% Isopropanol+0.1% v/v DEA/60% $CO_2$ Example 21a: First Eluted Peak (S)-3-(6-Amino-5-(3-methylisoxazol-5-yl)pyridin-3-yl)-4-methyl-N-((tetrahydrofuran-3-yl)oxy)benzenesulfonamide or (R)-3-(6-amino-5-(3-methylisoxazol-5-yl)pyridin-3-yl)-4-methyl-N-((tetrahydrofuran-3-yl)oxy)benzene sulfonamide SFC Rt 8.18 min;

LCMS: Rt 0.98 min; MS m/z 431.2 [M+H]+; Method: 2 minLowpHv03

$^1$H NMR (400 MHz, DMSO-d6) δ 10.39 (1H, br. s.), 8.16 (1H, d, J=2.3 Hz), 7.91 (1H, d, J=2.3 Hz), 7.72 (1H, dd, J=8.1, 1.8 Hz), 7.66 (1H, d, J=1.8 Hz), 7.58 (1H, d, J=8.1 Hz), 6.90 (1H, s), 6.52 (2H, s), 4.67 (1H, m), 3.79 (1H, m), 3.71-3.61 (3H, m), 2.39 (3H, s), 2.30 (3H, s), 2.05-1.89 (2H, m).

Example 21b: Second Eluted Peak (S)-3-(6-Amino-5-(3-methylisoxazol-5-yl)pyridin-3-yl)-4-methyl-N-((tetrahydrofuran-3-yl)oxy)benzenesulfonamide or (R)-3-(6-amino-5-(3-methylisoxazol-5-yl)pyridin-3-yl)-4-methyl-N-((tetrahydrofuran-3-yl)oxy)benzene sulfonamide SFC Rt 10.73 min;

LCMS: Rt 1.01 min; MS m/z 429.2 [M−H]−; Method: 2 minLowpHv03

NMR identical to Example 21a

Example 22

3-(6-Amino-5-(3-methylisoxazol-5-yl)pyridin-3-yl)-N-ethoxy-4-methylbenzenesulfonamide

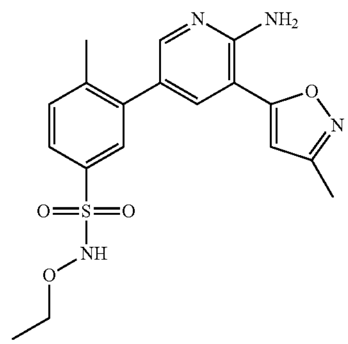 [SMILES: CCONS(=O)(=O)c1ccc(C)c(-c2cnc(N)c(-c3cc(C)no3)c2)c1]

Step 1: 3-(6-Amino-5-(3-methylisoxazol-5-yl)pyridin-3-yl)-N-ethoxy-4-methylbenzenesulfonamide To a solution of O-ethylhydroxylamine (15 mg, 0.246 mmol) and pyridine (75 μl, 0.927 mmol) in N,N-Dimethylacetamide (DMA) (1 mL) was added solid 3-(6-amino-5-(3-methylisoxazol-5-yl)pyridin-3-yl)-4-methylbenzene-1-sulfonyl chloride (Intermediate E3) (50 mg, 0.125 mmol). The resulting mixture was stirred overnight at room temperature then partitioned between DCM (3 mL) and sat. sodium bicarbonate (2 mL) and separated using a phase separator. Evaporated at ambient pressure and then further under reduced pressure. The resulting brown oily residue was purified by flash column chromatography (4 g silica, 3-7% methanol in DCM). Fractions eluting between 3-4% methanol were combined and evaporated under reduced pressure, then dried in the vacuum oven overnight. The pale yellow oil obtained was triturated with diethyl ether to give an off white solid which was collected by filtration and dried in a vacuum oven to afford the title compound;

LCMS: Rt 0.96 min; MS m/z 389.2 [M+H]+; Method: 2 minLowpHv01

$^1$H NMR (400 MHz, DMSO-d6) δ 10.30 (1H, br. s.), 8.16 (1H, d, J=2 Hz), 7.91 (1H, d, J=2 Hz), 7.73 (1H, d, J=8 Hz), 7.67 (1H, s), 7.57 (1H, d, J=8 Hz), 6.90 (1H, s), 6.52 (2H, s), 3.91 (2H, q, J=7 Hz), 2.39 (3H, s), 2.30 (3H, s), 1.10 (3H, t).

Example 23a: (R or S)-3-(6-Amino-5-(3-methylisoxazol-5-yl)pyridin-3-yl)-4-methyl-N-((tetrahydro-2H-pyran-3-yl)methyl)benzenesulfonamide and Example 23b: (R or S)-3-(6-amino-5-(3-methylisoxazol-5-yl)pyridin-3-yl)-4-methyl-N-((tetrahydro-2H-pyran-3-yl)methyl)benzenesulfonamide

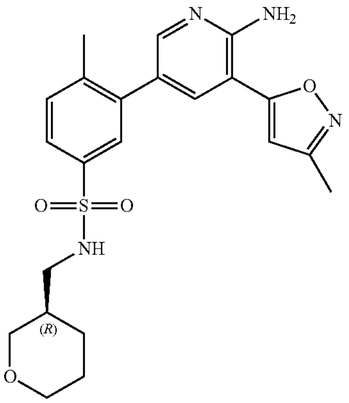

and

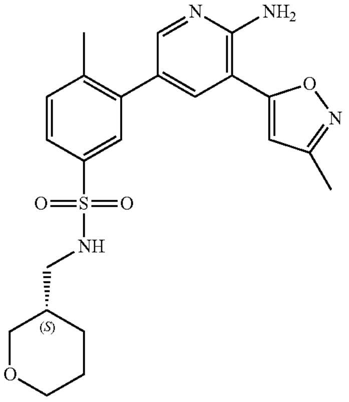

DIPEA (125 μL, 0.716 mmol) was added 3-(6-amino-5-(3-methylisoxazol-5-yl)pyridin-3-yl)-4-methylbenzene-1-sulfonyl chloride (Intermediate E3) (100 mg, 0.250 mmol) followed immediately by a freshly prepared solution of (tetrahydro-2H-pyran-3-yl)methanamine (30 mg, 0.260 mmol) in N,N-dimethylacetamide (2 mL). The resulting mixture was stirred at room temperature for 3 days, then partitioned between dichloromethane (6 mL) and 1M aqueous sodium carbonate (4 mL), shaken and separated using a phase separator. The organic phase was evaporated under reduced pressure. The resulting brown oily residue was purified by flash column chromatography (4 g silica, 2-6% (7M methanolic ammonia) in DCM). Fractions eluting at ~4% methanolic ammonia were combined and evaporated under reduced pressure, and resulting material submitted for chiral separation by SFC using the following conditions:

Sample concentration: 35 mg in 2 ml THF
Column: Chiralpak IA, 250×10 mm, 5 um @ 35 deg C.
Mobile phase: 40% Methanol+0.1% v/v DEA/60% CO2
Flow: 10 ml/min
Detection: UV @ 220 nm
Berger Minigram SFC System 2
Run Time: 18.00
Injection Volume: 100.000

Two fractions were obtained and analysed by analytical chiral SFC using the following conditions:

Run Time: 18.00
Injection Volume: 200.000
Column: Chiralpak IA, 250×10 mm, 5 um @ 35 deg C.
Mobile phase: 40% Methanol+0.1% v/v DEA/60% CO2
Flow: 10 ml/min
Detection: UV @ 220 nm
Berger Minigram SFC System 2

Example 23a: (R)-3-(6-Amino-5-(3-methylisoxazol-5-yl)pyridin-3-yl)-4-methyl-N-((tetrahydro-2H-pyran-3-yl)methyl)benzenesulfonamide or (S)-3-(6-amino-5-(3-methylisoxazol-5-yl)pyridin-3-yl)-4-methyl-N-((tetrahydro-2H-pyran-3-yl)methyl)benzenesulfonamide SFC Retention Time=Rt 11.1 min;

LCMS: Rt 0.95 min; MS m/z 443.2 [M+H]+; Method: 2 minLowpHv01

$^1$H NMR (400 MHz, DMSO-d6) δ 8.15 (1H, d, J=2.3 Hz), 7.90 (1H, d, J=2.3 Hz), 7.67 (1H, dd), 7.62 (1H, d), 7.58 (1H, t), 7.53 (1H, d, J=8 Hz), 6.90 (1H, s), 6.50 (2H, s), 3.73 (1H, m), 3.67 (1H, m), 3.27 (1H, m), 3.03 (1H, m), 2.63 (2H, m), 2.36 (3H, s), 2.30 (3H, s), 1.70 (1H, m), 1.60 (1H, brm.), 1.49 (1H, br m), 1.39 (1H, br m), 1.17 (1H, br m).

Example 23b: (R)-3-(6-Amino-5-(3-methylisoxazol-5-yl)pyridin-3-yl)-4-methyl-N-((tetrahydro-2H-pyran-3-yl)methyl)benzenesulfonamide or (S)-3-(6-amino-5-(3-methylisoxazol-5-yl)pyridin-3-yl)-4-methyl-N-((tetrahydro-2H-pyran-3-yl)methyl)benzenesulfonamide SFC Retention Time=14.1 min LCMS: Rt 1.02 min; MS m/z 443.2 [M+H]+; Method: 2 minLowpHv03

1H NMR (400 MHz, DMSO-d6) Example 23a

Example 24

(R)-3-(6-Amino-5-(3-methylisoxazol-5-yl)pyridin-3-yl)-N-(2-hydroxypropyl)-4-methylbenzenesulfonamide

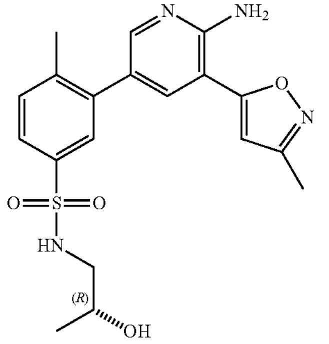

To a solution of (R)-1-aminopropan-2-ol (11 μl, 0.140 mmol) and DIPEA (70 μL, 0.401 mmol) in N,N-dimethylacetamide (1 mL) was added solid 3-(6-amino-5-(3-methylisoxazol-5-yl)pyridin-3-yl)-4-methylbenzene-1-sulfonyl chloride (Intermediate E3) (50 mg, 0.125 mmol) and the resulting mixture stirred overnight at room temperature. The reaction mixture was partitioned between DCM (3 mL) and sat. sodium bicarbonate (2 mL) and separated using a phase separator. The organic phase was loaded directly onto an Isolute® SCX-2 1 g column which had been primed with methanol. The column was washed with dichloromethane (~10 mL) and eluted with 2M methanolic ammonia (~4 mL). Ammoniacal fraction was evaporated under reduced pressure and further purified by flash column chromatography (4 g silica, 0-10% (7M methanolic ammonia) in DCM). Fractions containing product was evaporated under reduced pressure, then dried in the vacuum oven for 3 days to afford the title compound;

LCMS: Rt 0.79 min; MS m/z 403.3 [M+H]+; Method: 2 minLowpHv01

$^1$H NMR (400 MHz, DMSO-d6) δ 8.15 (1H, d, J=2.5 Hz), 7.90 (1H, d, J=2.5 Hz), 7.69-7.63 (2H, m), 7.52 (2H, m), 6.89 (1H, s), 6.49 (2H, s), 4.67 (1H, d, J=4.5 Hz), 3.60 (1H, m), 2.71-2.60 (2H, m), 2.36 (3H, s), 2.30 (3H, s), 1.00 (3H, d)

Example 25

3-(6-Amino-5-(3-methylisoxazol-5-yl)pyridin-3-yl)-4-methyl-N-(oxetan-3-ylmethyl)benzenesulfonamide

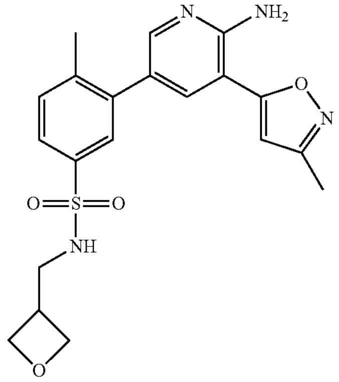 [SMILES: Cc1cc(-c2cc(-c3cc(S(=O)(=O)NCC4COC4)ccc3C)cnc2N)on1]

To oxetan-3-ylmethanamine (11 mg, 0.126 mmol) was added DIPEA (70 µL, 0.401 mmol) followed immediately by a freshly prepared solution of 3-(6-Amino-5-(3-methylisoxazol-5-yl)pyridin-3-yl)-4-methylbenzene-1-sulfonyl chloride (Intermediate E3) (50 mg, 0.125 mmol) in N,N-dimethylacetamide (1 mL). The resulting mixture was stirred at room temperature for 3 days, then partitioned between dichloromethane (3 mL) and 1M aqueous sodium carbonate (2 mL), shaken and separated using a phase separator. The organic phase was evaporated under reduced pressure to give a brown oily residue which was purified by flash column chromatography (4 g silica, 3-6% (7M methanolic ammonia) in DCM). Fractions containing product were combined and evaporated under reduced pressure, then dried in the vacuum oven overnight to give the title compound;

LCMS: Rt 0.83 min; MS m/z 415.4 [M+H]+; Method: 2 minLowpHv01

$^1$H NMR (400 MHz, DMSO-d6) δ 8.16 (1H, d, J=2 Hz), 7.91 (1H, d, J=2 Hz), 7.74 (1H, br.), 7.69 (1H, d), 7.64 (1H, s), 7.55 (1H, d, J=8 Hz), 6.90 (1H, s), 6.50 (2H, s), 4.54 (2H, t), 4.20 (2H, t), 3.06-2.95 (3H, m), 2.37 (3H, s), 2.30 (3H, s)

Example 26

3-(6-Amino-5-(1,3-di methyl-1H-pyrazol-4-yl)pyridin-3-yl)-N-(6-hydroxyspiro[3.3]heptan-2-yl)-4-methylbenzenesulfonamide

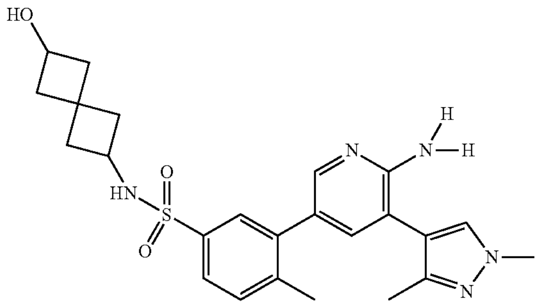 [SMILES: Cc1ccc(S(=O)(=O)NC2CC3(CC(O)C3)C2)cc1-c1cnc(N)c(-c2cn(C)nc2C)c1]

Step 1: N-(6-Hydroxyspiro[3.3]heptan-2-yl)-4-methyl-3-(4,4,5,5-tetramethyl-1,3,2-dioxaborolan-2-yl)benzenesulfonamide To a stirred mixture of 3-bromo-N-(6-hydroxyspiro[3.3]heptan-2-yl)-4-methylbenzene sulfonamide (Intermediate A8) (1.6 g, 4.44 mmol), bis(pinacolato)diboron (1.241 g, 4.89 mmol) and potassium acetate (0.654 g, 6.66 mmol) in dry DME (22 mL) at RT was added $PdCl_2(dppf).CH_2Cl_2$ adduct (0.181 g, 0.222 mmol). The mixture was heated at 90° C. overnight, then cooled to room temp, diluted with water (100 mL) and extracted with EtOAc (3×75 mL). The EtOAc extracts were combined, washed with sat. brine (75 mL), dried ($MgSO_4$), filtered and evaporated to give a yellow oil, which was purified by chromatography on silica gel using 0-100% EtOAc in isohexane as eluent. Fractions containing product were evaporated to give the title compound as an expanded foam;

LCMS: Rt=1.17 min; MS [M+H]+ 408.2; Method: 2 minLowpHv01.

Step 2: 5-Bromo-3-(1,3-dimethyl-1H-pyrazol-4-yl)pyridin-2-amine

To a microwave vial was added 2-amino-5-bromo-3-iodopyridine (200 mg, 0.669 mmol), 1,3-dimethyl-1H-pyrazole-4-boronic acid pinacol ester (150 mg, 0.676 mmol), 2M $Na_2CO_3$ aqueous solution (1004 µl, 2.007 mmol), [1,1'-bis(diphenylphosphino)ferrocene]dichloropalladium (II) complexed with DCM (27.3 mg, 0.033 mmol) and DME (2.0 ml) to give an orange suspension. The reaction mixture was heated in the microwave to 120° C. for 2 hours. The resulting solution of the title compound was used directly in the next step.

Step 3: 3-(6-Amino-5-(1,3-dimethyl-1H-pyrazol-4-yl)pyridin-3-yl)-N-(6-hydroxyspiro[3.3]heptan-2-yl)-4-methylbenzenesulfonamide To N-(6-hydroxyspiro[3.3]heptan-2-yl)-4-methyl-3-(4,4,5,5-tetramethyl-1,3,2-dioxaborolan-2-yl)benzenesulfonamide (step 1) (0.210 mmol), [1,1'-bis(diphenylphosphino)ferrocene]dichloropalladium (II) complexed with DCM (8.58 mg, 10.50 µmol), 2M aq. sodium carbonate (0.315 ml, 0.630 mmol) and 0.5 ml of the solution of 5-bromo-3-(1,3- dimethyl-1H-pyrazol-4-yl)pyridin-2-amine (step 2) was added DME (0.5 ml) and the resulting mixture heated to 150° C. for 3 hours using a microwave reactor. The reactions were purified using reverse-phase chromatography and a low pH modifier (TFA) with mass directed collection of fractions. Fractions containing product were evaporated under reduced pressure, redissolved in methanol (5 ml) and filtered through a MP-bicarbonate cartridge. The cartridge was flushed with 10 ml methanol and the filtrate under reduced pressure to afford the title compound;

LCMS: Rt 0.77 mins; MS m/z 468.3 [M+H]+; Method 2 minLowpHv02.

Example 27

3-(6-Amino-5-(3-methylisoxazol-5-yl)pyridin-3-yl)-N-(2,2-difluoroethyl)-4-methylbenzenesulfonamide

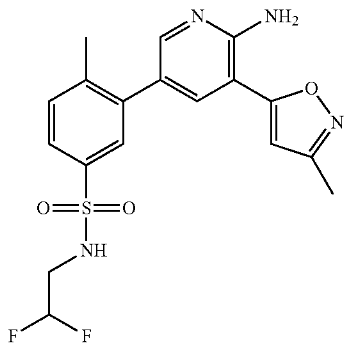 [SMILES: Cc1cc(-c2cc(-c3cc(S(=O)(=O)NCC(F)F)ccc3C)cnc2N)on1]

To 2,2-difluoroethanamine (11 mg, 0.136 mmol) was added DIPEA (70 μL, 0.401 mmol) followed immediately by a freshly prepared solution of 3-(6-amino-5-(3-methylisoxazol-5-yl)pyridin-3-yl)-4-methylbenzene-1-sulfonyl chloride (Intermediate E3) (50 mg, 0.125 mmol) in N,N-dimethylacetamide (1 mL). The resulting mixture was stirred at room temperature for 3 days then partitioned between dichloromethane (3 mL) and saturated aqueous sodium bicarbonate (2 mL), shaken and separated using a phase separator. The organic phase was evaporated under reduced pressure and the brown oily residue was purified by flash column chromatography (4 g silica, 0-10% methanol in DCM). Fractions containing product were combined and evaporated, then triturated with diethyl ether to afford the title compound; LCMS: Rt 0.91 min; MS m/z 409.2 [M+H]+; Method: 2 minLowpHv01

$^1$H NMR (400 MHz, DMSO-d6) δ 8.16 (2H, d, J=2.5 Hz), 7.91 (1H, d, J=2.5 Hz), 7.70 (1H, m), 7.66 (1H, d, J=2.0 Hz), 7.54 (1H, d, J=8 Hz), 6.90 (1H, s), 6.50 (2H, s), 6.00 (1H, tt, J=55, 4 Hz), 3.22 (2H, m), 2.37 (3H, s), 2.30 (3H, s).

Example 28

3-(6-Amino-5-(2-methylthiazol-5-yl)pyridin-3-yl)-N-(6-hydroxyspiro[3.3]heptan-2-yl)-4-methylbenzenesulfonamide

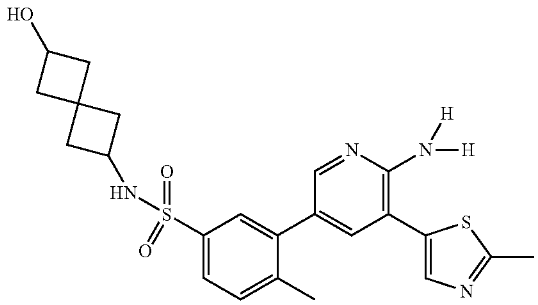 [SMILES: Cc1ncc(-c2cc(-c3cc(S(=O)(=O)NC4CC5(CC(O)C5)C4)ccc3C)cnc2N)s1]

Step 1: 5-Bromo-3-(2-methylthiazol-5-yl)pyridin-2-amine

A mixture of 2-amino-5-bromo-3-iodopyridine (350 mg, 1.171 mmol), 2-methylthiazole-5-boronic acid pinacol ester (266 mg, 1.183 mmol), 2M $Na_2CO_3$ aqueous solution (1.756 mL, 3.51 mmol), 1,1'-bis(diphenylphosphino)ferrocene]dichloropalladium(II) complexed with DCM (47.8 mg, 0.059 mmol) and DME (3.0 ml) was heated to 120° C. for 90 minutes in a microwave reactor.

The resulting reaction mixture of the title compound was used directly in the next step.

Step 2: 3-(6-Amino-5-(2-methylthiazol-5-yl)pyridin-3-yl)-N-(6-hydroxyspiro[3.3]heptan-2-yl)-4-methylbenzenesulfonamide A mixture of N-(6-hydroxyspiro[3.3]heptan-2-yl)-4-methyl-3-(4,4,5,5-tetramethyl-1,3,2-dioxaborolan-2-yl)benzenesulfonamide (Example 26 step 1)(0.215 mmol), 1,1'-bis(diphenylphosphino)ferrocene)dichloropalladium(II) complexed with DCM (7.96 mg, 9.75 μmol), 2M sodium carbonate (0.293 ml, 0.585 mmol) and 0.5 ml of a solution of 5-bromo-3-(2-methylthiazol-5-yl)pyridin-2-amine (reaction mixture step 1) in DME (0.5 ml) was heated to 150° C. for 3 hours in a microwave reactor. The reactions were purified using reverse-phase chromatography and a low pH modifier (TFA) with mass directed collection of fractions. Fractions containing product were filtered through a MP-bicarbonate cartridge. The cartridge was flushed with 10 ml methanol and the combined filtrates evaporated under reduced pressure to afford the title compound;

LCMS: Rt 0.77 min; MS m/z 471.2 [M+H]+; Method: 2 minLowpHv02

Example 29

3-(6-Amino-5-(3-methyl-1,2,4-oxadiazol-5-yl)pyridin-3-yl)-4-methyl-N-((tetrahydrofuran-3-yl)methyl) benzenesulfonamide

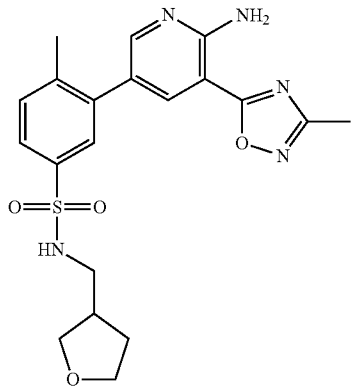 [SMILES: Cc1noc(-c2cc(-c3cc(S(=O)(=O)NCC4CCOC4)ccc3C)cnc2N)n1]

(Tetrahydrofuran-3-yl)methanamine (30 μL, 0.294 mmol) and pyridine (70 μL, 0.865 mmol) were added to a stirring mixture of 3-(6-amino-5-(3-methyl-1,2,4-oxadiazol-5-yl) pyridin-3-yl)-4-methylbenzene-1-sulfonyl chloride (Intermediate E2) (60 mg, 0.150 mmol) in THF (1 mL). The resulting mixture was stirred for three days, then diluted with DCM and saturated sodium bicarbonate (1 mL) was added. The phases were separated and the organic phase was evaporated under reduced pressure and residue purified by mass directed HPLC. Fractions containing product were evaporated under reduced pressure and the residue was partitioned between DCM and water, separated using a phase separator and evaporated under reduced pressure. The crude product was triturated with ethyl acetate to give a the title compound as a white solid;

LCMS: Rt 1.01 min; m/z 430.2 [M+H]+; Method: 2 minLowpHv01

$^1$H NMR (400 MHz, DMSO-d6) δ 8.36 (1H, d, J=2 Hz), 8.18 (1H, d, J=2 Hz), 7.73-7.65 (3H, m), 7.63-7.53 (3H, m), 3.69-3.53 (3H, m), 3.36 (1H, m), 2.74 (2H, m), 2.47 (3H, s), 2.38 (3H, s), 2.31-2.24 (1H, m), 1.93-1.84 (1H, m), 1.54-1.46 (1H, m).

Example 30

3-(6-Amino-5-(1-methyl-1H-pyrazol-4-yl)pyridin-3-yl)-4-methyl-N-(6-methylpyridin-2-yl)benzenesulfonamide

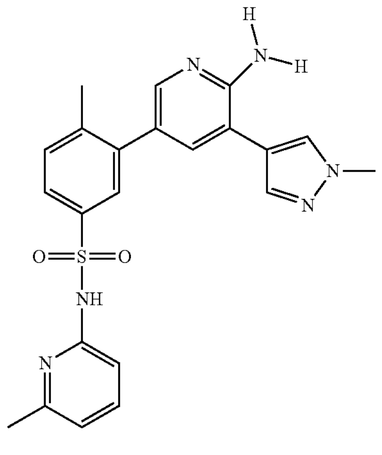

Step 1: 5-Bromo-3-(1-methyl-1H-pyrazol-4-yl)pyridin-2-amine

A mixture of 2-amino-5-bromo-3-iodopyridine (350 mg, 1.171 mmol), 1-methylpyrazole-4-boronic acid pinacol ester (246 mg, 1.183 mmol), 2M Na2CO3 aqueous solution (1756 μl, 3.51 mmol), [1,1'-bis(diphenylphosphino)ferrocene]dichloropalladium (II) complexed with DCM (47.8 mg, 0.059 mmol) and DME (3.0 ml) was heated to 130° C. for 2 hours in a microwave reactor. The resulting solution was used directly in the next step.

LCMS: Rt 0.58 mins; MS m/z 255.2 [M+H]+; Method: 2 minLowpHv02.

Step 2: 3-(6-Amino-5-(1-methyl-1H-pyrazol-4-yl) pyridin-3-yl)-4-methyl-N-(6-methylpyridin-2-yl) benzenesulfonamide A mixture of 4-methyl-N-(6-methylpyridin-2-yl)-3-(4,4,5,5-tetramethyl-1,3,2-dioxaborolan-2-yl)benzenesulfonamide (Intermediate B6) (0.198 mmol), 1,1'-bis(diphenylphosphino)ferrocene]dichloropalladium(II) complexed with DCM (8.07 mg, 9.88 μmol), 2M sodium carbonate (0.296 ml, 0.593 mmol) and 0.5 ml of the solution of 5-bromo-3-(1-methyl-1H-pyrazol-4-yl)pyridin-2-amine (step 1) in DME was heated to 150° C. for 3 hours in a microwave reactor. The reactions were purified using reverse-phase chromatography and a low pH modifier (TFA) with mass directed collection of fractions. Fractions containing product were evaporated under reduced pressure, redissolved in methanol (5 ml) and filtered through a MP-bicarbonate cartridge. The cartridge was flushed with 10 ml methanol and the filtrate under reduced pressure to afford the title compound;

LCMS: Rt 0.74 mins; MS m/z 435.2 [M+H]+; 2 minLowpHv02.

Example 31

3-(6-Amino-5-(3-methylisoxazol-5-yl)pyridin-3-yl)-N-cyclopropyl-4-methylbenzenesulfonamide

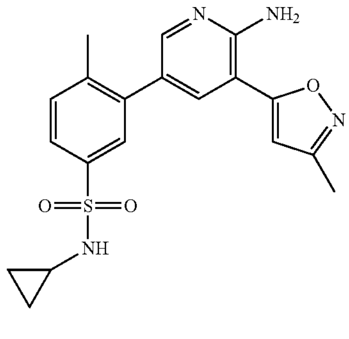 [SMILES: Cc1cc(-c2cc(-c3cc(S(=O)(=O)NC4CC4)ccc3C)cnc2N)on1]

To a solution of cyclopropanamine (10 μl, 0.144 mmol) and DIPEA (70 μL, 0.401 mmol) in N,N-dimethylacetamide (1 mL) was added solid 3-(6-amino-5-(3-methylisoxazol-5-yl)pyridin-3-yl)-4-methylbenzene-1-sulfonyl chloride (Intermediate E3) (50 mg, 0.125 mmol). The resulting mixture was stirred overnight at room temperature, then partitioned between DCM (3 mL) and sat. sodium bicarbonate (2 mL) and separated using a phase separator. Organic phase was loaded directly onto an Isolute® 1 g SCX-2 column which had been primed with methanol. The column was washed with dichloromethane (~10 mL) and eluted with 2M methanolic ammonia (~4 mL). Ammoniacal fraction was evaporated under reduced pressure and further purified by flash column chromatography (4 g silica, 0-10% (7M methanolic ammonia) in DCM). Fractions containing product were combined and evaporated under reduced pressure to give a yellow oil which was dried in the vacuum oven. The resulting oil was triturated with methanol to give an off white solid, which was dried in the vacuum oven to give the title compound;

LCMS: Rt 0.92 min; m/z 385.3 [M+H]+; Method: 2 minLowpHv01

$^1$H NMR (400 MHz, DMSO-d6) δ 8.15 (1H, d, J=2.5 Hz), 7.91 (1H, d, J=2.5 Hz), 7.85 (1H, s), 7.70 (1H, dd, J=8.0, 2 Hz), 7.64 (1H, d, J=2 Hz), 7.55 (1H, d, J=8 Hz), 6.90 (1H, s), 6.50 (2H, s), 2.38 (3H, s), 2.30 (3H, s), 2.12 (1H, m), 0.44-0.57 (2H, m), 0.35-0.44 (2H, m).

Example 32

3-(6-Amino-5-(3-methylisoxazol-5-yl)pyridin-3-yl)-4-methylbenzenesulfonamide

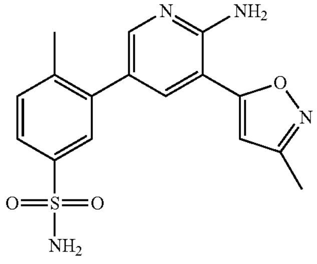 [SMILES: Cc1cc(-c2cc(-c3cc(S(N)(=O)=O)ccc3C)cnc2N)on1]

To a solution of 4-methyl-3-(4,4,5,5-tetramethyl-1,3,2-dioxaborolan-2-yl)benzenesulfonamide (Example 74, step 1) (110 mg, 0.370 mmol) in acetonitrile (2.5 mL) was added 5-bromo-3-(3-methyl-isoxazol-5-yl)-pyridin-2-ylamine (Intermediate C5) (73 mg, 0.287 mmol), bis(triphenylphosphine)palladium(II) chloride (10 mg, 0.014 mmol) and sodium carbonate (aq. 2.0M) (0.43 mL, 0.860 mmol). The reaction heated to 120° C. for 30 mins in a microwave reactor. Additional 4-methyl-3-(4,4,5,5-tetramethyl-1,3,2-dioxaborolan-2-yl)benzenesulfonamide (Example 74, step 1)(50 mg) and bis(triphenylphosphine)palladium(II) chloride (10 mg, 0.014 mmol) were added, and the mixture heated again to 120° C. for 30 mins in the microwave. The reaction mixture was diluted with 10% methanol in DCM, filtered through a 1 g Celite® column (filter material), then evaporated under reduced pressure and purified by flash column chromatography (12 g silica, 0-20% methanol in DCM). The product obtained was crystallised from ethyl acetate:ethanol (~1:4), then triturated from methanol to give a tan solid which was dried in the vacuum oven.

LCMS: Rt 0.71 min; m/z 345.5 [M+H]+; Method: 2 minLowpHv01

$^1$H NMR (400 MHz, DMSO-d6) δ 8.15 (1H, d, J 2.3 Hz); 7.89 (1H, d, J 2.3 Hz); 7.71 (1H, d) overlapping with 7.69 (1H, s); 7.51 (1H, d, J 7.6 Hz); 7.31 (2H, s); 6.90 (1H, s); 6.49 (2H, s); 2.36 (3H, s); 2.30 (3H, s).

Example 33

3-(6-Amino-5-(2-methyloxazol-5-yl)pyridin-3-yl)-4-methylbenzenesulfonamide

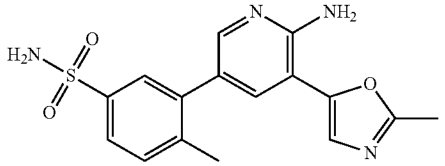 [SMILES: Cc1ncc(-c2cc(-c3cc(S(N)(=O)=O)ccc3C)cnc2N)o1]

To a solution of 4-methyl-3-(4,4,5,5-tetramethyl-1,3,2-dioxaborolan-2-yl)benzenesulfonamide (Example 74, step 1)(85 mg, 0.286 mmol) in 1,4-dioxane (2.5 mL) was added 5-bromo-3-(2-methyl-oxazol-5-yl)-pyridin-2-ylamine (Intermediate C4) (70 mg, 0.276 mmol), bis(triphenylphosphine)palladium(II) chloride (10 mg, 0.014 mmol) and sodium carbonate (aq. 2.0M) (0.43 mL, 0.860 mmol). The resulting mixture was heated to reflux for 1 hour, cooled then diluted with 10% methanol in DCM and passed through a 500 mg Si-TMT column, washing with further DCM. Combined filtrate and washings were evaporated under reduced pressure then redissolved in ~10% methanol in DCM and bound to silica gel for purification by flash column chromatography (4 g silica, 0-10% 7M methanolic ammonia in DCM, shallow gradient between 5 and 6% to separate close running impurity). The fractions containing product were combined and evaporated under reduced pressure, then triturated with diethyl ether/ethyl acetate mixture to give the title compound as a pale yellow solid which was dried in the vacuum oven;

LCMS: Rt 0.69 min; m/z 345.4 [M+H]+; Method: 2 minLowpHv03

$^1$H NMR (400 MHz, DMSO-d6) δ 8.04 (1H, d, J=2.3 Hz), 7.75-7.65 (3H, m), 7.53-7.48 (2H, m), 7.31 (2H, s), 6.30 (2H, s), 2.48 (3H, s), 2.34 (3H, s)

Example 34

3-(6-Amino-5-(1-(2,2,2-trifluoroethyl)-1H-pyrazol-4-yl)pyridin-3-yl)-N-(2-hydroxy-2-methylpropoxy)-4-methylbenzenesulfonamide hydrochloride

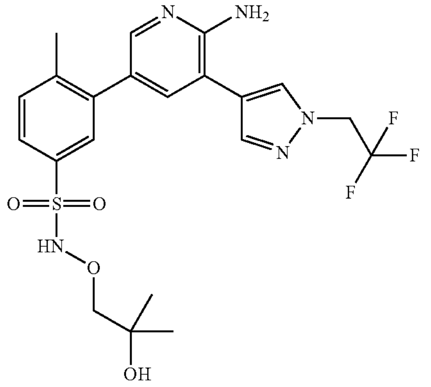 [SMILES: Cc1ccc(S(=O)(=O)NOCC(C)(C)O)cc1-c1cnc(N)c(-c2cnn(CC(F)(F)F)c2)c1]

Sodium carbonate (0.65 ml of a 2M solution, 1.3 mmol) was added to a mixture of 5-bromo-3-(1-(2,2,2-trifluoroethyl)-1H-pyrazol-4-yl)pyridin-2-amine (Intermediate C1) (140 mg, 0.436 mmol), N-(2-hydroxy-2-methylpropoxy)-4-methyl-3-(4,4,5,5-tetramethyl-1,3,2-dioxaborolan-2-yl)benzenesulfonamide [intermediate B4](168 mg, 0.436 mmol) and $PdCl_2$(dppf). $CH_2Cl_2$.adduct (18 mg, 0.022 mmol) in DME (5 ml). The mixture was de-gassed several times under nitrogen then heated with stirring at 80° C. for 2 h when LCMS indicated complete reaction.

The reaction mixture was allowed to cool, diluted with EtOAc and filtered through a Celite® pad (filter material) to remove aq. $NaHCO_3$. Chromatography on silica, eluting with EtOAc, gave the product as a colourless gum. The purified product was taken up in 4M HCl in dioxane (2 ml). After 5 min the volatiles were evaporated and the residue was triturated with EtOAc-diethyl ether to give the hydrochloride salt as a white amorphous solid;

LCMS: Rt 0.75 mins; MS m/z 500.3 [M+H]+; Method 2 minLowpHv10

$^1$H NMR (400 MHz, DMSO-d6) δ 10.45 (1H, s), 8.34 (1H, s), 8.09 (1H, s), 8.02 (2H, m), 7.78 (4H, m), 7.01 (1H, d), 5.20 (2H, m), 3.72 (2H, s), 2.40 (3H, s), 1.02 (6H, s).

Example 35

3-(6-Amino-5-(3-(2,2,2-trifluoroethyl)isoxazol-5-yl) pyridin-3-yl)-N-(2-hydroxy-2-methylpropyl)-4-methylbenzenesulfonamide hydrochloride

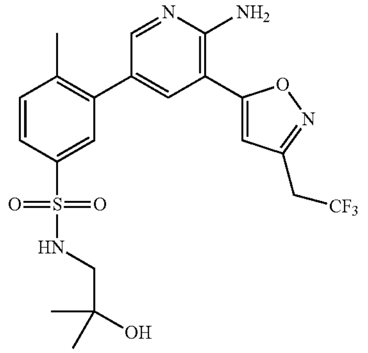 [SMILES: Cc1ccc(S(=O)(=O)NCC(C)(C)O)cc1-c1cnc(N)c(-c2cc(CC(F)(F)F)no2)c1]

To a 5 ml microwave vial was added N-(2-hydroxy-2-methyl-propyl)-4-methyl-3-(4,4,5,5-tetramethyl[1,3,2]dioxaborolan-2-yl)benzenesulfonamide (Intermediate B2) (229 mg, 0.621 mmol), 5-bromo-3-(3-(2,2,2-trifluoroethyl) isoxazol-5-yl)pyridin-2-amine [prepared analogously to Intermediate C12, by replacing propionaldehyde oxime with 3,3,3-trifluoropropanal oxime](200 mg, 0.621 mmol), $PdCl_2$(dppf).$CH_2Cl_2$ adduct (25.4 mg, 0.031 mmol) and sodium carbonate (0.776 ml, 1.552 mmol) in DME (4 ml). The mixture was heated in the biotage initiator microwave at 120° C. for 2 hours. The resulting mixture was extracted into ethyl acetate, washed with water, brine, the organic layer separated, dried over $MgSO_4$, filtered and the solvent removed under reduced pressure. The crude product was loaded onto silica and purified by flash column chromatography elution with iso hexane:ethyl acetate (0-100%) on a 12 g silica cartridge. The purified product was taken up in 4M HCl in dioxane (2 ml). After 5 min the volatiles were evaporated and the residue was recrystallised from hot EtOH to give a solid;

LCMS: Rt=1.01 mins MS m/z 485.1 [M+H]+; Method 2 minLowpHv01.

$^1$H NMR (400 MHz, DMSO-d6) δ 8.31 (1H, d), 8.27 (1H, mult), 7.73 (2H, mult), 7.55 (1H, d), 7.49 (1H, t), 7.23 (1H, s), 3.98 (2H, mult), 2.62 (2H, d), 2.37 (3H, s), 1.06 (6H, s).

$^{19}$F NMR (400 MHz, d6-DMSO) δ −63.21.

Example 35.1

3-(6-Amino-5-(3-propyl isoxazol-5-yl)pyridin-3-yl)-N-(2-hydroxy-2-methylpropyl)-4-methylbenzenesulfonamide hydrochloride

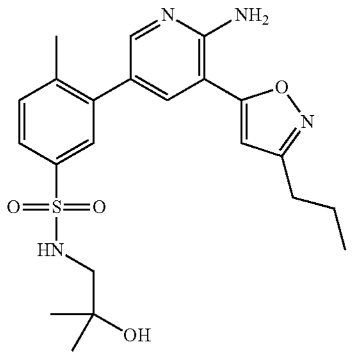 [SMILES: CCCc1cc(-c2cc(-c3cc(S(=O)(=O)NCC(C)(C)O)ccc3C)cnc2N)on1]

The title compound was prepared analogously to Example 35 using N-(2-hydroxy-2-methyl-propyl)-4-methyl-3-(4,4,5,5-tetramethyl[1,3,2]dioxaborolan-2-yl)benzenesulfonamide (Intermediate B2) and 5-bromo-3-(3-propylisoxazol-5-yl)pyridin-2-amine [prepared analogously to Intermediate C12, by replacing propionaldehyde oxime with butyraldehyde oxime.]

LCMS Rt=1.02 mins MS m/z 445.2 [M+H]+; Method 2 minLowpHv01.

Example 35.2 trans-3-(6-Amino-5-(3-(tert-butyl)isoxazol-5-yl) pyridin-3-yl)-N-(−4-hydroxycyclohexyl)-4-methylbenzenesulfonamide hydrochloride

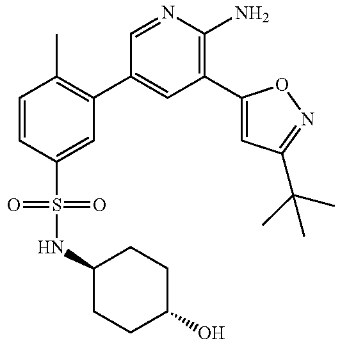 [SMILES: Cc1ccc(S(=O)(=O)N[C@H]2CC[C@H](O)CC2)cc1-c1cnc(N)c(-c2cc(C(C)(C)C)no2)c1]

The title compound was prepared analogously to Example 35 using trans N-(4-Hydroxy-cyclohexyl)-4-methyl-3-(4,4,5,5-tetramethyl-[1,3,2]dioxaborolan-2-yl)-benzenesulfonamide (Intermediate B5) and 5-bromo-3-(3-(tert-butyl)isoxazol-5-yl)pyridin-2-amine [prepared analogously to Intermediate C12, by replacing propionaldehyde oxime with pivalaldehyde oxime.]

LCMS Rt=1.02 mins MS m/z 485.3 [M+H]+; Method 2 minLowpHv01.

Example 35.3

3-(6-Amino-5-(3-cyclopropylisoxazol-5-yl)pyridin-3-yl)-N-(2-hydroxy-2-methylpropyl)-4-methylbenzenesulfonamide hydrochloride

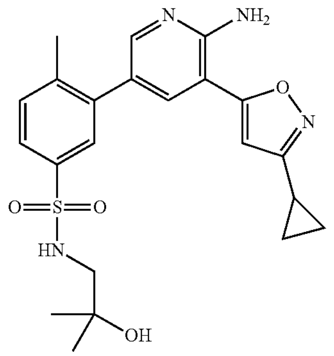 [SMILES: Cc1ccc(S(=O)(=O)NCC(C)(C)O)cc1-c1cnc(N)c(-c2cc(C3CC3)no2)c1]

The title compound was prepared analogously to Example 35 using N-(2-hydroxy-2-methyl-propyl)-4-methyl-3-(4,4,5,5-tetramethyl[1,3,2]dioxaborolan-2-yl)benzenesulfonamide (Intermediate B2) and 5-bromo-3-(3-cyclopropylisoxazol-5-yl)pyridin-2-amine [prepared analogously to Intermediate C12, by replacing propionaldehyde oxime with cyclopropanecarbaldehyde oxime.] The product was recrystallised from ethanol to afford the title compound;

$^1$H NMR (400 MHz, DMSO-d6) δ 8.24 (1H, d), 8.16 (1H, br), 7.73 (1H, dd), 7.71 (1H, d), 7.55 (1H, d), 7.49 (1H, t), 6.86 (1H, s), 2.62 (2H, d), 2.36 (3H, s), 2.09 (1H, mult), 1.07 (2H, mult), 1.06 (6H, s), 0.86 (2H, mult).

Example 35.4

3-(6-Amino-5-(3-isopropylisoxazol-5-yl)pyridin-3-yl)-N-(3-hydroxy-3-methyl butyl)-4-methylbenzenesulfonamide

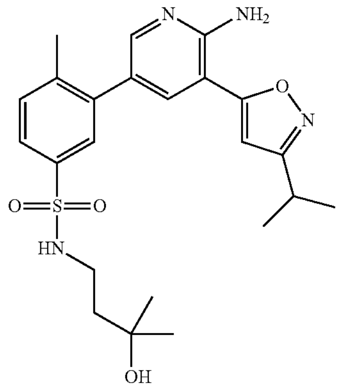 [SMILES: Cc1ccc(S(=O)(=O)NCCC(C)(C)O)cc1-c1cnc(N)c(-c2cc(C(C)C)no2)c1]

The title compound was prepared analogously to Example 35 using N-(3-hydroxy-3-methylbutyl)-4-methyl-3-(4,4,5,5-tetramethyl-1,3,2-dioxaborolan-2-yl)benzenesulfonamide (Intermediate B3), and 5-bromo-3-(3-isopropylisoxazol-5-yl)pyridin-2-amine (Intermediate C8)

The crude product was purified by mass directed preparative HPLC using a low pH gradient. The fractions were combined, extracted into DCM, washed with sat.sodium bicarbonate, the organic layer separated, dried over $MgSO_4$, filtered and the solvent removed under reduced pressure. The residue was dissolved in ethanol (1 ml) and allowed to dry in a flask at RT overnight to afford the title compound;

$^1$H NMR (400 MHz, DMSO-d6) δ 8.14 (1H, d), 7.92 (1H, d), 7.67 (1H, dd), 7.62 (1H, d), 7.54 (1H, d), 7.40 (1H, t), 7.01 (1H, s), 6.52 (2H, br), 4.27 (1H, s), 3.05 (1H, mult), 2.83 (2H, mult), 2.36 (3H, s), 1.50 (2H, mult), 1.28 (6H, d), 1.02 (6H, s).

Example 35.5

3-(6-Amino-5-(3-(tert-butyl)isoxazol-5-yl)pyridin-3-yl)-N-(2-hydroxy-2-methylpropyl)-4-methylbenzenesulfonamide hydrochloride

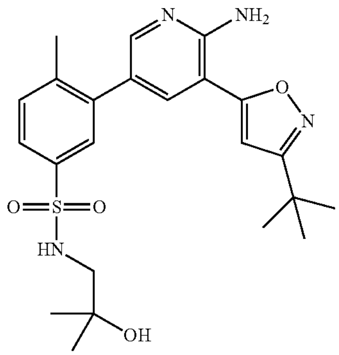 [SMILES: Cc1ccc(S(=O)(=O)NCC(C)(C)O)cc1-c1cnc(N)c(-c2cc(C(C)(C)C)no2)c1]

The title compound was prepared analogously to Example 35 using N-(2-hydroxy-2-methyl-propyl)-4-methyl-3-(4,4,5,5-tetramethyl[1,3,2]dioxaborolan-2-yl)benzenesulfonamide (Intermediate B2) and 5-bromo-3-(3-(tert-butyl)isoxazol-5-yl)pyridin-2-amine [prepared analogously to Intermediate C12 by replacing propionaldehyde oxime with pivalaldehyde oxime.]

LCMS Rt=1.06 mins MS m/z 459.3 [M+H]+; Method 2 minLowpHv01.

Example 35.6

3-(6-Amino-5-(3-isopropylisoxazol-5-yl)pyridin-3-yl)-N-(2-hydroxy-2-methylpropyl)-4-methylbenzenesulfonamide

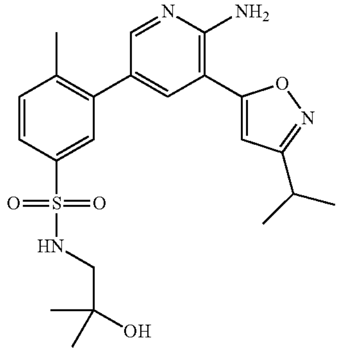 [SMILES: Cc1ccc(S(=O)(=O)NCC(C)(C)O)cc1-c1cnc(N)c(-c2cc(C(C)C)no2)c1]

The title compound was prepared analogously to Example 35 using N-(2-hydroxy-2-methyl-propyl)-4-methyl-3-(4,4,5,5-tetramethyl[1,3,2]dioxaborolan-2-yl)benzenesulfonamide (Intermediate B2) and 5-bromo-3-(3-isopropylisoxazol-5-yl)pyridin-2-amine (Intermediate C8);

$^1$H NMR (400 MHz, DMSO-d6) δ 8.15 (1H, d), 7.92 (1H, d), 7.68 (2H, mult), 7.52 (1H, d), 7.44 (1H, t), 7.02 (1H, s), 6.52 (2H, br), 4.39 (1H, s), 3.05 (1H, mult), 2.61 (2H, d), 2.36 (3H, s), 1.28 (6H, d), 1.06 (6H, s).

Example 36a: cis-3-(6-Amino-5-(3-methylisoxazol-5-yl)pyridin-3-yl)-N-((1s,3s)-3-hydroxycyclobutyl)-4-methylbenzenesulfonamide and Example 36b: trans-3-(6-aminoamino-5-(3-methylisoxazol-5-yl)pyridin-3-yl)-N-((1r,3r)-3-hydroxycyclobutyl)-4-methylbenzenesulfonamide

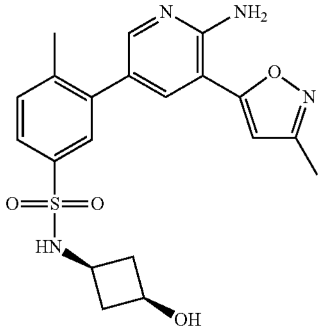

and

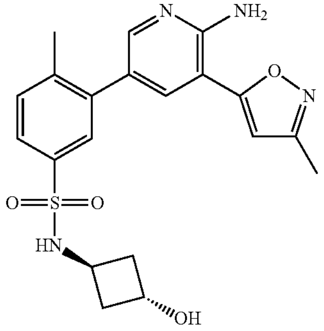

To a solution of DIPEA (0.144 ml, 0.825 mmol) and 3-aminocyclobutanol (23.95 mg, 0.275 mmol) in DMA (1 ml) was added 3-(6-amino-5-(3-methylisoxazol-5-yl)pyridin-3-yl)-4-methylbenzene-1-sulfonyl chloride (Intermediate E3) (50 mg, 0.137 mmol). The reaction was stirred at RT overnight. The resulting mixture was extracted into DCM, washed with sat. sodium bicarb, brine, the organic layer separated, dried over $MgSO_4$, filtered and the solvent removed under reduced pressure. The crude material was passed through a 1 g Isolute® SCX-2 cartridge, elution with 2M ammonia methanol solution to afford 3-(6-amino-5-(3-methylisoxazol-5-yl)pyridin-3-yl)-N-(3-hydroxycyclobutyl)-4-methylbenzenesulfonamide as a mixture of stereoisomers;

LCMS: Rt 0.81 mins; MS m/z 415.2 [M+H]+; Method 2 minLowpHv01.

Chiral separation of the stereomeric mixture of 3-(6-amino-5-(3-methylisoxazol-5-yl)pyridin-3-yl)-N-(3-hydroxycyclobutyl)-4-methylbenzenesulfonamide (step 1) was carried out under the following conditions:

Method Details:
Column: Chiralpak ID, 250×10 mm, 5 um @ 35 deg C.
5 um @ 35 deg C.
Mobile phase: 40% Isopropanol+0.1% DEA/60% $CO_2$
Flow: 10 ml/min
Detection: UV @ 220 nm
Instrument: Berger Minigram SFC2

Example 36a: cis-3-(6-Amino-5-(3-methylisoxazol-5-yl)pyridin-3-yl)-N-(−3-hydroxycyclobutyl)-4-methylbenzenesulfonamide First Eluted Peak:
$^1$H NMR (400 MHz, DMSO-d6) δ 8.14 (1H, d), 7.90 (1H, d), 7.81 (1H, d), 7.66 (1H, dd), 7.62 (1H, mult), 7.52 (1H, d), 6.90 (1H, s), 6.50 (2H, br), 5.00 (1H, d), 3.66 (1H, mult), 3.12 (1H, mult), 2.36 (3H, s), 2.31 (3H, s), 2.24 (2H, mult), 1.61 (2H, mult),

Example 36b: trans-3-(6-Amino-5-(3-methylisoxazol-5-yl)pyridin-3-yl)-N-(−3-hydroxycyclobutyl)-4-methylbenzenesulfonamide Second Eluted Peak: Trans Isomer:
$^1$H NMR (400 MHz, DMSO-d6) δ 8.13 (1H, d), 7.90 (1H, d), 7.84 (1H, d), 7.64 (1H, dd), 7.60 (1H, mult), 7.53 (1H, d), 6.90 (1H, s), 6.51 (2H, br), 4.92 (1H, d), 4.14 (1H, mult), 3.75 (1H, mult), 2.36 (3H, s), 2.30 (3H, s), 1.96 (2H, mult), 1.89 (2H, mult), Nuclear Overhauser Effect Spectroscopy (NOESY) confirmed that the first eluted compound was the cis isomer and second eluted compound was the trans isomer.

Example 37

(S)-3-(6-Amino-5-(3-methylisoxazol-5-yl)pyridin-3-yl)-N-(2-hydroxypropyl)-4-methylbenzenesulfonamide

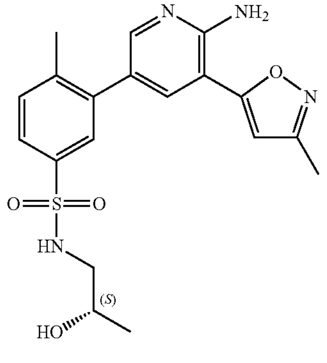

To a solution of DIPEA (0.072 ml, 0.412 mmol) and (S)-1-aminopropan-2-ol (commercially available; 10.32 mg, 0.137 mmol) in DMA (1 ml) was added 3-(6-amino-5-(3-methylisoxazol-5-yl)pyridin-3-yl)-4-methylbenzene-1-sulfonyl chloride (Intermediate E3) (50 mg, 0.137 mmol).

The reaction was stirred at RT overnight. The resulting mixture was extracted into DCM, washed with water, brine, the organic layer separated, dried over $MgSO_4$, filtered and the solvent removed under reduced pressure. The crude material was passed through a 1 g Isolute® SCX-2 cartridge, elution with 2M ammonia methanol solution. The crude product was purified by flash column chromatography elution with 0-10% methanol in TBME on a 4 g silica cartridge. The required fractions were combined and the solvent removed under reduced pressure. The resulting oil was dried in a vacuum oven at 40° C. overnight to afford the title compound as an off white solid;

LCMS: Rt 0.78 mins; MS m/z 403.2 [M+H]+; Method 2 minLowpHv01

$^1$H NMR (400 MHz, DMSO-d6) δ 8.15 (1H, d), 7.90 (1H, d), 7.66 (2H, mult), 7.52 (2H, mult), 6.89 (1H, s), 6.49 (2H, br), 4.67 (1H, d), 3.60 (1H, mult), 2.66 (2H, mult), 2.36 (3H, s), 2.30 (3H, s), 1.00 (3H, d).

Examples 37.1 to Example 37.38 were prepared by methods analogous to that for the preparation of Example 37 starting from Intermediate E2 or E3 as appropriate, and amines obtained from commercial vendors as free base or hydrochloride salt. Purification was carried out by appropriate methods known in the art, for example flash column chromatography, strong cation exchange, trituration, crystallisation or combinations of the above.

Example 37.1

3-(6-Amino-5-(3-methylisoxazol-5-yl)pyridin-3-yl)-N-((4-(hydroxymethyl)tetrahydro-2H-pyran-4-yl)methyl)-4-methylbenzenesulfonamide

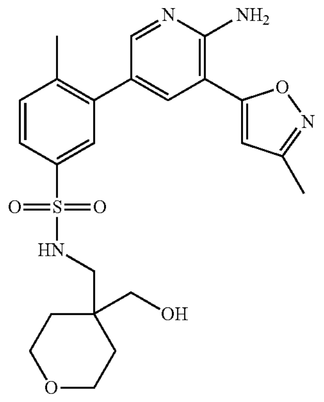 [SMILES: Cc1cc(-c2cc(-c3cc(S(=O)(=O)NCC4(CO)CCOCC4)ccc3C)cnc2N)on1]

LC-MS: Rt 0.81 mins; MS m/z 473.4 [M+H]+; Method 2 minLowpHv01

Example 37.2

5-(5-((3-Methoxy-3-methylazetidin-1-yl)sulfonyl)-2-methylphenyl)-3-(3-methyl-1,2,4-oxadiazol-5-yl)pyridin-2-amine

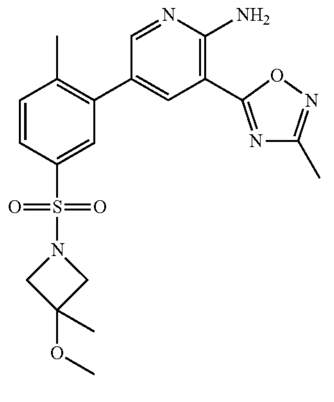 [SMILES: COC1(C)CN(S(=O)(=O)c2ccc(C)c(-c3cnc(N)c(-c4nc(C)no4)c3)c2)C1]

LCMS: Rt=1.11 mins; MS m/z 430.2 [M+H]+; Method 2 minLowpHv01

Example 37.3

3-(6-Amino-5-(3-methylisoxazol-5-yl)pyridin-3-yl)-N-((1-(hydroxymethyl)cyclohexyl)methyl)-4-methylbenzenesulfonamide

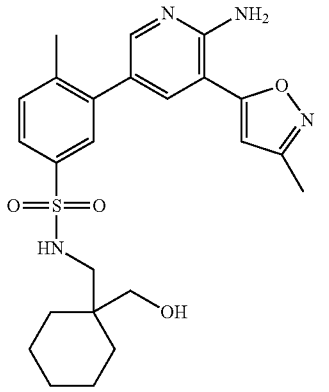 [SMILES: Cc1cc(-c2cc(-c3cc(S(=O)(=O)NCC4(CO)CCCCC4)ccc3C)cnc2N)on1]

LC-MS: Rt 1.06 mins; MS m/z 471.3 [M+H]+; Method 2 minLowpHv01

Example 37.4

(R)-3-(6-Amino-5-(3-methylisoxazol-5-yl)pyridin-3-yl)-4-methyl-N-(2-oxopiperidin-4-yl)benzenesulfonamide

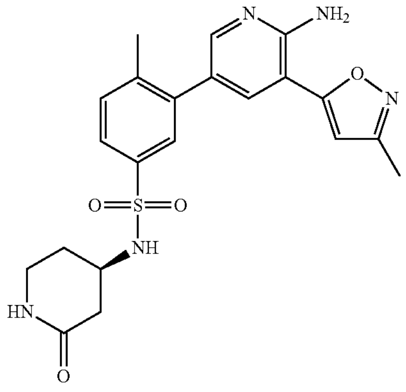 [SMILES: Cc1cc(-c2cc(-c3cc(S(=O)(=O)N[C@@H]4CCNC(=O)C4)ccc3C)cnc2N)on1]

LCMS: Rt=0.77 mins; MS m/z 442.4 [M+H]+; Method 2 minLowpHv01

Example 37.5

(R)-3-(6-Amino-5-(3-methyl-1,2,4-oxadiazol-5-yl)pyridin-3-yl)-4-methyl-N-((tetrahydrofuran-2-yl)methyl)benzenesulfonamide

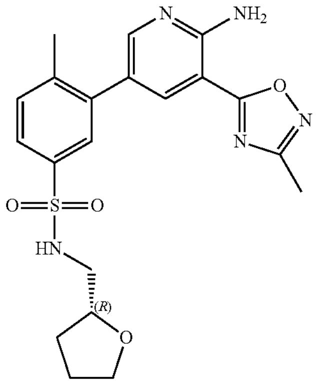

$^{1}$H NMR (400 MHz, MeOD-d4) δ 8.25 (1H, s) 8.23 (1H, s) 7.76 (1H, d) 7.74 (1H, s) 7.52 (1H, d) 3.93 (1H, m) 3.79 (1H, m) 3.69 (1H, m) 2.69 (2H, m) 2.49 (3H, s) 2.41 (3H, s) 1.89 (3H, m) 1.65 (1H, m)

Example 37.6

3-(6-Amino-5-(3-methylisoxazol-5-yl)pyridin-3-yl)-N-((1-(hydroxymethyl)cyclobutyl)methyl)-4-methylbenzenesulfonamide

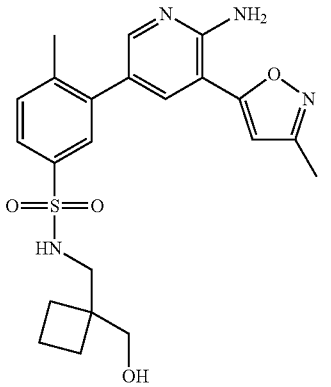 [SMILES: Cc1cc(-c2cc(-c3cc(S(=O)(=O)NCC4(CO)CCC4)ccc3C)cnc2N)on1]

LCMS: Rt=0.95 mins; MS m/z 443.3 [M+H]+; Method 2 minLowpHv01

Example 37.7

3-(6-Amino-5-(3-methylisoxazol-5-yl)pyridin-3-yl)-N-(3-hydroxy-2,2-dimethylpropyl)-4-methylbenzenesulfonamide

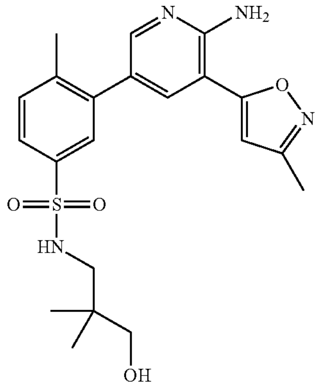 [SMILES: Cc1cc(-c2cc(-c3cc(S(=O)(=O)NCC(C)(C)CO)ccc3C)cnc2N)on1]

LCMS: Rt 0.86 min; m/z 431.4 [M+H]+; Method: 2 minLowpHv01

Example 37.8

3-(6-Amino-5-(3-methylisoxazol-5-yl)pyridin-3-yl)-4-methyl-N-(tetrahydro-2H-pyran-4-yl)benzenesulfonamide

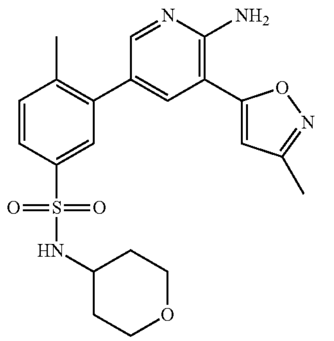 [SMILES: Cc1cc(-c2cc(-c3cc(S(=O)(=O)NC4CCOCC4)ccc3C)cnc2N)on1]

LC-MS: Rt 0.89 mins; MS m/z 429.2 [M+H]+; Method 2 minLowpHv01

Example 37.9

3-(6-Amino-5-(3-methylisoxazol-5-yl)pyridin-3-yl)-N-((1-hydroxycyclohexyl)methyl)-4-methylbenzene-sulfonamide: diethyl ether (1:1

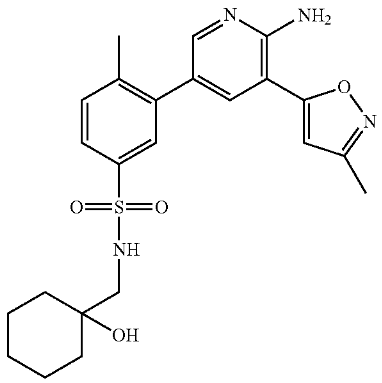 [SMILES: Cc1cc(-c2cc(-c3cc(S(=O)(=O)NCC4(O)CCCCC4)ccc3C)cnc2N)on1]

Note: the product was triturated in a DCM:$Et_2O$ mixture, resulting in the formation of a 1:1 complex with diethyl ether following overnight drying in a vacuum oven;

$^1$H NMR (400 MHz, DMSO-d6) δ 8.16 (1H, d), 7.91 (1H, d), 7.66-7.71 (2H, m), 7.50-7.55 (1H, m), 7.36 (1H, t), 6.90 (1H, s), 6.50 (2H, s), 4.13 (1H, s), 3.39 (2H, q)(ether solvate), 2.64 (2H, d), 2.37 (3H, s), 2.30 (3H, s), 1.29-1.58 (9H, m), 1.15 (1H, m), 1.10 (3H, t)(ether solvate).

Example 37.10

3-(6-Amino-5-(3-methyl-1,2,4-oxadiazol-5-yl)pyridin-3-yl)-N-((4-(hydroxymethyl)tetrahydro-2H-pyran-4-yl)methyl)-4-methylbenzenesulfonamide

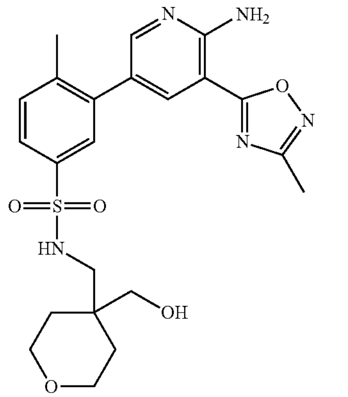 [SMILES: Cc1noc(-c2cc(-c3cc(S(=O)(=O)NCC4(CO)CCOCC4)ccc3C)cnc2N)n1]

LC-MS: Rt 0.95 mins; MS m/z 474.4 [M+H]+; Method 2 minLowpHv01

Example 37.11

3-(6-Amino-5-(3-methyl-1,2,4-oxadiazol-5-yl)pyridin-3-yl)-N-(2-(1-hydroxycyclopentyl)ethyl)-4-methylbenzenesulfonamide

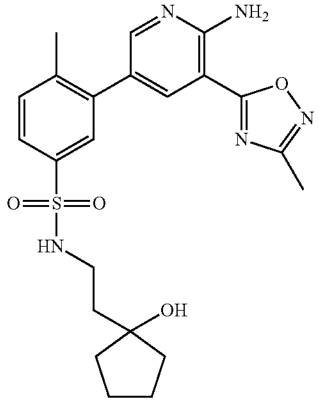 [SMILES: Cc1noc(-c2cc(-c3cc(S(=O)(=O)NCCC4(O)CCCC4)ccc3C)cnc2N)n1]

LCMS—Rt=1.07 mins; MS m/z 458.4 [M+H]+; Method 2 minLowpHv01

Example 37.12

(1-((3-(6-Amino-5-(3-methylisoxazol-5-yl)pyridin-3-yl)-4-methylphenyl)sulfonyl)azetidin-3-yl)methanol

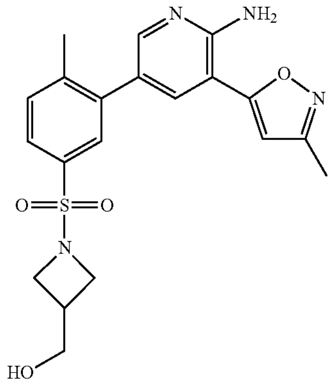 [SMILES: Cc1cc(-c2cc(-c3cc(S(=O)(=O)N4CC(CO)C4)ccc3C)cnc2N)on1]

LCMS—Rt=0.84 mins; MS m/z 415.2 [M+H]+; Method 2 minLowpHv01

Example 37.13

3-(6-Amino-5-(3-methyl-1,2,4-oxadiazol-5-yl)pyridin-3-yl)-N-((1-(hydroxymethyl)cyclopentyl)methyl)-4-methylbenzenesulfonamide

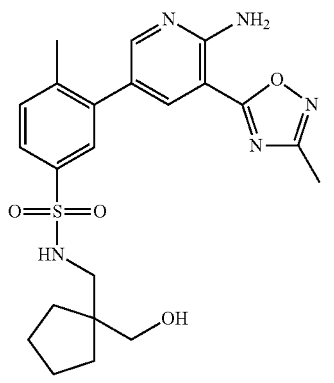 [SMILES: Cc1noc(-c2cc(-c3cc(S(=O)(=O)NCC4(CO)CCCC4)ccc3C)cnc2N)n1]

LCMS: Rt=1.09 mins; MS m/z 458.4 [M+H]+; Method 2 minLowpHv01

Example 37.14

3-(6-Amino-5-(3-methylisoxazol-5-yl)pyridin-3-yl)-4-methyl-N-(3,3,3-trifluoropropyl)benzenesulfonamide

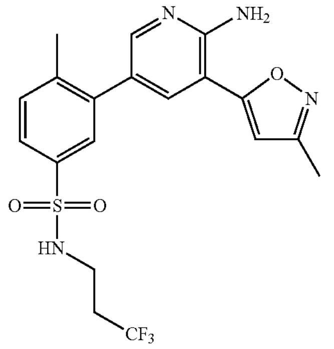 [SMILES: Cc1cc(-c2cc(-c3cc(S(=O)(=O)NCCC(F)(F)F)ccc3C)cnc2N)on1]

LCMS: Rt 0.99 mins; MS m/z 441.1 [M+H]+; Method 2 minLowpHv01.

Example 37.15

3-(6-Amino-5-(3-methyl-1,2,4-oxadiazol-5-yl)pyridin-3-yl)-N-((1-hydroxycyclobutyl)methyl)-4-methylbenzenesulfonamide

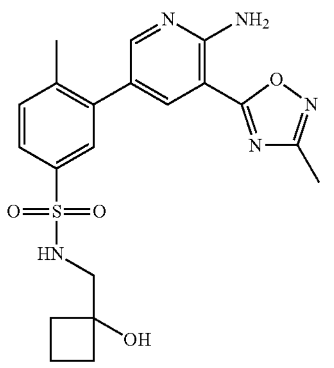 [SMILES: Cc1noc(-c2cc(-c3cc(S(=O)(=O)NCC4(O)CCC4)ccc3C)cnc2N)n1]

LCMS: Rt=1.00 mins; MS m/z 430.2 [M+H]+; Method 2 minLowpHv01

Example 37.16

3-(6-Amino-5-(3-methylisoxazol-5-yl)pyridin-3-yl)-N-(2-(1-hydroxycyclopentyl)ethyl)-4-methylbenzenesulfonamide

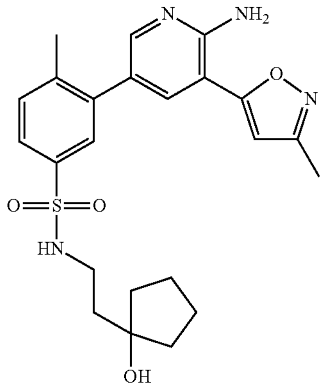 [SMILES: Cc1cc(-c2cc(-c3cc(S(=O)(=O)NCCC4(O)CCCC4)ccc3C)cnc2N)on1]

LCMS—Rt=0.96 mins; MS m/z 457.4 [M+H]+; Method 2 minLowpHv01

Example 37.17

3-(6-Amino-5-(3-methyl-1,2,4-oxadiazol-5-yl)pyridin-3-yl)-N-(3,3-difluorocyclobutyl)-4-methylbenzenesulfonamide

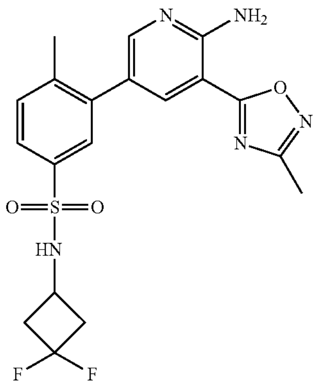 [SMILES: Cc1noc(-c2cc(-c3cc(S(=O)(=O)NC4CC(F)(F)C4)ccc3C)cnc2N)n1]

$^1H$ NMR (400 MHz, $CDCl_3$) δ 8.26 (1H, s) 8.23 (1H, s) 7.79 (1H, d) 7.75 (1H, s) 7.49 (1H, d) 6.96 (2H, s) 5.13 (1H, d) 3.79 (1H, m) 2.89 (2H, m) 2.53 (3H, s) 2.48 (2H, m) 2.41 (3H, s)

Example 37.18

3-(6-Amino-5-(3-methyl-1,2,4-oxadiazol-5-yl)pyridin-3-yl)-N-(3-hydroxy-2,2-dimethylpropyl)-4-methylbenzenesulfonamide hydrochloride

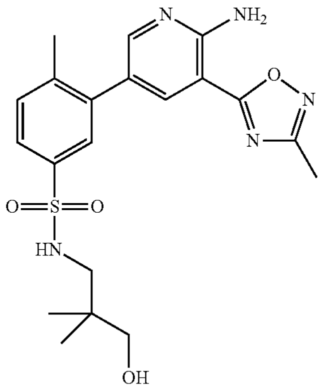 [SMILES: Cc1noc(-c2cc(-c3cc(S(=O)(=O)NCC(C)(C)CO)ccc3C)cnc2N)n1]

LCMS: Rt=1.05 mins; MS m/z 432.6 [M+H]+; Method 2 minLowpHv01

Example 37.19

3-(6-Amino-5-(3-methyl-1,2,4-oxadiazol-5-yl)pyridin-3-yl)-N-((1-hydroxycyclopropyl)methyl)-4-methylbenzenesulfonamide

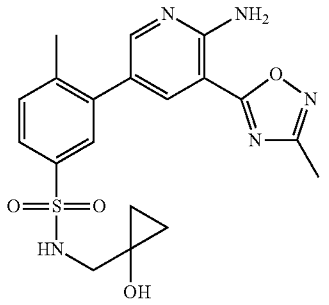 [SMILES: Cc1noc(-c2cc(-c3cc(S(=O)(=O)NCC4(O)CC4)ccc3C)cnc2N)n1]

LCMS: Rt 1.03 min; m/z 416.3 [M+H]+; Method 2 minLowpHv03

Example 37.20

5-(5-((3-Methoxy-3-methylazetidin-yl)sulfonyl)-2-methylphenyl)-3-(3-methylisoxazol-5-yl)pyridin-2-amine

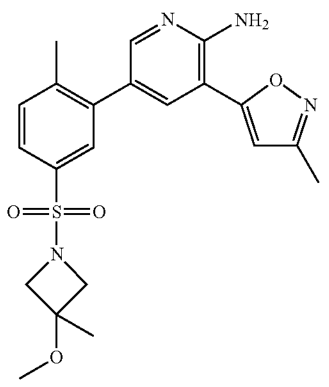 [SMILES: COC1(C)CN(S(=O)(=O)c2ccc(C)c(-c3cnc(N)c(-c4cc(C)no4)c3)c2)C1]

LCMS: Rt=0.98 mins; MS m/z 429.4 [M+H]+; Method 2 minLowpHv01

Example 37.21

3-(6-Amino-5-(3-methyl-1,2,4-oxadiazol-5-yl)pyridin-3-yl)-N-(2-hydroxy-1-(tetrahydrofuran-3-yl) ethyl)-4-methylbenzenesulfonamide

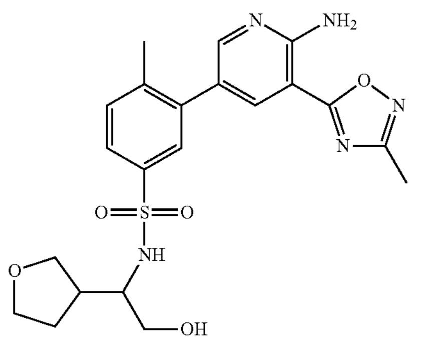 [SMILES: Cc1noc(-c2cc(-c3cc(S(=O)(=O)NC(CO)C4CCOC4)ccc3C)cnc2N)n1]

LCMS: Rt=1.02 mins; MS m/z 460.6 [M+H]+; Method 2 minLowpHv3.

Example 37.22

3-(6-Amino-5-(3-methylisoxazol-5-yl)pyridin-3-yl)-N-methoxy-N,4-dimethylbenzenesulfonamide

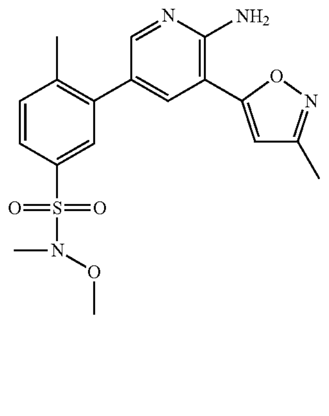 [SMILES: CON(C)S(=O)(=O)c1ccc(C)c(-c2cnc(N)c(-c3cc(C)no3)c2)c1]

$^1$H NMR (400 MHz, DMSO-d6) δ 8.16 (1H, d), 7.92 (1H, d), 7.72-7.74 (1H, m), 7.61-7.65 (2H, m), 6.90 (1H, s), 6.52 (2H, s), 3.73 (3H, s), 2.78 (3H, s), 2.40 (3H, s), 2.30 (3H, s).

Example 37.23

3-(6-Amino-5-(3-methylisoxazol-5-yl)pyridin-3-yl)-N-((1-(hydroxymethyl)cyclopentyl) methyl)-4-methylbenzenesulfonamide

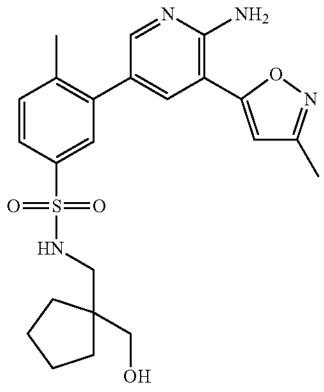 [SMILES: Cc1cc(-c2cc(-c3cc(S(=O)(=O)NCC4(CO)CCCC4)ccc3C)cnc2N)on1]

LCMS: Rt=1.00 mins; MS m/z 457.4 [M+H]+; Method 2 minLowpHv01

Example 37.24

(R)-1-((3-(6-Amino-5-(3-methylisoxazol-5-yl)pyridin-3-yl)-4-methylphenyl)sulfonyl)pyrrolidin-3-ol

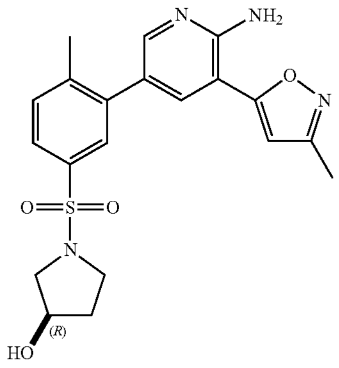

LCMS: Rt 0.83 min; m/z 415.4 [M+H]+; Method: 2 minLowpHv10

Example 37.25

(R)-3-(6-Amino-5-(3-methyl-1,2,4-oxadiazol-5-yl)pyridin-3-yl)-4-methyl-N-(2-oxopiperidin-4-yl)benzenesulfonamide

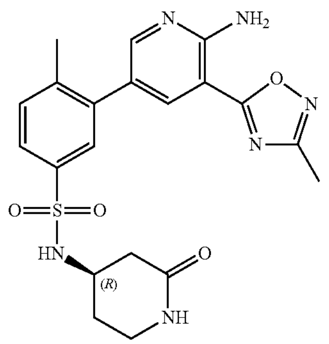

LCMS: Rt=0.87 mins; MS m/z 443.2 [M+H]+; Method 2 minLowpHv01

Example 37.26

3-(6-Amino-5-(3-methyl-1,2,4-oxadiazol-5-yl)pyridin-3-yl)-N-((1-(hydroxymethyl)cyclobutyl)methyl)-4-methylbenzenesulfonamide

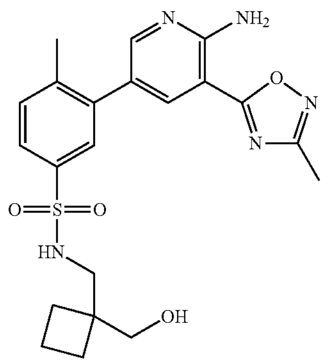 [SMILES: Cc1noc(-c2cc(-c3cc(S(=O)(=O)NCC4(CO)CCC4)ccc3C)cnc2N)n1]

LCMS—Rt=1.04 mins; MS m/z 444.2 [M+H]+; Method 2 minLowpHv01

Example 37.27

(R)-3-(6-Amino-5-(3-methylisoxazol-5-yl)pyridin-3-yl)-N-((1-ethyl pyrrolidin-2-yl)methyl)-4-methylbenzenesulfonamide

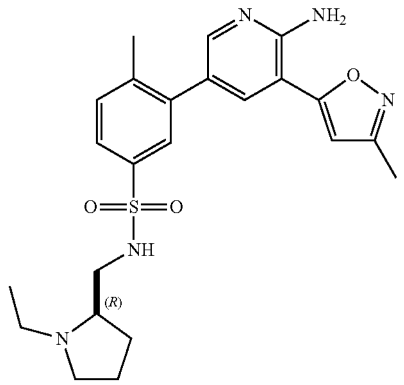

LCMS: Rt 0.63 min; m/z 456.4 [M+H]+; Method: 2 minLowpHv01

Example 37.28

1-((3-(6-Amino-5-(3-methylisoxazol-5-yl)pyridin-3-yl)-4-methylphenyl)sulfonyl)-3-methylazetidin-3-ol

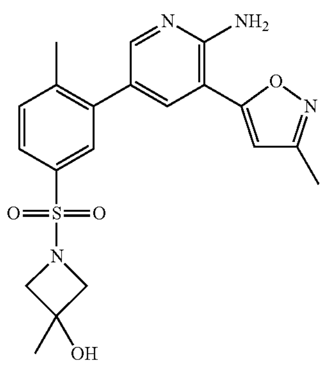 [SMILES: Cc1cc(-c2cc(-c3cc(S(=O)(=O)N4CC(C)(O)C4)ccc3C)cnc2N)on1]

LCMS Rt 0.82 mins; MS m/z 415.2 [M+H]+; Method 2 minLowpHv01.

Example 37.29

3-(6-Amino-5-(3-methyl-1,2,4-oxadiazol-5-yl)pyridin-3-yl)-N-(2-aminoethyl)-4-methylbenzenesulfonamide

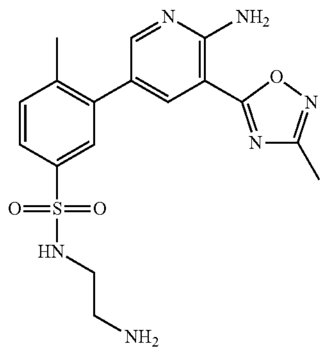

LCMS—Rt=0.66 mins; MS m/z 389.3 [M+H]+; Method 2 minLowpHv01

Example 37.30

3-(6-Amino-5-(3-methylisoxazol-5-yl)pyridin-3-yl)-N-(2-(1-hydroxycyclohexyl)ethyl)-4-methylbenzenesulfonamide

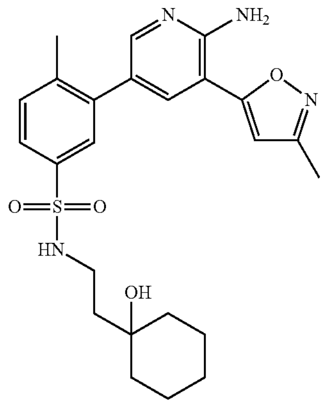 [SMILES: Cc1cc(-c2cc(-c3cc(S(=O)(=O)NCCC4(O)CCCCC4)ccc3C)cnc2N)on1]

LCMS: Rt 3.95 min; MS m/z 471.3, [M+H]+ Method: 10 minLowpH.

Example 37.31

3-(6-Amino-5-(3-methyl-1,2,4-oxadiazol-5-yl)pyridin-3-yl)-N-(2-(1-hydroxycyclohexyl)ethyl)-4-methylbenzenesulfonamide

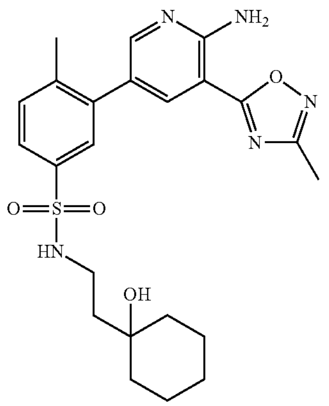 [SMILES: Cc1noc(-c2cc(-c3cc(S(=O)(=O)NCCC4(O)CCCCC4)ccc3C)cnc2N)n1]

LCMS: Rt 4.72 min; MS m/z 472.6 [M+H]+ Method: 10 minLowpH.

Example 37.32

(S)-1-((3-(6-Amino-5-(3-methyl-1,2,4-oxadiazol-5-yl)pyridin-3-yl)-4-methylphenyl)sulfonyl)pyrrolidin-3-ol hydrochloride

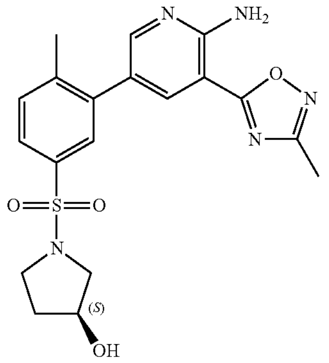

LCMS—Rt=1.04 mins; MS m/z 416.2 [M+H]+; 2 minLowpHv03.

Example 37.33

(S)-3-(6-Amino-5-(3-methylisoxazol-5-yl)pyridin-3-yl)-N-((1-ethyl pyrrolidin-2-yl)methyl)-4-methyl-benzenesulfonamide

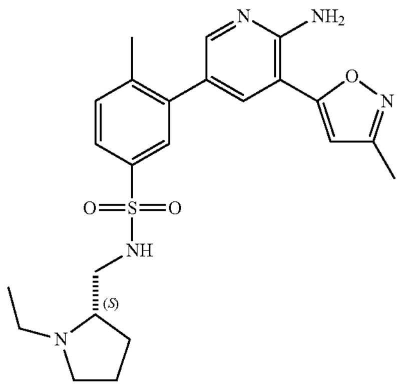

LCMS: Rt 0.66 min; m/z 454.5 [M−H]−; Method: 2 minLowpHv01

Example 37.34

3-(6-Amino-5-(3-methyl-1,2,4-oxadiazol-5-yl)pyridin-3-yl)-N-(1-isopropylpiperidin-4-yl)-4-methyl-benzenesulfonamide

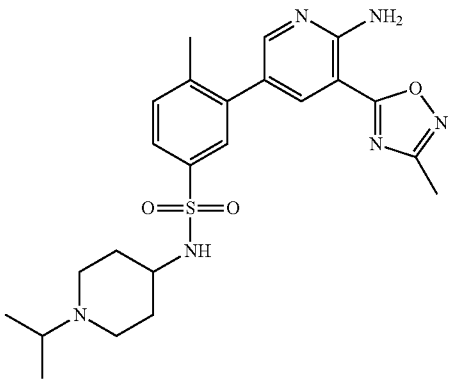 [SMILES: Cc1noc(-c2cc(-c3cc(S(=O)(=O)NC4CCN(C(C)C)CC4)ccc3C)cnc2N)n1]

$^1$H NMR (400 MHz, DMSO-d6) δ 8.35 (2H, s) 8.16 (1H, s) 7.71 (1H, s) 7.69 (1H, s) 7.64 (1H, d) 7.60 (2H, s) 7.53 (1H, d) 2.95 (1H, m) 2.64 (2H, m) 2.47 (3H, s) 2.38 (3H, s) 2.02 (2H, m) 1.57 (2H, m) 1.34 (2H, m) 0.90 (6H, d)

Example 37.35

3-(6-Amino-5-(3-methylisoxazol-5-yl)pyridin-3-yl)-N-((1-hydroxycyclobutyl)methyl)-4-methylbenzene-sulfonamide

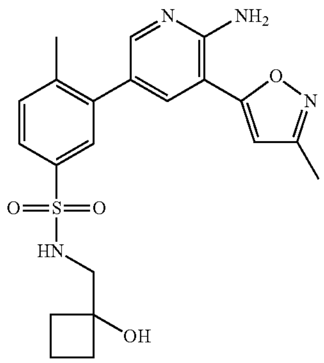 [SMILES: Cc1cc(-c2cc(-c3cc(S(=O)(=O)NCC4(O)CCC4)ccc3C)cnc2N)on1]

LCMS—Rt=0.90 mins; MS m/z 429.3 [M+H]+; 2 min-LowpHv01

Example 37.37a and 37.37b (R)-3-(6-Amino-5-(3-methylisoxazol-5-yl)pyridin-3-yl)-4-methyl-N-((tetrahydro-2H-pyran-2-yl)methyl) benzenesulfonamide and (S)-3-(6-amino-5-(3-methylisoxazol-5-yl)pyridin-3-yl)-4-methyl-N-((tetrahydro-2H-pyran-2-yl)methyl) benzenesulfonamide

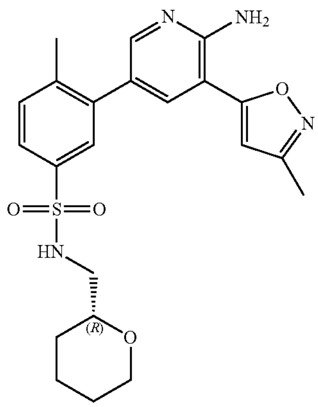

and

-continued

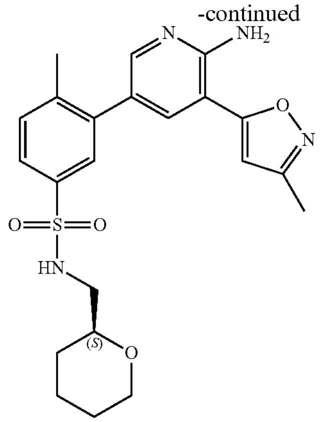

Enantiomers were separated by chiral SFC using the following conditions:

Sample concentration: 50 mg in 1 ml ethanol+4 ml THF (10 mg/ml)

Column: Chiralpak AD-H 250×10 mm, 5 um @ 35 deg C.

Mobile phase: 50% Isopropanol+0.1% v/v DEA/50% CO2

Flow: 10 ml/min

Detection: UV @ 220 nm

Instrument: Berger Minigram SFC1

Run time: 16 mins

Example 37.37a (R)-3-(6-Amino-5-(3-methylisoxazol-5-yl)pyridin-3-yl)-4-methyl-N-((tetrahydro-2H-pyran-2-yl)methyl)benzenesulfonamide or (S)-3-(6-amino-5-(3-methylisoxazol-5-yl)pyridin-3-yl)-4-methyl-N-((tetrahydro-2H-pyran-2-yl)methyl) benzenesulfonamide Collected 7.8-9.9 min Example 37.37b (R)-3-(6-Amino-5-(3-methylisoxazol-5-yl)pyridin-3-yl)-4-methyl-N-((tetrahydro-2H-pyran-2-yl)methyl)benzenesulfonamide or (S)-3-(6-amino-5-(3-methylisoxazol-5-yl)pyridin-3-yl)-4-methyl-N-((tetrahydro-2H-pyran-2-yl)methyl) benzenesulfonamide Collected 13-15.7 min Analytical Chiral SFC using the following method:

Chiralpak AD-3, 150×2.1 mm 3 um @ 40 C, 0.4 ml/min, UV @ 220 nm and 254 nm; 50%

Isopropanol+0.1% v/v DEA in CO2

Example 37.37a: Rt 6.40 min

Example 37.37b: Rt 12.28 min

Further analytical data for Example 37.37a:

LCMS: Rt 1.03 min; m/z 443.3 [M+H]+; Method: 2 minLowpHv01

$^1$H NMR (400 MHz, DMSO-d6) δ 8.15 (1H, d, J=2.5 Hz), 7.90 (1H, d, J=2.5 Hz), 7.69-7.63 (3H, m), 7.52 (1H, d), 6.90 (1H, s), 6.50 (2H, s), 3.79 (1H, d), 3.26-3.18 (2H, m), 2.76 (2H, m), 2.36 (3H, s), 2.30 (3H, s), 1.73 (1H, br. s.), 1.53 (1H, m), 1.44-1.33 (3H, m), 1.16-1.04 (1H, m).

Example 37.38

3-(6-Amino-5-(3-methyl-1,2,4-oxadiazol-5-yl)pyridin-3-yl)-N-(2,2-difluoropropyl)-4-methylbenzenesulfonamide

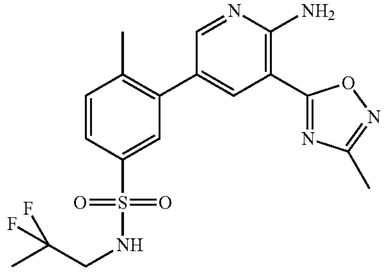 [SMILES: Cc1noc(-c2cc(-c3cc(S(=O)(=O)NCC(C)(F)F)ccc3C)cnc2N)n1]

LCMS—Rt=1.19 mins; MS m/z 424.3 [M+H]+; Method 2 minLowpHv03

Example 37.39

(S)-((3-(6-Amino-5-(3-methyl-1,2,4-oxadiazol-5-yl) pyridin-3-yl)-4-methylphenyl)sulfonyl)azetidin-3-yl) methanol

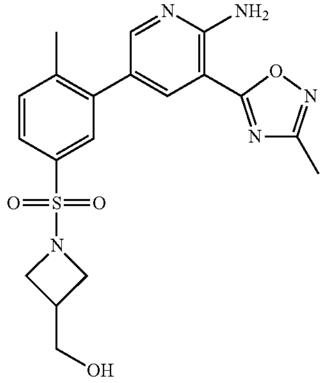 [SMILES: Cc1noc(-c2cc(-c3cc(S(=O)(=O)N4CC(CO)C4)ccc3C)cnc2N)n1]

LCMS: Rt=0.94 mins; MS m/z 416.1 [M+H]+; Method 2 minLowpHv01

Example 38

(S)-3-(6-Amino-5-(3-methylisoxazol-5-yl)pyridin-3-yl)-4-methyl-N-((tetrahydrofuran-3-yl)methyl)benzenesulfonamide

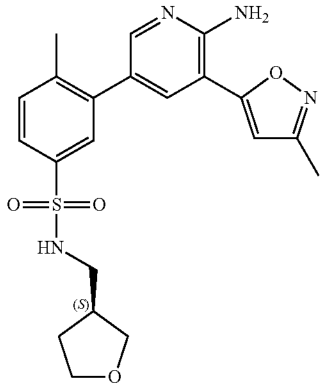

To a solution of DIPEA (0.072 ml, 0.412 mmol) and (S)-(tetrahydrofuran-2-yl)methanamine hydrochloride (18.91 mg, 0.137 mmol) in DMA (1 ml) was added 3-(6-amino-5-(3-methylisoxazol-5-yl)pyridin-3-yl)-4-methylbenzene-1-sulfonyl chloride (Intermediate E3) (50 mg, 0.137 mmol). The reaction mixture was stirred at RT overnight. The resulting mixture was extracted into DCM, washed with bicarb, brine, the organic layer separated, dried over $MgSO_4$, filtered and the solvent removed under reduced pressure. The crude material was passed through a 1 g Isolute® SCX-2 cartridge, elution with 2M ammonia methanol solution. The eluant was dried in the genevac overnight to afford the title compound as an off-white solid;

LCMS: Rt 0.86 mins; MS m/z 429.2 [M+H]+; Method 2 minLowpHv01.

$^1$H NMR (400 MHz, DMSO-d6) δ 8.15 (1H, d), 7.90 (1H, d), 7.68 (2H, mult), 7.63 (1H, d), 7.53 (1H, d), 6.89 (1H, s), 6.50 (2H, br), 3.62 (3H, mult), 3.36 (1H, mult),2.72 (2H, mult), 2.36 (3H, s), 2.30 (3H, s), 2.26 (1H, mult), 1.87 (1H, mult), 1.49 (1H, mult).

Example 39

3-(6-Amino-5-(3-methylisoxazol-5-yl)pyridin-3-yl)-4-methyl-N-(2,2,2-trifluoroethyl)benzenesulfonamide

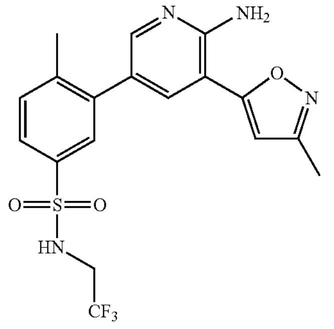 [SMILES: Cc1cc(-c2cc(-c3cc(S(=O)(=O)NCC(F)(F)F)ccc3C)cnc2N)on1]

To a solution of DIPEA (0.072 ml, 0.412 mmol) and 2,2,2-trifluoroethanamine (13.61 mg, 0.137 mmol) in DMA (Volume: 1 ml) was added 3-(6-amino-5-(3-methylisoxazol-5-yl)pyridin-3-yl)-4-methylbenzene-1-sulfonyl chloride (Intermediate E3) (50 mg, 0.137 mmol). The reaction was stirred at RT overnight. The mixture was extracted into DCM, washed with bicarb, brine, the organic layer separated, dried over $MgSO_4$, filtered and the solvent removed under reduced pressure. The crude material was passed through a 1 g Isolute® SCX-2 cartridge, elution with 2M ammonia methanol solution. The eluant was dried in the genevac overnight to afford the title compound;

LCMS: Rt 0.95 mins; MS m/z 427.3 [M+H]+; Method 2 minLowpHv01.

$^1$H NMR (400 MHz, DMSO-d6) δ 8.55 (1H, br), 8.16 (1H, d), 7.90 (1H, d), 7.71 (1H, dd), 7.68 (1H, d), 7.54 (1H, d), 6.89 (1H, s), 6.50 (2H, br), 3.70 (2H, mult), 2.38 (3H, s), 2.30 (3H, s). $^{19}$F NMR (400 MHz, d6-DMSO) δ −71.0.

Example 40

(S)-3-(6-Amino-5-(3-methylisoxazol-5-yl)pyridin-3-yl)-4-methyl-N-((tetrahydrofuran-2-yl)methyl)benzenesulfonamide

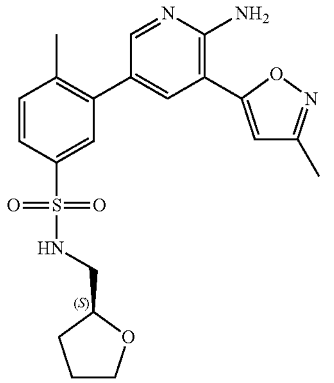

To a solution of DIPEA (0.072 ml, 0.412 mmol) and (S)-(tetrahydrofuran-2-yl)methanamine (13.90 mg, 0.137 mmol) in DMA (1 ml) was added 3-(6-amino-5-(3-methylisoxazol-5-yl)pyridin-3-yl)-4-methylbenzene-1-sulfonyl chloride (Intermediate E3) (50 mg, 0.137 mmol). The reaction was stirred at RT overnight. The reaction mixture was extracted into DCM, washed with water, brine, the organic layer separated, dried over $MgSO_4$, filtered and the solvent removed under reduced pressure. The crude material was passed through a 1 g Isolute® SCX-2 cartridge, elution with 2M ammonia methanol solution and the solvent removed under reduced pressure. The crude product was purified by flash column chromatography elution with TBME:MeOH (0-10%) on a 4 g silica cartridge. The required fractions were combined and the solvent removed under reduced pressure. The resulting oil was dried in a vac oven at 40° C. overnight to afford the title compound as an off white solid;

LCMS: Rt 0.89 mins; MS m/z 429.2 [M+H]+; Method 2 minLowpHv01.

$^1$H NMR (400 MHz, DMSO-d6) δ 8.15 (1H, d), 7.90 (1H, d), 7.66 (3H, mult), 7.52 (1H, d), 6.89 (1H, s), 6.49 (2H, br), 3.80 (1H, mult), 3.67 (1H, mult), 3.56 (1H, mult), 2.79 (2H, mult), 2.36 (3H, s), 2.30 (3H, s), 1.78 (3H, mult), 1.53 (1H, mult).

Example 41

3-(6-Amino-5-(3-(hydroxymethyl)isoxazol-5-yl)pyridin-3-yl)-N-(2-hydroxy-2-methylpropyl)-4-methylbenzenesulfonamide

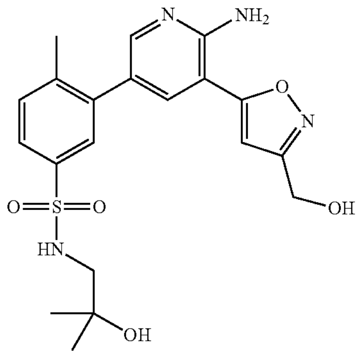 [SMILES: Cc1ccc(S(=O)(=O)NCC(C)(C)O)cc1-c1cnc(N)c(-c2cc(CO)no2)c1]

Step 1: 2-((Tert-butyldimethylsilyl)oxy)acetaldehyde oxime

To a mixture of 2-((tert-butyldimethylsilyl)oxy)acetaldehyde (1.7 g, 9.75 mmol) and $NaHCO_3$ (10.73 mL, 10.73 mmol) in MeOH (30 mL) was slowly added hydroxylamine hydrochloride (745 mg, 10.73 mmol) and the reaction stirred at RT for 2 hours. A clear solution was observed. The reaction was extracted into ether, washed with water, the organic layer separated, dried over $MgSO_4$, filtered and the solvent removed under reduced pressure to yield the title compound as a clear oil. Used without further purification in subsequent step.

Step 2: 2-((Tert-butyldimethylsilyl)oxy)-N-hydroxyacetimidoyl chloride

To a solution of 2-((tert-butyldimethylsilyl)oxy)acetaldehyde oxime (step 1) (1.81 g, 9.56 mmol) in DMF (30 mL) was added N-chlorosuccinimide (1.66 g, 12.43 mmol) slowly over 5 mins and the reaction stirred at RT for 1 hour. The reaction mixture was extracted into ether, washed with brine, the organic layer separated, dried over $MgSO_4$ and the solvent removed under reduced pressure to yield the title compound as a pale yellow oil. The crude compound was used in the next step without further purification Step 3: 5-Bromo-3-(3-(((tert-butyldimethylsilyl)oxy)methyl)isoxazol-5-yl)pyridin-2-amine To a suspension of 5-bromo-3-ethynylpyridin-2-amine (Intermediate C15) (500 mg, 2.54 mmol) and sodium ascorbate (0.254 ml, 0.254 mmol) in t-BuOH (10 ml) and water (10 ml) under $N_2$ was added copper(II) sulfate pentahydrate (13 mg, 0.051 mmol, 2 mol %) and $NaHCO_3$ (853 mg, 10.15 mmol) followed by 2-((tert-butyldimethylsilyl)oxy)-N-hydroxyacetimidoyl chloride (step 3) (1.7 g, 7.61 mmol, 3 eq) slowly over 15 mins. The mixture was stirred at RT overnight. The resulting mixture was extracted into DCM, washed with water, brine, the organic layer separated, dried over $MgSO_4$, filtered and the solvent removed under reduced pressure. The crude product was purified by flash column chromatography elution with iso-hexane:ethyl acetate (0-30%) on a 24 g silica cartridge. The required fractions were combined and the solvent removed under reduced pressure to afford the title compound;

LCMS: Rt=1.62 mins MS m/z 384.4 [M+H]+; Method 2 minLowpHv03.

Step 4. (5-(2-Amino-5-bromopyridin-3-yl)isoxazol-3-yl)methanol

A solution of 5-bromo-3-(3-(((tert-butyldimethylsilyl)oxy)methyl isoxazol-5-yl)pyridin-2-amine (step 3) (975 mg, 1.015 mmol) and TBAF (1M in THF) (1.015 ml, 1.015 mmol) in THF (10 ml) was stirred at RT for 15 mins, then extracted into DCM, washed with water, brine, the organic layer separated, dried over $MgSO_4$, filtered and the solvent removed under reduced pressure. The crude product was purified by flash column chromatography elution with iso-hexane:ethyl acetate (0-100%) on a 24 g silica cartridge. The required fractions were combined and the solvent removed under reduced pressure to yield the title compound as a yellow solid;

LCMS: Rt=0.81 mins MS m/z 270.1 [M+H]+; Method 2 minLowpHv03.

Step 5: 3-(6-Amino-5-(3-(hydroxymethyl)isoxazol-5-yl)pyridin-3-yl)-N-(2-hydroxy-2-methylpropyl)-4-methylbenzenesulfonamide A mixture of N-(2-hydroxy-2-methyl-propyl)-4-methyl-3-(4,4,5,5-tetramethyl[1,3,2]dioxaborolan-2-yl)benzenesulfonamide (Intermediate B2) (115 mg, 0.311 mmol), (5-(2-amino-5-bromopyridin-3-yl)isoxazol-3-yl)methanol (step 5) (80 mg, 0.296 mmol), [1,1'-bis(di-tert-butylphosphino)ferrocene]dichloropalladium(II) [Pd-118] (9.65 mg, 0.015 mmol) and $K_3PO_4$ (126 mg, 0.592 mmol) in dioxane (2 ml) and water (1 ml) was heated at 100° C. for 1 hour. The resulting mixture was extracted into ethyl acetate, washed with water, brine, the organic layer separated, dried over $MgSO_4$, filtered and the solvent removed under reduced pressure. The crude product was loaded onto silica and purified by flash column chromatography elution with TBME:MeOH (0-15%) on a 12 g silica cartridge. The required fractions were combined and the solvent removed under reduced pressure to yield a pale yellow residue. The product was further purified by mass directed preparative HPLC at low pH. The required fractions were combined, extracted into DCM, washed with sat. sodium bicarbonate, the organic layer separated, dried over $MgSO_4$, filtered and the solvent removed under reduced pressure. The resulting residue was dissolved in DCM (1 ml) and allowed to evaporate at ambient temp overnight to afford the title compound as an off white foam;

LCMS: Rt=0.84 mins MS m/z 433.3 [M+H]+; Method 2 minLowpHv03.

$^1H$ NMR (400 MHz, DMSO-d6) δ 8.16 (1H, d), 7.95 (1H, d), 7.67 (2H, mult), 7.51 (1H, d), 7.44 (1H, mult), 7.01 (1H, s), 6.51 (2H, s), 5.53 (1H, t), 4.56 (2H, d), 4.39 (1H, s), 2.61 (2H, d), 2.36 (3H, s), 1.05 (6H, s).

Example 42

3-(6-Amino-5-(3-(morpholine-4-carbonyl)isoxazol-5-yl)pyridin-3-yl)-N-(2-hydroxy-2-methylpropyl)-4-methylbenzenesulfonamide

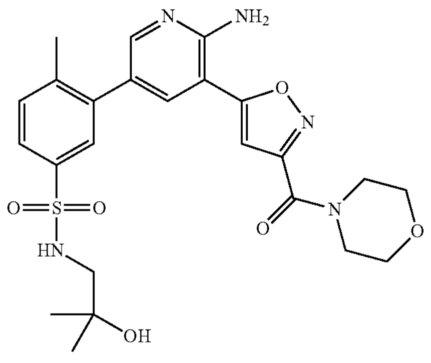 [SMILES: Cc1ccc(S(=O)(=O)NCC(C)(C)O)cc1-c1cnc(N)c(-c2cc(C(=O)N3CCOCC3)no2)c1]

Step 1: Ethyl 5-(2-amino-5-bromopyridin-3-yl)isoxazole-3-carboxylate

To a suspension of 5-bromo-3-ethynylpyridin-2-amine (Intermediate C15) (2.84 g, 14.41 mmol) and sodium ascorbate (1.441 ml, 1.441 mmol) in t-BuOH (50 ml) and water (50 ml) under $N_2$ was added copper(II) sulfate pentahydrate (72 mg, 0.288 mmol, 2 mol %) and $NaHCO_3$ (4.84 g, 57.7 mmol) followed by (Z)-ethyl 2-chloro-2-(hydroxyimino) acetate (2.2 g, 14.4 mmol, 1 eq) slowly over 15 mins. The resulting mixture was stirred at room temp for 1 hour. To the mixture was slowly added further (Z)-ethyl 2-chloro-2-(hydroxyimino)acetate (2.2 g, 14.4 mmol, 1 eq) over 15 mins and stirring continued for a further hour. Further (Z)-ethyl 2-chloro-2-(hydroxyimino)acetate (2.2 g, 14.4 mmol, 1 eq) was added over 15 mins and the mixture was stirred at RT overnight. The mixture was extracted into ethyl acetate, washed with water, brine, the organic layer separated, dried over $MgSO_4$, filtered and the solvent removed under reduced pressure. The crude product was purified by flash column chromatography elution with iso-hexane:ethyl acetate (0-40%) on a 80 g silica cartridge. The required fractions were combined and the solvent removed under reduced pressure. A solid crystallised on concentration. The solid was collected by filtration to yield the title compound as orange crystals;

LCMS: Rt=1.18 mins MS m/z 314.1 [M+H]+; Method 2 minLowpHv03.

Step 2: 5-(2-Amino-5-bromopyridin-3-yl)isoxazole-3-carboxylic acid

To a 100 mL round-bottomed flask was added ethyl 5-(2-amino-5-bromopyridin-3-yl)isoxazole-3-carboxylate (step 1) (1.4 g, 4.49 mmol) and lithium hydroxide (0.107 g, 4.49 mmol) in THF (24 ml) and water (8 ml) to give a orange suspension. The reaction was stirred at RT for 30 mins and turned red in colour. The mixture was acidified with 1M HCl and the resulting suspension filtered and dried in a vacuum oven overnight at 50° C. to afford the title compound as a beige solid;

LCMS: Rt=0.91 mins MS m/z 284.1 [M+H]+; Method 2 minLowpHv03.

Step 3: (5-(2-Amino-5-bromopyridin-3-yl)isoxazol-3-yl)(morpholino)methanone

To a 50 mL round-bottomed flask was added 5-(2-amino-5-bromopyridin-3-yl)isoxazole-3-carboxylic acid (step 2) (150 mg, 0.528 mmol), morpholine (0.055 mL, 0.634 mmol) and triethylamine (0.294 mL, 2.112 mmol) in DMF (5 mL) to give a white suspension. To the reaction mixture was added T3P® (0.467 ml, 0.792 mmol) dropwise over 5 mins. The reaction mixture was warmed to 30° C. under $N_2$ with stirred for 1 hour. The resulting mixture was extracted into ethyl acetate, washed with water, brine, the organic layer separated, dried over $MgSO_4$, filtered and the solvent removed under reduced pressure. The resulting pale yellow solid was triturated in iso-hexane:EtOAc (5:1) and the suspension filtered to yield the title compound as a yellow solid;

LCMS: Rt=0.99 mins MS m/z 355.2 [M+H]+; Method 2 minLowpHv03.

Step 4: 3-(6-Amino-5-(3-(morpholine-4-carbonyl)isoxazol-5-yl)pyridin-3-yl)-N-(2-hydroxy-2-methylpropyl)-4-methylbenzenesulfonamide To a 5 ml microwave vial was added N-(2-hydroxy-2-methyl-propyl)-4-methyl-3-(4,4,5,5-tetramethyl[1,3,2]dioxaborolan-2-yl)benzenesulfonamide (Intermediate B2) (160 mg, 0.433 mmol), (5-(2-amino-5-bromopyridin-3-yl)isoxazol-3-yl)(morpholino)methanone (step 3) (153 mg, 0.433 mmol), and $PdCl_2(dppf).CH_2Cl_2$-adduct (17.69 mg, 0.022 mmol) and sodium carbonate (0.542 ml, 1.083 mmol) in DME (4 ml). The reaction was heated in the biotage initiator microwave at 120° C. for 2 hours. The reaction was extracted into ethyl acetate, washed with water, brine, the organic layer separated, dried over $MgSO_4$, filtered and the solvent removed under reduced pressure. The crude product was loaded onto silica and purified by flash column chromatography elution with TBME:MeOH (0-15%) on a 12 g silica cartridge. The required fractions were combined and the solvent removed under reduced pressure to yield a pale yellow residue. The residue was dried in a vac oven at 50° C. overnight to yield the title compound as a light brown solid;

LCMS: Rt=0.92 mins MS m/z 516.7 [M+H]+; Method 2 minLowpHv03.

$^1H$ NMR (400 MHz, DMSO-d6) δ 8.20 (1H, d), 7.99 (1H, d), 7.68 (2H, mult), 7.52 (1H, d), 7.45 (1H, t), 7.24 (1H, s), 6.63 (2H, br), 4.40 (1H, s), 3.65 (8H, mult), 2.62 (2H, d), 2.37 (3H, s), 1.06 (6H, s).

Example 43

5-(2-Amino-5-(5-(N-(2-hydroxy-2-methylpropyl)sulfamoyl)-2-methylphenyl)pyridin-3-yl)-N,N-dimethylisoxazole-3-carboxamide

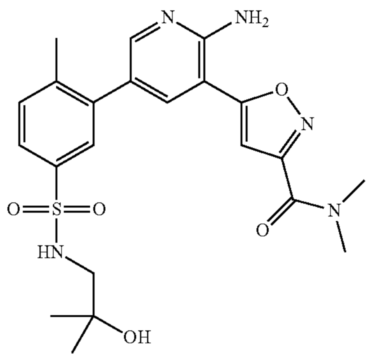 [SMILES: Cc1ccc(S(=O)(=O)NCC(C)(C)O)cc1-c1cnc(N)c(-c2cc(C(=O)N(C)C)no2)c1]

Step 1: 5-(2-Amino-5-bromopyridin-3-yl)-N,N-dimethylisoxazole-3-carboxamide

To a 50 mL round-bottomed flask was added 5-(2-amino-5-bromopyridin-3-yl)isoxazole-3-carboxylic acid (Example 42, step 2) (150 mg, 0.528 mmol), dimethylamine (2M in THF) (0.317 mL, 0.634 mmol) and triethylamine (0.294 mL, 2.112 mmol) in DMF (5 mL) to give a white suspension. To the reaction mixture was added T3P® (2.036 ml, 3.46 mmol) dropwise over 5 mins. The mixture was warmed to 30° C. under $N_2$ with stirring for 1 hour. The resulting mixture was extracted into ethyl acetate, washed with water, brine, the organic layer separated, dried over $MgSO_4$, filtered and the solvent removed under reduced pressure. The resulting red oil was sonicated in iso-hexane:EtOAc (5:1) until a solid formed. After filtration the title compound was isolated as a pink solid;

LCMS: Rt=0.98 mins MS m/z 311.4 [M+H]+; Method 2 minLowpHv03.

Step 2: 5-(2-Amino-5-(5-(N-(2-hydroxy-2-methylpropyl)sulfamoyl)-2-methylphenyl)pyridin-3-yl)-N,N-dimethylisoxazole-3-carboxamide To a 5 ml microwave vial was added N-(2-hydroxy-2-methyl-propyl)-4-methyl-3-(4,4,5,5-tetramethyl[1,3,2]dioxaborolan-2-yl)benzenesulfonamide (Intermediate B2) (138 mg, 0.373 mmol), 5-(2-amino-5-bromopyridin-3-yl)-N,N-dimethylisoxazole-3-carboxamide (step 1) (116 mg, 0.373 mmol) and $PdCl_2(dppf).CH_2Cl_2$-adduct (15.22 mg, 0.019 mmol) and sodium carbonate (0.466 ml, 0.932 mmol) in DME (4 ml). The reaction mixture was heated in the biotage initiator microwave at 120° C. for 2 hours. The resulting mixture was extracted into ethyl acetate, washed with water, brine, the organic layer separated, dried over $MgSO_4$, filtered and the solvent removed under reduced pressure. The crude product was loaded onto silica and purified by flash column chromatography elution with TBME:MeOH (0-15%) on a 12 g silica cartridge. The required fractions were combined and the solvent removed under reduced pressure to yield a pale yellow residue. The residue was dried in a vacuum oven at 50° C. overnight to yield the title compound as a light brown solid;

LCMS: Rt=0.88 mins MS m/z 474.5 [M+H]+; Method 2 minLowpHv03.

$^1$H NMR (400 MHz, DMSO-d6) δ 8.19 (1H, d), 8.00 (1H, d), 7.68 (2H, mult), 7.52 (1H, d), 7.44 (1H, t), 7.22 (1H, s), 6.62 (2H, br), 4.39 (1H, s), 3.13 (3H, s), 3.05 (3H, s), 2.62 (2H, d), 2.37 (3H, s), 1.06 (6H, s).

Example 44

3-(6-Amino-5-(3-methyl-1,2,4-oxadiazol-5-yl)pyridin-3-yl)-4-methyl-N-propoxybenzenesulfonamide

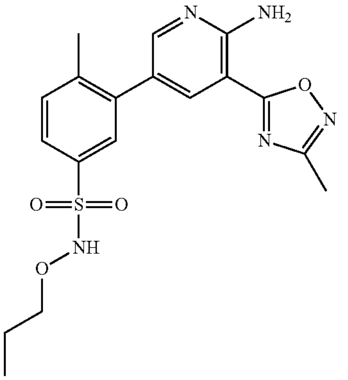 [SMILES: CCCONS(=O)(=O)c1ccc(C)c(-c2cnc(N)c(-c3nc(C)no3)c2)c1]

To a stirring solution of 3-(6-amino-5-(3-methyl-1,2,4-oxadiazol-5-yl)pyridin-3-yl)-4-methylbenzene-1-sulfonyl chloride (Intermediate E2) (50 mg, 0.125 mmol) in THF (1 mL) was added O-propylhydroxylamine (HCl salt) (30 mg, 0.269 mmol) and pyridine (0.1 mL, 1.236 mmol) and the resulting mixture stirred at room temperature overnight. The reaction mixture was diluted with DCM (3 mL) and saturated sodium bicarbonate (1 mL) was added. The pH was checked (7-8) and the organic layer separated using a phase separator, then evaporated under reduced pressure. The resulting yellow-orange oil was dissolved in minimum volume of DCM and precipitated by addition of hexane and sonication. The solid was collected and washed with 9:1 hexane:ethyl acetate, dried by filtration and further in the vacuum oven to give the title compound as a cream solid;

LCMS: Rt 1.15 min; m/z 404.4 [M+H]+; Method: 2 minLowpHv01

Example 45

3-(6-Amino-5-(3-methyl-1,2,4-oxadiazol-5-yl)pyridin-3-yl)-N-isopropoxy-4-methylbenzenesulfonamide

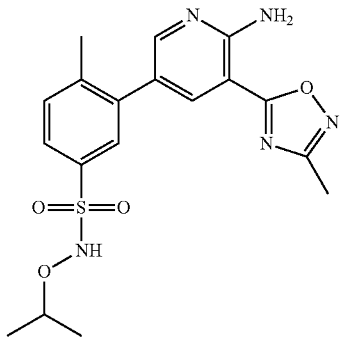 [SMILES: Cc1noc(-c2cc(-c3cc(S(=O)(=O)NOC(C)C)ccc3C)cnc2N)n1]

The title compound was prepared by a method analogous to the preparation of Example 44 starting from O-isopropylhydroxylamine (HCl salt);

LCMS: Rt 1.14 min; m/z 404.2 [M+H]+; Method: 2 minLowpHv01

Example 46

3-(6-Amino-5-(3-methyl-1,2,4-oxadiazol-5-yl)pyridin-3-yl)-N-methoxy-4-methylbenzenesulfonamide

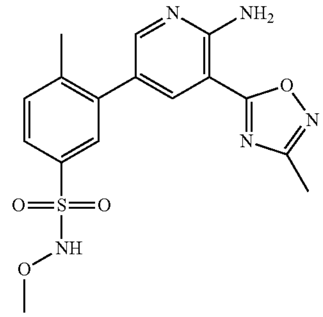 [SMILES: CONS(=O)(=O)c1ccc(C)c(-c2cnc(N)c(-c3nc(C)no3)c2)c1]

To a stirring solution of 3-(6-amino-5-(3-methyl-1,2,4-oxadiazol-5-yl)pyridin-3-yl)-4-methylbenzene-1-sulfonyl chloride (Intermediate E2) (50 mg, 0.125 mmol) in THF (1 mL) was added O-methylhydroxylamine (HCl salt) (25 mg, 0.299 mmol) and pyridine (0.1 mL, 1.236 mmol) and the resulting mixture stirred at room temperature overnight. The mixture was partitioned between DCM (2 mL) and saturated sodium bicarbonate (1 mL). The pH was checked pH (7-8) and the mixture was separated using a phase separator column. The organic phase was evaporated under reduced pressure and purification was carried out by by flash column chromatography (4 g silica, 0-10% methanol in DCM). The fractions containing product combined and evaporated under reduced pressure and triturated with DCM/ether, filtered and the solid dried in the vacuum oven to afford the title compound;

LCMS: Rt 1.03 min; m/z 376.4 [M+H]+; Method: 2 minLowpHv01

$^1$H NMR (400 MHz, DMSO-d6) δ 10.49 (1H, s), 8.36 (1H, d, J=2 Hz), 8.19 (1H, d, J=2 Hz), 7.75 (1H, d, J=8 Hz), 7.70 (1H, s), 7.64-7.57 (3H, m), 3.67 (3H, s), 2.47 (3H, s), 2.40 (3H, s).

Example 47

3-(6-Amino-5-(3-methyl-1,2,4-oxadiazol-5-yl)pyridin-3-yl)-N-(tert-butoxy)-4-methylbenzenesulfonamide

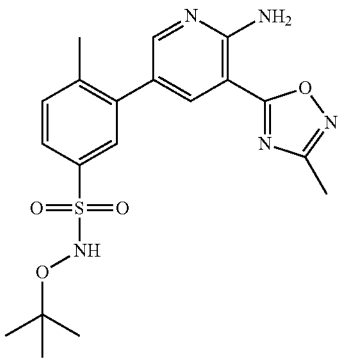 [SMILES: Cc1noc(-c2cc(-c3cc(S(=O)(=O)NOC(C)(C)C)ccc3C)cnc2N)n1]

The title compound was prepared by an analogous method to the synthesis of Example 46 using O-(tert-butyl)hydroxylamine (HCl salt);

LCMS: Rt 1.19 min; m/z 418.3 [M+H]+; Method: 2 minLowpHv01

Example 48

3-(6-Amino-5-(3-methyl-1,2,4-oxadiazol-5-yl)pyridin-3-yl)-4-methyl-N-(3,3,3-trifluoropropyl)benzenesulfonamide

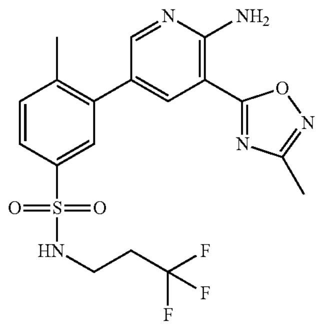 [SMILES: Cc1noc(-c2cc(-c3cc(S(=O)(=O)NCCC(F)(F)F)ccc3C)cnc2N)n1]

3,3,3-Trifluoropropan-1-amine (34 mg, 0.301 mmol) and pyridine (70 μL, 0.865 mmol) were added to a stirring mixture of 3-(6-amino-5-(3-methyl-1,2,4-oxadiazol-5-yl)pyridin-3-yl)-4-methylbenzene-1-sulfonyl chloride (Intermediate E2) in THF (1 mL) and the resulting mixture stirred for three days. The mixture was diluted with DCM and saturated sodium bicarbonate (1 mL) was added. The phases were separated and the organic phase evaporated under reduced pressure. The yellow sticky solid formed was triturated with hot ethyl acetate, which was then allowed to cool and the white solid collected, washing with further cold ethyl acetate to afford the title compound;

$^1$H NMR (400 MHz, DMSO-d6) δ 8.35 (1H, d, J=2 Hz), 8.18 (1H, d, J=2 Hz), 7.84 (1H, t, J=6 Hz), 7.71 (1H, dd, J=8, 2 Hz), 7.67 (1H, d, J=2 Hz), 7.62-7.55 (3H, m), 2.99 (2H, q, J=7 Hz), 2.47 (3H, s); overlapping with ~2.5-2.4 (2H, m); 2.38 (3H, s)

LCMS: Rt 1.13 min; m/z 442.2 [M+H]+; Method: 2 minLowpHv01

Example 49

3-(6-Amino-5-(3-methyl-1,2,4-oxadiazol-5-yl)pyridin-3-yl)-4-methyl-N-(tetrahydro-2H-pyran-4-yl)benzenesulfonamide

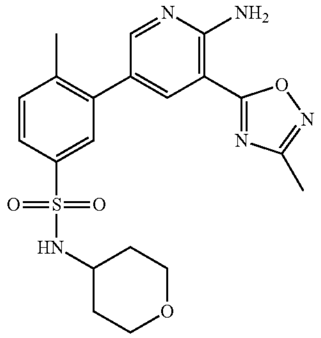 [SMILES: Cc1noc(-c2cc(-c3cc(S(=O)(=O)NC4CCOCC4)ccc3C)cnc2N)n1]

To a stirred mixture of 3-(6-amino-5-(3-methyl-1,2,4-oxadiazol-5-yl)pyridin-3-yl)-4-methylbenzene-1-sulfonyl chloride (Intermediate E2) (60 mg, 0.15 mmol) and tetrahydro-2H-pyran-4-amine (15.2 mg, 0.15 mmol) in dry THF (1 mL) at RT was added dry pyridine (70 μL, 0.865 mmol). The mixture was stirred at RT for 90 minutes, then diluted with 1M $Na_2CO_3$ (2 mL) and extracted with EtOAc (3×2 mL). The EtOAc extracts were combined, dried ($MgSO_4$), filtered and evaporated to give a yellow oil. The yellow oil was purified on 1 g Isolute® SCX-2 column, pre-washed with MeOH. After application of the compound, the column was eluted with MeOH then with 2M ammonia in MeOH to elute the product. Product-containing fractions were combined and evaporated to give the title compound;

LC-MS: Rt 0.98 mins; MS m/z 430.2 [M+H]+; Method 2 minLowpHv01

$^1$H NMR (400 MHz, DMSO-d6) δ 8.35 (1H, d), 8.17 (1H, d), 7.73 (3H, m), 7.60 (2H, br s), 7.54 (1H, d), 3.73 (2H, m), 3.25 (3H, m), 2.47 (3H, s), 2.38 (3H, s), 1.55 (2H, m), 1.37 (2H, m).

Example 50

3-(6-Amino-5-(3-methylisoxazol-5-yl)pyridin-3-yl)-N-((3-(hydroxymethyl)oxetan-3-yl)methyl)-4-methylbenzenesulfonamide

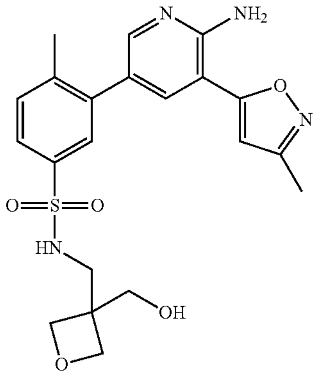 [SMILES: Cc1cc(-c2cc(-c3cc(S(=O)(=O)NCC4(CO)COC4)ccc3C)cnc2N)on1]

To a stirred mixture of 1-(aminomethyl)cyclopentanol (18 mg, 0.15 mmol) and DIPEA (131 μL, 0.75 mmol) in dry DMA (1 mL) at room temp was added 3-(6-amino-5-(3-methylisoxazol-5-yl)pyridin-3-yl)-4-methylbenzene-1-sulfonyl chloride (Intermediate E3) (60 mg, 0.15 mmol). The mixture was stirred at room temp overnight then diluted with DCM (2 mL) and washed with 1M $Na_2CO_3$ solution (2 mL). The DCM layer was recovered using a phase separator and evaporated to give a light brown solution of the product containing some DMA. The mixture was dissolved in the minimum amount of MeOH and purified using a 1 g Isolute® SCX-2 column previously equilibrated with MeOH. After elution with MeOH to remove DMA and any by-products, the product was eluted using 2M ammonia in MeOH. Evaporation under reduced pressure gave a off white solid which was triturated with EtOAc/isohexane and filtered to give the title compound as a colourless solid;

$^1$H NMR (400 MHz, DMSO-d6) δ 8.16 (1H, d), 7.92 (1H, d), 7.70 (2H, dd superimposed over br s), 7.67 (1H, d), 7.55 (1H, d), 6.90 (1H, s), 6.50 (2H, br s), 4.84 (1H, br t), 4.27 (4H, m), 3.53 (2H, d), 2.95 (2H, br s), 2.37 (3H, s), 2.30 (3H, s).

LC-MS: Rt 0.75 mins; MS m/z 445.2 [M+H]+; Method 2 minLowpHv01

Example 51

3-(6-Amino-5-(3-methyl-1,2,4-oxadiazol-5-yl)pyridin-3-yl)-N-((4-hydroxytetrahydro-2H-pyran-4-yl)methyl)-4-methylbenzenesulfonamide

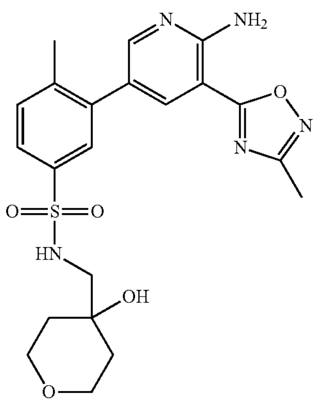 [SMILES: Cc1noc(-c2cc(-c3cc(S(=O)(=O)NCC4(O)CCOCC4)ccc3C)cnc2N)n1]

$^1$H NMR (400 MHz, DMSO-d6) δ 8.36 (1H, d), 8.19 (1H, d), 7.71 (2H, m), 7.60 (2H, br s), 7.54 (1H, d), 7.53 (1H, br), 4.45 (1H, s), 3.57 (4H, m), 2.69 (2H, br s), 2.47 (3H, s), 2.38 (3H, s), 1.55 (2H, m), 1.32 (2H, m).

LC-MS: Rt 0.93 mins; MS m/z 460.3 [M+H]+; Method 2 minLowpHv01

Example 52

3-(6-Amino-5-(3-methyl-1,2,4-oxadiazol-5-yl)pyridin-3-yl)-N-((3-(hydroxymethyl)oxetan-3-yl)methyl)-4-methylbenzenesulfonamide

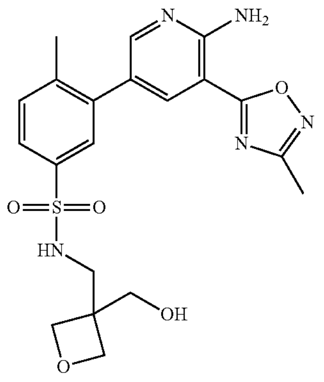 [SMILES: Cc1noc(-c2cc(-c3cc(S(=O)(=O)NCC4(CO)COC4)ccc3C)cnc2N)n1]

LC-MS: Rt 0.90 mins; MS m/z 446.2 [M+H]+; Method 2 minLowpHv01

$^1$H NMR (400 MHz, DMSO-d6) δ 8.37 (1H, d), 8.20 (1H, d), 7.72 (3H, m), 7.60 (2H, br s), 7.56 (1H, d), 4.85 (1H, br t), 4.28 (4H, m), 3.53 (2H, d), 2.96 (2H, br d), 2.47 (3H, s), 2.39 (3H, s).

Example 53

3-(6-Amino-5-(3-methylisoxazol-5-yl)pyridin-3-yl)-N-((1-hydroxycyclopentyl)methyl)-4-methylbenzenesulfonamide

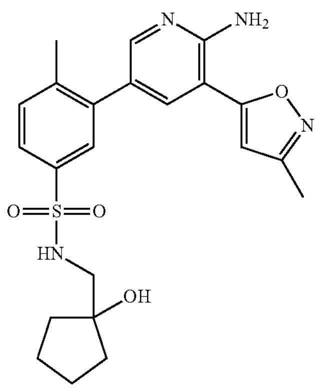 [SMILES: Cc1cc(-c2cc(-c3cc(S(=O)(=O)NCC4(O)CCCC4)ccc3C)cnc2N)on1]

To a stirred mixture of 1-(aminomethyl)cyclopentanol (18 mg, 0.15 mmol) and DIPEA (131 μL, 0.75 mmol) in dry DMA (1 mL) at room temp was added 3-(6-amino-5-(3-methylisoxazol-5-yl)pyridin-3-yl)-4-methylbenzene-1-sulfonyl chloride (Intermediate E3) (60 mg, 0.15 mmol). The mixture was stirred at room temp overnight whereupon LCMS showed clean conversion to the desired product with ca. 6% sulfonic acid by-product. The mixture was diluted with DCM (2 mL) and washed with 1M $Na_2CO_3$ solution (2 mL). The DCM layer was recovered using a phase separator and evaporated to give a light brown solution of the product containing some DMA. The mixture was dissolved in the minimum amount of MeOH and purified using a 1 g Isolute® SCX-2 column previously equilibrated with MeOH. After elution with MeOH to remove DMA and any by-products, the product was eluted using 2M ammonia in MeOH. Evaporation under reduced pressure gave a off white solid which was triturated with EtOAc/isohexane and filtered to give the title compound as a colourless solid;

$^1$H NMR (400 MHz, DMSO-d6) δ 8.16 (1H, d), 7.90 (1H, d), 7.68 (2H, m), 7.52 (1H, d), 7.46 (1H, br), 6.89 (1H, s), 6.49 (2H, br s), 4.31 (1H, s), 2.75 (2H, br s), 2.36 (3H, s), 2.30 (3H, s), 1.70-1.40 (8H, m). Contains 3% EtOAc.

LC-MS: Rt 0.91 mins; MS m/z 443.4 [M+H]+; Method 2 minLowpHv01

Example 54

3-(6-Amino-5-(3-methylisoxazol-5-yl)pyridin-3-yl)-N-((4-hydroxytetrahydro-2H-pyran-4-yl)methyl)-4-methylbenzenesulfonamide

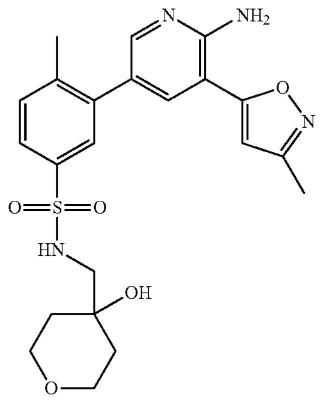 [SMILES: Cc1cc(-c2cc(-c3cc(S(=O)(=O)NCC4(O)CCOCC4)ccc3C)cnc2N)on1]

To a stirred mixture of 4-(aminomethyl)tetrahydro-2H-pyran-4-ol (20 mg, 0.15 mmol) and DIPEA (131 μL, 0.75 mmol) in dry DMA (1 mL) at RT was added 3-(6-amino-5-(3-methylisoxazol-5-yl)pyridin-3-yl)-4-methylbenzene-1-sulfonyl chloride (Intermediate E3) (60 mg, 0.15 mmol). The mixture was stirred at room temp overnight whereupon LCMS showed clean conversion to the desired product. The mixture was diluted with DCM (2 mL) and washed with 1M $Na_2CO_3$ solution (2 mL). The DCM layer was recovered using a phase separator and evaporated to give a light brown solution of the product containing some DMA. The mixture was dissolved in the minimum amount of MeOH and purified using a 1 g Isolute® SCX-2 column previously equilibrated with MeOH. After elution with MeOH to remove DMA and any by-products, the product was eluted using 2M ammonia in. Evaporation gave a off white solid which was triturated with EtOAc/isohexane and filtered to give the title compound as a colourless solid.

$^1$H NMR (400 MHz, DMSO-d6) δ 8.16 (1H, d), 7.91 (1H, d), 7.69 (2H, m), 7.53 (2H, d superimposed over br s), 6.90 (1H, s), 6.50 (2H, br s), 4.44 (1H, s), 3.57 (4H, m), 2.68 (2H, br s), 2.37 (3H, s), 2.31 (3H, s), 1.55 (2H, m), 1.32 (2H, m).

LC-MS: Rt 0.79 mins; MS m/z 459.2 [M+H]+; Method 2 minLowpHv01

Example 55 trans-3-(6-Amino-5-(3-methyl-1,2,4-oxadiazol-5-yl)pyridin-3-yl)-N-(3-hydroxycyclobutoxy)-4-methylbenzenesulfonamide

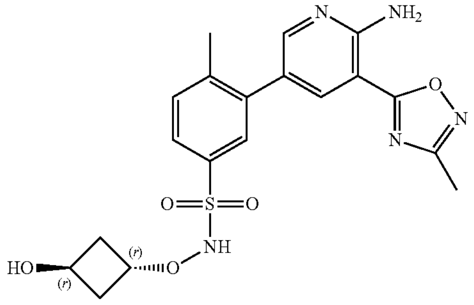

Step 1: 2-(3-((tert-butyldimethylsilyl)oxy)cyclobutoxy)isoindoline-1,3-dione

To a stirring solution of N-hydroxyphthalimide (0.806 g, 4.94 mmol) in THF (24.71 ml) at 0° C., 3-((tert-butyldimethylsilyl)oxy)cyclobutanol (1 g, 4.94 mmol) was added followed by triphenylphosphine (1.555 g, 5.93 mmol). Di-tert-butyl azodicarboxylate (1.138 g, 4.94 mmol) was added and the reaction mixture was allowed to warm up to RT overnight. The reaction mixture was diluted with EtOAc (100 ml), washed with water (100 ml), brine and dried over $MgSO_4$. The solvent was concentrated under reduced pressure. The triphenylphosphine oxide by-product was removed by adding $Et_2O$ (~10 ml) to obtain a solution and hexane was added until the solution became nearly cloudy. A solid crystallised upon standing and cooling to 0° C., the solid was collected by filtration and washed with hexane. The resulting mother liquor had further solid crystallised in it, when cooled again to 0° C. this solid was also removed by filtration. The solvent was concentrated under reduced pressure to give the title compound as a yellow oil;

$^1$H NMR (400 MHz, DMSO-d6) δ 7.82 (4H, s), 4.83 (1H, m), 4.62 (1H, m), 2.48-2.41 (2H, m) 2.14-2.07 (2H, m), 0.82 (9H, s), 0.00 (6H, s). $^1$H NMR indicates presence of triphenylphosphine oxide, material used in next step without further purification.

Step 2. O-(3-((tert-Butyldimethylsilyl)oxy)cyclobutyl)hydroxylamine

To a stirring solution of 2-(3-((tert-butyldimethylsilyl)oxy)cyclobutoxy)isoindoline-1,3-dione (impure product from step 1) (2 g, 5.76 mmol) in MeOH (28.8 ml), hydrazine hydrate (0.480 ml, 6.33 mmol) was added. The reaction mixture was stirred at RT for 5 hours, a precipitate was formed and the reaction mixture was filtered off. The solvent was concentrated under reduced pressure and the residue was titrated with DCM, the resulting gelatinous solid was filtered off to remove any residual phthalazine by-product. The filtrate was dried over $MgSO_4$ and the solvent was concentrated under reduced pressure. The resulting oil was dissolved in $Et_2O$ and hexane was added. A solid precipitate formed, the mixture was left to stand, the solvent was decanted away and concentrated under reduced pressure to give the title compound as a pale yellow oil;

$^1$H NMR (400 MHz, DMSO-d6) δ 4.40 (1H, m), 4.10 (1H, m), 2.24 (2H, m), 1.94 (2H, m), 0.84 (9H, s), 0.00 (6H, s). $NH_2$ signal not observed. $^1$H NMR indicates presence of triphenylphosphine oxide from previous step, material used in next step without further purification.

Step 3: 3-(6-Amino-5-(3-methyl-1,2,4-oxadiazol-5-yl)pyridin-3-yl)-N-(3-((tert-butyldimethylsilyl)oxy)cyclobutoxy)-4-methylbenzenesulfonamide To a stirring solution of O-(3-((tert-butyldimethylsilyl)oxy)cyclobutyl)hydroxylamine (impure product from step 2) (238 mg, 1.096 mmol) and DIPEA (239 μl, 1.371 mmol) in DMA (2741 μl) was added 3-(6-amino-5-(3-methyl-1,2,4-oxadiazol-5-yl)pyridin-3-yl)-4-methyl benzene-1-sulfonyl chloride (Intermediate E2) (200 mg, 0.548 mmol). The reaction mixture was stirred at RT overnight. The reaction mixture was added to water (50 ml) and extracted with EtOAc (50 ml). The organic phase was washed with brine (50 ml) and dried over $MgSO_4$. The solid was removed by filtration, washed with EtOAc and the solvent was concentrated under reduced pressure. The crude material was purified by flash column chromatography, eluting with 0-5% gradient of MeOH in DCM on a 4 g silica column, loading with DCM. Upon drying in a vacuum oven at 50° C. the resulting oil crystallised to give the title compound as a fine white solid;

LCMS: Rt 1.69 mins; MS m/z 546.7 [M+H]+; Method 2 minLowpH.

$^1$H NMR (400 MHz, $CDCl_3$) δ 8.28 (1H, d), 8.22 (1H, d), 7.82 (1H, dd), 7.76 (1H, d), 7.18 (1H, s), 4.67 (1H, m), 4.56-4.34* (1H, m), 2.49 (3H, s), 2.38 (3H, s), 2.36-2.31* (2H, m), 2.20-2.08* (2H, m), 0.82 (9H, s), −0.03 (6H, s). $NH_2$ and NH signal not observed. $^1$H NMR indicates presence of triphenylphosphine oxide from previous step and unreacted starting material amine, material used in next step without further purification.

*—signals for cyclobutane part of product believed to be in the region of the spectra stated but obscured by cyclobutane signals from starting material amine and other possible impurities.

Step 4: trans-3-(6-Amino-5-(3-methyl-1,2,4-oxadiazol-5-yl)pyridin-3-yl)-N-((1r,3r)-3-hydroxycyclobutoxy)-4-methylbenzenesulfonamide To a stirring solution of 3-(6-amino-5-(3-methyl-1,2,4-oxadiazol-5-yl)pyridin-3-yl)-N-(3-((tert-butyldimethylsilyl)oxy)cyclobutoxy)-4-methylbenzenesulfonamide (impure product from step 3) (15.8 mg, 0.029 mmol) in anhydrous THF (145 μl) was added TBAF, 1M in THF (43.4 μl, 0.043 mmol). The reaction mixture was stirred overnight at RT. The mixture was poured into water (20 ml) and extracted with EtOAc (20 ml). The organic layer was washed with brine (20 ml) and dried over $MgSO_4$. The solid was removed by filtration, washed with EtOAc and the solvent was concentrated under reduced pressure. The crude material was purified by flash column chromatography, eluting with a gradient 0-5% MeOH in DCM on a 4 g silica column, loading with DCM. The resulting oil was left to dry overnight in a vacuum oven at 50° C. to give a the title compound as a colourless oil;

LCMS: Rt 1.07 mins; MS m/z 432.6 [M+H]+; Method 2 minLowpH.

$^1$H NMR (400 MHz, $CDCl_3$) δ 8.15 (1H, d), 8.10 (1H, d), 7.77 (1H, dd), 7.67 (1H, d), 7.58 (1H, s), 7.41 (1H, d), 4.69 (1H, m), 4.44 (1H, m), 2.43 (3H, s), 2.41-2.36 (2H, m), 2.34 (3H, s), 2.12 (2H, m). $NH_2$ and NH signal not observed. NOESY NMR confirmed trans stereochemistry.

Example 56

3-(6-Amino-5-(3-methyl-1,2,4-oxadiazol-5-yl)pyridin-3-yl)-N-((3-hydroxyoxetan-3-yl)methyl)-4-methylbenzenesulfonamide

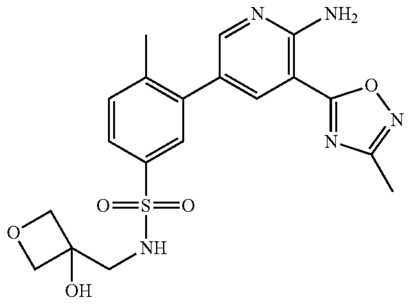 [SMILES: Cc1noc(-c2cc(-c3cc(S(=O)(=O)NCC4(O)COC4)ccc3C)cnc2N)n1]

Step 1: 3-(6-Amino-5-(3-methyl-1,2,4-oxadiazol-5-yl)pyridin-3-yl)-N-((3-hydroxyoxetan-3-yl)methyl)-4-methylbenzenesulfonamide To a stirring solution of 3-(aminomethyl)oxetan-3-ol (42.4 mg, 0.411 mmol) and DIPEA (120 μl, 0.685 mmol) in DMA (1371 μl) was added 3-(6-amino-5-(3-methyl-1,2,4-oxadiazol-5-yl)pyridin-3-yl)-4-methylbenzene-1-sulfonyl chloride (Intermediate E2) (100 mg, 0.274 mmol). The reaction mixture was stirred for 2 hours at RT. The reaction mixture was added to water (50 ml) and extracted with EtOAc (50 ml). The organic phase was washed with brine (50 ml) and dried over $MgSO_4$. The solid was removed by filtration, washed with EtOAc and the solvent was concentrated under reduced pressure. The crude material was purified by flash column chromatography, eluting with a gradient of 0-5% (2M $NH_3$ in MeOH) in DCM on a 12 g silica column, loading with DCM. The resulting oil was dried in a vacuum oven at 50° C. for 5 hours. Upon drying the oil crystallised to give the title compound as a yellow solid;

LCMS: Rt 0.98 mins; MS m/z 432.6 [M+H]+; Method 2 minLowpH.

$^1$H NMR (400 MHz, DMSO-d6) δ 8.37 (1H, d), 8.20 (1H, d), 7.77 (1H, t), 7.73 (2H, m), 7.60 (2H, br s), 7.55 (1H, m), 5.85 (1H, s), 4.37 (4H, q), 2.99 (2H, d), 2.47 (3H, s), 2.38 (3H, s).

Example 57

3-(6-Amino-5-(3-methyl-1,2,4-oxadiazol-5-yl)pyridin-3-yl)-4-methyl-N-((tetrahydrofuran-2-yl)methyl) benzenesulfonamide

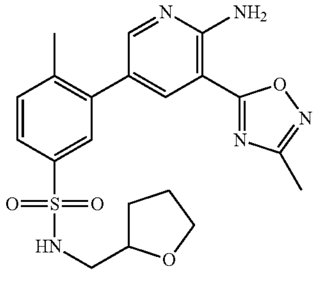 [SMILES: Cc1noc(-c2cc(-c3cc(S(=O)(=O)NCC4CCCO4)ccc3C)cnc2N)n1]

LCMS: Rt 1.05 min; m/z 430.2 [M+H]+; Method: 2 minLowpHv01

$^1$H NMR (400 MHz, DMSO-d6) δ 8.36 (1H, br. s.), 8.18 (1H, br. s.), 7.68 (3H, br. m), 7.64-7.50 (3H, m), 3.81 (1H, m), 3.68 (1H, m), 3.57 (1H, m), 2.80 (2H, br), 2.47 (3H, s overlapping with solvent peak), 2.38 (3H, s), 1.85 (1H, m), 1.77 (2H, m), 1.55 (1H, m).

Example 58

3-(6-Amino-5-(1-methyl-1H-pyrrol-3-yl)pyridin-3-yl)-N-(2-hydroxy-2-methylpropyl)-4-methylbenzenesulfonamide hydrochloride

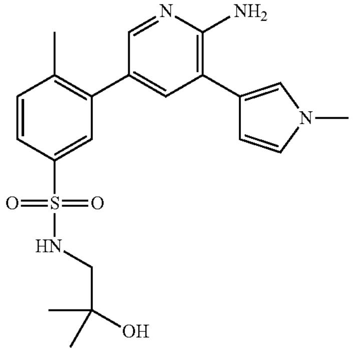

The title compound was prepared analogously to Example 4 using 1-methyl-3-(4,4,5,5-tetramethyl-1,3,2-dioxaborolan-2-yl)-1H-pyrrole and 3-(6-amino-5-bromopyridin-3-yl)-N-(2-hydroxy-2-methylpropyl)-4-methylbenzenesulfonamide (Intermediate EE1). The residue was taken up in 4M HCl in dioxane, the solvent removed under reduced pressure, ethanol (2 ml) added and the product recrystallised in the fridge overnight. After filtration a pale brown solid was obtained which was dried in the oven for 2 hours;

$^1$H NMR (400 MHz, DMSO-d6) δ 7.99 (1H, d), 7.91 (1H, d), 7.74 (1H, dd), 7.72 (1H, mult), 7.69 (2H, br), 7.56 (1H, d), 7.50 (1H, t), 7.26 (1H, mult), 6.92 (1H, mult), 6.43 (1H, mult), 3.68 (3H, s), 2.62 (2H, d), 2.37 (3H, s), 1.06 (6H, s).

Rt=0.72 mins MS m/z 415.3 [M+H]+; Method 2 minLowpHv01.

Example 59

3-(6-Amino-5-(2-methylthiazol-4-yl)pyridin-3-yl)-N-(2-hydroxy-2-methylpropyl)-4-methylbenzenesulfonamide

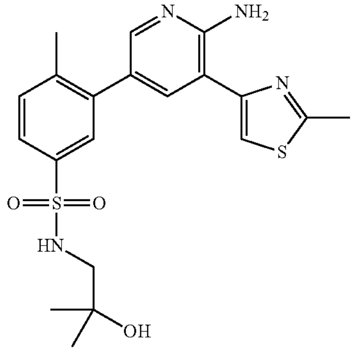 [SMILES: Cc1nc(-c2cc(-c3cc(S(=O)(=O)NCC(C)(C)O)ccc3C)cnc2N)cs1]

The title compound was prepared analogously to Example 4 using 2-methyl-4-(4,4,5,5-tetramethyl-1,3,2-dioxaborolan-2-yl)thiazole and 3-(6-amino-5-bromopyridin-3-yl)-N-(2-hydroxy-2-methylpropyl)-4-methylbenzenesulfonamide (Intermediate EE1);

$^1$H NMR (400 MHz, DMSO-d6) δ 8.00 (2H, mult), 7.97 (1H, d), 7.66 (2H, mult), 7.51 (1H, d), 7.44 (1H, t), 7.07 (2H, br), 4.39 (1H, s), 2.77 (3H, s), 2.61 (2H, d), 2.37 (3H, s), 1.06 (6H, s).

Example 60

3-(6-Amino-5-(4-methyl-1H-pyrazol-1-yl)pyridin-3-yl)-N-(2-hydroxy-2-methylpropyl)-4-methylbenzenesulfonamide

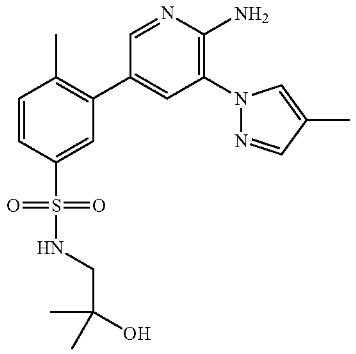 [SMILES: Cc1cnn(-c2cc(-c3cc(S(=O)(=O)NCC(C)(C)O)ccc3C)cnc2N)c1]

LCMS: Rt 0.89 min; m/z 416.6 [M+H]+; Method: 2 minLowpHv01

Example 61

3-(6-Amino-5-(1,5-dimethyl-1H-pyrazol-4-yl)pyridin-3-yl)-N-(2-hydroxy-2-methylpropyl)-4-methylbenzenesulfonamide

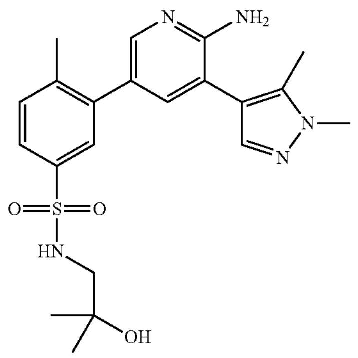 [SMILES: Cc1ccc(S(=O)(=O)NCC(C)(C)O)cc1-c1cnc(N)c(-c2cnn(C)c2C)c1]

The title compound was prepared analogously to Example 4 using 1,5-dimethyl-4-(4,4,5,5-tetramethyl-1,3,2-dioxaborolan-2-yl)-1H-pyrazole and 3-(6-amino-5-bromopyridin-3-yl)-N-(2-hydroxy-2-methylpropyl)-4-methylbenzenesulfonamide (Intermediate EE1);

LCMS: Rt 0.65 min; m/z 430.5 [M+H]+; Method: 2 minLowpHv01

$^1$H NMR (400 MHz, DMSO-d6) δ 7.94 (1H, d, J~2.4 Hz); 7.64-7.60 (2H, m); 7.50-7.41 (3H, m); 7.27 (1H, d, J~2.4 Hz); 5.74 (2H, s); 4.40 (1H, s); 3.78 (3H, s); 2.59 (2H, d); 2.37 (3H, s); 2.20 (3H, s); 1.04 (6H, s).

Example 62

3-(6-Amino-5-(5-methylisoxazol-4-yl)pyridin-3-yl)-N-(2-hydroxy-2-methylpropyl)-4-methylbenzenesulfonamide

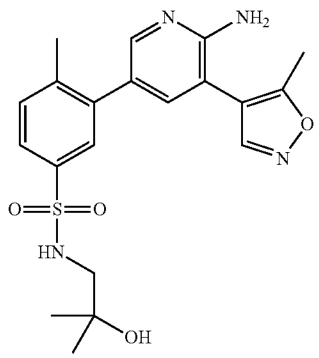 [SMILES: Cc1ccc(S(=O)(=O)NCC(C)(C)O)cc1-c1cnc(N)c(-c2cnoc2C)c1]

The title compound was prepared analogously to Example 4 using 5-methyl-4-(4,4,5,5-tetramethyl-1,3,2-dioxaborolan-2-yl)isoxazole and 3-(6-amino-5-bromopyridin-3-yl)-N-(2-hydroxy-2-methylpropyl)-4-methylbenzenesulfonamide (Intermediate EE1);

LCMS Rt=0.75 mins, MS m/z 417.3 [M+H]+; Method 2 minLowpHv01.

$^1$H NMR (400 MHz, DMSO-d6) δ 8.64 (1H, d), 8.02 (1H, d), 7.64 (2H, mult), 7.50 (1H, d), 7.42 (2H, mult), 6.03 (2H, br), 4.39 (1H, s), 2.61 (2H, d), 2.40 (3H, s), 2.37 (3H, s), 1.05 (6H, s).

Example 63

3-(6-Amino-5-(1-methyl-1H-1,2,3-triazol-4-yl)pyridin-3-yl)-N-(2-hydroxy-2-methylpropyl)-4-methylbenzenesulfonamide hydrochloride

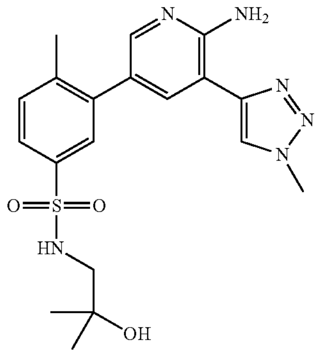 [SMILES: Cc1ccc(S(=O)(=O)NCC(C)(C)O)cc1-c1cnc(N)c(-c2cn(C)nn2)c1]

The title compound was prepared analogously to Example 35 using N-(2-hydroxy-2-methyl-propyl)-4-methyl-3-(4,4,5,5-tetramethyl[,3,2]dioxaborolan-2-yl)benzenesulfonamide (Intermediate B2), and 5-bromo-3-(1-methyl-1H-1,2,3-triazol-4-yl)pyridin-2-amine (minor isomer from Intermediate C11 preparation)

LCMS: Rt=0.65 mins MS m/z 417.5 [M+H]+; Method 2 minLowpHv01.

$^1$H NMR (400 MHz, DMSO-d6) δ 8.93 (1H, s), 8.45 (1H, br), 8.15 (1H, s), 7.77 (1H, d), 7.74 (1H, s), 7.59 (1H, d), 7.53 (1H, t), 4.17 (3H, s), 2.63 (2H, d), 2.38 (3H, s), 1.07 (6H, s).

Example 64

3-(6-Amino-5-(isoxazol-5-yl)pyridin-3-yl)-N-(2-hydroxy-2-methylpropyl)-4-methylbenzenesulfonamide

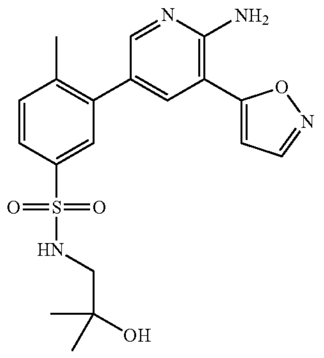 [SMILES: Cc1ccc(S(=O)(=O)NCC(C)(C)O)cc1-c1cnc(N)c(-c2ccno2)c1]

To a 25 mL round-bottomed flask was added N-(2-hydroxy-2-methylpropyl)-4-methyl-3-(4,4,5,5-tetramethyl-1,3,2-dioxaborolan-2-yl)benzenesulfonamide (Intermediate B2) (397 mg, 1.076 mmol), 5-bromo-3-(isoxazol-5-yl)pyridin-2-amine (prepared analogously to Intermediate C5) (246 mg, 1.025 mmol), [1,1'-bis(di-tert-butylphosphino)ferrocene]dichloropalladium(II) [Pd-118] (33.4 mg, 0.051 mmol) and $K_3PO_4$ (435 mg, 2.05 mmol) in dioxane (4 ml) and water (1 ml) to give a brown solution. The reaction mixture was heated at 100° C. for 1 hour. The resulting mixture was extracted into ethyl acetate, washed with water, brine, the organic layer separated, dried over $MgSO_4$, filtered and the solvent removed under reduced pressure. The crude product was loaded onto silica and purified by flash column chromatography eluting with TBME:MeOH (0-15%) on a 12 g silica cartridge. The product fractions were combined and the solvent removed under reduced pressure to yield a pale yellow residue. The product was further purified by mass directed prep chromatography using a Low pH gradient. The product fractions were combined, extracted into DCM, washed with sat. sodium bicarbonate solution, the organic layer separated, dried over $MgSO_4$, filtered and the solvent removed under reduced pressure to afford the title compound as a yellow solid.

LCMS: Rt=0.88 mins MS m/z 403.5 [M+H]+; Method 2 minLowpHv03.

$^1$H NMR (400 MHz, DMSO-d6) δ 8.71 (1H, d), 8.17 (1H, d), 7.97 (1H, d), 7.68 (2H, mult), 7.52 (1H, d), 7.44 (1H, t), 7.04 (1H, d), 6.55 (2H, br), 4.39 (1H, s), 2.61 (2H, d), 2.36 (3H, s), 1.06 (6H, s).

Example 65

3-(6-Amino-5-(3-(trifluoromethyl)isoxazol-5-yl)pyridin-3-yl)-N-(2-hydroxy-2-methylpropyl)-4-methylbenzenesulfonamide hydrochloride

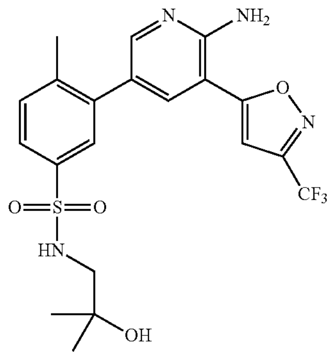 [SMILES: Cc1ccc(S(=O)(=O)NCC(C)(C)O)cc1-c1cnc(N)c(-c2cc(C(F)(F)F)no2)c1]

Step 1: 5-Bromo-3-((trimethylsilyl)ethynyl)pyridin-2-amine

To a mixture of 5-bromo-3-iodopyridin-2-amine (4.98 g, 16.66 mmol), copper(I) iodide (635 mg, 3.33 mmol), triethylamine (23.22 mL, 167 mmol) and $PdCl_2(PPh_3)_2$ (1.169 g, 1.666 mmol) in dry THF (70 mL) under nitrogen at 0° C. was added, dropwise, a solution of ethynyltrimethylsilane (1.8 g, 18.33 mmol) in dry THF (5 mL). The mixture was then allowed to warm to room temp and stirred at RT for 2 hours, whereupon TLC (isohexane/EtOAc (2:1)) showed complete consumption of the starting aminopyridine. The mixture was diluted with 5% citric acid (100 mL) and extracted with EtOAc (3×100 mL). The EtOAc extracts were combined, washed with sat. brine (100 mL), dried ($MgSO_4$), filtered and evaporated to give a dark brown oil. The crude product was purified by flash chromatography on 80 g silica gel using 0-30% EtOAc in isohexane over 12 min as eluent. The pure fractions were combined to the title compound;

LCMS: Rt=1.36 mins MS m/z 269.4 [M+H]+; Method 2 minLowpHv01.

Step 2: 5-Bromo-3-ethynylpyridin-2-amine

5-Bromo-3-((trimethylsilyl)ethynyl)pyridin-2-amine (2.36 g, 8.77 mmol) was suspended in MeOH (50 mL) and to this stirred mixture, $K_2CO_3$ (1.212 g, 8.77 mmol) was added. The mixture was stirred at room temp for 25 min. The reaction mixture was diluted with water (100 mL) and extracted with DCM (3×50 mL). The DCM layer was separated, washed with sat. brine (50 mL), dried ($MgSO_4$), filtered and evaporated to give the title compound as a brown solid;

LCMS: Rt=0.89 mins MS m/z 197.2/199.2 [M+H]+; Method 2 minLowpHv01.

Step 3: 2,2,2-Trifluoroacetaldehyde oxime

To a 50 mL round-bottomed flask was added 2,2,2-trifluoro-1-methoxyethanol (2 g, 15.38 mmol) and hydroxylamine hydrochloride (1.122 g, 16.15 mmol) in Methanol (3 mL) and water (7 ml) to give a colorless solution. To this at 0° C. was slowly added NaOH (50% solution, 3.69 g in 3.69 ml water). The reaction was warmed to RT with stirring for 18 hours. Hexane was added and the layers separated. The aqueous layer was acidified with 2M HCl (10 ml), extracted with ether (2×100 ml), the organic layers separated, combined, dried over $MgSO_4$, filtered and the solvent removed under reduced pressure to yield the title compound as a pale yellow oil;

$^1$H NMR (400 MHz, DMSO-d6) δ 8.70 (1H, s), 7.53 (1H, m).

Step 4: 2,2,2-Trifluoro-N-hydroxyacetimidoyl bromide

To a solution of 2,2,2-trifluoroacetaldehyde oxime (1.78 g, 6.81 mmol) in DMF (5 mL) was added N-bromosuccinimide (1.273 g, 7.15 mmol) dissolved in DMF (3 ml) over 5 mins. The reaction was allowed to stir at RT overnight. The reaction mixture was diluted with water, extracted into ether (2×50 ml), the organic layer separated, dried over MgSO4, filtered and the solvent removed under reduced pressure to yield the title compound as a yellow oil;

$^1$H NMR (400 MHz, DMSO-d6) δ 10.31 (1H, s).

Step 5: 5-Bromo-3-(3-(trifluoromethyl)isoxazol-5-yl)pyridin-2-amine

To a 50 mL round-bottomed flask was added 5-bromo-3-ethynylpyridin-2-amine (500 mg, 2.54 mmol), and sodium ascorbate (0.254 ml, 0.254 mmol) in t-BuOH (10 ml) and water (10 ml) under $N_2$ to give a brown suspension. To the mixture was added copper(II) sulfate pentahydrate (13 mg, 0.051 mmol, 2 mol %) and $NaHCO_3$ (923 mg, 10.99 mmol) followed by 2,2,2-trifluoro-N-hydroxyacetimidoyl bromide (1.239 g, 2.54 mmol) in 250 μl portions over 15 mins. The reaction mixture was stirred at RT for 1 hour. To the mixture was added 2,2,2-trifluoro-N-hydroxyacetimidoyl bromide (700 mg, 1.433 mmol) and stirring continued at RT overnight. The resulting mixture was extracted into ethyl acetate, washed with water, brine, the organic layer separated, dried over $MgSO_4$, filtered and the solvent removed under reduced pressure. The crude product was purified by flash column chromatography elution with iso hexane:ethyl acetate (0-20%) on a 12 g silica cartridge. The product fractions were combined and the solvent removed under reduced pressure to yield a yellow solid. The product was purified by a second flash column chromatography, elution with iso hexane:ethyl acetate (0-20%) on a 12 g silica cartridge. The fractions were combined and the solvent removed under reduced pressure to yield the title compound as a yellow solid;

LCMS: Rt=1.20 mins MS m/z 308.4 [M+H]+; Method 2 minLowpHv01.

Step 6: 3-(6-amino-5-(3-(trifluoromethyl)isoxazol-5-yl)pyridin-3-yl)-N-(2-hydroxy-2-methylpropyl)-4-methylbenzenesulfonamide hydrochloride To a 5 ml microwave vial was added N-(2-hydroxy-2-methyl-propyl)-4-methyl-3-(4,4,5,5-tetramethyl[1,3,2]dioxaborolan-2-yl)benzenesulfonamide (Intermediate B2), (171 mg, 0.464 mmol), 5-bromo-3-(3-(trifluoromethyl)isoxazol-5-yl)pyridin-2-amine (130 mg, 0.422 mmol) and $PdCl_2$(dppf).$CH_2Cl_2$ adduct (17.23 mg, 0.021 mmol) and sodium carbonate (0.528 ml, 1.055 mmol) in DME (4 ml). The reaction mixture was heated in the biotage initiator microwave at 120° C. for 2 hours. The resulting mixture was extracted into ethyl acetate, washed with water, brine, the organic layer separated, dried over $MgSO_4$, filtered and the solvent removed under reduced pressure. The crude product was loaded onto silica and purified by flash column chromatography elution with iso-hexane:ethyl acetate (0-100%) on a 12 g silica cartridge. The purified product was taken up in 4M HCl in dioxane (2 ml). After 5 min the volatiles were evaporated and the residue was recrystallised from hot EtOH to give a solid.

LCMS: Rt=1.06 mins MS m/z 471.4 [M+H]+; Method 2 minLowpHv01.

$^1$H NMR (400 MHz, DMSO-d6) δ 8.27 (1H, d), 8.15 (1H, d), 7.72 (1H, mult), 7.70 (1H, s), 7.67 (1H, s), 7.54 (1H, d), 7.47 (1H, t), 2.61 (2H, d), 2.37 (3H, s), 1.06 (6H, s).

$^{19}$F NMR (400 MHz, DMSO) δ −62.12.

Example 66

3-(6-Amino-5-(3-((dimethylamino)methyl)isoxazol-5-yl)pyridin-3-yl)-N-(2-hydroxy-2-methylpropyl)-4-methylbenzenesulfonamide

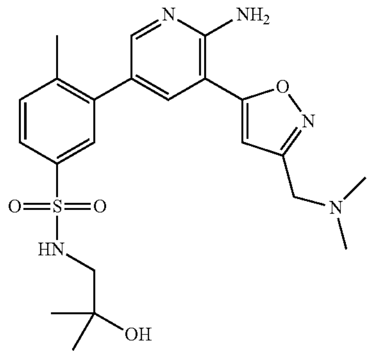 [SMILES: Cc1ccc(S(=O)(=O)NCC(C)(C)O)cc1-c1cnc(N)c(-c2cc(CN(C)C)no2)c1]

Step 1: (E)-2-Chloroacetaldehyde oxime, (Z)-2-chloroacetaldehyde oxime

To a 150 mL round-bottomed flask was added 2-chloroacetaldehyde (50% in water) (4.93 mL, 38.2 mmol) and sodium acetate (3.45 g, 42.0 mmol) in Water (50 mL) to give a colourless solution. To the mixture was slowly added hydroxylamine hydrochloride (2.92 g, 42 mmol) and the reaction stirred at RT for 1 hour. The resulting mixture was extracted with ether (2×100 ml), the organic layer separated, dried over $MgSO_4$, filtered and the solvent removed under reduced pressure to yield the title compound (as a mixture of Z and E isomers) as a clear oil;

$^1$H NMR (400 MHz, DMSO-d6) δ 11.96 (1H, s), 7.43 (1H, t), 4.26 (2H, d).

NMR indicated a 2:1 mix of the E and Z isomers. Only major isomer data given.

Step 2: 5-Bromo-3-(3-(chloromethyl)isoxazol-5-yl)pyridin-2-amine

To a 100 mL round-bottomed flask was added 5-bromo-3-ethynylpyridin-2-amine (Intermediate C15) (1.3 g, 6.60 mmol), and 2-chloroacetaldehyde oxime (mixture of isomers, from Step 1)(1.424 g, 9.90 mmol) in THF (15 ml) under N2 to give a brown solution. To the mixture at 0° C. was then added NaOCl (30 ml) dropwise over 90 mins. The mixture was stirred at RT overnight. The resulting mixture was extracted into DCM, washed with water, brine, the organic layer separated, dried over $MgSO_4$, filtered and the solvent removed under reduced pressure. The crude product was purified by flash column chromatography elution with iso-hexane:ethyl acetate (0-50%) on a 40 g silica cartridge. The product fractions were combined and the solvent removed under reduced pressure to yield the title compound as a brown oil;

LCMS: Rt=1.21 mins MS m/z 290.1 (Br isotope) [M+H]+; Method 2 minLowpHv03.

Step 3: 5-Bromo-3-(3-((dimethylamino)methyl)isoxazol-5-yl)pyridin-2-amine

To a 2-5 ml microwave vial was added 5-bromo-3-(3-(chloromethyl)isoxazol-5-yl)pyridin-2-amine (from step 2) (290 mg, 1.005 mmol) and dimethylamine (2M in THF) (1.005 mL, 2.010 mmol) in THF (3 mL) to give a brown solution. The reaction mixture was heated in a biotage initiator microwave at 80° C. for 2 hours. The crude mixture was extracted into ethyl acetate, washed with brine, the organic layer separated, dried over $MgSO_4$, filtered and the solvent removed under reduced pressure to yield the title compound as a brown oil;

LCMS: Rt=0.46 mins MS m/z 297.2 (Br isotope) [M+H]+; Method 2 minLowpHv03.

The material was taken on crude.

Step 4: 3-(6-Amino-5-(3-((dimethylamino)methyl)isoxazol-5-yl)pyridin-3-yl)-N-(2-hydroxy-2-methylpropyl)-4-methylbenzenesulfonamide To a 25 mL round-bottomed flask was added N-(2-hydroxy-2-methyl-propyl)-4-methyl-3-(4,4,5,5-tetramethyl[1,3,2]dioxaborolan-2-yl)benzenesulfonamide (Intermediate B2) (320 mg, 0.866 mmol), 5-bromo-3-(3-((dimethylamino)methyl)isoxazol-5-yl)pyridin-2-amine (from step 3) (245 mg, 0.824 mmol), [1,1'-bis(di-tert-butylphosphino)ferrocene]dichloropalladium(II) [Pd-118] (26.9 mg, 0.041 mmol) and $K_3PO_4$ (350 mg, 1.649 mmol) in dioxane (8 ml) and water (2 ml) to give a brown solution. The reaction mixture was heated at 100° C. for 1 hour. The resulting mixture was extracted into DCM, washed with water, brine, the organic layer separated, dried over $MgSO_4$, filtered and the solvent removed under reduced pressure. The crude product was purified by mass directed preparative chromatography using a low pH solvent gradient. The product fractions were combined, extracted into DCM, washed with sat. sodium bicarbonate solution, the organic layer separated, dried over $MgSO_4$, filtered and the solvent removed under reduced pressure to yield the title compound as a light brown solid;

LCMS: Rt=0.67 mins MS m/z 460.3 [M+H]+; Method 2 minLowpHv03.

$^1$H NMR (400 MHz, DMSO-d6) 8.16 (1H, d), 7.97 (1H, d), 7.68 (2H, mult), 7.52 (1H, d), 7.42 (1H, t), 7.00 (1H, s), 6.50 (2H, br), 4.37 (1H, s), 3.54 (2H, s), 2.63 (2H, d), 2.37 (3H, s), 2.23 (6H, s), 1.06 (6H, s).

Example 67

3-(6-Amino-5-(2-methyloxazol-5-yl)pyridin-3-yl)-N-((3-(hydroxymethyl)oxetan-3-yl)methyl)-4-methylbenzenesulfonamide

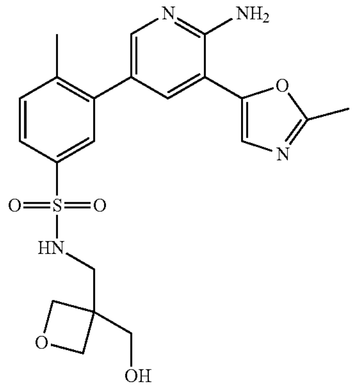 [SMILES: Cc1ncc(-c2cc(-c3cc(S(=O)(=O)NCC4(CO)COC4)ccc3C)cnc2N)o1]

Step 1: 3-Bromo-N-((3-(Hydroxymethyl)oxetan-3-yl)methyl)-4-methylbenzenesulfonamide 3-Bromo-4-methylbenzene-1-sulfonyl chloride (2.09, 7.76 mmol) in DMA (10 ml) was added dropwise to a stirred solution of (3-(aminomethyl)oxetan-3-yl)methanol (1.0 g, 8.54 mmol) and DIPEA (4.0 ml, 5.3 mmol) in DMA (5 ml) at 00° C. The reaction was allowed to warm to RT. After 15 min the reaction mixture was diluted with EtOAc and washed with aq. $NaHCO_3$ followed by brine. The organic extract was separated, dried over $MgSO_4$ and the solvent removed to give an oil which solidified to an oily solid. Trituation with EtOAc and diethyl ether gave a white crystalline solid which was collected by filtration. The solvent was removed from the filtrate to give an oil which was purified by chromatography on silica, eluting with EtOAc to give more white crystalline solid;

LCMS: Rt 1.01 mins; MS m/z 352.5 [M+H]+; Method 2 minLowpHv03

$^1$H NMR (400 MHz, DMSO-d6) δ 7.98 (1H, s), 7.85 (1H, t), 7.73 (1H, d), 7.61 (1H, d), 4.86 (1H, t), 4.27 (4H, m), 3.52 (2H, d), 2.93 (2H, d), 2.42 (3H, s).

Step 2: N-((3-(Hydroxymethyl)oxetan-3-yl)methyl)-4-methyl-3-(4,4,5,5-tetramethyl-1,3,2-dioxaborolan-2-yl)benzenesulfonamide Bis(pinacolato)diboron (1.2 g, 4.71 mmol) was added to a stirred mixture of 3-bromo-N-((3-(hydroxymethyl)oxetan-3-yl)methyl)-4-methylbenzenesulfonamide (Step 1) (1.5 g, 4.28 mmol), $PdCl_2$(dppf).DCM adduct (0.175 g, 0.21 mmol) and potassium acetate (0.63 g, 6.42 mmol) in dry DME (20 ml). The mixture was de-gassed several times under nitrogen then heated with stirring under nitrogen at 50° C. for 18 hours followed by 90° C. for 3 hours. The solvent was removed and the residue was diluted with EtOAc and washed with aq. $NaHCO_3$ followed by brine. The organic extract was separated, dried over $MgSO_4$, and the solvent removed under reduced pressure to give an oil. Chromatography on silica, eluting with EtOAc, followed by triturating of the resulting oil with diethyl ether gave the product as a white crystalline solid;

LCMS: Rt 1.25 mins; MS m/z 398.6 [M+H]+; Method 2 minLowpHv03

$^1$H NMR (400 MHz, $CDCl_3$) δ 8.24 (1H, s), 7.80 (1H, d), 7.35 (1H, d), 5.03 (1H, br s), 4.39 (4H, m), 4.00 (2H, s), 3.35 (2H, d), 2.62 (3H, s), 2.35 (1H, br s), 1.38 (12H, s).

Step 3: 3-(6-Amino-5-(2-methyloxazol-5-yl)pyridin-3-yl)-N-((3-(hydroxymethyl)oxetan-3-yl)methyl)-4-methylbenzenesulfonamide To a mixture of 5-bromo-3-(2-methyl-oxazol-5-yl)-pyridin-2-ylamine (intermediate C4) (100 mg, 0.394 mmol) in DME was added N-((3-(hydroxymethyl)oxetan-3-yl)methyl)-4-methyl-3-(4,4,5,5-tetramethyl-1,3,2-dioxaborolan-2-yl)benzenesulfonamide (step 2) (156 mg, 0.394 mmol), $Na_2CO_3$ (aq. 2.0M) (590 μl, 1.181 mmol) and bis(triphenylphosphine)palladium(II) chloride (13.81 mg, 0.020 mmol). The reaction was microwaved at 120° C. for 1 hour. The resulting mixture was added to water (50 ml) and the product was extracted into EtOAc (50 ml). The organic phase was washed with brine, dried over $MgSO_4$ and concentrated to dryness. The crude product was purified by flash column chromatography, eluting with 0-10% gradient of MeOH in DCM on a 4 g Si-column to afford the title compound;

LCMS: Rt=0.75 mins; MS m/z 445.5 [M+H]+; Method 2 minLowpHv03

$^1$H NMR (400 MHz, DMSO-d6) δ 8.05 (1H, d), 7.74 (1H, d), 7.73 (1H, brs), 7.70 (1H, dd), 7.65 (1H, d), 7.54 (1H, d), 7.50 (1H, s), 6.30 (2H, s), 4.84 (1H, br t), 4.27 (4H, q), 3.52 (2H, d), 2.95 (2H, br m), 2.48 (3H, s), 2.36 (3H, s).

Example 68

3-(6-Amino-5-(2-methylthiazol-5-yl)pyridin-3-yl)-N-((3-(hydroxymethyl)oxetan-3-yl)methyl)-4-methylbenzenesulfonamide

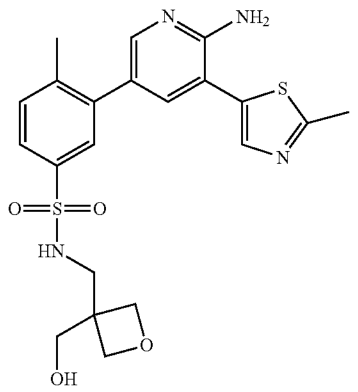 [SMILES: Cc1ncc(-c2cc(-c3cc(S(=O)(=O)NCC4(CO)COC4)ccc3C)cnc2N)s1]

To a mixture of 5-bromo-3-(2-methylthiazol-5-yl)pyridin-2-amine (Intermediate C6) (100 mg, 0.370 mmol) in DME (1851 μl) was added N-((3-(hydroxymethyl)oxetan-3-yl)methyl)-4-methyl-3-(4,4,5,5-tetramethyl-1,3,2-dioxaborolan-2-yl)benzenesulfonamide (Example 67, step 2) (147 mg, 0.370 mmol), $Na_2CO_3$ (aq. 2.0M) (555 μl, 1.110 mmol) and bis(triphenylphosphine) palladium(II) chloride (12.99 mg, 0.019 mmol). The reaction mixture was microwaved at 120° C. for 1 hour. The resulting mixture was added to water (50 ml) and the product extracted into EtOAc (50 ml). The organic phase was washed with brine, dried over $MgSO_4$ and concentrated to dryness. The crude product was purified by flash column chromatography, eluting with 0-10% gradient of MeOH in DCM on a 4 g Si-column to afford the title compound;

LCMS: Rt=0.75 mins; MS m/z 461.5 [M+H]+; Method 2 minLowpHv03

$^1$H NMR (400 MHz, DMSO-d6) δ 8.04 (1H, d), 7.83 (1H, s), 7.71 (1H, br m), 7.68 (1H, dd), 7.64 (1H, d), 7.52 (2H, m), 6.14 (2H, s), 4.84 (1H, br t), 4.27 (4H, q), 3.52 (2H, d), 2.94 (2H, d), 2.69 (3H, s), 2.37 (3H, s).

Example 69

3-(6-Amino-5-(2-methyloxazol-5-yl)pyridin-3-yl)-4-methyl-N-((3-methyloxetan-3-yl)methyl)benzenesulfonamide

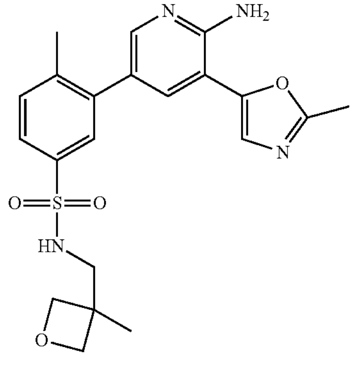 [SMILES: Cc1ncc(-c2cc(-c3cc(S(=O)(=O)NCC4(C)COC4)ccc3C)cnc2N)o1]

To a mixture of 5-bromo-3-(2-methyl-oxazol-5-yl)-pyridin-2-ylamine (Intermediate C4) (100 mg, 0.394 mmol) in DME was added 4-methyl-N-(3-methyl-oxetan-3-ylmethyl)-3-(4,4,5,5)tetramethyl-[1,3,2] dioxaborolan-2-yl)-benzenesulfonamide (Intermediate B7) (150 mg, 0.394 mmol), $Na_2CO_3$ (aq. 2.0M) (590 μl, 1.181 mmol) and bis(triphenylphosphine)palladium(II) chloride (13.81 mg, 0.020 mmol). The mixture was microwaved at 120° C. for 1 hour. The resulting mixture was added to water (50 ml) and the product extracted into EtOAc (50 ml). The organic phase was washed with brine, dried over $MgSO_4$ and concentrated to dryness. The crude product was purified by flash column chromatography, eluting with 0-10% gradient of MeOH in DCM on a 4 g Si-column to afford the title compound;

LCMS: Rt=0.85 mins; MS m/z 429.4 [M+H]+; Method 2 minLowpHv03

$^1$H NMR (400 MHz, DMSO-d6) δ 8.05 (1H, d), 7.78 (1H, t), 7.74 (1H, d), 7.70 (1H, dd), 7.65 (1H, d), 7.54 (1H, d), 7.50 (1H, s), 6.30 (2H, s), 4.31 (2H, d), 4.16 (2H, d), 2.92 (2H, d), 2.48 (3H, s), 2.36 (3H, s), 1.20 (3H, s).

Example 70

3-(6-Amino-5-(3-(difluoromethyl)-1,2,4-oxadiazol-5-yl)pyridin-3-yl)-N-((1r,4r)-4-hydroxycyclohexyl)-4-methylbenzenesulfonamide hydrochloride

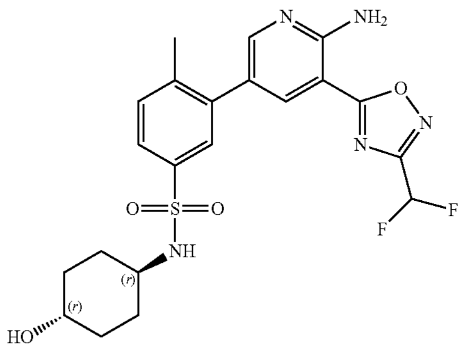 [SMILES: Cc1ccc(S(=O)(=O)N[C@H]2CC[C@H](O)CC2)cc1-c1cnc(N)c(-c2nc(C(F)F)no2)c1]

Step 1: (Z)-2,2-Difluoro-N'-hydroxyacetimidamide

To a stirring solution of 2,2-difluoroacetonitrile (1 g, 12.98 mmol) in EtOH (2.5 ml), under $N_2$, was added hydroxylamine (50% wt in water) (1.029 g, 15.58 mmol) dropwise over 30 mins and the mixture was stirred for 24 hours at RT. The resulting mixture was concentrated under reduced pressure and added to water (70 ml). The product was extracted into EtOAc (3×60 ml) and the combined extracts were washed with, brine, dried over $MgSO_4$ and concentrated to dryness to afford the title compound;

$^1$H NMR (400 MHz, DMSO-d6) δ 9.92 (1H, s), 6.10 (1H, t), 5.89 (1H, br s).

Step 2: 5-Bromo-3-(3-(difluoromethyl)-1,2,4-oxadiazol-5-yl)pyridin-2-amine

To a stirring suspension of 2-amino-5-bromonicotinic acid (500 mg, 2.304 mmol) in DCM (11.5 ml) was added 1-chloro-N,N,2-trimethyl-1-propenylamine (Ghosez's reagent) (0.366 ml, 2.76 mmol). The reaction mixture was left stirring for 1.5 hrs. 2,2-Difluoro-N'-hydroxyacetimidamide (step 1) (507 mg, 4.61 mmol) was added followed by DIPEA (0.805 ml, 4.61 mmol) and the mixture was stirred overnight. T3P® (4.04 ml, 6.91 mmol) was added and the mixture was heated using microwave radiation for 135 mins at 100° C. The mixture was added to water (100 ml) and the product extracted into EtOAc (2×90 ml). The organic phase was washed with brine, dried over $MgSO_4$ and concentrated to dryness. The crude product was purified by flash column chromatography, eluting with 0-10% gradient of (2M $NH_3$ in MeOH) in DCM on a 24 g Si-column to afford the title compound;

LCMS: Rt=1.11 mins; MS m/z 291.4 [M+H]+; Method 2 minLowpHv01

$^1$H NMR (400 MHz, DMSO-d6) δ 8.43 (1H, d), 8.39 (1H, d), 7.55 (2H, br s), 7.47 (1H, t).

Step 3: 3-(6-Amino-5-(3-(difluoromethyl)-1,2,4-oxadiazol-5-yl)pyridin-3-yl)-N-((1r,4r)-4-hydroxy-cyclohexyl)-4-methylbenzenesulfonamide hydrochloride To a solution of trans-N-(4-hydroxy-cyclohexyl)-4-methyl-3-(4,4,5,5-tetramethyl-[1,3,2]dioxaborolan-2-yl)-benzenesulfonamide (Intermediate B5) (163 mg, 0.412 mmol) in DME (1718 μl) was added 5-bromo-3-(3-(difluoromethyl)-1,2,4-oxadiazol-5-yl)pyridin-2-amine (step 2) (100 mg, 0.344 mmol), bis(triphenylphosphine)palladium (II) chloride (12.06 mg, 0.017 mmol) and $Na_2CO_3$ (aq. 2.0M) (515 μl, 1.031 mmol). The mixture was microwaved at 120° C. for 90 mins. A further 0.05 eq of bis(triphenylphosphine)palladium(II) chloride (12.06 mg, 0.017 mmol) was added and reaction was microwaved at 120° C. for 60 mins. The resulting mixture was added to water (50 ml) and the product extracted into EtOAc (2×50 ml). The organic phase was washed with brine, dried over $MgSO_4$ and Si-TMT resin to remove Pd. The solids were removed by filtration, washed with EtOAc and the filtrate was concentrated to dryness. The crude product was purified by flash column chromatography, eluting with 0-10% gradient of (2M $NH_3$ in MeOH) in DCM on a 12 g Si-column, loading with DCM. The resulting oil was dissolved in MeOH (1 ml) and 4M HCl in dioxane (1 ml) was added. The mixture was concentrated to dryness and the resulting gum recrystallized from hot EtOH (~2 ml). Upon cooling a solid crystallized which was collected by filtration and dried to afford the title compound;

LCMS: Rt=1.00 mins; MS m/z 480.4 [M+H]+; Method 2 minLowpHv01

$^1$H NMR (400 MHz, DMSO-d6) δ 8.42 (1H, d), 8.30 (1H, d), 7.80-7.67 (2H, br m), 7.59 (1H, d), 7.54 (1H, d), 7.49 (1H, t), 3.29 (1H, m), 2.93 (1H, m), 2.38 (3H, s), 1.67 (4H, dd), 1.13 (4H, m).

Example 71

3-(6-Amino-5-(3-(difluoromethyl)-1,2,4-oxadiazol-5-yl)pyridin-3-yl)-N-(2-hydroxy-2-methylpropyl)-4-methylbenzenesulfonamide hydrochloride

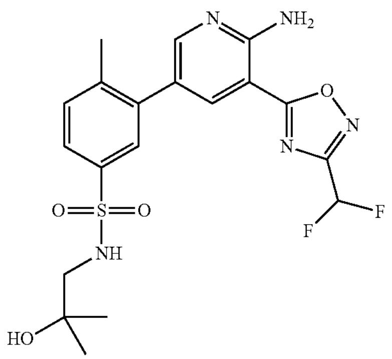 [SMILES: Cc1ccc(S(=O)(=O)NCC(C)(C)O)cc1-c1cnc(N)c(-c2nc(C(F)F)no2)c1]

To a solution of N-(2-hydroxy-2-methyl-propyl)-4-methyl-3-(4,4,5,5-tetramethyl[1,3,2]dioxaborolan-2-yl)benzenesulfonamide (Intermediate B2) (152 mg, 0.412 mmol) in DME (1.7 ml) was added 5-bromo-3-(3-(difluoromethyl)-1,2,4-oxadiazol-5-yl)pyridin-2-amine (Example 70, step 2) (100 mg, 0.344 mmol), bis(triphenylphosphine)palladium (II) chloride (12.06 mg, 0.017 mmol) and $Na_2CO_3$ (aq. 2.0M) (515 μl, 1.031 mmol). The mixture was microwaved at 120° C. for 90 mins. A further 0.05 eq of bis(triphenylphosphine)palladium(II) chloride (12.06 mg, 0.017 mmol) was added and reaction was microwaved at 120° C. for 60 mins. The mixture was added to water (50 ml) and the product extracted into EtOAc (2×50 ml). The organic phase was washed with brine, dried over $MgSO_4$ and Si-TMT resin to remove Pd. The solids were removed by filtration, washed with EtOAc and the filtrate concentrated under reduced pressure. The crude product was purified by flash column chromatography, eluting with 0-10% gradient of (2M $NH_3$ in MeOH) in DCM on a 12 g Si-column. The resulting oil was dissolved MeOH (1 ml) and 4M HCl in dioxane (1 ml) was added. The mixture was concentrated to dryness and the resulting gum recrystallized from hot EtOAc:EtOH (2:1) (~4 ml). Upon cooling a solid crystallized which was collected by filtration and dried to afford the title compound;

LCMS: Rt=1.04 mins; MS m/z 454.6 [M+H]+; Method 2 minLowpHv01

1H NMR (400 MHz, DMSO-d6) δ 8.44 (1H, d), 8.31 (1H, d), 7.75-7.69 (2H, br m), 7.55 (1H, d), 7.49 (1H, t), 7.47 (1H, d), 6.29-5.29 (3H, br s), 2.63 (2H, d), 2.38 (3H, s), 1.07 (6H, s).

Example 72

3-(6-Amino-5-(3-methyl-1,2,4-oxadiazol-5-yl)pyridin-3-yl)-4-methyl-N-(6-methylpyridin-2-yl)benzenesulfonamide

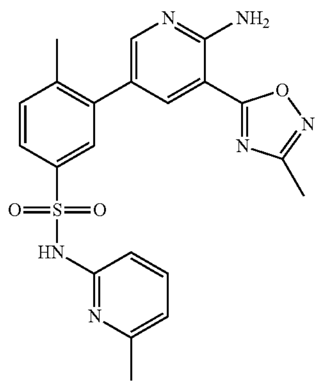 [SMILES: Cc1cccc(NS(=O)(=O)c2ccc(C)c(-c3cnc(N)c(-c4nc(C)no4)c3)c2)n1]

To a solution of 4-methyl-N-(6-methylpyridin-2-yl)-3-(4,4,5,5-tetramethyl-1,3,2-dioxaborolan-2-yl)benzenesulfonamide (Intermediate B6) (152 mg, 0.392 mmol) in DME (1960 μl) was added 5-bromo-3-[1,2,4]oxadiazol-5-yl-pyridin-2-ylamine (Intermediate C3) (100 mg, 0.392 mmol), bis(triphenylphosphine)palladium(II) chloride (13.76 mg, 0.020 mmol) and $Na_2CO_3$ (aq. 2.0M) (588 μl, 1.176 mmol). The reaction mixture was microwaved at 120° C. for 90 mins. The resulting mixture was added to water (50 ml) and product extracted into EtOAc (2×50 ml). The organic phase was washed with brine, dried over $MgSO_4$ and Si-TMT resin was added to remove Pd. The solids were removed by filtration, washed with EtOAc and the filtrate concentrated to dryness. The crude product was purified by flash column chromatography, eluting with 0-10% gradient of (2M $NH_3$ in MeOH) in DCM on a 12 g Si-column, loading with DCM. The resulting oil was dissolved in MeOH (1 ml) and 4M HCl in dioxane was added (1 ml). The mixture was concentrated to dryness, then triturated in $Et_2O$ and dried. The product was loaded onto 10 g cartridge of Isolute® SCX-2, flushed with MeOH (50 ml) and then eluted with 2M $NH_3$ in MeOH (50 ml). The ammonia phase was concentrated to dryness to afford the title compound;

LCMS: Rt=0.99 mins; MS m/z 437.6 [M+H]+; Method 2 minLowpHv01

$^1$H NMR (400 MHz, DMSO-d6) δ 8.30 (1H, d), 8.11 (1H, d), 7.74 (1H, m), 7.63 (1H, t), 7.58 (2H, s), 7.47 (1H, d), 7.07 (1H, d), 6.69 (1H, d), 2.47 (3H, s), 2.33 (3H, s), 2.31 (3H, s).

Example 73

3-(6-Amino-5-(3-methylisoxazol-5-yl)pyridin-3-yl)-N-(2-hydroxyethyl)-4-methylbenzenesulfonamide

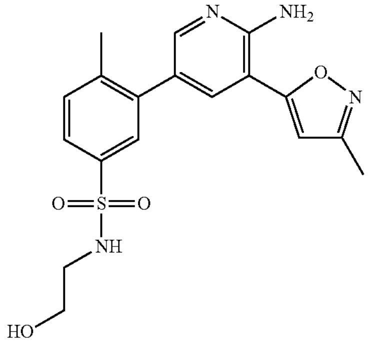 [SMILES: Cc1cc(-c2cc(-c3cc(S(=O)(=O)NCCO)ccc3C)cnc2N)on1]

To a stirring solution of 3-(6-amino-5-(3-methylisoxazol-5-yl)pyridin-3-yl)-4-methylbenzene-1-sulfonyl chloride (Intermediate E3) (50 mg, 0.125 mmol) in DMA (625 μl), under $N_2$, was added 2-aminoethanol (11.28 μl, 0.187 mmol) & DIPEA (87 μl, 0.5 mmol). The reaction mixture was stirred for 4 hours at RT. The resulting mixture was added to water (10 ml) and the product extracted into EtOAc (15 ml). The organic extract was collected via pipetting EtOAc into a phase separator and concentrating to dryness. The crude product was purified by flash column chromatography, eluting with 0-10% gradient of (2.0M $NH_3$ in MeOH) in DCM. The resulting solid was triturated in $Et_2O$ and dried to afford the title compound.

LCMS: Rt=0.79 mins; MS m/z 389.2 [M+H]+; Method 2 minLowpHv01

$^1$H NMR (400 MHz, DMSO-d6) δ 8.16 (1H, d), 7.91 (1H, d), 7.68 (1H, d), 7.65 (1H, s), 7.56 (1H, s), 7.53 (1H, d), 6.90 (1H, s), 6.50 (2H, d), 3.68 (1H, t), 3.38 (2H, q), 2.80 (2H, t), 2.37 (3H, s), 2.30 (3H, s).

Example 74

3-(6-Amino-5-(2-methylthiazol-5-yl)pyridin-3-yl)-4-methylbenzenesulfonamide

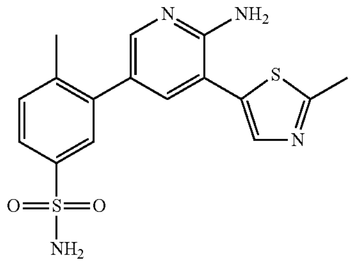 [SMILES: Cc1ncc(-c2cc(-c3cc(S(N)(=O)=O)ccc3C)cnc2N)s1]

Step 1: 4-methyl-3-(4,4,5,5-tetramethyl-1,3,2-dioxaborolan-2-yl)benzenesulfonamide A stirring mixture of 3-bromo-4-methylbenzenesulfonamide (5.7 g, 22.79 mmol), KOAc (3.35 g, 34.2 mmol), $PdCl_2(dppf).CH_2Cl_2$ adduct (0.931 g, 1.139 mmol), and 4,4,4',4',5,5,5',5'-octamethyl-2,2'-bi(1,3,2-dioxaborolane) (5.79 g, 22.79 mmol) in DME (114 ml), under $N_2$, was heated at 90° C. for overnight. The mixture was added to water (200 ml) and the product extracted into EtOAc (2×200 ml). The organic extracts were combined, washed with brine, dried over $MgSO_4$. The solids were removed by filtration, washed with EtOAc and the filtrate concentrated under reduced pressure. The crude black oil was diluted with DCM (20 ml) and left to stand. The resulting precipitate was collected by filtration and washed with minimal DCM to remove any brown colouration to afford the title compound. Upon cooling and standing more precipitate formed from the mother liquors. This was collected and washed with DCM to give batch two of the title compound;

LCMS: Rt=1.22 mins; MS m/z 298.2 [M+H]+; Method 2 minLowpHv01

$^1$H NMR (400 MHz, DMSO-d6) δ 8.09 (1H, d), 7.78 (1H, d), 7.39 (1H, d), 7.28 (2H, s), 2.53 (3H, s), 1.33 (12H, s).

Step 2: 3-(6-Amino-5-(2-methylthiazol-5-yl)pyridin-3-yl)-4-methylbenzenesulfonamide To a mixture of 5-bromo-3-(2-methyl-thiazol-5-yl)-pyridin-2-ylamine (Intermediate C6) (100 mg, 0.370 mmol) in DME (3702 μl) was added for 4-methyl-3-(4,4,5,5-tetramethyl-1,3,2-dioxaborolan-2-yl)benzenesulfonamide (step 1) (110 mg, 0.370 mmol), $Na_2CO_3$ (aq. 2.0M) (555 μl, 1.110 mmol) and bis(triphenylphosphine)palladium(II) chloride (12.99 mg, 0.019 mmol). The mixture was microwaved at 120° C. for 1 hour. The resulting mixture was added to water (100 ml), and product extracted into EtOAc (2×80 ml). The organic extract was washed with brine, dried over $MgSO_4$ and Si-TMT resing was added. The solids were removed by filtration and the filtrate was concentrated under reduced pressure. The crude product was purified by adding MeOH (5 ml) to the resulting clear oil. Upon heating the oil dissolved, the solution was allowed to cool to RT and the resulting solid was collected by filtration, washed with MeOH and dried to afford the title compound;

LCMS: Rt=0.68 mins; MS m/z 361.4 [M+H]+; Method 2 minLowpHv03

$^1$H NMR (400 MHz, DMSO-d6) δ 8.02 (1H, d), 7.83 (1H, d), 7.68 (1H, s), 7.66 (1H, s), 7.48 (2H, m), 7.28 (2H, s), 6.13 (2H, s), 2.69 (3H, s), 2.35 (3H, s).

Example 75

3-(6-Amino-5-(3-methyl-1,2,4-oxadiazol-5-yl)pyridin-3-yl)-4-methylbenzenesulfonamide

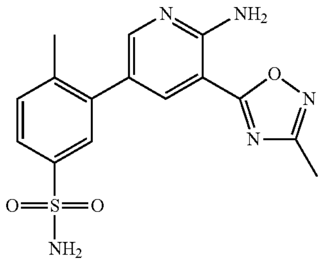 [SMILES: Cc1noc(-c2cc(-c3cc(S(N)(=O)=O)ccc3C)cnc2N)n1]

To a solution of 4-methyl-3-(4,4,5,5-tetramethyl-1,3,2-dioxaborolan-2-yl)benzenesulfonamide (Example 74, step 1) (140 mg, 0.470 mmol) in DME (2 ml) was added 5-bromo-3-[1,2,4]oxadiazol-5-yl-pyridin-2-ylamine (Intermediate C3) (100 mg, 0.392 mmol), bis(triphenylphosphine)palladium(II) chloride (13.76 mg, 0.020 mmol) and $Na_2CO_3$ (aq. 2.0M) (588 μl, 1.176 mmol). The reaction mixture was microwaved at 120° C. for 30 mins. The mixture was added to water (50 ml) and the product extracted into EtOAc (2×50 ml). The organic extract was washed with brine, dried over $MgSO_4$ and Si-TMT resin to remove Pd. The solids were removed by filtration, washed with EtOAc and the filtrate concentrated under reduced pressure. The crude product was purified by flash column chromatography, eluting with 0-10% gradient (2M $NH_3$ in MeOH) in DCM on a 12 g Si-column, loading with DCM to afford the title compound;

LCMS Rt=0.92 mins; MS m/z 346.5 [M+H]+; Method 2 minLowpHv01

$^1$H NMR: (400 MHz, DMSO-d6) δ 8.35 (1H, d), 8.17 (1H, d), 7.72 (2H, m), 7.60 (2H, s), 7.52 (1H, d), 7.32 (2H, s), 2.47 (3H, s), 2.37 (3H, s).

Example 76a: cis-3-(6-Amino-5-(3-methyl-1,2,4-oxadiazol-5-yl)pyridin-3-yl)-N-(-3-(hydroxymethyl)cyclobutyl)-4-methylbenzenesulfonamide and Example 76b trans-3-(6-amino-5-(3-methyl-1,2,4-oxadiazol-5-yl)pyridin-3-yl)-N-((1r,3r)-3-(hydroxymethyl)cyclobutyl)-4-methylbenzenesulfonamide

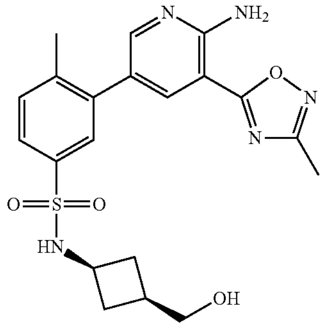

and

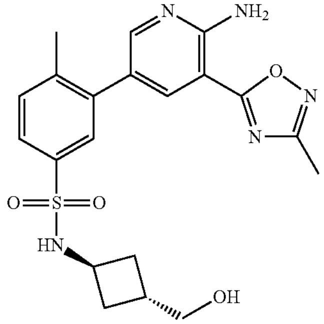

A mixture of cis and trans-3-(6-amino-5-(3-methyl-1,2,4-oxadiazol-5-yl)pyridin-3-yl)-N-(-3-(hydroxymethyl)cyclobutyl)-4-methylbenzenesulfonamide was prepared analogously to Example 37 from 3-(6-amino-5-(3-methyl-1,2,4-oxadiazol-5-yl)pyridin-3-yl)-4-methylbenzene-1-sulfonyl chloride (Intermediate E2) and (3-aminocyclobutyl)methanol.HCl. The mixture was separated into the individual isomers using SFC chromatography.

Method Details:

Column: Chiralcel AD-H 250×10 mm, 5 um @ 35 deg C.;

Mobile phase: 40% isopropanol+0.1% v/v DEA/60% $CO_2$;

Flow: 10 ml/min;

Detection: UV @ 220 nm;
Berger Minigram SFC System 2

Example 76a: First Eluted Peak

SFC Retention Time=6.71 mins cis-3-(6-amino-5-(3-methyl-1,2,4-oxadiazol-5-yl)pyridin-3-yl)-N-((1s,3s)-3-(hydroxymethyl)cyclobutyl)-4-methylbenzenesulfonamide LCMS: Rt=1.05 mins; MS m/z 430.2 [M+H]+; Method 2 minLowpHv03

$^1$H NMR (400 MHz, MeOD-d4) δ 8.25 (2H, s), 7.77 (1H, dd), 7.73 (1H, d), 7.53 (1H, d), 3.68 (1H, m), 3.41 (2H, d), 2.50 (3H, s), 2.41 (3H, s), 2.16 (2H, m), 2.04 (1H, m), 1.56 (2H, m).

Example 76b: Second Eluted Peak

SFC Retention Time=8.72 mins trans-3-(6-amino-5-(3-methyl-1,2,4-oxadiazol-5-yl)pyridin-3-yl)-N-((1s,3s)-3-(hydroxymethyl)cyclobutyl)-4-methylbenzenesulfonamide as the second eluting peak Rt; 8.72 mins LCMS: Rt=1.01 mins; MS m/z 430.2 [M+H]+; Method 2 minLowpHv03

$^1$H NMR (400 MHz, MeOD-d4) δ 8.25 (2H, s), 7.76 (1H, dd), 7.72 (1H, d), 7.53 (1H, d), 3.87 (1H, m), 3.51 (2H, d), 2.50 (3H, s), 2.41 (3H, s), 2.25 (1H, m), 1.97 (4H, m).

Assignment of cis or trans determined by NOESY NMR.

Example 77 trans-3-(2-Amino-2'-methyl-[3,4'-bipyridin]-5-yl)-N-(-4-(hydroxymethyl)cyclohexyl)-4-methylbenzenesulfonamide hydrochloride

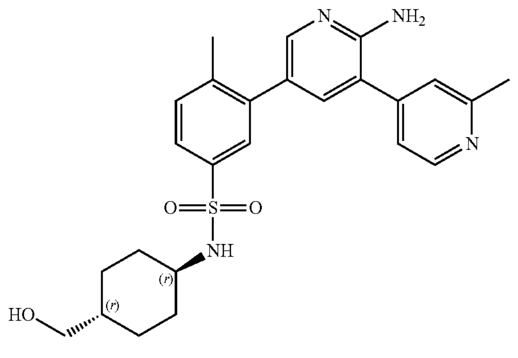 [SMILES: Cc1cc(-c2cc(-c3cc(S(=O)(=O)N[C@H]4CC[C@H](CO)CC4)ccc3C)cnc2N)ccn1]

Step 1: 5-Bromo-2'-methyl-[3,4'-bipyridin]-2-amine

To a solution of 2-methyl-4-(4,4,5,5-tetramethyl-1,3,2-dioxaborolan-2-yl)pyridine (1.246 g, 5.69 mmol) in DME (28.4 ml) was added 5-bromo-3-iodopyridin-2-amine (1.7 g, 5.69 mmol), bis(triphenylphosphine)palladium(II) chloride (0.200 g, 0.284 mmol) and $Na_2CO_3$ (aq. 2.0M) (8.53 ml, 17.06 mmol). The reaction mixture was heated at 90° C. and stirred for 24 hours. The mixture was added to water (100 ml) and the product extracted into EtOAc (2×100 ml). The organic extract was washed with brine, dried over $MgSO_4$. The solids were removed by filtration, washed with EtOAc and the filtrate concentrated under reduced pressure. The crude product was purified by sonification in DCM (~2 ml). The resulting solid was collected by filtration washed with DCM and dried to afford the title compound;

LCMS: Rt=0.69 mins; MS m/z 264.2 [M+H]+; Method 2 minLowpHv01

$^1$H NMR (400 MHz, DMSO-d6) δ 8.50 (1H, d), 8.07 (1H, d), 7.56 (1H, d), 7.35 (1H, s), 7.28 (1H, d), 6.08 (2H, s). Methyl expected to be under DMSO Step 2: trans-3-Bromo-N-(-4-(hydroxymethyl)cyclohexyl)-4-methylbenzenesulfonamide To a stirring solution of trans-4-aminocyclohexyl)methanol (1.5 g, 11.61 mmol) in DMF (58.0 ml), under $N_2$, was added 3-bromo-4-methylbenzene-1-sulfonyl chloride (3.13 g, 11.61 mmol) & DIPEA (4.46 ml, 25.5 mmol). The reaction mixture was stirred for 24 hours at room temperature. The mixture was concentrated to dryness, added to 0.1M HCl (150 ml) and product extracted into EtOAc (200 ml). The organic extract was washed with sat. $Na_2CO_3$ (150 ml), brine, dried over $MgSO_4$, and concentrated under reduced pressure to afford the title compound;

LCMS: Two peaks observed Rt 1.08, 0.95 mins; MS m/z 364.1 [M+H]+; Method 2 minLowpHv01

$^1$H NMR (400 MHz, DMSO-d6) δ 7.95 (1H, s), 7.71 (2H, d), 7.57 (1H, d), 4.33 (1H, t), 3.13 (2H, t), 2.87 (1H, m), 2.42 (3H, s), 1.63 (4H, d), 1.19 (1H, m), 1.11 (2H, q), 0.81 (2H, q).

Step 3: N-(trans-4-(Hydroxymethyl)cyclohexyl)-4-methyl-3-(4,4,5,5-tetramethyl-1,3,2-dioxaborolan-2-yl)benzenesulfonamide A stirring mixture of 3-bromo-N-(trans-4-(hydroxymethyl)cyclohexyl)-4-methyl benzenesulfonamide (step 2) (4.1 g, 11.32 mmol), KOAc (1.666 g, 16.98 mmol), $PdCl_2$ (dppf).$CH_2Cl_2$ adduct (0.462 g, 0.566 mmol), and 4,4,4',4',5,5,5',5'-octamethyl-2,2'-bi(1,3,2-dioxaborolane) (3.16 g, 12.45 mmol) in DME (56.6 ml), under $N_2$, was heated at 90° C. overnight. The mixture was added to water (100 ml) and product extracted into EtOAc (100 ml). The organic extract was washed with brine, dried over $MgSO_4$. The solids were removed by filtration, washed with EtOAc and the filtrate concentrated under reduced pressure. The crude product was purified by flash column chromatography, eluting with 0-100% gradient of EtOAc in hexane on a 80 g Si-column to afford the title compound.

LCMS: Rt=1.27 mins; MS m/z 410.4 [M+H]+; Method 2 minLowpHv01

$^1$H NMR (400 MHz, DMSO-d6) δ 8.05 (1H, d), 7.76 (1H, dd), 7.59 (1H, d), 7.39 (1H, d), 4.33 (1H, t), 3.12 (2H, t), 2.82 (1H, m), 2.54 (3H, s), 1.62 (4H, d), 1.33 (12H, s), 1.17 (1H, m), 1.10 (2H, q), 0.78 (2H, q).

Step 4: trans-3-(2-Amino-2'-methyl-[3,4'-bipyridin]-5-yl)-N-((1r,4r)-4-(hydroxymethyl)cyclohexyl)-4-methylbenzenesulfonamide hydrochloride To a solution of N-(trans-4-(hydroxymethyl)cyclohexyl)-4-methyl-3-(4,4,5,5-tetramethyl-1,3,2-dioxaborolan-2-yl) benzenesulfonamide (step 3) (280 mg, 0.683 mmol) in DME (3414 μl) was added 5-bromo-2'-methyl-[3,4'-bipyridin]-2-amine (step 1) (150 mg, 0.683 mmol), bis(triphenylphosphine)palladium(II) chloride (23.96 mg, 0.034 mmol) and $Na_2CO_3$ (aq. 2.0M) (1024 μl, 2.049 mmol). The reaction mixture was microwaved at 120° C. for 30 mins. The mixture was added to water (60 ml) and product extracted into EtOAc (2×60 ml). The organic extract was washed with brine, dried over $MgSO_4$ and Si-TMT resin to remove Pd. The solids were removed by filtration, washed with EtOAc and the filtrate concentrated under reduced pressure. The crude product was purified by flash column chromatography, eluting with 0-10% gradient of (2M $NH_3$ in MeOH) in DCM on a 12 g Si-column. The resulting oil was dissolved in MeOH (1 ml) and 4.0M HCl in dioxane was added (1 ml). The mixture was concentrated to under reduced pressure and product crystallized from i-PrOH (~10 ml). The resulting solid collected by filtration, washed with iPrOH, and dried to afford the title compound.

LCMS: Rt=0.62 mins; MS m/z 467.7 [M+H]+; Method 2 minLowpHv01

$^1$H NMR (400 MHz, DMSO-d6) δ 8.83 (1H, d), 8.24 (1H, s), 8.03 (1H, s), 7.98-7.90 (2H, br m), 7.77-7.67 (2H, br m), 7.63 (1H, s), 7.55 (3H, d on top of br hump), 3.78 (1H, t), 3.13 (2H, d), 2.89 (1H, m), 2.75 (3H, s), 2.38 (3H, s), 1.65 (4H, m), 1.24-1.08 (3H, m), 0.79 (2H, q).

Example 78 trans-3-(6-Amino-5-(3-(2,2,2-trifluoroethyl)-1,2,4-oxadiazol-5-yl)pyridin-3-yl)-N-((1r,4r)-4-hydroxy-cyclohexyl)-4-methylbenzenesulfonamide

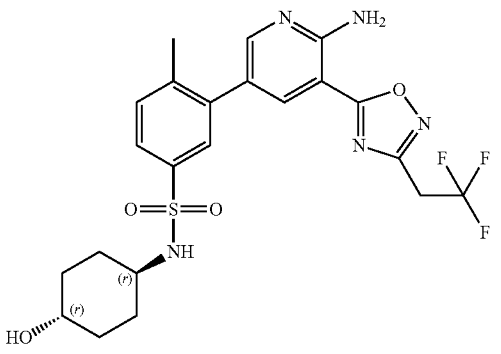 [SMILES: Cc1ccc(S(=O)(=O)N[C@H]2CC[C@H](O)CC2)cc1-c1cnc(N)c(-c2nc(CC(F)(F)F)no2)c1]

Step 1: (Z)-3,3,3-Trifluoro-N'-hydroxypropanimid-amide

To a stirring solution of 3,3,3-trifluoropropanenitrile (2 g, 18.34 mmol) in EtOH (3.67 ml), under $N_2$, was added hydroxylamine (50% wt in water) (1.454 g, 22.01 mmol) dropwise over 30 mins. The reaction mixture was stirred for 72 hours at room temperature. The mixture was concentrated and added to water (70 ml). The product was extracted into EtOAc (100 ml). The organic extract was washed with, brine, dried over $MgSO_4$, and filtrate concentrated under reduced pressure to afford the title compound;

$^1$H NMR (400 MHz, DMSO-d6) δ 9.32 (1H, s), 5.62 (2H, s), 3.01 (2H, q).

Step 2: 5-Bromo-3-(3-(2,2,2-trifluoroethyl)-1,2,4-oxadiazol-5-yl)pyridin-2-amine To a stirring suspension of 2-amino-5-bromonicotinic acid (2.3 g, 10.60 mmol) in DCM (53.0 ml), 1-chloro-N,N,2-trimethyl-1-propenylamine (Ghosez's reagent) (1.683 ml, 12.72 mmol) was added. The reaction mixture was left stirring for 1.5 hours. 3,3,3-trifluoro-N'-hydroxypropanimidamide (step 1) (1.656 g, 11.66 mmol) was then added followed by DIPEA (3.70 ml, 21.20 mmol). The reaction mixture was stirred overnight. T3P® (18.56 ml, 31.8 mmol) was added to the mixture and this was microwaved for 3 hours at 100° C. The mixture was added to water (100 ml) and product extracted into EtOAc (2×90 ml). The organic extracts were washed with brine, dried over $MgSO_4$ and the filtrate was concentrated under reduced pressure. The crude product was purified by adding MeOH (~10 ml). The mixture was sonicated and the resulting solid collected by filtration, washed with MeOH and dried to afford the title compound;

LCMS: Rt=1.17 mins; MS m/z 325.0 [M+H]+; Method 2 minLowpHv01

$^1$H NMR (400 MHz, DMSO-d6) δ 8.40 (1H, d), 8.35 (1H, d), 7.59 (2H, br s), 4.21 (2H, q).

Step 3: trans-3-(6-Amino-5-(3-(2,2,2-trifluoroethyl)-1,2,4-oxadiazol-5-yl)pyridin-3-yl)-N-((1r,4r)-4-hydroxycyclohexyl)-4-methylbenzenesulfonamide To a solution of trans N-(4-hydroxy-cyclohexyl)-4-methyl-3-(4,4,5,5-tetramethyl-[1,3,2]dioxaborolan-2-yl)-benzenesulfonamide (Intermediate B5) (147 mg, 0.371 mmol) in DME (1548 μl) was added 5-bromo-3-(3-(2,2,2-trifluoroethyl)-1,2,4-oxadiazol-5-yl)pyridin-2-amine (Step 2) (100 mg, 0.310 mmol), bis(triphenylphosphine)palladium (II) chloride (10.86 mg, 0.015 mmol) and $Na_2CO_3$ (aq. 2.0M) (464 μl, 0.929 mmol). The reaction mixture was microwaved at 120° C. for 90 mins. A further 0.05 eq of bis(triphenylphosphine)palladium(II) chloride (10.86 mg, 0.015 mmol) was added and reaction mixture was microwaved at 120° C. for 60 mins. The mixture was added to water (50 ml) and the product extracted into EtOAc (2×50 ml). The organic extract was washed with brine, dried over $MgSO_4$ and Si-TMT resin to remove Pd. The solids were removed by filtration, washed with EtOAc and the filtrate concentrated under reduced pressure. The crude product was purified by flash column chromatography, eluting with 0-10% gradient of MeOH in DCM on a 12 g Si-column to afford the title compound.

LCMS: Rt=1.12 mins; MS m/z 512.3 [M+H]+; Method 2 minLowpHv01

$^1$H NMR (400 MHz, DMSO-d6) δ 8.83 (1H, d), 8.21 (1H, d), 7.75-7.67 (2H, m), 7.61 (2H, br s), 7.55 (2H, q), 4.48 (1H, s), 4.22 (2H, q), 3.28 (1H, m), 2.93 (1H, m), 2.38 (3H, s), 1.72 (2H, m), 1.62 (2H, m), 1.13 (4H, m).

Example 79

3-(6-Amino-5-(3-(2,2,2-trifluoroethyl)-1,2,4-oxadiazol-5-yl)pyridin-3-yl)-N-(3-hydroxy-3-methylbutyl)-4-methylbenzenesulfonamide

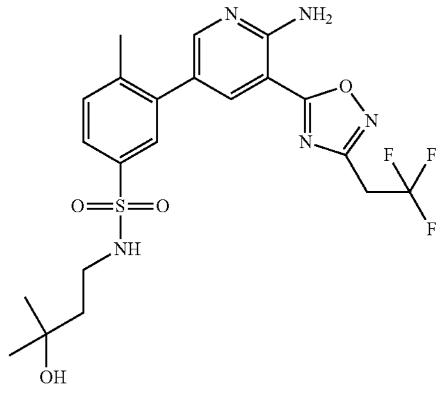 [SMILES: Cc1ccc(S(=O)(=O)NCCC(C)(C)O)cc1-c1cnc(N)c(-c2nc(CC(F)(F)F)no2)c1]

The title compound was prepared analogously to Example 78 starting from N-(3-hydroxy-3-methylbutyl)-4-methyl-3-(4,4,5,5-tetramethyl-1,3,2-dioxaborolan-2-yl)benzenesulfonamide (Intermediate B3) and 5-bromo-3-(3-(2,2,2-trifluoroethyl)-1,2,4-oxadiazol-5-yl)pyridin-2-amine (Example 78, step 2);

LCMS: Rt=1.18 mins; MS m/z 500.3 [M+H]+; Method 2 minLowpHv01

$^1$H NMR (400 MHz, DMSO-d6) δ 8.39 (1H, d), 8.22 (1H, d), 7.72-7.53 (5H, m), 7.41 (1H, t), 4.28 (1H, s), 4.22 (2H, q), 2.84 (2H, m), 2.38 (3H, s), 1.51 (2H, m), 1.03 (6H, s).

Example 80

3-(6-Amino-5-(3-cyclopropyl-1,2,4-oxadiazol-5-yl)pyridin-3-yl)-N-(2-hydroxy-2-methylpropyl)-4-methylbenzenesulfonamide hydrochloride

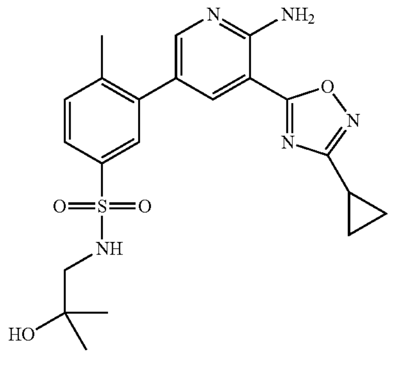 [SMILES: Cc1ccc(S(=O)(=O)NCC(C)(C)O)cc1-c1cnc(N)c(-c2nc(C3CC3)no2)c1]

The title compound was prepared analogously to Example 78 starting from N-(2-hydroxy-2-methylpropyl)-4-methyl-3-(4,4,5,5-tetramethyl-1,3,2-dioxaborolan-2-yl)benzenesulfonamide (Intermediate B2) and 5-bromo-3-(3-cyclopropyl-1,2,4-oxadiazol-5-yl)pyridin-2-amine (prepared analogously to Intermediate C3). The resulting oil was dissolved in MeOH (1 ml) and 4.0M HCl in dioxane was added (1 ml). The mixture was concentrated under reduced pressure and the solid recrystallized from hot EtOH/EtOAc (1:1) (~2 ml). Upon cooling a white solid crystallized, this was collected by filtration and dried to afford the title compound;

LCMS: Rt=1.09 mins; MS m/z 444.5 [M+H]+; Method 2 minLowpHv01

$^1$H NMR (400 MHz, DMSO-d6) δ 8.38 (1H, s), 8.26 (1H, s), 7.71 (2H, s), 7.54 (1H, d), 7.48 (1H, t), 2.63 (2H, d), 2.37 (3H, s), 2.24 (1H, m), 1.14 (4H, m), 1.06 (6H, s).

Example 81

3-(6-Amino-5-(1H-1,2,4-triazol-1-yl)pyridin-3-yl)-N-(2-hydroxy-2-methylpropyl)-4-methylbenzenesulfonamide hydrochloride

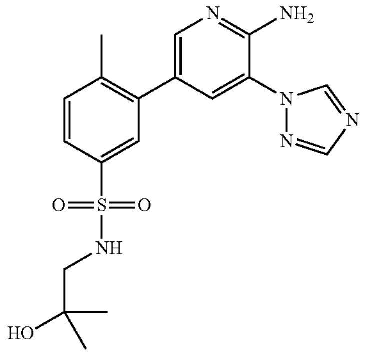 [SMILES: Cc1ccc(S(=O)(=O)NCC(C)(C)O)cc1-c1cnc(N)c(-n2cncn2)c1]

Step 1: 5-Bromo-3-(1H-1,2,4-triazol-1-yl)pyridin-2-amine

A mixture of 5-bromo-3-iodopyridin-2-amine (1 g, 3.35 mmol), 1H-1,2,4-triazole (0.254 g, 3.68 mmol), N,N-dimethylglycine (0.034 g, 0.335 mmol), $Cs_2CO_3$ (3.27 g, 10.04 mmol) and CuI (0.064 g, 0.335 mmol) in DMA (16.73 mL) was microwaved at 150° C. for 2 hours. The mixture was added to water (100 ml) and product extracted into EtOAc (2×90 ml). The organic extracts were washed with brine, dried over $MgSO_4$ and concentrated under reduced pressure. The crude product was purified by flash column chromatography, eluting with a modified 0-10% gradient (2M $NH_3$ in MeOH) in DCM on a 40 g Si-column. The product was dissolved in MeOH (5 ml) and loaded onto a pre-soaked Isolute® SCX-2 cartridge (10 g). The column was flushed with MeOH (50 ml) and the product eluted with 2.0M $NH_3$ in MeOH (40 ml). Ammonia/MeOH removed under reduced pressure to afford the title compound;

LCMS: Rt=0.67 mins; MS m/z 240.0 [M+H]+; Method 2 minLCv003

Material taken on crude directly to the next step, purity estimated at ~70%

Step 2: 3-(6-Amino-5-(1H-1,2,4-triazol-1-yl)pyridin-3-yl)-N-(2-hydroxy-2-methylpropyl)-4-methylbenzenesulfonamide hydrochloride To a solution of N-(2-hydroxy-2-methylpropyl)-4-methyl-3-(4,4,5,5-tetramethyl-1,3,2-dioxaborolan-2-yl)benzenesulfonamide (Intermediate B2) (154 mg, 0.417 mmol) in DME (2083 μL) was added 5-bromo-3-(1H-1,2,4-triazol-1-yl)pyridin-2-amine (Step 1) (100 mg, 0.417 mmol), bis(triphenylphosphine)palladium(II) chloride (14.62 mg, 0.021 mmol) and $Na_2CO_3$ (aq. 2.0M) (625 μL, 1.250 mmol). The reaction mixture was microwaved at 120° C. for 30 mins. The mixture was added to water (50 ml) and the product extracted into EtOAc (60 ml). The organic extract was washed with brine, dried over $MgSO_4$ and Si-TMT resin to remove Pd. The solids were removed by filtration, washed with EtOAc and the filtrate concentrated under reduced pressure. The crude product was purified by flash column chromatography, eluting with a modified 0-10% gradient (2M $NH_3$ in MeOH) in DCM on a 12 g Si-column. The resulting oil was dissolved in DCM (1 ml) and 4.0M HCl in dioxane was added (1 ml), the mixture was concentrated under reduced pressure and the solid recrystallized from hot EtOH (~1 ml). Upon cooling a pale yellow solid crystallized which was collected by filtration, washed with EtOH and dried to afford the title compound.

LCMS: Rt=0.78 mins; MS m/z 403.7 [M+H]+; Method 2 minLowpHv01

$^1$H NMR (400 MHz, DMSO-d6) plus a drop of $D_2O$ δ 9.04 (1H, s), 8.35 (1H, s), 8.18 (1H, d), 8.08 (1H, d), 7.72 (1H, s), 7.71 (1H, s), 7.54 (1H, d), 2.60 (2H, s), 2.37 (3H, s), 1.05 (6H, s).

Example 82a: cis-3-(6-Amino-5-(2-methyloxazol-5-yl)pyridin-3-yl)-N-((1s,3s)-3-hydroxycyclobutyl)-4-methylbenzenesulfonamide and Example 82b trans-3-(6-amino-5-(2-methyloxazol-5-yl)pyridin-3-yl)-N-((1r,3r)-3-hydroxycyclobutyl)-4-methylbenzenesulfonamide

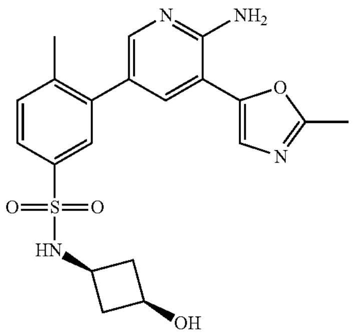

and

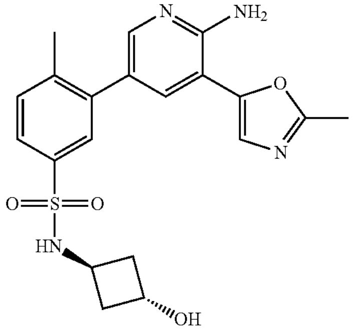

Step 1: 3-(6-Amino-5-(2-methyloxazol-5-yl)pyridin-3-yl)-N-(3-hydroxycyclobutyl)-4-methylbenzenesulfonamide To a mixture of 5-bromo-3-(2-methyloxazol-5-yl)pyridin-2-amine (Intermediate C4)(150 mg, 0.590 mmol) in DME (3 ml) was added N-(3-hydroxycyclobutyl)-4-methyl-3-(4,4,5,5-tetramethyl-1,3,2-dioxaborolan-2-yl)benzenesulfonamide (Intermediate B9)(217 mg, 0.590 mmol), $Na_2CO_3$ (aq. 2.0M) (886 μl, 1.771 mmol) and bis(triphenylphosphine) palladium(II) chloride (20.72 mg, 0.030 mmol). The reaction mixture was microwaved at 120° C. for 1 hour. The mixture was added to water (50 ml) and the product extracted into EtOAc (50 ml). The organic extract was washed with brine, dried over $MgSO_4$ and concentrated under reduced pressure. The crude product was purified by flash column chromatography, eluting with 0-10% gradient of (2M $NH_3$ in MeOH) in DCM on a 12 g Si-column to give the title compound as a mixture of stereoisomers;

LCMS: Rt=0.72, 0.74 mins; MS m/z 415.3 [M+H]+; Method 2 minLowpHv03

Step 5 cis-3-(6-Amino-5-(2-methyloxazol-5-yl)pyridin-3-yl)-N-((1s,3s)-3-hydroxycyclobutyl)-4-methylbenzenesulfonamide and trans-3-(6-amino-5-(2-methyloxazol-5-yl)pyridin-3-yl)-N-((1r,3r)-3-hydroxycyclobutyl)-4-methylbenzenesulfonamide The mixture was separated into the individual geometrical isomers using SFC chromatography.

Method Details:

Column: Chiralpak IC 250×10 mm, 5 um;

Mobile phase: 50% isopropanol+0.1% v/v DEA/50% $CO_2$;

Flow: 10 ml/min;

Detection: UV @ 220 nm;

System: Berger Minigram SFC 2

Example 82a: First Eluted Peak

SFC Retention Time=1.44 mins cis-3-(6-Amino-5-(2-methyloxazol-5-yl)pyridin-3-yl)-N-(3-hydroxycyclobutyl)-4-methylbenzenesulfonamide as the first eluting compound LCMS; Rt=0.81 mins; MS m/z 415.3 [M+H]+; Method 2 minLowpHv03

$^1$H NMR (400 MHz, DMSO-d6) δ 8.02 (1H, d), 7.82 (1H, d), 7.72 (1H, d), 7.65 (1H, d), 7.60 (1H, d), 7.51 (2H, m), 6.32 (2H, s), 5.01 (1H, d), 3.66 (1H, m), 3.12 (1H, m), 2.49 (3H, s), 2.35 (3H, s), 2.23 (2H, m), 1.58 (2H, m).

Example 82b: Second Eluted Peak

SFC Retention Time=15.81 mins trans-3-(6-amino-5-(2-methyloxazol-5-yl)pyridin-3-yl)-N-(3-hydroxycyclobutyl)-4-methylbenzenesulfonamide LCMS; Rt=0.76 mins; MS m/z 415.3 [M+H]+; Method 2 minLowpHv03

$^1$H NMR (400 MHz, DMSO-d6) δ 8.03 (1H, d), 7.86 (1H, d), 7.72 (1H, d), 7.64 (1H, dd), 7.57 (1H, d), 7.52 (1H, s), 7.51 (1H, s) 6.32 (2H, s), 4.93 (1H, d), 4.13 (1H, m), 3.74 (1H, m), 2.49 (3H, s), 2.35 (3H, s), 1.98 (2H, m), 1.78 (2H, m).

Assignment of compounds as cis or trans isomers made using NOESY NMR

Example 83 cis/trans-3-(6-Amino-5-(2-methylthiazol-5-yl)pyridin-3-yl)-N-((3-hydroxycyclobutyl)methyl)-4-methylbenzenesulfonamide

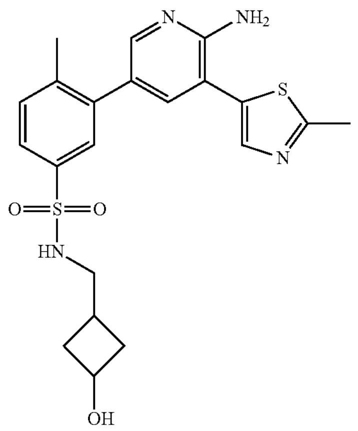 [SMILES: Cc1ncc(-c2cc(-c3cc(S(=O)(=O)NCC4CC(O)C4)ccc3C)cnc2N)s1]

Step 1: 3-(2-methylthiazol-5-yl)-5-(o-tolyl)pyridin-2-amine

To a mixture of 5-bromo-3-(2-methylthiazol-5-yl)pyridin-2-amine (Intermediate C6) (750 mg, 2.78 mmol) in DME (13.900 ml) was added o-tolylboronic acid (377 mg, 2.78 mmol), $Na_2CO_3$ (aq. 2.0M) (4.16 ml, 8.33 mmol) and bis(triphenylphosphine)palladium(II) chloride (97 mg, 0.139 mmol). The reaction mixture was microwaved at 120° C. for 1 hour.

Bis(triphenylphosphine)palladium(II) chloride (97 mg, 0.139 mmol) and o-tolylboronic acid (150 mg) was added and reaction mixture was microwaved at 120° C. for 1 hour. The mixture was added to water (100 ml) and the product extracted into EtOAc (100 ml). The organic extract was washed with brine, dried over $MgSO_4$ and concentrated under reduced pressure. The crude product was purified by flash column chromatography, eluting with 0-10% gradient of MeOH in DCM on a 24 g Si-column to give the title compound which was used without further purification;

LCMS; Rt=0.90 mins; MS m/z 282.2 [M+H]+; Method 2 minLowpHv03

Step 2: 3-(6-Amino-5-(2-methylthiazol-5-yl)pyridin-3-yl)-4-methylbenzene-1-sulfonyl chloride To a cooled (0° C.) stirring solution of 3-(2-methylthiazol-5-yl)-5-(o-tolyl)pyridin-2-amine (Step 1) (550 mg, 1.955 mmol) in $CHCl_3$ (9.77 ml), under $N_2$, was added chlorosulphonic acid (3.142 ml, 46.9 mmol) dropwise. The reaction mixture was stirred for 1 hour at 0° C. then allowed to warm to room temperature and stirred for 16 hours. The reaction was quenched by dropwise addition of the mixture into a stirring mixture of cold (ice bath) sat. $NaHCO_3$ (80 ml) and DCM (60 ml). The DCM extract was collected via a phase separator, washed with brine and dried over $MgSO_4$. 4M HCl in dioxane (1.5 ml) was added to the DCM and the solution concentrated under reduced pressure to give the title compound which was used directly in the next without further purification;

Step 3: 3-(6-Amino-5-(2-methylthiazol-5-yl)pyridin-3-yl)-N-((3-hydroxycyclobutyl)methyl)-4-methylbenzenesulfonamide To a stirring solution of 3-(aminomethyl)cyclobutanol (48.6 mg, 0.480 mmol) in DMA (1201 μl), under $N_2$, was added DIPEA (126 μl, 0.721 mmol) and 3-(6-amino-5-(2-methylthiazol-5-yl)pyridin-3-yl)-4-methylbenzene-1-sulfonyl chloride.HCl (Step 2) (100 mg, 0.240 mmol). The reaction mixture was stirred for 24 hours at room temperature. The mixture was added to water (15 ml) and product extracted into EtOAc (2×10 ml). The organic extracts were combined, washed with sat. $NaHCO_3$, brine and concentrated under reduced pressure. The crude product was purified by flash column chromatography, eluting with 0-10% gradient of (2M $NH_3$ in MeOH) in DCM on a 4 g Si-column. The resulting oil was sonicated in $Et_2O$ until a fine precipitate was formed, $Et_2O$ was decanted away from solid and solid dried to give the title compound;

LCMS: Rt=0.77 mins; MS m/z 445.2 [M+H]+; Method 2 minLowpHv03

$^1H$ NMR (400 MHz, DMSO-d6) δ 8.03 (1H, d), 7.83 (1H, s), 7.63 (1H, dd), 7.60 (1H, s), 7.51 (3H, m), 6.15 (2H, s), 4.92 (1H, s), 3.83 (1H, q), 5.07 (2H, m), 2.69 (3H, s), 2.36 (3H, s), 2.15 (2H, m), 1.72 (1H, m), 1.39 (2H, m).

Example 83a: cis-3-(6-Amino-5-(2-methylthiazol-5-yl)pyridin-3-yl)-N-(–3-hydroxycyclobutyl)methyl)-4-methylbenzenesulfonamide and Example 83b: trans-3-(6-amino-5-(2-methylthiazol-5-yl)pyridin-3-yl)-N-((–3-hydroxycyclobutyl)methyl)-4-methylbenzenesulfonamide

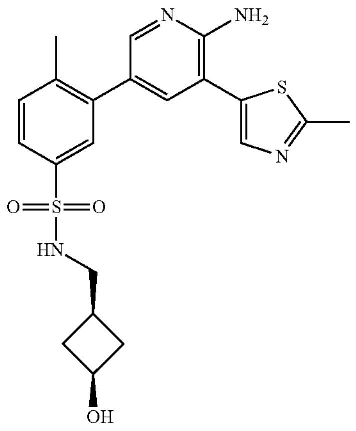

cis-isomer

-continued

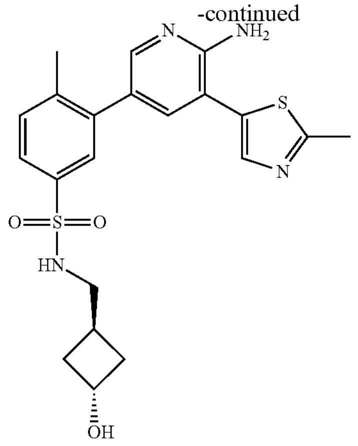

trans-isomer

Chiral separation of the mixture of cis-/trans-3-(6-amino-5-(2-methylthiazol-5-yl)pyridin-3-yl)-N-((3-hydroxycyclobutyl)methyl)-4-methylbenzenesulfonamide (Example 83) using Supercritical Fluid Chromatography afforded the individual enantiomers:

Method Details:

Column: Phenomenex LUX-C2 250×10 mm, 5 um @ 35 deg C.

Mobile phase: 45% Methanol+0.1% v/vDEA/55% $CO_2$

Flow: 10 ml/min

Detection: UV @ 220 nm

Instrument: Berger Minigram SFC1

Example 83a: cis-3-(6-amino-5-(2-methylthiazol-5-yl)pyridin-3-yl)-N-(3-hydroxycyclobutyl)methyl)-4-methylbenzenesulfonamide SFC Retention Time=16.40 mins LCMS: Rt=0.79 mins; MS m/z 446.5 [M+H]+; Method: 2 minLowpHv03

Example 83b: trans-3-(6-amino-5-(2-methylthiazol-5-yl)pyridin-3-yl)-N-((3-hydroxycyclobutyl)methyl)-4-methylbenzenesulfonamide SFC Retention Time=21.07 mins LCMS: Rt=0.81 mins; MS m/z 445.3 [M+H]+; Method 2 minLowpHv03

Example 83.1

(1-((3-(6-Amino-5-(2-methylthiazol-5-yl)pyridin-3-yl)-4-methylphenyl)sulfonyl)azetidin-3-yl)methanol

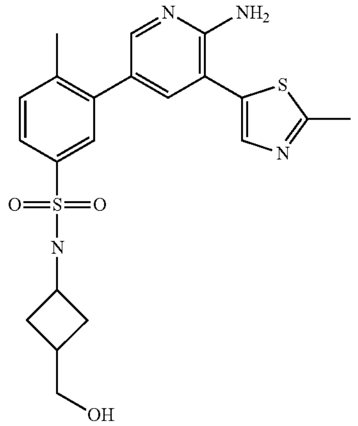 [SMILES: Cc1ncc(-c2cc(-c3cc(S(=O)(=O)NC4CC(CO)C4)ccc3C)cnc2N)s1]

The title compound was prepared analogously to Example 83 using azetidin-3-ylmethanol.

LCMS: Rt=0.79 mins; MS m/z 431.2 [M+H]+; Method 2 minLowpHv3

$^1$H NMR (400 MHz, DMSO-d6) δ 8.05 (1H, d), 7.84 (1H, s), 7.67 (1H, dd), 7.61 (1H, d), 7.51 (2H, m), 6.16 (2H, s), 4.68 (1H, t), 3.72 (2H, t), 3.46 (2H, m), 3.24 (2H, t), 2.69 (3H, s), 2.49 (1H, m), 2.40 (3H, s).

Example 83.2

3-(6-Amino-5-(2-methylthiazol-5-yl)pyridin-3-yl)-4-methyl-N-(oxetan-3-ylmethyl)benzenesulfonamide

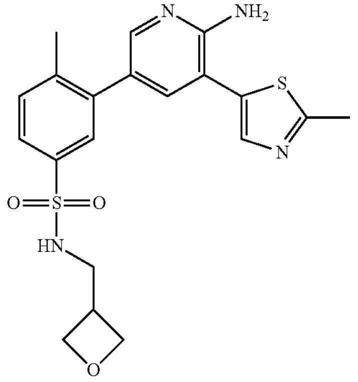 [SMILES: Cc1ncc(-c2cc(-c3cc(S(=O)(=O)NCC4COC4)ccc3C)cnc2N)s1]

The title compound was prepared analogously to Example 83 using oxetan-3-ylmethanamine.

LCMS: Rt=0.83 mins; MS m/z 431.3 [M+H]+; Method 2 minLowpHv03

$^1$H NMR (400 MHz, DMSO-d6) δ 8.04 (1H, d), 7.84 (1H, s), 7.72 (1H, br s), 7.66 (1H, dd), 7.61 (1H, d), 7.52 (2H, m), 6.16 (2H, s), 4.52 (2H, t), 4.18 (2H, t), 3.06-2.91 (3H, m), 2.69 (3H, s), 2.36 (3H, s).

Example 83.3

3-(6-amino-5-(2-methylthiazol-5-yl)pyridin-3-yl)-N-((3-hydroxyoxetan-3-yl)methyl)-4-methylbenzenesulfonamide

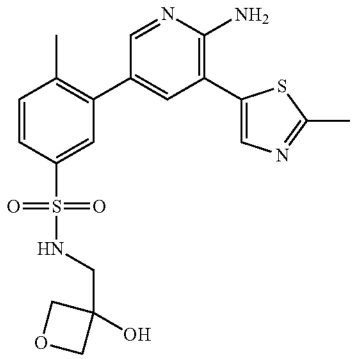 [SMILES: Cc1ncc(-c2cc(-c3cc(S(=O)(=O)NCC4(O)COC4)ccc3C)cnc2N)s1]

To a stirring solution of 3-(aminomethyl)oxetan-3-ol (24.8 mg, 0.240 mmol) in DMA (0.6 mL), under nitrogen, was added DIPEA (62.9 μl, 0.360 mmol) and 3-(6-Amino- 5-(2-methylthiazol-5-yl)pyridin-3-yl)-4-methylbenzene-1-sulfonyl chloride (Example 83, Step 2) (50 mg, 0.120 mmol). The reaction mixture was stirred for 24 hours at room temperature, then added to water (15 mL) and product extracted into EtOAc (2×10 mL). Organic phases were combined, washed with sat. $NaHCO_3$, brine and concentrated to dryness. Crude was purified by flash column chromatography, eluting with a 0-10% gradient of (2M NH3 in MeOH) in DCM on a 4 g silica column, loading with DCM. The resulting oil was sonicated in diethyl ether until a fine precipitate was formed. Diethyl ether was decanted away from solid and solid dried in vacuo to give the title compound as a white solid.

LCMS: Rt=0.78 mins; MS m/z 447.2 [M+H]+; Method 2 minLowpHv03

$^1$H NMR (400 MHz, DMSO-d6) δ 8.04 (1H, d), 7.83 (1H, s), 7.76 (1H, br s), 7.68 (2H, m), 7.51 (2H, m), 6.15 (2H, s), 5.85 (1H, br s), 4.35 (4H, q), 2.96 (2H, br s), 2.69 (3H, s), 2.36 (3H, s).

Example 83.4

3-(6-Amino-5-(2-methylthiazol-5-yl)pyridin-3-yl)-N-(3-hydroxy-2,2-dimethylpropyl)-4-methylbenzenesulfonamide

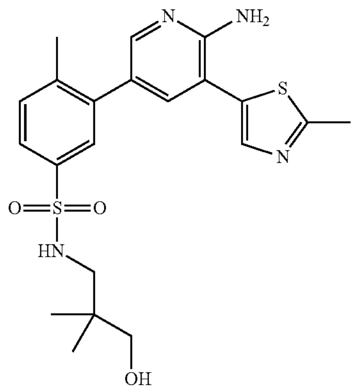 [SMILES: Cc1ncc(-c2cc(-c3cc(S(=O)(=O)NCC(C)(C)CO)ccc3C)cnc2N)s1]

The title compound was prepared analogously to Example 83 using 3-amino-2,2-dimethylpropan-1-ol.

LCMS: Rt=0.90 mins; MS m/z 447.3 [M+H]+; Method 2 minLowpHv03

$^1$H NMR (400 MHz, DMSO-d6) δ 8.03 (1H, d), 7.83 (1H, s), 7.64 (2H, m), 7.50 (2H, m), 7.34 (1H, br s), 6.15 (2H, s), 4.45 (1H, br s), 3.08 (2H, d), 2.69 (3H, s), 2.54 (2H, br m), 2.35 (3H, s), 0.76 (6H, s).

Example 83.5

3-(6-Amino-5-(2-methylthiazol-5-yl)pyridin-3-yl)-N-(2-hydroxyethyl)-4-methylbenzenesulfonamide

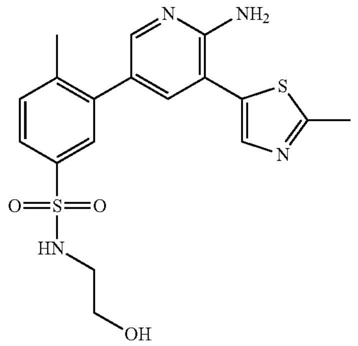 [SMILES: Cc1ncc(-c2cc(-c3cc(S(=O)(=O)NCCO)ccc3C)cnc2N)s1]

The title compound was prepared analogously to Example 83 using 2-aminoethanol.

LCMS: Rt=0.71 mins; MS m/z 405.1 [M+H]+; Method 2 minLowpHv03

$^1$H NMR (400 MHz, DMSO-d6) δ 8.03 (1H, d), 7.83 (1H, s), 7.65 (1H, dd), 7.62 (1H, m), 7.54 (1H, t), 7.51 (2H, m), 6.15 (2H, s), 4.69 (1H, t), 4.62 (2H, m), 2.78 (2H, q), 2.69 (3H, s), 2.36 (3H, s).

Example 84 cis-3-(6-Amino-5-(3-methylisoxazol-5-yl)pyridin-3-yl)-N-(((1s,3s)-3-hydroxycyclobutyl)methyl)-4-methylbenzenesulfonamide

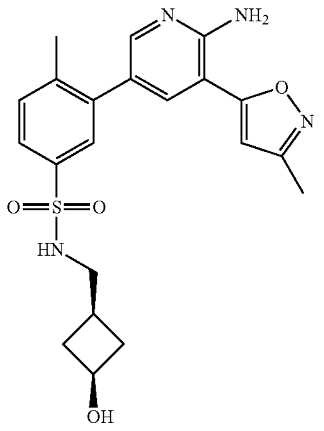 [SMILES: Cc1cc(-c2cc(-c3cc(S(=O)(=O)NC[C@H]4C[C@@H](O)C4)ccc3C)cnc2N)on1]

To a stirred solution of 3-(aminomethyl)cyclobutanol (30.3 mg, 0.300 mmol) in N,N-dimethylacetamide (2 mL) was added N,N-diisopropylethylamine (0.175 mL, 0.999 mmol) followed by 3-(6-Amino-5-(3-methylisoxazol-5-yl)pyridin-3-yl)-4-methylbenzene-1-sulfonyl chloride (Intermediate E3) (100 mg, 0.250 mmol). The reaction mixture was stirred at RT for 16 hrs. The reaction mixture was poured into DCM and washed with 1M $Na_2CO_3$. The organic phase was separated by means of a phase separator. The solvent was removed under reduced pressure. The resulting oil was dissolved in MeOH and passed through a 1 g Isolute® SCX-2 cartridge. The cartridge was washed through with MeOH and the resulting solution from this cartridge was discarded. The cartridge was eluted with 7M ammonia in methanol and the ammoniacal fractions were reduced to dryness to give the title compound.

The structure was confirmed as cis by NOESY NMR spectroscopy;

LCMS: Rt. 2.56 min; MS m/z 429.5 [M+H]+; Method 8 minLowpHv01.

$^1$H NMR (400 MHz, DMSO-d6) δ 8.15 (1H, d), 7.90 (1H, d), 7.69-7.61 (2H, m), 7.53 (2H, d), 6.90 (1H, s), 6.50 (2H, s), 4.89 (1H, d), 3.89-3.80 (1H, m), 2.73 (2H, br. s.), 2.36 (3H, s), 2.30 (3H, s), 2.21-2.12 (2H, m), 1.79-1.69 (1H, m), 1.45-1.36 (2H, m)

Example 85

5-(6-Amino-5-(3-methyl-1,2,4-oxadiazol-5-yl)pyridin-3-yl)-2-fluoro-N-(2-hydroxy-2-methylpropyl)-4-methylbenzenesulfonamide

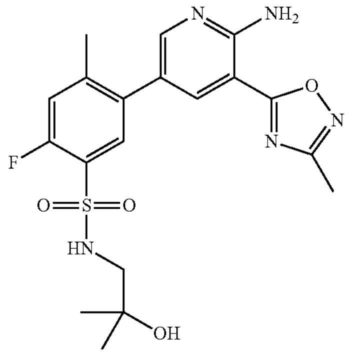 [SMILES: Cc1noc(-c2cc(-c3cc(S(=O)(=O)NCC(C)(C)O)c(F)cc3C)cnc2N)n1]

Step 1: 5-Bromo-2-fluoro-N-(2-hydroxy-2-methylpropyl)-4-methylbenzenesulfonamide To a stirring solution of 5-bromo-2-fluoro-4-methylbenzene-1-sulfonyl chloride (1 g, 3.48 mmol) in DCM (15 mL) was added 1-amino-2-methylpropan-2-ol (0.341 g, 3.83 mmol) and triethylamine (0.969 mL, 6.96 mmol). The reaction mixture was stirred for 3 hours and then diluted with DCM and washed with 1M HCl. The resulting mixture was washed with saturated sodium bicarbonate solution, dried over $MgSO_4$, filtered and the solvent evaporated to give the title compound as a white solid;

LCMS: Rt. 1.02 min; MS m/z 341.0, [M+H]+; Method: 2 minLowpHv01.

$^1$H NMR (400 MHz, DMSO-d6) δ 7.88 (1H, d) 7.84 (1H, t) 7.53 (1H, d) 2.79 (2H, d) 2.41 (3H, s) 1.05 (6H, s)

Step 2: 5-(6-Amino-5-(3-methyl-1,2,4-oxadiazol-5-yl)pyridin-3-yl)-2-fluoro-N-(2-hydroxy-2-methylpropyl)-4-methylbenzenesulfonamide To a microwave vial was added 4,4,4',4',5,5,5',5'-octamethyl-2,2'-bi(1,3,2-dioxaborolane) (82 mg, 0.323 mmol), 5-bromo-3-[1,2,4]oxadiazol-5-yl-pyridin-2-ylamine (Intermediate C3) (75.0 mg, 0.294 mmol), $PdCl_2$(dppf).$CH_2Cl_2$ adduct (12.00 mg, 0.015 mmol), potassium acetate (43.3 mg, 0.441 mmol) in DME (2 mL). The vial was placed in the microwave for 1 hour at 120° C. To the reaction mixture was added $PdCl_2$(dppf).$CH_2Cl_2$ adduct (12.00 mg, 0.015 mmol), 5-bromo-2-fluoro-N-(2-hydroxy-2-methylpropyl)-4-methylbenzenesulfonamide (step 1) (100 mg, 0.294 mmol) and $Na_2CO_3$ (0.441 mL, 0.882 mmol) and the vial was placed in the microwave for 30 minutes at 120° C. The reaction mixture was diluted with ethyl acetate and washed with water. The organic layer was collected, dried over $MgSO_4$, filtered and the solvent removed on a rotary evaporator to give a brown oil. The crude product was dissolved in DMSO and purified by preparative LCMS to give the title compound;

LCMS: Rt. 3.93 min; MS m/z 436.0, [M+H]+; Method: 10 minLowpH.

$^1$H NMR (400 MHz, MeOD-d4) δ 8.20 (1H, s) 8.18 (1H, s) 7.70 (1H, d) 7.29 (1H, d) 2.95 (2H, s) 2.48 (3H, s) 2.37 (3H, s) 1.20 (6H, s)

Example 86

(R)-3-(6-Amino-5-(3-methyl-1,2,4-oxadiazol-5-yl)pyridin-3-yl)-4-methyl-N-((tetrahydrofuran-3-yl)methyl)benzenesulfonamide

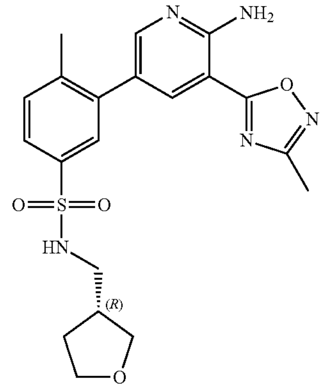

To (R)-4-methyl-N-((tetrahydrofuran-3-yl)methyl)-3-(4,4,5,5-tetramethyl-1,3,2-dioxaborolan-2-yl)benzenesulfonamide (Intermediate B8) (75 mg, 0.197 mmol), 5-bromo-3-[1,2,4]oxadiazol-5-yl-pyridin-2-ylamine (Intermediate C3) (50.2 mg, 0.197 mmol), potassium phosphate (84 mg, 0.393 mmol) and [1,1'-bis(di-tert-butylphosphino)ferrocene]dichloropalladium(III) (6.41 mg, 9.83 μmol) in 1,4-dioxane (2 mL), water (0.500 mL) was added. The reaction mixture was stirred at 1100° C. for 15 mins in the microwave. The reaction mixture was poured into water and the product was extracted using EtOAc. The organic layer was separated and washed with sat. $NaHCO_3$, water and brine then dried over $MgSO_4$. Si-TMT resin was added to the filtrate and this was stirred for 1 hr and filtered. The solvent was removed under reduced pressure. The crude product was columned by ISCO chromatography, eluting in a 0% to 5% TBME:MeOH gradient, on a 4 g silica cartridge. The product fractions were combined and the solvent was removed to give a clear oil. $Et_2O$ was added to the oil and the product precipitated out. The product was filtered and dried to give the title compound of a white solid;

LCMS: Rt 3.41 min; MS m/z 430.2 [M+H]+; Method 8 minLowpHv01

$^1$H NMR (400 MHz, $CDCl_3$) δ 8.25 (2H, m), 7.83-7.73 (2H, m), 7.47 (1H, d), 6.95 (2H, broad s), 4.85 (1H, t), 3.87 (1H, m), 3.80-3.68 (2H, m), 3.54-3.47 (1H, m), 3.01 (2H, t), 2.55 (3H, s), 2.45 (1H, m), 2.40 (3H, s), 2.05 (1H, m), 1.60 (1H, m).

Example 87

(S)-3-(6-Amino-5-(3-methyl-1,2,4-oxadiazol-5-yl)pyridin-3-yl)-4-methyl-N-((tetrahydrofuran-3-yl)methyl)benzenesulfonamide

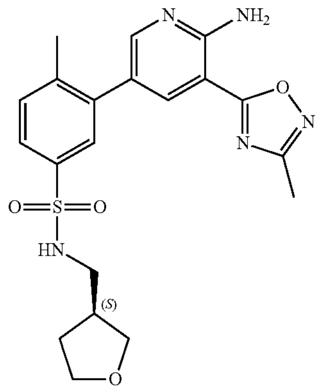

To a microwave vial was added (S)-3-bromo-4-methyl-N-((tetrahydrofuran-3-yl)methyl)benzene sulfonamide (prepared analogously to the (R) isomer described in Step 1 of Intermediate B8 by replacement of (R)-(tetrahydrofuran-3-yl)methanamine hydrochloride with the (S)-isomer) (564 mg, 1.687 mmol), 4,4,4',4',5,5,5',5'-octamethyl-2,2'-bi(1,3,2-dioxaborolane) (471 mg, 1.856 mmol), $PdCl_2$(dppf).$CH_2Cl_2$ adduct (276 mg, 0.337 mmol), potassium acetate (248 mg, 2.53 mmol) in DME (2 mL). The vial was placed in the microwave for 1 hour at 120° C. To the reaction mixture was added $PdCl_2$(dppf).$CH_2Cl_2$ adduct (276 mg, 0.337 mmol), 5-bromo-3-[1,2,4]oxadiazol-5-yl-pyridin-2-ylamine (Intermediate C3) and 2M sodium carbonate (2.53 mL, 5.06 mmol) and the vial was placed in the microwave for 45 minutes at 120° C. The reaction mixture was poured into water and the product was extracted using EtOAc. The organic layer was separated and washed with sat $NaHCO_3$, water and brine then dried over $MgSO_4$. Si-TMT resin was added to the filtrate and this was stirred for 1 hr and filtered. The solvent was removed under reduced pressure. The crude product was columned by ISCO chromatography, eluting in a 0% to 5% TBME:MeOH gradient, on a 40 g silica cartridge, crude product was dry loaded on the column. The product fractions were combined and the solvent was removed to give a clear oil. $Et_2O$ was added to the oil and the product precipitated out. The product was filtered and dried to afford the title compound as an off a white solid;

LCMS: Rt 2.76 min; MS m/z 430.5 [M+H]+; Method 8 minLowpHv01

$^1H$ NMR (400 MHz, DMSO-d6) −δ 8.36 (1H, d), 8.18 (1H, d), 7.5-7.8 (6H, m), 3.53-3.70 (3H, m), 3.29-3.42 (1H, m), 2.73 (2H, m), 2.47 (3H, s), 2.38 (3H, s), 2.21-2.34 (1H, m), 1.88 (1H, m), 1.50 (1H, m).

Example 88

5-(6-Amino-5-(3-methylisoxazol-5-yl)pyridin-3-yl)-2-chloro-N-(2-hydroxy-2-methylpropyl)-4-methylbenzenesulfonamide

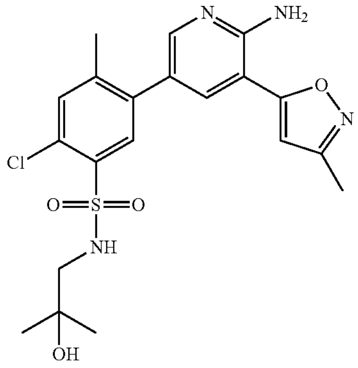 [SMILES: Cc1cc(-c2cc(-c3cc(S(=O)(=O)NCC(C)(C)O)c(Cl)cc3C)cnc2N)on1]

Step 1: 5-Bromo-2-chloro-N-(2-hydroxy-2-methylpropyl)-4-methylbenzenesulfonamide To a round bottom flask was added 1-bromo-4-chloro-2-methylbenzene (2 g, 9.73 mmol) in $CHCl_3$ (50 mL). The reaction mixture was cooled to 0° C. and chlorosulfonic acid (15.64 mL, 234 mmol) was added carefully. The reaction mixture was left stirring and warmed slowly to RT for 3 hours. The reaction mixture was carefully added to ice cold water and extracted with DCM. The organic layer was passed through a phase separator and the solvent was evaporated on the rotary evaporator. The product was dissolved in about DCM (20 ml) and to this was added 1-amino-2-methylpropan-2-ol (0.954 g, 10.71 mmol) in triethylamine (2.71 mL, 19.47 mmol). The reaction mixture was stirred at RT overnight for 20 hours. The reaction mixture was diluted with DCM and washed with 1M HCl and saturated brine. The organic layer was collected, dried over $MgSO_4$, filtered and the solvent removed under reduced pressure to give the title compound as a white solid;

LCMS: Rt 1.19 min; MS m/z 356.0 [M+H]+; Method 2 minLowpHv03

Step 2: 5-(6-Amino-5-(3-methylisoxazol-5-yl)pyridin-3-yl)-2-chloro-N-(2-hydroxy-2-methylpropyl)-4-methylbenzenesulfonamide To a microwave vial was added 5-bromo-2-chloro-N-(2-hydroxy-2-methylpropyl)-4-methylbenzenesulfonamide (250 mg, 0.701 mmol), 4,4,4',4',5,5,5',5'-octamethyl-2,2'-bi(1,3,2-dioxaborolane) (196 mg, 0.771 mmol), $PdCl_2$(dppf).$CH_2Cl_2$ adduct (28.6 mg, 0.035 mmol), potassium acetate (103 mg, 1.051 mmol) in DME (4 ml). The vial was placed in the microwave at 120° C. for one hour. To the RM was added 5-bromo-3-(3-methyl-isoxazol-5-yl)-pyridin-2-ylamine (Intermediate C5) (178 mg, 0.701 mmol), $Na_2CO_3$ (1.051 ml, 2.103 mmol) and $PdCl_2$(dppf).$CH_2Cl_2$ adduct (28.6 mg, 0.035 mmol). The reaction mixture was diluted with EtOAc and washed with water. The organic layer was collected and Si-TMT resin was added. The reaction mixture was left stirring for 15 minutes. The solid was filtered and the solvent removed under reduced pressure to give a brown oil. The crude product was triturated in MeOH and the solid was filtered. The solid was then loaded onto an Isolute® SCX-2 column and the column was washed with MeOH and the collected fraction was discarded. The column was eluted with $MeOH/NH_3$ and the fraction was collected and the solvent removed under reduced pressure to give a white solid. The collected solid was dried in the oven overnight to afford the title compound;

LCMS: Rt 3.07 min; MS m/z 451.3 [M+H]+; Method 8 minLowpHv01

$^1$H NMR (400 MHz, DMSO-d6) –δ 8.15 (1H, s) 7.91 (1H, s) 7.74 (1H, s) 7.65 (1H, s) 6.90 (1H, s) 6.53 (2H, s) 6.52 (1H, s) 4.42 (1H, s) 2.79 (2H, s) 2.34 (3H, s) 2.30 (3H, s) 1.06 (6H, s)

Example 89

5-(6-Amino-5-(3-methyl-1,2,4-oxadiazol-5-yl)pyridin-3-yl)-2-chloro-N-(2-hydroxy-2-methylpropyl)-4-methylbenzenesulfonamide

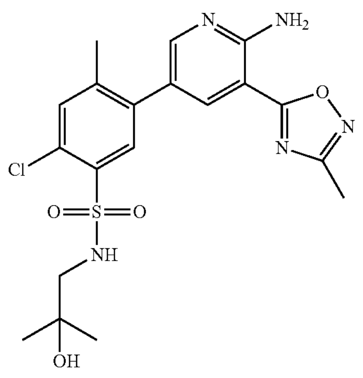 [SMILES: Cc1noc(-c2cc(-c3cc(S(=O)(=O)NCC(C)(C)O)c(Cl)cc3C)cnc2N)n1]

The title compound was prepared analogously to Example 88 starting from 5-bromo-3-(3-methyl-1,2,4-oxadiazol-5-yl)pyridin-2-amine (Intermediate C3);

LCMS: Rt 3.53 min; MS m/z 452.3 [M+H]+; Method 8 minLowpHv01

$^1$H NMR (400 MHz, DMSO-d6) –δ 8.35 (1H, s) 8.20 (1H, s) 7.77 (1H, s) 7.66 (1H, s) 7.62 (2H, s) 7.55 (1H, s) 4.42 (1H, s) 2.80 (2H, s) 2.47 (3H, s) 2.36 (3H, s) 1.06 (6H, s).

Example 90

3-(6-Amino-5-(5-methylthiazol-2-yl)pyridin-3-yl)-N-(2-hydroxy-2-methylpropyl)-4-methylbenzenesulfonamide

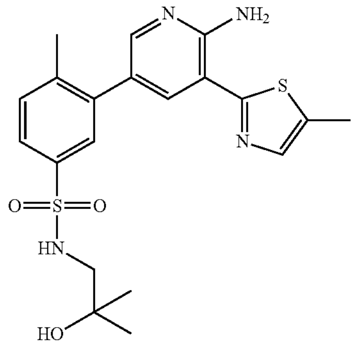 [SMILES: Cc1cnc(-c2cc(-c3cc(S(=O)(=O)NCC(C)(C)O)ccc3C)cnc2N)s1]

Step 1: 3-(5-methylthiazol-2-yl)pyridin-2-amine

2-Aminopyridine-3-boronic acid pinacol ester (200 mg, 0.909 mmol), 2-bromo-5-methylthiazole (147 mg, 0.826 mmol) and potassium phosphate (351 mg, 1.652 mmol) was added to a 2-5 ml microwave vial. 1,4-dioxane (3305 μl), water (826 μl) and Pd-118 (25.4 mg, 0.041 mmol) was added and the reaction mixture was heated in a microwave reactor at 'very high' absorbance level for 90 minutes at 120° C. The reaction mixture was added to water (50 ml) and extracted with EtOAc (50 ml). The organic phase was washed with brine (50 ml) and dried over $MgSO_4$. The solid was filtered off, washed with EtOAc and the solvent was concentrated under reduced pressure. The crude residue was purified by flash column chromatography, eluting with a gradient of 0-5% MeOH in DCM using a 12 g silica column, loading with DCM. The appropriate fractions were concentrated under reduced pressure to give the title compound as a light brown solid;

LCMS: Rt 0.53 mins; MS m/z 191.7 [M+H]+; Method 2 minLowpHv03.

$^1$H NMR (400 MHz, DMSO-d6) δ 8.05 (1H, dd), 7.85 (1H, dd), 7.61 (1H, d), 7.52 (2H, br s), 6.65 (1H, q). Aromatic methyl signal believed to be under DMSO solvent peak.

Step 2: 5-Bromo-3-(5-methylthiazol-2-yl)pyridin-2-amine 3-(5-methylthiazol-2-yl)pyridin-2-amine (from step 1) (80 mg, 0.418 mmol) was dissolved in dry THF (5 ml). At 0° C., under an atmosphere of $N_2$, NBS (82 mg, 0.460 mmol) was added and the reaction mixture was allowed to warm up to RT. The resulting mixture was stirred for 2 hours at RT. EtOAc (25 ml) was added to the reaction mixture, the organic phase was washed with 0.1 M NaOH solution (2×25 ml), brine (25 ml) and dried over $MgSO_4$. The solid was filtered off, washed with EtOAc and the solvent was concentrated under reduced pressure to give the title compound as a brown solid;

LCMS: Rt 1.27 mins, MS m/z 272.3 [M+H]+; 2 minLowpHv03.

$^1$H NMR (400 MHz, $CDCl_3$) δ 8.08 (1H, d), 7.93 (1H, d), 7.51 (1H, d), 7.35 (2H, br s), 2.55 (3H, d).

Step 3: 3-(6-Amino-5-(5-methylthiazol-2-yl)pyridin-3-yl)-N-(2-hydroxy-2-methylpropyl)-4-methylbenzenesulfonamide 5-Bromo-3-(5-methylthiazol-2-yl)pyridin-2-amine (from Step 2) (40 mg, 0.148 mmol), N-(2-hydroxy-2-methylpropyl)-4-methyl-3-(4,4,5,5-tetramethyl-1,3,2-dioxaborolan-2-yl)benzenesulfonamide (Intermediate B2) (60.1 mg, 0.163 mmol) and potassium phosphate (62.9 mg, 0.296 mmol) was added to a 0.5-2 ml microwave vial. 1,4-Dioxane (592 μl), water (148 μl) and Pd-118 (4.56 mg, 7.40 μmol) was added and the reaction mixture was heated in a microwave reactor at 'very high' absorbance level for 90 minutes at 120° C. The reaction mixture was added to water (50 ml) and extracted with EtOAc (50 ml). The organic phase was washed with brine (50 ml), dried over $MgSO_4$, the solid was filtered off, washed with EtOAc and the solvent was concentrated under reduced pressure. The crude residue was purified by flash column chromatography, eluting with a gradient of 0-5% MeOH in DCM using a 4 g silica column, loading with DCM. The resulting pale orange oil was triturated with $Et_2O$:hexane (~2:1), the resulting solid was filtered off and washed with $Et_2O$. The solid was dried in a vacuum oven at 50° C. for 4 hours to give the title compound as a light brown solid;

LCMS: Rt 0.96 mins, MS m/z 433.8 [M+H]+; Method 2 minLowpHv03.

$^1H$ NMR (400 MHz, DMSO-d6) δ 8.11 (1H, d), 7.85 (1H, d), 7.73 (2H, br s), 7.68-7.65 (3H, m), 7.52 (1H, d), 7.45 (1H, t), 4.39 (1H, s), 2.62 (2H, d), 2.37 (3H, s), 1.06 (6H, s). One 3H-methyl signal not observed—likely obscured by DMSO solvent peak.

Example 91

3-(6-Amino-5-(5-methylthiazol-2-yl)pyridin-3-yl)-N-(3-hydroxy-3-methylbutyl)-4-methylbenzenesulfonamide

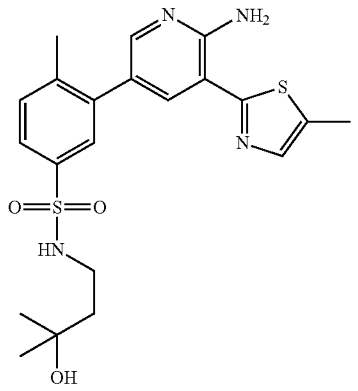 [SMILES: Cc1cnc(-c2cc(-c3cc(S(=O)(=O)NCCC(C)(C)O)ccc3C)cnc2N)s1]

5-Bromo-3-(5-methylthiazol-2-yl)pyridin-2-amine (Example 90 step 2) (40 mg, 0.148 mmol), N-(3-hydroxy-3-methylbutyl)-4-methyl-3-(4,4,5,5-tetramethyl-1,3,2-dioxaborolan-2-yl)benzenesulfonamide (Intermediate B3) (62.4 mg, 0.163 mmol) and potassium phosphate (62.9 mg, 0.296 mmol) was added to a 0.5-2 ml microwave vial. 1,4-Dioxane (592 μl), water (148 μl) and Pd-118 (4.56 mg, 7.40 μmol) was added and the reaction mixture was heated in a microwave reactor at 'very high' absorbance level for 90 minutes at 120° C. The reaction mixture was added to water (50 ml) and extracted with EtOAc (50 ml). The organic phase was washed with brine (50 ml) and dried over $MgSO_4$. The solid was filtered off, washed with EtOAc and the solvent was concentrated under reduced pressure. The crude residue was purified by flash column chromatography, eluting with a gradient of 0-5% MeOH in DCM using a 4 g silica column, loading with DCM. The resulting orange oil was triturated with $Et_2O$:hexane (~2:1) and the resulting solid was filtered off and washed with $Et_2O$. The solid was left to dry in a vacuum oven at 50° C. for 4 hours to give the title compound as a cream solid;

LCMS: Rt 0.97 mins, MS m/z 447.3 [M+H]+; 2 minLowpHv03.

$^1H$ NMR (400 MHz, DMSO-d6) δ 8.10 (1H, d), 7.85 (1H, d), 7.73 (2H, br s), 7.68-7.63 (3H, m), 7.54 (1H, d), 7.41 (1H, t), 4.27 (1H, s), 2.86-2.81 (2H, m), 2.38 (3H, s), 1.51 (2H, t), 1.02 (6H, s). One 3H-methyl signal not observed—likely obscured by DMSO solvent peak as for related compound Example 90.

Example 92

3-(6-Amino-5-(2-methylthiazol-4-yl)pyridin-3-yl)-N-((1r,4r)-4-hydroxycyclohexyl)-4-methylbenzenesulfonamide

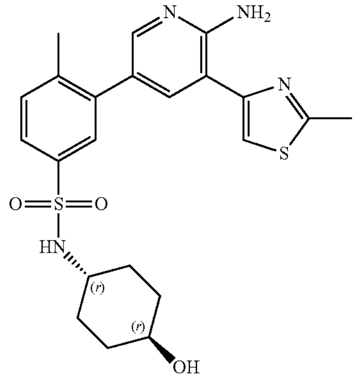 [SMILES: Cc1nc(-c2cc(-c3cc(S(=O)(=O)N[C@H]4CC[C@H](O)CC4)ccc3C)cnc2N)cs1]

5-Bromo-3-(2-methylthiazol-4-yl)pyridin-2-amine (Intermediate C6) (100 mg, 0.370 mmol), trans N-(4-Hydroxycyclohexyl)-4-methyl-3-(4,4,5,5-tetramethyl-[1,3,2]dioxaborolan-2-yl)-benzenesulfonamide (Intermediate B5) (161 mg, 0.407 mmol) and potassium phosphate (157 mg, 0.740 mmol) was added to a 0.5-2 ml microwave vial. 1,4-Dioxane (1481 μl), water (370 μl) and Pd-118 (11.40 mg, 0.019 mmol) was added and the reaction mixture was heated in a microwave reactor at 'very high' absorbance level for 90 minutes at 120° C. The reaction mixture was added to water (50 ml) and extracted with EtOAc (50 ml). The organic phase was washed with brine (50 ml) and dried over $MgSO_4$. The solid was filtered off, washed with EtOAc and the solvent was concentrated under reduced pressure. The crude residue was purified by flash column chromatography, eluting with a gradient of 0-5% MeOH in DCM using a 12 g silica column, loading with DCM and by reverse phase preparative HPLC (method 'Low pH 10-35% gradient'). The contents of the appropriate preparative vials were added to saturated $NaHCO_3$ solution (20 ml) and the aqueous phase was extracted with DCM (2×20 ml). The organic phase was separated using a phase separator and the solvent was concentrated under reduced pressure. The resulting colourless oil was triturated with $Et_2O$:hexane (~2:1) and the resulting solid was filtered off and washed with $Et_2O$. The solid was left to dry in a vacuum oven at 50° C. overnight to give the title compound as a white solid;

LCMS: Rt 0.78 mins, MS m/z 459.7 [M+H]+; 2 minLowpHv03.

$^1H$ NMR (400 MHz, DMSO-d6) δ 8.00 (1H, s), 7.98 (1H, d), 7.96 (1H, d), 7.68 (1H, s), 7.65 (1H, s), 7.55 (1H, d), 7.50 (1H, d), 7.07 (2H, s), 4.46 (1H, d), 3.33-3.25 (1H, m), 2.95-2.87 (1H, m), 2.77 (3H, s), 2.47 (3H, s), 1.72-1.60 (4H, m), 1.21-1.03 (4H, m).

Example 93

3-(6-Amino-5-(2-methylthiazol-4-yl)pyridin-3-yl)-N-(3-hydroxy-3-methylbutyl)-4-methylbenzenesulfonamide

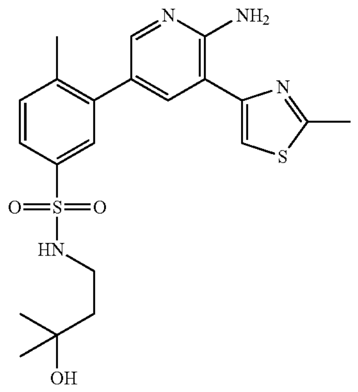 [SMILES: Cc1nc(-c2cc(-c3cc(S(=O)(=O)NCCC(C)(C)O)ccc3C)cnc2N)cs1]

5-Bromo-3-(2-methylthiazol-4-yl)pyridin-2-amine (Example 92, step 1) (100 mg, 0.370 mmol), N-(3-hydroxy-3-methylbutyl)-4-methyl-3-(4,4,5,5-tetramethyl-1,3,2-dioxaborolan-2-yl)benzenesulfonamide (Intermediate B3) (156 mg, 0.407 mmol) and potassium phosphate (157 mg, 0.740 mmol) was added to a 0.5-2 ml microwave vial. 1,4-Dioxane (1481 µl), water (370 µl) and Pd-118 (11.40 mg, 0.019 mmol) were added and the reaction mixture was heated in a microwave reactor at 'very high' absorbance level for 90 minutes at 120° C. The reaction mixture was added to water (50 ml) and extracted with EtOAc (50 ml). The organic phase was washed with brine (50 ml), dried over $MgSO_4$. The solid was filtered off, washed with EtOAc and the solvent was concentrated under reduced pressure. The crude residue was purified by flash column chromatography, eluting with a gradient of 0-10% MeOH in DCM using a 12 g silica column, loading with DCM and by reverse phase preparative HPLC (method 'Low pH 10-35% gradient'). The product fractions were added to saturated $NaHCO_3$ solution (10 ml) and the aqueous phase was extracted with DCM (2×10 ml). The organic phase was separated using a phase separator and the solvent was concentrated under reduced pressure to give the title compound as a white solid;

LCMS: Rt 0.82 mins, MS m/z 447.3 [M+H]+; 2 minLowpHv03.

$^1$H NMR (400 MHz, $CDCl_3$) δ 7.97 (1H, d), 7.86 (1H, d), 7.80 (1H, dd), 7.77 (1H, d), 7.48 (1H, s) 7.45 (1H, d), 7.24 (2H, br s), 5.69 (1H, t), 3.17 (2H, q), 2.82 (3H, s), 2.40 (3H, s), 1.68 (2H, t), 1.21 (6H, s).

Example 94a 3-(6-amino-5-(oxazol-5-yl)pyridin-3-yl)-N-(2-hydroxy-2-methylpropyl)-4-methylbenzenesulfonamide And Example 94b 3-(6-amino-5-(oxazol-2-yl)pyridin-3-yl)-N-(2-hydroxy-2-methylpropyl)-4-methylbenzenesulfonamide

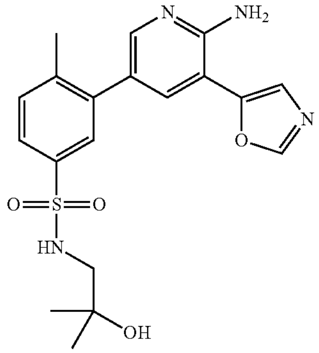

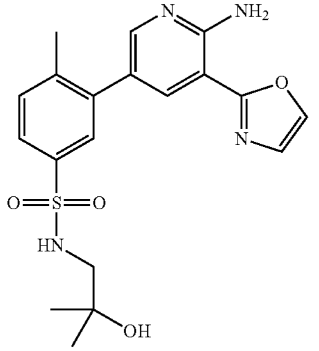

To a mixture of pivalic acid (23 µl, 0.200 mmol), potassium carbonate (207 mg, 1.500 mmol), $Pd(OAc)_2$ (5.6 mg, 0.025 mmol), di(adamantan-1-yl)(butyl)phosphine (17.9 mg, 0.050 mmol) and 3-(6-amino-5-bromopyridin-3-yl)-N-(2-hydroxy-2-methylpropyl)-4-methyl benzenesulfonamide (intermediate EE1) (207 mg, 0.5 mmol was added dry DMA (2.3 mL) followed by oxazole (66 µl, 1.003 mmol). The mixture was de-oxygenated using a stream of nitrogen and heated under nitrogen at 110° C. for 16 hours. The reaction was cooled to room temperature and purified by chromatography on silica (80 g, dry loaded onto silica, eluting with THF/iso hexane 30-65%). Two products were obtained, but both contained impurities. Impure 3-(6-amino-5-(oxazol-5-yl)pyridin-3-yl)-N-(2-hydroxy-2-methylpropyl)-4-methylbenzenesulfonamide (example 94a) was purified by ion exchange [SCX-2 10 g, washing with MeOH and eluting with ammonia 2M in MeOH], and further purified by trituration with ethyl acetate/diethyl ether to give 3-(6-amino-5-(oxazol-5-yl)pyridin-3-yl)-N-(2-hydroxy-2-methylpropyl)-4-methylbenzenesulfonamide (Example 94a) as an off white solid.

LCMS: Rt 2.24 min; MS m/z 403.2 [M+H]+; Method: 8 minLowpHv01

$^1$H NMR (400 MHz, $CDCl_3$) δ 8.10 (1H, d, J=2.3 Hz), 8.03, (1H, s), 7.79-7.72 (3H, m), 7.47-7.42 (2H, m), 5.35 (2H, br s), 4.99-4.96 (1H, m), 2.96-2.94 (2H, m), 2.40 (3H, s), 1.27 (6H, s).

Impure 3-(6-amino-5-(oxazol-2-yl)pyridin-3-yl)-N-(2-hydroxy-2-methylpropyl)-4-methylbenzenesulfonamide (example 94b) was purified by ion exchange [SCX-2 10 g, washing with MeOH and eluting with ammonia 2M in MeOH], and then further purified by mass directed HPLC to give 3-(6-amino-5-(oxazol-2-yl)pyridin-3-yl)-N-(2-hydroxy-2-methylpropyl)-4-methylbenzenesulfonamide (example 94b) as a white solid.

LCMS: Rt 0.89 min, m/z 403.3 [M+H]+; Method Name: 2 minLowpHv03

Example 95 trans-3-(6-amino-5-(3-methylisoxazol-5-yl)pyridin-3-yl)-N-((1r,3r)-3-hydroxycyclobutoxy)-4-methylbenzenesulfonamide

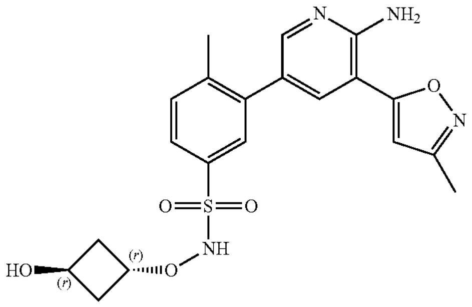 [SMILES: Cc1cc(-c2cc(-c3cc(S(=O)(=O)NO[C@H]4C[C@H](O)C4)ccc3C)cnc2N)on1]

To a stirring solution of O-(3-((tert-butyldimethylsilyl)oxy)cyclobutyl)hydroxylamine (impure product from Example 55, step 2) (358 mg, 1.649 mmol) and DIPEA (360 μl, 2.061 mmol) in DMA (4.1 mL) was added 3-(6-amino-5-(3-methylisoxazol-5-yl)pyridin-3-yl)-4-methylbenzene-1-sulfonyl chloride (Intermediate E3) (300 mg, 0.825 mmol). The reaction mixture was stirred at room temperature overnight, then added to water (50 mL) and extracted with EtOAc (2×50 ml). The organic phase was washed with saturated brine (50 mL) and dried over $MgSO_4$. The solid was removed by filtration, washed with EtOAc and the solvent was concentrated under reduced pressure. The crude material was purified by flash column chromatography, eluting with a gradient of 0-5% MeOH in DCM on a 24 g silica column, loading with DCM. The resulting orange oil was left to dry in a vacuum oven at 50° C. over the weekend.

To a solution of the resulting material in anhydrous THF (2.77 mL) was added TBAF, 1M in THF (832 μl, 0.832 mmol). The reaction mixture was stirred at room temperature overnight, then poured into water (50 ml) and extracted with EtOAc (2×100 ml). The organic layer was washed with saturated brine (50 ml) and dried over $MgSO_4$. The solid was removed by filtration, washed with EtOAc and the solvent was concentrated under reduced pressure. The crude material was purified by flash column chromatography, eluting with a gradient 0-5% MeOH in DCM on a 12 g silica column, loading with DCM. The resulting white solid was left to dry overnight in a vacuum oven at 50° C. Further purification by chiral supercritical fluid chromatography (Chiralcel AS-H 250×10 mm, 5 μm; 40% IPA+0.1% DEA/60% CO2) gave the title compound (trans stereoisomer).

LCMS: Rt 0.93 mins; MS m/z 431.2 [M+H]+; Method: 2 minLowpHv03

$^1$H NMR (400 MHz, d6-DMSO) δ 10.30 (1H, s), 8.16 (1H, s), 7.92 (1H, s), 7.72 (1H, d), 7.66 (1H, s), 7.57 (1H, d), 6.90 (1H, s), 6.52 (2H, s), 5.07 (1H, d), 4.54 (1H, m), 4.20 (1H, m), 2.39 (3H, s), 2.30 (3H, s), 2.21 (2H, m), 2.00 (2H, m).

Example 96 trans-3-(6-amino-5-(3-methylisoxazol-5-yl)pyridin-3-yl)-N-(3-hydroxycyclopentyl)-4-methylbenzenesulfonamide

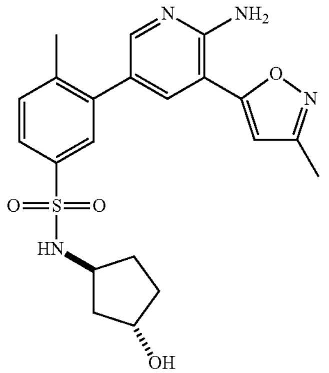

and

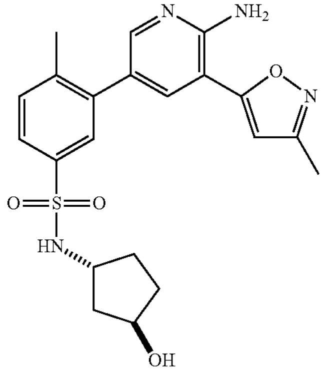

To a stirring solution of trans-3-aminocyclopentanol hydrochloride (68.8 mg, 0.500 mmol) in DMA (1.25 mL), under nitrogen, was added DIPEA (175 μl, 0.999 mmol) and 3-(6-amino-5-(3-methylisoxazol-5-yl)pyridin-3-yl)-4-methylbenzene-1-sulfonyl chloride (Intermediate E3) (100 mg, 0.250 mmol). The reaction mixture was stirred for 24 hours at room temperature, then added to water (50 ml) and product extracted into ethyl acetate (50 ml). Organic extract was washed with brine and concentrated under reduced pressure then purified by flash column chromatography, eluting with 0-10% gradient of (2M $NH_3$ in MeOH) in DCM on a 12 g Si-column, loading with DCM. The resulting oil was sonicated in diethyl ether until a fine precipitate was formed. Some of the excess diethyl ether was decanted away from solid and solid dried under reduced pressure to give a white solid.

LCMS: Rt 0.89 mins; MS m/z 429.4 [M+H]+; Method: 2 minLowpHv03

$^1$H NMR (400 MHz, d6-DMSO) δ 8.14 (1H, s), 7.90 (1H, s), 7.68 (1H, d), 7.64 (1H, s), 7.59 (1H, d), 7.53 (1H, d), 6.90 (1H, s), 6.51 (2H, s), 4.44 (1H, d), 4.05 (1H, br s), 3.62 (1H, q), 3.37 (3H, s), 2.30 (3H, s), 1.79 (2H, m), 1.57 (1H, m), 1.43 (1H, m), 1.29 (2H, m).

Example 97

3-(6-amino-5-(2-methylthiazol-5-yl)pyridin-3-yl)-N-((1r,4r)-4-hydroxycyclohexyl)-4-methylbenzenesulfonamide

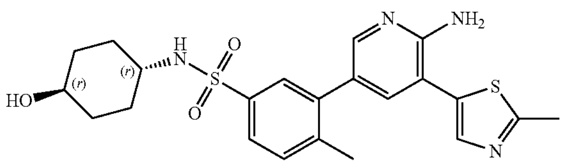 [SMILES: Cc1ncc(-c2cc(-c3cc(S(=O)(=O)N[C@H]4CC[C@H](O)CC4)ccc3C)cnc2N)s1]

Prepared by analogy to Example 28 starting from trans N-(4-hydroxy-cyclohexyl)-4-methyl-3-(4,4,5,5-tetramethyl-[1,3,2]dioxaborolan-2-yl)-benzenesulfonamide (Intermediate B5).

LCMS: Rt 0.74 min; m/z 459.2 [M+H]+; Method: 2 minLowpHv02

Example 98

3-(6-amino-5-(2-methyloxazol-5-yl)pyridin-3-yl)-N-((1r,4r)-4-hydroxycyclohexyl)-4-methylbenzenesulfonamide hydrochloride

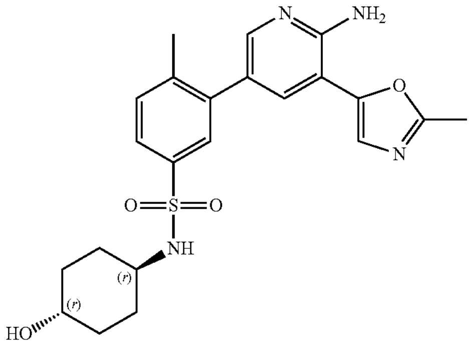 [SMILES: Cc1ncc(-c2cc(-c3cc(S(=O)(=O)N[C@H]4CC[C@H](O)CC4)ccc3C)cnc2N)o1]

Prepared by analogy to Example 69 starting from trans N-(4-hydroxy-cyclohexyl)-4-methyl-3-(4,4,5,5-tetramethyl-[1,3,2]dioxaborolan-2-yl)-benzenesulfonamide (Intermediate B5).

Resulting oil was dissolved in a small amount of MeOH (1 mL) and HCl in Dioxane was added (1 mL)

The mixture was concentrated to dryness and solid recrystallised from hot EtOH (~2 mL). Upon addition of EtOAc (~2 mL), cooling and scratching with a spatula a white solid crystalised which was collected by filtration and dried.

LCMS: Rt 0.74 mins; MS m/z 443.5 [M+H]+; Method: 2 minLowpHv01

$^1$H NMR (400 MHz, d6-DMSO) δ 8.18 (2H, m), 8.05-7.80 (1H, br s), 7.76 (1H, d), 7.72 (1H, s), 7.67 (1H, s), 7.63 (1H, d), 7.56 (1H, s), 4.03 (1H, q), 3.45 (1H, q), 3.30 (1H, m), 2.93 (1H, m), 2.36 (3H, s), 1.71 (2H, m), 1.64 (2H, m), 1.25-1.00 (4H, m). One methyl signal obscured by DMSO peak.

Example 99

5-(6-amino-5-(3-methylisoxazol-5-yl)pyridin-3-yl)-2-fluoro-N-(2-hydroxy-2-methylpropoxy)-4-methylbenzenesulfonamide

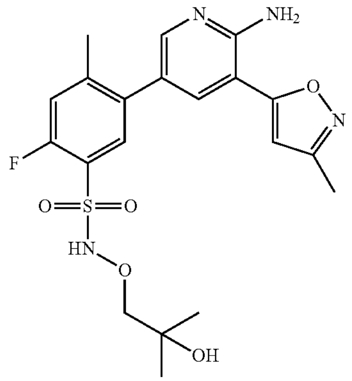 [SMILES: Cc1cc(-c2cc(-c3cc(S(=O)(=O)NOCC(C)(C)O)c(F)cc3C)cnc2N)on1]

Step 1: 5-bromo-2-fluoro-N-(2-hydroxy-2-methylpropoxy)-4-methylbenzenesulfonamide To 5-bromo-2-fluoro-4-methylbenzene-1-sulfonyl chloride (200 mg, 0.696 mmol) was added 1-(aminooxy)-2-methylpropan-2-ol (1.46 g, 13.91 mmol) and the resulting mixture was stirred at room temperature for 24 hours, then diluted with EtOAc and extracted with 1M sodium hydroxide solution. The aqueous layer was neutralised with HCl and extracted with ethyl acetate. The organic layer was dried over magnesium sulfate, filtered and the solvent removed under reduced pressure to give a yellow oil which was purified by flash column chromatography, eluting with a 0% to 60% hexanes:EtOAc gradient, on a 4 g silica cartridge. The relevant fractions were combined and evaporated to give a white solid.

LCMS: Rt 1.17 min; m/z 356.4 [M+H]+ Method: 2 minLowpHv03.

Step 2: 5-(6-amino-5-(3-methylisoxazol-5-yl)pyridin-3-yl)-2-fluoro-N-(2-hydroxy-2-methylpropoxy)-4-methylbenzenesulfonamide A mixture of 5-bromo-2-fluoro-N-(2-hydroxy-2-methylpropoxy)-4-methylbenzenesulfonamide (Step 1) (80 mg, 0.225 mmol), bis(pinacolato)diboron (62.7 mg, 0.247 mmol), potassium acetate (33.1 mg, 0.337 mmol), $PdCl_2$(dppf).$CH_2Cl_2$ adduct (9.2 mg, 0.011 mmol) in DME (3 ml) was heated in the microwave for 1 hour at 120° C. 5-bromo-3-(3-methyl-isoxazol-5-yl)-pyridin-2-ylamine (Intermediate C5) (57.1 mg, 0.225 mmol), $PdCl_2$(dppf).$CH_2Cl_2$ adduct (9.2 mg, 0.011 mmol) and 2M sodium carbonate (0.337 ml, 0.674 mmol) were added and the resulting mixture heated in the microwave at 120° C. for one hour. The RM was diluted with EtOAc and washed with water. The organic layer was collected and Si-TMT was added. The solid was removed by filtration and the solvent removed on a rotary evaporator to give a brown oil. The crude product was purified by flash column chromatography, eluting with a 0% to 10% DCM: MeOH/NH3 gradient, on a 4 g silica cartridge. The relevant fractions were combined and the solvent was removed to give an off white solid.

LCMS: Rt 2.96 min; m/z 451.2, [M+H]+. Method: 8 minLowpHv01

$^1$H NMR (400 MHz, DMSO-$d_6$) δ10.64 (1H, s), 8.12 (1H, s), 7.88 (1H, s), 7.61 (1H, d), 7.49 (1H, d), 6.88 (1H, s), 6.52 (2H, s), 4.50 (1H, s), 3.71 (2H, s), 2.37 (3H, s), 2.31 (3H, s), 1.04 (6H, s).

Example 100

5-(6-amino-5-(3-methyl-1,2,4-oxadiazol-5-yl pyridin-3-yl)-N-(2-hydroxy-2-methylpropyl)-2,4-dimethylbenzenesulfonamide

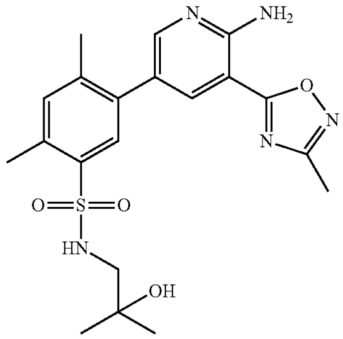 [SMILES: Cc1noc(-c2cc(-c3cc(S(=O)(=O)NCC(C)(C)O)c(C)cc3C)cnc2N)n1]

Step 1: 5-bromo-N-(2-hydroxy-2-methylpropyl)-2,4-dimethylbenzenesulfonamide

To a solution of 1-amino-2-methylpropan-2-ol (123 mg, 1.375 mmol) and DIPEA (0.240 mL, 1.375 mmol) in THF (6 mL) cooled (ice bath) was added dropwise a solution of 5-bromo-2,4-dimethylbenzene-1-sulfonyl chloride (390 mg, 1.375 mmol) in THF (6 mL). The RM was stirred for 16 hrs at RT, then diluted with EtOAc, washed with 1M HCl, sat.$NaHCO_3$, water, brine and dried over $MgSO_4$. The solvent was evaporated under reduced pressure to give the title compound.

LCMS: Rt 1.08 min; m/z 336.2 [M−H]−; Method: 2 minLowpHv01

Step 2: 5-(6-amino-5-(3-methyl-1,2,4-oxadiazol-5-yl)pyridin-3-yl)-N-(2-hydroxy-2-methylpropyl)-2,4-dimethylbenzenesulfonamide To a mixture of 5-bromo-N-(2-hydroxy-2-methylpropyl)-2,4-dimethylbenzenesulfonamide (79 mg, 0.235 mmol), $PdCl_2$(dppf).$CH_2Cl_2$ adduct (9.6 mg, 0.012 mmol), potassium acetate (34.6 mg, 0.353 mmol) was added a solution of bis(pinacolato)diboron (65.7 mg, 0.259 mmol) in DME (2 ml). The resulting mixture was heated in the microwave for 1 hour at 120° C. To the RM was added a solution of 5-bromo-3-[1,2,4]oxadiazol-5-yl-pyridin-2-ylamine (Intermediate C3) (60 mg, 0.235 mmol) in DME (2 ml), $Na_2CO_3$ (0.353 ml, 0.706 mmol) and $PdCl_2$(dppf). $CH_2Cl_2$ adduct (9.6 mg, 0.012 mmol). The resulting mixture was heated in the microwave for 1 hour at 120° C. The RM was washed through a Si-TMT cartridge with acetonitrile. The solvent was removed from the crude product under reduced pressure (Genevac) to give dark brown solid.

The crude solid was dissolved in 1 ml DMSO and purified by preparative HPLC. Fractions containing product were evaporated (Genevac), and redissolved in MeOH, then washed through a Si—CO3 column in order to free base the compounds. The solvent was then evaporated (Genevac) to give the title compound.

LCMS: Rt 3.42 min; m/z 432.8 [M+H]+; Method 8 minLowpHv01

$^1$H NMR (400 MHz, DMSO-d6) δ 8.33 (1H, s) 8.15 (1H, s) 7.65 (1H, s) 7.55 (2H, s) 7.45 (1H, s) 7.35 (1H, s) 4.38 (1H, s) 2.71 (2H, s) 2.58 (3H, s) 2.45 (3H, s) 2.32 (3H, s) 1.03 (6H, s)

Example 101.1

3-(6-amino-5-(3-methylisoxazol-5-yl)pyridin-3-yl)-N-(trans-4-hydroxytetrahydrofuran-3-yl)-4-methylbenzenesulfonamide:trifluoroacetic acid 1:1

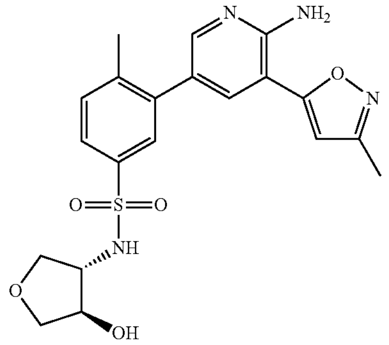

and

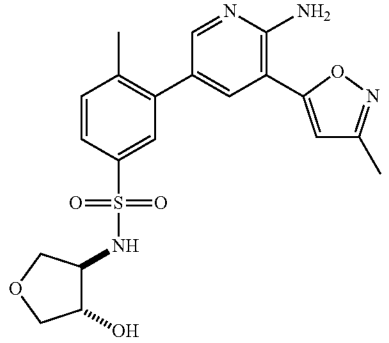

LCMS: Rt 0.73 mins; MS m/z 431.5 [M+H]+; Method 2 minLowpHv01.

Example 101.2

3-(6-amino-5-(3-methylisoxazol-5-yl)pyridin-3-yl)-N-((trans)-2-hydroxycyclopentyl)-4-methylbenzenesulfonamide

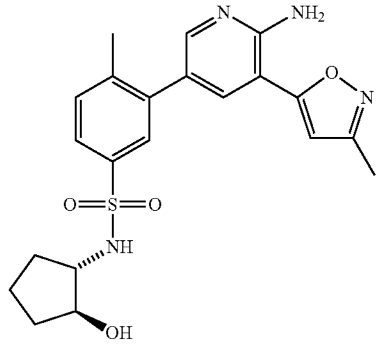

and

-continued

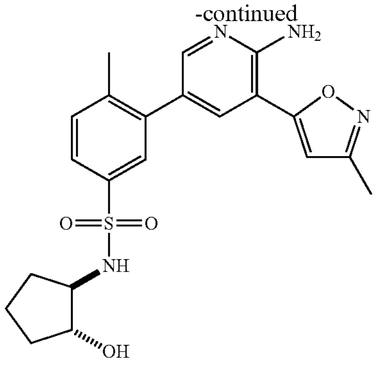

LCMS: Rt 0.8 mins; MS m/z 429.5 [M+H]+; Method 2 minLowpHv0.

Example 101.3 trans-1-((3-(6-amino-5-(3-methylisoxazol-5-yl)pyridin-3-yl)-4-methylphenyl)sulfonyl)-4-methylpyrrolidin-3-ol

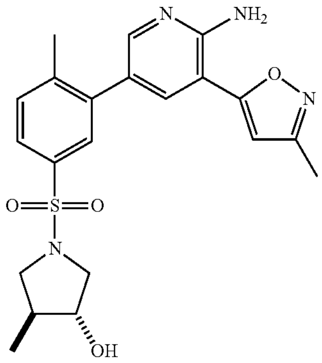

and

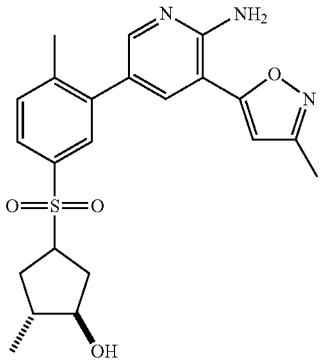

LCMS: Rt 0.82 mins; MS m/z 429.5 [M+H]+; Method 2 minLowpHv10.

Example 102

3-(6-amino-5-(5-methyl-1,3,4-thiadiazol-2-yl)pyridin-3-yl)-N-(2-hydroxy-2-methylpropyl)-4-methylbenzenesulfonamide

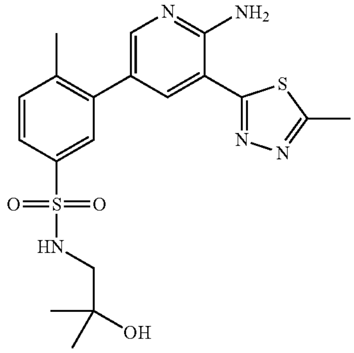 [SMILES: Cc1nnc(-c2cc(-c3cc(S(=O)(=O)NCC(C)(C)O)ccc3C)cnc2N)s1]

Step 1: N'-acetyl-2-amino-5-bromonicotinohydrazide

To a mixture of 2-amino-5-bromonicotinic acid (2 g, 9.22 mmol), acetohydrazide (0.819 g, 11.06 mmol) and TEA (5.14 ml, 36.9 mmol) in DMF (60 ml) under N2 was added T3P (50% in DMF) (8.23 ml, 27.6 mmol) over 5 mins and the reaction left stirring at room temperature for 3 days.

The resulting mixture was added to 1M HCl (10 ml) and extracted into EtOAc, washed with 1M NaOH (10 ml), brine and dried over magnesium sulfate before being concentrated under reduced pressure. The acidic washings were neutralised by addition of NaOH and extracted again into EtOAc, washed with brine, dried over magnesium sulfate and concentrated under reduced pressure. Used without further purification.

LCMS: Rt=0.38 mins MS m/z $[M+H]^+$=273.3 (smaller Br isotope reported) Method: 2 minLowpHv01

Step 2: 5-bromo-3-(5-methyl-1,3,4-thiadiazol-2-yl)pyridin-2-amine

To a stirring dispersion of N'-acetyl-2-amino-5-bromonicotinohydrazide (Step 1, 100 mg, 0.366 mmol) in THF (1.8 mL) was added Lawesson's reagent (222 mg, 0.549 mmol). Reaction was heated to 70° C. for 3 hours. To a further solution of N'-acetyl-2-amino-5-bromonicotinohydrazide (Step 1, 1 g, 3.66 mmol) in THF (18.3 mL) was added Lawesson's reagent (1.925 g, 4.76 mmol).

Reaction was heated to 60° C. for 3 hours. Combined reaction mixtures were filtered to remove solids and the filtate was concentrated under reduced pressure then purified by flash column chromatography (silica, ethyl acetate/hexane gradients). The resulting gummy solid was diluted with sat. $NaHCO_3$ and product extracted into EtOAc. This mixture was stirred for 30 mins, and the organic extract was washed with brine, dried over magnesium sulfate and concentrated under reduced pressure to give white solid which was used without further purification in subsequent steps LCMS: Rt 1.03 mins; MS m/z 273.4 [M+H]+, larger of Br isotopes reported; Method: 2 minLowpHv03.

Step 3: 3-(6-amino-5-(5-methyl-1,3,4-thiadiazol-2-yl)pyridin-3-yl)-N-(2-hydroxy-2-methylpropyl)-4-methylbenzenesulfonamide To a mixture of 5-bromo-3-(5-methyl-1,3,4-thiadiazol-2-yl)pyridin-2-amine (Step 2, 90 mg, 0.332 mmol) in DME (1.6 mL) was added N-(2-hydroxy-2-methyl-propyl)-4-methyl-3-(4,4,5,5-tetramethyl[1,3,2] dioxaborolan-2-yl) benzenesulfonamide (Intermediate B2) (123 mg, 0.332 mmol), 2M aqueous sodium carbonate (498 μl, 0.996 mmol) and bis(triphenylphosphine)palladium(II) chloride (11.65 mg, 0.017 mmol). The reaction was heated in the microwave at 120° C. for 1 hour. Further bis(triphenylphosphine)palladium(II) chloride (35 mg, 0.051 mmol) was added and reaction heated in the microwave for 4 hours at 140° C. The resulting mixture was added to water (50 ml), and product extracted into EtOAc (2×50 ml). The organic extracts were combined, washed with brine, dried over magnesium sulfate containing Si-TMT to remove Pd and concentrated under reduced pressure. Crude product was purified by triturating with 5% MeOH in DCM to give 22 mg of yellow solid.

LCMS: Rt=0.94 mins; MS m/z 434.5 [M+H]+; Method 2 minLowpHv03

$^1$H NMR (400 MHz, d6-DMSO) δ 8.20 (1H, s), 7.91 (1H, s), 7.73 (2H, s), 7.69 (2H, s), 7.53 (1H, d), 7.45 (1H, t), 4.40 (1H, s), 2.78 (3H, s), 2.63 (2H, d), 2.37 (3H, s), 1.07 (6H, s).

Example 103a: (R or S)-3-(6-amino-5-(3-methylisoxazol-5-yl)pyridin-3-yl)-4-methyl-N-(1,1,1-trifluoro-3-hydroxypropan-2-yl)benzenesulfonamide and Example 103b: (R or S)-3-(6-amino-5-(3-methylisoxazol-5-yl)pyridin-3-yl)-4-methyl-N-(1,1,1-trifluoro-3-hydroxypropan-2-yl)benzenesulfonamide

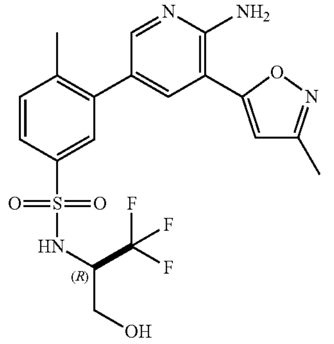

and

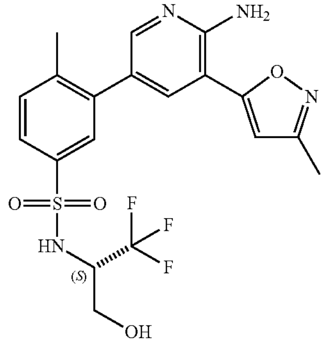

To a stirring solution of 2-amino-3,3,3-trifluoropropan-1-ol.HCl (83 mg, 0.500 mmol) in DMA (1.25 mL), under nitrogen, was added DIPEA (175 μl, 0.999 mmol) and 3-(6-amino-5-(3-methylisoxazol-5-yl)pyridin-3-yl)-4-methylbenzene-1-sulfonyl chloride (Intermediate E3) (100 mg, 0.250 mmol). The reaction mixture was stirred for 24 hours at RT, then added to water (50 ml) and product extracted into EtOAc (50 ml). Organic extract was washed with brine and concentrated under reduced pressure. Crude product was purified by automated flash column chromatography, eluting with 0-10% gradient of (2M NH3 in MeOH) in DCM on a 12 g Si-column, loading with DCM. The resulting oil was sonicated in diethyl ether until a fine precipitate was formed. Some of the excess diethyl ether was decanted away from solid and solid dried in vacuo. Chiral separation of the racemate formed using Supercritical Fluid Chromatography (Chiralpak AS-H, 250×10 mm, 5 um, Mobile phase: 40% IPA+0.1% DEA/60% CO2, Flow: 10 ml/min, Detection: UV @ 220 nm) afforded the individual enantiomers (Examples 103a and 103b). Fractions collected were analysed by analytical chiral SFC (Chiralpak AS-H, 250×10 mm, 5 um, Mobile phase: 40% IPA+0.1% DEA/60% CO2, Flow: 10 ml/min, Detection: UV @ 220 nm).

Example 103a: First Eluted Peak (R)-3-(6-amino-5-(3-methylisoxazol-5-yl)pyridin-3-yl)-4-methyl-N-(1,1,1-trifluoro-3-hydroxypropan-2-yl)benzenesulfonamide or (S)-3-(6-amino-5-(3-methylisoxazol-5-yl)pyridin-3-yl)-4-methyl-N-(1,1,1-trifluoro-3-hydroxypropan-2-yl)benzenesulfonamide SFC (Chiralpak AS-H, 250×10 mm, 5 um, Mobile phase: 40% IPA+0.1% DEA/60% CO2, Flow: 10 ml/min, Detection: UV @ 220 nm): Rt 2.40 min LCMS: Rt=1.00 mins; MS m/z 457.3 [M+H]+; 2 minLowpHv03

$^1$H NMR (400 MHz, DMSO-d6) δ 8.46 (1H, s), 8.14 (1H, s), 7.89 (1H, m), 7.73 (1H, s), 7.71 (1H, s), 7.52 (1H, d), 6.89 (1H, s), 6.50 (2H, s), 5.04 (1H, t), 4.02 (1H, m), 3.50 (1H, t), 3.41 (1H, t), 2.37 (3H, s), 2.31 (3H, s).

Example 103b: Second Eluted Peak (R)-3-(6-amino-5-(3-methylisoxazol-5-yl)pyridin-3-yl)-4-methyl-N-(1,1,1-trifluoro-3-hydroxypropan-2-yl)benzenesulfonamide or (S)-3-(6-amino-5-(3-methylisoxazol-5-yl)pyridin-3-yl)-4-methyl-N-(1,1,1-trifluoro-3-hydroxypropan-2-yl)benzenesulfonamide SFC (Chiralpak AS-H, 250×10 mm, 5 um, Mobile phase: 40% IPA+0.1% DEA/60% CO2, Flow: 10 ml/min, Detection: UV @ 220 nm): Rt 2.95 min LCMS: Rt=0.98 mins; MS m/z 457.2 [M+H]+; 2 minLowpHv03

$^1$H NMR (400 MHz, DMSO-d6) is the same as that for its enantiomer Example 103a The following examples 104.1 to 104.16 were prepared by analogy to Example 19 starting from an appropriate commercially available amine and 3-(6-amino-5-(2-methyloxazol-5-yl)pyridin-3-yl)-4-methylbenzene-1-sulfonyl chloride (Intermediate E4).

Mass spectra were run on LCMS system Agilent 1100 HPLC/Micromass ZMD Mass Spectrometer using electrospray ionization and Waters XBridge C18 column

| Ex # | Structure | Name | RT (min) | MS [M + H]+ |
|---|---|---|---|---|
| 104.1 | 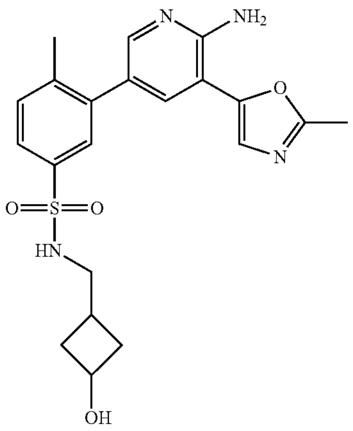 [SMILES: Cc1ncc(-c2cc(-c3cc(S(=O)(=O)NCC4CC(O)C4)ccc3C)cnc2N)o1] | 3-(6-amino-5-(2-methyloxazol-5-yl)pyridin-3-yl)-N-((3-hydroxycyclobutyl) methyl)-4-methylbenzenesulfon-amide | 4.09 | 429.50 |
| 104.2 | 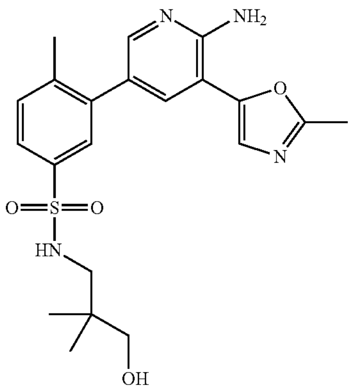 [SMILES: Cc1ncc(-c2cc(-c3cc(S(=O)(=O)NCC(C)(C)CO)ccc3C)cnc2N)o1] | 3-(6-amino-5-(2-methyloxazol-5-yl)pyridin-3-yl)-N-(3-hydroxy-2,2-dimethylpropyl)-4-methylbenzenesulfon-amide | 4.26 | 431.53 |
| 104.3 | 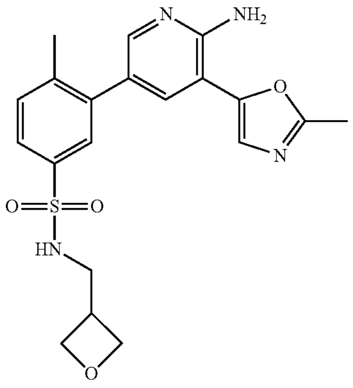 [SMILES: Cc1ncc(-c2cc(-c3cc(S(=O)(=O)NCC4COC4)ccc3C)cnc2N)o1] | 3-(6-amino-5-(2-methyloxazol-5-yl)pyridin-3-yl)-4-methyl-N-(oxetan-3-ylmethyl)benzenesulfon-amide | 4.14 | 415.52 |
| 104.4 | 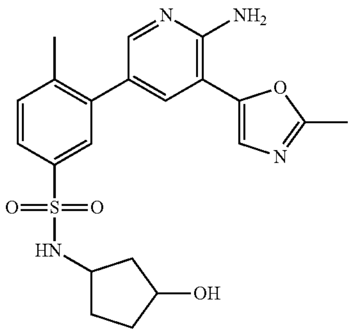 [SMILES: Cc1ncc(-c2cc(-c3cc(S(=O)(=O)NC4CCC(O)C4)ccc3C)cnc2N)o1] | (+/−)trans-3-(6-amino-5-(2-methyloxazol-5-yl)pyridin-3-yl)-N-(3-hydroxycyclopentyl)-4-methylbenzenesulfon-amide | 4.05 | 429.56 |

-continued

| Ex # | Structure | Name | RT (min) | MS [M + H]+ |
|---|---|---|---|---|
| 104.5 | 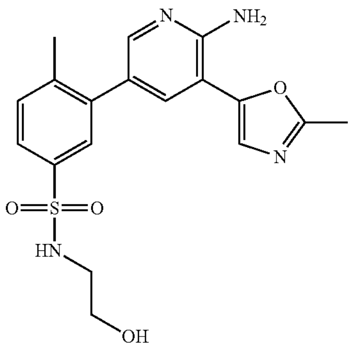 [SMILES: Cc1ncc(-c2cc(-c3cc(S(=O)(=O)NCCO)ccc3C)cnc2N)o1] | 3-(6-amino-5-(2-methyloxazol-5-yl)pyridin-3-yl)-N-(2-hydroxyethyl)-4-methylbenzenesulfonamide | 4.01 | 389.53 |
| 104.6 | 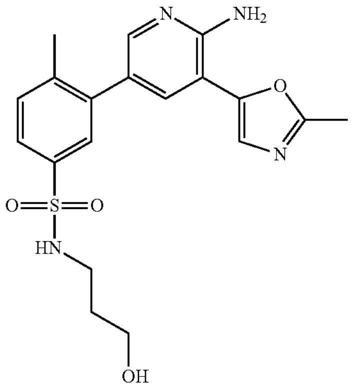 [SMILES: Cc1ncc(-c2cc(-c3cc(S(=O)(=O)NCCCO)ccc3C)cnc2N)o1] | 3-(6-amino-5-(2-methyloxazol-5-yl)pyridin-3-yl)-N-(3-hydroxypropyl)-4-methylbenzenesulfonamide | 3.92 | 403.54 |
| 104.7 | 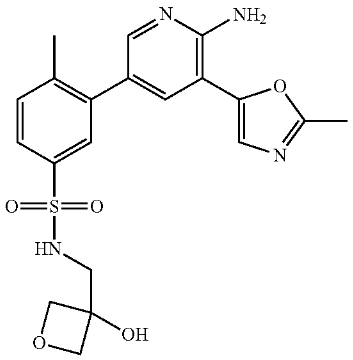 [SMILES: Cc1ncc(-c2cc(-c3cc(S(=O)(=O)NCC4(O)COC4)ccc3C)cnc2N)o1] | 3-(6-amino-5-(2-methyloxazol-5-yl)pyridin-3-yl)-N-((3-hydroxyoxetan-3-yl)methyl)-4-methylbenzenesulfonamide | 4.03 | 431.55 |
| 104.8 | 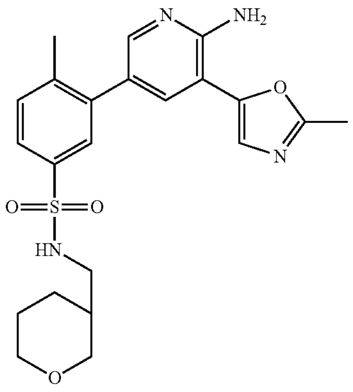 [SMILES: Cc1ncc(-c2cc(-c3cc(S(=O)(=O)NCC4CCCOC4)ccc3C)cnc2N)o1] | 3-(6-amino-5-(2-methyloxazol-5-yl)pyridin-3-yl)-4-methyl-N-((tetrahydro-2H-pyran-3-yl)methyl)benzenesulfonamide | 4.41 | 443.60 |

-continued

| Ex # | Structure | Name | RT (min) | MS [M + H]+ |
|---|---|---|---|---|
| 104.9 | 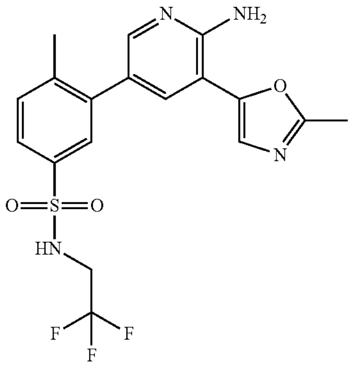 [SMILES: Cc1ncc(-c2cc(-c3cc(S(=O)(=O)NCC(F)(F)F)ccc3C)cnc2N)o1] | 3-(6-amino-5-(2-methyloxazol-5-yl)pyridin-3-yl)-4-methyl-N-(2,2,2-trifluoroethyl)benzene-sulfonamide | 4.57 | 427.53 |
| 104.10 | 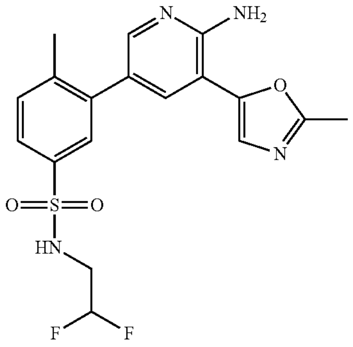 [SMILES: Cc1ncc(-c2cc(-c3cc(S(=O)(=O)NCC(F)F)ccc3C)cnc2N)o1] | 3-(6-amino-5-(2-methyloxazol-5-yl)pyridin-3-yl)-N-(2,2-difluoroethyl)-4-methylbenzenesulfon-amide | 4.28 | 409.53 |
| 104.11 | 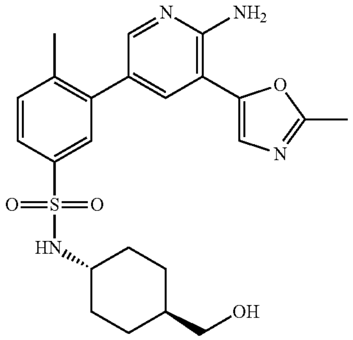 [SMILES: Cc1ncc(-c2cc(-c3cc(S(=O)(=O)N[C@H]4CC[C@H](CO)CC4)ccc3C)cnc2N)o1] | 3-(6-amino-5-(2-methyloxazol-5-yl)pyridin-3-yl)-N-((1r,4r)-4-(hydroxymethyl)cyclo-hexyl)-4-methylbenzenesulfon-amide | 4.24 | 457.65 |
| 104.12 | 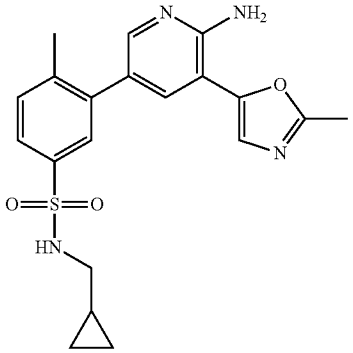 [SMILES: Cc1ncc(-c2cc(-c3cc(S(=O)(=O)NCC4CC4)ccc3C)cnc2N)o1] | 3-(6-amino-5-(2-methyloxazol-5-yl)pyridin-3-yl)-N-(cyclopropylmethyl)-4-methylbenzenesulfon-amide | 4.52 | 399.58 |

-continued

| Ex # | Structure | Name | RT (min) | MS [M + H]+ |
|---|---|---|---|---|
| 104.13 | 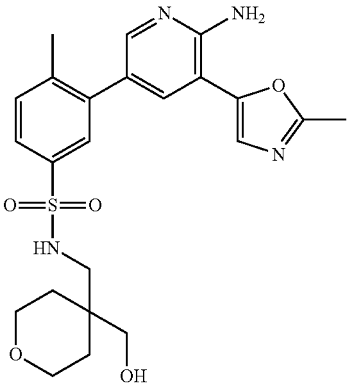 [SMILES: Cc1ncc(-c2cc(-c3cc(S(=O)(=O)NCC4(CO)CCOCC4)ccc3C)cnc2N)o1] | 3-(6-amino-5-(2-methyloxazol-5-yl)pyridin-3-yl)-N-((4-(hydroxymethyl)tetra-hydro-2H-pyran-4-yl)methyl)-4-methylbenzenesulfon-amide | 4.13 | 473.65 |
| 104.14 | 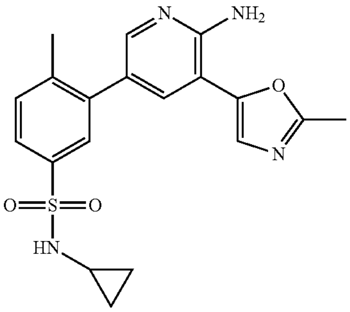 [SMILES: Cc1ncc(-c2cc(-c3cc(S(=O)(=O)NC4CC4)ccc3C)cnc2N)o1] | 3-(6-amino-5-(2-methyloxazol-5-yl)pyridin-3-yl)-N-cyclopropyl-4-methylbenzenesulfon-amide | 4.44 | 385.61 |
| 104.15 | 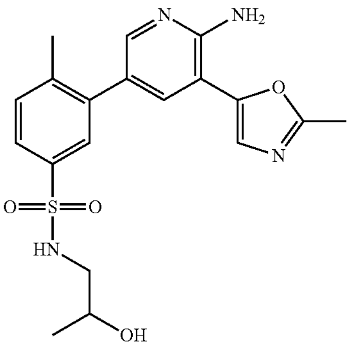 [SMILES: Cc1ncc(-c2cc(-c3cc(S(=O)(=O)NCC(C)O)ccc3C)cnc2N)o1] | rac-3-(6-amino-5-(2-methyloxazol-5-yl)pyridin-3-yl)-N-(2-hydroxypropyl)-4-methylbenzenesulfon-amide | 4.26 | 403.63 |
| 104.16 | 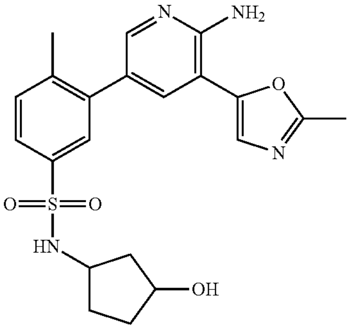 [SMILES: Cc1ncc(-c2cc(-c3cc(S(=O)(=O)NC4CCC(O)C4)ccc3C)cnc2N)o1] | (+/−)-cis-3-(6-amino-5-(2-methyloxazol-5-yl)pyridin-3-yl)-N-(3-hydroxycyclopentyl)-4-methylbenzenesulfon-amide | 4.09 | 429.54 |

Example 105

3-(6-amino-5-(5-methyl-1,3,4-thiadiazol-2-yl)pyridin-3-yl)-N-(3-hydroxy-3-methyl butyl)-4-methylbenzenesulfonamide

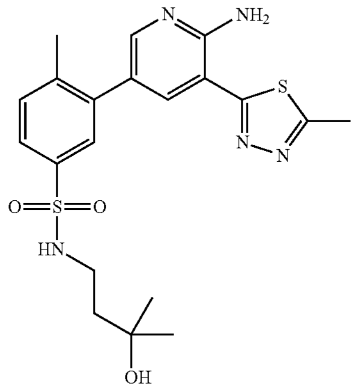 [SMILES: Cc1nnc(-c2cc(-c3cc(S(=O)(=O)NCCC(C)(C)O)ccc3C)cnc2N)s1]

The title compound was prepared by analogy to example 102, using N-(3-hydroxy-3-methylbutyl)-4-methyl-3-(4,4,5,5-tetramethyl-1,3,2-dioxaborolan-2-yl)benzenesulfonamide (Intermediate B3).

LCMS: Rt=0.97 mins; MS m/z 448.3 [M+H]+; Method 2 minLowpHv03

$^1$H NMR (400 MHz, DMSO-d6) δ 8.19 (1H, d), 7.91 (1H, d), 7.73 (2H, s), 7.69 (1H, d), 7.65 (1H, s), 7.55 (1H, d), 7.41 (1H, s), 4.28 (1H, s), 2.84 (2H, br. s), 2.78 (3H, s), 2.37 (3H, s), 1.51, (2H, t), 1.03 (6H, s).

Example 106

3-(6-amino-5-(2-methyl-2H-1,2,3-triazol-4-yl)pyridin-3-yl)-N-(3-hydroxy-3-methylbutyl)-4-methylbenzenesulfonamide

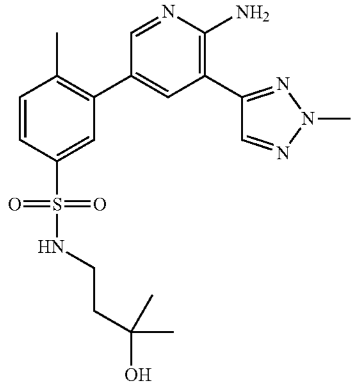 [SMILES: Cc1ccc(S(=O)(=O)NCCC(C)(C)O)cc1-c1cnc(N)c(-c2cnn(C)n2)c1]

The title compound was prepared by analogy to example 4.4, using N-(3-hydroxy-3-methylbutyl)-4-methyl-3-(4,4,5,5-tetramethyl-1,3,2-dioxaborolan-2-yl)benzenesulfonamide (Intermediate B3).

LCMS: Rt=0.72 mins; MS m/z 431.7 [M+H]+; Method 2 minLowpHv1.

$^1$H NMR (400 MHz, DMSO-d6) δ 8.56 (2H, mult), 8.18 (2H, br.s.), 7.75 (1H, d), 7.72 (1H, br.s.), 7.60 (1H, d), 7.49 (1H, t), 4.29 (3H, s), 2.84 (2H, mult), 2.38 (3H, s), 1.52 (2H, mult), 1.03 (6H, s).

Example 107

3-(6-amino-5-(2-methyloxazol-5-yl)pyridin-3-yl)-N-(2-hydroxy-2-methylpropoxy)-4-methylbenzenesulfonamide hydrochloride

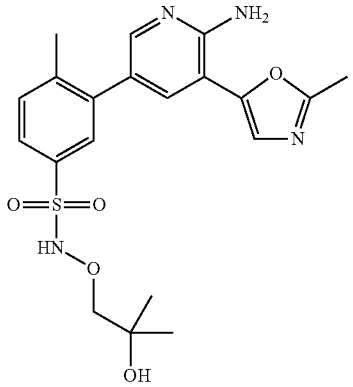 [SMILES: Cc1ncc(-c2cc(-c3cc(S(=O)(=O)NOCC(C)(C)O)ccc3C)cnc2N)o1]

LCMS: Rt=0.77 mins; MS m/z 433.3 [M+H]+; 2 minLowpHv01

$^1$H NMR (400 MHz, DMSO-d6) δ 10.46 (1H, s), 8.17 (1H, s), 8.12 (1H, s), 7.80 (1H, d), 7.74 (1H, s), 7.63 (2H, m), 3.72 (2H, s), 2.39 (3H, s), 1.05 (6H, s).

A CH3 is under the DMSO & the NH2/NH3 (salt) cannot be seen. Broad water peak

Example 108

Rac-3-(6-amino-5-(3-methyl-1,2,4-oxadiazol-5-yl)pyridin-3-yl)-N-(2-hydroxypropyl)-4-methylbenzenesulfonamide

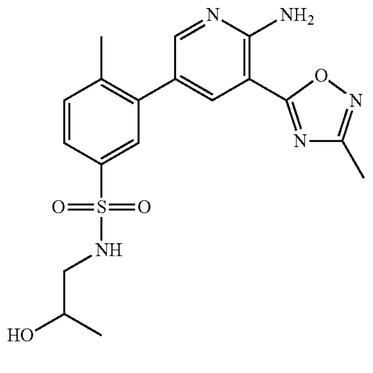 [SMILES: Cc1noc(-c2cc(-c3cc(S(=O)(=O)NCC(C)O)ccc3C)cnc2N)n1]

To a stirring mixture of 1-aminopropan-2-ol (20 mg, 0.266 mmol) and 3-(6-amino-5-(3-methyl-1,2,4-oxadiazol-5-yl)pyridin-3-yl)-4-methylbenzene-1-sulfonyl chloride (Intermediate E2) (50 mg, 0.125 mmol) in THF (1 mL) was added pyridine (50 μl, 0.618 mmol) and the resulting mixture stirred for 24 h at room temperature. The reaction mixture was diluted with DCM and washed with water. Organic phase collected and dried by passing through a phase separator. Evaporated under reduced pressure and purified by mass directed HPLC to give the title compound as a white solid.

LCMS: Rt 0.91 min; m/z 404.2 [M+H]+; Method: 2 minLowpHv01

$^1$H NMR (400 MHz, DMSO-d6) δ 8.36 (1H, d, J=2.5 Hz), 8.19 (1H, d, J=2.5 Hz), 7.71-7.67 (2H, m), 7.63-7.5 (4H, m), 4.68 (1H, d, J=5 Hz), 3.61 (1H, m), 2.72-2.59 (2H, m), 2.47 (3H, s), 2.38 (3H, s), 1.01 (3H, d).

Example 109

5-(6-amino-5-(3-methylisoxazol-5-yl)pyridin-3-yl)-2-fluoro-N-(2-hydroxy-2-methylpropyl)-4-methyl-benzenesulfonamide

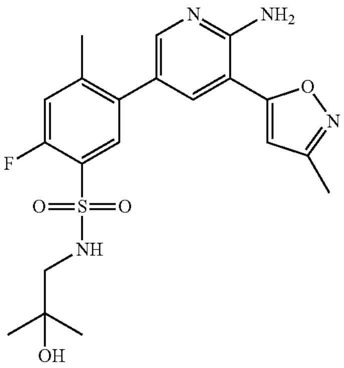 [SMILES: Cc1cc(-c2cc(-c3cc(S(=O)(=O)NCC(C)(C)O)c(F)cc3C)cnc2N)on1]

The title compound was prepared by analogy to Example 85 using 5-bromo-3-(3-methyl-isoxazol-5-yl)-pyridin-2-ylamine (Intermediate C5).

LCMS: Rt 2.86 min; m/z 435.6 [M+H]+. Method: 8 minLowpHv01.

$^1$H NMR (400 MHz, DMSO-d6) δ 8.13 (1H, s), 7.89 (1H, s) 7.67 (1H, s) 7.58 (1H, d) 7.43 (1H, d) 6.89 (1H, s) 6.49 (2H, s) 4.42 (1H, s) 2.80 (2H, m) 2.34 (3H, s) 2.30 (3H, s) 1.07 (6H, s)

Example 110

3-(6-amino-5-(1-methyl-1H-pyrazol-3-yl)pyridin-3-yl)-N-(2-hydroxy-2-methylpropyl)-4-methylbenzenesulfonamide

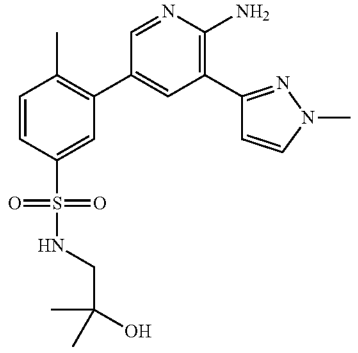 [SMILES: Cc1ccc(S(=O)(=O)NCC(C)(C)O)cc1-c1cnc(N)c(-c2ccn(C)n2)c1]

LCMS: Rt 2.05 min; m/z 416.6 [M+H]+; Method 8 minLowpHv01

$^1$H NMR (400 MHz, $CDCl_3$) δ 7.96 (1H, s), 7.79-7.67 (3H, m), 7.46-7.37 (2H, m), 6.66 (2H, br. s.), 6.58 (1H, m), 5.71 (1H, t, J=6.4 Hz), 3.98 (3H, s), 2.94 (2H, d, J=6.4 Hz), 2.38 (3H, s), 1.27 (6H, s). One proton not observed—likely OH masked by a water peak.

Example 111

3-(6-amino-5-(3-methylisoxazol-5-yl)pyridin-3-yl)-N-(2-hydroxy-2-methylpropyl)benzenesulfonamide

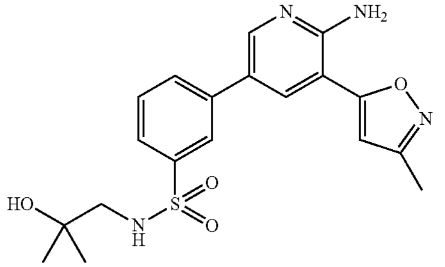 [SMILES: Cc1cc(-c2cc(-c3cccc(S(=O)(=O)NCC(C)(C)O)c3)cnc2N)on1]

A mixture of bis(pinacolato)diboron (0.152 g, 0.600 mmol), 3-bromo-N-(2-hydroxy-2-methylpropyl)benzene-sulfonamide (prepared by analogy to intermediate A2, 0.154 g, 0.5 mmol), and potassium acetate (0.074 g, 0.750 mmol) and $PdCl_2(dppf).CH_2Cl_2$ adduct (0.082 g, 0.100 mmol) was heated in the microwave at 120° C. for 1 hr. The resulting mixture was added to 5-bromo-3-(3-methyl-isoxazol-5-yl)-pyridin-2-ylamine (Intermediate C5, 63.5 mg, 0.250 mmol), sodium carbonate 2M aq (0.375 mL, 0.750 mmol) and $PdCl_2(dppf).CH_2Cl_2$ adduct (40.8 mg, 0.050 mmol) in DME (6 mL) to give a black suspension. The RM was degassed and put under nitrogen atmosphere, and heated to 120° C. for 45 min in the microwave, then stirred with 0.6 g of Si-TMT for 15 min. Silica was added and solvents evaporated. The product was purified by flash column chromagraphy using a 12 g silica flash column eluting on a gradient of 0-10% MeOH/DCM. Fractions were combined and concentrated. The resulting solid was triturated in ethyl acetate and filtered to give 3 crops. The 3 crops were combined, suspended in diethyl ether and evaporated to give the title compound.

$^1$H NMR (400 MHz, $CD_3OD$) δ 8.43 (1H, d), 8.22 (1H, d), 8.10 (1H, m), 7.89 (1H, d), 7.83 (1H, d), 7.66 (1H, t), 6.79 (1H, s), 2.82 (2H, s), 2.38 (3H, s), 1.19 (6H, s) LC-MS: Rt 2.70 mins; MS m/z 403.4 [M+H]+; 8 minLowpHv01

Example 112

3-(6-amino-5-(2-methyloxazol-5-yl)pyridin-3-yl)-N-((1S,3S)-3-hydroxycyclohexyl)-4-methylbenzenesulfonamide

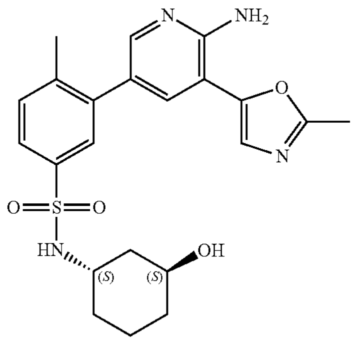

The title compound was prepared by analogy to Example 19 starting from the appropriate amine (may be prepared as described in Brocklehurst et al., *Org. Proc. Res. Dev,* 2011, 15, 294-300) and 3-(6-amino-5-(2-methyloxazol-5-yl)pyridin-3-yl)-4-methylbenzene-1-sulfonyl chloride (Intermediate E4).

LCMS: Rt=0.81 mins; MS m/z 443.4 [M+H]+; Method: 2 minLowpHv03

Example 113

5-(6-amino-5-(3-methyl-1,2,4-oxadiazol-5-yl)pyridin-3-yl)-4-fluoro-N-(2-hydroxy-2-methylpropyl)-2-methylbenzenesulfonamide

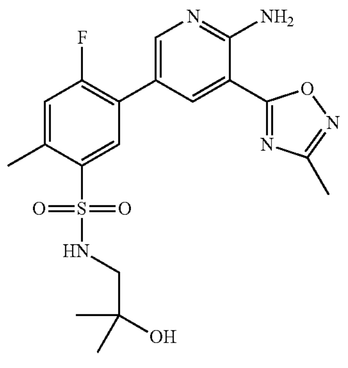 [SMILES: Cc1noc(-c2cc(-c3cc(S(=O)(=O)NCC(C)(C)O)c(C)cc3F)cnc2N)n1]

Prepared by analogy to Example 99 Step 2 using 5-bromo-3-[1,2,4]oxadiazol-5-yl-pyridin-2-ylamine (Intermediate C3) and 5-bromo-4-fluoro-N-(2-hydroxy-2-methylpropyl)-2-methylbenzenesulfonamide (which was itself prepared by analogy to intermediate A2 starting from 5-bromo-4-fluoro-2-methylbenzene-1-sulfonyl chloride).

$^1$H NMR (400 MHz, d6-DMSO) δ 8.52 (1H, m), 8.35 (1H, m), 7.97 (1H, d), 7.68 (2H, s), 7.63 (1H, s), 7.43 (1H, d), 4.41 (1H, s), 2.76 (2H, s), 2.62 (3H, s), 2.47 (3H, s), 1.05 (6H, s).

LCMS: Rt=3.49 mins; MS m/z 436.4 [M+H]+; Method: 8 minLowpHv01

The following examples 114.1 to 114.4 were prepared by analogy to Example 19 starting from an appropriate commercially available amine and 3-(6-amino-5-(2-methyloxazol-5-yl)pyridin-3-yl)-4-methylbenzene-1-sulfonyl chloride (Intermediate E4). LCMS data is using method 2 minLowpHv03.

| Ex # | Structure | Name | RT (min) | MS [M + H]+ |
|---|---|---|---|---|
| 114.1 | 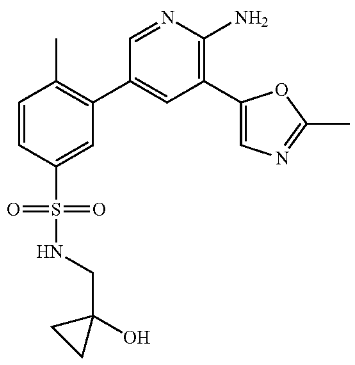 [SMILES: Cc1ncc(-c2cc(-c3cc(S(=O)(=O)NCC4(O)CC4)ccc3C)cnc2N)o1] | 3-(6-amino-5-(2-methyloxazol-5-yl)pyridin-3-yl)-N-((1-hydroxycyclopropyl) methyl)-4-methylbenzenesulfonamide | 0.80 | 415.3 |
| 114.2 | 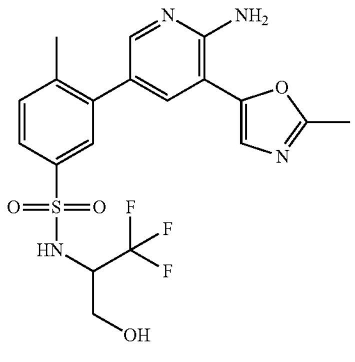 [SMILES: Cc1ncc(-c2cc(-c3cc(S(=O)(=O)NC(CO)C(F)(F)F)ccc3C)cnc2N)o1] | 3-(6-amino-5-(2-methyloxazol-5-yl)pyridin-3-yl)-4-methyl-N-(1,1,1-trifluoro-3-hydroxypropan-2-yl)benzenesulfonamide | 0.87 | 457.4 |

-continued

| Ex # | Structure | Name | RT (min) | MS [M + H]+ |
|---|---|---|---|---|
| 114.3 | 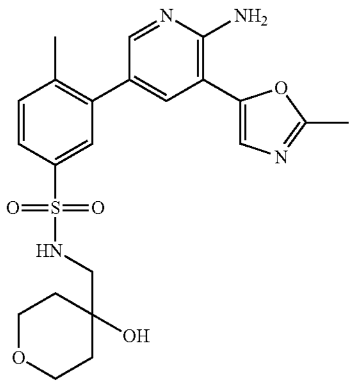 [SMILES: Cc1ncc(-c2cc(-c3cc(S(=O)(=O)NCC4(O)CCOCC4)ccc3C)cnc2N)o1] | 3-(6-amino-5-(2-methyloxazol-5-yl)pyridin-3-yl)-N-((4-hydroxytetrahydro-2H-pyran-4-yl)methyl)-4-methylbenzenesulfonamide | 0.78 | 459.4 |
| 114.4 | 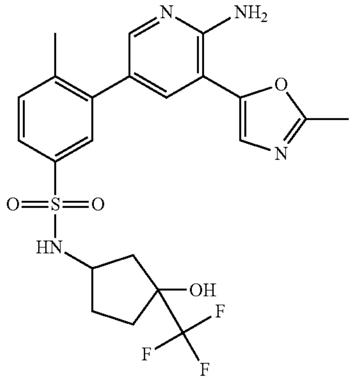 [SMILES: Cc1ncc(-c2cc(-c3cc(S(=O)(=O)NC4CCC(O)(C(F)(F)F)C4)ccc3C)cnc2N)o1] | 3-(6-amino-5-(2-methyloxazol-5-yl)pyridin-3-yl)-N-(3-hydroxy-3-(trifluoromethyl)cyclopentyl)-4-methylbenzenesulfonamide | 0.99 | 497.4 |

Example 115

3-(6-Amino-5-(2-cyclopropyloxazol-5-yl)pyridin-3-yl)-N-(2-hydroxy-2-methylpropyl)-4-methylbenzenesulfonamide

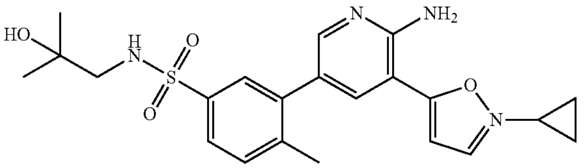

5-Bromo-3-(2-cyclopropyloxazol-5-yl)pyridin-2-amine (Intermediate F, 100 mg, 0.357 mmol), potassium acetate (52.6 mg, 0.535 mmol), 2M sodium carbonate (0.535 ml, 1.071 mmol), and $PdCl_2(dppf).CH_2Cl_2$ adduct (14.58 mg, 0.018 mmol) were added into DME (4 ml) to give a brown/orange solution. The reaction mixture was heated in the microwave under an atmosphere of nitrogen at 120° C. for 45 min. The reaction mixture was diluted with EtOAc (20 mL) and water (20 mL). The organic phase was washed with $NaHCO_3$ (20 mL). The organic phase was dried with $MgSO_4$, filtered and concentrated. The product dissolved in DCM (10 mL) and was scavenged with Si-TMT resin (2,4,6-trimercaptotriazine silica, 1 g loose resin), filtered and concentrated under reduced pressure. The product was purified by silica flash column chromagraphy eluting on a gradient of 50-100% EtOAc/hexane. Fractions were combined and concentrated to afford a yellow oil $^1$H NMR (400 MHz), $CDCl_3$ δ 8.05 (1H, s), 7.78 (1H, d), 7.73 (1H, s), 7.69 (1H, s), 7.45 (1H, d), 7.24 (1H, s), 5.32 (2H, s), 5.17 (1H, m), 2.94 (2H, d), 2.39 (3H, s), 2.16 (1H, m), 2.5-1.5 (1H, broad exchangeable), 1.28 (6H, s), 1.15 (4H, m).

LC-MS: Rt 2.63 mins; MS m/z 443/444/445 {M+H}+; Method 8 minLowpHv01

Preparation of Intermediates

Bromides (A)

Intermediate A1

3-Bromo-N-(3-hydroxypropyl)-4-methylbenzenesulfonamide

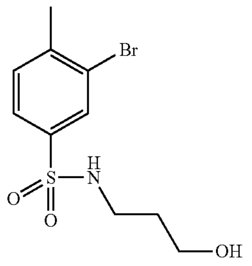 [SMILES: Cc1ccc(S(=O)(=O)NCCCO)cc1Br]

To a stirring solution of 3-bromo-4-methylbenzene-1-sulfonyl chloride (2 g, 7.42 mmol) in THF (37 mL) under $N_2$ was added 3-amino-1-propanol (0.568 ml, 7.42 mmol), DIPEA (1.56 ml, 8.9 mmol) and the resulting mixture was stirred at RT for 24 hours. The solvent was removed under reduced pressure and the crude material was added to 0.1M HCl (100 ml). The mixture was extracted with EtOAc (150 ml) and the organic extract was washed with sat. $Na_2CO_3$ (60 ml), brine, dried over $MgSO_4$ and concentrated under reduced pressure to afford the title compound;

LCMS: Rt 0.89 mins; MS m/z 310.1 [M+H]+; Method 2 minLC_v003

Intermediate A2

3-Bromo-N-(2-hydroxy-2-methylpropyl)-4-methylbenzenesulfonamide

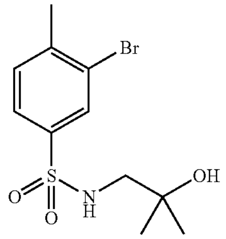 [SMILES: Cc1ccc(S(=O)(=O)NCC(C)(C)O)cc1Br]

To a stirring solution of 1-amino-2-methylpropan-2-ol (17.86 g, 200 mmol) in THF (500 ml), was added DIPEA (42.0 ml, 240 mmol) followed by 3-bromo-4-methylbenzene-1-sulfonyl chloride (54 g, 200 mmol). The reaction was exothermic, going up to 45° C. after the addition of the sulfonyl chloride. The reaction returned to 20° C. after 10 mins. The reaction mixture was stirred for a further 30 mins at RT, then the solvent was removed under reduced pressure. The crude product was diluted in EtOAc and washed with 0.1M HCl, sat. $NaHCO_3$, brine, dried over $MgSO_4$, and concentrated to dryness. The resulting solid was put in the vacuum oven overnight to give 61.31 g of a yellow solid;

LCMS: Rt 0.99 min; MS m/z 322.3 [M−H]−; Method 2 minLowpHv01

Intermediate A3

3-Bromo-N-(3-hydroxy-3-methyl-butyl)-4-methylbenzenesulfonamide

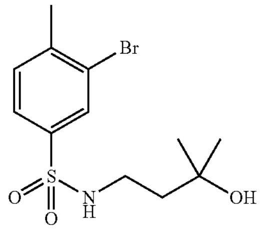 [SMILES: Cc1ccc(S(=O)(=O)NCCC(C)(C)O)cc1Br]

To a stirring solution of 3-bromo-4-methylbenzene-1-sulfonyl chloride (100 g, 371 mmol) in THF (500 ml) under nitrogen, was added 4-amino-2-methylbutan-2-ol (38.3 g, 371 mmol) in THF (50 mL) and DIPEA (78 ml, 445 mmol). The reaction mixture was stirred at room temperature overnight, then concentrated under reduced pressure and partitioned between ethyl acetate (500 mL) and 0.1M HCl (450 mL). The organic phase was dried over magnesium sulfate, filtered and concentrated under reduced pressure to give a yellow oil. The oil solidified upon cooling. DCM (100 mL) was added, then a thick precipitate formed. This precipitae was filtered and washed with DCM and Diethylether to afford a white cake, which was dried in the vacuum oven to give 90.18 grams of the title compound;

LCMS: Rt 0.97 min; MS m/z 334.1 and 336.0 [M−H]−, Br isotopes; Method: 2 minLowpH The filtrate was concentrated under reduced pressure and treated with diethyl ether. The precipitate was filtered and washed with diethylether. The resulting white solid was dried in the vacuum oven at 40° C. to give a further 11 grams of the title compound.

Intermediate A4

3-Bromo-N-(2-hydroxy-2-methylpropoxy)-4-methylbenzenesulfonamide

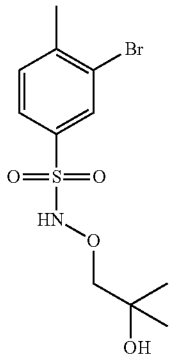 [SMILES: Cc1ccc(S(=O)(=O)NOCC(C)(C)O)cc1Br]

To a solution of 1-(aminooxy)-2-methylpropan-2-ol (2 g, 19.02 mmol) in THF (50 ml) at 00° C. under $N_2$ was added pyridine (1.692 ml, 20.93 mmol). To this mixture was added dropwise a solution of 3-bromo-4-methylbenzene-1-sulfonyl chloride (5.13 g, 19.02 mmol) in THF (50.0 ml) The mixture was stirred at 0° C. for 4 hrs then allowed to warm to rt overnight. The solvent was removed in vacuo and the residue was dissolved in EtOAc and washed with saturated aq. $NaHCO_3$ followed by 0.1M HCl then brine. The organic extract was dried over $MgSO_4$ and the solvent removed under reduced pressure to give the title compound;

LCMS: Rt 1.09 mins; MS m/z 338.3 [M+H]+; Method 2 minLowpHv01.

$^1H$ NMR (400 MHz, DMSO-d6) δ 10.53 (1H, s), 7.98 (1H, d), 7.75 (1H, dd), 7.65 (1H, d), 3.70 (2H, s), 2.45 (3H, s), 1.05 (6H, s).

Intermediate A6

3-Bromo-4-methyl-N-(6-methyl-pyridin-2-yl)-benzenesulfonamide

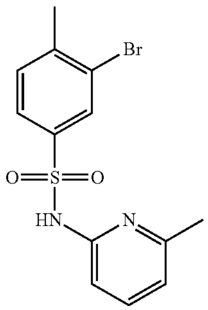 [SMILES: Cc1cccc(NS(=O)(=O)c2ccc(C)c(Br)c2)n1]

A solution of 3-bromo-4-methylbenzene-1-sulfonyl chloride (10 g, 37.1 mmol) and 6-methylpyridin-2-amine (4.01 g, 37.1 mmol) in pyridine (100 ml) was stirred at room temp for 3 hours. The mixture was dissolved in ethyl acetate, washed with $Na_2CO_3$, brine, the organic layer separated, dried over $MgSO_4$, filtered and the solvent removed under reduced pressure to yield a brown solid. The solid was triturated in ethyl acetate and the resulting suspension sonicated for 5 mins. The off-white solid was filtered off and the process repeated. The desired product was isolated as an off-white solid (9.35 g);

1H NMR (400 MHz, DMSO-d6) δ~13.3 (<1H, broad), 7.98 (1H, broad), 7.73 (1H, d), 7.66 (1H, dd), 7.49 (1H, d), 7.03 (1H, broad), 6.67 (1H, broad), 2.37 (3H, s), 2.32 (3H, s).

The compounds of the following tabulated intermediates were prepared analogously to the above intermediates from the appropriate starting compounds:

TABLE A

| Int. | Structure | Name | $[M + H]^+$/NMR |
|---|---|---|---|
| A5 | 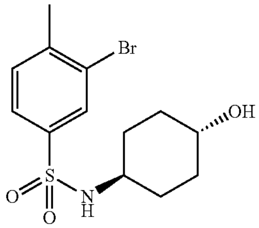 [SMILES: Cc1ccc(S(=O)(=O)N[C@H]2CC[C@H](O)CC2)cc1Br] | trans 3-Bromo-N-(4-hydroxy-cyclohexyl)-4-methylbenzenesulfonamide | LCMS: Rt 1.01 mins; MS m/z 348.1 [M + H]+; 2minLC_v003 |
| A7 | 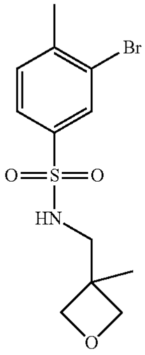 [SMILES: Cc1ccc(S(=O)(=O)NCC2(C)COC2)cc1Br] | 3-Bromo-4-methyl-N-(3-methyl-oxetan-3-ylmethyl)-benzenesulfonamide | LCMS: Rt 1.10 mins; MS m/z 336.1 [M + H]+; Method 2minLowpHv01 |
| A8 | 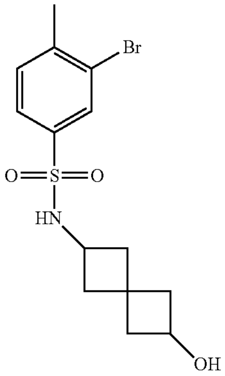 [SMILES: Cc1ccc(S(=O)(=O)NC2CC3(CC(O)C3)C2)cc1Br] | 3-Bromo-N-(6-hydroxy-spiro[3.3]hept-2-yl)-4-methyl-benzenesulfonamide | LCMS: Rt 1.01 mins; MS m/z 360.3 [M + H]+; Method 2minLowpHv01 |

TABLE A-continued

| Int. | Structure | Name | [M + H]⁺/NMR |
|---|---|---|---|
| A9 | 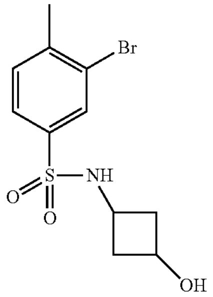 [SMILES: Cc1ccc(S(=O)(=O)NC2CC(O)C2)cc1Br] | 3-Bromo-N-(3-hydroxycyclobutyl)-4-methylbenzene-sulfonamide | LCMS: Rt 0.93, 0.95 mins; MS m/z 320.2 [M + H]+; 2minLowpHv01 |

Boronic Esters (B)

Intermediate B1

N-(3-Hydroxypropyl)-4-methyl-3-(4,4,5,5-tetramethyl-1,3,2-dioxaborolan-2-yl)benzenesulfonamide

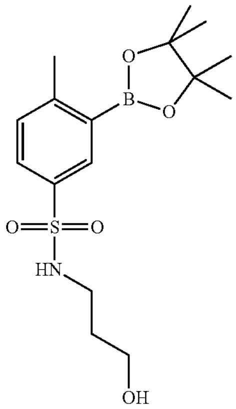 [SMILES: Cc1ccc(S(=O)(=O)NCCCO)cc1B1OC(C)(C)C(C)(C)O1]

A mixture comprising 3-bromo-N-(3-hydroxypropyl)-4-methylbenzenesulfonamide (Intermediate A1) (2.25 g, 7.30 mmol), KOAc (1.075 g, 10.95 mmol), $PdCl_2(dppf).CH_2Cl_2$ adduct (0.298 g, 0.365 mmol) and bis(pinacolato)diboron (2.039 g, 8.03 mmol) in DME (36.5 mL) under $N_2$ was stirred at 90° C. for 5 hours. The resulting mixture was added to water (100 ml) and extracted with EtOAc (2×100 ml). The combined organic extracts were washed with brine, dried over $MgSO_4$ and concentrated under reduced pressure. Purification by chromatography on silica eluting with 0-100% gradient EtOAc in iso-hexane afforded the title compound;

LCMS: Rt 1.03 mins; MS m/z 356.5 [M+H]+; 2 min-LC_v003

Intermediate B2

N-(2-Hydroxy-2-methylpropyl)-4-methyl-3-(4,4,5,5-tetramethyl-1,3,2-dioxaborolan-2-yl)benzenesulfonamide

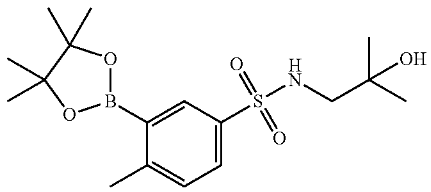 [SMILES: Cc1ccc(S(=O)(=O)NCC(C)(C)O)cc1B1OC(C)(C)C(C)(C)O1]

To a 1000 ml flask was added 3-bromo-N-(2-hydroxy-2-methylpropyl)-4-methylbenzene sulfonamide (Intermediate A2) (85 g, 264 mmol), bis(pinacolato)diboron (73.7 g, 290 mmol), potassium acetate (38.8 g, 396 mmol) and $PdCl_2$ (dppf)-$CH2Cl_2$ adduct (10.77 g, 13.19 mmol) in DME (400 ml) to give a yellow suspension. The reaction mixture was heated at 90° C. for 6 hours then RT overnight. The resulting mixture was filtered through Celite® (filter material) and the filtrate was diluted with ethyl acetate, washed with brine, the organic layer separated, dried over $MgSO_4$, filtered and the solvent removed under reduced pressure. The crude product was purified by ISCO chromatography, eluting in a 0% to 80% iso-hexane:EtOAc gradient on a 1.5 kg silica cartridge (dry loading). The product fractions were combined and the solvent removed under reduced pressure to yield a light brown oil. The oil was diluted with iso-hexane and a white precipitate formed. The suspension was sonicated for 2 hrs and filtered to yield a white solid. The solid was dried in the vacuum oven at 40° C. for 1 hr to afford the title compound as an off white solid;

LCMS: Rt 1.20 min; MS m/z 370.3 [M+H]+; Method 2 minLowpHv01

The compounds of the following tabulated intermediates were prepared analogously to Intermediate B1 from the appropriate starting compounds:

TABLE B

| Int. | Structure | Name | [M + H]$^+$/NMR |
|---|---|---|---|
| B3 | 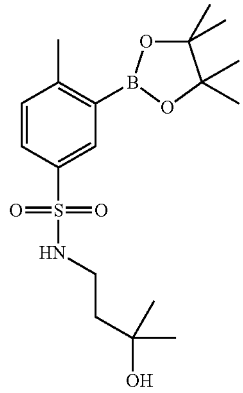 [SMILES: Cc1ccc(S(=O)(=O)NCCC(C)(C)O)cc1B1OC(C)(C)C(C)(C)O1] | N-(3-Hydroxy-3-methylbutyl)-4-methyl-3-(4,4,5,5-tetramethyl-1,3,2-dioxaborolan-2-yl)benzenesulfonamide | LCMS: Rt 1.10 mins; MS m/z 384.5 [M + H]+; Method 2minLC_v003 |
| B4 | 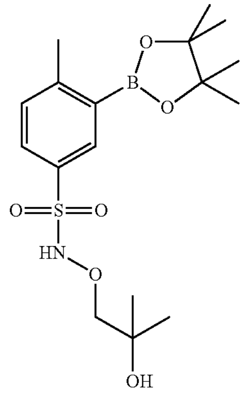 [SMILES: Cc1ccc(S(=O)(=O)NOCC(C)(C)O)cc1B1OC(C)(C)C(C)(C)O1] | N-(2-Hydroxy-2-methyl-propoxy)-4-methyl-3-(4,4,5,5-tetramethyl-[1,3,2]dioxaborolan-2-yl)benzenesulfonamide | LCMS: Rt 1.24 mins; MS m/z 386.5 [M + H]+; Method 2minLowpHv01 |
| B5 | 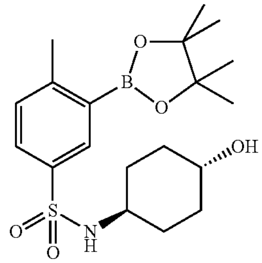 [SMILES: Cc1ccc(S(=O)(=O)N[C@H]2CC[C@H](O)CC2)cc1B1OC(C)(C)C(C)(C)O1] | trans N-(4-Hydroxycyclohexyl)-4-methyl-3-(4,4,5,5-tetramethyl-1,3,2-dioxaborolan-2-yl)benzenesulfonamide | LCMS: Rt 1.14 mins; MS m/z 396.3 [M + H]+; Method 2minLC_v003 |
| B6 | 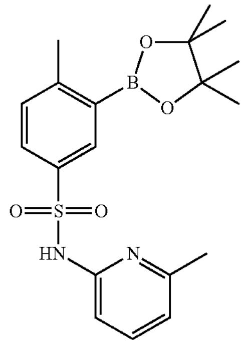 | 4-Methyl-N-(6-methylpyridin-2-yl)-3-(4,4,5,5-tetramethyl-1,3,2-dioxaborolan-2-yl)benzenesulfonamide | LCMS: Rt 1.09 mins MS m/z 396.3 [M + H]+; Method 2minLowpH |

TABLE B-continued

| Int. | Structure | Name | [M + H]+/NMR |
|---|---|---|---|
| B7 | 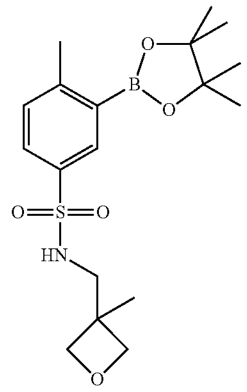 [SMILES: Cc1ccc(S(=O)(=O)NCC2(C)COC2)cc1B1OC(C)(C)C(C)(C)O1] | 4-Methyl-N-(3-methyl-oxetan-3-ylmethyl)-3-(4,4,5,5)tetramethyl-[1,3,2]dioxaborolan-2-yl)-benzenesulfonamide | LCMS: Rt 1.22 mins MS m/z 382.6 [M + H]+; Method 2minLC_v003 |

Intermediate B8

(R)-4-methyl-N-((tetrahydrofuran-3-yl)methyl)-3-(4,4,5,5-tetramethyl-1,3,2-dioxaborolan-2-yl)benzenesulfonamide

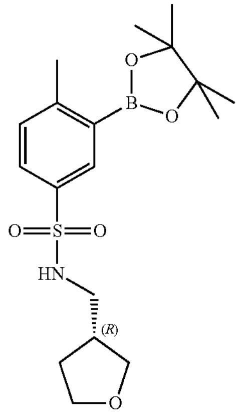

Step 1: (R)-3-Bromo-4-methyl-N-((tetrahydrofuran-3-yl)methyl)benzenesulfonamide

A solution of (R)-(tetrahydrofuran-3-yl)methanamine hydrochloride (2.72 g, 19.77 mmol) in DMA (60 ml) was cooled in an ice bath under nitrogen and treated with DIPEA (6.90 ml, 39.5 mmol). To this mixture was added dropwise a solution of 3-bromo-4-methylbenzene-1-sulfonyl chloride (4.8 g, 17.79 mmol) in DMA (50 ml) using a dropping funnel. The resulting mixture was allowed to warm to RT overnight and then partitioned between EtOAc and water. The organic portion was separated and washed with 1M HCl, sat. $NaHCO_3$, dried ($MgSO_4$), filtered and concentrated under reduced pressure to afford the title compound;

LCMS; Rt 1.09 min; MS m/z 334.0 [M+H]+ Method 2 minLowpHv01

Step 2: (R)-4-methyl-N-((tetrahydrofuran-3-yl)methyl)-3-(4,4,5,5-tetramethyl-1,3,2-dioxaborolan-2-yl)benzenesulfonamide The title compound was prepared from (R)-3-bromo-4-methyl-N-((tetrahydrofuran-3-yl)methyl)benzenesulfonamide (step 1) analogously to Intermediate B1;

LCMS; Rt 1.24, 85%, MS m/z 382.3 [M+H]+ Method 2 minLowpHv01

Intermediate B9

N-(3-Hydroxycyclobutyl)-4-methyl-3-(4,4,5,5-tetramethyl-1,3,2-dioxaborolan-2-yl)benzenesulfonamide

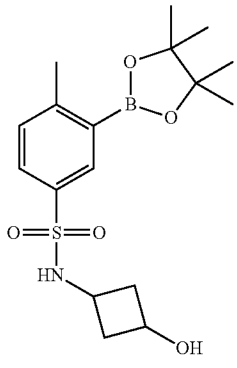 [SMILES: Cc1ccc(S(=O)(=O)NC2CC(O)C2)cc1B1OC(C)(C)C(C)(C)O1]

Step 1: 3-Aminocyclobutanol

To a cooled (0° C.) stirring solution of tert-butyl 3-oxocyclobutylcarbamate (1 g, 5.40 mmol) in EtOH (27.0 mL), under $N_2$, was added $NaBH_4$ (0.204 g, 5.40 mmol) portion wise. The reaction mixture was stirred 30 mins then allowed to warm to room temperature. After 3 hours, the reaction was quenched by dropwise addition of water (100 ml) and the product extracted into EtOAc (2×100 ml). The organic extracts were combined, washed with brine, dried over $MgSO_4$, and concentrated under reduced pressure. To the resulting mixture was added 2.0M HCl in MeOH (27.0 mL, 54.0 mmol). The solution was stirred for 3 h at room temperature and the mixture was concentrated under reduced pressure to afford the title compound as a mixture or stereoisomers which was used as crude directly in the next step.

Step 2: 3-Bromo-N-(3-hydroxycyclobutyl)-4-methylbenzenesulfonamide

To a stirring solution of 3-aminocyclobutanol (480 mg, 3.88 mmol) in DMF (24.300 ml), under $N_2$, was added 3-bromo-4-methylbenzene-1-sulfonyl chloride (1047 mg, 3.88 mmol) and DIPEA (1.492 ml, 8.55 mmol). The reaction mixture was stirred for 24 hours at room temperature. The mixture was concentrated under reduced pressure and added to 0.1M HCl (150 ml) and product extracted into EtOAc (200 ml). The organic extract was washed with sat. $Na_2CO_3$ (150 ml), brine, dried over $MgSO_4$ and concentrated under reduced pressure to afford the title compound as a mixture of stereoisomers;

LCMS: Rt 0.93, 0.95 mins; MS m/z 320.2 [M+H]+; Method 2 minLowpHv01

Step 3: N-(3-Hydroxycyclobutyl)-4-methyl-3-(4,4,5,5-tetramethyl-1,3,2-dioxaborolan-2-yl)benzenesulfonamide A stirring mixture of 3-bromo-N-(3-hydroxycyclobutyl)-4-methylbenzenesulfonamide (1.2 g, 3.75 mmol), KOAc (0.552 g, 5.62 mmol), $PdCl_2$(dppf).$CH_2Cl_2$ adduct (0.153 g, 0.187 mmol) and 4,4,4',4',5,5,5',5'-octamethyl-2,2'-bi(1,3,2-dioxaborolane) (1.047 g, 4.12 mmol) in DME (18.74 mL), under $N_2$, was heated at 90° C. for 16 hours. The mixture was added to water (100 ml) and the product extracted into EtOAc (100 ml). The organic extract was washed with brine and dried over $MgSO_4$. The solids were removed by filtration, washed with EtOAc and the filtrate was concentrated under reduced pressure. The crude product was purified by flash column chromatography, eluting with 0-100% gradient of EtOAc in hexane on a 40 g Si-column to give the title compound as a mixture of stereoisomers;

LCMS: Rt=1.13 mins; MS m/z 368.2 [M+H]+; Method 2 minLowpHv01

Intermediate C1

5-Bromo-3-[1-(2,2,2-trifluoro-ethyl)-1H-pyrazol-4-yl]-pyridin-2-ylamine

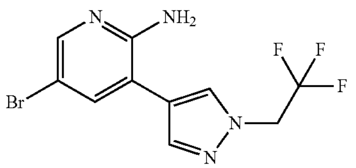 [SMILES: Nc1ncc(Br)cc1-c1cnn(CC(F)(F)F)c1]

Sodium carbonate (2.76 ml of a 2M solution, 5.52 mmol) was added to a mixture of 5-bromo-3-iodopyridin-2-amine (0.55 g, 1.84 mmol), 4-(4,4,5,5-tetramethyl-1,3,2-dioxoborolan-2-yl)-1-(2,2,2-trifluoroethyl)-1H-pyrazole (0.61 g, 2.21 mmol) (Intermediate D1) and $Pd(PPh_3)_2Cl_2$ (0.065 g, 0.092 mmol) in toluene (7 ml) and ethanol (3.5 ml). The mixture was heated at 90° C. After 3 h the reaction was complete by LCMS. The reaction mixture was diluted with EtOAc and washed with brine. The organic extract was dried over $MgSO_4$ and the crude product absorbed on silica. Chromatography on silica, eluting with EtOAc, gave the product as a grey solid (0.36 g, 58%);

LCMS: Rt 1.00 mins; MS m/z 321.3 [M+H]+; Method 2 minLC_v003

$^1$H NMR (400 MHz, $CDCl_3$) 8.15 (1H, brs), 7.82 (1H, s), 7.78 (1H, s), 7.55 (1H, s), 4.7 (2H, m)

Intermediate C2

5-Bromo-3-(1-methyl-1H-pyrazol-4-yl)pyridin-2-amine

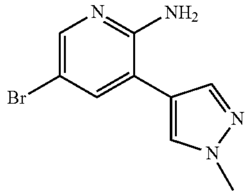

The title compound was prepared from 1-methyl-4-(4,4,5,5-tetramethyl-1,3,2-dioxaborolan-2-yl)-1H-pyrazole and 5-bromo-3-iodopyridin-2-amine under analogous conditions to those of Intermediate C1.

$^1$H NMR (400 MHz, MeOH-d4) δ 7.93 (1H, d) 7.92 (1H, s), 7.74 (1H, s), 7.64 (1H, d), 3.97 (3H, s).

Intermediate C3

5-Bromo-3-[1,2,4]oxadiazol-5-yl-pyridin-2-ylamine

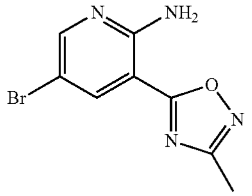

To a stirring solution of 2-amino-5-bromonicotinic acid (1 g, 4.61 mmol) in THF (24 mL), under $N_2$, was added acetamide oxime (0.410 g, 5.53 mmol) & DIPEA (1.610 mL, 9.22 mmol) followed by HATU. Reaction was stirred for 24 hours at RT. A further 0.5 Eq of HATU was added and reaction continued overnight. The reaction mixture was added to water (100 ml) and product extracted into EtOAc (2×100 ml). The organic phases were combined, washed with, brine, dried over $MgSO_4$, and concentrated to dryness. The residue was added to toluene (50 ml) and heated to 90° C. overnight. The reaction mixture was concentrated and added to water (100 ml). The product was extracted into EtOAc (2×100 ml). The organic phases were combined, washed with brine, dried over $MgSO_4$, and concentrated to dryness. The crude product was purified by flash column chromatography, eluting with a modified 0-10% gradient (2M $NH_3$ in MeOH) in DCM on a 40 g si-column, loading via dry loading to give 500 mg of pale yellow solid;

LCMS: Rt 0.97 mins; MS m/z 256.6 [M+H]+; Method 2 minLowpH

Intermediate C4

5-Bromo-3-(2-methyl-oxazol-5-yl)-pyridin-2-ylamine

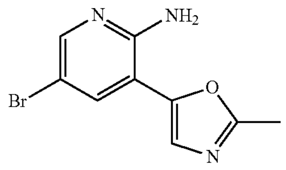

To a 100 mL Kolben flask, fitted with thermometer and overhead stirring and flushed with nitrogen, was charged 5-bromo-3-iodopyridin-2-amine (5.0 g, 16.73 mmol), 2-methyl-5-(4,4,5,5-tetramethyl-1,3,2-dioxaborolan-2-yl) oxazole (commercially available, Boropharm) (3.50 g, 16.73 mmol) and $PdCl_2$(dtbpf) (0.273 g, 0.418 mmol). The solids were part suspended in DL-α-Tocopherol methoxypolyethylene glycol succinate solution (2 wt. % in $H_2O$, 35 ml). The contents were vigorously stirred for 15 min to obtain a finely suspended slurry and to this was added dropwise over 10 min triethylamine (9.33 ml, 66.9 mmol). The reaction mixture was allowed to stir overnight at room temperature and then warmed to 30° C. in an oil bath for 4 hours and stirred for a further 3 hours. Additional 2-methyl-5-(4,4,5,5-tetramethyl-1,3,2-dioxaborolan-2-yl)oxazole (150 mg) was added and mixture was allowed to stir overnight. Additional 2-methyl-5-(4,4,5,5-tetramethyl-1,3,2-dioxaborolan-2-yl) oxazole (250 mg) was added and reaction mixture was warmed to 30° C. overnight. After cooling to 20° C., the reaction mixture was diluted with EtOAc (150 mL) and water (100 mL). The dark brown organic layer was extracted and the aqueous phase was washed with further EtOAc/5% MeOH (100 mL). The combined organic layers were washed with sat. brine, dried over $MgSO_4$, filtered under suction, and concentrated under reduced pressure to give a dark brown, crude solid. The crude product was dissolved up in DCM (1% MeOH) and loaded directly onto a 220 g silica column, equilibrated with iso-hexane/EtOAc (30%). The product was eluted using 30-100% EtOAc in iso-hexane. The product fractions were combined and concentrated under reduced pressure to give title compound as a pale yellow solid, dried over the weekend.

LCMS: Rt=0.94 min; MS m/z 254.3 [M+H]+; Method: 2 minLowpHv03

Intermediate C5

5-Bromo-3-(3-methyl-isoxazol-5-yl)-pyridin-2-ylamine

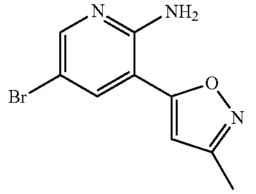

Step 1: 4-(2-Amino-5-bromopyridin-3-yl)but-3-yn-2-ol

5-Bromo-3-iodopyridin-2-amine (60 g, 201 mmol) was dissolved in 2-MeTHF (700 mL) with triethylamine (280 mL, 2007 mmol) to give an orange solution. The solution was flushed with nitrogen before bis(triphenylphosphine) palladium chloride (7.04 g, 10.04 mmol) was added followed by copper(I) iodide (3.82 g, 20.07 mmol). After stirring for a few minutes, but-3-yn-2-ol (17.31 mL, 221 mmol) in 2-MeTHF was added. The reaction was left to stir for 90 minutes, then filtered through Celite® (filter material). The Celite® was washed with 2-MeTHF (500 mL), then suspended in EtOAc (500 mL), stirred for 15 minutes and filtered. The solid was washed with EtOAc until solvent colourless (~500 mL) and all filtrates were combined and concentrated under reduced pressure, to leave a viscous dark brown oil which solidified overnight. Attempts to dissolve in DCM (250 mL) left a lot of undissolved material; the addition of MeOH (50 mL) and EtOAc (100 mL) left a finely divided precipitate. The DCM was removed under reduced pressure and the suspension diluted with a further 250 mL EtOAc before filtration to remove the solid. Silica (200 mL) was added to the dark brown solution and the solvent was removed under reduced pressure. The resulting free flowing solid was purified by column chromatography (silica, 1500 g/Gradient elution: EtOAc/hexanes). The product fractions were combined and concentrated to give the title compound as a red/orange solid;

LC-MS: Rt=2.59 minutes; MS m/z 241.3/243.3 Br isotope pattern [M+H]+ Method: 8 minLowpHv01

Step 2: 4-(2-Amino-5-bromopyridin-3-yl)but-3-yn-2-one

A solution of 4-(2-amino-5-bromopyridin-3-yl)but-3-yn-2-ol (step 1) (40.0 g, 166 mmol) in DCM (1 L) was stirred vigorously and manganese dioxide (144 g, 1659 mmol) was added in one portion. Further DCM (250 mL) was added and the resulting dark suspension was stirred at room temperature overnight then filtered through Whatman Grade 2 filter paper (×2). The retained solid was washed with DCM (250 mL) and filtered; the wash filtrate and reaction filtrates were combined and concentrated under reduced pressure, to give the title compound as a dark brown solid;

LC-MS: Rt=1.03 minutes; MS m/z 239.0/241.0 [M+H]+ Br isotope pattern; Method 2 minLowpHv03

Step 3: 5-Bromo-3-(3-methyl-isoxazol-5-yl)-pyridin-2-ylamine

Literature Reference: Synlett, 2010, No. 5, pp 0777-0781.

4-(2-Amino-5-bromopyridin-3-yl)but-3-yn-2-one (Step 2) (36.5 g, 153 mmol) and hydroxylamine hydrochloride (11.67 g, 168 mmol) were combined in MeOH (750 mL) with stirring, to give a dark orange/brown solution. $NaHCO_3$ (1M; aqueous) (153 mL, 153 mmol) was added in one portion and the reaction mixture was left to stir at room temperature overnight, then slowly poured into 2.5 L of vigorously stirring water. After 30 minutes, the mixture was filtered, and evaporated under reduced pressure. The resulting brown solid (28.5 g) was dissolved in acetic acid (500 mL) with stirring. 1M HCl (150 mL, 150 mmol) was added and the dark brown solution was stirred with heating at 70° C. (external temperature) overnight. The reaction was allowed to cool to room temperature, then diluted by pouring into a vigorously stirring mixture of water (2 L) and DCM (2 L). The vigorous stirring was continued while the pH was adjusted to ~6 by the slow addition of 5M NaOH(aq), then pH~8 by the slow and cautious addition of solid sodium bicarbonate (120 g). The mixture was filtered through Celite® (filter material) then separated. The aqueous layer was extracted with a further 2×1 L DCM. The combined organics were passed through a phase separator and concentrated under reduced pressure to give a brown solid. The brown solid was dissolved in DCM (500 mL) and adsorbed onto silica (60 g) by concentrating under reduced pressure to dryness. The material was purified by column chromatography (silica 750 g/30% EtOAc in hexanes). The product fractions were combined and concentrated under reduced pressure, then recrystallised from hexane:ethyl acetate (4:1 v/v) to give the title compound as a bright yellow solid;

$^1$H NMR (400 MHz, DMSO-d6) 8.17 (1H, d), 8.02 (1H, d), 6.90 (1H, s), 6.51 (2H, br s), 2.30 (3H, s).

Intermediate C6

5-Bromo-3-(2-methyl-thiazol-5-yl)-pyridin-2-ylamine

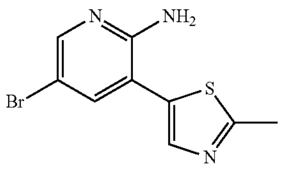

A mixture of $Pd(PPh_3)_2Cl_2$ (0.12 g, 0.171 mmol), 2-methyl-5-(4,4,5,5-tetramethyl-1,3,2-dioxaborolan-2-yl) thiazole (0.78 g, 3.46 mmol) and 5-bromo-3-iodopyridin-2-amine (1 g, 3.35 mmol) in sodium carbonate 2M aqueous solution (5 ml, 10.00 mmol), toluene (13.00 ml), and ethanol (6.5 ml) was heated to 70° C. overnight. The reaction was diluted with water and DCM, the phases were separated (phase separator) and the organic solvents removed under reduced pressure. The product was purified by flash column chromatography (ISCO, 80 g silica, 0-10% methanol in TBME) to give 230 mg of pale brown solid.

LCMS: Rt 0.84 min; MS m/z 270.1 and 272.1 [M+H]+, Br isotopes; Method 2 minLowpHv01.

Intermediate C7

5-Bromo-2'-methyl-[3,4']bipyridinyl-2-ylamine

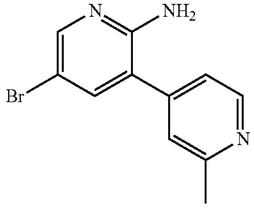

The title compound was prepared from 2-methyl-4-(4,4,5,5-tetramethyl-1,3,2-dioxaborolan-2-yl)pyridine and 5-bromo-3-iodopyridin-2-amine under analogous conditions to those of Intermediate C6.

LCMS: Rt 0.52 min; MS m/z 264 and 266.1 [M+H]+, Br isotopes; Method 2 minLowpH.

Intermediate C8

5-Bromo-3-(3-isopropyl-1,2,4-oxadiazol-5-yl)pyridin-2-amine

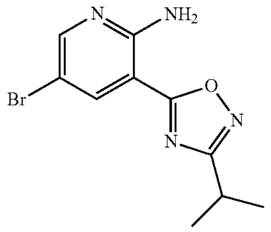 [SMILES: CC(C)c1noc(-c2cc(Br)cnc2N)n1]

The title compound was prepared analogously to Intermediate C3 from 2-amino-5-bromo nicotinic acid and (Z)-N'-hydroxyisobutyrimidamide;

LCMS: Rt 1.28 mins; MS m/z 283.4 [M+H]+; Method 2 minLowpH

Intermediate C9

5-Bromo-3-(5-methyloxazol-2-yl)pyridin-2-amine

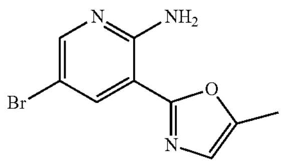

Step 1: 2-Amino-5-bromo-N-(prop-2-yn-1-yl)nicotinamide

To a stirring solution of 2-amino-5-bromonicotinic acid (1 g, 4.61 mmol) in THF (23.0 ml), under $N_2$ was added HATU (3.15 g, 8.29 mmol) and DIPEA (1.610 ml, 9.22 mmol) followed by prop-2-yn-1-amine (0.354 ml, 5.53 mmol). The reaction mixture was stirred at 50° C. for 24 hours. The resulting mixture was added to water (100 ml) and the product was extracted into EtOAc (100 ml). The organic portion was washed with brine, dried over $MgSO_4$ and concentrated to dryness. To the crude residue was added DCM (~15 ml) and the mixture was sonicated. The resulting solid was filtered, washed with DCM and dried to afford the title compound;

LCMS: Rt 0.75 mins; MS m/z 256.3[M+H]+; Method 2 minLowpH

Step 2: 5-Bromo-3-(5-methyloxazol-2-yl)pyridin-2-amine

To a stirring dispersion of 2-amino-5-bromo-N-(prop-2-yn-1-yl)nicotinamide (step 1) (500 mg, 1.968 mmol) in DCM (19.7 ml) under N2 was added gold(III) chloride (59.7 mg, 0.197 mmol) and the resulting mixture was stirred for 3 hours at RT. The mixture was added to sat. $NaHCO_3$ (100 ml) and extracted with DCM (100 ml). The organic portion was collected using a phase separator and concentrated to dryness. To the crude residue was added 10:1 mixture of DCM:MeOH (~5 ml). The mixture was sonicated and any solids were removed by filtration through Celite® (filter material). The organic portion was concentrated in vacuo and purification of the crude residue by chromatography on silica eluting with 0-100% EtOAc in iso-hexane afforded the title compound;

LCMS: Rt 1.15 mins; MS m/z 256.3 [M+H]+; Method 2 minLowpH

Intermediate C10

5-Bromo-3-(3-ethyl-1,2,4-oxadiazol-5-yl)pyridin-2-amine

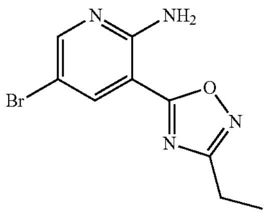

The title compound was prepared analogously to Intermediate C3 from 2-amino-5-bromo nicotinic acid and (Z)-N'-hydroxypropionimidamide;

LCMS: Rt 1.18 mins; MS m/z 271.4 [M+H]+; Method 2 minLowpH

Intermediate C11

5-Bromo-3-(2-methyl-2H-1,2,3-triazol-4-yl)pyridin-2-amine

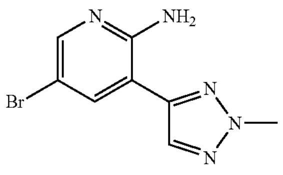

Step 1: 5-Bromo-3-(1H-1,2,3-triazol-4-yl)pyridin-2-amine

To a 150 mL round-bottomed flask was added 5-bromo-3-ethynyl-pyridin-2-ylamine (Intermediate C15)(1.50 g, 7.61 mmol), sodium ascorbate (0.761 ml, 0.761 mmol) and copper(II) sulfate pentahydrate (0.019 g, 0.076 mmol) in t-Butanol (20 ml) and water (40 ml) under $N_2$ to give a brown suspension. To this was added trimethylsilyl azide (3.58 ml, 27 mmol) and the reaction heated at 90° C. for 30 hours and allowed to cool to RT overnight. The resulting mixture was filtered to afford Batch 1 of the title compound;

LCMS; Rt 0.59 mins; MS m/z 240.1 [M+H]+; Method 2 minLowpHv01.

The filtrate was extracted with ethyl acetate and washed with 1M NaOH to extract the product into the aqueous. The aqueous layer was neutralised with 1M HCl to pH7 and the product extracted into ethyl acetate. The organic portion was washed with brine, dried over $MgSO_4$, filtered and the solvent removed under reduced pressure to yield an orange solid of the title compound (Batch 2):

LCMS: Rt 0.63 mins; MS m/z 240.3 [M+H]+; Method 2 minLowpHv01.

Step 2: 5-Bromo-3-(2-methyl-2H-1,2,3-triazol-4-yl)pyridin-2-amine

A mixture comprising 5-bromo-3-(1H-1,2,3-triazol-4-yl)pyridin-2-amine (step 1, batches 1 and 2) (395 mg, 1.645 mmol) and TBAF (1M in THF) (4.94 mL, 4.94 mmol) in THF (15 ml) at 0° C. was treated with iodomethane (0.309 mL, 4.94 mmol) to give a yellow solution. The reaction mixture was stirred at 0° C. for 30 mins. The resulting mixture was extracted with EtOAc. The organic extract was washed with water, brine, dried over MgSO4, filtered and the solvent removed under reduced pressure. The crude product was loaded onto silica and purified by flash column chromatography, elution with iso hexane:ethyl acetate (0-100%) on a 24 g silica cartridge to afford the title compound as the major isomer and 5-bromo-3-(1-methyl-1H-1,2,3-triazol-4-yl)pyridin-2-amine as the minor isomer;

Major Isomer:

5-Bromo-3-(2-methyl-2H-1,2,3-triazol-4-yl)pyridin-2-amine

LCMS: Rt=0.84 mins MS m/z 256.4 [M+H]+; Method 2 minLowpHv01.

Minor Isomer:

5-Bromo-3-(1-methyl-1H-1,2,3-triazol-4-yl)pyridin-2-amine

LCMS: Rt=0.60 mins MS m/z 256.3 [M+H]+; Method 2 minLowpHv01.

Intermediate C12

5-Bromo-3-(3-ethylisoxazol-5-yl)pyridin-2-amine

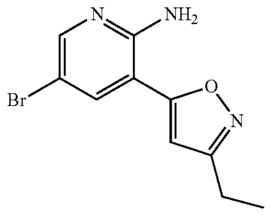

Step 1: (Z)-N-Hydroxypropionimidoyl chloride

To a cooled to (0° C.) solution of (E)-propionaldehyde oxime (1 g, 13.68 mmol) in DMF (20 mL) was added N-chlorosuccinimide (2.375 g, 17.79 mmol) in small portions over 5 mins maintaining the temperature below 10° C. Upon complete addition the reaction was allowed to warm to RT with stirring for 1 hour and then left to stand in a fridge over 2 days. The mixture was diluted with water (50 ml) and extracted with diethyl ether (2×50 ml). The combined organic extracts were dried over $MgSO_4$, filtered and concentrated under reduced pressure to yield the title compound as a pale blue oil;

$^1H$ NMR (400 MHz, DMSO-d6) δ 11.50 (1H, s), 2.50 (2H, q), 1.12 (3H, t). (Trace of DMF present)

Step 2:
5-Bromo-3-(3-ethylisoxazol-5-yl)pyridin-2-amine

To a 50 mL round-bottomed flask was added 5-bromo-3-ethynylpyridin-2-amine (Intermediate C15) (500 mg, 2.54 mmol) and sodium ascorbate (0.254 ml, 0.254 mmol) in tBuOH (10 ml) and water (10 ml) under $N_2$ to give a brown suspension. To the mixture was then added copper(II) sulfate pentahydrate (13 mg, 0.051 mmol, 2 mol %) and $KHCO_3$ (1.1 g, 10.99 mmol) followed by (Z)-N-hydroxypropionimidoyl chloride (1.092 g, 10.15 mmol) in 100 mg portions over 1 hour. After stirring at RT overnight, the reaction mixture was extracted with EtOAc. The combined organic extracts were washed with water, brine, dried over $MgSO_4$, filtered and concentrated under reduced pressure. The crude product was purified by flash column chromatography, elution with iso hexane:ethyl acetate (0-30%) on a 24 g silica cartridge to afford the title compound as a yellow solid;

LCMS: Rt=1.06 mins MS m/z 268.4 [M+H]+; Method 2 minLowpHv01.

Intermediate C13

5-Bromo-3-(3-methylisothiazol-5-yl)pyridin-2-amine

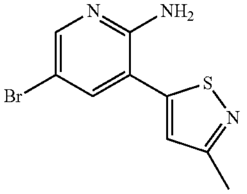

Step 1: 4-(2-Amino-5-bromopyridin-3-yl)but-3-yn-2-one

To 5-bromo-3-trimethylsilanylethynyl-pyridin-2-ylamine (Intermediate C15, step 1) (8.95 g, 33.2 mmol) in DCM (10 mL) at −20° C. (external temperature) in a chloroform/dry ice bath, acetyl chloride (2.364 mL, 33.2 mmol) was added to give a yellow solution. $AlCl_3$ (13.30 g, 100 mmol) was added to the reaction while vigorously stirring. After 30 mins the reaction was allowed to warm to RT and stirred for a further 60 mins. The reaction mixture was diluted with DCM and washed sequentially with 1M NaOH, water and brine. The organic layer was separated, dried over $MgSO_4$, filtered and concentrated under reduced pressure. The crude product was loaded onto silica and purified by flash column chromatography, elution with ethyl acetate in iso-hexane (0-50%) on a 330 g silica cartridge. The product fractions were combined and concentrated under reduced pressure to yield the title compound as a yellow solid;

Step 2:
5-Bromo-3-(3-methylisothiazol-5-yl)pyridin-2-amine

To a stirred suspension of 4-(2-amino-5-bromopyridin-3-yl)but-3-yn-2-one (step 1)(100 mg, 0.356 mmol) in water (2 mL) at 0° C. was added hydroxylamine-O-sulfonic acid (40 mg, 0.356 mmol). The mixture was stirred at 0° C. for 30 mins. THF (1 ml) was added and the mixture was stirred for a further 30 minutes at 0° C. Solid sodium bicarbonate (30 mg, 0.356 mmol) was added, followed by sodium hydrogen sulfide (0.28 mL of a 1.4M aqueous solution, 0.39 mmol) and the mixture was allowed to warm to RT and stirred at RT for 3 hour. Further NaSH (0.279 mL of a 1.4 M aq. solution, 0.39 mmol) was added and the mixture was stirred for 1 hour at RT. The mixture was diluted with water (10 mL) and DCM (10 mL) was added. The DCM layer was recovered using a phase separator and concentrated to give a yellow oil.

The crude product was purified using chromatography on 12 g silica gel using Isco, eluting with 0-80% EtOAc in iso-hexanes over 10 minutes to afford the title compound;

LC-MS: Rt 0.98 mins; MS m/z 270.1/272.1 [M+H]+; Method 2 minLowpHv01

$^1$H NMR (400 MHz, $CDCl_3$) δ 8.15 (1H, d), 7.62 (1H, d), 7.18 91H, s), 4.88 (2H, br s), 2.55 (3H, s).

Intermediate C14

5-Bromo-3-(5-methyl-1,3,4-oxadiazol-2-yl)pyridin-2-amine

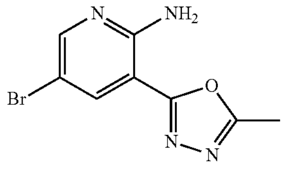

A stirred mixture of 2-amino-5-bromonicotinic acid (200 mg, 0.922 mmol) in $POCl_3$ (2 ml) was treated with acetohydrazide (68.3 mg, 0.922 mmol) and stirred under $N_2$ at 100° C. for 1 hour. The resulting mixture was added dropwise to crushed ice over 10 minutes and left for 5 minutes. The mixture was neutralized by addition of 2M NaOH and extracted with DCM (3×30 ml). The combined organic extracts were dried over $MgSO_4$, filtered and concentrated under reduced pressure. Purification of the crude residue by chromatography on silica eluting with 0-100% EtOAc in iso-hexane afforded the title compound as a white solid;

LCMS: Rt=0.88 mins MS m/z 255.3 [M+H]+; Method 2 minLowpHv01.

Intermediate C15

5-bromo-3-ethynylpyridin-2-amine

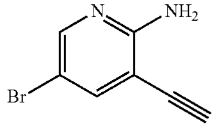

Step 1:
5-bromo-3-((trimethylsilyl)ethynyl)pyridin-2-amine

To a stirring solution of 5-bromo-3-iodopyridin-2-amine (10 g, 33.5 mmol) and triethylamine (46.6 ml, 335 mmol) in THF was added bis(triphenylphosphine)palladium(II) chloride (2.35 g, 3.35 mmol) and copper(I) iodide (1.27 g, 6.69 mmol). Whilst maintaining the temperature below 10° C., ethynyltrimethylsilane (5.2 ml, 36.8 mmol) was added slowly before warming to room temperature with stirring for 30 mins. The reaction was concentrated under reduced pressure, diluted with ethyl acetate, and the organics washed with citric acid, brine, the organic layer separated, dried over magnesium sulfate, filtered and the solvent removed under reduced pressure. The product was loaded onto silica and purified by flash column chromatography eluting with iso hexane:ethyl acetate (0-30%) on an 80 g silica column. The required fractions were combined and the solvent removed under reduced pressure to yield a brown solid (8.4 g).

LCMS:Rt=1.36 mins; MS m/z 269.3 [M+H]+; Method 2 minLowpHv01.

Step 2: 5-bromo-3-ethynylpyridin-2-amine

A mixture of 5-bromo-3-((trimethylsilyl)ethynyl)pyridin-2-amine (from Step 1) and potassium carbonate (4.31 g, 31.2 mmol) in methanol (150 mL) was stirred at room temperature for 30 mins. The resulting mixture was concentrated under reduced pressure, extracted into DCM, washed with water, brine, the organic layer separated, dried over $MgSO_4$, filtered and the solvent removed under reduced pressure to yield a brown solid (5.15 g).

$^1H$ NMR (400 MHz, DMSO) δ (ppm) 8.02 (1H, d), 7.72 (1H, d), 6.42 (2H, br s), 4.56 (1H, s).

The product contained an estimated 15% by weight of impurity, presumed triphenylphosphine oxide from Pd catalyst from Step 1, but was used without further purification.

Heterocyclic Boronic Esters (D)

Intermediate D1

4-(4,4,5,5-tetramethyl-1,3,2-dioxoborolan-2-yl)-1-(2,2,2-trifluoroethyl)-1H-pyrazole

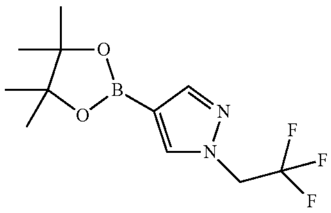 [SMILES: CC1(C)OB(c2cnn(CC(F)(F)F)c2)OC1(C)C]

A stirred mixture of 4-(4,4,5,5-tetramethyl-1,3,2-dioxaborolan-2-yl)-1H-pyrazole (0.56 g, 2.89 mmol), 2,2,2-trifluoroethyl trifluoromethanesulfonate (0.633 ml, 4.39 mmol) and cesium carbonate (2.81 g, 8.62 mmol) in acetonitrile (20 ml) was heated at 60° C. After 2 h the solvent was removed under reduced pressure and the residue was partitioned between EtOAc and water. The organic extract was dried over $MgSO_4$ and the solvent was removed under reduced pressure to afford the title compound as a gum;

LCMS: Rt 1.00 mins; MS m/z 277.4 [M+H]+; Method 2 minLC_v003

$^1H$ NMR (400 MHz, $CDCl_3$) δ 7.88 (1H, s), 7.82 (1H, s), 4.73 (2H, q), 1.35 (12H, s).

Intermediate E1

3-(6-Amino-5-bromopyridin-3-yl)-N-(3-hydroxy-3-methylbutyl)-4-methyl benzene sulfonamide

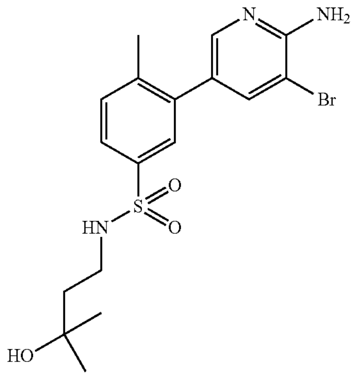 [SMILES: Cc1ccc(S(=O)(=O)NCCC(C)(C)O)cc1-c1cnc(N)c(Br)c1]

Step 1: 3-(6-Aminopyridin-3-yl)-N-(3-hydroxy-3-methylbutyl)-4-methylbenzenesulfonamide To a mixture of 5-bromopyridin-2-amine (200 mg, 1.16 mmol) and N-(3-hydroxy-3-methylbutyl)-4-methyl-3-(4,4,5,5-tetramethyl-1,3,2-dioxaborolan-2-yl)benzenesulfonamide (Intermediate B3) (487 mg, 1.27 mmol) in DME (3.5 mL) in a 5 mL microwave tube equipped with stirrer bar was added $PdCl_2(dppf).CH_2Cl_2$ adduct (94 mg, 0.12 mmol) and a solution of sodium carbonate (368 mg, 3.47 mmol) in water (1 mL). The tube was capped and the mixture was heated at 90° C. for 1 hour. The mixture was diluted with water and extracted with EtOAc (3×25 mL). The EtOAc extracts were combined and washed with sat. brine (50 mL), dried ($MgSO_4$), filtered and evaporated to give a brown syrup. The crude product was dissolved in the minimal amount of MeOH and applied to a 10 g Isolute SCX-2 column previously equilibrated with methanol. The column was eluted with MeOH until the eluate had no UV254 active content. The eluant was then switched to 2M ammonia in MeOH to elute the title compound;

LCMS: Rt 0.57 mins; MS m/z 350.3[M+H]+; Method 2 minLowpH

Step 2: 3-(6-Amino-5-bromopyridin-3-yl)-N-(3-hydroxy-3-methylbutyl)-4-methylbenzene sulfonamide To a stirred solution of 3-(6-aminopyridin-3-yl)-N-(3-hydroxy-3-methylbutyl)-4-methyl benzenesulfonamide (step 1) (168 mg, 0.48 mmol) in dry DCM (5 mL) at RT was added N-bromosuccinimide (94 mg, 0.53 mmol). The reaction was stirred at RT for 1 hour. The mixture was diluted with 50% sodium bicarbonate and the DCM layer was recovered by filtration through a phase separator. The DCM was evaporated to give a brown gum. The crude product was dissolved in the minimum amount of MeOH and applied to a 1 g Isolute SCX-2 column, pre-equilibrated with MeOH. The column was eluted with MeOH until the eluate was non-UV254 active. The eluant was then switched to 2M ammonia in MeOH to elute the title compound;

LCMS: Rt 0.85 mins; MS m/z 428/430[M+H]+; Method 2 minLowpH.

Intermediate EE1

3-(6-Amino-5-bromopyridin-3-yl)-N-(2-hydroxy-2-methylpropyl)-4-methyl benzenesulfonamide

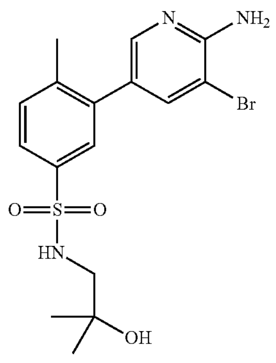 [SMILES: Cc1ccc(S(=O)(=O)NCC(C)(C)O)cc1-c1cnc(N)c(Br)c1]

A mixture of N-(2-hydroxy-2-methylpropyl)-4-methyl-3-(4,4,5,5-tetramethyl-1,3,2-dioxaborolan-2-yl)benzenesulfonamide (Intermediate B2) (3.5 g, 9.48 mmol), 3-bromo-5-iodopyridin-2-amine (2.5 g, 8.36 mmol), bis (triphenylphosphine)palladium dichloride (0.25 g, 0.356 mmol) in 1,2-dimethoxyethane (40 ml) and 2M sodium carbonate (12 ml, 24.00 mmol) was heated to reflux for 3 hours. After cooling to room temperature and diluting with 10% methanol in DCM, the mixture was filtered through 10 g Celite®, washing with further 10% methanol in DCM (leaving aqueous behind). The combined organic extracts were evaporated under reduced pressure, bound to silica and purified by flash column chromatography (220 g silica, 65-90% ethyl acetate in iso-hexane). The appropriate fractions were concentrated under reduced pressure in two batches. The brown sticky foam obtained from each were separately taken up in ethyl acetate and methanol and allowed to slowly evaporate overnight. Large apparent crystals were formed in each solution and these were collected washing with ethyl acetate to afford the title compound;

LCMS: Rt 0.88 min; m/z 416.1 and 414.1 [M+H]+, Br isotopes; Method: 2 minLowpHv01

Intermediate E2

3-(6-Amino-5-(3-methyl-1,2,4-oxadiazol-5-yl)pyridin-3-yl)-4-methylbenzene-1-sulfonyl chloride

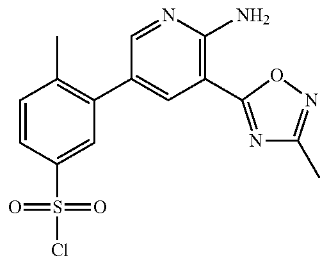 [SMILES: Cc1noc(-c2cc(-c3cc(S(=O)(=O)Cl)ccc3C)cnc2N)n1]

Step 1: 3-(3-methyl-1,2,4-oxadiazol-5-yl)-5-o-tolylpyridin-2-amine

To a solution of o-tolylboronic acid (533 mg, 3.92 mmol) in DME (9801 μL) was added 5-bromo-3-[1,2,4]oxadiazol-5-yl-pyridin-2-ylamine (Intermediate C3) (500 mg, 1.960 mmol), bis(triphenylphosphine)palladium(II) chloride (68.8 mg, 0.098 mmol) and $Na_2CO_3$ (aq. 2.0M) (2940 μL, 5.88 mmol). The reaction was heated in a microwave at 120° C. for 30 mins. The reaction mixture was added to water (100 ml), and the product extracted into EtOAc (2×80 ml). The organic phase was washed with brine, dried over $MgSO_4$. The solids were removed by filtration, washed with EtOAc and concentrated under reduced pressure. The crude product was purified by flash column chromatography, eluting with 0-10% gradient of (2M $NH_3$ in MeOH) in DCM on a 125 g si-column, followed by crystallization from MeOH to give a white solid (160 mg, 30.7%)

LCMS: Rt 1.16 mins; MS m/z 267.2 [M+H]+; Method 2 minLowpHv01.

Step 2: 3-(6-Amino-5-(3-methyl-1,2,4-oxadiazol-5-yl)pyridin-3-yl)-4-methylbenzene-1-sulfonyl chloride Chlorosulfonic acid (966 μl, 14.42 mmol) was added dropwise to a cooled stirring solution of 3-(3-methyl-1,2,4-oxadiazol-5-yl)-5-(o-tolyl)pyridin-2-amine (step 1) (160 mg, 0.601 mmol) in $CHCl_3$ (Volume: 3 ml), under $N_2$, at 0°. The reaction was stirred for 1 h at 0° C. then allowed to warm to RT and stirred overnight. The Reaction mixture was quenched with dropwise addition into a stirring mixture of sat. $NaHCO_3$ (50 ml) and DCM (50 ml). The DCM phase was collected via a phase separator. 1M HCl in dioxane (2 ml) was added to the DCM and the solution was concentrated to dryness to give the title compound (170 mg, 70.5%);

LCMS: Rt 1.10 mins; MS m/z 365.0 [M−H]−; Method 2 minLowpHv01

Intermediate E3

3-(6-Amino-5-(3-methylisoxazol-5-yl)pyridin-3-yl)-4-methylbenzene-1-sulfonyl chloride

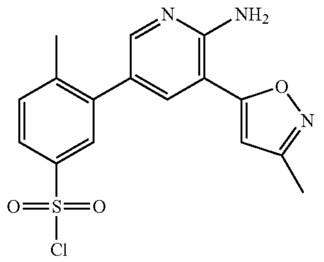 [SMILES: Cc1cc(-c2cc(-c3cc(S(=O)(=O)Cl)ccc3C)cnc2N)on1]

The title compound was prepared from 5-bromo-3-(3-methyl-isoxazol-5-yl)-pyridin-2-ylamine (Intermediate C5) analogously to Intermediate E2 steps 1 and 2.

LCMS: Rt 1.19 mins; MS m/z 364.3 [M+H]+; Method 2 minlowpHv01

Intermediate E4

3-(6-amino-5-(2-methyloxazol-5-yl)pyridin-3-yl)-4-methylbenzene-1-sulfonyl chloride

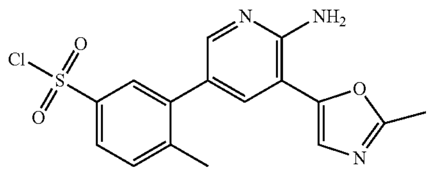 [SMILES: Cc1ncc(-c2cc(-c3cc(S(=O)(=O)Cl)ccc3C)cnc2N)o1]

Step 1: 3-(2-methyloxazol-5-yl)-5-(o-tolyl)pyridin-2-amine

To a solution of 3-bromo-5-iodopyridin-2-amine (1.430 g, 4.78 mmol) in DME (24 mL) was added 2-methyl-5-(4,4,5,5-tetramethyl-1,3,2-dioxaborolan-2-yl)oxazole (1 g, 4.78 mmol), bis(triphenylphosphine)palladium(II) chloride (0.168 g, 0.239 mmol) and $Na_2CO_3$ (aq. 2.0M) (9.57 ml, 19.13 mmol). The reaction was heated at 85° C. overnight.

A further 0.05 eq of bis(triphenylphosphine)palladium(II) chloride (0.168 g, 0.239 mmol) and 2-methyl-5-(4,4,5,5-tetramethyl-1,3,2-dioxaborolan-2-yl)oxazole (1 g, 4.78 mmol) was added and reaction was heated at 85° C. for 8 hours. Reaction was added to water (150 ml), and product extracted into EtOAc (2×120 ml). The organic extract was washed with brine, dried over $MgSO_4$, filtered, solid washed with EtOAc and combined organics concentrated under reduced pressure. Crude was purified by automated flash Si-chromatography, eluting with 0-10% gradient of (2M $NH_3$ in MeOH) in DCM on a 40 g Si-column, loading with DCM to give 550 mg of the title compound as an orange solid LCMS: Rt 0.85 mins; no consistent mass ion observed; Method: 2 minLowpHv01

$^1$H NMR (400 MHz, DMSO-d6) δ 7.99 (1H, d), 7.69 (1H, d), 7.49 (1H, s), 7.33-7.20 (4H, m), 6.18 (2H, s), 2.48 (3H, s), 2.27 (3H, s).

Step 2: 3-(6-amino-5-(2-methyloxazol-5-yl)pyridin-3-yl)-4-methylbenzene-1-sulfonyl chloride To a cooled stirring solution of 3-(2-methyloxazol-5-yl)-5-(o-tolyl)pyridin-2-amine (Step 1, 530 mg, 1.998 mmol) in $CHCl_3$ (10 mL), under $N_2$, at 0° C. was added chlorosulfonic acid (3.21 ml, 47.9 mmol) dropwise. Reaction was stirred for 1 hour at 0° C. then allowed to warm to RT and stirred overnight. The now biphasic solution was quenched by drop wise addition into a stirring mixture of cold sat. $NaHCO_3$ (200 ml) and DCM (200 ml). DCM extract was collected via a phase separator and 4M HCl in dioxane (8 ml) was added before the solution was concentrated to dryness under reduced pressure to give 900 mg of the title compound as a yellow solid.

An aliquot of sulfonyl chloride was quenched into pyrrolidine, diluted with MeOH and analyzed by LCMS to give >90% of the corresponding sulfonamide indicating that the desired sulfonyl chloride had been formed. LCMS: Rt 0.90 mins; MS m/z 399.3 [M+H]+; Method: 2 minLowpHv01

Intermediate F

5-Bromo-3-(2-cyclopropyloxazol-5-yl)pyridin-2-amine

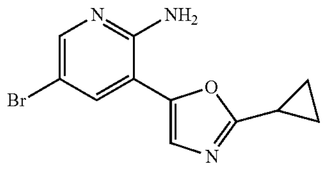 [SMILES: Nc1ncc(Br)cc1-c1cnc(C2CC2)o1]

In a 10 mL round-bottomed flask was 5-bromo-3-iodopyridin-2-amine (2 g, 6.69 mmol), 2-cyclopropyloxazole-4-carboxylic acid (1.537 g, 10.04 mmol), $Pd(PPh_3)_2Cl_2$ (0.470 g, 0.669 mmol) and silver carbonate (2.399 g, 8.70 mmol) in N-methyl-2-pyrrolidone (10 ml) to give a brown suspension. The reaction mixture was heated at 170° C. for 18 h. The reaction mixture was diluted with EtOAc (50 mL) and water (50 mL). The biphasic solution was filtered to remove solid particulates. The organics were washed with $NaHCO_3$ (50 mL), dried $MgSO_4$, filtered and concentrated under reduced pressure. The product was purified by silica flash column chromatography eluting on a gradient of 0-50% EtOAc/hexane. Fractions were combined and concentrated to afford a brown oil (154 mg).

LC-MS: Rt 1.10 mins; MS m/z 281/282/283 {M+H}+; Method 2 minLowpHv03

$^1$H NMR (400 MHz), $CDCl_3$) δ 8.11 (1H, s), 7.82 (1H, s), 7.21 (1H, s), 5.15 (2H, s), 2.16 (1H, m), 1.17 (6H, m).

Pharmaceutical Use and Assays

The compounds of the present invention and their pharmaceutically acceptable salts may be useful as pharmaceuticals. In particular, the compounds are suitable PI 3-kinase gamma isoform selective inhibitors and may be tested in the following assays.

Abbreviations:

ADP: Adenosine diphosphate

ATP: Adenosine triphosphate

BSA: Bovine serum albumin

DMEM: Dulbecco's modified Eagle's medium

DMSO: Dimethylsulfoxide

DTT: Dithiothreitol

CHAPS: 3-[(3-cholamidopropyl)dimethylammonio]-1-propanesulfonate

EDTA: Ethylenediaminetetraacetic acid

EGTA: Ethylene glycol tetraacetic acid

FACS: Fluorescence-activated cell sorting

FBS: Fetal bovine serum

HBSS: Hank's Balanced Salt Solution

HEPES: 4-(2-Hydroxyethyl)piperazine-1-ethanesulfonic acid

HTRF: Homogeneous Time Resolved Fluorescence

MIP1α: Macrophage Inflammatory Protein form 1α (also known as CCL3)

PBS: phosphate-buffered saline

RPMI: Roswell Park Memorial Institute medium

TR-FRET: Time-Resolved Fluorescence Resonance Energy Transfer

Kinase Glo Luminescent Kinase Assay (Kglo) for PI 3-Kinase Alpha (A), PI 3-Kinase Beta (B), Vps34 (C), PI 4-Kinase Beta (D)

The luminescence-based ATP detection reagent Kinase-Glo was obtained from Promega, (Cat. No. V6714, Lot No. 236161) through Catalys, Wallisellen, Switzerland. L-alpha-phosphatidylinositol (PI, liver, bovine) was obtained from Avanti Polar Lipid (Cat. No. 840042C, Lot#LPI-274), phosphatidylinositol-4,5-bisphosphate (PIP(4,5)2) was obtained from Avanti Polar Lipid (Cat. No. 840046X). L-α-phosphatidylserine (PS) was obtained from Avanti Polar Lipid (Cat. No. 840032C), n-octylglucoside from Avanti Polar Lipid (Cat. No. 10634425001). Luminescence is a well established readout to determine ATP concentrations and can thus be used to follow the activity of many kinases regardless of their substrate. The Kinase Glo Luminescent Kinase Assay (Promega, Madison, Wis., USA) is a homogeneous HTS method of measuring kinase activity by quantifying the amount of ATP remaining in solution following a kinase reaction.

50 nL of compound dilutions were dispensed onto black 384-well low volume Non Binding Styrene (NBS) plates (Costar Cat. No. NBS#3676). L-α-phosphatidylinositol (PI), provided as 10 mg/ml solution in methanol, was transferred into a glass tube and dried under a nitrogen beam. It was then resuspended in 3% OctylGlucoside (1-O-n-octyl-beta-D-glucopyranoside) by vortexing and stored at 4° C. 5 μl of a mix of PI/OctylGlucoside with the PI 3-kinase alpha and PI 3-kinase beta subtypes, or Vps34 or PI 4-kinase beta were added. Kinase reactions were started by the addition of 5 μl of an ATP-mix containing in a final volume 10 μl 10 mM TRIS-HCl pH 7.5, 3 mM $MgCl_2$, 50 mM NaCl, 0.05% CHAPS, 1 mM DTT and 1 μM ATP at room temperature. Reactions were stopped with 10 μl of KinaseGlo and plates were read 10 mins later in a Synergy2 reader using an integration time of 0.1 seconds per well. 2.5 μM of NVP-BGT226 (1-(3-(trifluoromethyl)-4-(piperazin-1-yl)phenyl)-8-(6-methoxypyridin-3-yl)-3-methyl-1H-imidazo[4,5-c]quinolin-2(3H)-one) was added to the assay plates to generate the 100% inhibition of the kinase reaction, and the 0% inhibition was given by the solvent vehicle (90% DMSO in water). (1-(3-(trifluoromethyl)-4-(piperazin-1-yl)phenyl)-8-(6-methoxypyridin-3-yl)-3-methyl-1H-imidazo[4,5-c]quinolin-2(3H)-one) was used as a reference compound and included in all assay plates in the form of 16 dilution points in duplicate.

$IC_{50}$ values of the percentage inhibition of each compound at 8 concentrations (10, 3.0, 1.0, 0.3, 0.1, 0.030, 0.010 and 0.003 μM) n=2 were derived by fitting a sigmoidal dose-response curve to a plot of assay readout over inhibitor concentration as described. All fits were performed with the program XLfit4 (ID Business Solutions, Guildford, UK).

TR-FRET Adapta Assay for PI 3-Kinase Gamma (E), PI 3-Kinase Delta (F)

The TR-FRET Adapta™ Universal Kinase Assay Kit was purchased from Invitrogen Corporation (Carlsbad, Calif., USA) (Cat. No. PV5099). The kit contains the following reagents: Adapta Eu-anti-ADP Antibody (Europium labeled anti-ADP antibody in HEPES buffered saline, Cat. No. PV5097), Alexa Fluor® 647-labeled ADP tracer (Alexa Fluor® 647-labeled ADP tracer in HEPES buffered saline, Cat. No. PV5098), TR-FRET dilution buffer pH 7.5 (Cat. No. PV3574).

PIK3CD substrate phosphatidylinositol (PI) was obtained from Invitrogen (vesicules consisting of 2 mM phosphatidylinositol (PI) in 50 mM HEPES pH7.5; Cat. No. PV5371). PIK3CG substrate phosphatidylinositol-4,5-bisphosphate (PIP(4,5)2 was obtained from Invitrogen (PIP2:PS large unilamellar vesicules consisting of 1 mM PIP2:19 mM PS in 50 mM HEPES pH7.5, 3 mM $MgCl_2$, 1 mM EGTA; Cat. No. PV5100).

Time-Resolved Fluorescence Resonance Energy Transfer (TR-FRET) is a technology based on energy transfer between two adjacent dyes, from an excited electron in one dye (the donor) to an electron of an adjacent dye (the acceptor) through resonance, then released as a photon. This energy transfer is detected by an increase in the fluorescence emission of the acceptor, and a decrease in the fluorescence emission of the donor. TR-FRET assays for protein kinases use a long-lifetime lanthanide Terbium or Europium chelates as the donor species which overcome interference from compound autofluorescence or light scatter from precipitated compounds, by introducing a delay after excitation by a flashlamp excitation source. Results are often expressed as a ratio of the intensities of the acceptor and donor fluorophores. The ratiometric nature of such a value corrects for differences in assay volumes between wells, as well as corrects for quenching effects due to colored compounds. The Adapta™ assay can be divided into two phases: a kinase reaction phase and an ADP detection phase. In the kinase reaction phase, all kinase reaction components are added to the well and the reaction is allowed to incubate for a set period of time specific for each kinase. After the reaction, a detection solution of Eu-labeled anti-ADP antibody, Alexa Fluor® 647-labeled ADP tracer, and EDTA (to stop the kinase reaction) are added to the assay well. ADP formed by the kinase reaction will displace the Alexa Fluor® 647-labeled ADP tracer from the antibody, resulting in a decrease in TR-FRET signal. In the presence of an inhibitor, the amount of ADP formed by the kinase reaction is reduced, and the resulting intact antibody-tracer interaction maintains a high TR-FRET signal. In the Adapta™ assay, the donor (Europium-anti-ADP antibody) is excited at 340 nm and will transfer its energy to the acceptor (Alexa Fluor® 647-labeled ADP tracer). The emission from the Alexa Fluor® 647 can be monitored with a filter centered at 665 nm because it is located between the emission peaks of the donor, which is measured at 615/620 nm.

50 nL of compound dilutions were dispensed onto white 384-well small volume polystyrene plate. Then 5 μl of either PI 3-kinase gamma or PI 3-kinase delta and lipid substrate (PI or PIP2: PS) followed by 5 μl of ATP (final assay volume 10 μl) are incubated at RT. The standard reaction buffer for the Adapta™ TR-FRET assay contained 10 mM Tris-HCl pH 7.5, 3 mM $MgCl_2$, 50 mM NaCl, 1 mM DTT, 0.05% CHAPS ((3-[(3-cholamidopropyl)dimethylammonio]-1-propanesulfonate). Reactions were stopped with 5 μl of a mixture of EDTA containing the Eu-labeled anti-ADP antibody and the Alexa Fluor® 647-labeled ADP tracer in TR-FRET dilution buffer. Plates are read 15 to 60 mins later in a Synergy2 reader using an integration time of 0.4 seconds and a delay of 0.05 seconds. Control for the 100% inhibition of the kinase reaction was performed by replacing the PI 3-kinase by the standard reaction buffer. The control for the 0% inhibition was given by the solvent vehicle of the compounds (90% DMSO in $H_2O$). The standard compound 1-(3-(trifluoromethyl)-4-(piperazin-1-yl)phenyl)-8-(6-methoxypyridin-3-yl)-3-methyl-1H-imidazo[4,5-c]quinolin-2(3H)-one (NVP-BGT226) was used as a reference compound and included in all assay plates in the form of 16 dilution points in duplicate.

Data are analyzed using Excel fit software or Graphpad Prism. $IC_{50}$ values were derived by fitting a sigmoidal dose-response curve to a plot of assay readout over inhibitor concentration. All fits were performed with the program XLfit4 (ID Business Solutions, Guildford, UK). Determination of $IC_{50}$ values of the percentage inhibition of each compound at 8 concentrations (usually 10, 3.0, 1.0, 0.3, 0.1, 0.030, 0.010 and 0.003 μM) n were derived by fitting a sigmoidal dose-response curve to a plot of assay readout over inhibitor concentration. All fits were performed with the program XLfit4 (ID Business Solutions, Guildford, UK).

Lanthascreen™ Kinase Binding Assay for mTOR (G)

Binding Assays are based on the binding and displacement of an Alexa Fluor® 647-labeled, ATP-competitive kinase inhibitors to the kinase of interest. Invitrogen's "Kinase Tracers" have been developed to address a wide range of kinase targets and are based on ATP-competitive kinase inhibitors, making them suitable for detection of any compounds that bind to the ATP site or to an allosteric site altering the conformation of the ATP site.

In the Lanthascreen™ kinase binding assay, the donor ($Eu^{3+}$-anti-GST (glutathione S-transferase) antibody) is excited at 340 nm and will transfer its energy to the acceptor (Alexa Fluor® 647-labeled ATP-competitive kinase inhibitor=Tracer-314). The emission from the Tracer-314 (Alexa Fluor® 647 inhibitor) can be monitored with a filter centered at 665 nm because it is located between the emission peaks of the donor, which is measured at 615/620 nm. The binding of both, the Tracer-314 and $Eu^{3+}$-anti-GST antibody, to the kinase results in a high degree of FRET from the $Eu^{3+}$-donor fluorophore to the Alexa-Fluor® 647-acceptor fluorophore on the Tracer-314. Binding of an inhibitor to the kinase competes for binding with the tracer, resulting in a loss of FRET.

50 nL of compound dilutions were dispensed onto white 384-well small volume polystyrene plate. Then 5 μl of GST-mTOR and Europium-anti-GST antibody followed by 5 μl of tracer-314 (final assay volume 10 μl) are incubated at RT. The standard reaction buffer for the Lanthascreen™ kinase binding assay contained 50 mM HEPES pH 7.5, 5 mM MgCl2, 1 mM EGTA, 0.01% Pluronic F-127. Plates are read 60 mins later in a Synergy2 reader using an integration time of 0.2 microseconds and a delay of 0.1 microseconds.

To calculate the emission ratio, the signal emitted at 665 nm from the acceptor (Alexa Fluor® 647-labeled Tracer-314) is divided by the signal emitted at 620 nm from the donor ($Eu^{3+}$ anti-GST antibody).

Control for the 0% inhibition was given by the solvent vehicle of the compounds (90% DMSO in $H_2O$). Control for the relative 100% inhibition was performed by adding 10 μM in the mix containing GST-mTOR and Europium anti-GST antibody. An additional control for the absolute 0% inhibition is given by $Eu^{3+}$ anti-GST antibody without GST-mTOR. Standard compounds for the lipid kinase panel profiling were used as a reference and included in all assay plates in the form of 8 dilution points.

Cellular Assays for PI 3-Kinase Alpha (H1), Beta (I1) and Delta (J1): Surefire Format AlphaScreen (Amplified Luminescent Proximity Homogeneous Assay, ALPHA, Perkin Elmer) is a non-radioactive bead-based proximity assay technology to study biomolecular interactions in a homogenous microtiter plate format. The brand name SureFire denotes AlphaScreen assays that are adapted to quantify the phosphorylation of endogenous cellular proteins in cell lysates, by using matched antibody pairs, which consist of an anti-phospho-kinase and an anti-kinase antibody. The assay allows characterization of kinase signaling in cells as well as measurement of kinase inhibitor effects.

Rat-1 cell lines stably overexpressing activated PI 3-kinase class I isoforms Rat-1 pBABEpuro Myr-HA-hp110 delta clone 5 (Rat-1_PI3Kdelta) and Rat-1 pBABEpuro Myr-HA-hp110 alpha clone 6 (Rat-1_PI3Kalpha) and Rat-1 pBABEpuro Myr-HA-hp110 beta (Rat-1_PI3beta) were cultivated in complete growth medium (DMEM high glucose, 10% (v/v) fetal bovine serum, 1% (v/v) MEM NEAA, 10 mM HEPES, 2 mM L-glutamine, puromycin (10 μg/mL for Rat-1_PI3Kdelta and Rat-1_PI3Kalpha, 4 μg/mL for Rat-1_PI3beta), 1% (v/v) Pen/Strep) to 90% confluency at 37° C./5% $CO_2$/90% humidity in a humidified $CO_2$ incubator and were split twice a week.

The following materials were used for p-AKT(S473) detection in Rat-1 cell lysates: Dulbecco's modified Eagle's medium (DMEM) high glucose (Gibco Invitrogen, Basel, Switzerland, Cat. No. 41965), heat inactivated fetal bovine serum, qualified (HI FBS; Gibco Invitrogen, Basel, Switzerland, Lot. No. 16140), MEM non essential amino acids (NEAA; Gibco Invitrogen, Basel, Switzerland, Cat. No. 11140), HEPES (Gibco Invitrogen, Basel, Switzerland, Cat. No. 15630), penicillin/streptomycin (Pen/Strep, 100×; Gibco Invitrogen, Basel, Switzerland, Cat. No. 15140-122), L-glutamine (Gibco Invitrogen, Basel, Switzerland, Cat. No. 25030), puromycin (Sigma Aldrich, Buchs, Switzerland, Cat. No. P9620), DMSO (MERCK, Dietikon, Switzerland, Cat. No. 8.02912.2500), $H_2O$, MilliQ-$H_2O$ unless otherwise stated (MILLIPORE QGARDOOR1, Millipore, Zug, Switzerland), bovine serum albumine (BSA; Sigma Aldrich, Buchs, Switzerland Cat. No. A8412), SureFire p-Akt 1/2 (Ser473) Assay Kit (PerkinElmer, Schwerzenbach, Switzerland, Cat. No. TGRAS50K). The p-Akt (S473) SureFire assay measures the phosphorylation of endogenous cellular Akt 1/2 at Ser473 in cell lysates. Using Rat-1 cells stably expressing myr-HA-tagged versions of the human PI3Kdelta, PI3Kalpha, or PI3Kbeta p110 catalytic subunit isoforms, the assay was developed as a two-plate protocol in a 384-well format.

For compound testing, the cells were seeded at a density of 4000 (Rat-1_PI3Kdelta), 7500 (Rat-1_PI3Kalpha), or 6200 (Rat-1_PI3Kbeta) cells in 20 μl complete growth medium into cell culture treated 384-well plates and were grown at 37° C./5% $CO_2$/90% humidity for 24 h. Shortly before compound transfer, the complete medium was removed, 30 μl assay buffer (DMEM high glucose, 1×MEM NEAA, 10 mM HEPES, 2 mM L-glutamine, 0.1% (w/v) BSA) was added and 10 μl of the compound predilutions were transferred to the cells. After treatment with compound for 1 h, the cells were lysed by the addition of 20 μl lysis buffer supplemented with 0.24% (w/v) BSA. Detection of p-AKT (Ser473) was performed with the SureFire p-Akt 1/2 (Ser473) Assay Kit according to the manufacturer's instructions using 5 μl of cell lysate in a total detection volume of 12 μl.

$IC_{50}$ values of the percentage inhibition of each compound at 8 concentrations (usually 10, 3.0, 1.0, 0.3, 0.1, 0.030, 0.010 and 0.003 μM) n=2 were derived by fitting a sigmoidal dose-response curve to a plot of assay readout over inhibitor concentration as described. All fits were performed with the program XLfit4 (ID Business Solutions, Guildford, UK).

Cellular Assays for PI 3-Kinase Alpha (H2), Beta (I2) and Delta (J2): HTRF (Homogeneous Time Resolved Fluorescence) Format The following materials were used for p-AKT(S473) detection in Rat-1 cell lysates: Dulbecco's modified Eagle's medium (DMEM), high Glucose, GlutaMAX™, Pyruvate (Gibco Invitrogen, Basel, Switzerland, Cat. No. 31966), Dialyzed Fetal Bovine Serum (FBS) US origin (Gibco Invitrogen, Basel, Switzerland, Cat. No. 36400, Lot. No. 776683), MEM non essential amino acids (NEAA; Gibco Invitrogen, Basel, Switzerland, Cat. No. 11140), HEPES (Gibco Invitrogen, Basel, Switzerland, Cat. No. 15630), Penicillin/Streptomycin (Pen/Strep, 100×; Gibco Invitrogen, Basel, Switzerland, Cat. No. 15140-122), Puromycin (Sigma Aldrich, Buchs, Switzerland, Cat. No. P9620), DMSO (MERCK, Dietikon, Switzerland, Cat. No. 8.02912.2500), H2O, MilliQ-H2O unless otherwise stated (MILLIPORE QGARDOOR1, Millipore, Zug, Switzerland), HTRF Phospho-AKT (Ser473) Assay Kit (Cisbio, Codolet, France, Cat. No. 64AKSPEH)

The Rat-1 cell lines stably overexpressing activated PI3K class I isoforms Rat-1 pBABEpuro Myr-HA-hp110 delta clone 6 (Rat-1_PI3Kdelta) and Rat-1 pBABEpuro Myr-HA-hp110 alpha clone 6 (Rat-1_PI3Kalpha) and Rat-1 pBABEpuro Myr-HA-hp110 beta clone 1-E8 (Rat-1_PI3Kbeta) were used. All cell lines were cultivated in complete growth medium (DMEM high glucose GlutaMAX™ Pyruvate, 10% (v/v) fetal bovine serum, 0.1 mM MEM NEAA, 25 mM HEPES, puromycin 10 μg/mL, 100 U/ml Penicillin, 100 μg/ml Streptomycin) to 90% confluency at 37° C./5% CO2/90% humidity in a humidified CO2 incubator and were split twice a week.

Semi-automated preparation of cell lysates: For low (inhibited) controls, 0.9 mM NVP-BGT226-AF-1 in 90% (v/v) DMSO was added to the compound master plate. For compound testing, the cells were seeded at a density of 4000 (Rat-1_PI3Kdelta), 8000 (Rat-1_PI3Kalpha), or 6500 (Rat-1_PI3Kbeta) cells in 30 μl complete growth medium into cell culture treated 384-well plates and were grown at 37° C./5% CO2/90% humidity for 24 h. 10 μl of the compound predilutions were transferred to the cells. After treatment with compound for 1 h, medium was removed and cells were lysed by the addition of 20 μl lysis buffer supplemented with blocking buffer. Detection of p-AKT(Ser473) was performed with the HTRF pAKT (Ser473) assay kit according to the manufacturer's instructions using 16 μl of cell lysate in a total detection volume of 20 μl.

Cellular U937 AKT Assay for PI 3-Kinase Gamma (K1)

The U937 monocyte cell line is maintained in a basal medium of RPMI 1640 supplemented with 10% heat inactivated FBS, 100 U/ml Penicillin, 100 ug/ml streptomycin and 2 mM L-glutamine (Invitrogen). U937 suspension culture is maintained by seeding cells at a density of $0.125\times10^6$ cells per ml in fresh medium every three or four days. Cells are incubated at 37° C., 5% CO2. Three or four days prior to assay, cells are seeded at a density of $0.25\times10^6$ cells per ml in a total volume of 40 ml in a T162 culture flask.

Before beginning the cell manipulations described below, the MSD (Meso Scale Discovery) assay plate is blocked by addition of 150 μl/well blocking buffer supplied and incubated with shaking for a minimum of one hour at room temperature. All steps of the assay must be performed quickly, with accurately timed incubation periods and observing temperature controls where indicated.

Cells seeded at $0.25\times10^6$/ml 3 or 4 days prior to the assay are aspirated, transferred to a 50 ml falcon tube, counted and centrifuged for eight minutes at 300 g at room temperature. Supernatant is aspirated, the cell pellet resuspended and washed once in HBSS (Hank's Balanced Salt Solution) by centrifugation for eight minutes at 300 g at room temperature. The cell pellet is resuspended in HBSS to a concentration of $4\times10^6$ per ml, and 100 μL of cell suspension added to each well of a flat-bottomed 96-well tissue culture plate. Assay plates are incubated for 1.5 hours at 37° C., 5% $CO_2$ to allow background AKT phosphorylation to reduce before the compound stimulation step.

A 5 mM stock concentration of compound is prepared in 100% DMSO; from this a 1 in 125 dilution is made in HBSS giving a top compound concentration of 40 μM, 0.8% DMSO. Compound titrations are prepared in a fresh flat-bottomed, 96-well plate, by 10-fold serial dilution of 40 μM into HBSS 0.8% DMSO; pipette tips are replaced after each dilution is made. Compound concentrations at this stage are 4-times the final concentration required in the assay plate. Cells are stimulated with compound or HBSS 0.8% DMSO by direct transfer of 50 μl/well from the compound dilution plate. The assay plate containing compound-treated cells is then incubated for 30 minutes at 37° C. A standard plate layout is used for all experiments.

Compound-treated cells, in addition to positive control wells ("max MIP1α"), are stimulated with 50 μL per well of 40 ng/ml MIP1α (R&D Systems catalogue number 270-LD, lyophilized stock reconstituted to 50 μg/ml with PBS 0.1% BSA). Negative control wells ("min HBSS"), are stimulated with 50 μl/well of HBSS in the absence of MIP1α. Final compound concentrations are now diluted 4-fold giving a top concentration of 10 μM; where added, the final concentration of MIP1α is 10 ng/ml. Cells are incubated with MIP1α for 3 minutes, at 37° C., 5% CO2. After the three minute stimulation period, the assay plate is kept ice cold at all times. Assay plates are centrifuged for 2 minutes at 300 g, 4° C. and supernatant is removed by gently inverting, and then blotting the plate on tissue. Cells are then washed by gentle addition of 150 μL/well of ice cold HBSS and centrifugation at 300 g, for 5 minutes at 4° C. Supernatant is aspirated and the plate blotted as described above. The plate is placed on ice and cells are immediately treated with 35 μL per well of ice cold lysis buffer, prepared according to the kit instructions (per assay plate, to 5 ml of Tris lysis buffer add 100 μl of 50× protease inhibitor solution and 50 μl of each 100× phosphatase inhibitor solutions I and II). Plates are incubated on ice for 20 minutes before centrifugation at 841 g for 5 minutes, 4° C.

Block buffer is aspirated from the MSD plate, and the plate washed four times with 300 μl/well Tris wash buffer. 25 μL of cell lysate is then transferred from the assay plate to the washed MSD plate which is sealed and incubated at room temperature for one hour with shaking. The plate is washed four times with 300 μL per well of Tris wash buffer before addition of 25 μL per well of sulfo-tag anti-total AKT/pAKT detection antibody (60 μl of 50× antibody stock is diluted in 1 ml block buffer mixed with 2 ml wash buffer) and incubated at room temperature for one hour with shaking. The plate is washed four times with 300 μl per well of Tris wash buffer and 150 μl per well of Read buffer is added, taking care to avoid the introduction of bubbles. The plate is immediately read using an MSD SECTOR Imager 6000. Results are exported in Excel and the percentage of phosphorylated AKT is calculated using the equation: % Phosphoprotein=((2*Phospho signal)/(Phospho signal+Total signal))*100. Compound-mediated inhibition of AKT phosphorylation is analysed using Prizm V Graphpad software.

Cellular U937 AKT Assay for PI 3-Kinase Gamma (K2)

Materials used: Bio-Rad TC10™ automated cell counter, Bio-RAD counting slides (#145-0011), Trypan blue solution 0.4% (#T8154 Sigma), diluted 1:2 in PBS), Bioconcept Multidrop combi, Versette automated liquid handler (Thermo scientific), HTRF Phospho-AKT (Ser473) 10,000 tests assay kit (cisbio #64AKSPEH), ProxiPlate-384 Plus, White, TC treated (Perkin Elmer #6008239)

384-well tissue culture treated plate (BD Falcon #353289), RPMI+GlutaMAX (Life Technologies #61870-010), FBS dialyzed (Life Technologies #26400), Penicillin/Streptomycin (Life Technologies #15140), HBSS 1× (Life Technologies #14025-050), Wortmannin (Sigma-Aldrich # W1628), stock solution 10 mM in 90% DMSO, Recombinant Human CCL3/MIP1α (R&D Systems #270-LD) (stock solution 10 μg/ml), RUBYstar Microplate Reader (BMG Labtech #8)

U937 cells are split every 3-4 days: $5\times10^6$ cells/flask (175 $cm^2$) in 40 ml. 3-4 days before the assay, cells should be seeded: 4-5 flasks with 107 cells in 40 ml.

Semi-automated preparation of cell lysates: Cells were resuspended in HBSS, seeded (200,000 cells/well/60 μl) into a 384-well plate and incubated in a humidified 37° C., 5% CO2 incubator for 1.5 hours. The compounds were diluted with HBSS and 40 μl were added to the starved cells (except for wells 24 I-P). 10 μM Wortmanin was added to the negative control (wells 24 I-P). The cells were then incubated for 30 minutes at 37° C. and 5% CO2.

Stimulation occurred during 3 minutes by addition of 20 μl MIP1α (final 10 ng/ml, diluted in HBSS) in the incubator. Wells 24 A-H were only stimulated with HBSS.

The stimulation was then stopped by putting the cell plates on ice (filled with cold water). The cells were then centrifuged at 1200 rpm and 4° C. for 3 minutes.

80 μl of supernatant was removed. The cells were again centrifuged at 1200 rpm and 4° C. for 3 minutes. The supernatant was then removed by turning plates upside down and 30 μl of lysis buffer were added. The plate was incubated at room temperature for 30 minutes under shaking. 16 μl were then transferred to a ProxiPlate Plus 384-well. 4 μl of the master mix (each conjugate diluted 1:20 with detection reagent) were added to each well and the plate was kept in the dark at room temperature for 4 hours. Fluorescence was measured at 665 nm and 620 nm with a RUBYstar Reader.

Whole Blood Neutrophil Shape Change Assay (L)

A flow cytometry based method used to measure the inhibition of IL-8 (interleukin-8)-induced neutrophil shape change in human whole blood.

Reagents, Material & Equipment

Sterile Distilled Water, Baxter # UKF117

10× CellFIX solution, BECTON DICKINSON Biosciences #340181

IL-8, R&D Systems #208-IL

DMSO, Hybri-Max, Sigma-Aldrich # D2650

Dulbecco's Phosphate Buffered Saline 1× [+]$CaCL_2$, $MgCL_2$, gibco by life technologies #14040

Albumin Solution from Bovine Serum (30%), Sigma Aldrich # A9576-50 ml

Ammonium Chloride $NH_4CL$, Sigma Aldrich # A0171

Potassium Bicarbonate $KHCO_3$, Sigma Aldrich # P9144

K2 EDTA Vacutainers, Becton Dickinson Vacutainer® #367525

96-well Polypropylene deep-well plates, VWR # PORV219009

96 well Plates, V-bottom with lid, Costar #3894

96 well Polypropylene Plates, Round Bottom, Greiner #650261 (for HIGH THROUGHPUT SAMPLER FACS)

120 μl pre-sterilized Biohit Filter Tips, Biohit #790101F

350 μl pre-sterilized Biohit Tips, Biohit #790350

1200 μl pre-sterilized Biohit Tips, Biohit #791202

Biohit e1200 Electronic 8-channel Pipette

Biohit e120 Electronic 8-channel Pipette

Eppendorf Research Plus 100-1000 μl Pipette

Eppendorf Research Plus 20-200 μl Pipette

Becton Dickinson Biosciences FACS Canto II Flow Cytometer with high throughput sampler.

IL-8 was made up to 2 μM stocks in 0.1% bovine serum albumin/PBS and stored at −80° C. On the day IL-8 was diluted in PBS (phosphate buffered saline) 10 minutes before use. IL-8 was used at final concentration of 2 nM and a concentration range from 0.003 to 200 nM for the donor dose response curve.

Assay fixative solution was prepared fresh each day from 10× concentrated CellFIX™ solution diluted 1:10 in sterile distilled water and then 1:4 with PBS. Assay fixative solution was kept on ice prior to use.

A 10× lysis buffer was prepared in advance by dissolving 20.75 g $NH_4Cl$ and 2.5 g $KHCO_3$ in 250 ml sterile $H_2O$. This 10× lysis buffer was filtered under sterile conditions and stored for up to two weeks at 4° C. On the day a 1× lysis solution was prepared with sterile distilled $H_2O$ and kept on ice prior to use.

The test compounds were prepared as 10 mM stock solutions in 100% DMSO and were stored at 4° C. Once in use for an assay 10 mM stock compounds were thawed and stored at RT protected from light. Compound dilutions were prepared fresh on the day. The first series of dilutions in 100% DMSO were done first thing in the morning. Only once blood had been collected and arrived in laboratory was the next set of dilutions into PBS carried out (1:10 PBS, 10% DMSO). This limited the exposure of diluted compound to plastic and made sure the exposure timing was consistent between assays. Compounds were added to the deep 96 well plates at 10× the final desired concentration (with addition of blood final [DMSO]=1%).

Table 3 illustrates the compound dilution series used in human whole blood neutrophil shape change assay.

TABLE 3

| 100% DMSO Serial Dil'n 1 in 4 | 10% DMSO 1 in 10 PBS | 1% DMSO Assay Plate | $_{example}$Well ID* |
|---|---|---|---|
| 10000 μM | 1000 μM | 100 μM | B2; CPD + IL-8 |
| 2500 | 250 | 25 | B3; CPD + IL-8 |
| 625 | 62.5 | 6.25 | B4; CPD + IL-8 |
| 156.25 | 15.62 | 1.56 | B5; CPD + IL-8 |
| 39.0625 | 3.9 | 0.39 | B6; CPD + IL-8 |
| 9.765625 | 0.97 | 0.097 | B7; CPD + IL-8 |
| 2.441406 | 0.24 | 0.024 | B8; CPD + IL-8 |
| 0.610352 | 0.06 | 0.006 | B9; CPD + IL-8 |
| 100% DMSO | 10% DMSO | 1% DMSO | B10; +IL-8 |
| 100% DMSO | 10% DMSO | 1% DMSO | B11; +PBS |

On the day of running the assay, assay fixative buffer and 1× lysis solutions were prepared and stored on ice. Compound dilutions in 100% DMSO were prepared as described previously. Human whole blood was collected in K2 EDTA Vacutainers. Once blood was in the laboratory, compound dilutions into PBS were carried out as described previously and depicted in Table 1.

10 μl of 10× final compound concentration was added to appropriate wells of a deep 96-well plate except controls where 10 μl of 10% DMSO was added in place of compound, as outlined in the dilution series in Table 1. The outer wells of the deep well assay plate were filled with 1200 μl of sterile distilled $H_2O$ in an effort to limit edge effects (rows A1-H1, A1-A12, A12-H12).

An IL-8 dose response was determined for each blood donor examined, to monitor the donor response to IL-8. At this step in assay preparation for the IL-8 dose response samples 10 μl of PBS was added to designated wells. In addition the assay window without DMSO was also assessed each day. For such samples at this step in assay preparation 10 μl of PBS was added in the place of 10% DMSO.

80 μl of whole blood was added to compound/10% DMSO/PBS and mixed once gently upon addition. Lids were placed on the 96 well plates and samples were incubated for 15 minutes at 37° C. in a water-bath.

Following the compound pre-incubation 10× final IL-8 was added to appropriate wells (10 μl of 20 nM working stock IL-8, final IL-8 concentration in blood=2 nM) and 10 μl of PBS was added to the un-stimulated controls. 10× final dose response range IL-8 was also added to designated wells (final concentration range on assay plate was 200 nM to 0.0005 nM, 1:5 serial dilution in PBS). The IL-8 and PBS were added to appropriate wells across all assay plates in the same sequence as the blood to compound addition. Once added to all assay plates, samples were mixed quickly once to ensure even distribution of IL-8. Samples were incubated for 5 minutes at 37° C. in a water-bath. Following the incubation sample plates were transferred to ice where 250 μl of chilled Assay Fixative Buffer was added promptly to all wells.

Samples were incubated on ice for 7 minutes (no mixing). Following fixation 1.2 ml of 1× Lysis Solution was then added promptly to each well. Once added samples were mixed once and incubated on ice for 30 minutes to achieve uniform red blood cells lysis. After lysis, 200 μl of sample was transferred to a 96 well microplate on ice. Samples were acquired using the HTS on high throughput mode on a Becton Dickinson FACS Canto II. Granulocytes were identified based on differential side scatter (SSC) and forward scatter (FSC) characteristics. Neutrophils were distinguished from eosinophils using the phycoerythrin channel, as the latter have higher auto-fluorescence.

The mean FSC value for the neutrophil population was taken as measure of cell shape change (the greater the FSC value meant the greater the degree of shape change). Data was presented as % shape change over basal for the IL-8 dose response curve and assay window controls and presented as % inhibition of shape change for compound treated samples.

% Shape Change Above Basal

Subtract the un-stimulated control FSC reading from agonist FSC readings, divide results by the un-stimulated FSC value and multiply by 100 to give % shape change above basal.

% inhibition $$\% \text{ inhibition}=(X-Y)/X*100$$

X=IL-8 FSC response minus the un-stimulated control (basal) FSC.

Y=IL-8 FSC response in compound treated samples minus the un-stimulated control (basal) FSC.

The % inhibition values were plotted on the Y-axis against compound concentration on the x-axis, to give $IC_{50}$ values.

Microsomal Clearance Assay (M)

The experiments were performed in 96-well glass plates at 37° C. on an automated Tecan EVO platform. Test compounds at a concentration of 10 mM in pure DMSO were diluted 1:1000 in water to 10 μM. This solution (30 μL) was added to 120 μL of rat liver microsomal protein (1.25 mg/mL) suspended in phosphate buffer (pH 7.4). Reactions were initiated by the addition of 150 μL of a cofactor solution containing 2 mM NADPH. At specific reaction time points (0, 5, 20, and 30 min), aliquots (50 μL) were removed and reactions were terminated by the addition to acetonitrile (100 μL) containing the analytical internal standards (1 μM alprenolol and 1.6 μM chlorzoxazone) and stored at −20° C. for at least 1 h to allow complete precipitation of proteins. The samples were then centrifuged at 5000 g at 4° C. for 35 min, and 20 μL of the supernatants were analyzed by LC-MS/MS for quantitation of the remaining test article. The percentage of test compound remaining, relative to time zero minute incubation, is used to estimate the in vitro elimination-rate constant ($k_{mic}$), which is used to calculate the in vitro metabolic clearance rates.

The biochemical assay data for examples 1-115 is provided in the following Table 4:

TABLE 4

| Biochemical assay data | | | | | | | |
|---|---|---|---|---|---|---|---|
| Example | Assay A PI3Kα IC50 (μM) | Assay B PI3Kβ IC50 (μM) | Assay C VPS34 IC50 (μM) | Assay D PI4Kβ IC50 (μM) | Assay E PI3Kγ IC50 (μM) | Assay F PI3Kδ IC50 (μM) | Assay G mTOR IC50 (μM) |
| 1 | 0.19 | 4.05 | >9.1 | 1.95 | 0.007 | 0.17 | 2.37 |
| 2 | 0.53 | 3.15 | >9.1 | 5.40 | 0.065 | 0.46 | >9.1 |
| 3 | 0.77 | 2.04 | >9.1 | 1.08 | 0.044 | 0.07 | 3.11 |
| 4 | 0.19 | 1.87 | 1.95 | 1.44 | 0.011 | 0.08 | 2.63 |
| 4.1 | 0.28 | 1.60 | 6.60 | 3.90 | 0.018 | 0.46 | 9.5 |
| 4.2 | 0.21 | 0.90 | >10 | 0.65 | 0.008 | 0.38 | 1.3 |
| 4.3 | 0.26 | 7.20 | >10 | 1.70 | 0.021 | 2.70 | 7.3 |
| 4.4 | 0.56 | 2.95 | >10 | 8.20 | 0.212 | 1.85 | >10 |
| 4.5 | 0.25 | 2.80 | >10 | 5.25 | 0.575 | 0.48 | >10 |
| 4.6 | 0.52 | 4.10 | >10 | 2.70 | 0.021 | 1.90 | 1.4 |
| 4.7 | 0.30 | 4.70 | >10 | 1.70 | | 0.85 | 7.7 |
| 4.8 | 0.57 | 4.65 | >10 | 3.15 | 0.150 | 0.21 | >10 |
| 4.9 | 0.62 | 4.50 | >10 | >10 | 0.046 | 1.00 | >10 |
| 5 | 0.08 | 1.15 | >9.55 | 4.90 | 0.011 | 0.06 | 6.5 |
| 5.1 | 1.25 | 6.45 | >10 | 4.40 | 0.028 | 1.10 | 8.2 |
| 5.2 | 0.19 | 1.30 | >10 | 0.90 | 0.007 | 0.28 | >10 |
| 5.3 | 1.40 | 5.00 | >10 | 7.50 | 0.026 | 0.42 | >10 |
| 5.4 | 0.25 | 3.10 | >10 | 2.20 | 0.022 | 0.57 | 3 |
| 5.5 | 0.32 | 1.00 | >10 | 4.00 | 0.021 | 0.39 | >10 |
| 5.5a | 0.76 | 2.90 | >10 | 4.60 | 0.110 | 0.95 | >10 |
| 5.6 | 0.70 | 4.50 | >10 | 7.80 | 0.011 | 0.35 | >10 |
| 6 | 0.40 | 2.30 | >10 | 2.73 | 0.036 | 0.62 | 6.85 |
| 7 | 0.95 | 3.80 | >10 | 3.98 | 0.024 | 0.82 | 8.1 |
| 8 | 0.06 | 0.43 | >10 | 6.10 | 0.004 | 0.08 | >10 |

TABLE 4-continued

| Biochemical assay data | | | | | | | |
|---|---|---|---|---|---|---|---|
| Example | Assay A PI3Kα IC50 (μM) | Assay B PI3Kβ IC50 (μM) | Assay C VPS34 IC50 (μM) | Assay D PI4Kβ IC50 (μM) | Assay E PI3Kγ IC50 (μM) | Assay F PI3Kδ IC50 (μM) | Assay G mTOR IC50 (μM) |
| 8.1 | 0.02 | 0.36 | >10 | 2.80 | 0.017 | 0.08 | 0.98 |
| 8.2 | 0.04 | 2.10 | >10 | 5.10 | 0.005 | 0.08 | 8.2 |
| 9 | 0.30 | >9.10 | 0.89 | 1.92 | 0.014 | 0.22 | 5.9 |
| 10 | 0.90 | 4.30 | >9.8 | >9.8 | 0.040 | 0.55 | 4.2 |
| 11 | 0.07 | 0.29 | >10 | 5.10 | 0.012 | 0.05 | >10 |
| 12 | 0.16 | 0.23 | >10 | 5.30 | 0.008 | 0.27 | >10 |
| 13 | 0.14 | 0.85 | >10 | 4.40 | 0.016 | 0.11 | 1.6 |
| 14 | 0.17 | 1.10 | >10 | 2.60 | 0.013 | 0.10 | >10 |
| 15 | 0.62 | 4.20 | 1.62 | 3.39 | 0.012 | 0.24 | 7.9 |
| 16 | 0.10 | 6.36 | >9.1 | 4.66 | 0.087 | 0.26 | >9.1 |
| 17 | 0.30 | 1.40 | 8.10 | 1.50 | 0.010 | 0.17 | 8.5 |
| 18 | 0.09 | 3.84 | >9.1 | >9.1 | 0.058 | 0.47 | >9.1 |
| 19 | 0.04 | 0.10 | >10 | 1.30 | <0.003 | 0.11 | >10 |
| 19.1 | 0.55 | >10 | >10 | 4.00 | 0.140 | 1.80 | |
| 19.2 | 0.68 | 1.90 | >10 | 3.70 | 0.044 | 0.29 | |
| 19.3 | 1.30 | 0.68 | >10 | 1.20 | 0.039 | 0.14 | |
| 19.4 | 0.46 | 1.70 | >10 | 2.10 | 0.051 | 0.51 | |
| 19.5 | 2.10 | 9.20 | >10 | 2.30 | 0.190 | 1.70 | |
| 19.6 | 0.70 | 4.90 | >10 | 1.50 | 0.150 | 1.10 | |
| 19.7 | 0.41 | 3.90 | >10 | 3.20 | 0.078 | 0.53 | |
| 19.8 | 3.00 | >10 | >10 | 2.20 | 0.230 | 1.20 | |
| 19.9 | 1.60 | 9.50 | >10 | 1.90 | 0.200 | 1.40 | |
| 19.10 | 0.42 | 3.50 | >10 | 3.70 | 0.028 | 0.57 | |
| 19.11 | 0.32 | | >10 | 5.10 | 0.056 | 0.42 | |
| 19.12 | 0.24 | 2.60 | >10 | 4.30 | 0.027 | 0.62 | |
| 19.13 | 0.61 | 3.10 | >10 | 1.60 | 0.048 | 0.82 | |
| 19.15 | 0.79 | >10 | >10 | 0.90 | 0.050 | 1.40 | |
| 19.16 | 0.40 | 0.98 | >10 | 1.50 | 0.014 | 0.28 | |
| 19.17 | 1.00 | >10 | >10 | 1.40 | 0.130 | 2.80 | |
| 19.18 | 0.76 | >10 | >10 | 3.80 | 0.180 | 1.30 | |
| 19.19 | 3.10 | 6.10 | >10 | 8.50 | 0.380 | 3.60 | |
| 19.20 | 2.80 | >10 | >10 | 4.20 | 0.400 | 2.90 | |
| 19.21 | 0.66 | 3.4 | >10 | 1.6 | 0.016 | 0.54 | |
| 19.22 | 2 | 5.8 | >10 | 8.6 | 0.51 | 1.4 | |
| 20 | 0.08 | 1.20 | >10 | 1.60 | 0.016 | 0.39 | 4.05 |
| 21a | 0.13 | 0.68 | >10 | 0.98 | 0.013 | 0.04 | |
| 21b | 0.07 | 0.88 | >10 | 1.71 | 0.005 | 0.09 | |
| 22 | 0.21 | 2.70 | >10 | 0.94 | 0.032 | 0.20 | |
| 23a | 0.26 | 2.55 | >10 | 2.10 | 0.027 | 0.12 | |
| 23b | 0.26 | 1.20 | >10 | 3.00 | 0.047 | 0.13 | |
| 24 | 0.28 | 2.40 | >10 | 2.40 | 0.041 | 0.28 | |
| 25 | 0.40 | 4.40 | >10 | 1.30 | 0.043 | 0.43 | |
| 26 | 0.22 | 3.00 | >10 | 3.40 | 0.067 | 1.10 | 0.32 |
| 27 | 0.66 | 4.40 | >10 | 2.40 | 0.070 | 0.86 | |
| 28 | 0.05 | 0.45 | 2.00 | 0.68 | 0.130 | 0.20 | 0.13 |
| 29 | 0.42 | 5.60 | >10 | 9.90 | 0.140 | 1.10 | >10 |
| 30 | 0.33 | 1.50 | >10 | 3.10 | 0.010 | 0.99 | 4.7 |
| 31 | 0.53 | 3.63 | >10 | 1.26 | 0.033 | 0.74 | |
| 32 | 1.06 | 7.05 | >10 | 5.75 | 0.062 | 1.15 | >10 |
| 33 | 0.13 | 3.20 | 3.90 | 4.45 | 0.096 | 0.68 | |
| 34 | 0.07 | 0.85 | >10 | 1.30 | 0.059 | 0.04 | |
| 35 | 0.71 | 2.90 | >10 | 0.82 | 0.016 | 0.40 | |
| 35.1 | 0.41 | 4.20 | >10 | 2.20 | 0.008 | 0.47 | |
| 35.2 | 0.27 | 6.70 | >10 | 0.63 | 0.009 | 0.09 | |
| 35.3 | 0.39 | 3.50 | >10 | 1.30 | 0.033 | 0.59 | |
| 35.4 | 0.18 | 3.10 | >10 | 1.00 | 0.033 | 0.51 | >10 |
| 35.5 | 1.10 | 8.80 | >10 | 1.20 | 0.071 | 0.28 | |
| 35.6 | 1.00 | 8.00 | >10 | 2.80 | 0.041 | 0.54 | 6.3 |
| 36a | 0.39 | 2.20 | >10 | 1.40 | 0.021 | 0.75 | |
| 36b | 0.26 | 5.30 | >10 | 0.96 | 0.021 | 0.45 | |
| 37 | 0.89 | 4.00 | >10 | 3.40 | 0.035 | 0.55 | |
| 37.1 | 0.34 | 5.50 | >10 | 3.50 | <0.003 | >10 | 8.8 |
| 37.2 | 1.40 | >10 | >10 | >10 | <0.003 | 0.49 | >10 |
| 37.3 | 0.14 | 2.10 | >10 | 1.80 | 0.004 | | 3 |
| 37.4 | 0.57 | 6.70 | >10 | 2.40 | 0.013 | 1.20 | |
| 37.5 | 0.16 | 5.30 | >10 | 8.00 | 0.018 | 0.27 | |
| 37.6 | 0.25 | 0.80 | >10 | 2.20 | 0.027 | 0.38 | |
| 37.7 | 0.47 | 2.30 | >10 | 1.20 | 0.032 | 0.60 | |
| 37.8 | 0.30 | 4.80 | >10 | 5.70 | 0.033 | 0.45 | 6.4 |
| 37.9 | 0.15 | 0.47 | >10 | 1.70 | 0.043 | 0.18 | |
| 37.10 | 0.56 | 9.10 | >10 | >10 | 0.043 | 0.50 | |
| 37.11 | 0.19 | 1.30 | >10 | 8.10 | 0.046 | 1.20 | >10 |
| 37.12 | 0.81 | 6.70 | >10 | 3.40 | 0.060 | 1.10 | |
| 37.13 | 0.35 | 2.80 | >10 | 5.00 | 0.063 | 0.50 | >10 |

TABLE 4-continued

| Biochemical assay data | | | | | | | |
|---|---|---|---|---|---|---|---|
| Example | Assay A PI3Kα IC50 (μM) | Assay B PI3Kβ IC50 (μM) | Assay C VPS34 IC50 (μM) | Assay D PI4Kβ IC50 (μM) | Assay E PI3Kγ IC50 (μM) | Assay F PI3Kδ IC50 (μM) | Assay G mTOR IC50 (μM) |
| 37.14 | 0.36 | 4.30 | >10 | 1.40 | 0.071 | 0.04 | |
| 37.15 | 0.29 | 3.90 | >10 | 5.40 | 0.078 | 0.16 | >10 |
| 37.16 | 0.07 | 1.20 | >10 | 0.90 | 0.086 | 0.04 | |
| 37.17 | 0.47 | 2.80 | >10 | 8.60 | 0.100 | 0.45 | |
| 37.18 | 0.47 | 0.22 | >10 | >10 | 0.110 | 0.41 | >10 |
| 37.19 | 0.54 | 4.90 | >10 | 8.60 | 0.120 | 0.46 | |
| 37.20 | 1.80 | 9.00 | >10 | 5.10 | 0.130 | 2.00 | |
| 37.21 | 1.80 | 10.00 | >10 | >10 | 0.120 | 0.99 | |
| 37.22 | 0.62 | 2.40 | >10 | 1.70 | 0.150 | 0.46 | |
| 37.23 | 0.13 | 2.20 | >10 | 2.10 | 0.160 | 0.36 | |
| 37.24 | 1.70 | 6.30 | >10 | 2.90 | 0.200 | 0.51 | |
| 37.25 | 3.80 | >10 | >10 | >10 | 0.220 | 1.80 | >10 |
| 37.26 | 0.72 | 3.10 | >10 | >10 | 0.280 | 1.60 | >10 |
| 37.27 | 1.40 | 2.70 | >10 | 4.80 | 0.290 | 0.12 | |
| 37.28 | 0.58 | 3.80 | >10 | 2.80 | 0.310 | 0.64 | |
| 37.29 | 0.91 | 0.91 | >10 | 7.10 | 0.350 | 0.61 | >10 |
| 37.30 | 0.10 | 1.50 | >10 | 1.90 | 0.620 | 0.11 | |
| 37.31 | 0.05 | 2.50 | >10 | 6.20 | 0.690 | 0.26 | |
| 37.32 | 1.10 | >10 | >10 | 8.50 | 0.700 | 1.50 | |
| 37.33 | 2.50 | 6.50 | >10 | >10 | 0.770 | 0.18 | |
| 37.34 | 1.40 | >10 | >10 | >10 | 5.500 | 0.42 | |
| 37.35 | 0.59 | 3.30 | >10 | 3.20 | | 1.20 | >10 |
| 37.37a | 0.39 | 4.10 | >10 | 3.80 | 0.046 | 0.49 | |
| 37.37b | 0.42 | 1.50 | >10 | 3.20 | 0.017 | 0.80 | |
| 37.38 | 0.55 | >10 | >10 | 7.50 | 0.250 | 0.37 | |
| 37.39 | 1.80 | 3.30 | >10 | 4.80 | 0.410 | 2.30 | >10 |
| 38 | 0.32 | 4.70 | >10 | 3.10 | 0.038 | 0.07 | |
| 39 | 0.45 | 3.70 | >10 | 1.30 | 0.096 | 0.29 | |
| 40 | 0.44 | 4.00 | >10 | 3.20 | | 0.38 | |
| 41 | 0.76 | 0.63 | >10 | 2.00 | 0.028 | 0.55 | |
| 42 | 0.89 | >10 | >10 | 2.90 | 0.056 | 1.10 | |
| 43 | 2.60 | >10 | >10 | 1.30 | 0.066 | 1.90 | |
| 44 | 0.05 | 1.60 | >10 | 3.55 | 0.029 | 0.07 | >10 |
| 45 | 0.23 | 2.60 | >10 | 7.40 | 0.110 | 0.06 | 9.1 |
| 46 | 0.39 | >10 | >10 | >10 | 0.067 | 0.18 | |
| 47 | 0.10 | 0.89 | >10 | 4.40 | 0.094 | | 4 |
| 48 | 0.30 | 5.10 | >10 | 6.00 | 0.073 | 0.11 | >10 |
| 49 | 0.27 | 2.10 | >10 | 6.80 | 0.089 | 0.14 | 8.1 |
| 50 | 1.60 | 4.40 | >10 | 4.70 | 0.045 | 0.48 | |
| 51 | 0.42 | 1.80 | >10 | >10 | 0.061 | 0.60 | |
| 52 | 1.10 | >10 | >10 | >10 | 0.086 | 1.40 | |
| 53 | 0.68 | 2.20 | >10 | 2.30 | 0.093 | 0.09 | |
| 54 | 0.79 | 4.50 | >10 | 5.20 | 0.100 | 0.20 | |
| 55 | 0.09 | 1.20 | >10 | 4.70 | 0.008 | 0.02 | |
| 56 | 1.30 | 6.30 | >10 | >10 | 0.080 | 0.20 | |
| 57 | 1.70 | >10 | >10 | >10 | 0.190 | 0.98 | 2.4 |
| 58 | 1.30 | >10 | >10 | 3.20 | 0.120 | 0.72 | |
| 59 | 0.83 | 9.20 | >10 | >10 | 0.280 | 0.71 | |
| 60 | 9.40 | >10 | >10 | >10 | 0.880 | >10 | >10 |
| 61 | 1.10 | 1.30 | >10 | 1.70 | 1.700 | 5.80 | 6.7 |
| 62 | 1.20 | >10 | >10 | 6.60 | 2.600 | 5.00 | >10 |
| 63 | 2.20 | 5.10 | >10 | 9.60 | 0.355 | 0.54 | 5.3 |
| 64 | 0.34 | 0.95 | >10 | 2.20 | 0.049 | 0.65 | |
| 65 | 2.30 | 9.50 | >10 | 5.20 | 0.215 | 0.59 | >10 |
| 66 | 1.80 | 1.30 | >10 | >10 | 0.140 | 1.20 | |
| 67 | 0.22 | 2.30 | 9.50 | 2.30 | 0.009 | 1.20 | |
| 68 | 0.50 | 2.80 | 8.40 | 2.50 | 0.023 | 1.40 | |
| 69 | 0.32 | 2.20 | 4.40 | 2.40 | 0.034 | 0.74 | |
| 70 | 0.58 | 4.40 | >10 | 8.20 | 0.047 | 1.10 | >10 |
| 71 | 2.60 | >10 | >10 | 10.00 | 0.047 | 5.90 | >10 |
| 72 | 1.20 | 1.30 | >10 | >10 | 0.062 | 0.40 | 0.37 |
| 73 | 0.24 | 1.00 | >10 | 1.10 | | 0.52 | >10 |
| 74 | 0.52 | 5.90 | 2.20 | 5.00 | 0.060 | 1.60 | |
| 75 | 0.66 | >10 | >10 | >10 | 0.075 | 2.70 | 8.2 |
| 76a | 0.35 | 3.85 | >10 | 7.00 | 0.069 | 0.53 | |
| 76b | 0.21 | 4.10 | >10 | 6.80 | 0.038 | 0.40 | |
| 77 | 0.03 | 1.70 | >10 | 2.10 | 0.031 | 1.20 | >10 |
| 78 | 0.09 | 2.50 | >10 | 0.49 | 0.018 | 0.10 | |
| 79 | 0.13 | 5.40 | >10 | 2.80 | 0.034 | 0.12 | |
| 80 | 0.90 | 4.65 | >10 | 3.55 | 0.200 | 1.15 | >10 |
| 81 | 7.50 | 6.30 | >9.8 | >9.775 | 1.800 | 6.18 | 6.6 |
| 82a | 0.14 | 1.03 | 3.85 | 1.35 | 0.041 | 0.19 | |
| 82b | 0.23 | 1.70 | 2.50 | 1.50 | 0.038 | 0.21 | |
| 83.1 | 0.40 | 2.50 | 4.60 | 2.50 | 0.170 | 1.30 | |

TABLE 4-continued

| Biochemical assay data | | | | | | | |
|---|---|---|---|---|---|---|---|
| Example | Assay A PI3Kα IC50 (μM) | Assay B PI3Kβ IC50 (μM) | Assay C VPS34 IC50 (μM) | Assay D PI4Kβ IC50 (μM) | Assay E PI3Kγ IC50 (μM) | Assay F PI3Kδ IC50 (μM) | Assay G mTOR IC50 (μM) |
| 83.2 | 0.40 | 6.20 | 6.20 | 2.40 | 0.039 | 0.66 | |
| 83.3 | 0.57 | 3.00 | 9.70 | 1.70 | | 0.90 | |
| 83.4 | 0.35 | 2.10 | 2.20 | 1.30 | 0.038 | 0.64 | |
| 83.5 | 0.43 | 3.40 | 5.20 | 2.80 | 0.086 | 1.50 | |
| 84 | 0.27 | 4.45 | >10 | 2.65 | 0.008 | 0.15 | |
| 85 | 0.30 | 1.30 | >10 | >10 | 0.020 | 0.65 | |
| 86 | 0.22 | 2.90 | >10 | 6.30 | 0.065 | 0.29 | |
| 87 | 0.29 | 1.70 | >10 | 6.10 | 0.140 | 0.14 | |
| 88 | 0.06 | 0.27 | >10 | 0.31 | 0.013 | 0.07 | |
| 89 | 0.10 | 0.23 | >10 | 1.50 | 0.015 | 0.13 | |
| 90 | 0.16 | 0.88 | >10 | 0.75 | 0.012 | 0.32 | |
| 91 | 0.16 | 0.22 | >10 | 0.79 | 0.016 | 0.08 | |
| 92 | 1.60 | 1.90 | >10 | 5.10 | 0.013 | 0.27 | |
| 93 | 0.88 | 4.80 | >10 | 7.50 | 0.057 | 0.45 | |
| 94a | 0.81 | 1.80 | >10 | 3.80 | 0.180 | 2.80 | 3.30 |
| 94b | 0.75 | | >10 | 1.30 | 0.076 | 0.73 | |
| 95 | 0.10 | 0.69 | >10 | 0.86 | 0.014 | 0.09 | >10 |
| 96 | 1.10 | 1.38 | >10 | 2.80 | 0.009 | 0.63 | |
| 97 | 0.16 | 1.10 | 3.80 | 1.34 | 0.012 | 0.52 | 6.5 |
| 98 | 0.21 | 1.70 | 2.50 | 0.83 | 0.015 | 0.21 | 7.9 |
| 99 | 0.18 | 1.70 | >10 | 1.20 | 0.022 | 0.41 | |
| 100 | 0.26 | 2.25 | >10 | 4.25 | 0.024 | 0.60 | |
| 101.1 | 0.52 | 4.70 | >10 | 1.20 | 0.040 | 0.97 | >10 |
| 101.2 | 0.44 | 1.10 | >10 | 1.40 | 0.040 | 0.36 | >10 |
| 101.3 | 0.80 | 5.10 | >10 | 3.60 | 0.130 | 0.79 | |
| 102 | 3.10 | 1.75 | >10 | 8.60 | 0.055 | 1.40 | |
| 103a | 0.62 | 5.00 | >10 | 0.77 | 0.045 | 1.20 | |
| 103b | 0.50 | >10 | >10 | 2.00 | 0.072 | 0.72 | |
| 104.1 | 0.18 | >10 | 1.10 | 2.40 | 0.120 | 2.20 | |
| 104.2 | 0.31 | >10 | 3.30 | 1.10 | 0.280 | 8.90 | |
| 104.3 | 0.58 | 2.7 | 4.7 | 4.6 | 0.087 | 2.5 | |
| 104.4 | 0.19 | 1 | 4 | 2.8 | 0.062 | 2.7 | |
| 104.5 | 0.35 | >10 | 2.00 | 3.10 | 0.230 | 2.00 | |
| 104.6 | 0.22 | >10 | 1.90 | 2.20 | 0.092 | 2.40 | |
| 104.7 | 0.31 | >10 | 3.20 | 1.80 | 0.013 | >10 | |
| 104.8 | 0.15 | 0.8 | 4.8 | 2 | 0.056 | 0.59 | |
| 104.9 | 0.22 | 1.3 | 1.6 | 1.2 | 0.091 | 1.7 | |
| 104.10 | 0.27 | 1.1 | 1.5 | 1.6 | 0.048 | 1.6 | |
| 104.11 | 0.03 | | 0.30 | 0.50 | 0.007 | 0.61 | |
| 104.12 | 0.13 | 0.95 | 1.4 | 2.1 | 0.070 | 1.5 | |
| 104.13 | 0.24 | 1.8 | >10 | 3.4 | 0.110 | 2.2 | |
| 104.14 | 0.21 | 1.7 | 1.2 | 1.2 | 0.072 | 1.3 | |
| 104.15 | 0.19 | >10 | 1.60 | 1.90 | 0.030 | 5.00 | |
| 104.16 | 0.14 | >10 | 1.20 | 1.30 | 0.047 | 3.40 | |
| 105 | 1.3 | 7.6 | >10 | 2.9 | 0.0094 | 0.68 | |
| 106 | 0.33 | 2.7 | >10 | 6.4 | 0.013 | 0.72 | 7.6 |
| 107 | 0.05 | 0.46 | >10 | 0.66 | 0.024 | 0.032 | |
| 108 | 0.64 | 7.3 | >10 | 5.9 | 0.041 | 0.14 | >10 |
| 109 | 0.79 | 2 | >10 | 5 | 0.0455 | 2 | |
| 110 | 2.75 | 9.5 | >10 | >10 | 0.15 | 1.28 | |
| 111 | 0.58 | >10.00 | 2.9 | 1.7 | 1.4 | 2.3 | |
| 112 | 0.14 | 0.66 | 3.5 | 0.73 | 0.038 | 0.41 | |
| 113 | 1.15 | 8.85 | >10 | 2.45 | 0.305 | 2.6 | |
| 114.1 | 0.25 | 1.4 | 3.4 | 4.5 | 0.077 | 1.2 | — |
| 114.2 | 0.41 | 2.8 | 4.4 | 2.3 | 0.120 | 1.3 | — |
| 114.3 | 0.59 | 8.4 | >10 | 8.1 | 0.120 | 1.7 | — |
| 114.4 | 0.08 | 1.2 | 1.2 | 0.63 | 0.049 | 0.19 | — |
| 115 | 0.28 | 1.3 | 6.8 | 0.62 | 0.013 | 0.38 | — |

The following compounds were found to be inactive in assay E:

3-(6-amino-5-(3-methyl-1,2,4-oxadiazol-5-yl)pyridin-3-yl)-N-(2-hydroxy-2-methylpropyl)-5-methylbenzenesulfonamide;

3-(6-amino-5-(3-methyl-1,2,4-oxadiazol-5-yl)pyridin-3-yl)-N-(2-hydroxy-2-methylpropyl)-5-(trifluoromethyl)benzenesulfonamide;

3-(6-amino-5-(3-methyl-1,2,4-oxadiazol-5-yl)pyridin-3-yl)-N-(2-hydroxy-2-methylpropyl)-4-(trifluoromethyl)benzenesulfonamide.

TABLE 5

Cellular data in isoform-specific assays (Assays H, I, J, K1, K2), whole blood neutrophil shape change data (WBSC, Assay L) and intrinsic clearance data in rat liver microsomes (RLM, Assay M).

| Example | Assay H PI3Kα IC50 (μM) | Assay I PI3Kβ IC50 (μM) | Assay J PI3Kδ IC50 (μM) | Assay K1 PI3Kγ IC50 (μM) | Assay K2 PI3Kγ IC50 (μM) | Assay L WBSC IC50 (μM) | Assay M RLM CI(int) ($\mu L.min^{-1}.mg^{-1}$) |
|---|---|---|---|---|---|---|---|
| 1 | 7.08 | 5.98 | 2.78 | 0.064 | | 2.19 | 67 |
| 2 | 7.75 | 9.19 | 3.92 | 0.267 | | 0.84 | 28 |
| 3 | 1.91 | 3.03 | 1.64 | 0.223 | | 0.50 | 82 |
| 4 | 1.25 | 2.31 | 1.33 | 0.046 | | 0.28 | 71 |
| 4.1 | | | | 0.041 | | | 26 |
| 4.2 | >10 | 4.89 | 1.44 | 0.035 | | | 19 |
| 4.3 | | | | 0.190 | | 1.02 | 34 |
| 4.4 | >10 | >10 | 2.20 | 0.158 | 0.384 | 0.94 | 41 |
| 4.5 | >10 | >10 | 4.65 | 0.038 | | 0.59 | 31 |
| 4.6 | 6.23 | >3 | 2.46 | 0.063 | | 1.77 | 84 |
| 4.7 | 6.40 | >3 | 1.53 | 0.068 | | | 201 |
| 4.8 | >10 | 4.47 | 1.42 | 0.110 | | | 93 |
| 4.9 | >10 | >10 | 5.34 | 0.213 | | 3.16 | 125 |
| 5 | 0.74 | 1.44 | 0.59 | 0.055 | | 0.25 | 100 |
| 5.1 | 8.94 | >3 | 4.04 | 0.169 | | 4.99 | 109 |
| 5.2 | 0.63 | >3 | 0.29 | 0.023 | | | 94 |
| 5.3 | 7.56 | >10 | 3.97 | 0.200 | 0.881 | | 77 |
| 5.4 | | >10 | >10 | 0.012 | | 0.38 | 50 |
| 5.5 | 4.43 | >10 | 0.84 | 0.140 | | | 67 |
| 5.5a | >10 | 2.18 | 1.32 | | | | 55 |
| 5.6 | | | | 0.281 | 1.151 | | 50 |
| 6 | 7.84 | 4.67 | 2.27 | 0.114 | 0.141 | 0.99 | 60 |
| 7 | 5.88 | 6.73 | 3.45 | 0.108 | 0.247 | 0.84 | 46 |
| 8 | 0.65 | 4.68 | 0.42 | | | 0.92 | 154 |
| 8.1 | 0.31 | 0.98 | 0.28 | 0.018 | 0.054 | 0.53 | 153 |
| 8.2 | 0.54 | 1.43 | 0.33 | | 0.178 | 0.63 | 132 |
| 9 | 5.19 | 5.12 | 3.43 | 0.156 | 0.144 | 1.28 | 34 |
| 10 | 6.63 | 4.03 | 1.81 | 0.202 | 0.224 | 0.95 | 46 |
| 11 | 0.15 | 0.72 | 0.14 | 0.018 | 0.052 | 0.44 | 55 |
| 12 | 1.46 | 3.94 | 0.90 | 0.020 | 0.076 | 0.38 | 48 |
| 13 | 1.13 | >10 | 1.13 | 0.040 | 0.286 | 0.66 | 77 |
| 14 | 1.53 | 4.48 | 0.75 | 0.022 | 0.108 | 0.88 | 112 |
| 15 | 5.92 | 8.93 | 3.54 | 0.240 | 0.313 | 1.91 | 39 |
| 16 | 2.38 | 8.25 | 4.76 | 0.263 | | 2.47 | 72 |
| 17 | 3.31 | >10 | 1.63 | 0.037 | | 2.62 | 199 |
| 18 | 2.03 | >10 | 3.68 | 0.180 | 0.610 | 1.20 | 150 |
| 19 | 0.22 | 0.75 | 0.18 | 0.017 | 0.075 | 0.61 | 103 |
| 19.1 | 9.29* | >10* | 3.45* | | | | 254 |
| 19.2 | >10* | >10* | 2.56* | | 0.032 | | 152 |
| 19.3 | >10* | >10* | 4.75* | — | 0.544 | — | 17 |
| 19.4 | >10* | >10* | 2.18* | | 2.395 | 29.13 | 13 |
| 19.5 | >10* | >10* | 6.33* | | | | 340 |
| 19.6 | >10* | >10* | 7.34* | | | | 386 |
| 19.7 | >10* | >10* | 1.56* | 0.067 | 0.341 | | 615 |
| 19.8 | >10* | >10* | 4.04* | | | | 113 |
| 19.9 | 5.44* | >10* | 2.83* | | | | >924 |
| 19.10 | 7.3* | >10* | 2.17* | 0.085 | 0.309 | | 59 |
| 19.11 | >10* | >10* | >10* | | 0.807 | | 505 |
| 19.12 | 1.64* | >10* | 1.1* | | 0.193 | | 670 |
| 19.13 | 6.33* | >10* | 3.55* | | 0.367 | | 352 |
| 19.15 | >10* | >10* | 2.78* | 0.232 | 0.602 | | 145 |
| 19.16 | 3.72* | >10* | 2.18* | 0.042 | 0.093 | 1.86 | 61 |
| 19.17 | >10* | >10* | >10* | | 0.223 | | 98 |
| 19.18 | 9.53* | >10* | 6.59* | | | | 634 |
| 19.19 | >10* | >10* | >10* | | | | 568 |
| 19.20 | >10* | >10* | 7.04* | | | | |
| 19.21 | 2.91* | >10* | 1.78* | 0.065 | 0.260 | 8.26 | 412 |
| 12.22 | >10* | >10* | 3.01* | | | | |
| 20 | 0.41 | >3 | 0.27 | 0.011 | 0.057 | 0.38 | 50 |
| 21a | 0.74 | | 0.36 | | 0.047 | | 84 |
| 21b | 0.97 | 1.84 | 0.46 | 0.020 | 0.023 | | 91 |
| 22 | 0.51 | 2.40 | 0.48 | | | | |
| 23a | 2.59 | >3 | 1.43 | | 0.192 | | 57 |
| 23b | 3.17 | >3 | 1.44 | | | | 504 |
| 24 | 2.91 | 6.62 | 0.71 | 0.078 | 0.077 | 2.22 | 43 |
| 25 | 2.81 | >10 | 1.19 | 0.094 | 0.174 | 1.03 | 78 |
| 26 | | | | | | | 30 |
| 27 | 2.57 | >10 | 1.12 | 0.048 | | 2.66 | 81 |
| 28 | | | | 0.014 | 0.058 | | 31 |
| 29 | 0.67 | >10 | 1.28 | | | | 50 |
| 30 | — | — | — | — | 0.238 | — | 45 |
| 31 | 1.94 | >10 | 0.77 | 0.089 | 0.220 | | 331 |

TABLE 5-continued

Cellular data in isoform-specific assays (Assays H, I, J, K1, K2), whole blood neutrophil shape change data (WBSC, Assay L) and intrinsic clearance data in rat liver microsomes (RLM, Assay M).

| Example | Assay H PI3Kα IC50 (μM) | Assay I PI3Kβ IC50 (μM) | Assay J PI3Kδ IC50 (μM) | Assay K1 PI3Kγ IC50 (μM) | Assay K2 PI3Kγ IC50 (μM) | Assay L WBSC IC50 (μM) | Assay M RLM CI(int) ($\mu L.min^{-1}.mg^{-1}$) |
|---|---|---|---|---|---|---|---|
| 32 | 8.92 | 4.10 | 1.17 | 0.194 | | 5.93 | 26 |
| 33 | >10 | >10 | >10 | 0.174 | 0.300 | 19.35 | 47 |
| 34 | 0.54 | 1.24 | 0.71 | | 0.033 | 0.54 | 43 |
| 35 | 3.61 | >10 | 1.73 | 0.085 | | 6.09 | 49 |
| 35.1 | >10 | >3 | 3.77 | | | | 126 |
| 35.2 | >3 | 6.39 | 0.54 | | 0.169 | | 105 |
| 35.3 | >10 | >10 | >3 | 0.091 | | 4.81 | 87 |
| 35.4 | 1.25 | 2.29 | 0.94 | | | | 239 |
| 35.5 | >10 | 7.37 | 1.24 | 0.132 | 0.322 | | 136 |
| 35.6 | >10 | 4.18 | 1.36 | | 0.092 | | 102 |
| 36a | >10 | >10 | 2.72 | 0.103 | 0.718 | 2.90 | 38 |
| 36b | >10 | 9.63 | 2.48 | 0.043 | 0.049 | | 87 |
| 37 | 5.15 | 1.54 | 3.48 | 0.079 | 0.304 | 0.67 | 41 |
| 37.1 | 5.83 | 4.22 | 8.53 | 0.049 | | | 235 |
| 37.2 | >10 | >10 | 4.15 | 0.957 | | | 732 |
| 37.3 | 1.71 | >10 | 1.23 | | | | >924 |
| 37.4 | >10 | >10 | >10 | 1.077 | 0.585 | — | 28 |
| 37.5 | 1.88 | >3 | 0.94 | 0.262 | | | 649 |
| 37.6 | 2.86 | >10 | 1.06 | | | | 312 |
| 37.7 | 3.27 | 8.33 | 1.65 | | 0.103 | | 108 |
| 37.8 | >10 | >10 | 0.93 | | | | 243 |
| 37.9 | 2.35 | 3.26 | 1.63 | | | | 872 |
| 37.10 | 1.41 | >10 | 1.99 | 0.075 | | | 206 |
| 37.11 | 0.90 | 2.52 | 0.90 | | | | 623 |
| 37.12 | 7.62 | >10 | 2.76 | 0.405 | 0.831 | | 71 |
| 37.13 | 2.21 | 3.86 | 1.24 | | | | 752 |
| 37.14 | | | | 0.056 | | | 425 |
| 37.15 | 2.07 | 3.61 | 0.79 | | | | 196 |
| 37.16 | 1.16 | 6.00 | 0.92 | | | | 512 |
| 37.17 | >10 | >10 | >10 | | | | 142 |
| 37.18 | >10 | 3.36 | 1.34 | | | | 92 |
| 37.19 | 7.97 | >10 | 2.35 | 0.245 | | | 67 |
| 37.20 | 9.32 | >10 | 3.75 | | | | 514 |
| 37.21 | >10 | 2.52 | >10 | 0.846 | 0.813 | | 80 |
| 37.22 | 7.26 | >10 | 2.07 | | | | 379 |
| 37.23 | 2.91 | >10 | 1.07 | | | | >924 |
| 37.24 | >10 | >10 | 2.82 | | | | 103 |
| 37.25 | | | | | | | 26 |
| 37.26 | 2.23 | 2.89 | 1.42 | | | | 231 |
| 37.27 | 4.62 | 5.72 | 0.63 | | | 0.69 | 280 |
| 37.28 | | | | | | | |
| 37.29 | | | | | | | 14 |
| 37.30 | 2.67 | 5.38 | 1.86 | | | | 512 |
| 37.31 | 1.00 | >10 | 1.10 | | | | >924 |
| 37.32 | >10 | >10 | >10 | | | | 207 |
| 37.33 | 4.79 | >10 | 0.59 | | | | |
| 37.34 | >10 | >10 | 1.90 | | | | 221 |
| 37.35 | 3.57 | >10 | 1.42 | — | 0.101 | — | 157 |
| 37.37a | >10 | >3 | 5.07 | | | | 695 |
| 37.37b | >10 | >3 | 6.61 | 0.121 | 0.292 | | >924 |
| 37.38 | >10 | >10 | >10 | | | | 471 |
| 37.39 | >10 | >10 | 1.15 | | | | 93 |
| 38 | >10 | 4.23 | 2.64 | 0.055 | | 0.65 | 158 |
| 39 | | | | 0.084 | | 2.00 | 41 |
| 40 | | | 0.071 | 0.457 | | | |
| 41 | >10 | >10 | >10 | | 0.185 | | 20 |
| 42 | >10 | >10 | >10 | 0.127 | 0.088 | 0.90 | 41 |
| 43 | >10 | >10 | >10 | 0.166 | 0.259 | 3.33 | 39 |
| 44 | 0.30 | >10 | 0.38 | | | | 353 |
| 45 | >10 | 2.93 | 0.59 | | | | 180 |
| 46 | 1.46 | >10 | 1.42 | | | | |
| 47 | >10 | >10 | 0.37 | | | | 200 |
| 48 | >10 | >10 | 1.17 | | | | 464 |
| 49 | >10 | 9.56 | 0.66 | | | | 203 |
| 50 | >10 | >10 | >10 | 0.074 | | 0.64 | 38 |
| 51 | 1.56 | >10 | 1.04 | 0.073 | | 1.23 | 96 |
| 52 | >10 | >10 | 6.47 | 0.275 | | 1.75 | 46 |
| 53 | >10 | 6.07 | 1.89 | | 0.224 | | |
| 54 | >10 | >10 | >10 | 0.056 | 0.206 | 1.02 | 19 |
| 55 | 0.32 | 0.41 | 0.36 | 0.011 | 0.034 | | 80 |
| 56 | >10 | 7.63 | >10 | 0.138 | 0.177 | 1.71 | 44 |
| 57 | 3.23 | 8.72 | 2.93 | | | | 278 |

TABLE 5-continued

Cellular data in isoform-specific assays (Assays H, I, J, K1, K2), whole blood neutrophil shape change data (WBSC, Assay L) and intrinsic clearance data in rat liver microsomes (RLM, Assay M).

| Example | Assay H PI3Kα IC50 (μM) | Assay I PI3Kβ IC50 (μM) | Assay J PI3Kδ IC50 (μM) | Assay K1 PI3Kγ IC50 (μM) | Assay K2 PI3Kγ IC50 (μM) | Assay L WBSC IC50 (μM) | Assay M RLM CI(int) ($\mu L.min^{-1}.mg^{-1}$) |
|---|---|---|---|---|---|---|---|
| 58 | >10 | >10 | 1.53 | | | | 89 |
| 59 | >10 | >10 | 2.18 | | | | 74 |
| 60 | | | | | | | |
| 61 | >10* | >10* | >10* | | | | 26 |
| 62 | >10 | >10 | 7.00 | | | | 47 |
| 63 | >3 | >10 | >10 | | | | 18 |
| 64 | 4.12 | 2.92 | 2.92 | | 0.206 | | 367 |
| 65 | >10 | >10 | 2.80 | | | | 55 |
| 66 | | | | | | | 89 |
| 67 | >10 | >10 | | 0.158 | 0.101 | 0.67 | 14 |
| 68 | >10 | >10 | | 0.196 | 0.161 | 0.63 | 26 |
| 69 | >10 | 2.70 | | 0.077 | 0.156 | 0.74 | 74 |
| 70 | >6.5 | >3 | 3.18 | | 0.103 | | 44 |
| 71 | >6.5 | >3 | >10 | 0.233 | 0.626 | | 19 |
| 72 | 5.20 | 1.78 | 1.49 | 0.067 | | 19.35 | 102 |
| 73 | 2.53 | >10 | 1.19 | — | 0.098 | — | 30 |
| 74 | >10 | >10 | | 0.161 | 0.141 | 16.66 | 26 |
| 75 | 7.86 | 0.85 | 4.59 | 0.472 | | | 59 |
| 76a | 3.04 | 2.83 | 0.69 | | | | 124 |
| 76b | 1.59 | 9.22 | 0.54 | | | | 107 |
| 77 | 3.58 | >10 | >10 | 0.054 | | 0.92 | 93 |
| 78 | >10 | >10 | 1.38 | 0.042 | | 1.97 | 85 |
| 79 | 0.34 | >10 | 0.44 | | | | 164 |
| 80 | 5.86 | 2.97 | 1.27 | 0.092 | | | 118 |
| 81 | >10 | 4.20 | >10 | | | | 25 |
| 82a | 8.77* | 7.45* | 2.08* | | 0.076 | 0.60 | 24 |
| 82b | 4.94* | >10* | 1.58* | | 0.228 | | 132 |
| 83a | 5.1* | 7.52* | 2.15* | | | | 72 |
| 83.1 | | | | | 0.526 | | 65 |
| 83.2 | | | | | 0.145 | | 77 |
| 83.3 | | | | | | 0.76 | 38 |
| 83.4 | | | | | 0.407 | | 99 |
| 83.5 | | | | | 0.393 | | 29 |
| 84 | 7.03 | >10 | 5.27 | 0.056 | 0.101 | | 90 |
| 85 | >10 | 2.98 | 0.95 | 0.123 | 0.198 | 1.42 | 45 |
| 86 | | | | | | | 249 |
| 87 | 4.35* | >10* | 0.63* | | 0.264 | | 322 |
| 88 | 1.43* | 2.08* | 0.42* | | 0.379 | | 108 |
| 89 | 0.73* | 1.62* | 0.23* | | 0.237 | | 144 |
| 90 | >10 | 3.57 | >10 | | | | 202 |
| 91 | 4.36 | 2.47 | 2.10 | | | | 457 |
| 92 | >10 | >10 | 2.53 | | 0.130 | | 89 |
| 93 | >10 | >10 | 2.79 | | | | 326 |
| 94a | 3.86* | >10* | 1.2* | | 0.082 | 0.72 | 40 |
| 94b | >10* | >10* | 3.02* | | 0.900 | | 57 |
| 95 | 0.38* | 2.88* | 0.09* | | 0.024 | 0.24 | <3.42 |
| 96 | 5.84* | >10* | 1.25* | | 0.183 | 0.60 | 68 |
| 97 | 2.84 | >10 | 1.79 | | 0.021 | | 41 |
| 98 | 3.46 | 2.55 | 1.32 | 0.015 | | 0.31 | 30 |
| 99 | 1.4* | 7.15* | 0.63* | — | 0.047 | — | 33 |
| 100 | 4.14 | >10 | 1.51 | 0.259 | 0.067 | 3.24 | 67 |
| 101.1 | >10* | >10* | 7.92* | — | 0.109 | — | 27 |
| 101.2 | >10* | >10* | 2.54* | — | 0.181 | — | 75 |
| 101.3 | >10* | >10* | >10* | 0.094 | — | — | 148 |
| 102 | >10* | >10* | 3.92* | — | 0.218 | 0.98 | 43 |
| 103a | 6.74* | >10* | 1.85* | — | 0.113 | 1.35 | 45 |
| 103b | 8.57* | >10* | 2.80* | — | 0.056 | 1.80 | 36 |
| 104.1 | 3.25* | >10* | 1.95* | — | — | — | — |
| 104.2 | 2.93* | 3.26* | 1.52* | — | — | — | — |
| 104.3 | 5.63* | — | 3.2* | — | 0.292 | — | — |
| 104.4 | 5.24* | 7.89* | 4.06* | — | 0.137 | — | 37 |
| 104.5 | 6.62* | >10* | 2.45* | — | — | — | — |
| 104.6 | 5.29* | >10* | 2.35* | — | — | — | 24 |
| 104.7 | >10* | >10* | 9.48* | — | 0.235 | — | — |
| 104.8 | 2.55* | — | 1.02* | — | 0.166 | — | — |
| 104.9 | 2.62* | 3.49* | 1.42* | — | 0.197 | — | 111 |
| 104.10 | 1.1* | 8.99* | 1.13* | — | 0.072 | — | — |
| 104.11 | 1.59* | 2.63* | 0.71* | — | 0.074 | — | 74 |
| 104.12 | 1.79* | 3.81* | 0.98* | — | 0.161 | — | 338 |
| 104.13 | >10* | >10* | 5.66* | — | — | — | 51 |
| 104.14 | 1.46* | 6.47* | 0.89* | — | 0.200 | — | 383 |
| 104.15 | 3.58* | 5.2* | 1.48* | — | 0.152 | — | <3.4 |

TABLE 5-continued

Cellular data in isoform-specific assays (Assays H, I, J, K1, K2), whole blood neutrophil shape change data (WBSC, Assay L) and intrinsic clearance data in rat liver microsomes (RLM, Assay M).

| Example | Assay H PI3Kα IC50 (μM) | Assay I PI3Kβ IC50 (μM) | Assay J PI3Kδ IC50 (μM) | Assay K1 PI3Kγ IC50 (μM) | Assay K2 PI3Kγ IC50 (μM) | Assay L WBSC IC50 (μM) | Assay M RLM CI(int) (μL.min$^{-1}$.mg$^{-1}$ |
|---|---|---|---|---|---|---|---|
| 104.16 | 3.52* | 5.06* | 1.25* | — | 0.167 | — | — |
| 105 | 6.38* | 6.59* | 1.19* | | 0.242 | 1.92 | 115 |
| 106 | 1.14 | 1.02 | 0.55 | | | | 96 |
| 107 | 0.75 | 3.36 | 0.56 | 0.01 | | | 83 |
| 108 | >10 | 3.31 | 1.11 | 0.173 | | | 44 |
| 109 | >10 | >10 | 7.79 | 0.207 | 0.278 | | 66 |
| 110 | 9.31* | >10* | 4.07* | — | 0.891 | — | 36 |
| 111 | >10* | >3* | 1.64* | | 3.58 | 13.7 | 78 |
| 112 | — | — | — | — | — | — | 94 |
| 114.1 | — | — | — | — | — | — | 43 |
| 114.2 | — | — | — | — | — | — | 34 |
| 114.3 | — | — | — | — | — | — | 85 |
| 114.4 | — | — | — | — | — | — | 214 |
| 115.0 | — | — | — | — | — | — | 109 |

For assays H, I and J, non-asterisked data denotes data generated in versions H1, I1, J1 (Surefire format) of these assays and asterisked data denotes data generated in versions H2, I2, J2 (HTRF format) of these assays. Two closely related assay formats were used to generate PI3K gamma isoform cellular activities (IC50s). The table includes all data from both formats (Assays K1 and K2).

The following tables 6 and 7 give data generated in the above assays for compounds disclosed in the prior art.

TABLE 6

| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| 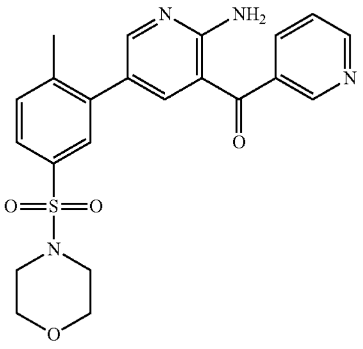 (i) | 0.25 | 1.24 | >9.4 | 3.16 | 0.064 | 0.63 | — |
| 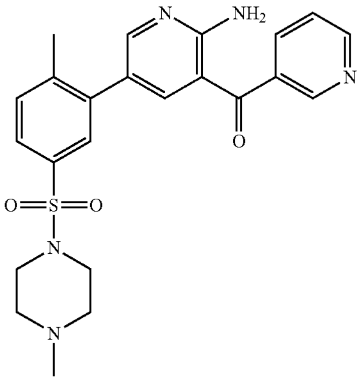 [SMILES: Cc1ccc(S(=O)(=O)N2CCOCC2)cc1-c1cnc(N)c(C(=O)c2cccnc2)c1] (ii) | 1.50 | 2.00 | >10 | 3.00 | 2.00 | >10 | — |

TABLE 6-continued
| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| 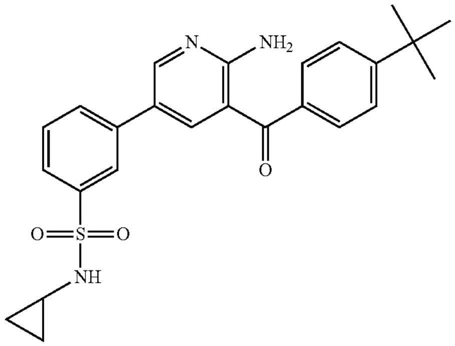 (iii) | 0.02 | 1.70 | 0.70 | 0.30 | 1.200 | 2.30 | — |
| 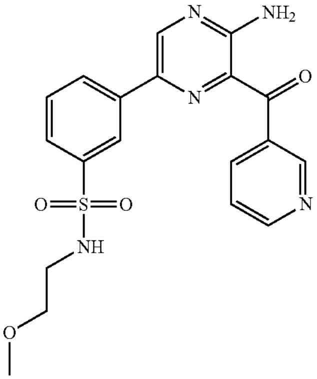 (iv) | 0.49 | 1.27 | 1.76 | 3.76 | 0.060 | 1.50 | — |
| 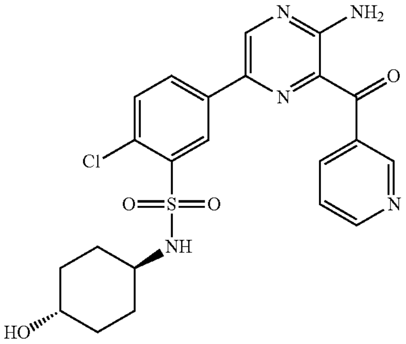 (v) | 0.07 | 0.14 | 0.91 | 0.16 | 0.247 | 1.97 | — |

TABLE 6-continued
| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| 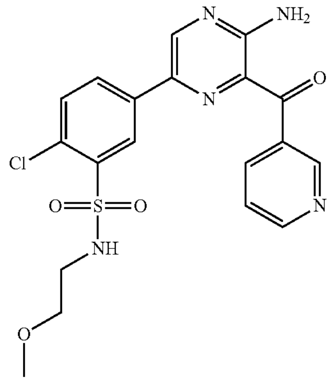 (vi) | 0.09 | 0.19 | 2.38 | 0.61 | 0.034 | 0.45 | — |
| 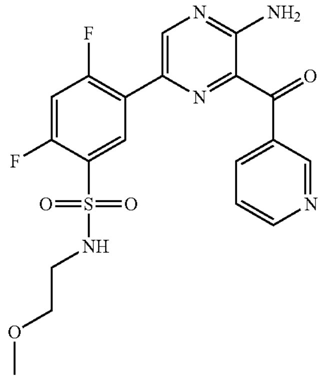 (vii) | — | — | — | — | — | — | — |
| 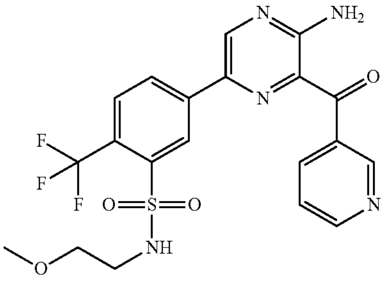 (viii) | 0.06 | 0.46 | — | 0.29 | — | — | — |
| 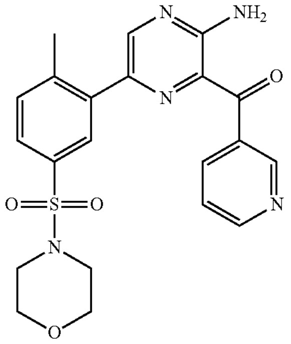 (ix) | 0.78 | 0.63 | 6.31 | 4.01 | 0.007 | 0.08 | — |

TABLE 6-continued
| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| 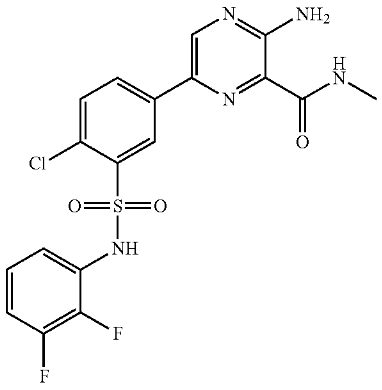 (x) | 0.46 | 0.70 | 1.80 | 0.54 | 0.110 | 1.40 | 2.50 |
| 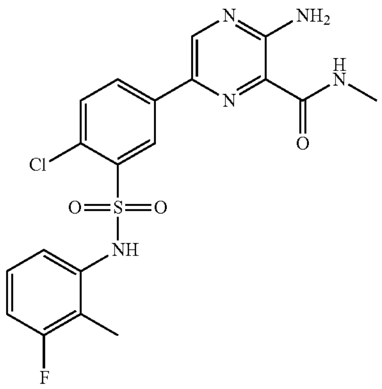 (xi) | 1.20 | 1.60 | 1.60 | 0.41 | 0.031 | 1.00 | 4.50 |
| 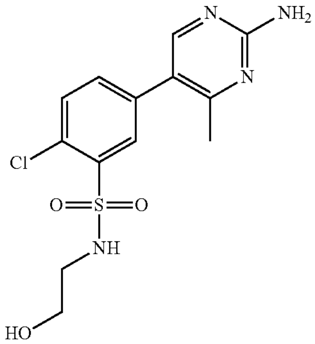 (xii) | 3.32 | 1.19 | | | 0.753 | 6.01 | — |
Compounds (i)-(ix) are disclosed in WO09/115517, compounds (x) and (xi) are disclosed in Leahy et al., *J. Med. Chem.*, 2012, 55 (11), pp 5467-5482 and compound (xii) is disclosed in WO09/013348.
TABLE 7
| Compound | Assay H PI3Kα | Assay I PI3Kβ | Assay J PI3Kδ | Assay K1 PI3Kγ | Assay K2 PI3Kγ | Assay L WBSC | Assay M RLM CI(int) |
|---|---|---|---|---|---|---|---|
| (i) | 0.97 | 3.77 | 1.10 | 0.526 | 0.838 | 2.39 | 47 |
| (ii) | >10* | >10* | 0.58* | — | 9.48 | 11.32 | 233 |
| (iii) | — | — | — | — | — | — | 219 |
| (iv) | 0.93 | 3.96 | 1.36 | 0.128 | 0.264 | 2.06 | 465 |

TABLE 7-continued

| Compound | Assay H PI3Kα | Assay I PI3Kβ | Assay J PI3Kδ | Assay K1 PI3Kγ | Assay K2 PI3Kγ | Assay L WBSC | Assay M RLM CI(int) |
|---|---|---|---|---|---|---|---|
| (v) | 0.18 | 0.23 | 0.15 | — | — | 0.71 | 173 |
| (vi) | 0.17 | 0.26 | 0.17 | 0.182 | — | — | 630 |
| (vii) | — | — | — | — | — | — | 283 |
| (viii) | — | — | — | — | — | — | — |
| (ix) | 0.85 | 2.29 | 1.26 | 0.020 | — | 2.34 | 267 |
| (x) | >10 | >10 | 2.87 | 0.352 | — | >100 | — |
| (xi) | 5.41 | 5.58 | 5.87 | 0.539 | — | >44 | 271 |
| (xii) | >10* | 4.37* | 5.55* | — | — | 15.12 | 9 |

The numbering (i)-(xii) refers to the compounds in Table 6. For assays H, I and J, non-asterisked data denotes data generated in versions H1, I1, J1 of these assays and asterisked data denotes data generated in versions H2, I2, J2 of these assays.

The invention claimed is:

1. A compound of formula (I)

(I)

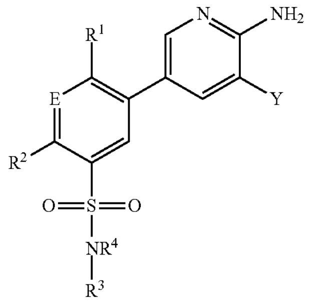

or a pharmaceutically acceptable salt thereof, wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

$R^3$ is selected from (i) $C_{1-4}$ alkyl which is unsubstituted or substituted with 1 or more substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(ii) $C_{1-4}$ alkoxy which is unsubstituted or substituted with 1 or more substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) pyridyl wherein the pyridyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$; and (viii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is selected from the group consisting of oxazol-5-yl, thiazol-5-yl, thiazol-4-yl, isothiazol-5-yl, pyrazol-4-yl, pyrazol-1-yl, pyrid-4-yl,
1,2,4-triazol-1-yl,
1,2,3-triazol-4-yl,
1,2,4-oxadiazol-5-yl,
1,3,4-oxadiazol-2-yl,
isoxazol-5-yl,
isoxazol-4-yl, and
pyrrol-3-yl, each of which is unsubstituted or substituted with 1 to 3 substituents independently selected from $C_{1-4}$ alkyl, $C_{1-4}$ haloalkyl, —(C═O)—$C_{3-7}$ heterocyclyl, —($C_{0-3}$ alkyl)-NR'R" and —(C═O)—NR'R"; and R' and R" are independently selected from H and $C_{1-4}$ alkyl;

or a pharmaceutically acceptable salt thereof.

2. A compound of formula (I)

(I)

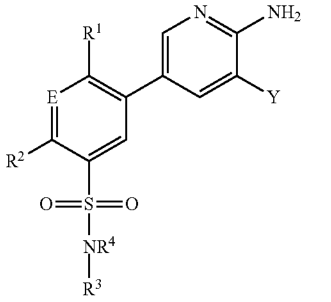

or a pharmaceutically acceptable salt thereof, wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

$R^3$ is selected from (i) $C_{1-4}$ alkyl which is unsubstituted or substituted with 1 or more substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(ii) $C_{1-4}$ alkoxy which is unsubstituted or substituted with 1 or more substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) pyridyl wherein the pyridyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$; and (viii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is selected from the group consisting of

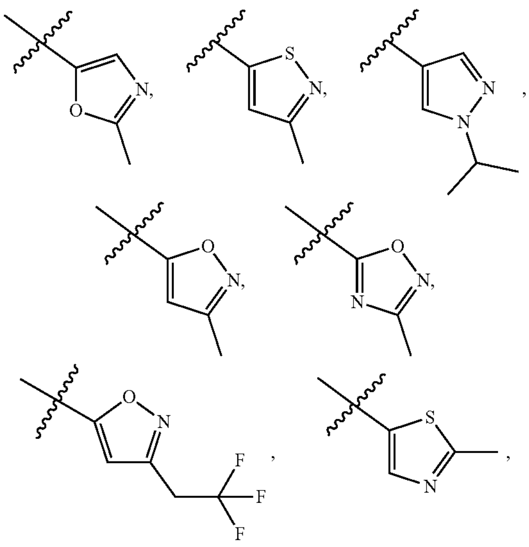

-continued
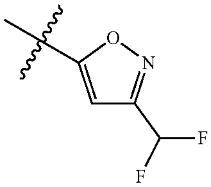 , 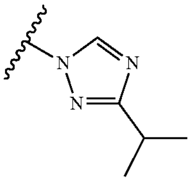 ,
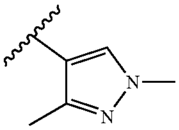 , 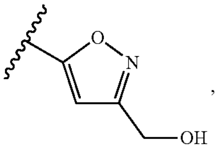 ,
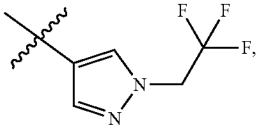 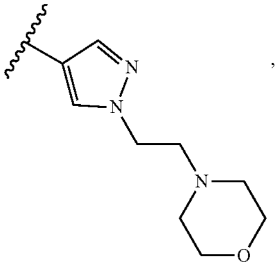 ,
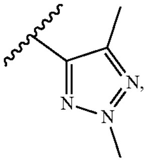 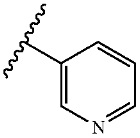 ,
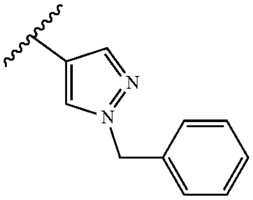 , 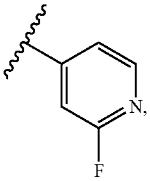
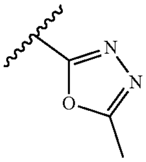 , 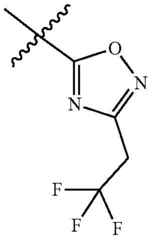 , 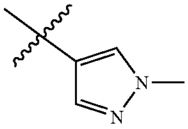 ,
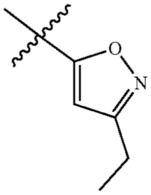 , 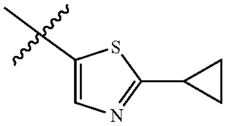 ,
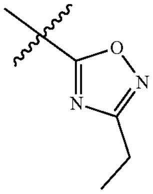 , 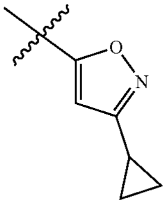 ,
-continued
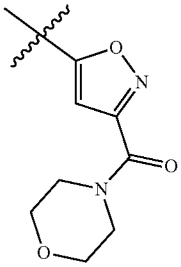 , 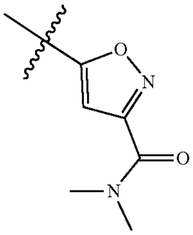 ,
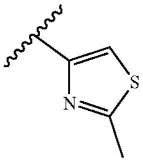 , 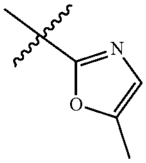 , 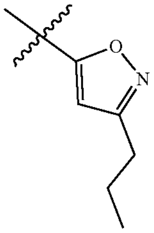 ,
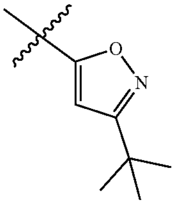 , 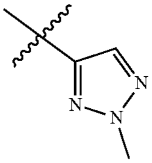 ,
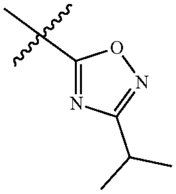 , 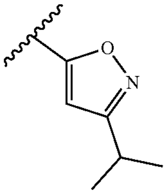 ,
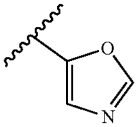 , 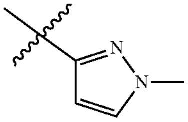 , 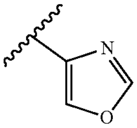 ,
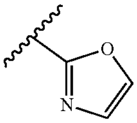 , 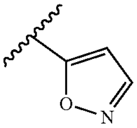 , 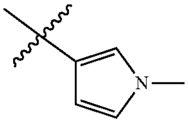 ,
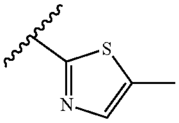 , 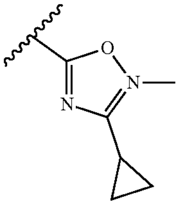 ,
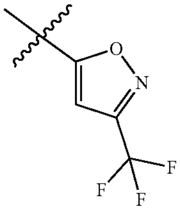 , 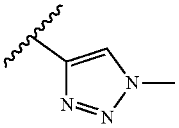 ,
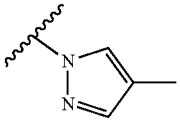 , 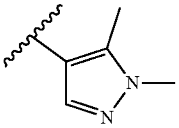 , -continued
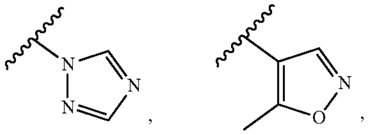
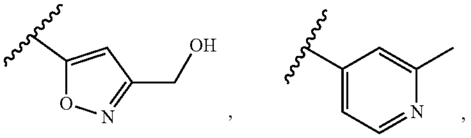
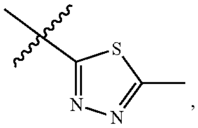
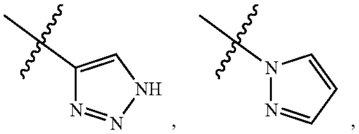
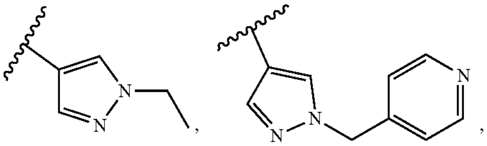
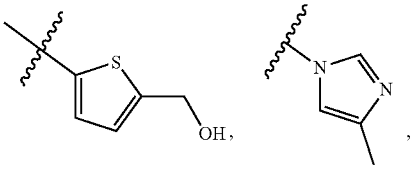
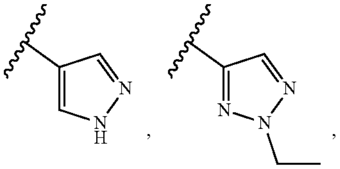
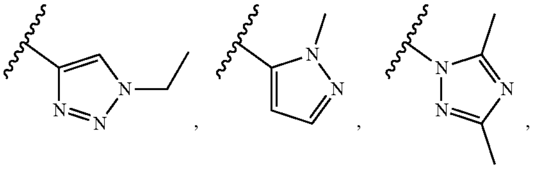
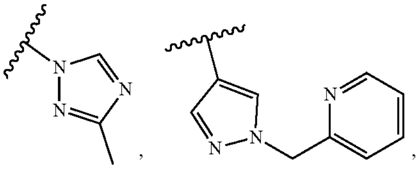
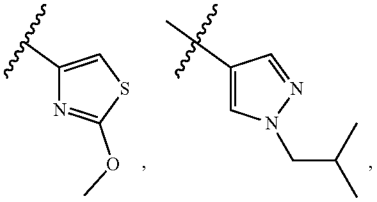
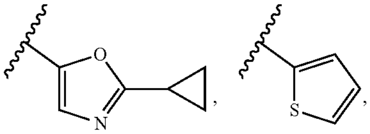
-continued
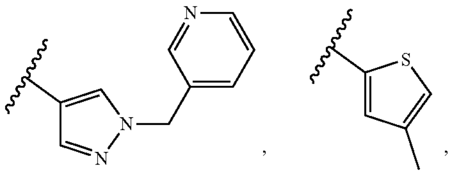
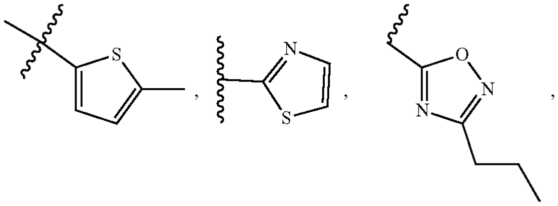
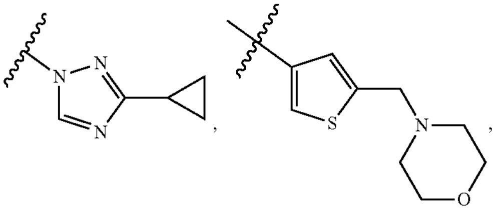
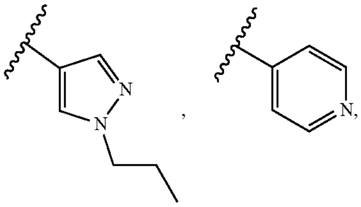
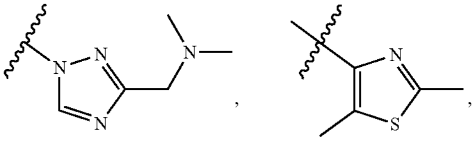
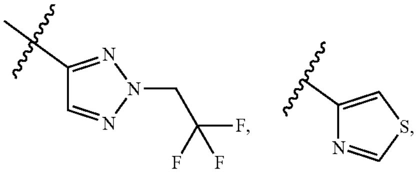
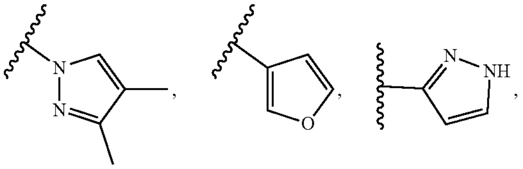
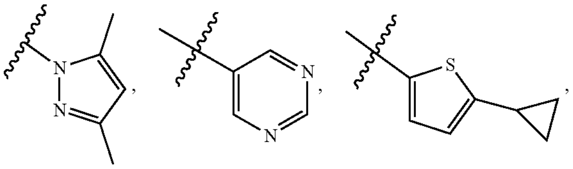
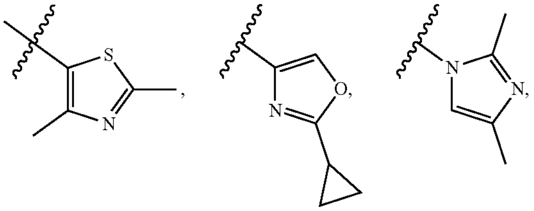

-continued
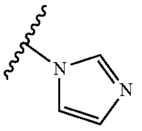 and 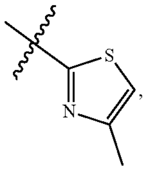,
or a pharmaceutically acceptable salt thereof.
3. The compound according to claim 2 formula (I)
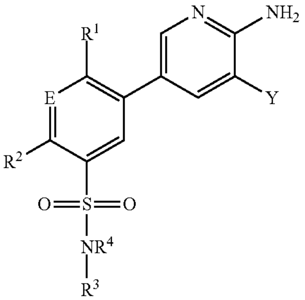
(I)
wherein
E is selected from N and $CR^E$;
$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;
Y is selected from the group consisting of
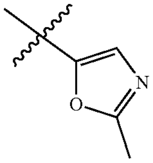, 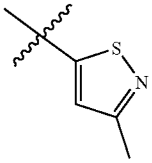,
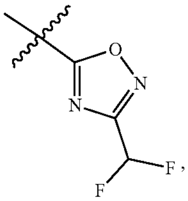, 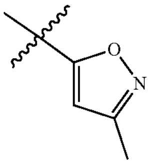, 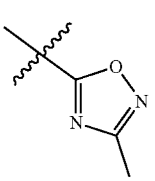,
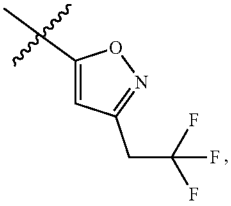, 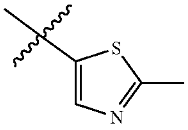,
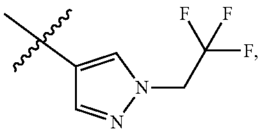, 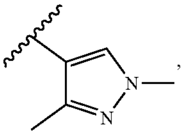,
-continued
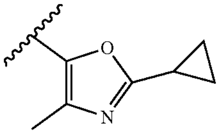, 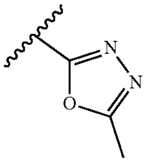,
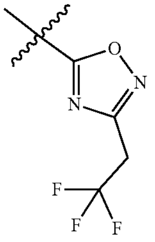, 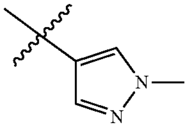,
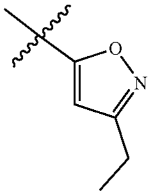, 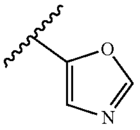, 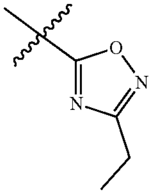,
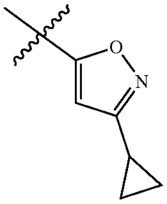, 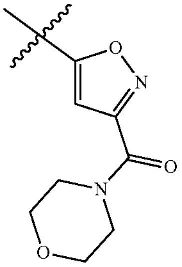,
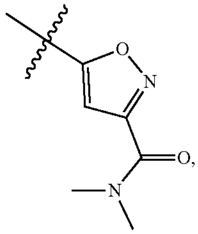, 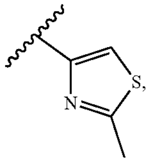,
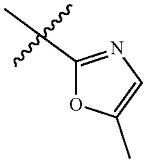, 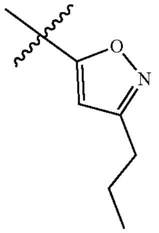,
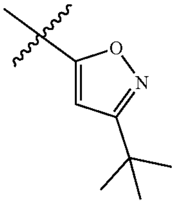, 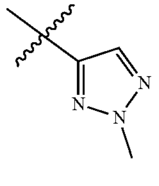,
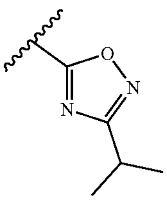, 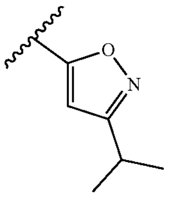, -continued
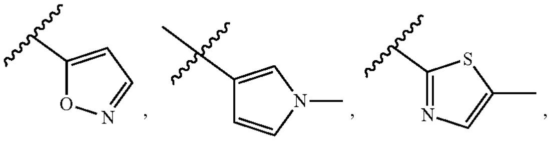
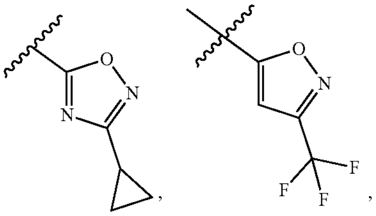
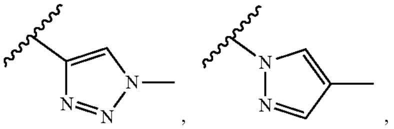
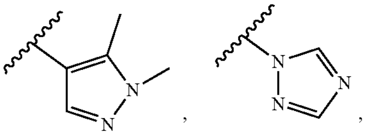
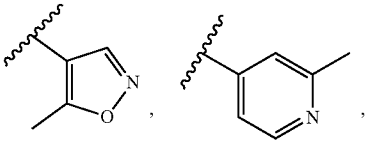
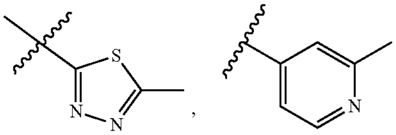 and
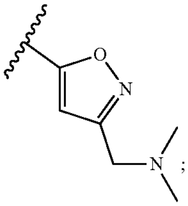;
$R^4$ is H and $R^3$ is selected from the group consisting of
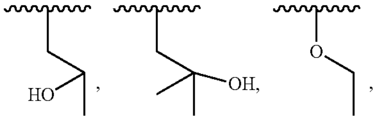
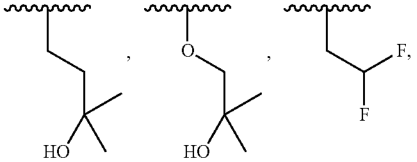
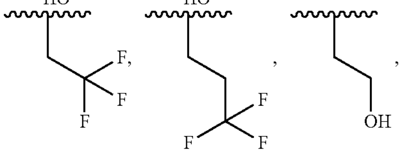
-continued
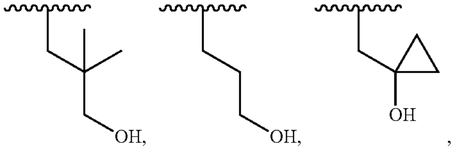
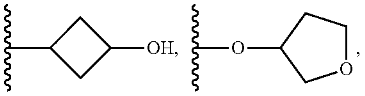
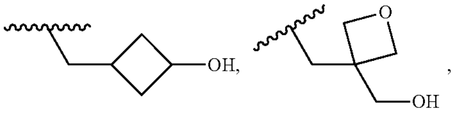
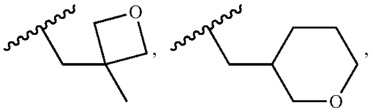
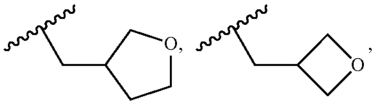
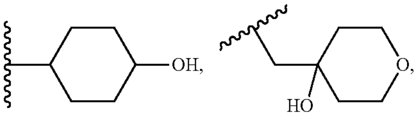
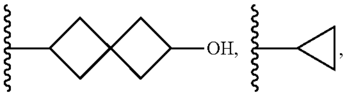
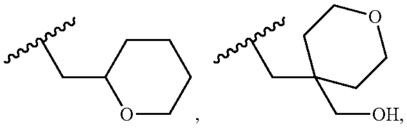
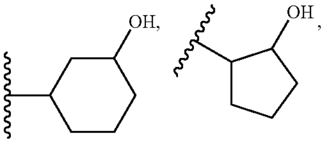
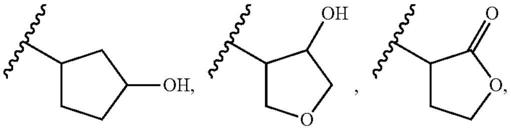
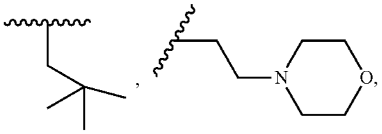
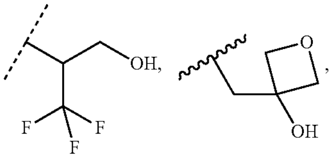
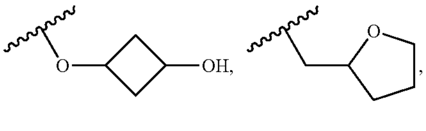

-continued

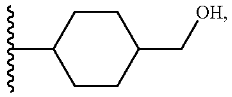
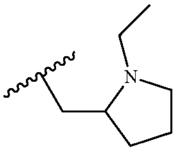
and

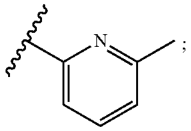

or $R^3$ and $R^4$ together with the nitrogen atom to which they are attached form a $C_{3-7}$ heterocyclyl selected from the group consisting of

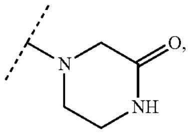
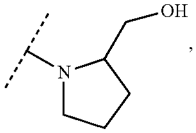
,

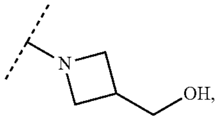
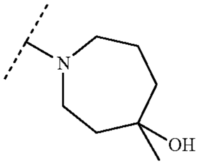
and

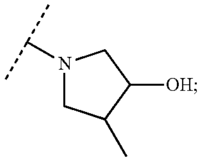

or a pharmaceutically acceptable salt thereof.

4. The compound according to claim 2 of formula (Ib)

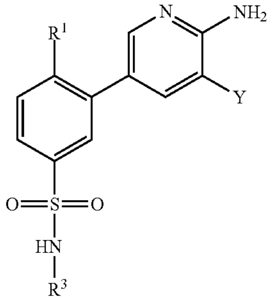
(Ib)

wherein $R^1$ is H or $C_{1-4}$ alkyl;

Y is selected from the group consisting of

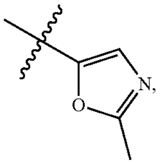
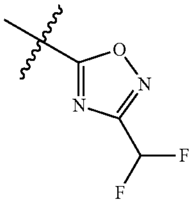
,

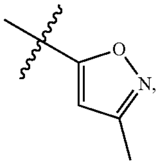
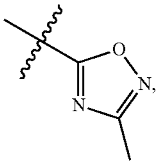
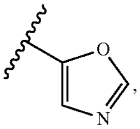

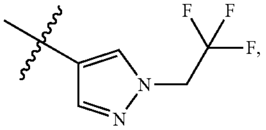
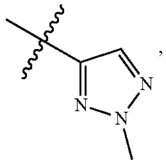
,

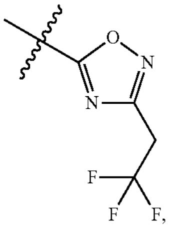
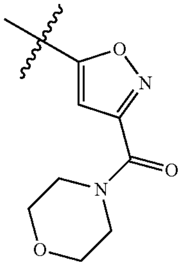
,

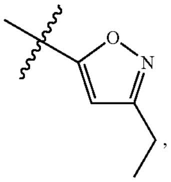
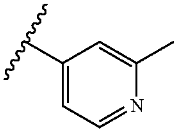
,

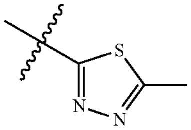
and
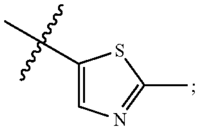

$R^3$ is selected from the group consisting of

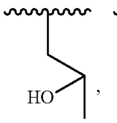
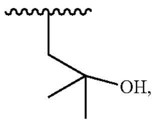
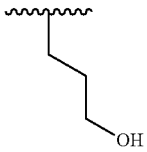
,

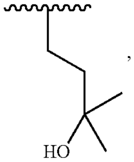
,
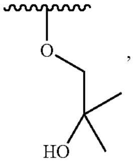
,
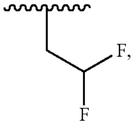

-continued

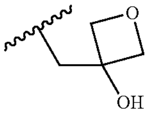, 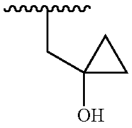, 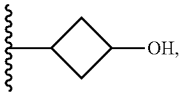

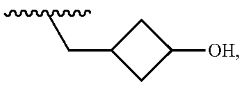 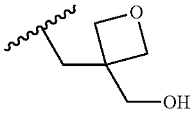,

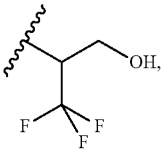 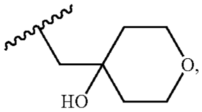

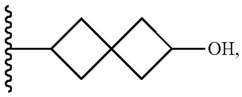 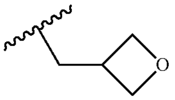 and

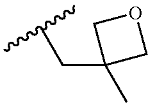;

or a pharmaceutically acceptable salt thereof.

5. A pharmaceutical composition, comprising:

a therapeutically effective amount of the compound or salt according to claim 1 and one or more pharmaceutically acceptable carriers.

6. A pharmaceutical combination, comprising:

a therapeutically effective amount of the compound or salt according to claim 1 and a second active agent.

7. A method of treating a disorder or disease mediated by the activation of PI 3-kinase gamma isoform, comprising administering to a subject having said disorder or disease a therapeutically effective amount of a compound or salt according to claim 1.

8. The method of claim 7, wherein the disorder or disease is selected from the group consisting of respiratory diseases, allergies, rheumatoid arthritis, osteoarthritis, rheumatic disorders, psoriasis, ulcerative colitis, Crohn's disease, septic shock, cancer, atherosclerosis, allograft rejection following transplantation, diabetes, stroke, obesity and restenosis.

9. The compound according to claim 4, wherein $R^1$ is $C_{1-4}$ alkyl, or a pharmaceutically acceptable salt thereof.

10. The compound according to claim 4, wherein $R^1$ is methyl, or a pharmaceutically acceptable salt thereof.

11. A compound selected from the following 3-(6-amino-5-(1-(2,2,2-trifluoroethyl)-1H-pyrazol-4-yl) pyridin-3-yl)-4-methyl-N-(6-methylpyridin-2-yl)benzenesulfonamide;

3-(6-amino-5-(1-methyl-1H-pyrazol-4-yl)pyridin-3-yl)-N-(3-hydroxy-3-methylbutyl)-4-methylbenzenesulfonamide;

3-(6-amino-5-(1-(2,2,2-trifluoroethyl)-1H-pyrazol-4-yl) pyridin-3-yl)-N-(3-hydroxy-3-methylbutyl)-4-methylbenzenesulfonamide;

3-(6-amino-5-(2-methylthiazol-5-yl)pyridin-3-yl)-N-(3-hydroxy-3-methylbutyl)-4-methylbenzenesulfonamide;

3-(6-amino-5-(1-methyl-1H-pyrazol-4-yl)pyridin-3-yl)-N-((1 r,4r)-4-hydroxycyclohexyl)-4-methylbenzenesulfonamide;

3-(6-amino-5-(1-(2,2,2-trifluoroethyl)-1H-pyrazol-4-yl) pyridin-3-yl)-N-((1r,4r)-4-hydroxycyclohexyl)-4-methylbenzenesulfonamide;

3-(2-amino-2'-methyl-3,4'-bipyridin-5-yl)-N-((1 r,4r)-4-hydroxycyclohexyl)-4-methylbenzenesulfonamide;

3-(6-amino-5-(2-methyl-2H-1,2,3-triazol-4-yl)pyridin-3-yl)-N-(2-hydroxy-2-methylpropyl)-4-methylbenzenesulfonamide;

3-(6-amino-5-(2-methyl-2H-1,2,3-triazol-4-yl)pyridin-3-yl)-N-((1r,4r)-4-hydroxycyclohexyl)-4-methylbenzenesulfonamide;

3-(6-amino-5-(3-ethylisoxazol-5-yl)pyridin-3-yl)-N-(2-hydroxy-2-methylpropyl)-4-methylbenzenesulfonamide;

(R)-3-(6-amino-5-(3-methylisoxazol-5-yl)pyridin-3-yl)-4-methyl-N-((tetrahydrofuran-3-yl)methyl)benzenesulfonamide;

3-(6-amino-5-(3-methylisothiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-4-methyl-N-((3-methyloxetan-3-yl)methyl)benzenesulfonamide;

3-(6-amino-5-(3-methyl-1,2,4-oxadiazol-5-yl)pyridin-3-yl)-N-(3-hydroxy-3-methylbutyl)-4-methylbenzenesulfonamide;

3-(6-amino-5-(3-isopropyl-1,2,4-oxadiazol-5-yl)pyridin-3-yl)-N-(2-hydroxy-2-methylpropyl)-4-methylbenzenesulfonamide;

3-(6-amino-5-(5-methyloxazol-2-yl)pyridin-3-yl)-N-((1r,4r)-4-hydroxycyclohexyl)-4-methylbenzenesulfonamide;

3-(6-amino-5-(3-ethyl-1,2,4-oxadiazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1r,4r)-4-hydroxycyclohexyl)-4-methylbenzenesulfonamide;

3-(6-amino-5-(3-methyl-1,2,4-oxadiazol-5-yl)pyridin-3-yl)-N-(3-hydroxycyclobutyl)-4-methylbenzenesulfonamide;

3-(6-amino-5-(3-methyl-1,2,4-oxadiazol-5-yl)pyridin-3-yl)-N-((1s,3s)-3-hydroxycyclobutyl)-4-methylbenzenesulfonamide;

3-(6-amino-5-(5-methyl-1,3,4-oxadiazol-2-yl)pyridin-3-yl)-N-(3-hydroxy-3-methylbutyl)-4-methylbenzenesulfonamide;

3-(6-amino-5-(2-methyloxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-N-(6-hydroxyspiro[3.3]heptan-2-yl)-4-methylbenzenesulfonamide;

3-(6-amino-5-(3-methyl-1,2,4-oxadiazol-5-yl)pyridin-3-yl)-N-(6-hydroxyspiro[3.3]heptan-2-yl)-4-methylbenzenesulfonamide;

3-(6-amino-5-(3-methyl-1,2,4-oxadiazol-5-yl)pyridin-3-yl)-N-(6-hydroxyspiro[3.3]heptan-2-yl)-4-methylbenzenesulfonamide;

3-(6-amino-5-(2-methylthiazol-5-yl)pyridin-3-yl)-N-(3-hydroxypropyl)-4-methylbenzenesulfonamide;

3-(6-amino-5-(3-methyl-1,2,4-oxadiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-N-(2-hydroxy-2-methylpropoxy)-4-methylbenzenesulfonamide;

3-(6-amino-5-(3-methyl-1,2,4-oxadiazol-5-yl)pyridin-3-yl)-N-((1 r,4r)-4-hydroxycyclohexyl)-4-methylbenzenesulfonamide;

3-(6-amino-5-(2-methyloxazol-5-yl)pyridin-3-yl)-N-(3-hydroxy-3-methylbutyl)-4-methylbenzenesulfonamide;

3-(6-amino-5-(3-methylisoxazol-5-yl)pyridin-3-yl)-N-(3-hydroxy-3-methylbutyl)-4-methylbenzenesulfonamide;

3-(6-amino-5-(2-methylthiazol-5-yl)pyridin-3-yl)-N-(2-hydroxy-2-methylpropyl)-4-methylbenzenesulfonamide;

3-(2-amino-2'-methyl-3,4'-bipyridin-5-yl)-N-(3-hydroxy-3-methylbutyl)-4-methylbenzenesulfonamide;

3-(6-amino-5-(3-methylisoxazol-5-yl)pyridin-3-yl)-4-methyl-N-((3-methyloxetan-3-yl)methyl)benzenesulfonamide;

3-(2-amino-3,4'-bipyridin-5-yl)-N-(3-hydroxy-3-methylbutyl)-4-methylbenzenesulfonamide;

3-(6-amino-5-(3-methyl-1,2,4-oxadiazol-5-yl)pyridin-3-yl)-N-((1r,4r)-4-(hydroxymethyl)cyclohexyl)-4-methylbenzenesulfonamide;

5-(5-(6-oxa-2-azaspiro[3.4]octan-2-ylsulfonyl)-2-methylphenyl)-3-(3-methylisoxazol-5-yl)pyridin-2-amine;

3-(6-amino-5-(3-methylisoxazol-5-yl)pyridin-3-yl)-4-methyl-N-(2-oxotetrahydrofuran-3-yl)benzenesulfonamide;

3-(6-amino-5-(3-methylisoxazol-5-yl)pyridin-3-yl)-N-((1r,4r)-4-aminocyclohexyl)-4-methylbenzenesulfonamide;

3-(6-amino-5-(3-methylisoxazol-5-yl)pyridin-3-yl)-N-((3R,4R)-4-hydroxypyrrolidin-3-yl)-4-methylbenzenesulfonamide;

(S)-5-(2-methyl-5-(3-methylmorpholinosulfonyl)phenyl)-3-(3-methylisoxazol-5-yl)pyridin-2-amine;

(R)-5-(2-methyl-5-(3-methylmorpholinosulfonyl)phenyl)-3-(3-methylisoxazol-5-yl)pyridin-2-amine;

3-(6-amino-5-(3-methylisoxazol-5-yl)pyridin-3-yl)-4-methyl-N-neopentylbenzenesulfonamide;

3-(6-amino-5-(3-methylisoxazol-5-yl)pyridin-3-yl)-N-tert-butyl-4-methylbenzenesulfonamide 5-(5-(2,2-dimethylpyrrolidin-1-ylsulfonyl)-2-methylphenyl)-3-(3-methylisoxazol-5-yl)pyridin-2-amine;

3-(6-amino-5-(3-methylisoxazol-5-yl)pyridin-3-yl)-N-((1-hydroxycyclopropyl)methyl)-4-methylbenzenesulfonamide;

3-(6-amino-5-(3-methylisoxazol-5-yl)pyridin-3-yl)-N-(1-methoxy-3-methylbutan-2-yl)-4-methylbenzenesulfonamide;

3-(6-amino-5-(3-methylisoxazol-5-yl)pyridin-3-yl)-4-methyl-N-(2-(tetrahydro-2H-pyran-4-yl)ethyl)benzenesulfonamide;

(S)-3-(6-amino-5-(3-methylisoxazol-5-yl)pyridin-3-yl)-N-(1-cyclopropylethyl)-4-methylbenzenesulfonamide;

(S)-(1-(3-(6-amino-5-(3-methylisoxazol-5-yl)pyridin-3-yl)-4-methylphenylsulfonyl)pyrrolidin-2-yl)methanol;

3-(6-amino-5-(3-methylisoxazol-5-yl)pyridin-3-yl)-N-((1S,3S)-3-hydroxycyclohexyl)-4-methylbenzenesulfonamide;

4-(3-(6-amino-5-(3-methylisoxazol-5-yl)pyridin-3-yl)-4-methylphenylsulfonyl)piperazin-2-one;

5-(5-(4-(methoxymethyl)piperidin-1-ylsulfonyl)-2-methylphenyl)-3-(3-methylisoxazol-5-yl)pyridin-2-amine;

5-(5-(3-(dimethylamino)azetidin-1-ylsulfonyl)-2-methylphenyl)-3-(3-methylisoxazol-5-yl)pyridin-2-amine;

(R)-5-(5-(3-(methoxymethyl)morpholinosulfonyl)-2-methylphenyl)-3-(3-methylisoxazol-5-yl)pyridin-2-amine;

3-(6-amino-5-(3-methylisoxazol-5-yl)pyridin-3-yl)-N-(2-hydroxy-2-methylpropoxy)-4-methylbenzenesulfonamide;

3-(6-amino-5-(3-methylisoxazol-5-yl)pyridin-3-yl)-4-methyl-N-(tetrahydrofuran-3-yloxy)benzenesulfonamide;

3-(6-amino-5-(3-methylisoxazol-5-yl)pyridin-3-yl)-4-methyl-N-(tetrahydrofuran-3-yloxy)benzenesulfonamide;

3-(6-amino-5-(3-methylisoxazol-5-yl)pyridin-3-yl)-N-ethoxy-4-methylbenzenesulfonamide;

3-(6-amino-5-(3-methylisoxazol-5-yl)pyridin-3-yl)-4-methyl-N-((tetrahydro-2H-pyran-3-yl)methyl)benzenesulfonamide;

3-(6-amino-5-(3-methylisoxazol-5-yl)pyridin-3-yl)-4-methyl-N-((tetrahydro-2H-pyran-3-yl)methyl)benzenesulfonamide;

(R)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-4-methyl-N-(oxetan-3-ylmethyl)benzenesulfonamide;

3-(6-amino-5-(1,3-dimethyl-1H-pyrazol-4-yl)pyridin-3-yl)-N-(6-hydroxyspiro[3.3]heptan-2-yl)-4-methylbenzenesulfonamide;

3-(6-amino-5-(3-methylisoxazol-5-yl)pyridin-3-yl)-N-(2,2-difluoroethyl)-4-methylbenzenesulfonamide;

3-(6-amino-5-(2-methylthiazol-5-yl)pyridin-3-yl)-N-(6-hydroxyspiro[3.3]heptan-2-yl)-4-methylbenzenesulfonamide;

3-(6-amino-5-(3-methyl-1,2,4-oxadiazol-5-yl)pyridin-3-yl)-4-methyl-N-((tetrahydrofuran-3-yl)methyl)benzenesulfonamide;

3-(6-amino-5-(1-methyl-1H-pyrazol-4-yl)pyridin-3-yl)-4-methyl-N-(6-methylpyridin-2-yl)benzenesulfonamide;

3-(6-amino-5-(3-methylisoxazol-5-yl)pyridin-3-yl)-N-cyclopropyl-4-methylbenzenesulfonamide;

3-(6-amino-5-(3-methylisoxazol-5-yl)pyridin-3-yl)-4-methylbenzenesulfonamide;

3-(6-amino-5-(2-methyloxazol-5-yl)pyridin-3-yl)-4-methylbenzenesulfonamide;

3-(6-amino-5-(1-(2,2,2-trifluoroethyl)-1H-pyrazol-4-yl)pyridin-3-yl)-N-(2-hydroxy-2-methylpropoxy)-4-methylbenzenesulfonamide 3-(6-amino-5-(3-(2,2,2-trifluoroethyl)isoxazol-5-yl)pyridin-3-yl)-N-(2-hydroxy-2-methylpropyl)-4-methylbenzenesulfonamide;

3-(6-amino-5-(3-propylisoxazol-5-yl)pyridin-3-yl)-N-(2-hydroxy-2-methylpropyl)-4-methylbenzenesulfonamide;

3-(6-amino-5-(3-tert-butylisoxazol-5-yl)pyridin-3-yl)-N-((1r,4r)-4-hydroxycyclohexyl)-4-methylbenzenesulfonamide;

3-(6-amino-5-(3-cyclopropylisoxazol-5-yl)pyridin-3-yl)-N-(2-hydroxy-2-methylpropyl)-4-methylbenzenesulfonamide;

3-(6-amino-5-(3-isopropylisoxazol-5-yl)pyridin-3-yl)-N-(3-hydroxy-3-methylbutyl)-4-methylbenzenesulfonamide;

3-(6-amino-5-(3-tert-butylisoxazol-5-yl)pyridin-3-yl)-N-(2-hydroxy-2-methylpropyl)-4-methylbenzenesulfonamide;

3-(6-amino-5-(3-isopropylisoxazol-5-yl)pyridin-3-yl)-N-(2-hydroxy-2-methylpropyl)-4-methylbenzenesulfonamide;

3-(6-amino-5-(3-methylisoxazol-5-yl)pyridin-3-yl)-N-((1s,3s)-3-hydroxycyclobutyl)-4-methylbenzenesulfonamide;

3-(6-amino-5-(3-methylisoxazol-5-yl)pyridin-3-yl)-N-((1r,3r)-3-hydroxycyclobutyl)-4-methylbenzenesulfonamide;

(S)-3-(6-amino-5-(3-methylisoxazol-5-yl)pyridin-3-yl)-N-(2-hydroxypropyl)-4-methylbenzenesulfonamide;

3-(6-amino-5-(3-methylisoxazol-5-yl)pyridin-3-yl)-N-((4-(hydroxymethyl)tetrahydro-2H-pyran-4-yl)methyl)-4-methylbenzenesulfonamide;

5-(5-(3-methoxy-3-methylazetidin-1-ylsulfonyl)-2-methylphenyl)-3-(3-methyl-1,2,4-oxadiazol-5-yl)pyridin-2-amine;

3-(6-amino-5-(3-methylisoxazol-5-yl)pyridin-3-yl)-N-((1-(hydroxymethyl)cyclohexyl)methyl)-4-methylbenzenesulfonamide;

(R)-3-(6-amino-5-(3-methylisoxazol-5-yl)pyridin-3-yl)-4-methyl-N-(2-oxopiperidin-4-yl)benzenesulfonamide;

(R)-3-(6-amino-5-(3-methyl-1,2,4-oxadiazol-5-yl)pyridin-3-yl)-4-methyl-N-((tetrahydrofuran-2-yl)methyl)benzenesulfonamide;

3-(6-amino-5-(3-methylisoxazol-5-yl)pyridin-3-yl)-N-((1-(hydroxymethyl)cyclobutyl)methyl)-4-methylbenzenesulfonamide;

3-(6-amino-5-(3-methylisoxazol-5-yl)pyridin-3-yl)-N-(3-hydroxy-2,2-dimethylpropyl)-4-methylbenzenesulfonamide;

3-(6-amino-5-(3-methylisoxazol-5-yl)pyridin-3-yl)-4-methyl-N-(tetrahydro-2H-pyran-4-yl)benzenesulfonamide;

3-(6-amino-5-(3-methylisoxazol-5-yl)pyridin-3-yl)-N-((1-hydroxycyclohexyl)methyl)-4-methylbenzenesulfonamide;

3-(6-amino-5-(3-methyl-1,2,4-oxadiazol-5-yl)pyridin-3-yl)-N-((4-(hydroxymethyl)tetrahydro-2H-pyran-4-yl)methyl)-4-methylbenzenesulfonamide;

3-(6-amino-5-(3-methyl-1,2,4-oxadiazol-5-yl)pyridin-3-yl)-N-(2-(1-hydroxycyclopentyl)ethyl)-4-methylbenzenesulfonamide;

(1-(3-(6-amino-5-(3-methylisoxazol-5-yl)pyridin-3-yl)-4-methylphenylsulfonyl)azetidin-3-yl)methanol;

3-(6-amino-5-(3-methyl-1,2,4-oxadiazol-5-yl)pyridin-3-yl)-N-((1-(hydroxymethyl)cyclopentyl)methyl)-4-methylbenzenesulfonamide;

3-(6-amino-5-(3-methylisoxazol-5-yl)pyridin-3-yl)-4-methyl-N-(3,3,3-trifluoropropyl)benzenesulfonamide;

3-(6-amino-5-(3-methyl-1,2,4-oxadiazol-5-yl)pyridin-3-yl)-N-((1-hydroxycyclobutyl)methyl)-4-methylbenzenesulfonamide;

3-(6-amino-5-(3-methylisoxazol-5-yl)pyridin-3-yl)-N-(2-(1-hydroxycyclopentyl)ethyl)-4-methylbenzenesulfonamide;

3-(6-amino-5-(3-methyl-1,2,4-oxadiazol-5-yl)pyridin-3-yl)-N-(3,3-difluorocyclobutyl)-4-methylbenzenesulfonamide;

3-(6-amino-5-(3-methyl-1,2,4-oxadiazol-5-yl)pyridin-3-yl)-N-(3-hydroxy-2,2-dimethylpropyl)-4-methylbenzenesulfonamide;

3-(6-amino-5-(3-methyl-1,2,4-oxadiazol-5-yl)pyridin-3-yl)-N-((1-hydroxycyclopropyl)methyl)-4-methylbenzenesulfonamide;

5-(5-(3-methoxy-3-methylazetidin-1-ylsulfonyl)-2-methylphenyl)-3-(3-methylisoxazol-5-yl)pyridin-2-amine;

3-(6-amino-5-(3-methyl-1,2,4-oxadiazol-5-yl)pyridin-3-yl)-N-(2-hydroxy-1-(tetrahydrofuran-3-yl)ethyl)-4-methylbenzenesulfonamide;

3-(6-amino-5-(3-methylisoxazol-5-yl)pyridin-3-yl)-N-methoxy-N,4-dimethylbenzenesulfonamide;

3-(6-amino-5-(3-methylisoxazol-5-yl)pyridin-3-yl)-N-((1-(hydroxymethyl)cyclopentyl)methyl)-4-methylbenzenesulfonamide;

(R)-1-(3-(6-amino-5-(3-methylisoxazol-5-yl)pyridin-3-yl)-4-methylphenylsulfonyl)pyrrolidin-3-ol;

(R)-3-(6-amino-5-(3-methyl-1,2,4-oxadiazol-5-yl)pyridin-3-yl)-4-methyl-N-(2-oxopiperidin-4-yl)benzenesulfonamide;

3-(6-amino-5-(3-methyl-1,2,4-oxadiazol-5-yl)pyridin-3-yl)-N-((1-(hydroxymethyl)cyclobutyl)methyl)-4-methylbenzenesulfonamide;

(R)-3-(6-amino-5-(3-methylisoxazol-5-yl)pyridin-3-yl)-N-((1-ethylpyrrolidin-2-yl)methyl)-4-methylbenzenesulfonamide;

1-(3-(6-amino-5-(3-methylisoxazol-5-yl)pyridin-3-yl)-4-methylphenylsulfonyl)-3-methylazetidin-3-ol;

3-(6-amino-5-(3-methyl-1,2,4-oxadiazol-5-yl)pyridin-3-yl)-N-(2-aminoethyl)-4-methylbenzenesulfonamide;

3-(6-amino-5-(3-methylisoxazol-5-yl)pyridin-3-yl)-N-(2-(1-hydroxycyclohexyl)ethyl)-4-methylbenzenesulfonamide;

3-(6-amino-5-(3-methyl-1,2,4-oxadiazol-5-yl)pyridin-3-yl)-N-(2-(1-hydroxycyclohexyl)ethyl)-4-methylbenzenesulfonamide;

(S)-1-(3-(6-amino-5-(3-methyl-1,2,4-oxadiazol-5-yl)pyridin-3-yl)-4-methylphenylsulfonyl)pyrrolidin-3-ol;

(S)-3-(6-amino-5-(3-methylisoxazol-5-yl)pyridin-3-yl)-N-((1-ethylpyrrolidin-2-yl)methyl)-4-methylbenzenesulfonamide;

3-(6-amino-5-(3-methyl-1,2,4-oxadiazol-5-yl)pyridin-3-yl)-N-(1-isopropylpiperidin-4-yl)-4-methylbenzenesulfonamide;

3-(6-amino-5-(3-methylisoxazol-5-yl)pyridin-3-yl)-N-((1-hydroxycyclobutyl)methyl)-4-methylbenzenesulfonamide;

3-(6-amino-5-(3-methylisoxazol-5-yl)pyridin-3-yl)-4-methyl-N-((tetrahydro-2H-pyran-2-yl)methyl)benzenesulfonamide;

3-(6-amino-5-(3-methylisoxazol-5-yl)pyridin-3-yl)-4-methyl-N-((tetrahydro-2H-pyran-2-yl)methyl)benzenesulfonamide;

3-(6-amino-5-(3-methyl-1,2,4-oxadiazol-5-yl)pyridin-3-yl)-N-(2,2-difluoropropyl)-4-methylbenzenesulfonamide;

(1-(3-(6-amino-5-(3-methyl-1,2,4-oxadiazol-5-yl)pyridin-3-yl)-4-methylphenylsulfonyl)azetidin-3-yl)methanol;

(S)-3-(6-amino-5-(3-methylisoxazol-5-yl)pyridin-3-yl)-4-methyl-N-((tetrahydrofuran-3-yl)methyl)benzenesulfonamide;

3-(6-amino-5-(3-methylisoxazol-5-yl)pyridin-3-yl)-4-methyl-N-(2,2,2-trifluoroethyl)benzenesulfonamide;

(S)-3-(6-amino-5-(3-methylisoxazol-5-yl)pyridin-3-yl)-4-methyl-N-((tetrahydrofuran-2-yl)methyl)benzenesulfonamide;

3-(6-amino-5-(3-(hydroxymethyl)isoxazol-5-yl)pyridin-3-yl)-N-(2-hydroxy-2-methylpropyl)-4-methylbenzenesulfonamide;

3-(6-amino-5-(3-(morpholine-4-carbonyl)isoxazol-5-yl)pyridin-3-yl)-N-(2-hydroxy-2-methylpropyl)-4-methylbenzenesulfonamide;

5-(2-amino-5-(5-(N-(2-hydroxy-2-methylpropyl)sulfamoyl)-2-methylphenyl)pyridin-3-yl)-N,N-dimethylisoxazole-3-carboxamide;

3-(6-amino-5-(3-methyl-1,2,4-oxadiazol-5-yl)pyridin-3-yl)-4-methyl-N-propoxybenzenesulfonamide;

3-(6-amino-5-(3-methyl-1,2,4-oxadiazol-5-yl)pyridin-3-yl)-N-isopropoxy-4-methylbenzenesulfonamide 3-(6-amino-5-(3-methyl-1,2,4-oxadiazol-5-yl)pyridin-3-yl)-N-methoxy-4-methylbenzenesulfonamide;

3-(6-amino-5-(3-methyl-1,2,4-oxadiazol-5-yl)pyridin-3-yl)-N-tert-butoxy-4-methylbenzenesulfonamide;

3-(6-amino-5-(3-methyl-1,2,4-oxadiazol-5-yl)pyridin-3-yl)-4-methyl-N-(3,3,3-trifluoropropyl)benzenesulfonamide;

3-(6-amino-5-(3-methyl-1,2,4-oxadiazol-5-yl)pyridin-3-yl)-4-methyl-N-(tetrahydro-2H-pyran-4-yl)benzenesulfonamide;

3-(6-amino-5-(3-methylisoxazol-5-yl)pyridin-3-yl)-N-((3-(hydroxymethyl)oxetan-3-yl)methyl)-4-methylbenzenesulfonamide;

3-(6-amino-5-(3-methyl-1,2,4-oxadiazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((3-(hydroxymethyl)oxetan-3-yl)methyl)-4-methylbenzenesulfonamide;

3-(6-amino-5-(3-methylisoxazol-5-yl)pyridin-3-yl)-N-((1-hydroxycyclopentyl)methyl)-4-methylbenzenesulfonamide;

3-(6-amino-5-(3-methylisoxazol-5-yl)pyridin-3-yl)-N-((4-hydroxytetrahydro-2H-pyran-4-yl)methyl)-4-methylbenzenesulfonamide;

3-(6-amino-5-(3-methyl-1,2,4-oxadiazol-5-yl)pyridin-3-yl)-N-((1r,3r)-3-hydroxycyclobutoxy)-4-methylbenzenesulfonamide;

3-(6-amino-5-(3-methyl-1,2,4-oxadiazol-5-yl)pyridin-3-yl)-N-((3-hydroxyoxetan-3-yl)methyl)-4-methylbenzenesulfonamide;

3-(6-amino-5-(3-methyl-1,2,4-oxadiazol-5-yl)pyridin-3-yl)-4-methyl-N-((tetrahydrofuran-2-yl)methyl)benzenesulfonamide;

3-(6-amino-5-(1-methyl-1H-pyrrol-3-yl)pyridin-3-yl)-N-(2-hydroxy-2-methylpropyl)-4-methylbenzenesulfonamide;

3-(6-amino-5-(2-methylthiazol-4-yl)pyridin-3-yl)-N-(2-hydroxy-2-methylpropyl)-4-methylbenzenesulfonamide;

3-(6-amino-5-(4-methyl-1H-pyrazol-1-yl)pyridin-3-yl)-N-(2-hydroxy-2-methylpropyl)-4-methylbenzenesulfonamide;

3-(6-amino-5-(1,5-dimethyl-1H-pyrazol-4-yl)pyridin-3-yl)-N-(2-hydroxy-2-methylpropyl)-4-methylbenzenesulfonamide;

3-(6-amino-5-(5-methylisoxazol-4-yl)pyridin-3-yl)-N-(2-hydroxy-2-methylpropyl)-4-methylbenzenesulfonamide;

3-(6-amino-5-(1-methyl-1H-1,2,3-triazol-4-yl)pyridin-3-yl)-N-(2-hydroxy-2-methylpropyl)-4-methylbenzenesulfonamide;

3-(6-amino-5-(isoxazol-5-yl)pyridin-3-yl)-N-(2-hydroxy-2-methylpropyl)-4-methylbenzenesulfonamide;

3-(6-amino-5-(3-(trifluoromethyl)isoxazol-5-yl)pyridin-3-yl)-N-(2-hydroxy-2-methylpropyl)-4-methylbenzenesulfonamide;

3-(6-amino-5-(3-((dimethylamino)methyl)isoxazol-5-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((3-(hydroxymethyl)oxetan-3-yl)methyl)-4-methylbenzenesulfonamide;

3-(6-amino-5-(2-methylthiazol-5-yl)pyridin-3-yl)-N-((3-(hydroxymethyl)oxetan-3-yl)methyl)-4-methylbenzenesulfonamide;

3-(6-amino-5-(2-methyloxazol-5-yl)pyridin-3-yl)-4-methyl-N-((3-methyloxetan-3-yl)methyl)benzenesulfonamide;

3-(6-amino-5-(3-(difluoromethyl)-1,2,4-oxadiazol-5-yl)pyridin-3-yl)-N-((1r,4r)-4-hydroxycyclohexyl)-4-methylbenzenesulfonamide;

3-(6-amino-5-(3-(difluoromethyl)-1,2,4-oxadiazol-5-yl)pyridin-3-yl)-N-(2-hydroxy-2-methylpropyl)-4-methylbenzenesulfonamide;

3-(6-amino-5-(3-methyl-1,2,4-oxadiazol-5-yl)pyridin-3-yl)-4-methyl-N-(6-methylpyridin-2-yl)benzenesulfonamide;

3-(6-amino-5-(3-methylisoxazol-5-yl)pyridin-3-yl)-N-(2-hydroxyethyl)-4-methylbenzenesulfonamide;

3-(6-amino-5-(2-methylthiazol-5-yl)pyridin-3-yl)-4-methylbenzenesulfonamide;

3-(6-amino-5-(3-methyl-1,2,4-oxadiazol-5-yl)pyridin-3-yl)-4-methylbenzenesulfonamide;

3-(6-amino-5-(3-methyl-1,2,4-oxadiazol-5-yl)pyridin-3-yl)-N-((1s,3s)-3-(hydroxymethyl)cyclobutyl)-4-methylbenzenesulfonamide;

3-(6-amino-5-(3-methyl-1,2,4-oxadiazol-5-yl)pyridin-3-yl)-N-((1r,3r)-3-(hydroxymethyl)cyclobutyl)-4-methylbenzenesulfonamide;

3-(2-amino-2'-methyl-3,4'-bipyridin-5-yl)-N-((1r,4r)-4-(hydroxymethyl)cyclohexyl)-4-methylbenzenesulfonamide;

3-(6-amino-5-(3-(2,2,2-trifluoroethyl)-1,2,4-oxadiazol-5-yl)pyridin-3-yl)-N-((1r,4r)-4-hydroxycyclohexyl)-4-methylbenzenesulfonamide;

3-(6-amino-5-(3-(2,2,2-trifluoroethyl)-1,2,4-oxadiazol-5-yl)pyridin-3-yl)-N-(3-hydroxy-3-methylbutyl)-4-methylbenzenesulfonamide;

3-(6-amino-5-(3-cyclopropyl-1,2,4-oxadiazol-5-yl)pyridin-3-yl)-N-(2-hydroxy-2-methylpropyl)-4-methylbenzenesulfonamide;

3-(6-amino-5-(1H-1,2,4-triazol-1-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((1r,3r)-3-hydroxycyclobutyl)-4-methylbenzenesulfonamide;

3-(6-amino-5-(2-methyloxazol-5-yl)pyridin-3-yl)-N-((1s,3s)-3-hydroxycyclobutyl)-4-methylbenzenesulfonamide;

3-(6-amino-5-(2-methylthiazol-5-yl)pyridin-3-yl)-N-((3-hydroxycyclobutyl)methyl)-4-methylbenzenesulfonamide;

(1-(3-(6-amino-5-(2-methylthiazol-5-yl)pyridin-3-yl)-4-methylphenylsulfonyl)azetidin-3-yl)methanol;

3-(6-amino-5-(2-methylthiazol-5-yl)pyridin-3-yl)-4-methyl-N-(oxetan-3-ylmethyl)benzenesulfonamide;

3-(6-amino-5-(2-methylthiazol-5-yl)pyridin-3-yl)-N-((3-hydroxyoxetan-3-yl)methyl)-4-methylbenzenesulfonamide 3-(6-amino-5-(2-methylthiazol-5-yl)pyridin-3-yl)-N-(3-hydroxy-2,2-dimethylpropyl)-4-methylbenzenesulfonamide;

3-(6-amino-5-(2-methylthiazol-5-yl)pyridin-3-yl)-N-(2-hydroxyethyl)-4-methylbenzenesulfonamide;

3-(6-amino-5-(3-methylisoxazol-5-yl)pyridin-3-yl)-N-(((1s,3s)-3-hydroxycyclobutyl)methyl)-4-methylbenzenesulfonamide;

5-(6-amino-5-(3-methyl-1,2,4-oxadiazol-5-yl)pyridin-3-yl)-2-fluoro-N-(2-hydroxy-2-methylpropyl)-4-methylbenzenesulfonamide;

(R)-3-(6-amino-5-(3-methyl-1,2,4-oxadiazol-5-yl)pyridin-3-yl)-4-methyl-N-((tetrahydrofuran-3-yl)methyl)benzenesulfonamide;

(S)-3-(6-amino-5-(3-methyl-1,2,4-oxadiazol-5-yl)pyridin-3-yl)-4-methyl-N-((tetrahydrofuran-3-yl)methyl)benzenesulfonamide;

5-(6-amino-5-(3-methylisoxazol-5-yl)pyridin-3-yl)-2-chloro-N-(2-hydroxy-2-methylpropyl)-4-methylbenzenesulfonamide;

5-(6-amino-5-(3-methyl-1,2,4-oxadiazol-5-yl)pyridin-3-yl)-2-chloro-N-(2-hydroxy-2-methylpropyl)-4-methylbenzenesulfonamide;

3-(6-amino-5-(5-methylthiazol-2-yl)pyridin-3-yl)-N-(2-hydroxy-2-methylpropyl)-4-methylbenzenesulfonamide;

3-(6-amino-5-(5-methylthiazol-2-yl)pyridin-3-yl)-N-(3-hydroxy-3-methylbutyl)-4-methylbenzenesulfonamide;

3-(6-amino-5-(2-methylthiazol-4-yl)pyridin-3-yl)-N-((1r,4r)-4-hydroxycyclohexyl)-4-methylbenzenesulfonamide;

3-(6-amino-5-(2-methylthiazol-4-yl)pyridin-3-yl)-N-(3-hydroxy-3-methylbutyl)-4-methylbenzenesulfonamide;

3-(6-amino-5-(oxazol-5-yl)pyridin-3-yl)-N-(2-hydroxy-2-methylpropyl)-4-methylbenzenesulfonamide;

3-(6-amino-5-(2-methyloxazol-5-yl)pyridin-3-yl)-N-((1-hydroxycyclopropyl)methyl)-4-methylbenzenesulfonamide;

3-(6-amino-5-(2-methyloxazol-5-yl)pyridin-3-yl)-4-methyl-N-(2,2,2-trifluoroethyl)benzenesulfonamide;

3-(6-amino-5-(2-methyloxazol-5-yl)pyridin-3-yl)-N-(2-hydroxypropyl)-4-methylbenzenesulfonamide;

3-(6-amino-5-(2-methyloxazol-5-yl)pyridin-3-yl)-N-(2,2-difluoroethyl)-4-methylbenzenesulfonamide;

3-(6-amino-5-(2-methyloxazol-5-yl)pyridin-3-yl)-N-(3-hydroxy-2,2-dimethylpropyl)-4-methylbenzenesulfonamide;

3-(6-amino-5-(2-methyloxazol-5-yl)pyridin-3-yl)-4-methyl-N-(oxetan-3-ylmethyl)benzenesulfonamide;

3-(6-amino-5-(2-methyloxazol-5-yl)pyridin-3-yl)-4-methyl-N-((tetrahydrofuran-3-yl)methyl)benzenesulfonamide;

3-(6-amino-5-(2-methyloxazol-5-yl)pyridin-3-yl)-N-((3-hydroxycyclobutyl)methyl)-4-methylbenzenesulfonamide; and 3-(6-amino-5-(2-methyloxazol-5-yl)pyridin-3-yl)-N-cyclopropyl-4-methylbenzenesulfonamide;

3-(6-amino-5-(3-methylisoxazol-5-yl)pyridin-3-yl)-N-((1r,3r)-3-hydroxycyclobutoxy)-4-methylbenzenesulfonamide;

trans-3-(6-amino-5-(3-methylisoxazol-5-yl)pyridin-3-yl)-N-(3-hydroxycyclopentyl)-4-methylbenzenesulfonamide;

3-(6-amino-5-(2-methylthiazol-5-yl)pyridin-3-yl)-N-((1r,4r)-4-hydroxycyclohexyl)-4-methylbenzenesulfonamide;

3-(6-amino-5-(2-methyloxazol-5-yl)pyridin-3-yl)-N-((1r,4r)-4-hydroxycyclohexyl)-4-methylbenzenesulfonamide hydrochloride;

5-(6-amino-5-(3-methylisoxazol-5-yl)pyridin-3-yl)-2-fluoro-N-(2-hydroxy-2-methylpropoxy)-4-methylbenzenesulfonamide;

5-(6-amino-5-(3-methyl-1,2,4-oxadiazol-5-yl)pyridin-3-yl)-N-(2-hydroxy-2-methylpropyl)-2,4-dimethylbenzenesulfonamide;

3-(6-amino-5-(3-methylisoxazol-5-yl)pyridin-3-yl)-N-(trans-4-hydroxytetrahydrofuran-3-yl)-4-methylbenzenesulfonamide:trifluoroacetic acid;

3-(6-amino-5-(3-methylisoxazol-5-yl)pyridin-3-yl)-N-((trans)-2-hydroxycyclopentyl)-4-methylbenzenesulfonamide;

trans-1-((3-(6-amino-5-(3-methylisoxazol-5-yl)pyridin-3-yl)-4-methylphenyl)sulfonyl)-4-methylpyrrolidin-3-ol;

3-(6-amino-5-(5-methyl-1,3,4-thiadiazol-2-yl)pyridin-3-yl)-N-(2-hydroxy-2-methylpropyl)-4-methylbenzenesulfonamide;

(R)-3-(6-amino-5-(3-methylisoxazol-5-yl)pyridin-3-yl)-4-methyl-N-(1,1,1-trifluoro-3-hydroxypropan-2-yl)benzenesulfonamide;

(S)-3-(6-amino-5-(3-methylisoxazol-5-yl)pyridin-3-yl)-4-methyl-N-(1,1,1-trifluoro-3-hydroxypropan-2-yl)benzenesulfonamide;

3-(6-amino-5-(2-methyloxazol-5-yl)pyridin-3-yl)-N-((3-hydroxycyclobutyl)methyl)-4-methylbenzenesulfonamide;

3-(6-amino-5-(2-methyloxazol-5-yl)pyridin-3-yl)-N-(3-hydroxy-2,2-dimethylpropyl)-4-methylbenzenesulfonamide;

3-(6-amino-5-(2-methyloxazol-5-yl)pyridin-3-yl)-4-methyl-N-(oxetan-3-ylmethyl)benzenesulfonamide;

(+/−)trans-3-(6-amino-5-(2-methyloxazol-5-yl)pyridin-3-yl)-N-(3-hydroxycyclopentyl)-4-methylbenzenesulfonamide;

3-(6-amino-5-(2-methyloxazol-5-yl)pyridin-3-yl)-N-(2-hydroxyethyl)-4-methylbenzenesulfonamide;

3-(6-amino-5-(2-methyloxazol-5-yl)pyridin-3-yl)-N-(3-hydroxypropyl)-4-methylbenzenesulfonamide;

3-(6-amino-5-(2-methyloxazol-5-yl)pyridin-3-yl)-N-((3-hydroxyoxetan-3-yl)methyl)-4-methylbenzenesulfonamide;

3-(6-amino-5-(2-methyloxazol-5-yl)pyridin-3-yl)-4-methyl-N-((tetrahydro-2H-pyran-3-yl)methyl)benzenesulfonamide;

3-(6-amino-5-(2-methyloxazol-5-yl)pyridin-3-yl)-4-methyl-N-(2,2,2-trifluoroethyl)benzenesulfonamide;

3-(6-amino-5-(2-methyloxazol-5-yl)pyridin-3-yl)-N-(2,2-difluoroethyl)-4-methylbenzenesulfonamide;

3-(6-amino-5-(2-methyloxazol-5-yl)pyridin-3-yl)-N-((1r,4r)-4-(hydroxymethyl)cyclohexyl)-4-methylbenzenesulfonamide;

3-(6-amino-5-(2-methyloxazol-5-yl)pyridin-3-yl)-N-(cyclopropylmethyl)-4-methylbenzenesulfonamide;

3-(6-amino-5-(2-methyloxazol-5-yl)pyridin-3-yl)-N-((4-(hydroxymethyl)tetrahydro-2H-pyran-4-yl)methyl)-4-methylbenzenesulfonamide;

3-(6-amino-5-(2-methyloxazol-5-yl)pyridin-3-yl)-N-cyclopropyl-4 methylbenzenesulfonamide;

rac-3-(6-amino-5-(2-methyloxazol-5-yl)pyridin-3-yl)-N-(2-hydroxypropyl)-4-methylbenzenesulfonamide;

(+/−)-cis-3-(6-amino-5-(2-methyloxazol-5-yl)pyridin-3-yl)-N-(3-hydroxycyclopentyl)-4-methylbenzenesulfonamide;

or a pharmaceutically acceptable salt thereof.

12. The compound according to claim 11, wherein the compound is 3-(6-amino-5-(2-methyloxazol-5-yl)pyridin-3-yl)-N-(2-hydroxy-2-methylpropyl)-4-methylbenzenesulfonamide or a pharmaceutically acceptable salt thereof.

13. A pharmaceutical composition, comprising a compound or salt according to claim 2 and one or more pharmaceutically acceptable carriers.

14. A pharmaceutical combination, comprising a compound or salt according to claim 2 and a second active agent.

* * * * *